US012559521B2

(12) United States Patent
Wang et al.

(10) Patent No.: US 12,559,521 B2
(45) Date of Patent: Feb. 24, 2026

(54) PSMA IMAGING AGENTS

(71) Applicant: Siemens Medical Solutions USA, Inc., Malvern, PA (US)

(72) Inventors: Eric Wang, San Diego, CA (US); Hartmuth C. Kolb, Playa Del Rey, CA (US); Anna Katrin Szardenings, San Diego, CA (US); Changhui Liu, Los Angeles, CA (US); Joseph C. Walsh, Pacific Palisades, CA (US); Gang Chen, San Diego, CA (US); Anjana Sinha, San Diego, CA (US); Dhanalakshmi Kasi, Silver Spring, MD (US); Chul Yu, Los Angeles, CA (US); Umesh B. Gangadharmath, Folsom, CA (US); Wei Zhang, Los Angeles, CA (US); Tieming Zhao, Placentia, CA (US); Vani P. Mocharla, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 18/809,625

(22) Filed: Aug. 20, 2024

(65) Prior Publication Data

US 2024/0409580 A1 Dec. 12, 2024

Related U.S. Application Data

(60) Division of application No. 16/999,563, filed on Aug. 21, 2020, now Pat. No. 12,139,554, which is a continuation of application No. 15/975,296, filed on May 9, 2018, now Pat. No. 10,894,807, which is a continuation of application No. 14/917,127, filed as application No. PCT/US2012/051674 on Aug. 21, 2012, now Pat. No. 10,011,632.

(60) Provisional application No. 61/563,987, filed on Nov. 28, 2011, provisional application No. 61/525,877, filed on Aug. 22, 2011.

(51) Int. Cl.

| | |
|---|---|
| ***A61K 51/08*** | (2006.01) |
| ***A61K 51/04*** | (2006.01) |
| ***C07D 207/16*** | (2006.01) |
| ***C07D 209/48*** | (2006.01) |
| ***C07D 213/81*** | (2006.01) |
| ***C07D 213/82*** | (2006.01) |
| ***C07D 233/78*** | (2006.01) |
| ***C07D 233/96*** | (2006.01) |
| ***C07D 239/60*** | (2006.01) |
| ***C07D 249/04*** | (2006.01) |
| ***C07D 249/06*** | (2006.01) |
| ***C07D 251/30*** | (2006.01) |
| ***C07D 263/34*** | (2006.01) |
| ***C07D 277/56*** | (2006.01) |
| ***C07D 401/12*** | (2006.01) |
| ***C07D 403/06*** | (2006.01) |
| ***C07D 403/12*** | (2006.01) |
| ***C07D 405/12*** | (2006.01) |
| ***C07K 5/02*** | (2006.01) |
| ***C07K 5/062*** | (2006.01) |
| ***C07K 5/072*** | (2006.01) |
| *A61K 38/00* | (2006.01) |

(52) U.S. Cl.

CPC ........ *C07K 5/0215* (2013.01); *A61K 51/0402* (2013.01); *A61K 51/0453* (2013.01); *A61K 51/0497* (2013.01); *A61K 51/088* (2013.01); *C07D 207/16* (2013.01); *C07D 209/48* (2013.01); *C07D 213/81* (2013.01); *C07D 213/82* (2013.01); *C07D 233/78* (2013.01); *C07D 233/96* (2013.01); *C07D 239/60* (2013.01); *C07D 249/04* (2013.01); *C07D 249/06* (2013.01); *C07D 251/30* (2013.01); *C07D 263/34* (2013.01); *C07D 277/56* (2013.01); *C07D 401/12* (2013.01); *C07D 403/06* (2013.01); *C07D 403/12* (2013.01); *C07D 405/12* (2013.01); *C07K 5/06026* (2013.01); *C07K 5/06113* (2013.01); *A61K 38/00* (2013.01)

(58) Field of Classification Search

None

See application file for complete search history.

(56) References Cited

U.S. PATENT DOCUMENTS

| | | | |
|---|---|---|---|
| 2010/0178246 A1 | 7/2010 | Babich et al. | |
| 2013/0034494 A1 | 2/2013 | Babich et al. | |

FOREIGN PATENT DOCUMENTS

| | | |
|---|---|---|
| WO | 2010014933 | 2/2010 |
| WO | 2012078534 | 6/2012 |

OTHER PUBLICATIONS

Barinka, Cyril, et al. "Interactions between human glutamate carboxypeptidase II and urea-based inhibitors: structural characterization." Journal of medicinal chemistry 51.24 (2008): 7737-7743.

Banerjee, Sangeeta Ray, et al. "A modular strategy to prepare multivalent inhibitors of prostate-specific membrane antigen (PSMA)." Oncotarget 2.12 (2011): 1244.

(Continued)

*Primary Examiner* — Alicia L Otton

(57) ABSTRACT

Compounds for targeting and agents for imaging, prostate-specific membrane antigen (PSMA) are disclosed. Methods of synthesizing compounds and imaging agents, as well as methods for imaging PSMA are also disclosed. The imaging agents disclosed are suitable for PET and SPECT imaging.

6 Claims, 14 Drawing Sheets

(56) References Cited

OTHER PUBLICATIONS

International Search Report and Written Opinion for International Application No. PCT/US2012/051674, International Filing Date Aug. 21, 2012, Date of Mailing Nov. 15, 2012, 10 pages.
STN Registry database entry for CAS RN 949575-22-8, entry date Oct. 8, 2007, accessed May 18, 2024.
STN Registry entry for CAS Registry No. 1069138-65-3, accessed via STNext Nov. 15, 2023, Entry Date Oct. 31, 2008.
STN Registry Entry for CAS RN 68157-45-4, Entered STN May 14, 2004, accessed May 6, 2023.

COMPARISON OF THREE TRACERS IN THE SAME ANIMAL: H03111119
(PC3 AND 22RV1) SCAN TYPE: 2 HR UPTAKE, 15 MIN STATIC SCAN
THIRD PARTY COMPOUND
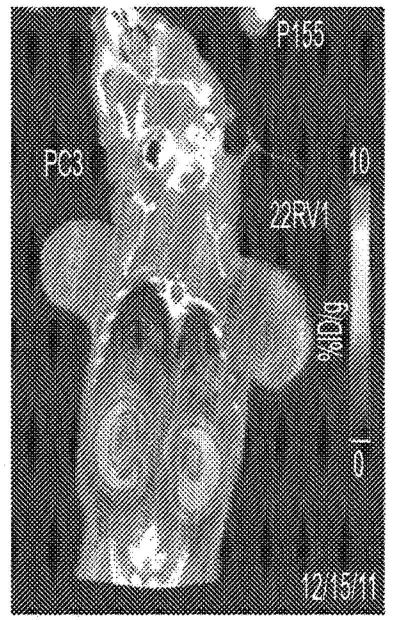
| | %ID/g | T/M |
|---|---|---|
| 22RV1 | 2.3 | **20.9** |
| PC3 | 0.20 | **1.8** |
| MUSCLE | 0.11 | - |
SIEMENS (P246)
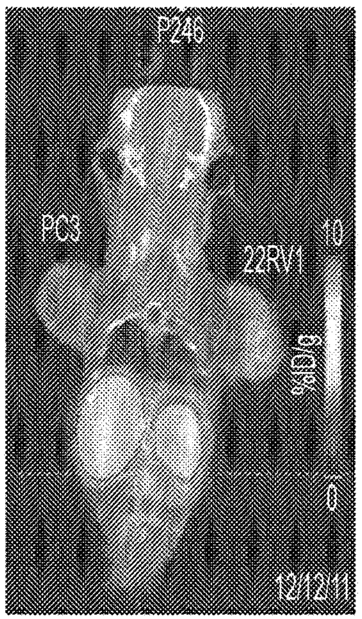
| | %ID/g | T/M |
|---|---|---|
| 22RV1 | 2.2 | **23.9** |
| PC3 | 0.81 | **8.8** |
| MUSCLE | 0.092 | - |
SIEMENS (P238)
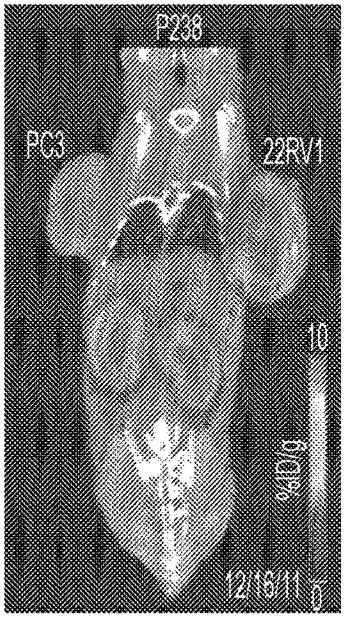
| | %ID/g | T/M |
|---|---|---|
| 22RV1 | 3.4 | **85** |
| PC3 | 0.256 | **6.4** |
| MUSCLE | 0.040 | - |
FIG. 1

COMPARISON OF THREE TRACERS IN THE SAME ANIMAL: H09181131
(DU145 AND 22RV1) SCAN TYPE: 2 HR UPTAKE, 15 MIN STATIC SCAN
THIRD PARTY COMPOUND
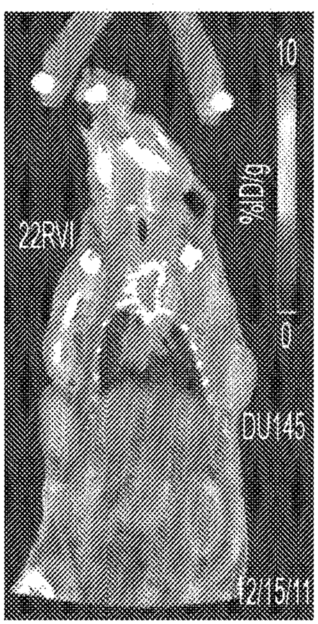
| | %ID/g | T/M |
|---|---|---|
| 22RV1 | 3.2 | **16** |
| DU145 | 0.18 | **0.9** |
| MUSCLE | 0.20 | - |
SIEMENS (P246)
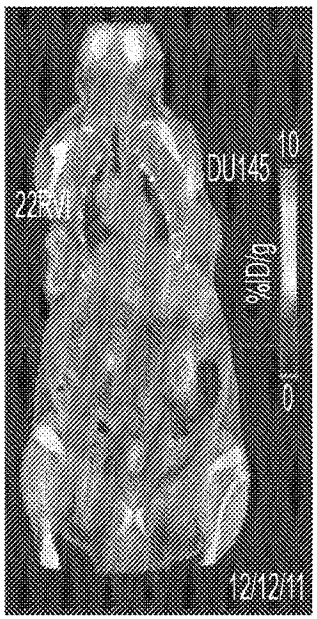
| | %ID/g | T/M |
|---|---|---|
| 22RV1 | 4.7 | **17.5** |
| DU145 | 0.242 | **0.9** |
| MUSCLE | 0.268 | - |
SIEMENS (P238)
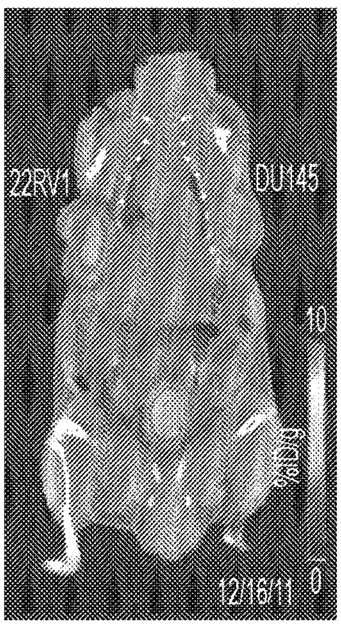
| | %ID/g | T/M |
|---|---|---|
| 22RV1 | 2.7 | **79.4** |
| DU145 | 0.035 | **1.02** |
| MUSCLE | 0.034 | - |
FIG. 2

| 120 MIN | %ID/g | T/M |
|---|---|---|
| 22RV1 | 4.56 | 26.7 |
| DU145 | 0.36 | 2.1 |
| MUSCLE | 0.17 | |

[F18]-P292: 2h DYNAMIC SCAN, AND 4h UPTAKE, 15 MIN SCAN(5-3 AND 5-17-12)
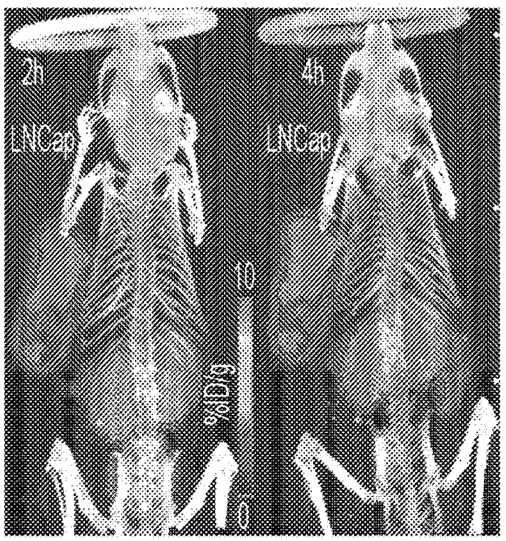
H10281187
| | %ID/g 2h | %ID/g 4h |
|---|---|---|
| LNCAP | 5.6 | 5.9 |
| MUSCLE | 0.1 | 0.07 |
| KIDNEYS | 39 | 28 |
| BLADDER | 397 | 43 |
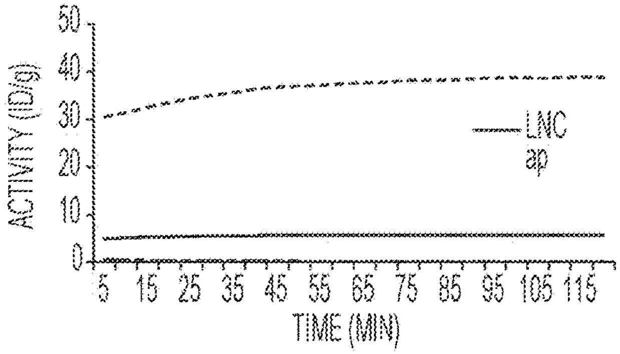
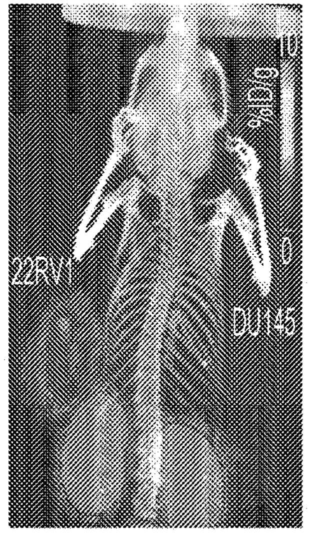
TM01301225
| 120 MIN | %ID/g | T/M |
|---|---|---|
| 22RV1 | 3.31 | 18.62 |
| DU145 | 0.33 | 1.88 |
| MUSCLE | 0.18 | |
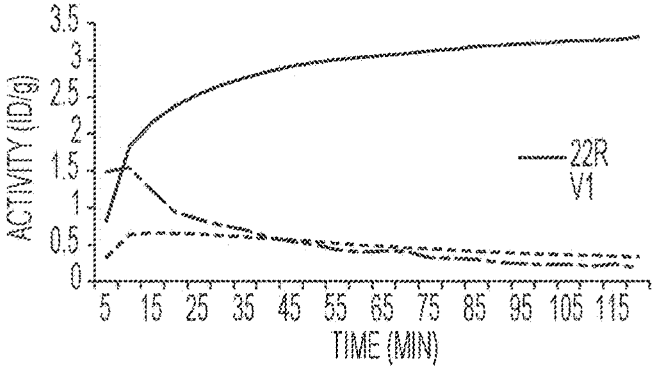
FIG. 5

[F18]-P155

| | 30 MIN | 60 MIN | 120 MIN |
|---|---|---|---|
| LNCaP | 10.6 | 15.6 | 28.3 |

[F18]-P246

| | 30 MIN | 60 MIN | 120 MIN |
|---|---|---|---|
| LNCaP | 13.4 | 36.5 | 72.6 |

NEGATIVE CONTROL: P297
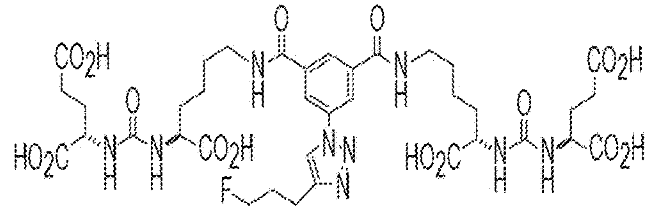
P246 (Ki 0.16 nM)
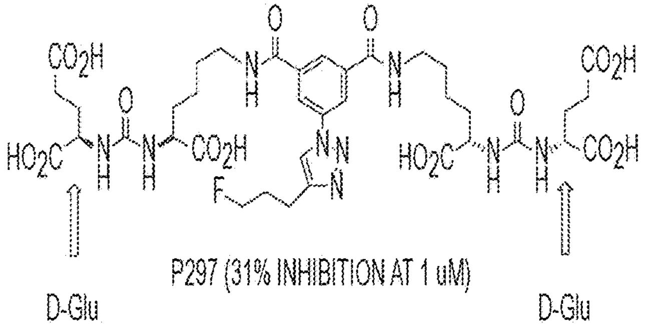
P297 (31% INHIBITION AT 1 uM)
D-Glu D-Glu
- CONVERSION OF NATURAL L-Glu (P246) TO D-Glu ISOMER (P297) RESULTS IN >3,000 FOLD DROP IN PSMA INHIBITION
- NO TUMOR (SALIVARY GLAND) UPTAKE
- KIDNEY: SIGNAL IN ONE ANIMAL DUE TO RENAL CLEARANCE, OTHER TWO ANIMALS HAVE NO SIGNAL
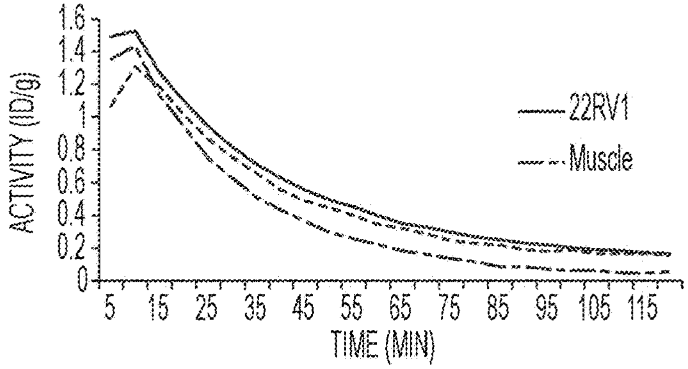
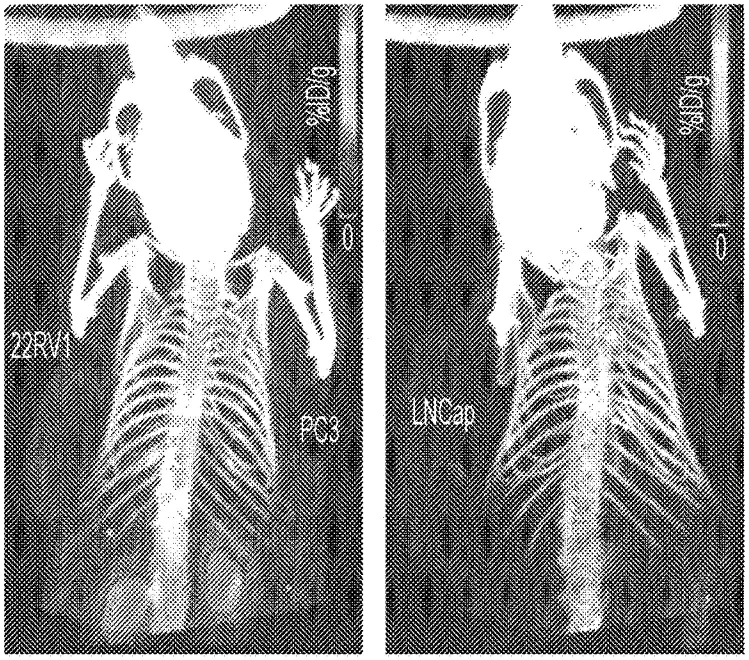
FIG. 7

CORRELATION OF KD (CELL BASED) WITH Ki (ENZYMATIC) FOR P238, P246, P292, P155

| | | | | Ki (nM) | Kd (nM) |
|---|---|---|---|---|---|
| P155 | 3.1 | 2.8 | 1.8 | 2.57 | 6 |
| P238 | 0.4 | 0.1 | | 0.25 | 15 |
| P246 | 0.2 | 0.4 | 0.2 | 0.27 | 7 |
| P292 | 0.7 | | | 0.70 | 9 |

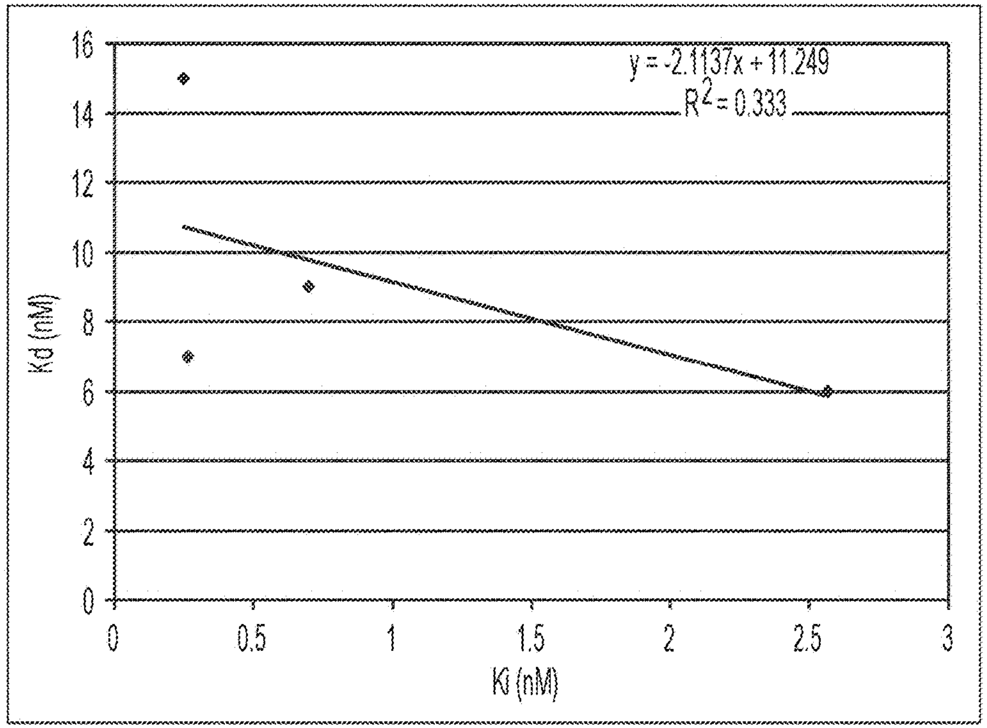

- THESE 4 TRACERS REPRESENT A VERY NARROW RANGE: Kis 0.2 TO 2.5 AND KDs 6-15 nM
- WITHIN THIS RANGE, THERE IS NO CORRELATION BETWEEN THE CELL BASED MEASURED KDs WITH Kis (ENZYMATIC MEASUREMENT) FOR 4 PSMA TRACERS
- THE KDs REFLECT THE BINDING OF THE TRACERS TO THE CELL MEMBRANE PLUS ANY NON-SPECIFIC BINDING TO OTHER PROTEINS
- THE Kis ARE MEASURED USING PURE ENZYME IN BUFFER IN A COMPETITION EXPERIMENT WITH THE NAAG SUBSTRATE

FIG. 9

DATE: 3/23/12
TRACER: P285
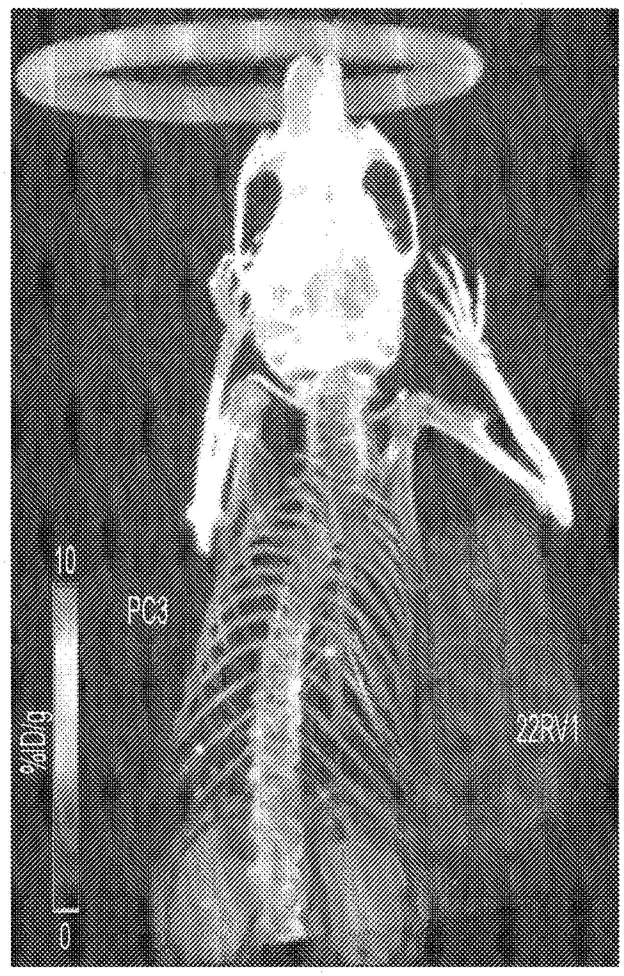
ANIMAL #: H09201159
TUMOR: 22RV1 AND PC3
SCAN: 3061
SCAN TYPE: 120 MIN DYNAMIC SCAN
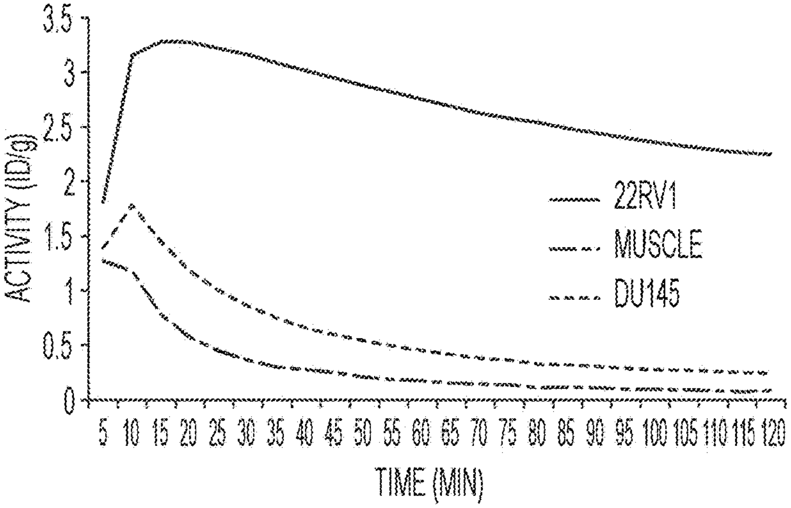
| 120 MIN | %ID/g | T/M |
|---|---|---|
| 22RV1 | 2.25 | 26.56 |
| PC3 | 0.24 | 2.88 |
| MUSCLE | 0.08 | |
FIG. 10

DATE: 3/23/12
TRACER: P285

ANIMAL #: H08111259
TUMOR: 22RV1 AND PC3
SCAN: 3062
SCAN TYPE: 2 HR UPTAKE, 15 MIN STATIC SCAN

| | %ID/g | T/M |
|---|---|---|
| 22RV1 | 1.5 | 75 |
| PC3 | 0.09 | 4.5 |
| MUSCLE | 0.02 | - |

DATE: 3/23/12
TRACER: P285

ANIMAL #: H08111290
TUMOR: 22RV1 AND DU145
SCAN: 3063
SCAN TYPE: 2HR UPTAKE, 15 MIN STATIC SCAN

| | %ID/g | T/M |
|---|---|---|
| 22RV1 | 1.7 | 283.33 |
| PC3 | 0.08 | 13.33 |
| MUSCLE | 0.006 | - |

PSMA TRACER OVERVIEW

| ID | THIRD PARTY COMPOUND | P238 | P246 | P267 | P292 |
|---|---|---|---|---|---|
| MW | 441.4 | 963.3 | 895.8 | 929.9 | 1060.5 |
| PSMA Ki [nM] | 1.8-3 | 0.1-0.4 | 0.16-0.3 | 0.8 | 0.7 |
| KD (BIACORE) P258 (MONOMER) ON CHIP | 440 pM (SD=5, N=3) | 163 pM (SD=23, N=6) | 160 pM (SD=10, N=3) | 64 pM (SD=3, N=3) | 50 pM (SD=3, N=3) |
| KD (BIACORE) P294 (DIMER) ON CHIP | 51 pM (SD=4, N=3) | 44 pM (SD=4, N=3) | 41 pM (SD=6, N=3) | 78 pM (SD=12, N=3) | 23 pM (SD=2, N=3) |
| KD (CELL BASED, LNCaP) | 6 nM | 15 nM | 7 nM | | 9 nM |
| AV. %ID/g IN 22RV1 (120 MIN) | 3.2 (SEM=0.41; N=7) | 5.3 (SEM=0.46,N=17) | 3.8 (SEM=0.29,N=13) | 3.8 (SEM=0.26,N=8) | 3.9 (SEM=0.38,N=10) |
| AV. %ID/g IN MUSCLE | 0.1 (SEM=0.05,N=10) | 0.1 (SEM=0.01,N=18) | 0.13 (SEM=0.02,N=15) | 0.17 (0.02) | 0.1 (0.020) |
| ABDOMEN %ID/g | 0.69 (SD=0.27,N=7) | 0.55 (SD=0.22,N=5) | 0.64 (SD=0.06,N=5) | 0.61 (SD=0.09,N=5) | 0.57(SD=0.18,N=6) |
| 4 HOUR PET SCAN (T, KIDNEY, BLADDER) | YES, SAME AS 2h | YES, SAME AS 2h | | | YES, SAME AS 2h |
| REACHING PLATEAU (TIME TO <0.05% ID/GCHANGE) 22RV1 IN MIN | 90 min (N=1) | 54(SD=5.48,N=5) | | | 47(SD=7.58,N=5) |
| MUSCLE CLEARANCE RATE (TIME TO <0.05% ID/gCHANGE) MIN | | 49(SD=9.62,N=5) | | | 46(SD=8.22,N=5) |
| CORR. %ID/g WITH WESTERN BLOT | | | | | |
| METABOLISM (HUMAN HEPATOCYTES) | STABLE | STABLE | STABLE | STABLE | |
| IN VIVO METABOLISM (MICE) | STABLE | STABLE | STABLE | | STABLE |
| PK (MOUSE) CONFIRM PET RESULTS? | YES | YES | YES | YES | YES |
| TUMOR BLOCKING | BLOCKED WITH P155, PMPA, P246 | BLOCKED WITH P155, PMPA, P246 | | | BLOCKED WITH P155, PMPA, P292 |
| RAT-PROSTATE PET/AUTORAD: NO BACKGRD | YES | YES | YES | YES | |

FIG. 13

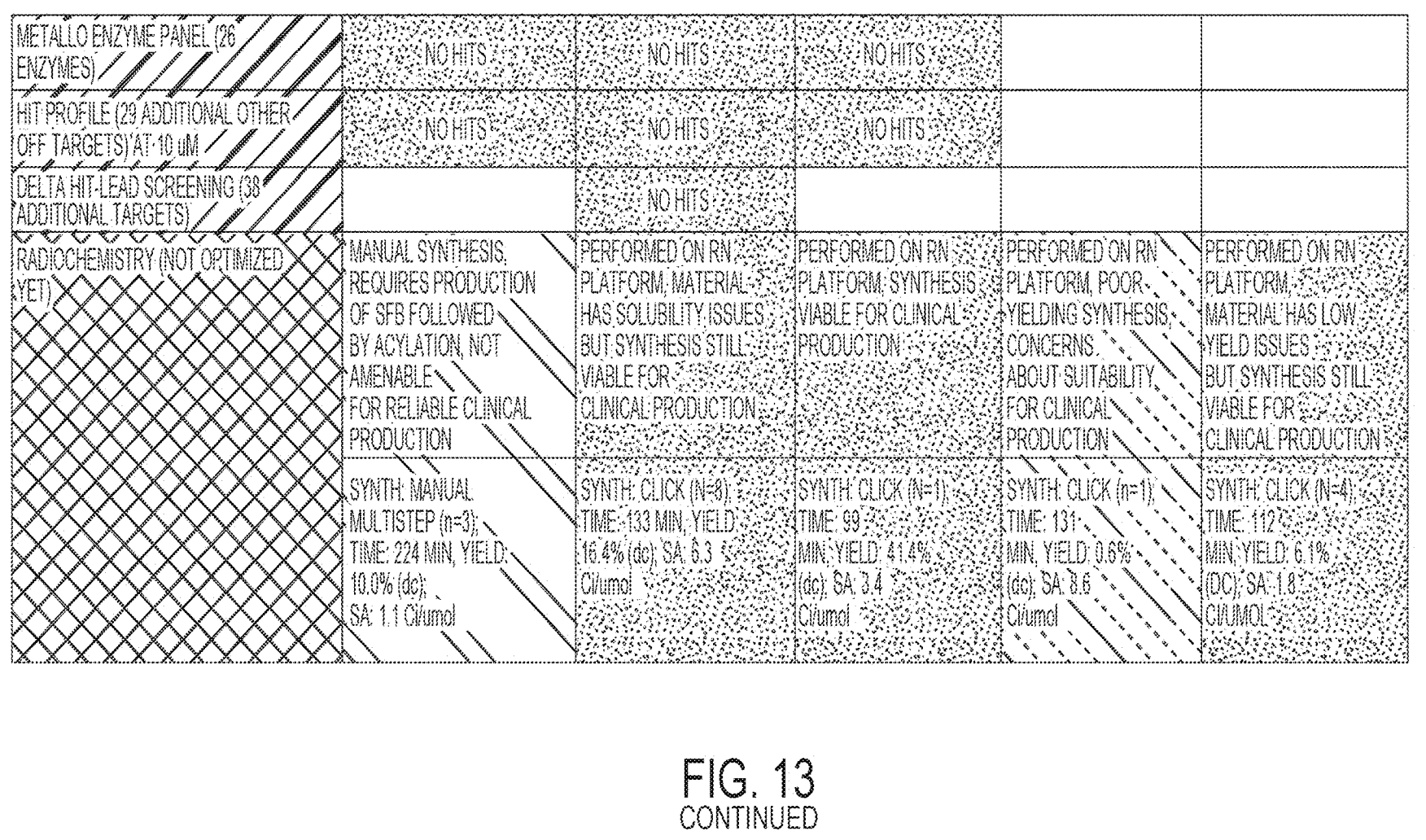

| | | | | | |
|---|---|---|---|---|---|
| METALLO ENZYME PANEL (26 ENZYMES) | NO HITS | NO HITS | NO HITS | | |
| HIT PROFILE (29 ADDITIONAL OTHER OFF TARGETS) AT 10 uM | NO HITS | NO HITS | NO HITS | | |
| DELTA HIT-LEAD SCREENING (38 ADDITIONAL TARGETS) | | NO HITS | | | |
| RADIOCHEMISTRY (NOT OPTIMIZED YET) | MANUAL SYNTHESIS, REQUIRES PRODUCTION OF SFB FOLLOWED BY ACYLATION, NOT AMENABLE FOR RELIABLE CLINICAL PRODUCTION | PERFORMED ON RN PLATFORM; MATERIAL HAS SOLUBILITY ISSUES BUT SYNTHESIS STILL VIABLE FOR CLINICAL PRODUCTION | PERFORMED ON RN PLATFORM; SYNTHESIS VIABLE FOR CLINICAL PRODUCTION | PERFORMED ON RN PLATFORM, POOR-YIELDING SYNTHESIS, CONCERNS ABOUT SUITABILITY FOR CLINICAL PRODUCTION | PERFORMED ON RN PLATFORM, MATERIAL HAS LOW YIELD ISSUES BUT SYNTHESIS STILL VIABLE FOR CLINICAL PRODUCTION |
| | SYNTH: MANUAL MULTISTEP (n=3); TIME: 224 MIN, YIELD: 10.0% (dc); SA: 1.1 Ci/umol | SYNTH: CLICK (N=8); TIME: 133 MIN, YIELD 16.4% (dc); SA: 6.3 Ci/umol | SYNTH: CLICK (N=1); TIME: 99 MIN, YIELD: 41.4% (dc); SA: 3.4 Ci/umol | SYNTH: CLICK (n=1); TIME: 131 MIN, YIELD: 0.6% (dc); SA: 8.6 Ci/umol | SYNTH: CLICK (N=4); TIME: 112 MIN, YIELD: 6.1% (DC); SA: 1.8 CI/UMOL |

FIG. 13
CONTINUED

PSMA IMAGING AGENTS

RELATED APPLICATIONS

This Divisional application claims priority to US application having Ser. No. 16/999,563, filed Aug. 21, 2020, which claims priority to US application having Ser. No. 15/975,296, filed May 9, 2018, now U.S. Pat. No. 10,894,807, granted Dec. 29, 2020, which claims priority to US application having Ser. No. 14/917,127 filed on Jun. 30, 2016, now U.S. Pat. No. 10,011,632, granted Jul. 3, 2018, which is a National Stage application of PCT/US2012/051674, filed Aug. 21, 2012, which claims priority to U.S. provisional patent application No. 61/525,877, filed on Aug. 22, 2011; and to U.S. provisional patent application No. 61/563,987, filed on Nov. 28, 2011; the entire contents of which is incorporated by reference herein.

FIELD OF THE INVENTION

The present invention relates to imaging; specifically, positron emission tomography (PET). More specifically, it relates to radiopharmaceuticals used in PET. More particularly, it relates to formulations for imaging, diagnosing and grading prostate cancer to find metastases and to monitor treatment.

BACKGROUND

Prostate cancer is a relatively common type of cancer and the second leading cause of death in men. There are currently no reliable, non-invasive diagnostic tests available for prostate cancer and the only way to fully confirm the diagnosis of prostate cancer is a biopsy. A PSA (prostate specific antigen) test is the only available tumor marker, but PSA blood levels can be elevated for a number of reasons and do not necessary correlate with prostate cancer. Also, there are rare types of aggressive prostate cancers that cannot be diagnosed with the PSA test. This test for screening therefore has limitations and is still controversial.

Further, prostate-related PET tracers known in the art; e.g., mAb PET tracers, are associated with low clearance (high blood activity) due to prolonged biologic half life of the antibody. This generally leads to low tumor-to-muscle ratios.

SUMMARY

In one embodiment, the invention is a compound of Formula I:

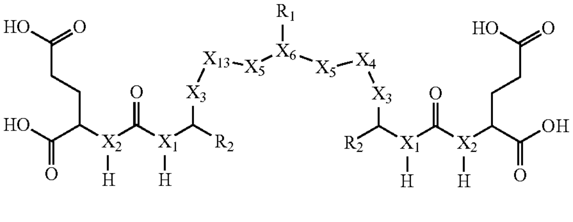

and pharmaceutically acceptable salts and isomers thereof, wherein:

$X_1$ is CH or N;

$X_2$ is CH or N;

$X_3$ is $(CH_2)_{1-6}$ wherein at least one $CH_2$ is optionally replaced by at least one of CONH or aryl;

$X_4$ is $(CH_2)_{1-5}$, where at least one $CH_2$ of $(CH_2)_{1-5}$ is optionally replaced by aryl, NH, and

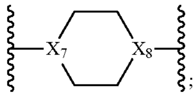

;

$X_5$ is selected from the group consisting of CONH, C(O), $(CH_2)_{1-2}$—C(O) and $(CH_2)_{1-2}$—CONH;

$X_6$ is aryl or CH;

$X_7$ is CH or N;

$X_8$ is CH or N;

$X_{13}$ is $(CH_2)_{1-5}$, where at least one $CH_2$ of $(CH_2)_{1-5}$ is optionally replaced by aryl, NH, and

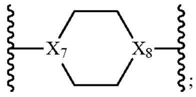

;

$R_1$ is selected from the group consisting of alkyne, $N_3$, $NO_2$, —$(CH_2)_{1-20}$—$R_3$ where at least one $CH_2$ of —$(CH_2)_{1-20}$—$R_3$ is optionally replaced by at least one of —O—, aryl, heteroaryl, NH or CONH and wherein at least one H of —$(CH_2)_{1-20}$—$R_3$ is optionally substituted with COOH or $NO_2$; and (—$CH_2$—$CH_2$—O—$)_{1-5}$—$NH_2$ where at least one $CH_2$ of (—$CH_2$—$CH_2$—O—$)_{1-5}$—$NH_2$ is optionally replaced by aryl or heteroaryl;

$R_2$ is selected from the group consisting of H, COOH or $CH_2$—COOH; and $R_3$ is selected from the group consisting of COOH, $N_3$, alkyne, protecting group, halo and radioisotope.

In another embodiment, the present invention is a compound of Formula Ia

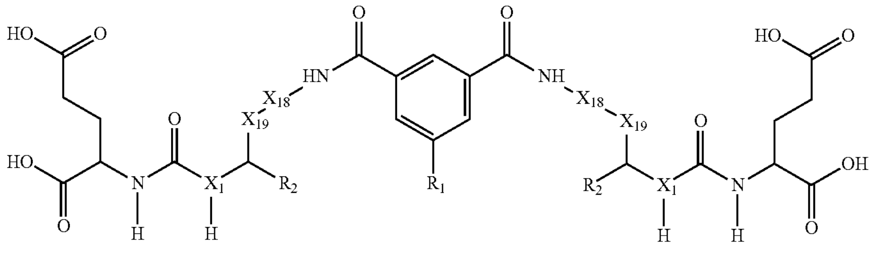

and pharmaceutically acceptable salts and isomers thereof, wherein:

$X_1$ is CH or N;

$X_{18}$ is selected from the group consisting of aryl or $CH_2$;

$X_{19}$ is selected from the group consisting of $(CH_2)_n$ and CONH—$(CH_2)_p$;

$R_1$ is selected from the group consisting of alkyne, $N_3$, $NO_2$, —$(CH_2)_{1-20}$—$R_3$ where at least one $CH_2$ of —$(CH_2)_{1-20}$—$R_3$ is optionally replaced by at least one of —O—, aryl, heteroaryl, NH or CONH and wherein at least one H of —$(CH_2)_{1-20}$—$R_3$ is optionally substituted with COOH or $NO_2$; and (—$CH_2$—$CH_2$—O—$)_{1-5}$—$NH_2$ where at least one $CH_2$ of (—$CH_2$—$CH_2$—O—$)_{1-5}$—$NH_2$ is optionally replaced by aryl or heteroaryl;

$R_2$ is selected from the group consisting of H, COOH or $CH_2$—COOH; and $R_3$ is selected from the group consisting of COOH, $N_3$, alkyne, protecting group, halo and radioisotope, wherein n is 1 or 3; and wherein p is 1, 2 or 4.

In another embodiment, the present invention is a compound of Formula Ib:

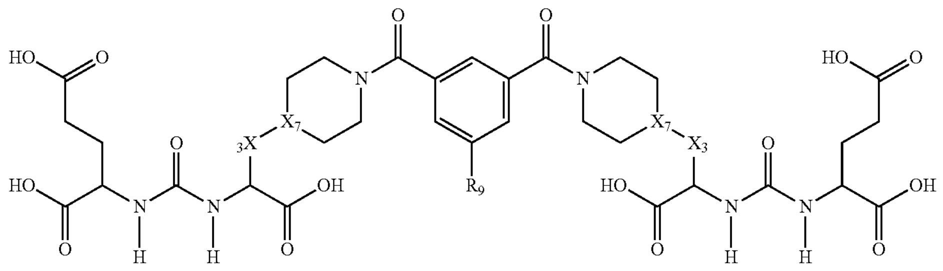

and pharmaceutically acceptable salts and isomers thereof, wherein:

$X_3$ is $(CH_2)_{1-6}$ wherein at least one $CH_2$ is optionally replaced by at least one of CONH or aryl;

$X_7$ is CH or N;

$R_9$ is —$(CH_2)_{1-10}$—$R_3$ where at least one $CH_2$ of —$(CH_2)_{1-10}$—$R_3$ is optionally replaced by at least one of aryl, heteroaryl or CONH; and $R_3$ is selected from the group consisting of COOH, $N_3$, alkyne, protecting group, halo and radioisotope In another embodiment, the present invention is a compound of Formula Ic:

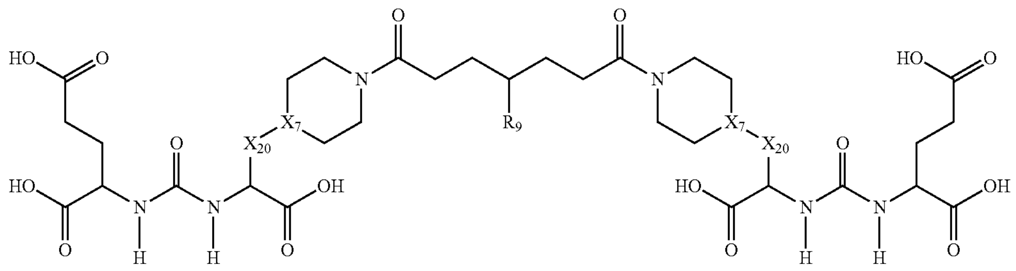

and pharmaceutically acceptable salts and isomers thereof, wherein:

$X_7$ is CH or N;

$X_{20}$ is selected from the group consisting of $(CH_2)_{1-5}$ and CONH—$(CH_2)_{1-5}$;

$R_9$ is —$(CH_2)_{1-10}$—$R_3$ where at least one $CH_2$ of —$(CH_2)_{1-10}$—$R_3$ is optionally replaced by at least one of aryl, heteroaryl or CONH; and $R_3$ is selected from the group consisting of COOH, $N_3$, alkyne, protecting group, halo and radioisotope In another embodiment, the present invention is a compound of Formula II:

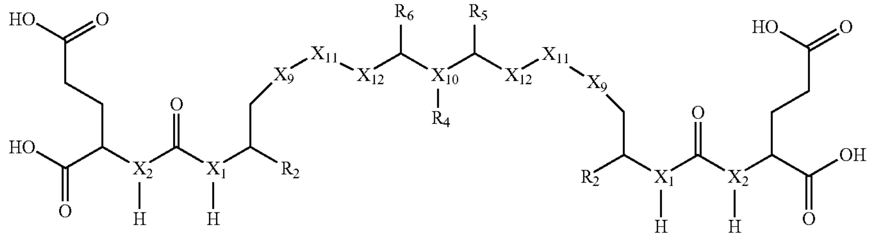

and pharmaceutically acceptable salts and isomers thereof, wherein:

$X_1$ is CH or N;

$X_2$ is CH or N;

$X_9$ is $(CH_2)_{1-5}$ where at least one $CH_2$ is optionally replaced by NH, $X_{10}$ is CH or N;

$X_{11}$ is selected from the group consisting of $(CH_2)$, aryl, or heteroaryl, wherein at least one H of the aryl or heteroaryl is optionally replaced by $NO_2$, $X_{12}$ is selected from the group consisting of O, CONH and $(CH_2)_{1-2}$ wherein at least one $CH_2$ is optionally replaced by NH;

$R_2$ is selected from the group consisting of H, COOH or $CH_2$—COOH;

$R_4$ is selected from the group consisting of H, alkyne, $N_3$, $NO_2$, —$(CH_2)_{1-20}$—$R_8$ where at least one $CH_2$ of —$(CH_2)_{1-20}$—$R_8$ is optionally replaced by at least one of —O—, aryl, heteroaryl, NH or CONH and wherein at least one H of —$(CH_2)_{1-20}$—$R_8$ is optionally substituted with COOH or $NO_2$;

$R_5$ is selected from the group consisting of H and —$(CH_2)_{1-10}$—$R_8$ where at least one $CH_2$ of —$(CH_2)_{1-10}$—$R_8$ is optionally replaced by at least one of —O—, aryl, heteroaryl or CONH;

$R_6$ is selected from the group consisting of H and —$(CH_2)_{1-10}$—$R_8$ where at least one $CH_2$ of —$(CH_2)_{1-10}$—$R_9$ is optionally replaced by at least one of —O—, aryl, heteroaryl or CONH; and $R_8$ is selected from the group consisting of COOH, $N_3$, alkyne, protecting group, halo and radioisotope.

In another embodiment, the present invention is a compound of Formula IIa:

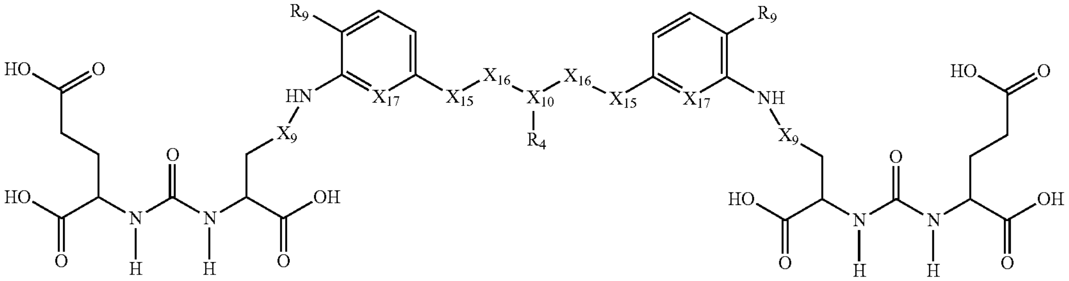

and pharmaceutically acceptable salts and isomers thereof, wherein:

$X_9$ is $(CH_2)_{1-5}$;

$X_{10}$ is CH or N;

$X_{15}$ is selected from the group consisting of O and NH;

$X_{16}$ is $(CH_2)_{1-2}$;

$X_{17}$ is N or CH;

$R_4$ is selected from the group consisting of H, alkyne, $N_3$, $NO_2$, $—(CH_2)_{1-20}—R_8$ where at least one $CH_2$ of $—(CH_2)_{1-20}—R_8$ is optionally replaced by at least one of —O—, aryl, heteroaryl, NH or CONH and wherein at least one H of $—(CH_2)_{1-20}—R_8$ is optionally substituted with COOH or $NO_2$;

$R_8$ is selected from the group consisting of COOH, $N_3$, alkyne, protecting group, halo and radioisotope; and $R_9$ is H or $NO_2$.

In another embodiment, the present invention is a compound of Formula III:

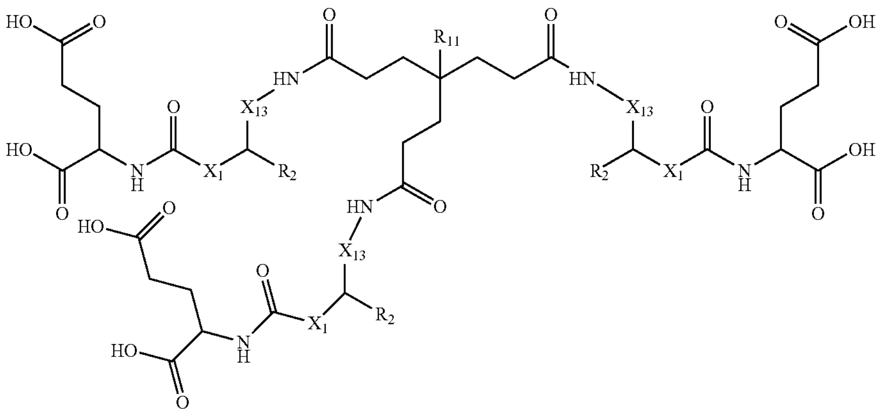

and pharmaceutically acceptable salts and isomers thereof, wherein:

$X_1$ is CH or N;

$X_{13}$ is $(CH_2)_{1-5}$ wherein at least one $CH_2$ is optionally replaced by aryl;

$R_2$ is selected from the group consisting of H, COOH or $CH_2—COOH$;

$R_{11}$ is selected from the group consisting of alkyne, $N_3$, $NO_2$, $(CH_2)_{1-10}—R_{12}$ wherein at least one $CH_2$ is optionally replaced by at least one of CONH, aryl or heteroaryl; and $R_{12}$ is selected from the group consisting of $N_3$, alkyne, protecting group, halo and radioisotope.

In another embodiment, the present invention is a compound of Formula IV:

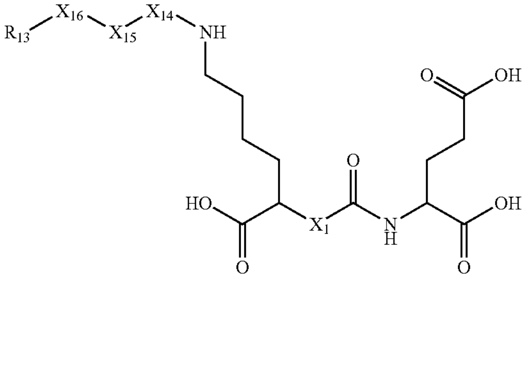

and pharmaceutically acceptable salts and isomers thereof, wherein:

$X_1$ is CH or N;

$X_{14}$ is selected from the group consisting of: C(O) and heteroaryl, wherein at least one H of the heteroaryl is substituted with $NO_2$;

$X_{15}$ is selected from the group consisting of: a bond, NH, $CH_2$, aryl, heteroaryl, cycloalkyl and heterocycloalkyl;

$X_{16}$ is at least one selected from the group consisting of: a bond, aryl, heteroaryl, $(CH_2)_{1-25}$, wherein at least one $CH_2$ of $(CH_2)_{1-12}$ is optionally replaced with heteroaryl, aryl, CONH, and —O—; and $R_{13}$ is selected from the group consisting of H, $NO_2$, $N_3$, alkyne, protecting group, halo and radioisotope.

In another embodiment, the present invention is a compound of Formula V:

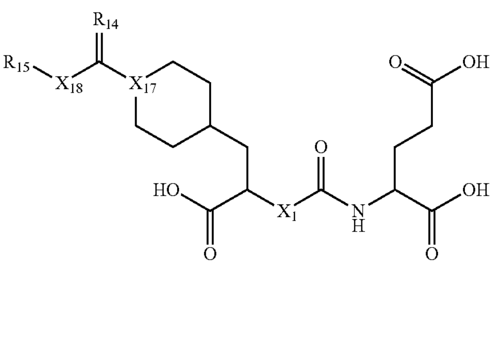

and pharmaceutically acceptable salts and isomers thereof, wherein:

$X_1$ is CH orN;

$X_{17}$ is selected from the group consisting of: N and CH;

$X_{18}$ is selected from the group consisting of: $(CH_2)_{1-10}$ wherein at least one $CH_2$ of $(CH_2)_{1-10}$ is optionally replaced by NH, aryl, heteroaryl and wherein at least one H is optionally substituted with $NO_2$; and $R_{14}$ is selected from the group consisting of O and S; and $R_{15}$ is selected from the group consisting of $N_3$, alkyne, protecting group, halo and radioisotope.

In another embodiment, the present invention is a compound of Formula V:

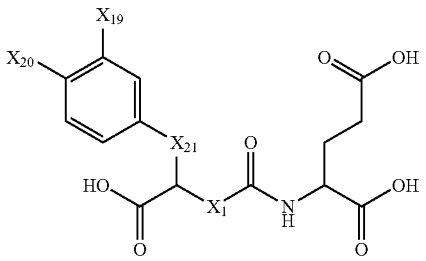

and pharmaceutically acceptable salts and isomers thereof, wherein:

$X_1$ is CH or N;

$X_{19}$ is selected from the group consisting of: H, $NO_2$, $(CH_2)_{1-10}$—$R_{16}$ wherein at least one $CH_2$ of $(CH_2)_{1-10}$ is optionally replaced by CONH, aryl, heteroaryl;

$X_{20}$ is selected from the group consisting of: H, $NO_2$, $(CH_2)_{1-10}$—$R_{16}$ wherein at least one $CH_2$ of $(CH_2)_{1-10}$ is optionally replaced by CONH, aryl, heteroaryl;

$X_{21}$ is selected from the group consisting of $(CH_2)_{1-3}$ wherein at least one $CH_2$ of $(CH_2)_{1-3}$ is optionally replaced by heteroaryl, $R_{14}$ is selected from the group consisting of O and S; and $R_{16}$ is selected from the group consisting of $N_3$, alkyne, protecting group, halo and radioisotope.

BRIEF DESCRIPTION OF THE FIGURES

FIG. 1 shows two scans using imaging agents according to embodiments of the present invention against scans using a third party tracer.

FIG. 2 shows two scans using imaging agents according to embodiments of the present invention against scans using a third party tracer.

FIG. 5 shows scans using a tracer of the present invention and accompanying data.

FIG. 7 shows Negative Control data for a tracer of the present invention.

FIG. 9 shows a comparison of Kd and Ki of tracers of the present invention.

FIGS. 10-12 show a scan using a tracer of the present invention.

FIG. 13 shows a table of data of tracers of the present invention versus a third party tracer.

DETAILED DESCRIPTION

Figure 3:
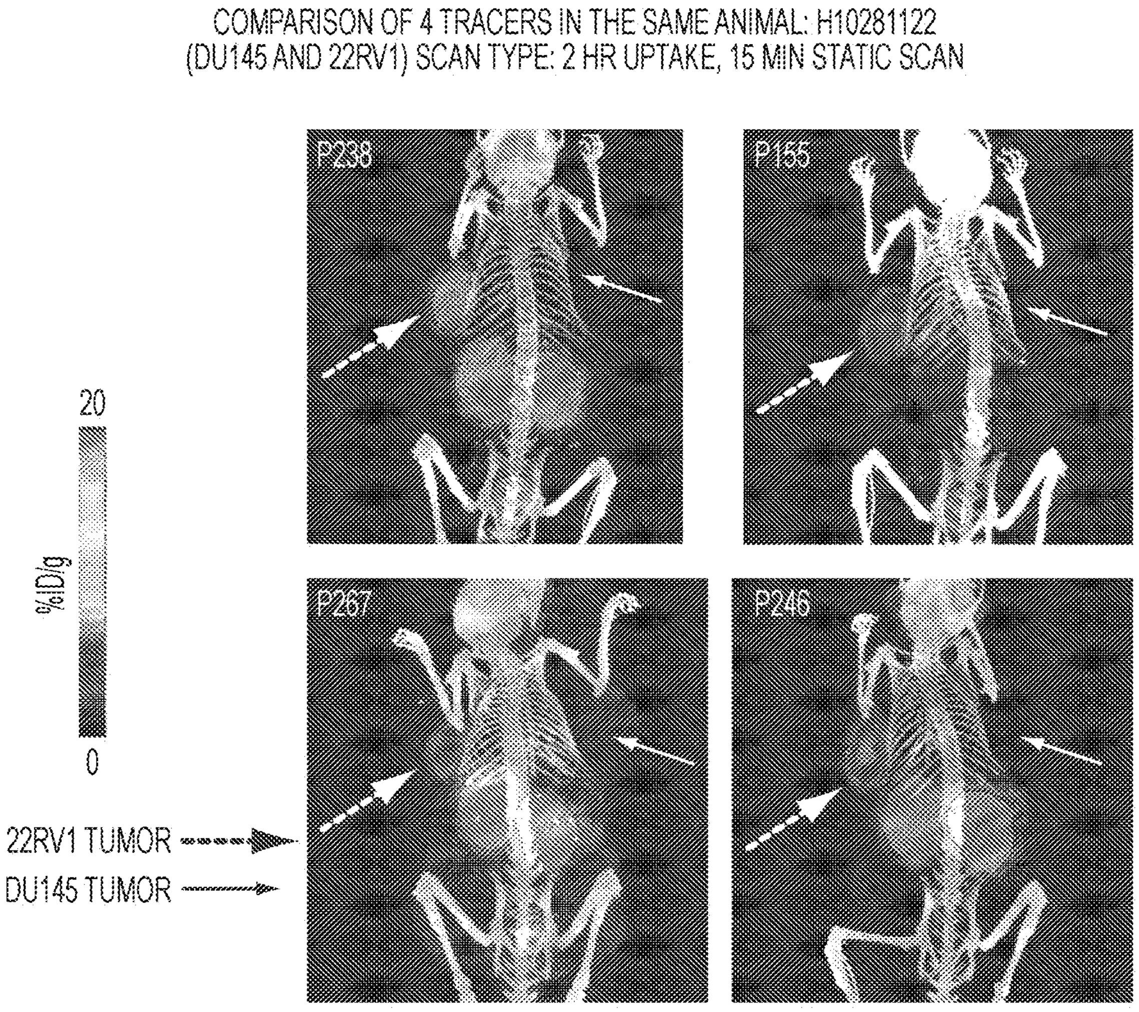
FIG. 3 shows a comparison of scans of four tracers of the present invention.
Figure 4:
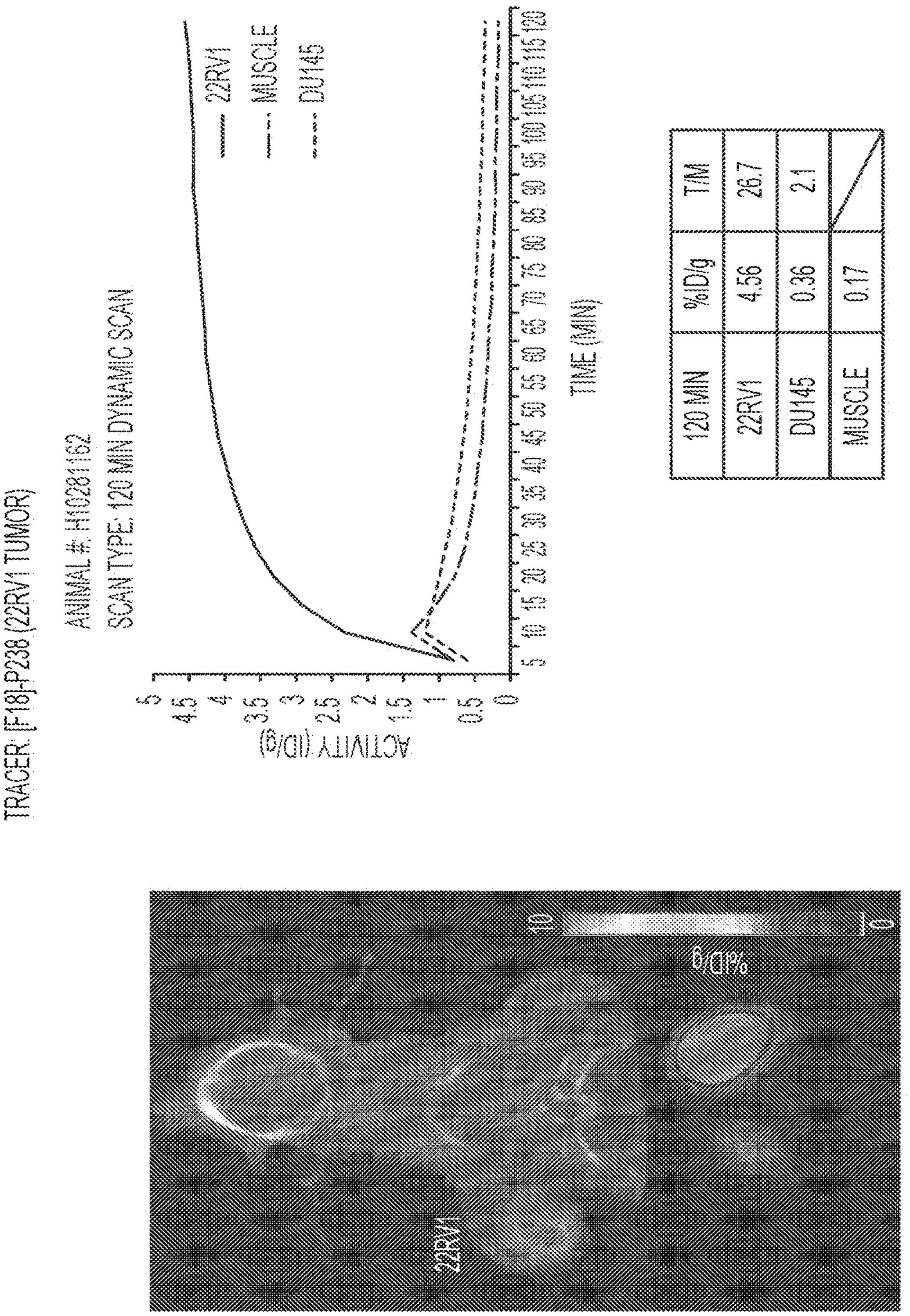
FIG. 4 shows a scan using a tracer of the present invention and accompanying data.
Figure 6:
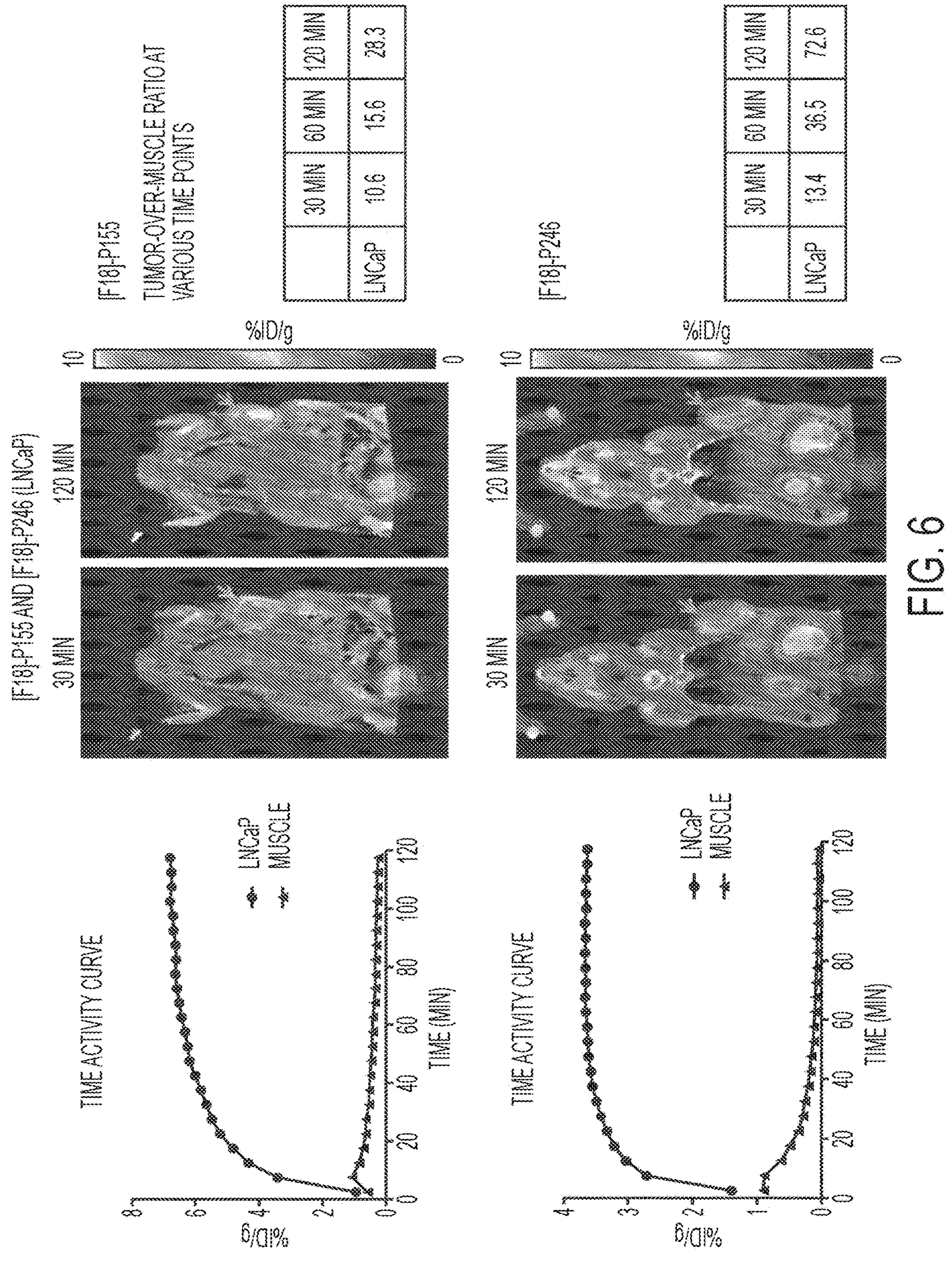
FIG. 6 shows scans using two tracers of the present invention and accompanying data.
Figure 8:
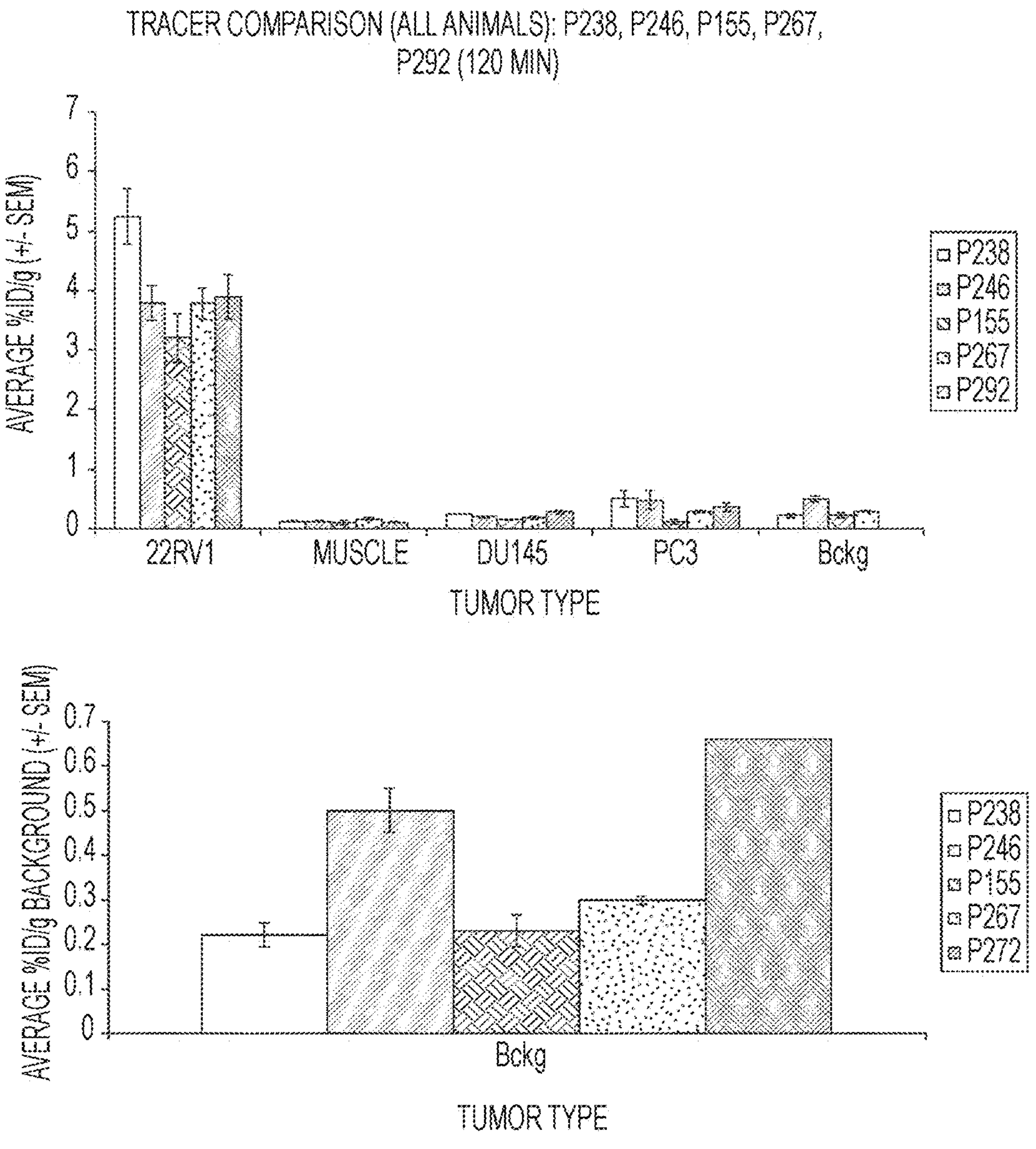
FIG. 8 shows comparative data for five tracers according the present invention.
Figure 11:
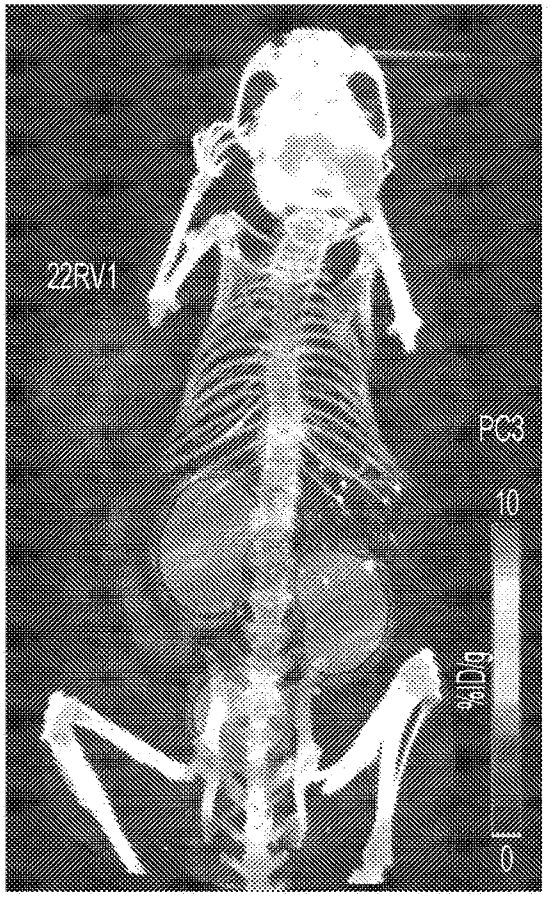
Figure 12:
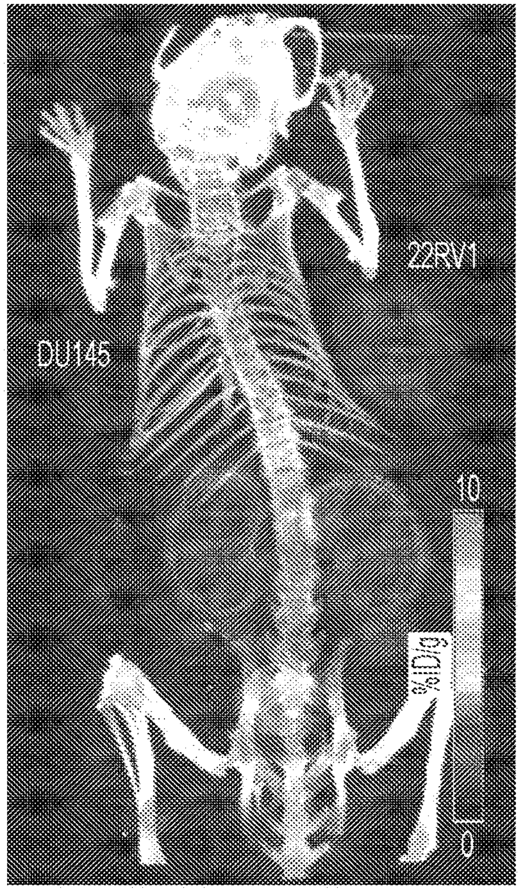

The following description will describe the invention in relation to advantageous embodiments thereof. The invention is in no way limited to these advantageous embodiments as they are purely included to exemplify the invention and the invention is intended to include possible variations and modifications as would be readily apparent to a person skilled in the art without departing from the scope of the invention.

Prostate-specific membrane antigen (PSMA) is a type 2 integral membrane glycoprotein found in prostate tissues and a few other tissues. Expression of PSMA increases proportional to tumor aggressiveness and there is a correlation between PSMA expression and severity of cancer. PSMA has shown to have glutamate carboxypeptidase II activity and catalyzes the hydrolytic cleavage of glutamates from peptides or small molecules. It has been determined that this enzymatic activity of PSMA can be exploited for the design of substrate-based inhibitors. Labeled with [F18], these in turn can be used as PET imaging agents to detect cells expressing PSMA. A PET scan with a PSMA tracer provides a non-invasive diagnostic tool to detect and grade the patient's prostate cancer and allow the physician to choose appropriate treatment methods.

Crystal structures of the active site have been published and show two zinc atoms coordinated by His and Glu/Asp residues, while Arg residues stabilize the C-terminal glutamate-containing substrate. In one embodiment of this invention, we provide substrate based inhibitors in which amide bonds may be replaced with non-hydrolyzable groups such as reverse amides, semi-carbazides, ureas, or heterocycles to name a few. In order to produce a PET ligand, [F18] may be introduced via "click chemistry," which is particularly suitable for labeling of these highly polar and acidic precursors and will provide an advantage over conventional labeling methods as the click reaction is a one step, fast, and high yielding step.

In some embodiments, the present invention is a urea based PET tracer. Many of these are strong inhibitors (Ki=24 nM) of PSMA and contain a triazole side chain generated through a click reaction, which allows for a fast radiosynthesis of the [F18] tracer. Generally, the compounds of the present invention have better PK/clearance profiles than existing compounds.

For the purposes of this application, unless otherwise stated in the specification, the following terms have the terminology cited below:

Alkyl refers to both straight and branched carbon chains; references to individual alkyl groups are specific for the straight chain (e.g. butyl=n-butyl). In one embodiment of alkyl, the number of carbons atoms is 1-20, in another embodiment of alkyl, the number of carbon atoms is 1-8 carbon atoms and in yet another embodiment of alkyl, the number of carbon atoms is 1-4 carbon atoms. Other ranges of carbon numbers are also contemplated depending on the location of the alkyl moiety on the molecule.

Alkynyl or alkyne refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in another embodiment of alkynyl, the number of carbon atoms is 2-8 and in yet another embodiment of alkynyl, the number of carbon atoms is 2-4. Other ranges of carbon-carbon double bonds and carbon numbers are also contemplated depending on the location of the alkenyl moiety on the molecule;

Aryl refers to a $C_6$-$C_{10}$ aromatic ring structure. In one embodiment of aryl, the moiety is phenyl, naphthyl, tetrahydronapthyl, phenylcyclopropyl and indanyl; in another embodiment of aryl, the moiety is phenyl.

Alkoxy refers to —O-alkyl, wherein alkyl is as defined in (1);

Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

Heterocycle, heterocyclic or heterocyclo refer to fully saturated or unsaturated, including aromatic (i.e. "hetaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

The present invention may include derivatives of Formulas I-VIII, which may be precursors to the fluorinated compounds. Such a precursor may include triflate trifluoromathanesulfonate (TFA).

Suitable protecting groups include, but are not limited to, Carbobenzyloxy (Cbz), tert-Butyloxycarbonyl (BOC), 9-Fluorenylmethyloxycarbonyl (FMOC), Benzoyl (Bz), Tosyl (Ts) and p-methoxybenzyl (PMB).

Unless otherwise noted, a compound represented as being substituted by an atom, such as the generic representation by the atom fluorine in fluoroalkyl, F-aryl or F—$CH_2$— for example, is intended to cover both the naturally occurring element $^{19}F$ (fluorine-19) as well as the $^{18}F$ (fluorine-18) isotope(s) of the element itself. Isotopes may be designated via any notation used in the art such as, by way of non-limiting example, fluorine-18, 18-F, $^{18}F$ F-18, etc.

The term "optionally substituted" or "substituted" refers to the specific substituents or groups wherein one to four hydrogen atoms in the group may be replaced by one to four substituents, for example, independently selected from the substituents amino, halo, cyano, nitro, hydroxyl, —SH, —$SC_{1-6}$alkyl, —C(O)$NH_2$, —C(S)$NH_2$, halo$C_{1-6}$alkyl, perhalo$C_{1-6}$alkyl, $C_{1-6}$alkyl, $C_{3-6}$cycloalkyl, $C_{3-12}$cycloalkyl, $C_{6-14}$aryl and heteroaryl, or as specifically disclosed herein. In addition, the substituents may also include alkyl, aryl, alkylene-aryl, hydroxy, alkoxy, aryloxy, perhaloalkoxy, heterocyclyl, azido, amino, guanidino, amidino, halo, alkylthio, oxo, acylalkyl, carboxy esters, carboxyl, carboxamido, acyloxy, aminoalkyl, alkylaminoaryl, alkylaminoalkyl, alkoxyaryl, arylamino, phosphono, sulfonyl, carboxamidoaryl, hydroxyalkyl, haloalkyl, alkoxyalkyl and perhaloalkyl. In addition, the term "optionally substituted" or "substituted" in reference to the variables $R^1$ through $R^{18}$ and X, includes groups substituted by one to four substituents, as identified above, which further comprise a positron or gamma emitter. Such positron emitters include, but are not limited to, $^{11}C$, $^{13}N$, $^{15}O$, $^{18}F$, $^{123}I$, $^{124}I$, $^{125}I$, $^{131}I$ and $^{77}Br$.

The phrase "optionally replaced" means that at least one atom or element (e.g., carbon) in a chain may be replaced with another, different atom, element or functional group, such as O, NH, CONH, aryl, heteroaryl, etc.

The phrase "is replaced" means that at least one atom or element (e.g., carbon) in a chain is replaced with another, different atom, element or functional group, such as O, NH, CONH, aryl, heteroaryl, etc.

The term "radiolabeled compound" as used herein refers to compounds having an atom or group that may provide a radiolabel or may be converted to a radiolabel, such as from a non-radioactive atom to a radionuclide that is active, such as for example, $^{11}C$, $^{13}N$, $^{15}O$, $^{18}F$, $^{123}I$, $^{124}I$, $^{125}I$, $^{131}I$ and $^{77}Br$. In addition, for the purpose of the present application, such "radiolabeled compound" may also refer to an atom or a group that comprises a non-active nuclide, such as a halogen, such as $^{19}F$ for example, wherein the compound may be used and administered in a therapeutically effective amount.

As used herein, the term "radiolabel," "radioactive isotope" or "radioactive element" refers to isotopes exhibiting radioactive decay (i.e., emitting positrons) and radiolabeling agents comprising a radioactive isotope. Non-limiting examples may include [$^{11}C$]methane, [$^{11}C$]carbon monoxide, [$^{11}C$]carbon dioxide, [$^{11}C$]phosgene, [$^{11}C$]urea, [$^{11}C$] cyanogen bromide, as well as various acid chlorides, carboxylic acids, alcohols, aldehydes and ketones containing carbon-11. Such isotopes or elements are also referred to in the art as radioisotopes or radionuclides. Radioactive isotopes are named herein using various commonly used combinations of the name or symbol of the element and its mass number (e.g., $^{18}F$, F-18, or fluorine-18). Exemplary radioactive isotopes include I-124, F-18 fluoride, C-11, N-13, and O-15, which have half-lives of 4.2 days, 110 minutes, 20 minutes, 10 minutes, and 2 minutes, respectively. The radioactive isotope is preferably dissolved in an organic solvent, such as a polar aprotic solvent. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and T1-201. Preferably, the radioactive isotope used in the present method is F-18. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

Compounds of the Formulas I-VIII may have optical centers and therefore may occur in different enantiomeric and diastereomeric configurations. The present invention includes all enantiomers, diastereomers, and other stereoisomers of such compounds of Formulas I-VIII, as well as racemic compounds and racemic mixtures and other mixtures of stereoisomers thereof.

The compounds of the present application may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Non-limiting examples of such inorganic acids are hydrochloric, hydrobromic, hydroiodic, nitric, carbonic, sulfuric and phosphoric acid. Appropriate organic acids may be selected from aliphatic (or alkyl), cycloalkyl, aromatic, arylalkyl, heterocyclic, carboxylic and sulfonic classes of organic acids, non-limiting examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include, but are not limited to, metallic salts made from aluminum, calcium, lithium, magnesium, potassium, sodium and zinc or organic salts made from amino acids, benzathine, N, NT-dibenzylethylenediamine, chloroprocaine, choline, diethanolamine, diethylamine, diolamine, ethylenediamine, meglumine-(N-methylglucamine), procaine and tromethamine. Ascorbic acid may also be used as an excipient. Hemisalts of acids and bases may also be formed, for example, hemisulphate and hemicalcium salts.

In another embodiment, there is provided a pharmaceutical composition for in vivo imaging of PSMA, comprising (a) a compound of any one of the above, and (b) a pharmaceutically acceptable carrier.

The pharmaceutical compositions of the invention may also be in the form of a sterile injectable preparation. Formulations suitable for parenteral administration include, by way of non-limiting example, aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

The compounds of the invention may be synthesized and/or radiolabeled using techniques known in the art.

In one embodiment, the compounds of the invention may be radiolabeled.

In another embodiment, the compounds are not comprised of a radioisotope.

In one embodiment, the invention is a compound of Formula I:

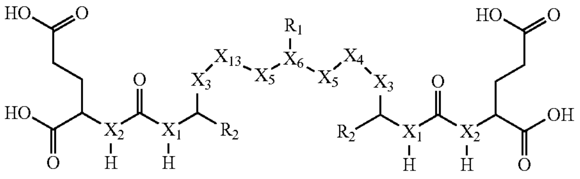

and pharmaceutically acceptable salts and isomers thereof, wherein:

$X_1$ is CH or N;

$X_2$ is CH or N;

$X_3$ is $(CH_2)_{1-6}$ wherein at least one $CH_2$ is optionally replaced by at least one of CONH or aryl;

$X_4$ is selected from the group consisting of aryl, NH, $CH_2$, and

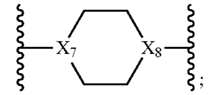

;

$X_5$ is selected from the group consisting of CONH, C(O), $(CH_2)_{1-2}$—C(O) and $(CH_2)_{1-2}$—CONH;

$X_6$ is aryl or CH;

$X_7$ is CH or N;

$X_8$ is CH or N;

$X_4$ is selected from the group consisting of aryl, NH, $CH_2$, and

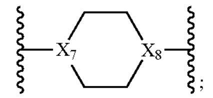

;

$R_1$ is selected from the group consisting of alkyne, $N_3$, $NO_2$, —$(CH_2)_{1-20}$—$R_3$ where at least one $CH_2$ of —$(CH_2)_{1-20}$—$R_3$ is optionally replaced by at least one of —O—, aryl, heteroaryl, NH or CONH and wherein at least one H of —$(CH_2)_{1-20}$—$R_3$ is optionally substituted with COOH or $NO_2$; and (—$CH_2$—$CH_2$—O—)$_{1-5}$—$NH_2$ where at least one $CH_2$ of (—$CH_2$—$CH_2$—O—)$_{1-5}$—$NH_2$ is optionally replaced by aryl or heteroaryl;

$R_2$ is selected from the group consisting of H, COOH or $CH_2$—COOH; and $R_3$ is selected from the group consisting of COOH, $N_3$, alkyne, protecting group, halo and radioisotope.

In one embodiment, in the compound of Formula I, $X_2$ is N.

In one embodiment, in the compound of Formula I, $X_1$ is N.

In one embodiment, in the compound of Formula I, $X_1$ is CH.

In one embodiment, in the compound of Formula I, $R_2$ is COOH.

In one embodiment, in the compound of Formula I, $R_2$ is H.

In one embodiment, in the compound of Formula I, $R_2$ is $CH_2$—COOH.

In one embodiment, in the compound of Formula I, $X_6$ is CH.

In one embodiment, in the compound of Formula I, $X_6$ is $C_6H_6$.

In one embodiment, in the compound of Formula I, $R_1$ is $N_3$.

In one embodiment, in the compound of Formula I, $R_1$ is —$(CH_2)_{1-10}$—$R_3$ where at least one $CH_2$ of —$(CH_2)_{1-20}$—$R_3$ is replaced by at least one of aryl, heteroaryl or CONH.

In one embodiment, in the compound of Formula I, at least one $CH_2$ of —$(CH_2)_{1-10}$—$R_3$ is replaced by $C_6H_6$.

In one embodiment, in the compound of Formula I, at least one $CH_2$ of —$(CH_2)_{1-10}$—$R_3$ is replaced by a triazole.

In one embodiment, in the compound of Formula I, $X_5$ is CONH.

In one embodiment, in the compound of Formula I, $X_5$ is $(CH_2)_{1-2}$—CONH.

In one embodiment, in the compound of Formula I, $X_4$ and $X_{13}$ are $C_6H_6$.

In one embodiment, in the compound of Formula I, $X_4$ and $X_{13}$ are $(CH_2)_{1-5}$.

In one embodiment, in the compound of Formula I, $X_5$ is C(O), $X_{13}$ is $C_6H_6$ and $X_4$ is $(CH_2)_{1-5}$, wherein one $CH_2$ of $(CH_2)_{1-5}$ is replaced by NH.

In one embodiment, in the compound of Formula I, $X_5$ is C(O), $X_4$ and $X_{13}$ are

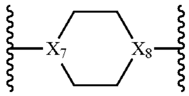, wherein $X_8$ is N.

In one embodiment, in the compound of Formula I, $X_5$ is C(O), $X_{13}$ is

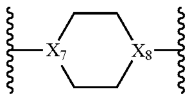, $X_8$ is N and $X_4$ is $(CH_2)_3$—NH.

In one embodiment, in the compound of Formula I, $X_3$ is $(CH_2)_{1-6}$.

In one embodiment, in the compound of Formula I, at least one $CH_2$ of $(CH_2)_{1-6}$ is replaced by CONH.

In one embodiment, in the compound of Formula I, $X_3$ is $CH_2$.

In one embodiment, in the compound of Formula I, at least one $CH_2$ of $(CH_2)_{1-6}$ is replaced by aryl.

In one embodiment, in the compound of Formula I, one $CH_2$ of $(CH_2)_{1-6}$ is replaced by CONH.

In one embodiment, in the compound of Formula I, $R_3$ is a radioisotope.

In one embodiment, in the compound of Formula I, $R_1$ is selected from the group consisting of:

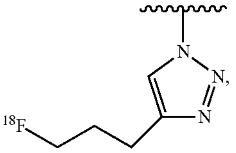

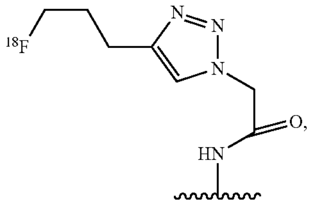, and

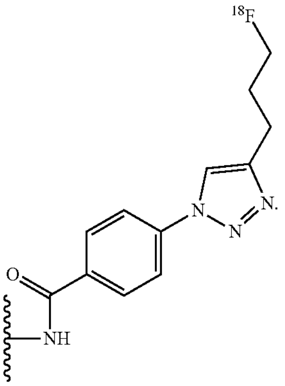

In one embodiment, in the compound of Formula I, $R_1$ is:

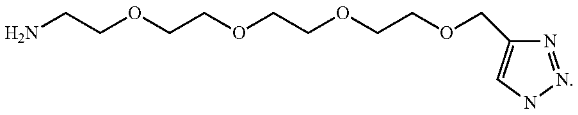 [SMILES: NCCOCCOCCOCCOCc1c[nH]nn1]

In one embodiment, the present invention is a compound that is:

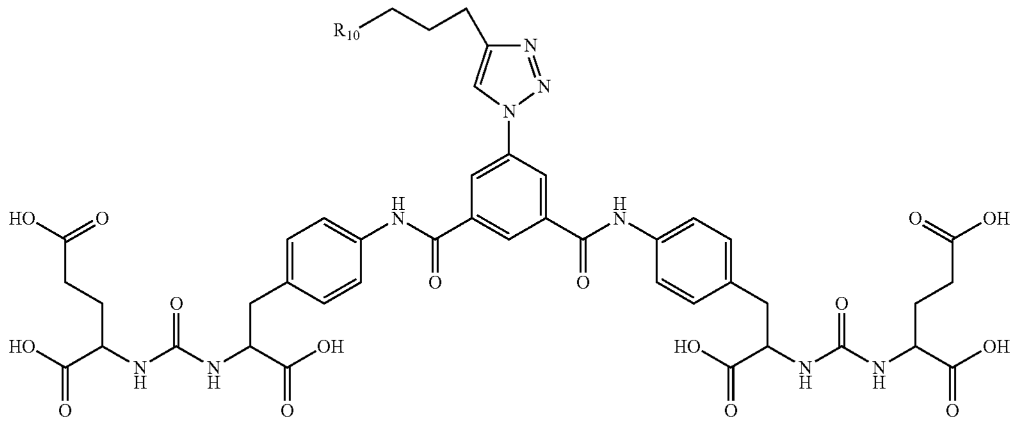

and pharmaceutically acceptable salts and isomers thereof, wherein $R_{10}$ is selected from the group consisting of radionuclide and halo.

In another embodiment, the present invention is a compound of Formula Ia:

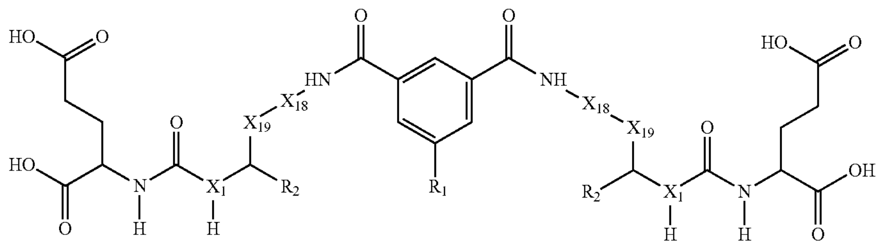

and pharmaceutically acceptable salts and isomers thereof, wherein:

$X_1$ is CH or N;

$X_{18}$ is selected from the group consisting of aryl or $CH_2$;

$X_{19}$ is selected from the group consisting of $(CH_2)_n$ and CONH—$(CH_2)_p$;

$R_1$ is selected from the group consisting of alkyne, $N_3$, $NO_2$, —$(CH_2)_{1-20}$—$R_3$ where at least one $CH_2$ of —$(CH_2)_{1-20}$—$R_3$ is optionally replaced by at least one of —O—, aryl, heteroaryl, NH or CONH and wherein at least one H of —$(CH_2)_{1-20}$—$R_3$ is optionally substituted with COOH or $NO_2$; and (—$CH_2$—$CH_2$—O—$)_{1-5}$—$NH_2$ where at least one $CH_2$ of (—$CH_2$—$CH_2$—O—$)_{1-5}$—$NH_2$ is optionally replaced by aryl or heteroaryl;

$R_2$ is selected from the group consisting of H, COOH or $CH_2$—COOH; and $R_3$ is selected from the group consisting of COOH, $N_3$, alkyne, protecting group, halo and radioisotope, wherein n is 1 or 3; and wherein p is 1, 2 or 4.

In one embodiment, in the compound of Formula Ia, $R_1$ is $N_3$.

In one embodiment, in the compound of Formula Ia, $R_1$ is selected from the group consisting of —$(CH_2)_{1-10}$—$R_3$ where at least one $CH_2$ of —$(CH_2)_{1-10}$—$R_3$ is optionally replaced by at least one of —O—, aryl, heteroaryl or CONH.

In one embodiment, in the compound of Formula Ia, $X_{18}$ is $CH_2$.

In one embodiment, in the compound of Formula Ia, $X_{18}$ is aryl.

In one embodiment, in the compound of Formula Ia, $X_{19}$ is $(CH_2)_n$.

In one embodiment, in the compound of Formula Ia, $X_{19}$ is CONH—$(CH_2)_p$.

In one embodiment, in the compound of Formula Ia, $X_1$ is N.

In one embodiment, in the compound of Formula Ia, $R_3$ is a radioisotope.

In another embodiment, the present invention is a compound of Formula Ib:

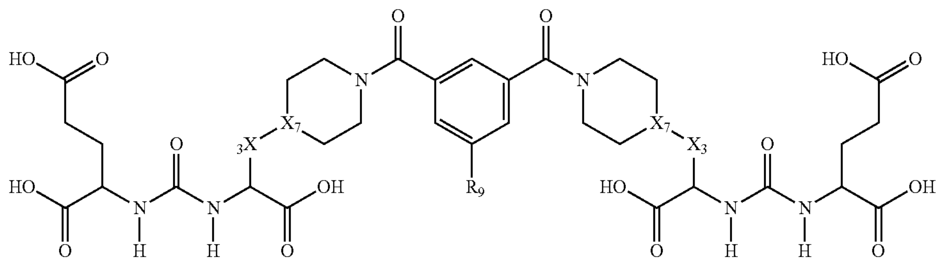

and pharmaceutically acceptable salts and isomers thereof, wherein:

$X_3$ is $(CH_2)_{1-6}$ wherein at least one $CH_2$ is optionally replaced by at least one of CONH or aryl;

$X_7$ is CH or N;

$R_9$ is $-(CH_2)_{1-10}-R_3$ where at least one $CH_2$ of $-(CH_2)_{1-10}-R_3$ is optionally replaced by at least one of aryl, heteroaryl or CONH; and $R_3$ is selected from the group consisting of COOH, $N_3$, alkyne, protecting group, halo and radioisotope.

In one embodiment, in the compound of Formula Ib, $X_7$ is N.

In one embodiment, in the compound of Formula Ib, $X_7$ is CH.

In one embodiment, in the compound of Formula Ib, $X_3$ is $CH_2$.

In one embodiment, in the compound of Formula Ib, $X_3$ is $(CH_2)_{1-6}$, wherein one $CH_2$ is replaced by CONH.

In one embodiment, in the compound of Formula Ib, $X_3$ is $(CH_2)_{2-6}$, wherein one $CH_2$ is replaced by aryl.

In one embodiment, in the compound of Formula Ib, $R_3$ is a radioisotope.

In one embodiment, in the compound of Formula Ib, $R_9$ is selected from the group consisting of:

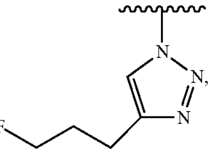

,

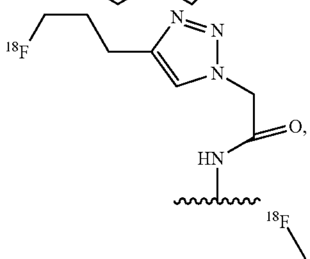

, and

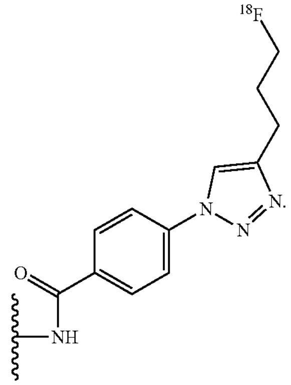

.

In another embodiment, the present invention is a compound of Formula Ic:

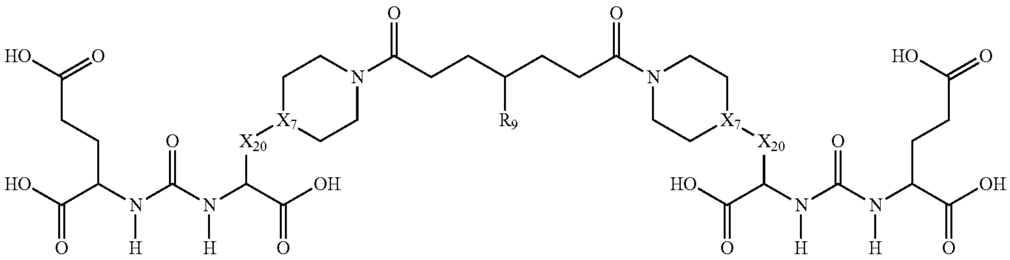

and pharmaceutically acceptable salts and isomers thereof, wherein:

$X_7$ is CH or N;

$X_{20}$ is selected from the group consisting of $(CH_2)_{1-5}$ and CONH—$(CH_2)_{1-5}$;

$R_9$ is —$(CH_2)_{1-10}$—$R_3$ where at least one $CH_2$ of —$(CH_2)_{1-10}$—$R_3$ is optionally replaced by at least one of aryl, heteroaryl or CONH; and $R_3$ is selected from the group consisting of COOH, $N_3$, alkyne, protecting group, halo and radioisotope.

In one embodiment, in the compound of Formula Ic, $X_7$ is N.

In one embodiment, in the compound of Formula Ic, $X_7$ is CH.

In one embodiment, in the compound of Formula Ic, $X_{20}$ is $CH_2$.

In one embodiment, in the compound of Formula Ic, $X_{20}$ is CONH—$(CH_2)_4$.

In one embodiment, in the compound of Formula Ic, $R_3$ is a radioisotope.

In one embodiment, in the compound of Formula Ic, $R_9$ is selected from the group consisting of:

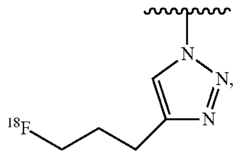

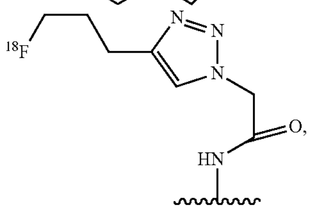

and

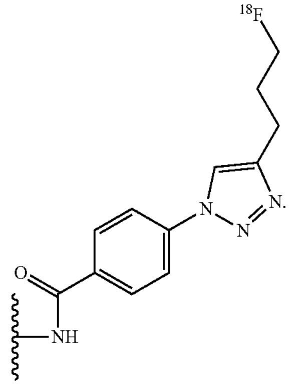

In another embodiment, the present invention is a compound of Formula II:

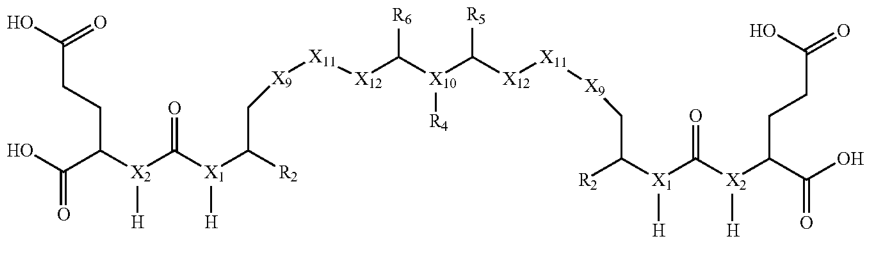

and pharmaceutically acceptable salts and isomers thereof, wherein:

$X_1$ is CH or N;

$X_2$ is CH or N;

$X_9$ is $(CH_2)_{1-5}$ where at least one $CH_2$ is optionally replaced by NH, $X_{10}$ is CH or N;

$X_{11}$ is selected from the group consisting of $(CH_2)$, aryl, or heteroaryl, wherein at least one H of the aryl or heteroaryl is optionally replaced by $NO_2$, $X_{12}$ is selected from the group consisting of 0, CONH and $(CH_2)_{1-2}$ wherein at least one $CH_2$ is optionally replaced by NH;

$R_2$ is selected from the group consisting of H, COOH or $CH_2$—COOH;

$R_4$ is selected from the group consisting of H, alkyne, $N_3$, $NO_2$, —$(CH_2)_{1-20}$—$R_8$ where at least one $CH_2$ of —$(CH_2)_{1-20}$—$R_8$ is optionally replaced by at least one of —O—, aryl, heteroaryl, NH or CONH and wherein at least one H of —$(CH_2)_{1-20}$—$R_8$ is optionally substituted with COOH or $NO_2$;

$R_5$ is selected from the group consisting of H and —$(CH_2)_{1-10}$—$R_8$ where at least one $CH_2$ of —$(CH_2)_{1-10}$—$R_8$ is optionally replaced by at least one of —O—, aryl, heteroaryl or CONH;

$R_6$ is selected from the group consisting of H and —$(CH_2)_{1-10}$—$R_8$ where at least one $CH_2$ of —$(CH_2)_{1-10}$—$R_9$ is optionally replaced by at least one of —O—, aryl, heteroaryl or CONH; and $R_8$ is selected from the group consisting of COOH, $N_3$, alkyne, protecting group, halo and radioisotope.

In one embodiment, in the compound of Formula II, $X_1$ is N; $X_2$ is N; $R_2$ is COOH; and $R_6$ is H.

In one embodiment, in the compound of Formula II, $X_{10}$ is CH.

In one embodiment, in the compound of Formula II, $X_{10}$ is N.

In one embodiment, in the compound of Formula II, $R_4$ is H, $R_6$ is H and $R_5$ is —$(CH_2)_{1-10}$—$R_8$ where at least one $CH_2$ of —$(CH_2)_{1-10}$—$R_8$ is replaced by heteroaryl and at least one $CH_2$ is replaced by CONH.

In one embodiment, in the compound of Formula II, the at least one heteroaryl of —$(CH_2)_{1-10}$—$R_8$ is a triazole.

In one embodiment, in the compound of Formula II, $R_5$ is H, $R_6$ is H and $R_4$ is —$(CH_2)_{1-10}$—$R_8$ where at least one $CH_2$ of —$(CH_2)_{1-10}$—$R_8$ is replaced by heteroaryl.

In one embodiment, in the compound of Formula II, at least one heteroaryl of —$(CH_2)_{1-10}$—$R_8$ is a triazole.

In one embodiment, in the compound of Formula II, $X_{12}$ is CONH.

In one embodiment, in the compound of Formula II, $X_{12}$ is O and $X_{11}$ is aryl.

In one embodiment, in the compound of Formula II, $X_{12}$ is NH and $X_{11}$ is heteroaryl.

In one embodiment, in the compound of Formula II, $X_{11}$ is $CH_2$.

In one embodiment, in the compound of Formula II, $X_9$ is $(CH_2)_{1-5}$, wherein at least one $CH_2$ is replaced by NH and wherein $X_{11}$ is aryl or heteroaryl.

In one embodiment, in the compound of Formula II, $R_8$ is a radioisotope.

In another embodiment, the present invention is a compound of Formula IIa:

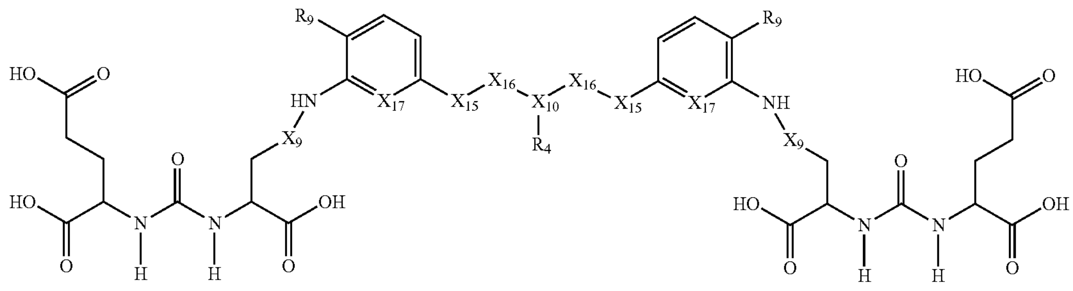

and pharmaceutically acceptable salts and isomers thereof, wherein:

$X_9$ is $(CH_2)_{1-5}$;

$X_{10}$ is CH or N;

$X_{15}$ is selected from the group consisting of 0 and NH;

$X_{16}$ is $(CH_2)_{1-2}$;

$X_{17}$ is N or CH;

$R_4$ is selected from the group consisting of H, alkyne, $N_3$, $NO_2$, $—(CH_2)_{1-20}—R_8$ where at least one $CH_2$ of $—(CH_2)_{1-20}—R_8$ is optionally replaced by at least one of —O—, aryl, heteroaryl, NH or CONH and wherein at least one H of $—(CH_2)_{1-20}—R_8$ is optionally substituted with COOH or $NO_2$;

$R_8$ is selected from the group consisting of COOH, $N_3$, alkyne, protecting group, halo and radioisotope; and $R_9$ is H or $NO_2$.

In one embodiment, in the compound of Formula IIa, $R_9$ is $NO_2$.

In one embodiment, in the compound of Formula IIa, $R_4$ is $—(CH_2)_{1-10}—R_8$ where at least one $CH_2$ of $—(CH_2)_{1-10}—R_8$ is replaced by a heteroaryl.

In one embodiment, in the compound of Formula IIa, the at least one heteroaryl of $—(CH_2)_{1-10}—R_8$ is a triazole.

In one embodiment, in the compound of Formula IIa, $X_{15}$ is O and $X_{17}$ is CH.

In one embodiment, in the compound of Formula IIa, $X_{10}$ is N, $X_{15}$ is NH.

In one embodiment, in the compound of Formula IIa, $R_8$ is a halo or radionuclide.

In one embodiment, in the compound of Formula IIa, $X_9$ is $(CH_2)_4$.

In one embodiment, the invention is a compound of Formula III:

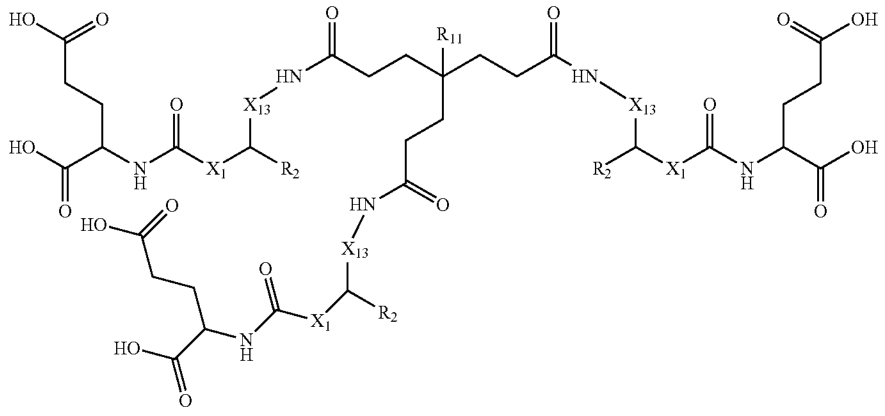

and pharmaceutically acceptable salts and isomers thereof, wherein:

$X_1$ is CH or N;

$X_3$ is $(CH_2)_{1-5}$ wherein at least one $CH_2$ is optionally replaced by aryl;

$R_2$ is selected from the group consisting of H, COOH or $CH_2—COOH$;

$R_{11}$ is selected from the group consisting of alkyne, $N_3$, $NO_2$, $(CH_2)_{1-10}—R_{12}$ wherein at least one $CH_2$ is optionally replaced by at least one of CONH, aryl or heteroaryl; and $R_{12}$ is selected from the group consisting of $N_3$, alkyne, protecting group, halo and radioisotope.

In one embodiment, in the compound of Formula III, $X_1$ is N.

In one embodiment, in the compound of Formula III, $X_1$ is CH.

In one embodiment, in the compound of Formula III, $X_{13}$ is $(CH_2)_2$ wherein at least one $CH_2$ is replaced by aryl.

In one embodiment, in the compound of Formula III, $X_{13}$ is $(CH_2)_4$.

In one embodiment, in the compound of Formula III, $R_{11}$ is $(CH_2)_{1-10}R_{12}$ wherein at least one $CH_2$ is replaced by at least one of CONH, aryl or heteroaryl.

In one embodiment, in the compound of Formula III, at least one $CH_2$ of $—(CH_2)_{1-10}—R_3$ is replaced by $C_6H_6$.

In one embodiment, in the compound of Formula III, at least one $CH_2$ of $—(CH_2)_{1-10}—R_3$ is replaced by a triazole.

In one embodiment, in the compound of Formula III, $R_{11}$ is selected from the group consisting of:

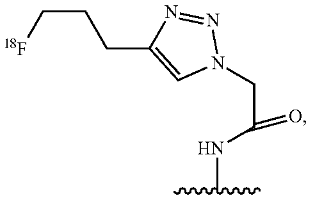

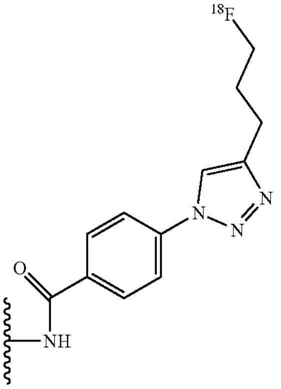

and

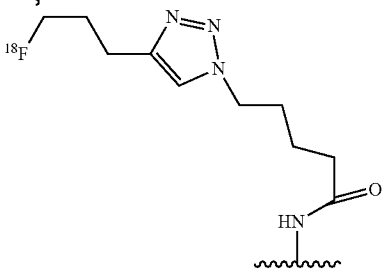

In one embodiment, in the compound of Formula III, $R_{12}$ is a radioisotope.

In one embodiment, the invention is a compound of Formula IV:

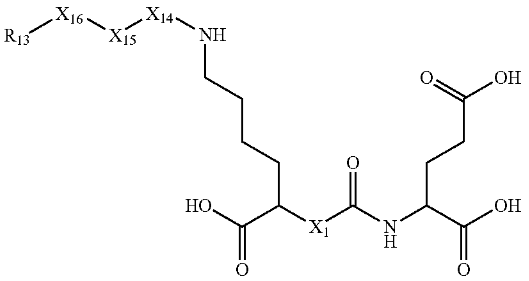

and pharmaceutically acceptable salts and isomers thereof, wherein:

$X_1$ is CH orN;

$X_{14}$ is selected from the group consisting of: C(O) and heteroaryl, wherein at least one H of the heteroaryl is substituted with $NO_2$;

$X_{15}$ is selected from the group consisting of: a bond, NH, $CH_2$, aryl, heteroaryl;

$X_{16}$ is at least one selected from the group consisting of: a bond, aryl, heteroaryl, $(CH_2)_{1-25}$, wherein at least one $CH_2$ of $(CH_2)_{1-25}$ is optionally replaced with heteroaryl, CONH, and —O—; and $R_{13}$ is selected from the group consisting of H, $NO_2$, $N_3$, alkyne, protecting group, halo and radioisotope.

In one embodiment, in the compound of Formula IV, $X_1$ is NH.

In one embodiment, in the compound of Formula IV, $X_{14}$ is

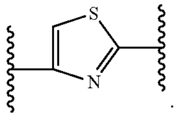 [SMILES: *c1csc(*)n1]

In one embodiment, in the compound of Formula IV, $X_{15}$ is $C_6H_6$.

In one embodiment, in the compound of Formula IV, $X_{16}$ is

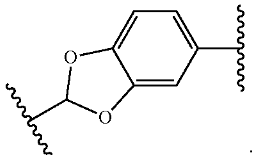 [SMILES: *c1ccc2c(c1)OC(*)O2]

In one embodiment, in the compound of Formula IV, $X_{15}$ is a bond.

In one embodiment, in the compound of Formula IV, $R_{13}$ is a radioisotope.

In one embodiment, the present invention is the following compound:

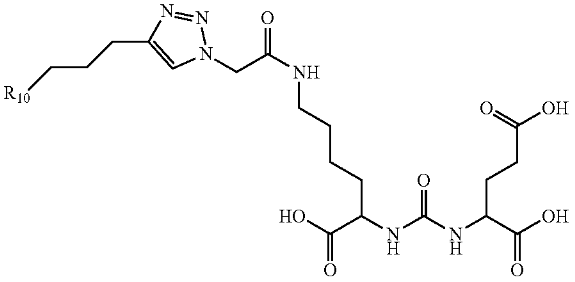

and pharmaceutically acceptable salts and isomers thereof, wherein $R_{10}$ is selected from the group consisting of radionuclide and halo.

In one embodiment, in the compound of Formula IV, $X_{14}$ is C(O) and $X_{15}$ is a sugar.

In one embodiment, the invention is a compound of Formula V:

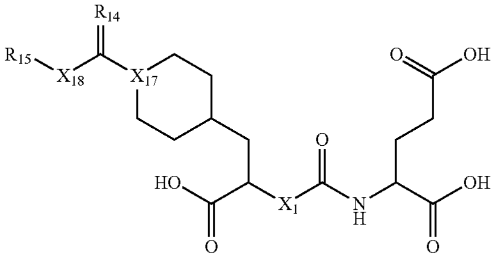

and pharmaceutically acceptable salts and isomers thereof, wherein:

$X_1$ is CH or N;

$X_{17}$ is selected from the group consisting of: N and CH;

$X_{18}$ is selected from the group consisting of: $(CH_2)_{1-10}$ wherein at least one $CH_2$ of $(CH_2)_{1-10}$ is optionally replaced by NH, aryl, heteroaryl and wherein at least one H is optionally substituted with $NO_2$;

$R_{14}$ is selected from the group consisting of O and S; and $R_{15}$ is selected from the group consisting of $N_3$, alkyne, protecting group, halo and radioisotope In one embodiment, the invention is a compound of Formula VI:

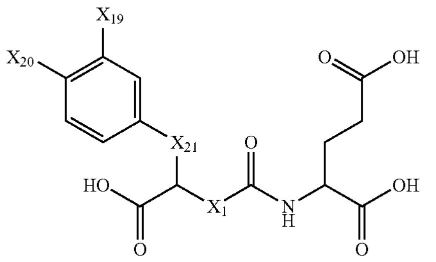

and pharmaceutically acceptable salts and isomers thereof, wherein:

$X_1$ is CH or N;

$X_{19}$ is selected from the group consisting of: H, $NO_2$, $(CH_2)_{1-10}$—$R_{16}$ wherein at least one $CH_2$ of $(CH_2)_{1-10}$ is optionally replaced by CONH, aryl, heteroaryl;

$X_{20}$ is selected from the group consisting of: H, $NO_2$, $(CH_2)_{1-10}$—$R_{16}$ wherein at least one $CH_2$ of $(CH_2)_{1-10}$ is optionally replaced by CONH, aryl, heteroaryl;

$X_{21}$ is selected from the group consisting of $(CH_2)_{1-3}$ wherein at least one $CH_2$ of $(CH_2)_{1-3}$ is optionally replaced by heteroaryl, $R_{14}$ is selected from the group consisting of O and S; and $R_{16}$ is selected from the group consisting of $N_3$, alkyne, protecting group, halo and radioisotope.

In one embodiment, in the compound of Formula VI, $X_1$ is N.

In one embodiment, in the compound of Formula VI, $X_{19}$ is H and $X_{20}$ is $(CH_2)_{1-10}$—$R_{16}$ wherein at least one $CH_2$ of $(CH_2)_{1-10}$ is replaced by CONH.

In one embodiment, in the compound of Formula VI, $X_{20}$ is H and $X_{19}$ is $(CH_2)_{1-10}$—$R_{16}$ wherein at least one $CH_2$ of $(CH_2)_{1-10}$ is replaced by CONH.

In one embodiment, in the compound of Formula VI, at least one $CH_2$ of $(CH_2)_{1-10}$—$R_{16}$ is replaced by triazole.

In one embodiment, in the compound of Formula VI, $R_{16}$ is a radioisotope.

In one embodiment, the invention is a compound of Formula VII:

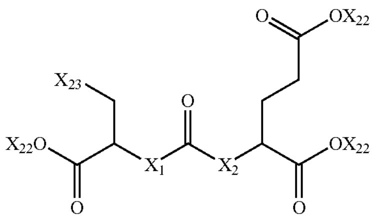

and pharmaceutically acceptable salts and isomers thereof, wherein:

$X_1$ is CH or N;

$X_2$ is CH or N;

$X_{22}$ is a protecting group; and $X_{23}$ is $(CH_2)_{1-10}$—$NH_2$ wherein at least one $CH_2$ of $(CH_2)_{1-10}$ is optionally replaced by at least one selected from the group consisting of S, O, NH, CONH, aryl, heteroaryl, cycloalkyl and heterocycloalkyl.

In one embodiment, in the compound of Formula VI, $X_{22}$ is t-butyl.

In one embodiment, the invention is a method of forming a compound comprising:

reacting a compound of Formula VII with

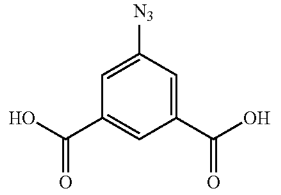 [SMILES: [N-]=[N+]=Nc1cc(C(=O)O)cc(C(=O)O)c1]

to form a first intermediate product;

coupling the first intermediate product with another compound of Formula VII to form a second intermediate product; and removing the protecting groups.

In another embodiment, the present invention is a compound of Formula VIII:

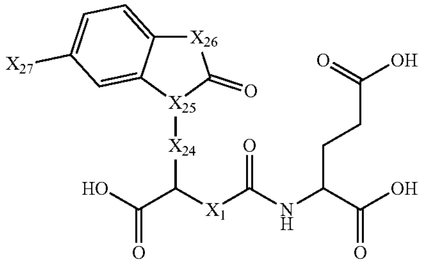

and pharmaceutically acceptable salts and isomers thereof, wherein:

$X_1$ is CH or N;

$X_{24}$ is selected from the group consisting of $(CH_2)_{1-6}$ wherein at least one $CH_2$ of $(CH_2)_{1-6}$ is optionally replaced by at least one selected from the group consisting of NH, O, S;

$X_{25}$ is N or CH;

$X_{26}$ is NH or $CH_2$;

$X_{27}$ is selected from the group consisting of: H, $NO_2$, $(CH_2)_{1-10}$—$R_{16}$ wherein at least one $CH_2$ of $(CH_2)_{1-10}$ is optionally replaced by O, CONH, aryl, heteroaryl; and $R_{16}$ is selected from the group consisting of $N_3$, alkyne, protecting group, halo and radioisotope.

In another embodiment, the present invention is a method of detecting comprising: administering a compound of any of Formulas I-VI and VIII to a mammal and scanning the mammal. The scanning may be performed after a predetermined time, using a PET or SPECT scanner.

In another embodiment, the present invention is a method of imaging PSMA comprising: administering a compound or a pharmaceutical composition of any of Formulas I-VI and VIII to a mammal and scanning the mammal. The scanning may be performed after a predetermined time, using a PET or SPECT scanner. The compound or composition may comprise a radiolabel.

In another embodiment, the present invention is a precursor to a hot or cold molecule, for example, a precursor to a radiotracer. The precursor preferably comprises an azide or an alkyne. More particularly, the azide or alkyne may be in the following positions: $R_1$, $R_3$, $R_4$, $R_8$, $R_{11}$, $R_{12}$, $R_{13}$, $R_{15}$ and $R_{16}$. In one embodiment, any of $R_1$, $R_3$, $R_4$, $R_8$, $R_{11}$, $R_{12}$, $R_{13}$, $R_{15}$ and $R_{16}$ comprises an azide. It is noted that precursors may also comprise leaving and/or protecting groups. Some examples of precursors are below.

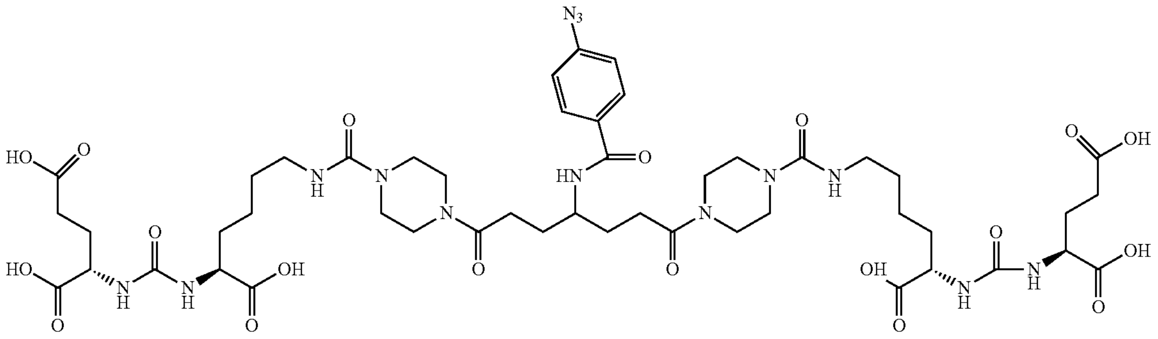

or

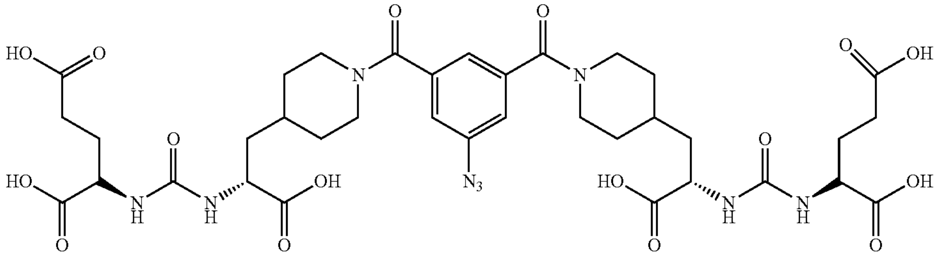

In another embodiment, the present invention is a method of synthesizing a tracer compound of Formulas I-VIII comprising: Reacting a compound of any of Formulas I-VIII, wherein in any of Formulas I-VIII, at least one H of $R_1$, $R_3$, $R_4$, $R_5$, $R_{11}$, $R_{12}$, $R_{13}$, $R_{15}$ and $R_{16}$ is replaced by either a first alkyne or a first azide with a second azide or second alkyne having a radioisotope or halo. In the example below, $R_{17}$ comprises an an alkyne or an azide, preferably, an alkyne if any of $R_1$, $R_3$, $R_4$, $R_8$, $R_{11}$, $R_{12}$, $R_{13}$, $R_{15}$ and $R_{16}$ comprises an azide.

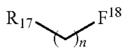

wherein $R_{16}$ is an azide if Formulas I-VIII comprises an alkyne or $R_{16}$ is an alkyne if Formulas I-VIII comprises an azide.

Table 1 shows compounds and their properties:

TABLE 1
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P001 | 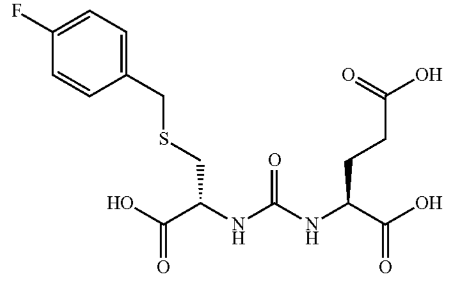 [SMILES: O=C(O)CC[C@H](NC(=O)N[C@@H](CSCc1ccc(F)cc1)C(=O)O)C(=O)O] | 402.39 | 402.1 | 0.32 | 97% | | 50 |
| P002 | 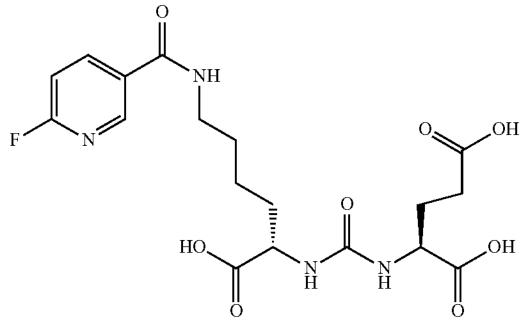 [SMILES: O=C(O)CC[C@H](NC(=O)N[C@@H](CCCCNC(=O)c1ccc(F)nc1)C(=O)O)C(=O)O] | 442.4 | 442.2 | −0.23 | 92% | | 15.6 |
| P003 | 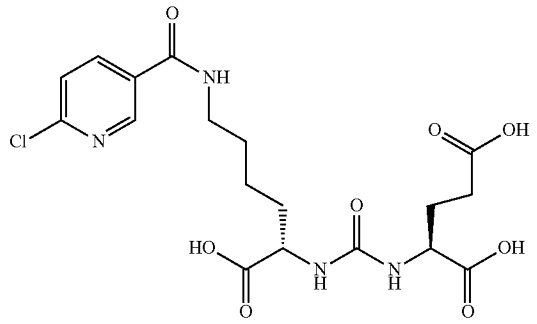 [SMILES: O=C(O)CC[C@H](NC(=O)N[C@@H](CCCCNC(=O)c1ccc(Cl)nc1)C(=O)O)C(=O)O] | 458.9 | 458.1 | 0.34 | 99% | | NA |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P004 | 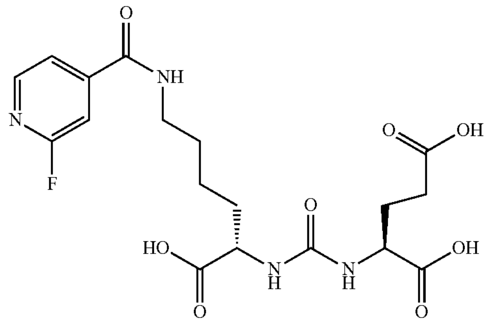 [SMILES: O=C(O)CC[C@H](NC(=O)N[C@@H](CCCCNC(=O)c1ccnc(F)c1)C(=O)O)C(=O)O] | 442.4 | 442.2 | −0.23 | 90% | | 15.6 |
| P005 | 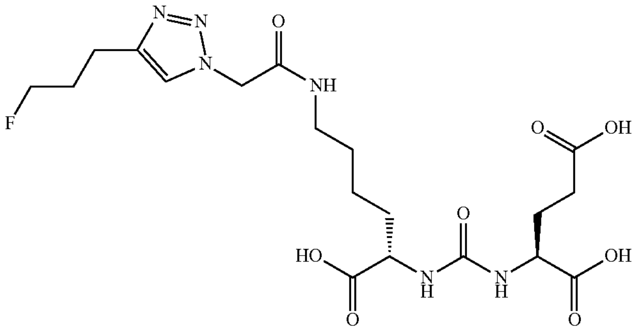 [SMILES: O=C(O)CC[C@H](NC(=O)N[C@@H](CCCCNC(=O)Cn1cc(CCCF)nn1)C(=O)O)C(=O)O] | 488.5 | 488.2 | −1.46 | 89% | | 40.7 |
| P006 | 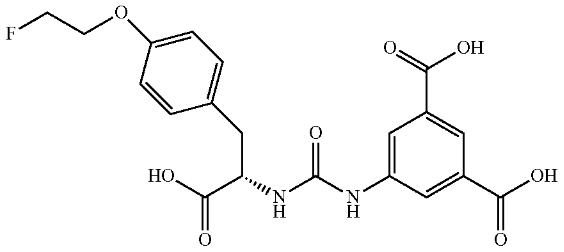 [SMILES: O=C(Nc1cc(C(=O)O)cc(C(=O)O)c1)N[C@@H](Cc1ccc(OCCF)cc1)C(=O)O] | 434.4 | 434.1 | 2.70 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P007 | 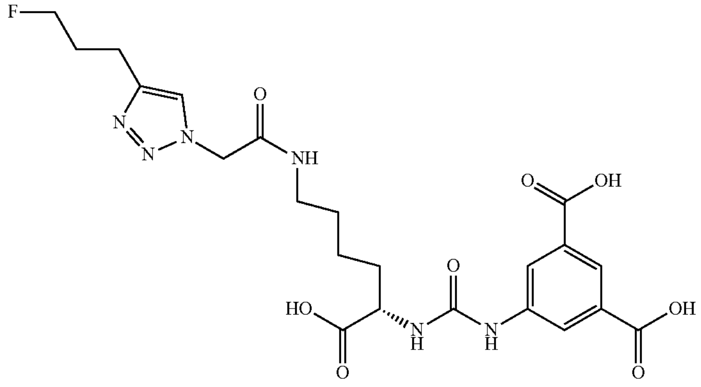 [SMILES: O=C(Cn1cc(CCCF)nn1)NCCCC[C@H](NC(=O)Nc1cc(C(=O)O)cc(C(=O)O)c1)C(=O)O] | 522.5 | 522.2 | 0.80 | 0% | | |
| P008 | 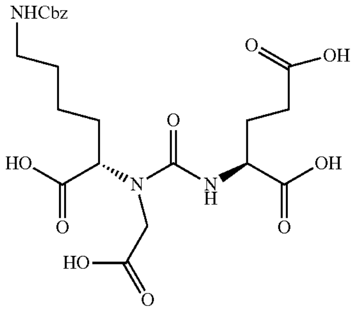 [SMILES: O=C(O)CC[C@H](NC(=O)N(CC(=O)O)[C@@H](CCCCNC(=O)OCc1ccccc1)C(=O)O)C(=O)O] | 511.5 | 511.2 | 1.52 | 21% | | |
| P009 | 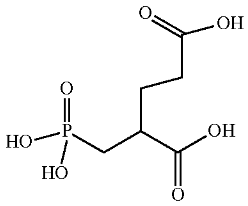 [SMILES: O=C(O)CCC(CP(=O)(O)O)C(=O)O] | 226.1 | 226 | −1.51 | 100% | | 6.6 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P010 | 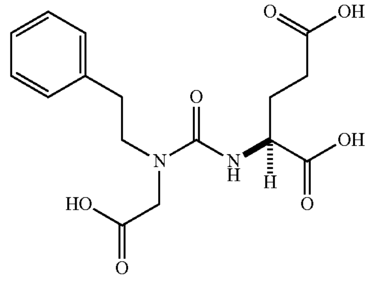 | 352.3 | 352.1 | −0.07 | 0% | | |
| P011 | 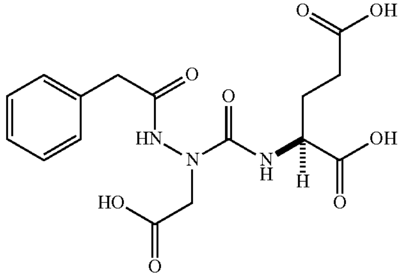 | 381.3 | 381.1 | −0.22 | 0% | | |
| P012 | 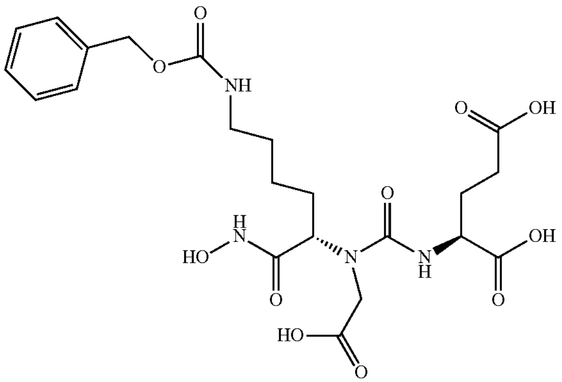 [SMILES: O=C(O)CC[C@H](NC(=O)N(CC(=O)O)[C@@H](CCCCNC(=O)OCc1ccccc1)C(=O)NO)C(=O)O] | 526.5 | 526.2 | 0.18 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P013 | 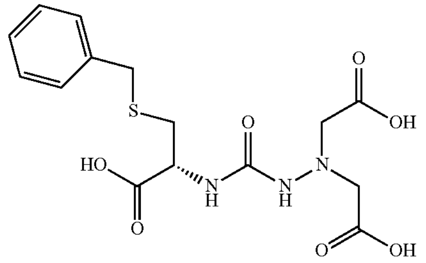 [SMILES: O=C(O)CN(CC(=O)O)NC(=O)N[C@@H](CSCc1ccccc1)C(=O)O] | 385.4 | 385.1 | 3.17 | 16% | | |
| P014 | 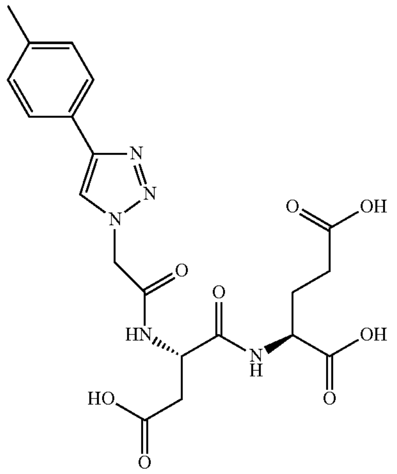 [SMILES: Cc1ccc(-c2cn(CC(=O)N[C@@H](CC(=O)O)C(=O)N[C@@H](CCC(=O)O)C(=O)O)nn2)cc1] | 461.4 | 461.2 | 0.21 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P015 | 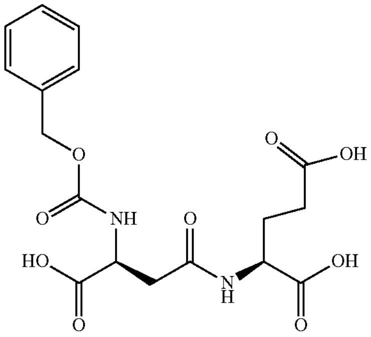 [SMILES: O=C(O)CC[C@H](NC(=O)C[C@H](NC(=O)OCc1ccccc1)C(=O)O)C(=O)O] | 396.4 | 396.1 | −0.04 | 0% | | |
| P016 | 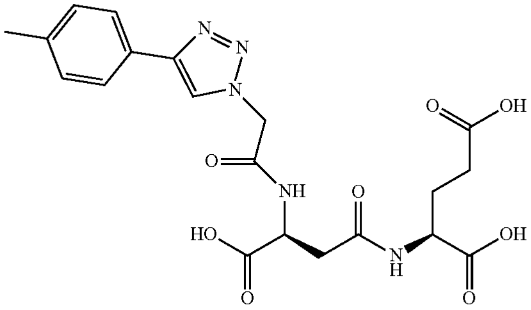 [SMILES: Cc1ccc(-c2cn(CC(=O)N[C@@H](CC(=O)N[C@@H](CCC(=O)O)C(=O)O)C(=O)O)nn2)cc1] | 461.4 | 461.2 | 0.28 | 12% | | |
| P017 | 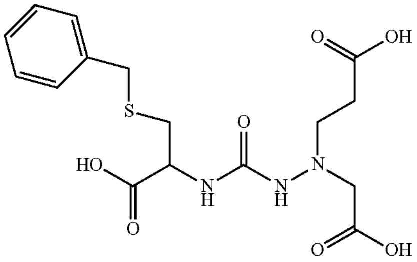 [SMILES: O=C(O)CCN(CC(=O)O)NC(=O)NC(CSCc1ccccc1)C(=O)O] | 399.4 | 399.1 | 2.92 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P018 | 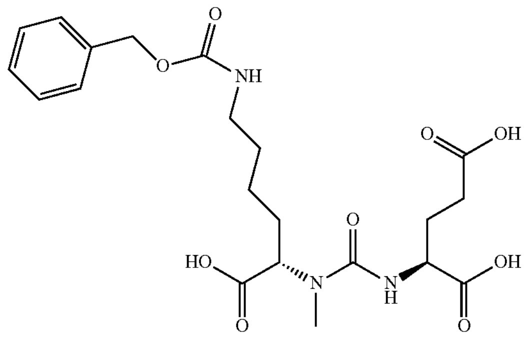 [SMILES: CN(C(=O)N[C@@H](CCC(=O)O)C(=O)O)[C@@H](CCCCNC(=O)OCc1ccccc1)C(=O)O] | 467.4 | 467.2 | 1.31 | 99% | | 15.6 |
| P019 | 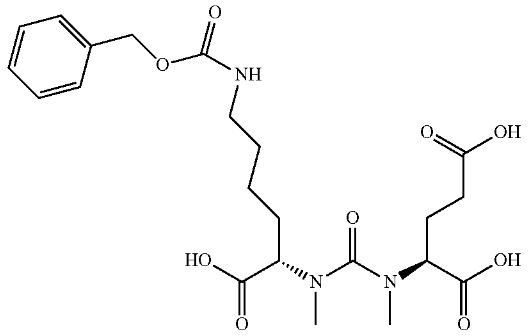 [SMILES: CN(C(=O)N(C)[C@@H](CCC(=O)O)C(=O)O)[C@@H](CCCCNC(=O)OCc1ccccc1)C(=O)O] | 467.4 | 467.2 | 1.31 | 97% | | 37.5 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P020 | 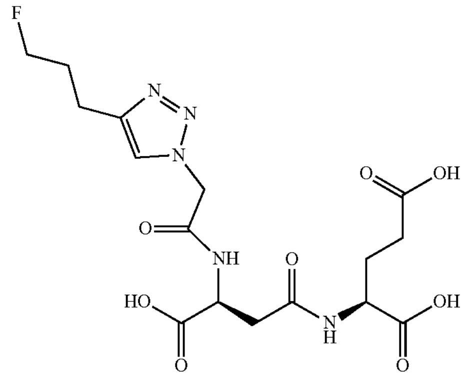 [SMILES: O=C(O)CC[C@H](NC(=O)C[C@H](NC(=O)Cn1cc(CCCF)nn1)C(=O)O)C(=O)O] | 431.4 | 431.2 | −1.72 | 0% | | |
| P021 | 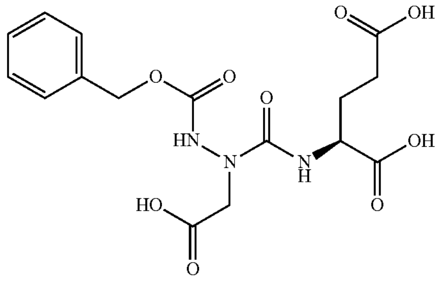 [SMILES: O=C(O)CC[C@H](NC(=O)N(CC(=O)O)NC(=O)OCc1ccccc1)C(=O)O] | 397.3 | 397.1 | −0.11 | 0% | | |
| P022 | 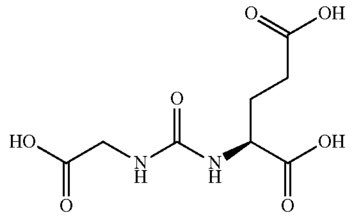 [SMILES: O=C(O)CC[C@H](NC(=O)NCC(=O)O)C(=O)O] | 248.2 | 248.1 | −1.23 | 77% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P023 | 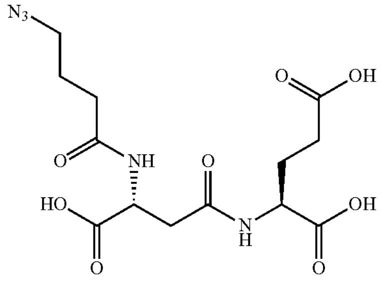 [SMILES: [N-]=[N+]=NCCCC(=O)N[C@H](CC(=O)N[C@@H](CCC(=O)O)C(=O)O)C(=O)O] | 373.1 | 373.1 | −0.36 | 24% | | |
| P024 | 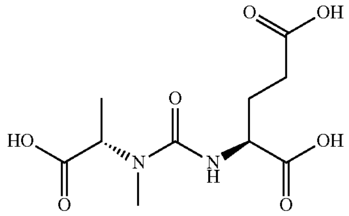 [SMILES: C[C@@H](C(=O)O)N(C)C(=O)N[C@@H](CCC(=O)O)C(=O)O] | 276.2 | 276.1 | −0.66 | 6% | | |
| P025 | 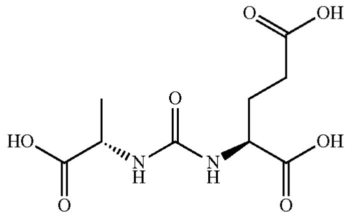 [SMILES: C[C@H](NC(=O)N[C@@H](CCC(=O)O)C(=O)O)C(=O)O] | 262.2 | 262.1 | −0.92 | 92% | | |
| P026 | 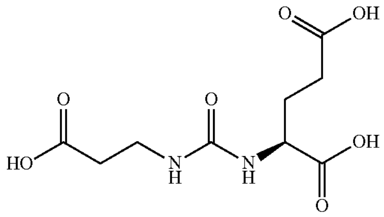 [SMILES: O=C(O)CCNC(=O)N[C@@H](CCC(=O)O)C(=O)O] | 262.2 | 262.1 | −1.22 | 2% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P027 | 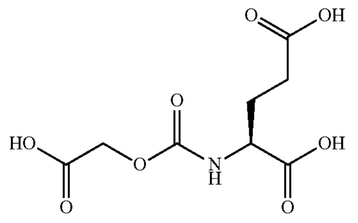 [SMILES: O=C(O)CC[C@H](NC(=O)OCC(=O)O)C(=O)O] | 249.2 | 249.1 | −1.17 | 31% | | |
| P028 | 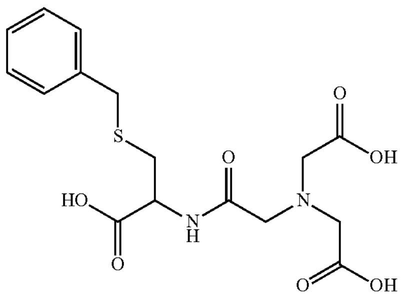 [SMILES: O=C(O)CN(CC(=O)O)CC(=O)NC(CSCc1ccccc1)C(=O)O] | 384.4 | 384.1 | 0.91 | 24% | | |
| P029 | 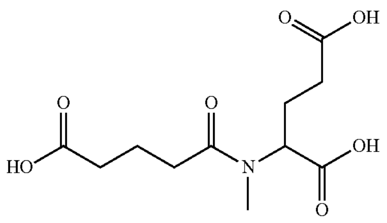 [SMILES: CN(C(=O)CCCC(=O)O)C(CCC(=O)O)C(=O)O] | 275.3 | 275.1 | −0.52 | 12% | | |
| P030 | 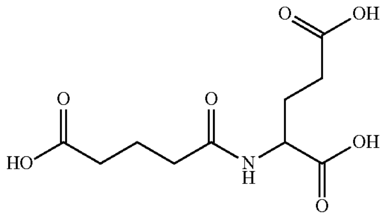 [SMILES: O=C(O)CCCC(=O)NC(CCC(=O)O)C(=O)O] | 261.2 | 261.1 | −1.09 | 2% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P031 | 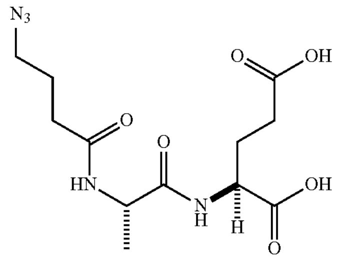 | 329.3 | 329.1 | −1.18 | 19% | | |
| P032 | 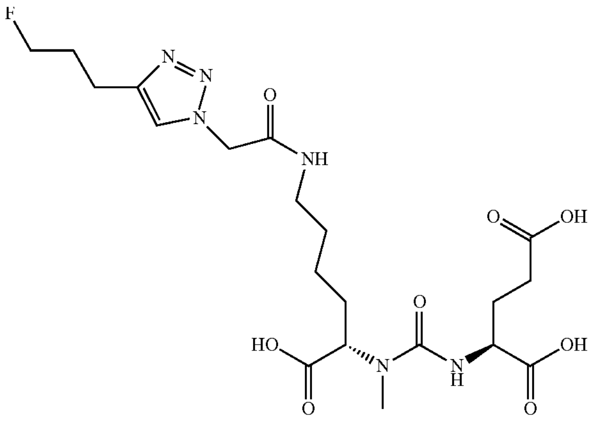 [SMILES: CN(C(=O)N[C@@H](CCC(=O)O)C(=O)O)[C@@H](CCCCNC(=O)Cn1cc(CCCF)nn1)C(=O)O] TFA | 599.5 | 502.2 | −0.99 | 50% | | |
| P033 | 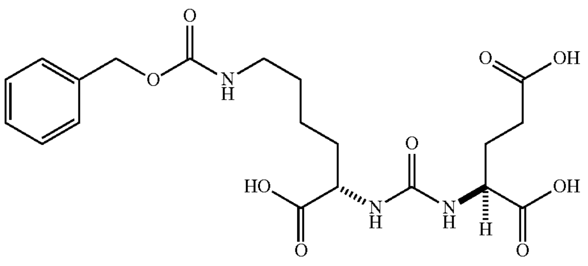 | 453.4 | 453.2 | −0.08 | 89% | | 0.78 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P034 | 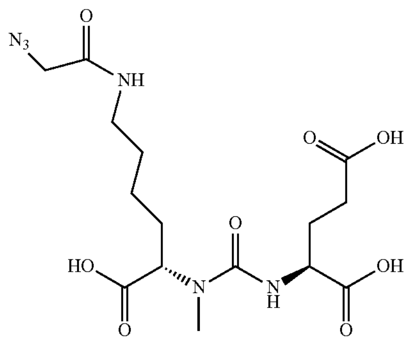 TFA | 513.4 | 416.4 | −0.43 | 70% | | |
| P035 | 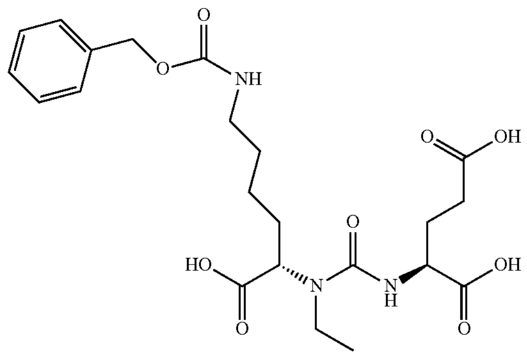 TFA | 578.5 | 481.2 | 1.83 | 0% | | |

TABLE 1-continued
| ID | Structure | MW | Exact Mass | CLogP | PSMA Blkg % (10 µM) | PSMA Blkg % (1.0 µM) | PSMA Ki (nM) |
|---|---|---|---|---|---|---|---|
| P036 | 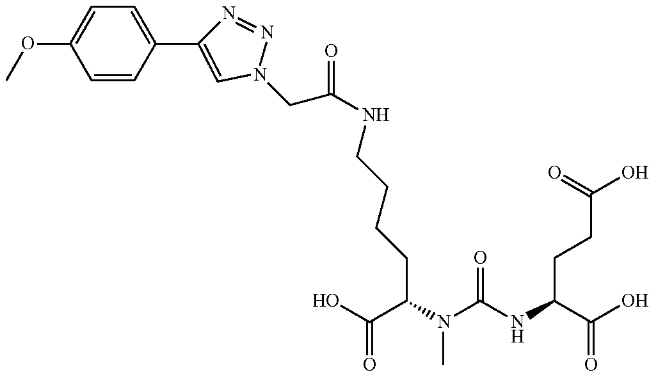 TFA | 645.6 | 548.2 | −0.49 | 68% | | |
| P037 | 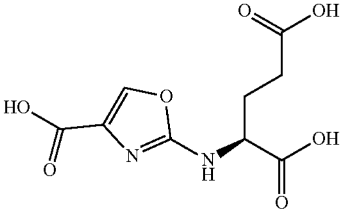 | 258.1 | 258 | −0.41 | 12% | | |
| P038 | 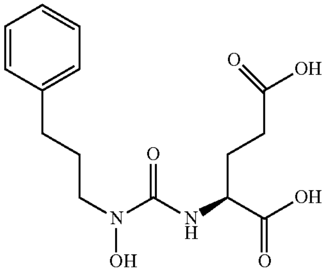 | 324.3 | 324.1 | 1.34 | 2% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P039 | 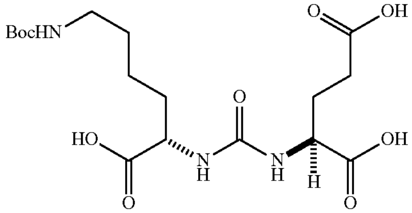 | 419.4 | 419.1 | −0.61 | 77% | | |
| P040 | 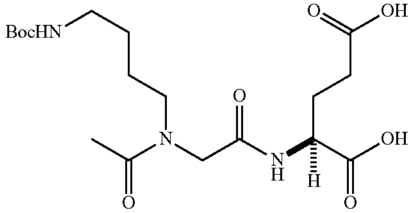 | 417.4 | 417.1 | −1.36 | 42% | | |
| P041 | 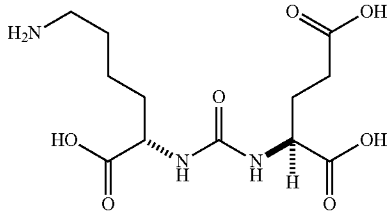 | 319.3 | 319.1 | −4.62 | 0% | | |
| P042 | 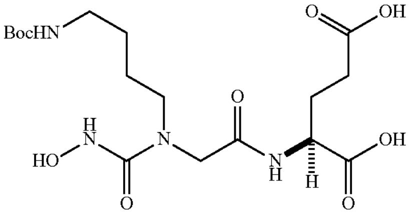 | 434.4 | 434.1 | −1.90 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P043 | 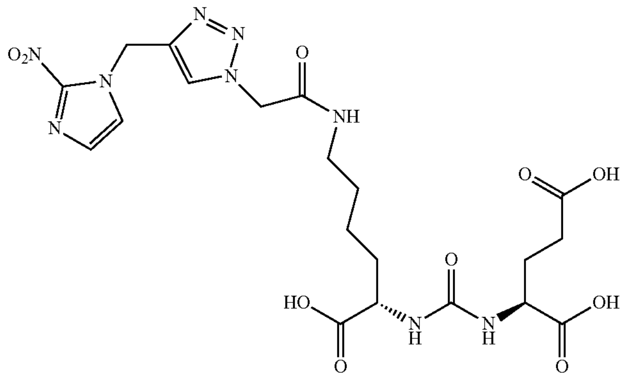 [SMILES: O=C(O)CC[C@H](NC(=O)N[C@@H](CCCCNC(=O)Cn1cc(Cn2ccnc2[N+](=O)[O-])nn1)C(=O)O)C(=O)O] | 553.5 | 553.2 | −2.11 | 77% | | |
| P044 | 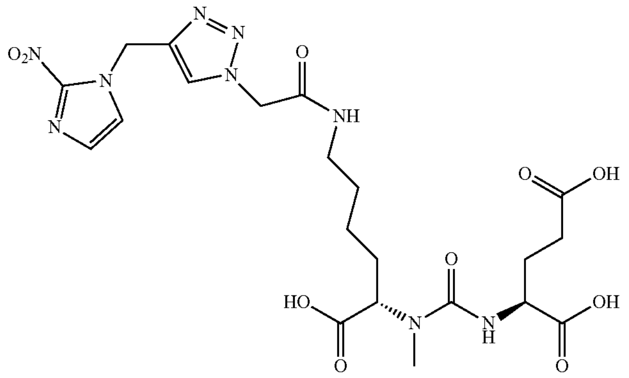 [SMILES: CN(C(=O)N[C@@H](CCC(=O)O)C(=O)O)[C@@H](CCCCNC(=O)Cn1cc(Cn2ccnc2[N+](=O)[O-])nn1)C(=O)O] | 567.5 | 567.2 | −1.85 | 62% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P045 | 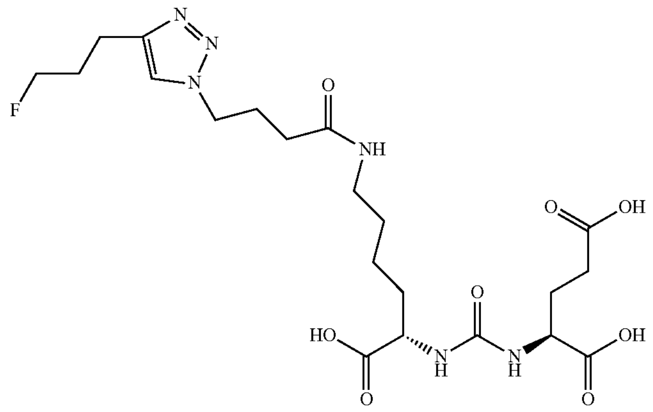 [SMILES: O=C(O)CC[C@H](NC(=O)N[C@@H](CCCCNC(=O)CCCn1cc(CCCF)nn1)C(=O)O)C(=O)O] | 516.5 | 516.2 | −1.00 | 95% | | 10.9 |
| P046 | 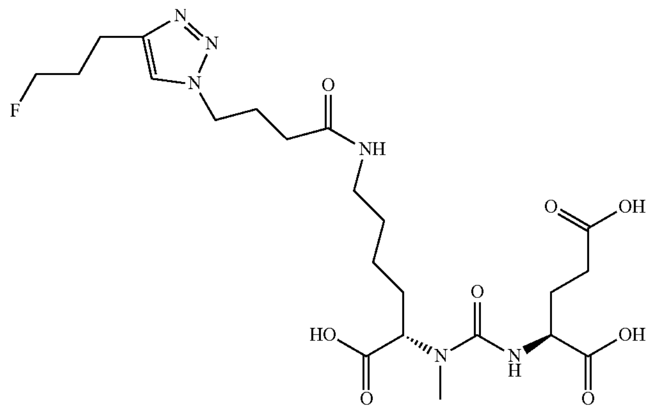 [SMILES: CN(C(=O)N[C@@H](CCC(=O)O)C(=O)O)[C@@H](CCCCNC(=O)CCCn1cc(CCCF)nn1)C(=O)O] | 530.6 | 530.3 | −0.75 | 80% | | 328 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P047 | 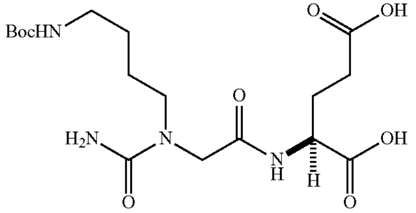 | 418.4 | 418.2 | −2.33 | 0% | | |
| P048 | 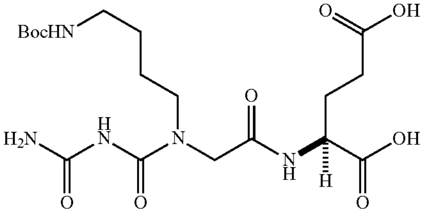 | 461.5 | 461.2 | −1.89 | 0% | | |
| P049 | 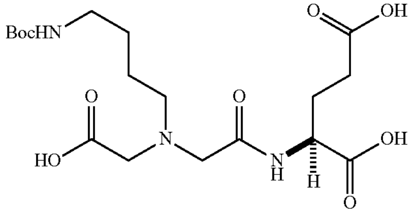 | 433.5 | 433.2 | −2.67 | 0% | | |
| P050 | 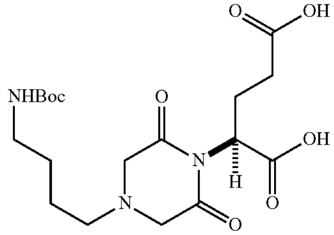 | 415.4 | 415.2 | −2.00 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P051 | 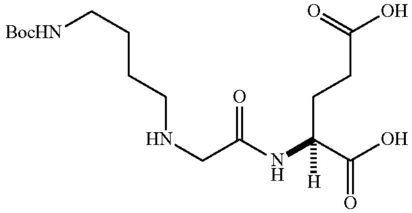 | 375.4 | 375.1 | −3.68 | 4% | | |
| P052 | 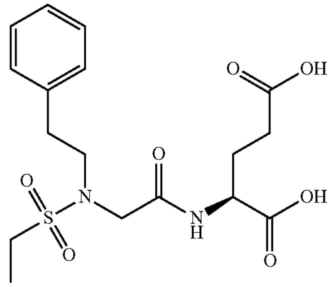 [SMILES: CCS(=O)(=O)N(CCc1ccccc1)CC(=O)N[C@@H](CCC(=O)O)C(=O)O] | 400.5 | 400.1 | 1.13 | 2% | | |
| P053 | 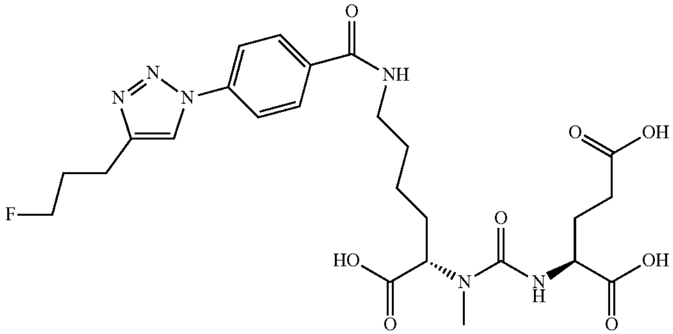 [SMILES: CN(C(=O)N[C@@H](CCC(=O)O)C(=O)O)[C@@H](CCCCNC(=O)c1ccc(-n2cc(CCCF)nn2)cc1)C(=O)O] | 564.6 | 564.2 | 1.20 | 94% | | 31.3 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P054 | 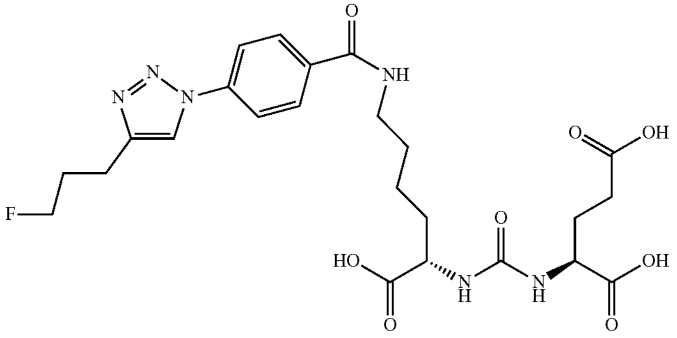 [SMILES: O=C(O)CC[C@H](NC(=O)N[C@@H](CCCCNC(=O)c1ccc(-n2cc(CCCF)nn2)cc1)C(=O)O)C(=O)O] | 550.5 | 550.2 | 0.94 | 100% | | 1.6 |
| P055 | 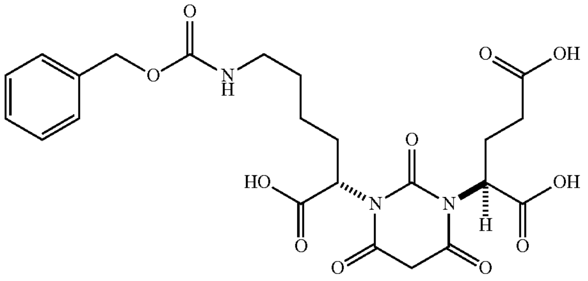 | 521.5 | 521.2 | 0.60 | 94% | | 344 |
| P056 | 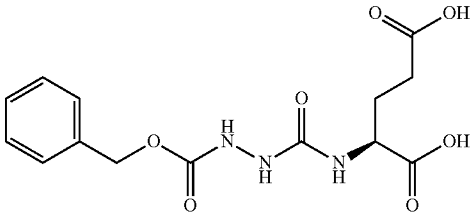 [SMILES: O=C(O)CC[C@H](NC(=O)NNC(=O)OCc1ccccc1)C(=O)O] | 339.3 | 339.1 | 0.22 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P057 | 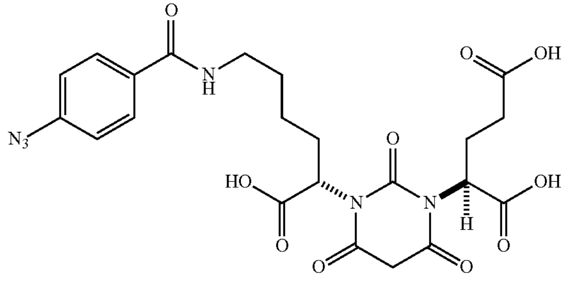 | 532.5 | 532.2 | 0.55 | 32% | | |
| P058 | 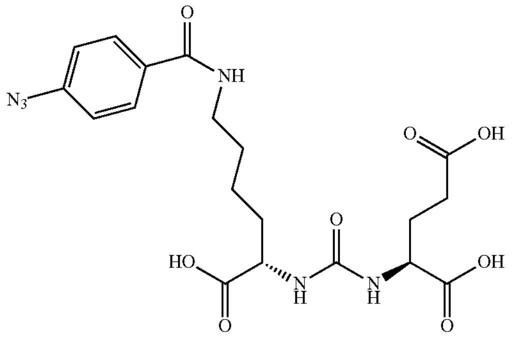 [SMILES: [N-]=[N+]=Nc1ccc(C(=O)NCCCC[C@H](NC(=O)N[C@@H](CCC(=O)O)C(=O)O)C(=O)O)cc1] | 464.4 | 464.2 | 1.00 | 100% | | |
| P059 | 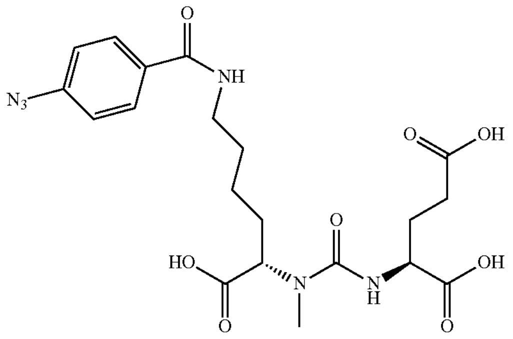 [SMILES: CN(C(=O)N[C@@H](CCC(=O)O)C(=O)O)[C@@H](CCCCNC(=O)c1ccc(N=[N+]=[N-])cc1)C(=O)O] | 478.4 | 478.2 | 1.25 | 99% | | 12.5 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P060 | 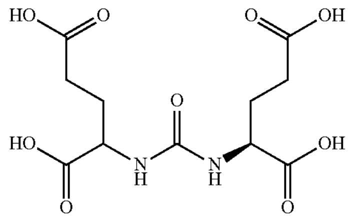 [SMILES: O=C(O)CCC(NC(=O)N[C@@H](CCC(=O)O)C(=O)O)C(=O)O] | 320.2 | 320.1 | −1.81 | 96% | | |
| P061 | 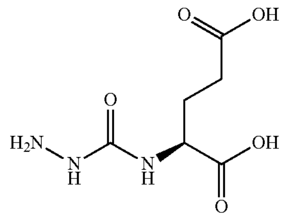 [SMILES: NNC(=O)N[C@@H](CCC(=O)O)C(=O)O] | 205.2 | 205.1 | −2.41 | 0% | | |
| P062 | 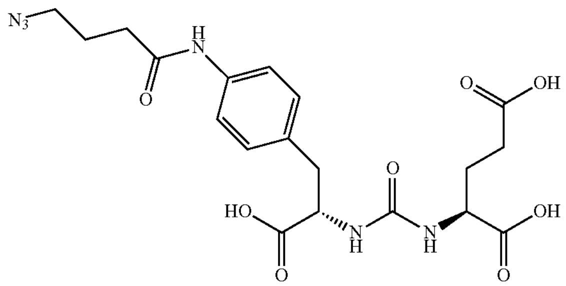 [SMILES: [N-]=[N+]=NCCCC(=O)Nc1ccc(C[C@H](NC(=O)N[C@@H](CCC(=O)O)C(=O)O)C(=O)O)cc1] | 464.3 | 464.2 | 1.02 | 97% | | |
| P063 | 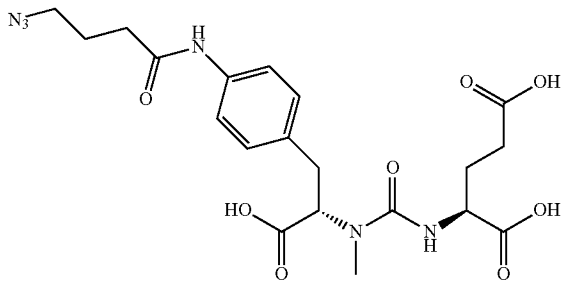 [SMILES: CN(C(=O)N[C@@H](CCC(=O)O)C(=O)O)[C@@H](Cc1ccc(NC(=O)CCCN=[N+]=[N-])cc1)C(=O)O] | 478.4 | 478.2 | 1.28 | 30% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P064 | 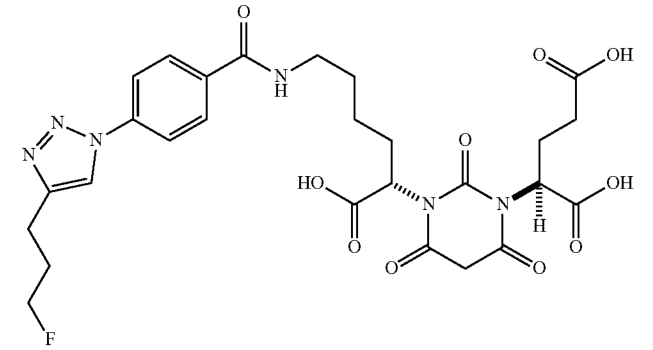 | 618.6 | 618.4 | 0.49 | 46% | | |
| P065 | 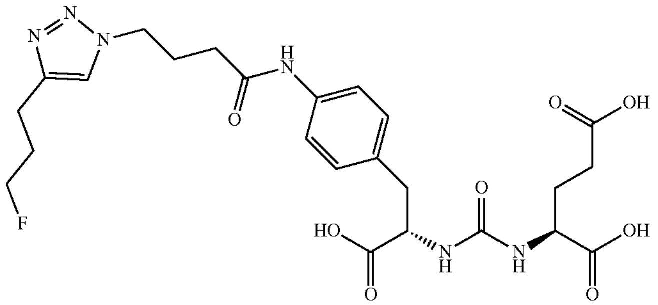 [SMILES: O=C(O)CC[C@H](NC(=O)N[C@@H](Cc1ccc(NC(=O)CCCn2cc(CCCF)nn2)cc1)C(=O)O)C(=O)O] | 550.5 | 550.2 | −0.04 | 96% | | 19.7 |
| P065 | 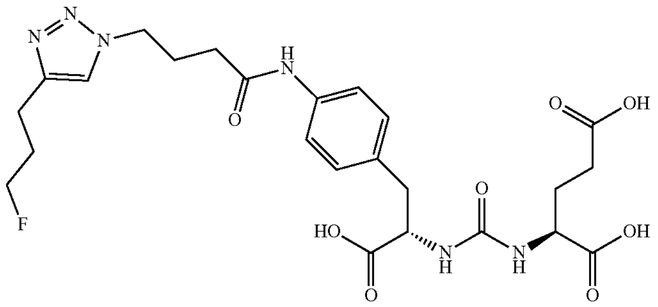 [SMILES: O=C(O)CC[C@H](NC(=O)N[C@@H](Cc1ccc(NC(=O)CCCn2cc(CCCF)nn2)cc1)C(=O)O)C(=O)O] | 550.5 | 550.2 | −0.04 | | 92% | 9.1 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P066 | 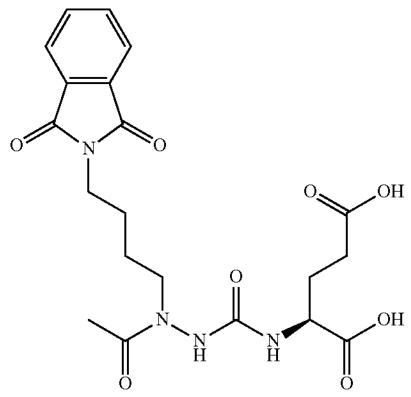 [SMILES: CC(=O)N(CCCCN1C(=O)c2ccccc2C1=O)NC(=O)N[C@@H](CCC(=O)O)C(=O)O] | 448.4 | 448.2 | 0.66 | 12% | | |
| P067 | 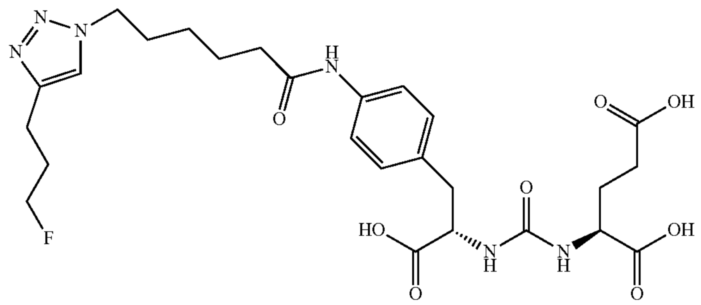 [SMILES: O=C(O)CC[C@H](NC(=O)N[C@@H](Cc1ccc(NC(=O)CCCCCn2cc(CCCF)nn2)cc1)C(=O)O)C(=O)O] | 578.6 | 578.2 | 0.48 | 52% | | |
| P068 | 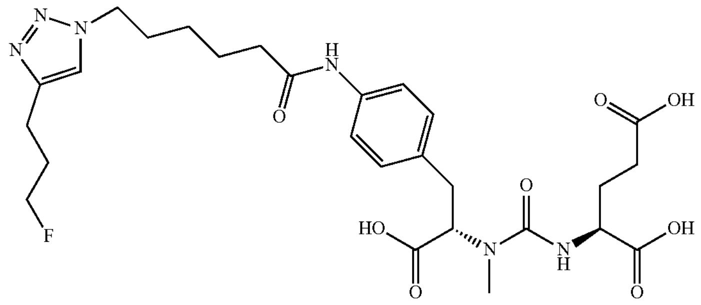 [SMILES: CN(C(=O)N[C@@H](CCC(=O)O)C(=O)O)[C@@H](Cc1ccc(NC(=O)CCCCCn2cc(CCCF)nn2)cc1)C(=O)O] | 592.6 | 592.3 | 0.73 | 27% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P069 | 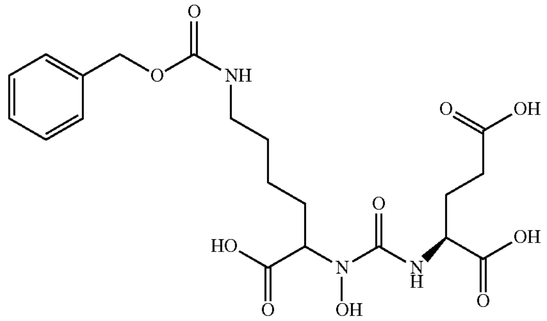 [SMILES: O=C(O)CC[C@H](NC(=O)N(O)C(CCCCNC(=O)OCc1ccccc1)C(=O)O)C(=O)O] | 469.4 | 469.2 | 1.06 | 94% | | 250 |
| P070 | 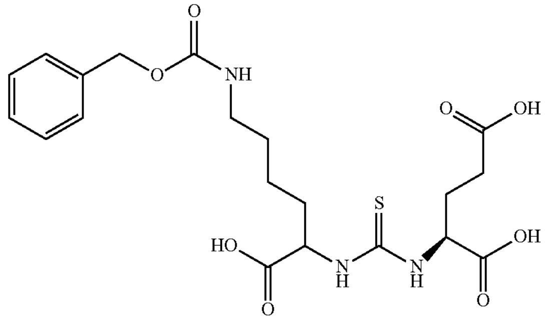 [SMILES: O=C(O)CC[C@H](NC(=S)NC(CCCCNC(=O)OCc1ccccc1)C(=O)O)C(=O)O] | 469.5 | 469.2 | 1.10 | 94% | | 59 |
| P071 | 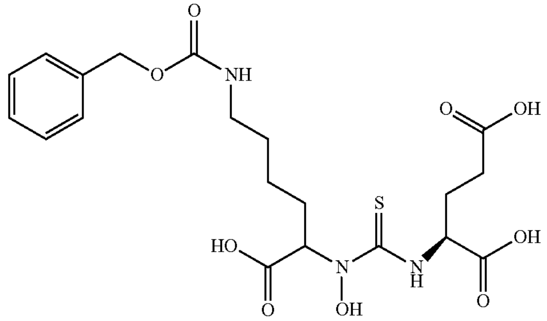 | 485.5 | 485.2 | 1.06 | 96% | | 31 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P072 | 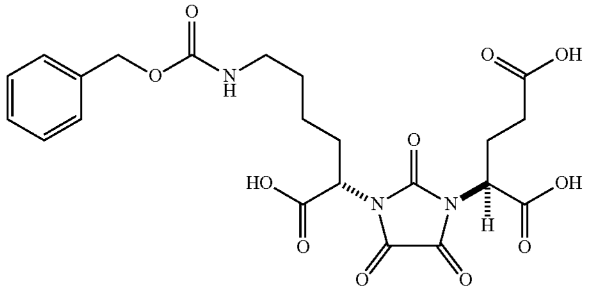 | 507.5 | 507.2 | 0.11 | 39% | | |
| P073 | 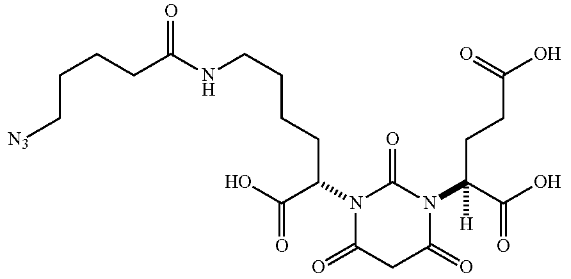 | 512.5 | 512.2 | −0.23 | 2% | | |
| P074 | 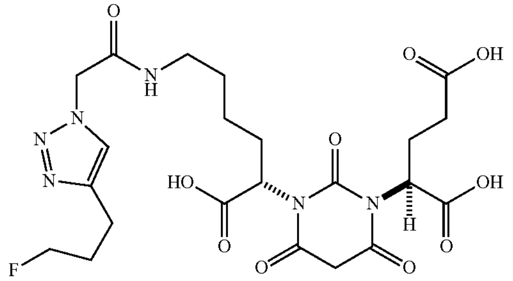 | 556.5 | 556.2 | −1.69 | 10% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P075 | 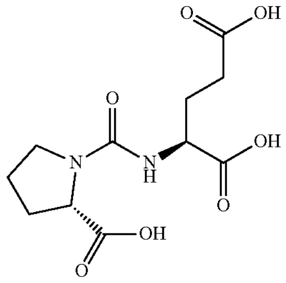 [SMILES: O=C(O)CC[C@H](NC(=O)N1CCC[C@H]1C(=O)O)C(=O)O] | 288.3 | 288.1 | −0.55 | 32% | | |
| P076 | 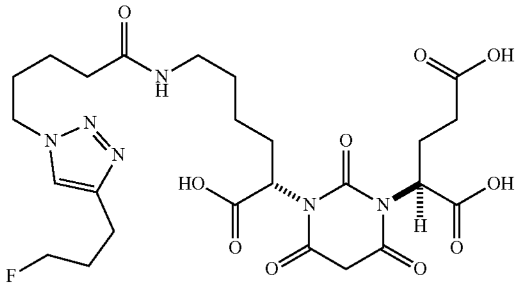 | 598.6 | 598.2 | −1.65 | 14% | | |
| P077 | 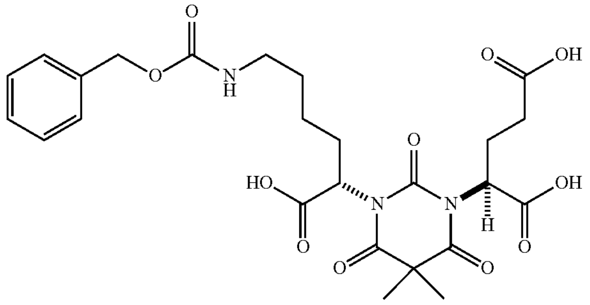 | 549.5 | 549.2 | 1.64 | 28% | | |

TABLE 1-continued
| ID | Structure | MW | Exact Mass | CLogP | PSMA Blkg % (10 µM) | PSMA Blkg % (1.0 µM) | PSMA Ki (nM) |
| --- | --- | --- | --- | --- | --- | --- | --- |
| P078 | 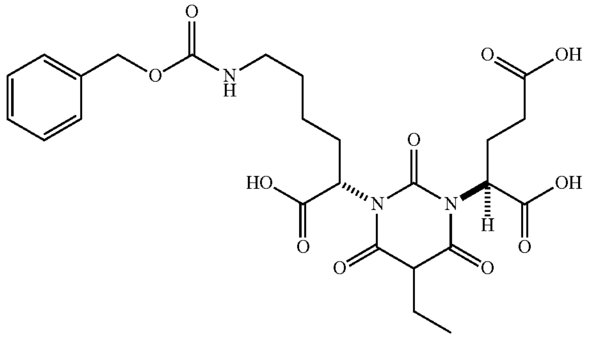 | 549.5 | 549.2 | 1.65 | 94% | | >312 |
| P079 | 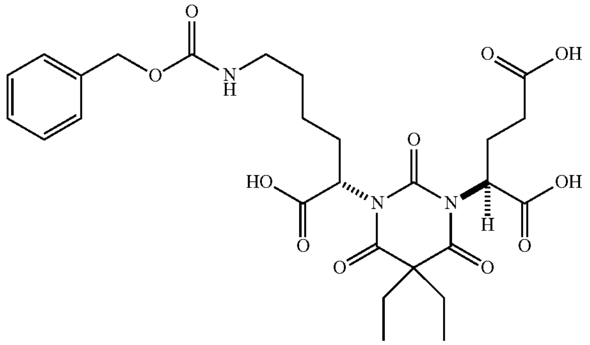 | 577.6 | 577.2 | 3.70 | 96% | | 313 |
| P080 | 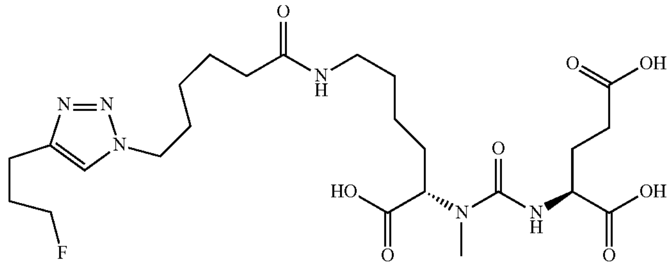 [SMILES: CN(C(=O)N[C@@H](CCC(=O)O)C(=O)O)[C@@H](CCCCNC(=O)CCCCCn1cc(CCCF)nn1)C(=O)O] | 518.6 | 518.4 | −0.41 | 90% | | 625 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P081 | 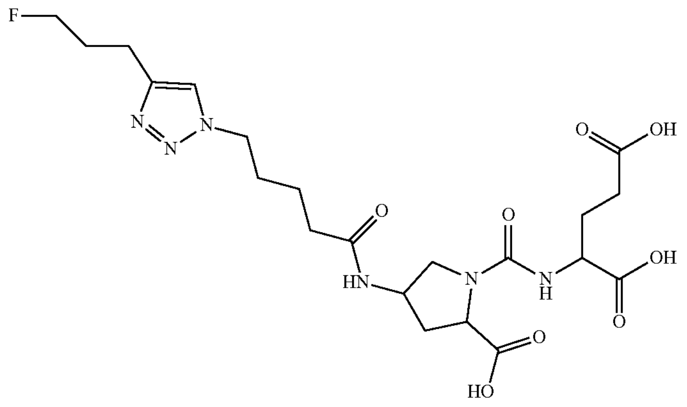 [SMILES: O=C(O)CCC(NC(=O)N1CC(NC(=O)CCCCn2cc(CCCF)nn2)CC1C(=O)O)C(=O)O] | 514.5 | 514.2 | −1.25 | 25% | | |
| P082 | 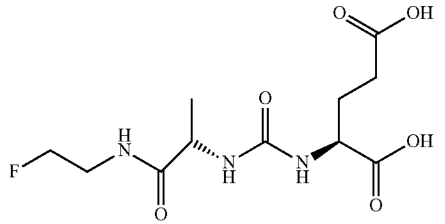 | 307.3 | 307.1 | −1.35 | 4% | | |
| P083 | 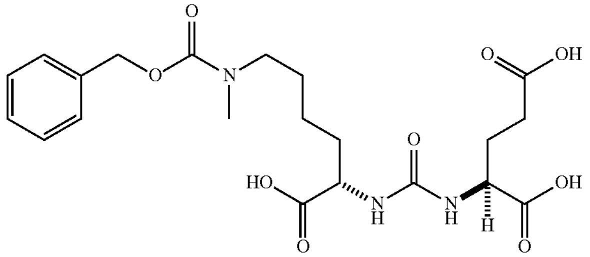 | 467.5 | 467.2 | 0.52 | 100% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P084 | 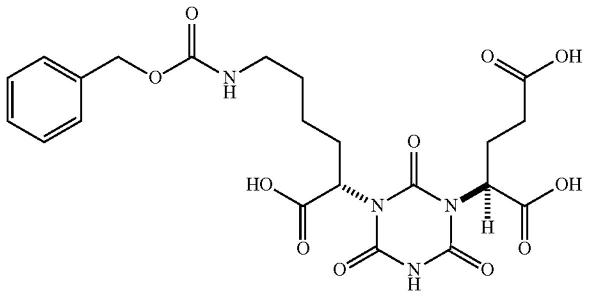 | 522.5 | 522.2 | 0.11 | 19% | | |
| P085 | 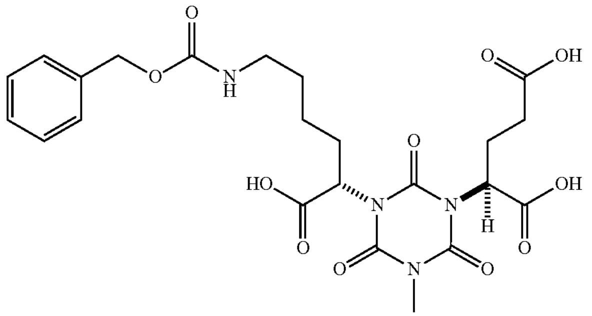 | 536.5 | 536.2 | 1.01 | 0% | | |
| P086 | 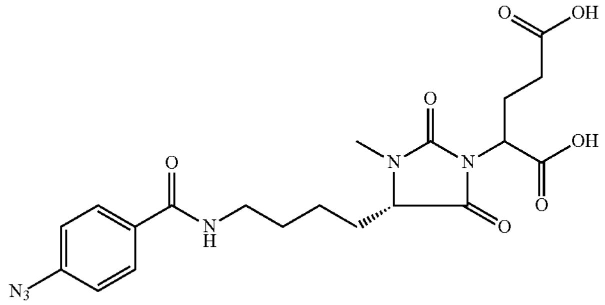 | 460.4 | 460.2 | 1.49 | 25% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P087 | 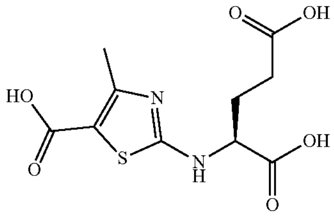 [SMILES: Cc1nc(N[C@@H](CCC(=O)O)C(=O)O)sc1C(=O)O] | 288.3 | 288 | 0.26 | 3% | | |
| P088 | 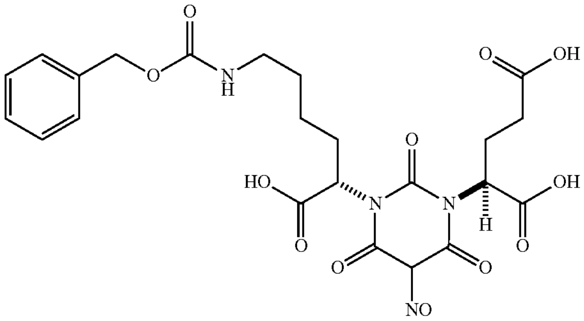 | 550.5 | 550.2 | 1.06 | 83% | | >407 |
| P089 | 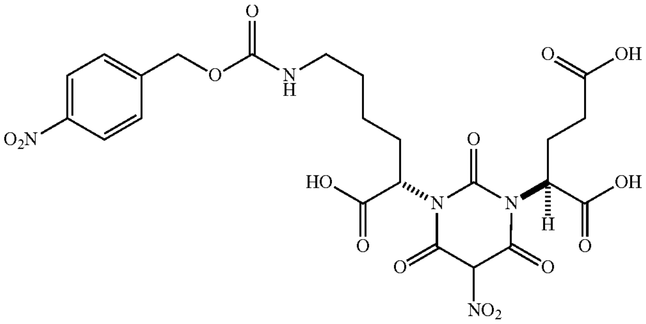 para:ortho = 3:1 | 611.5 | 611.1 | 0.73 | 88% | | >407 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P090 | 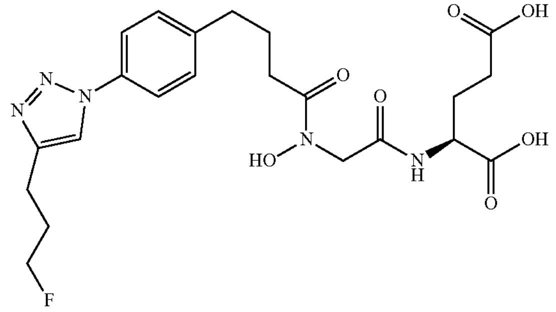 [SMILES: O=C(O)CC[C@H](NC(=O)CN(O)C(=O)CCCc1ccc(-n2cc(CCCF)nn2)cc1)C(=O)O] | 493.5 | 493.2 | 1.05 | 85% | | 313 |
| P091 | 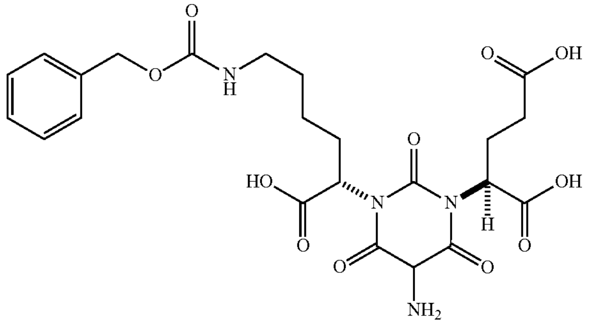 | 536.5 | 536.2 | −1.48 | 23% | | |
| P092 | 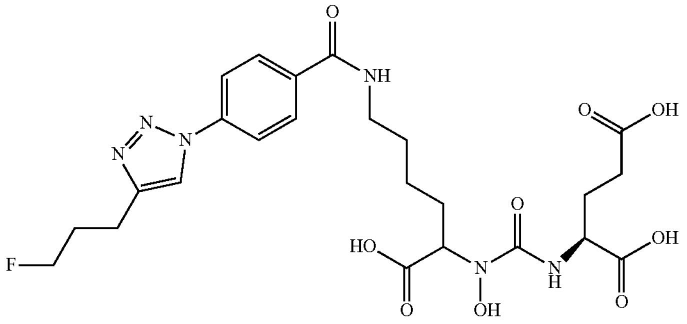 [SMILES: O=C(O)CC[C@H](NC(=O)N(O)C(CCCCNC(=O)c1ccc(-n2cc(CCCF)nn2)cc1)C(=O)O)C(=O)O] | 566.5 | 566.2 | 0.95 | 99% | | 31 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P093 | 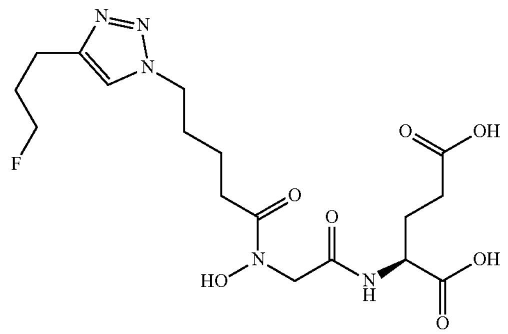 [SMILES: O=C(O)CC[C@H](NC(=O)CN(O)C(=O)CCCCn1cc(CCCF)nn1)C(=O)O] | 431.4 | 431.2 | −1.14 | 16% | | |
| P094 | 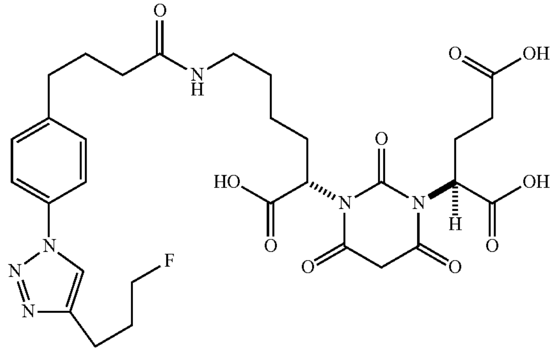 | 660.7 | 660.3 | 0.54 | 7% | | |
| P095 | 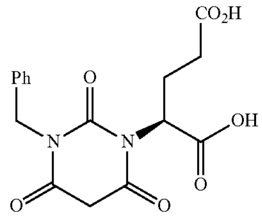 [SMILES: O=C(O)CC[C@@H](C(=O)O)N1C(=O)CC(=O)N(Cc2ccccc2)C1=O] | 348.3 | 348.1 | 0.95 | 4% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P096 | 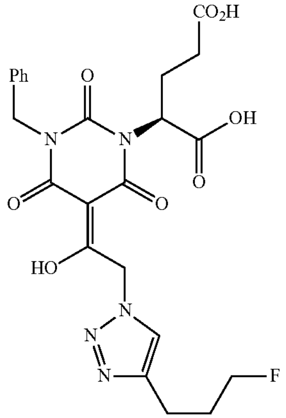 [SMILES: O=C(O)CC[C@@H](C(=O)O)N1C(=O)/C(=C(/O)Cn2cc(CCCF)nn2)C(=O)N(Cc2ccccc2)C1=O] | 517.5 | 517.2 | 0.67 | 3% | | |
| P097 | 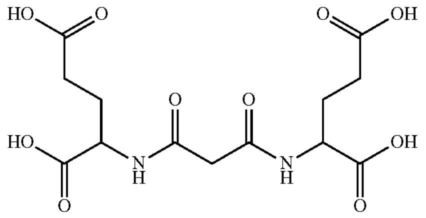 [SMILES: O=C(O)CCC(NC(=O)CC(=O)NC(CCC(=O)O)C(=O)O)C(=O)O] | 362.3 | 362.1 | −2.46 | fluorescence interference | | |
| P098 | 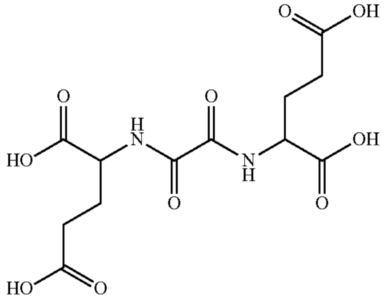 [SMILES: O=C(O)CCC(NC(=O)C(=O)NC(CCC(=O)O)C(=O)O)C(=O)O] | 348.3 | 348.1 | −2.01 | 23% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P099 | 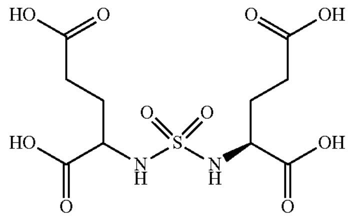 [SMILES: O=C(O)CCC(NS(=O)(=O)N[C@@H](CCC(=O)O)C(=O)O)C(=O)O] | 356.3 | 356.1 | −1.75 | 0% | | |
| P100 | 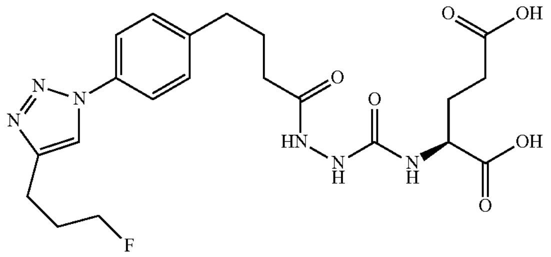 [SMILES: O=C(O)CC[C@H](NC(=O)NNC(=O)CCCc1ccc(-n2cc(CCCF)nn2)cc1)C(=O)O] | 548.5 | 548.2 | 0.80 | 3% | | |
| P101 | 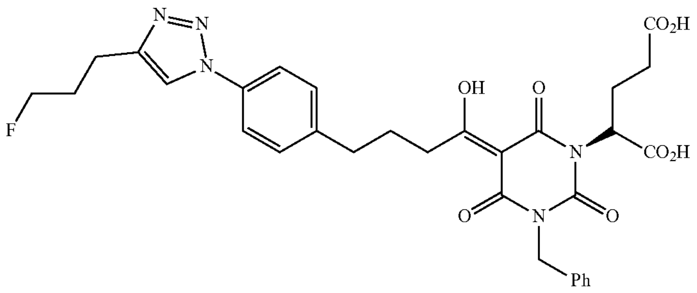 | 621.6 | 621.2 | 3.87 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P102 | 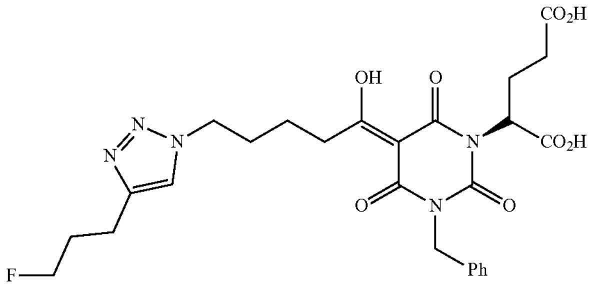 | 559.5 | 559.2 | 1.68 | 0% | | |
| P103 | 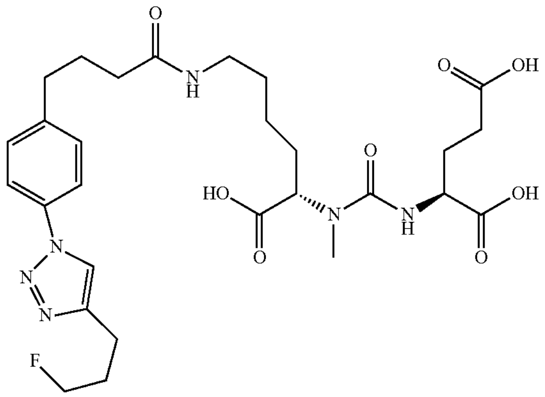 [SMILES: CN(C(=O)N[C@@H](CCC(=O)O)C(=O)O)[C@@H](CCCCNC(=O)CCCc1ccc(-n2cc(CCCF)nn2)cc1)C(=O)O] | 606.6 | 606.3 | 1.24 | 91% | | 235 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P104 | 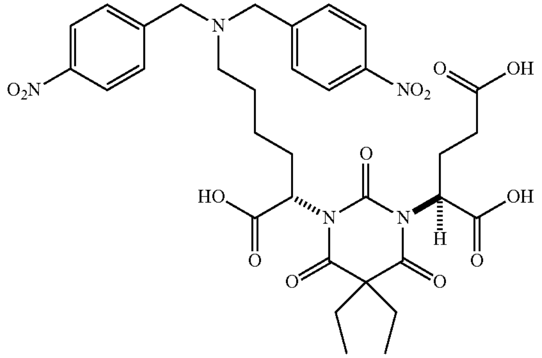 | 713.7 | 713.3 | 4.32 | 7% | | |
| P105 | 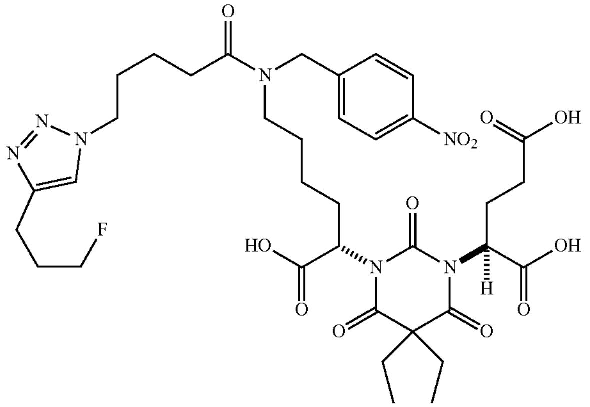 | 789.8 | 789.3 | | 5% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P106 | 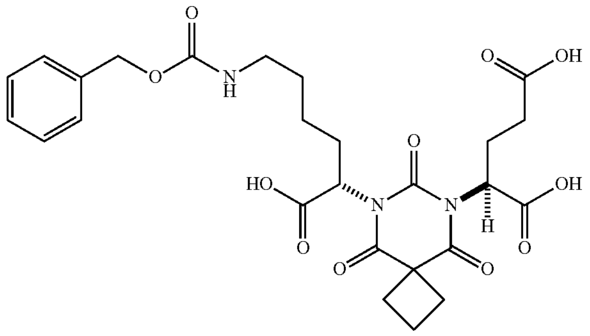 | 561.5 | 561.2 | 1.47 | 67% | | |
| P107 | 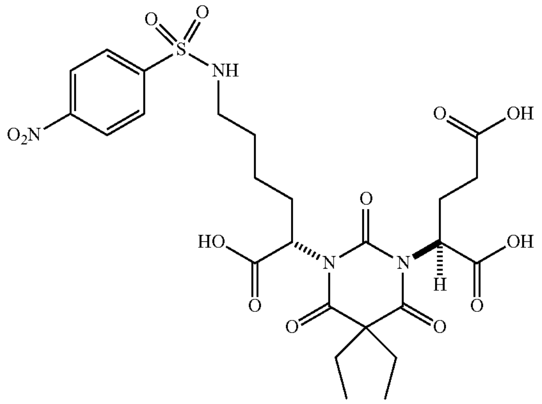 | 628.6 | 628.2 | 2.40 | 19% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P108 | 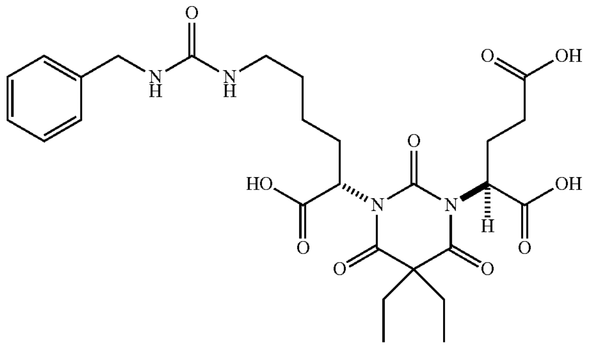 | 576.6 | 576.2 | 2.31 | 11% | | |
| P109 | 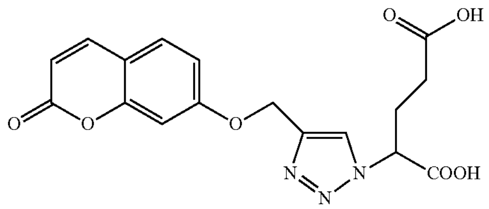 [SMILES: O=C(O)CCC(C(=O)O)n1cc(COc2ccc3ccc(=O)oc3c2)nn1] | 373.3 | 373.1 | 0.03 | 24% | | |
| P110 | 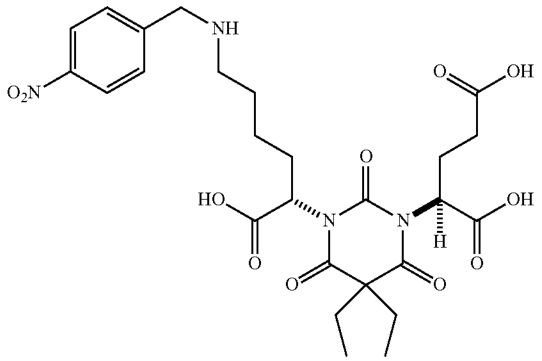 | 578.6 | 578.2 | 0.07 | 8% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P111 | 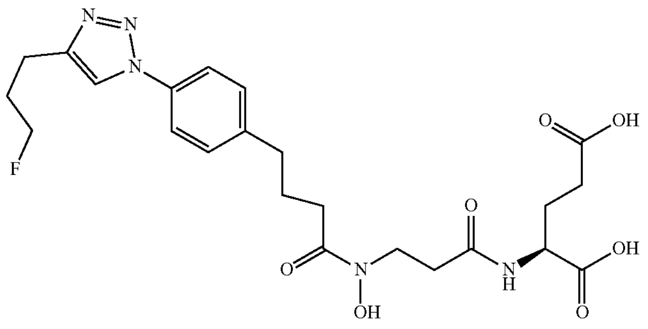 [SMILES: O=C(O)CC[C@H](NC(=O)CCN(O)C(=O)CCCc1ccc(-n2cc(CCCF)nn2)cc1)C(=O)O] | 507.5 | 507.2 | 1.30 | 9% | | |
| P112 | 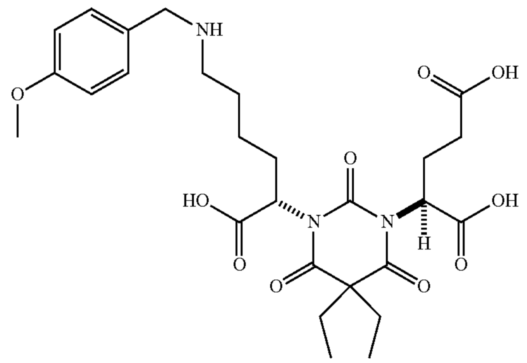 | 563.6 | 563.3 | 0.25 | 4% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P113 | 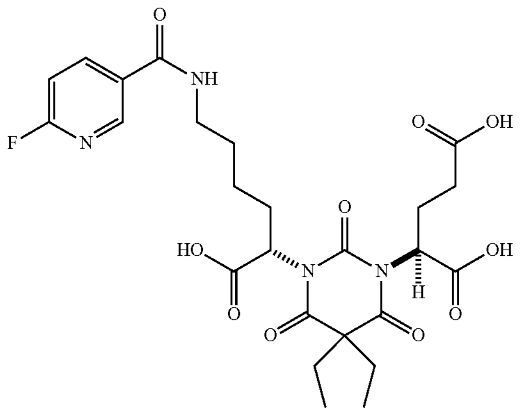 | 566.5 | 566.2 | 1.41 | 11% | | |
| P114 | 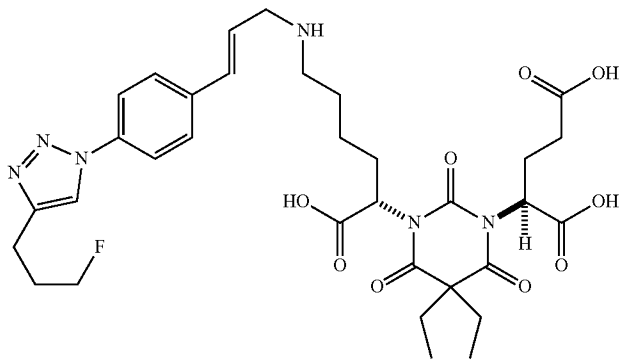 | 686.7 | 686.3 | 0.82 | 8% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P115 | 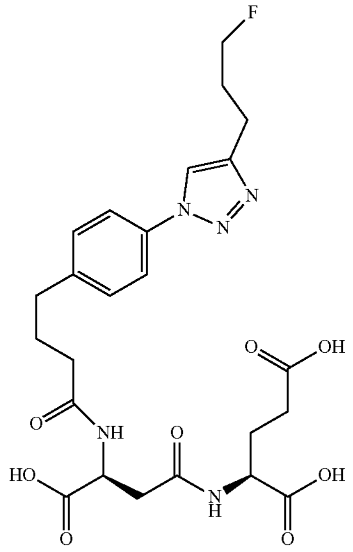 [SMILES: O=C(O)CC[C@H](NC(=O)C[C@H](NC(=O)CCCc1ccc(-n2cc(CCCF)nn2)cc1)C(=O)O)C(=O)O] | 535.5 | 535.2 | 0.51 | 36% | | |
| P116 | 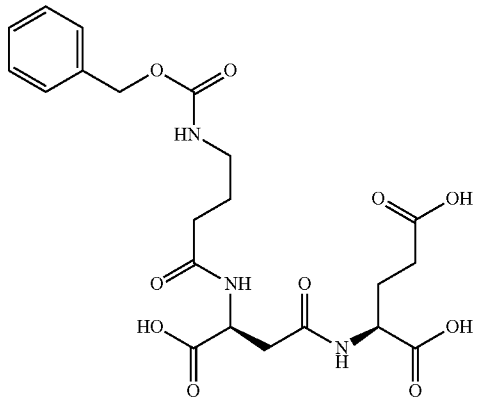 [SMILES: O=C(O)CC[C@H](NC(=O)C[C@H](NC(=O)CCCNC(=O)OCc1ccccc1)C(=O)O)C(=O)O] | 481.5 | 481.2 | 0.19 | 31% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P117 | 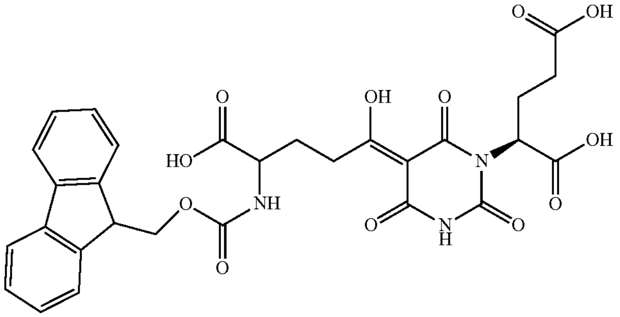 [SMILES: O=C(O)CC[C@@H](C(=O)O)N1C(=O)NC(=O)/C(=C(/O)CCC(NC(=O)OCC2c3ccccc3-c3ccccc32)C(=O)O)C1=O] | 609.6 | 609.3 | 0.23 | 18% | | |
| P118 | 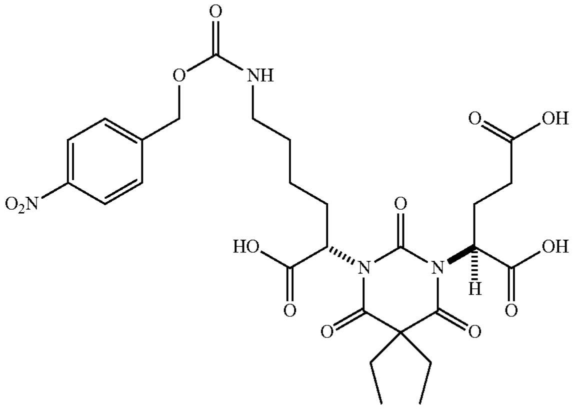 | 622.6 | 622.2 | 2.44 | 13% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P119 | 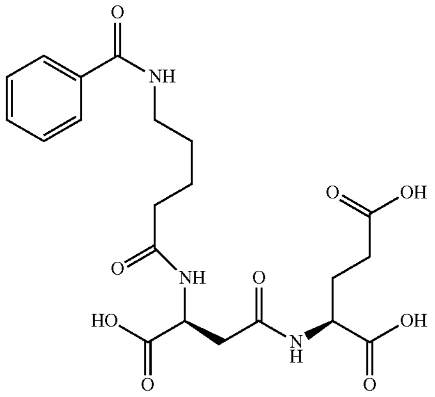 [SMILES: O=C(O)CC[C@H](NC(=O)C[C@H](NC(=O)CCCCNC(=O)c1ccccc1)C(=O)O)C(=O)O] | 465.5 | 465.2 | −0.89 | 26% | | |
| P120 | 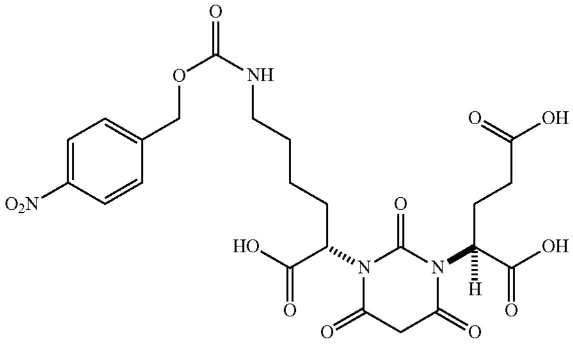 | 566.5 | 566.2 | 0.34 | 15% | | |
| P121 | 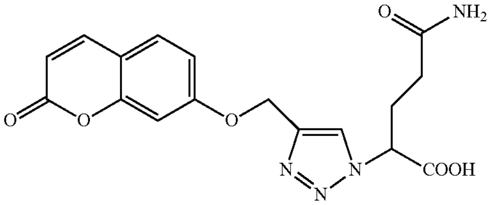 [SMILES: NC(=O)CCC(C(=O)O)n1cc(COc2ccc3ccc(=O)oc3c2)nn1] | 372.3 | 372.1 | −0.89 | 7% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P122 | 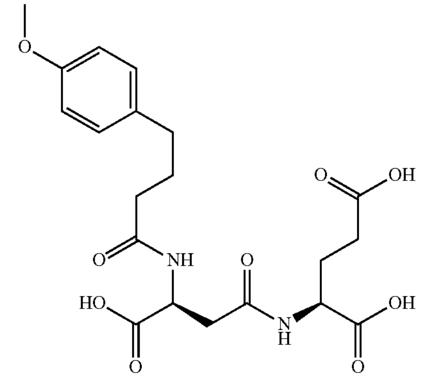 [SMILES: COc1ccc(CCCC(=O)N[C@@H](CC(=O)N[C@@H](CCC(=O)O)C(=O)O)C(=O)O)cc1] | 438.4 | 438.2 | 0.28 | 18% | | |
| P123 | 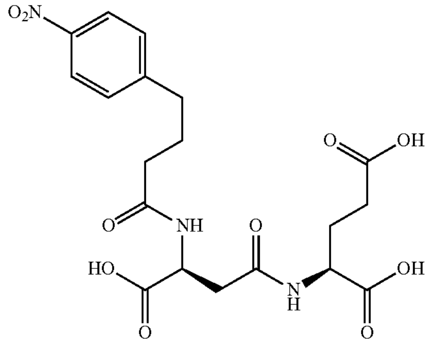 [SMILES: O=C(O)CC[C@H](NC(=O)C[C@H](NC(=O)CCCc1ccc([N+](=O)[O-])cc1)C(=O)O)C(=O)O] | 453.4 | 453.1 | 0.11 | 17% | | |
| P124 | 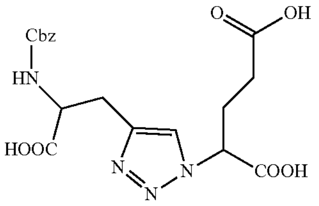 [SMILES: O=C(O)CCC(C(=O)O)n1cc(CC(NC(=O)OCc2ccccc2)C(=O)O)nn1] | 420.4 | 420.1 | −0.68 | 10% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P125 | 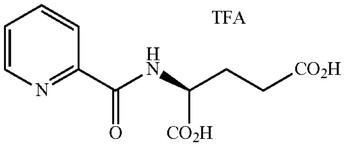 TFA | 349.2 | 349.1 | −0.66 | 2% | | |
| P126 | 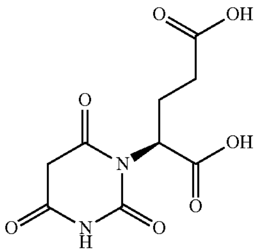 | 258.2 | 258.1 | −2.52 | 12% | | |
| P127 | 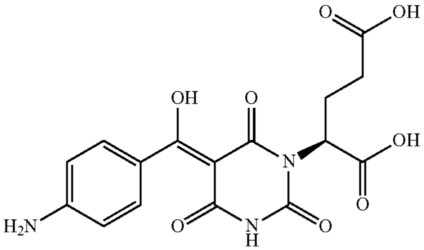 | 377.3 | 377.1 | −2.24 | 10% | | |
| P128 | 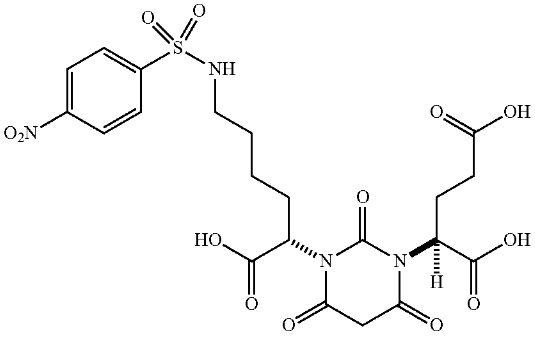 | 572.5 | 572.1 | 0.30 | 12% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P129 | 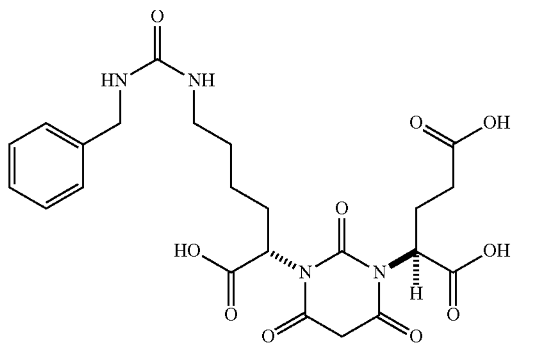 | 520.5 | 520.2 | 0.21 | 10% | | |
| P130 | 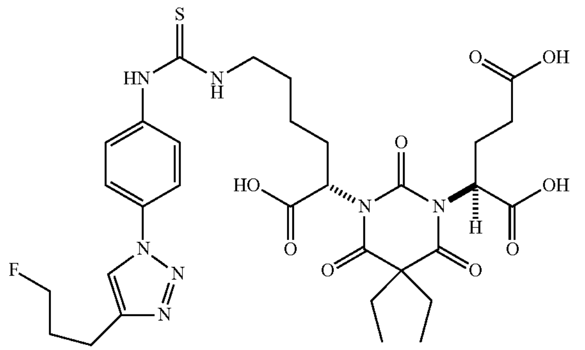 | 705.8 | 705.3 | 2.56 | 10% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P131 | 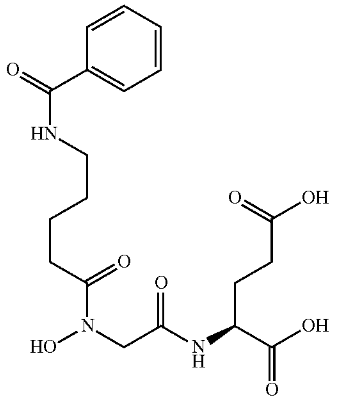 [SMILES: O=C(O)CC[C@H](NC(=O)CN(O)C(=O)CCCCNC(=O)c1ccccc1)C(=O)O] | 423.4 | 423.2 | −0.35 | 6% | | |
| P132 | 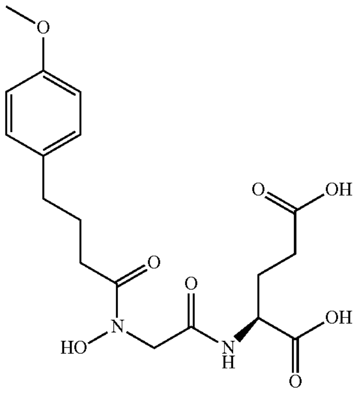 [SMILES: COc1ccc(CCCC(=O)N(O)CC(=O)N[C@@H](CCC(=O)O)C(=O)O)cc1] | 396.4 | 396.2 | 0.82 | 17% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P133 | 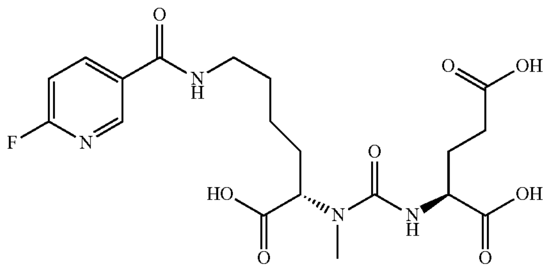 [SMILES: CN(C(=O)N[C@@H](CCC(=O)O)C(=O)O)[C@@H](CCCCNC(=O)c1ccc(F)nc1)C(=O)O] | 456.4 | 456.2 | 0.03 | 95% | | 125 |
| P134 | 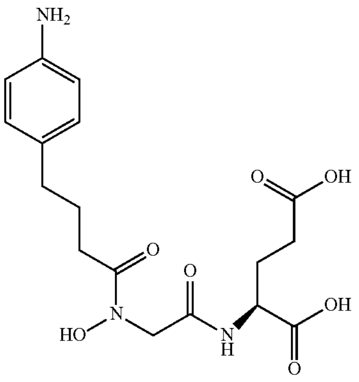 [SMILES: Nc1ccc(CCCC(=O)N(O)CC(=O)N[C@@H](CCC(=O)O)C(=O)O)cc1] | 381.4 | 381.2 | −0.32 | 37% | | |
| P135 | 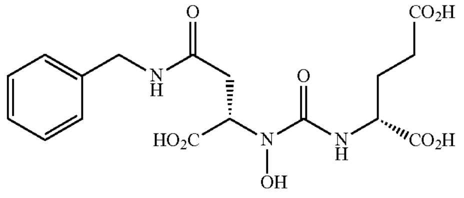 [SMILES: O=C(O)CC[C@@H](NC(=O)N(O)[C@@H](CC(=O)NCc1ccccc1)C(=O)O)C(=O)O] | 411.4 | 411.1 | −0.19 | 42% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P136 | 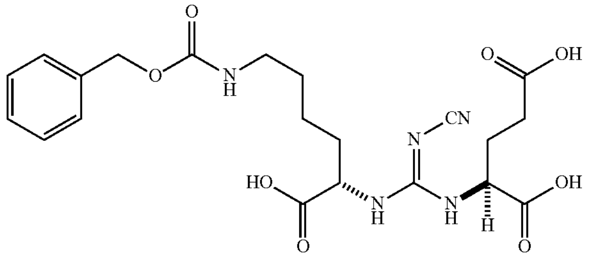 | 477.5 | 477.2 | −0.06 | 91% | | |
| P136 | 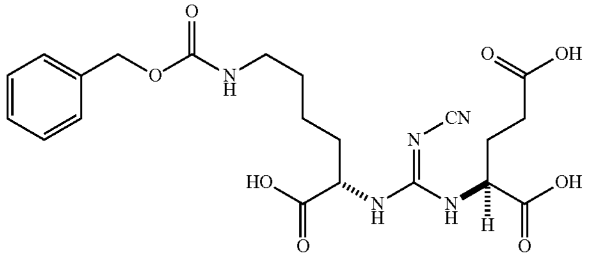 | 477.5 | 477.2 | −0.06 | 40% | | |
| P137 | 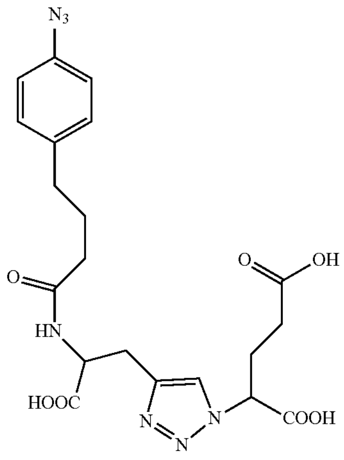 [SMILES: [N-]=[N+]=Nc1ccc(CCCC(=O)NC(Cc2cn(C(CCC(=O)O)C(=O)O)nn2)C(=O)O)cc1] | 473.4 | 473.2 | 0.02 | 3% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P138 | 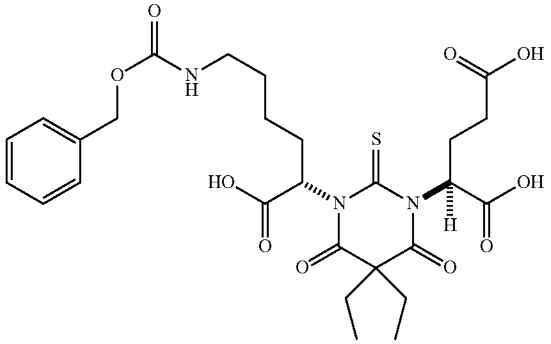 | 593.7 | 593.2 | 2.68 | 6% | | |
| P139 | 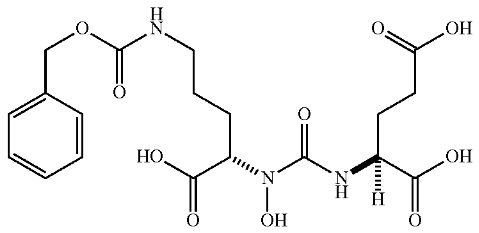 | 455.4 | 455.2 | −0.24 | 16% | | |
| P140 | 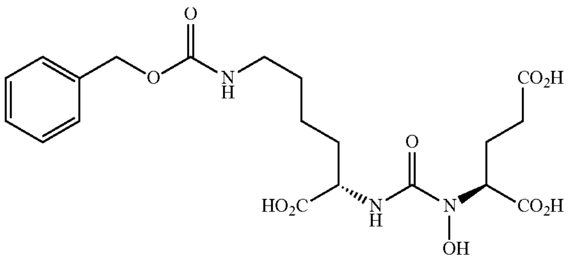 [SMILES: O=C(O)CC[C@@H](C(=O)O)N(O)C(=O)N[C@@H](CCCCNC(=O)OCc1ccccc1)C(=O)O] | 469.4 | 469.2 | 1.06 | 64% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P141 | 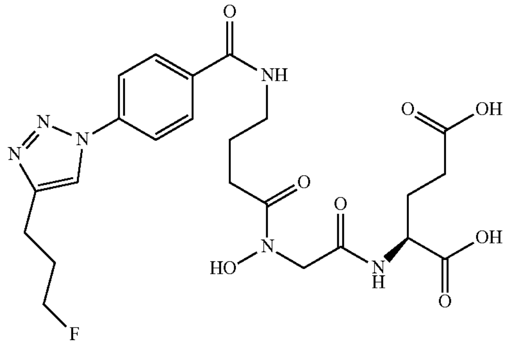 [SMILES: O=C(O)CC[C@H](NC(=O)CN(O)C(=O)CCCNC(=O)c1ccc(-n2cc(CCCF)nn2)cc1)C(=O)O] | 536.5 | 536.2 | 0.53 | 1% | | |
| P142 | 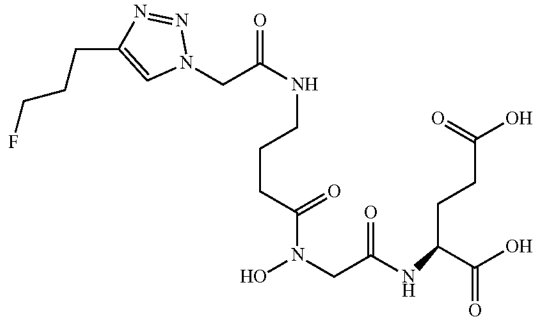 [SMILES: O=C(O)CC[C@H](NC(=O)CN(O)C(=O)CCCNC(=O)Cn1cc(CCCF)nn1)C(=O)O] | 474.4 | 474.2 | −1.48 | 5% | | |
| P143 | 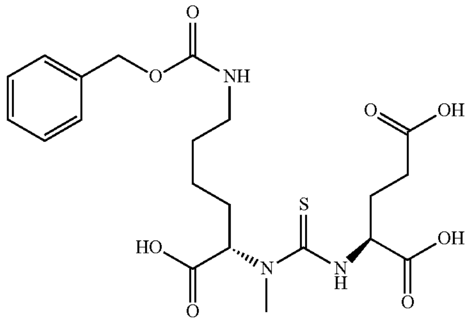 [SMILES: CN(C(=S)N[C@@H](CCC(=O)O)C(=O)O)[C@@H](CCCCNC(=O)OCc1ccccc1)C(=O)O] | 483.5 | 483.2 | 0.00 | 15% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P144 | 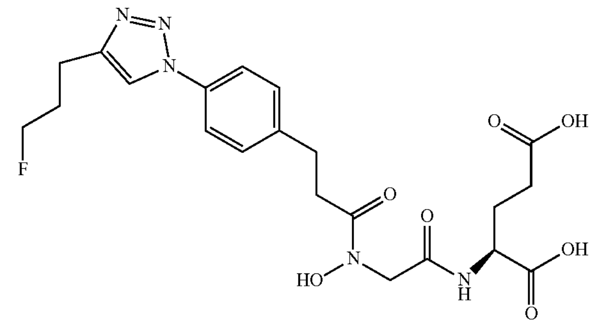 [SMILES: O=C(O)CC[C@H](NC(=O)CN(O)C(=O)CCc1ccc(-n2cc(CCCF)nn2)cc1)C(=O)O] | 479.5 | 479.2 | 0.67 | 7% | | |
| P145 | 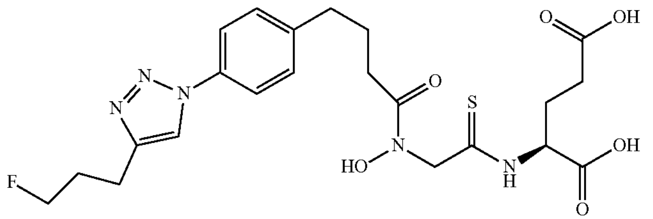 [SMILES: O=C(O)CC[C@H](NC(=S)CN(O)C(=O)CCCc1ccc(-n2cc(CCCF)nn2)cc1)C(=O)O] | 509.5 | 509.2 | 1.24 | 7% | | |
| P146 | 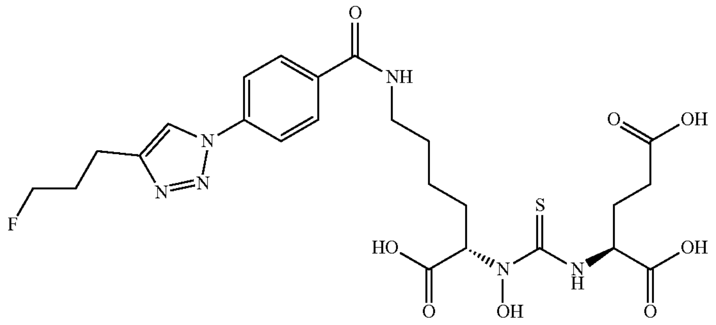 [SMILES: O=C(O)CC[C@H](NC(=S)N(O)[C@@H](CCCCNC(=O)c1ccc(-n2cc(CCCF)nn2)cc1)C(=O)O)C(=O)O] | 582.6 | 582.2 | 0.95 | 45% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P147 | 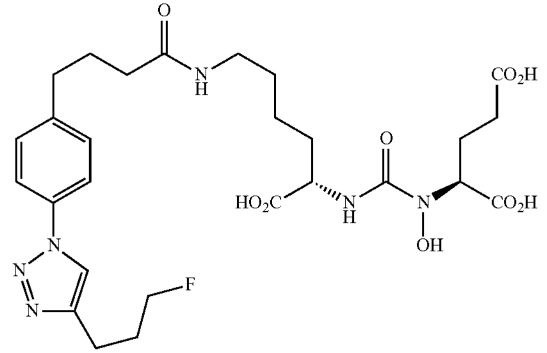 [SMILES: O=C(O)CC[C@@H](C(=O)O)N(O)C(=O)N[C@@H](CCCCNC(=O)CCCc1ccc(-n2cc(CCCF)nn2)cc1)C(=O)O] | 608.6 | 608.3 | 2.79 | 69% | | |
| P148 | 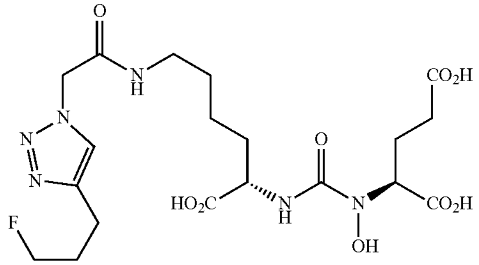 [SMILES: O=C(O)CC[C@@H](C(=O)O)N(O)C(=O)N[C@@H](CCCCNC(=O)Cn1cc(CCCF)nn1)C(=O)O] | 504.5 | 504.2 | −1.23 | 87% | | 250 |
| P149 | 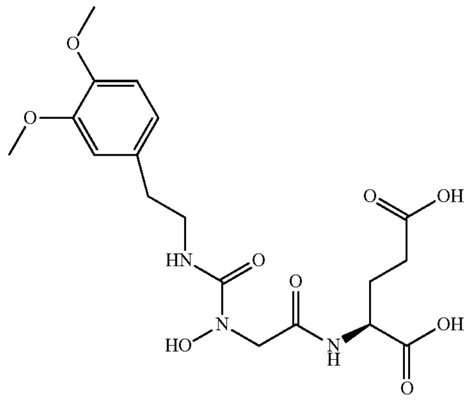 [SMILES: COc1ccc(CCNC(=O)N(O)CC(=O)N[C@@H](CCC(=O)O)C(=O)O)cc1OC] | 427.4 | 427.2 | 0.60 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P150 | 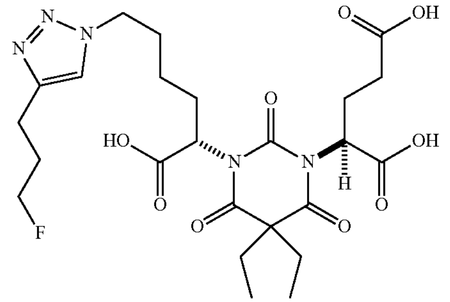 | 555.6 | 555.2 | 1.16 | 9% | | |
| P151 | 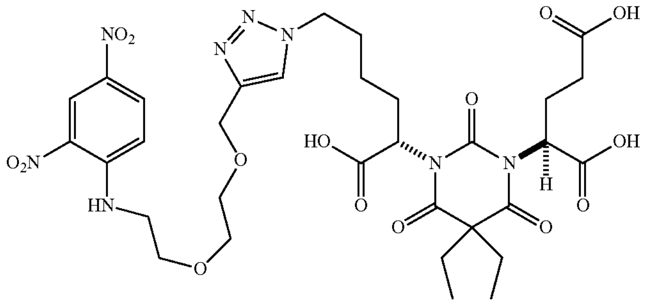 | 778.7 | 778.3 | 2.17 | 17% | | |
| P152 | 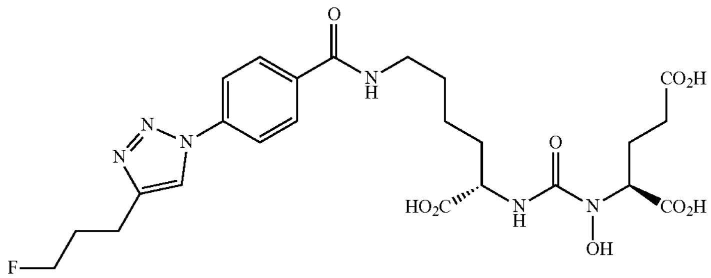 [SMILES: O=C(O)CC[C@@H](C(=O)O)N(O)C(=O)N[C@@H](CCCCNC(=O)c1ccc(-n2cc(CCCF)nn2)cc1)C(=O)O] | 566.5 | 566.2 | 0.95 | 93% | | 128 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P153 | 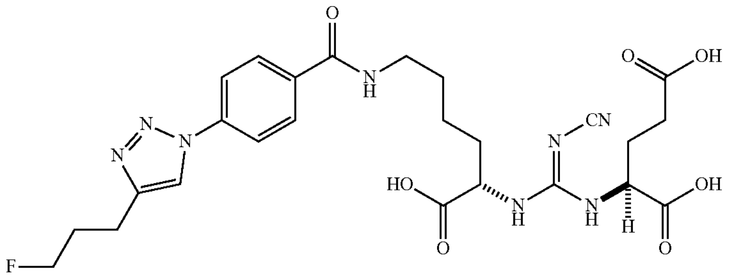 | 574.6 | 574.2 | −0.17 | 63% | | |
| P154 | 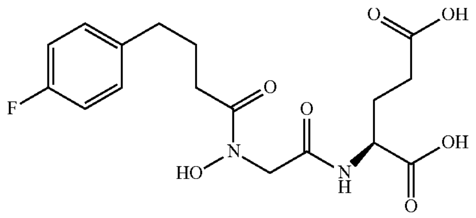 [SMILES: O=C(O)CC[C@H](NC(=O)CN(O)C(=O)CCCc1ccc(F)cc1)C(=O)O] | 384.4 | 384.1 | 1.05 | 50% | | |
| P155 | 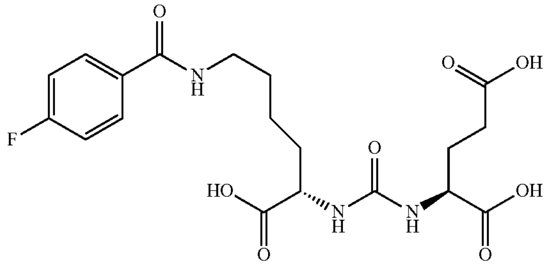 [SMILES: O=C(O)CC[C@H](NC(=O)N[C@@H](CCCCNC(=O)c1ccc(F)cc1)C(=O)O)C(=O)O] | 441.4 | 441.2 | 0.65 | 97% | | 3.1 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P156 | 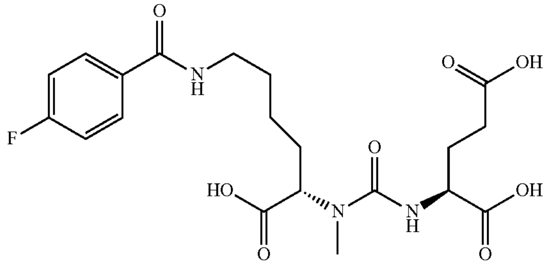 [SMILES: CN(C(=O)N[C@@H](CCC(=O)O)C(=O)O)[C@@H](CCCCNC(=O)c1ccc(F)cc1)C(=O)O] | 455.4 | 455.2 | 0.90 | 87% | | 219 |
| P157 | 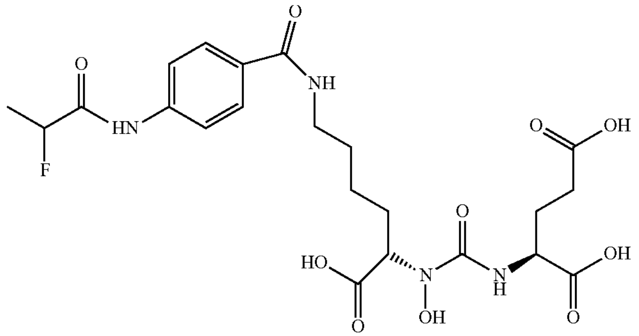 | 528.5 | 528.2 | 0.33 | 79% | | >313 |
| P158 | 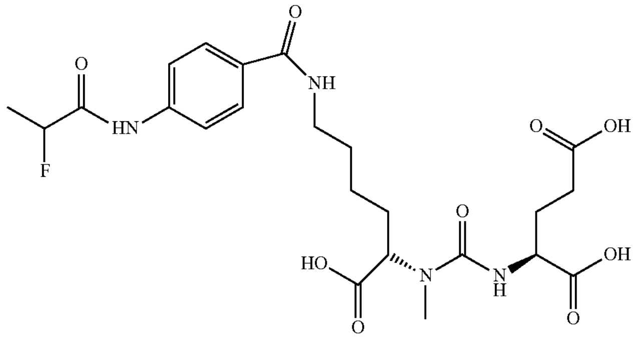 | 526.5 | 526.2 | 0.58 | 99% | | 34.4 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P159 | 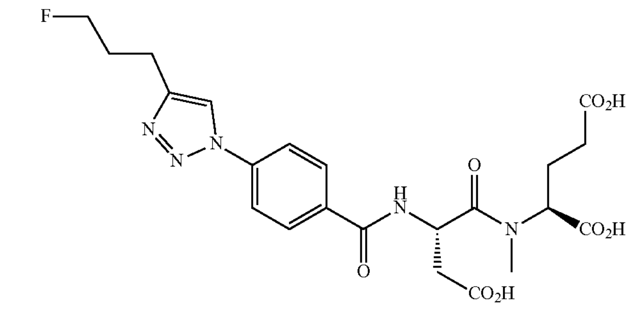 [SMILES: CN(C(=O)[C@H](CC(=O)O)NC(=O)c1ccc(-n2cc(CCCF)nn2)cc1)[C@@H](CCC(=O)O)C(=O)O] | 507.5 | 507.2 | 0.69 | 39% | | |
| P160 | 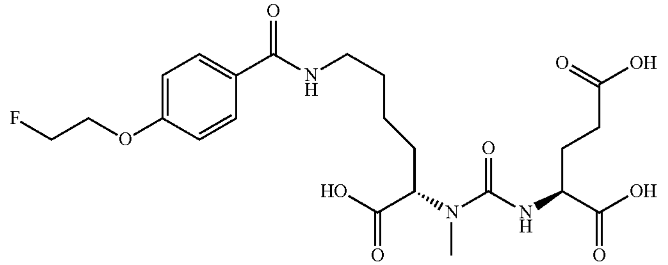 [SMILES: CN(C(=O)N[C@@H](CCC(=O)O)C(=O)O)[C@@H](CCCCNC(=O)c1ccc(OCCF)cc1)C(=O)O] | 499.5 | 499.2 | 1.01 | 88% | | 219 |
| P161 | 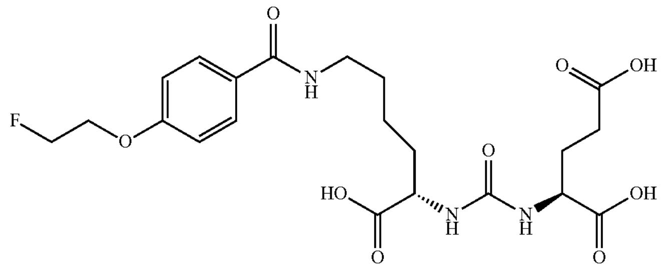 [SMILES: O=C(O)CC[C@H](NC(=O)N[C@@H](CCCCNC(=O)c1ccc(OCCF)cc1)C(=O)O)C(=O)O] | 485.5 | 485.2 | 0.76 | 96% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P162 | 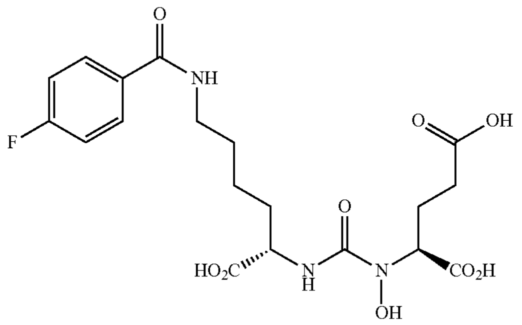 [SMILES: O=C(O)CC[C@@H](C(=O)O)N(O)C(=O)N[C@@H](CCCCNC(=O)c1ccc(F)cc1)C(=O)O] | 457.4 | 457.2 | 0.66 | 79% | | >531 |
| P163 | 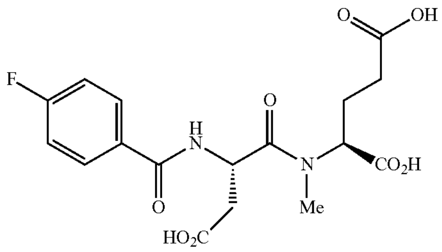 [SMILES: CN(C(=O)[C@H](CC(=O)O)NC(=O)c1ccc(F)cc1)[C@@H](CCC(=O)O)C(=O)O] | 398.3 | 398.1 | 0.39 | 0% | | |
| P164 | 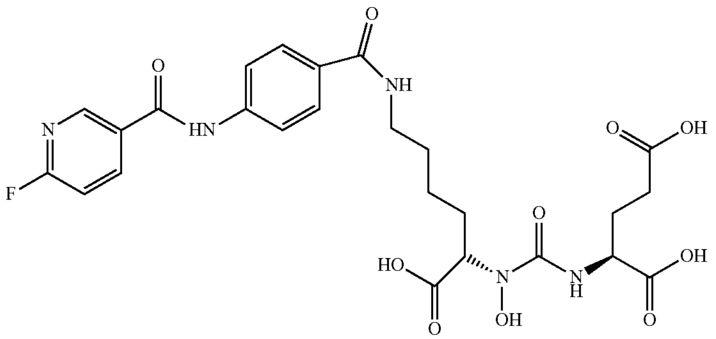 | 577.5 | 577.2 | 0.35 | 80% | | >407 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P165 | 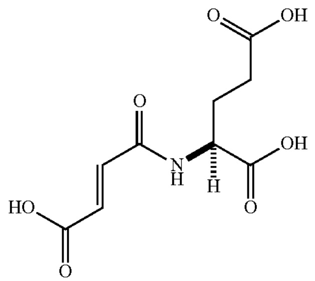 | 245.2 | 245.1 | −2.50 | 11% | | |
| P166 | 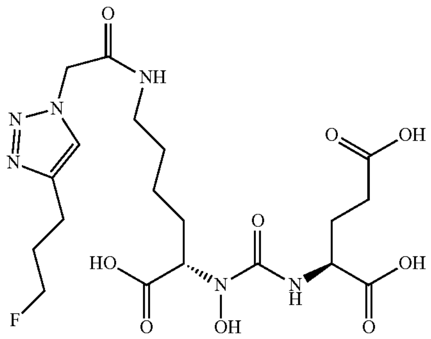 [SMILES: O=C(O)CC[C@H](NC(=O)N(O)[C@@H](CCCCNC(=O)Cn1cc(CCCF)nn1)C(=O)O)C(=O)O] | 504.5 | 5.4.2 | −1.23 | 87% | | >375 |
| P167 | 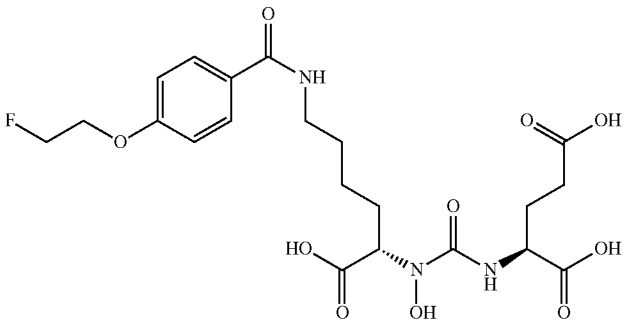 [SMILES: O=C(O)CC[C@H](NC(=O)N(O)[C@@H](CCCCNC(=O)c1ccc(OCCF)cc1)C(=O)O)C(=O)O] | 501.5 | 501.2 | 0.77 | 93% | | >657 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P168 | 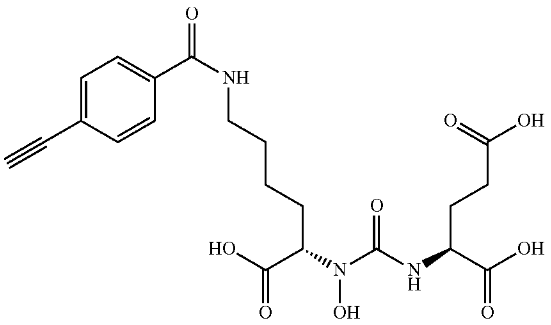 [SMILES: C#Cc1ccc(C(=O)NCCCC[C@@H](C(=O)O)N(O)C(=O)N[C@@H](CCC(=O)O)C(=O)O)cc1] | 463.4 | 463.2 | 0.59 | 98% | | |
| P169 | 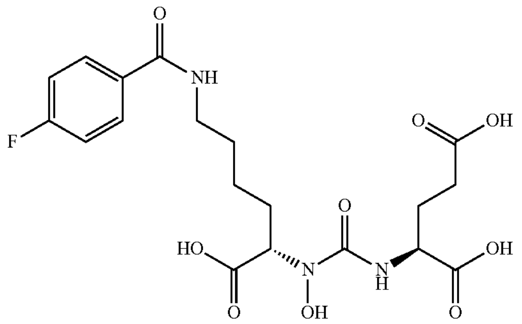 [SMILES: O=C(O)CC[C@H](NC(=O)N(O)[C@@H](CCCCNC(=O)c1ccc(F)cc1)C(=O)O)C(=O)O] | 457.4 | 457.2 | 0.66 | 79% | | 156 |
| P170 | 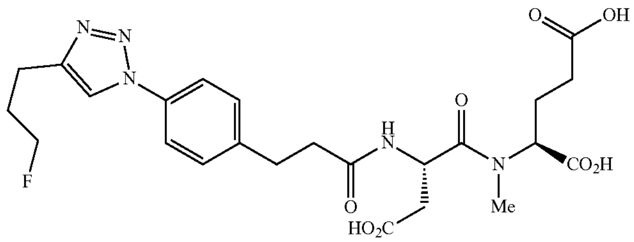 | 535.5 | 535.2 | 1.55 | 58% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P171 | 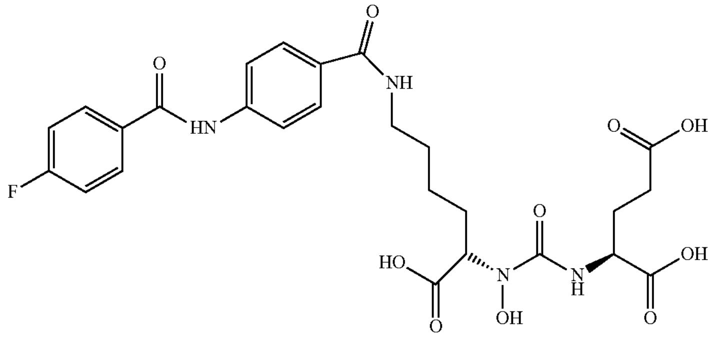 | 576.5 | 576.2 | 1.33 | 87% | | |
| P172 | 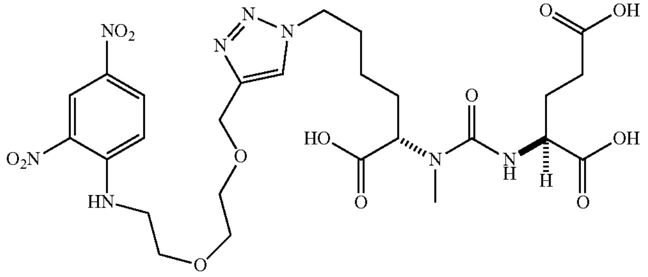 | 668.6 | 668.2 | −0.41 | 95% | | 313 |
| P173 | 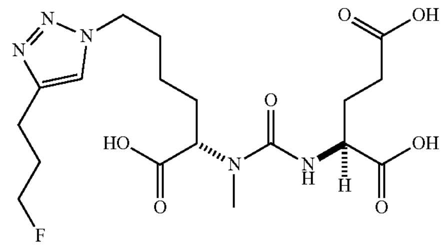 | 445.4 | 445.2 | −1.42 | 31% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P174 | 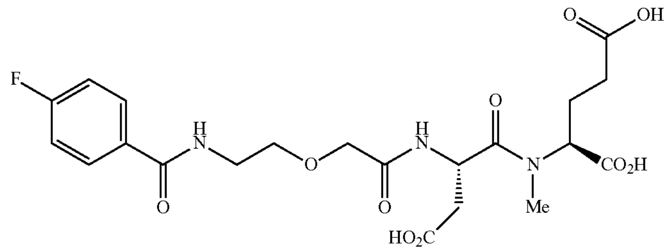 [SMILES: CN(C(=O)[C@H](CC(=O)O)NC(=O)COCCNC(=O)c1ccc(F)cc1)[C@@H](CCC(=O)O)C(=O)O] | 499.4 | 499.2 | 0.01 | 1% | | |
| P175 | 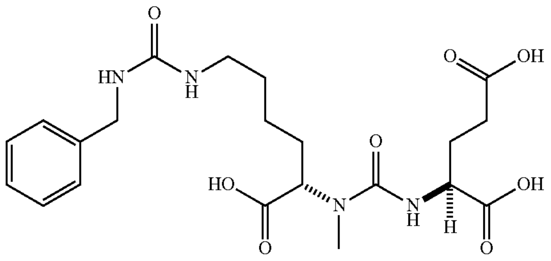 | 466.5 | 466.2 | −0.27 | 18% | | |
| P176 | 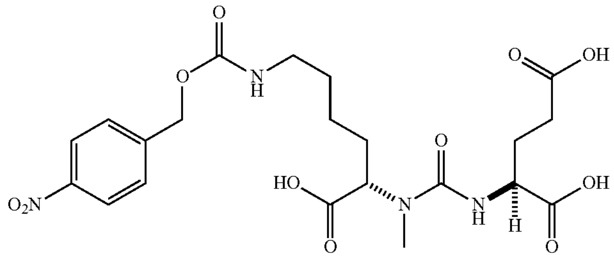 | 512.5 | 512.2 | −0.14 | 77% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P177 | 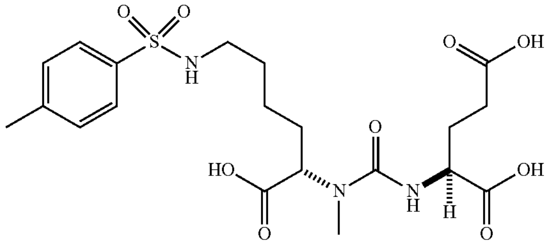 | 487.5 | 487.2 | −0.07 | 38% | | |
| P178 | 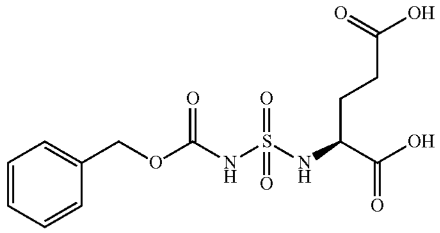 [SMILES: O=C(O)CC[C@H](NS(=O)(=O)NC(=O)OCc1ccccc1)C(=O)O] | 360.3 | 360.1 | 0.76 | 1% | | |
| P179 | 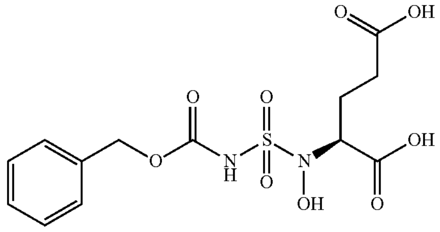 [SMILES: O=C(O)CC[C@@H](C(=O)O)N(O)S(=O)(=O)NC(=O)OCc1ccccc1] | 376.3 | 376.1 | 0.51 | 4% | | |
| P180 | 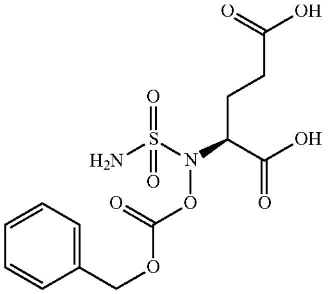 [SMILES: NS(=O)(=O)N(OC(=O)OCc1ccccc1)[C@@H](CCC(=O)O)C(=O)O] | 376.3 | 376.1 | 0.51 | 5% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P181 | 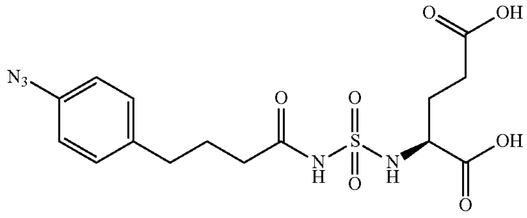 [SMILES: [N-]=[N+]=Nc1ccc(CCCC(=O)NS(=O)(=O)N[C@@H](CCC(=O)O)C(=O)O)cc1] | 413.4 | 413.1 | 1.74 | 39% | | |
| P182 | 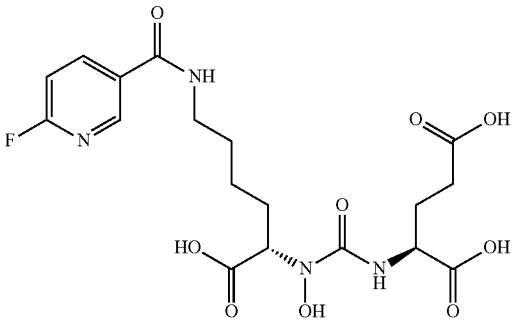 | 458.4 | 458.1 | −0.21 | 92% | | |
| P183 | 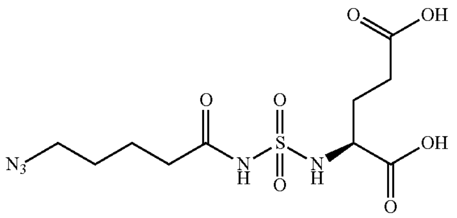 [SMILES: [N-]=[N+]=NCCCCC(=O)NS(=O)(=O)N[C@@H](CCC(=O)O)C(=O)O] | 351.3 | 351.1 | 0.68 | 36% | | |
| P184 | 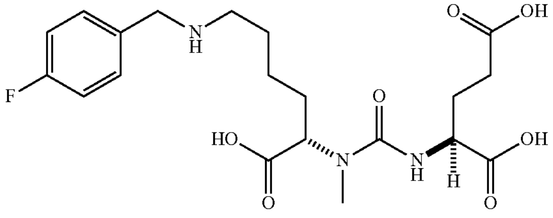 | 441.5 | 441.2 | −2.11 | 10% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P185 | 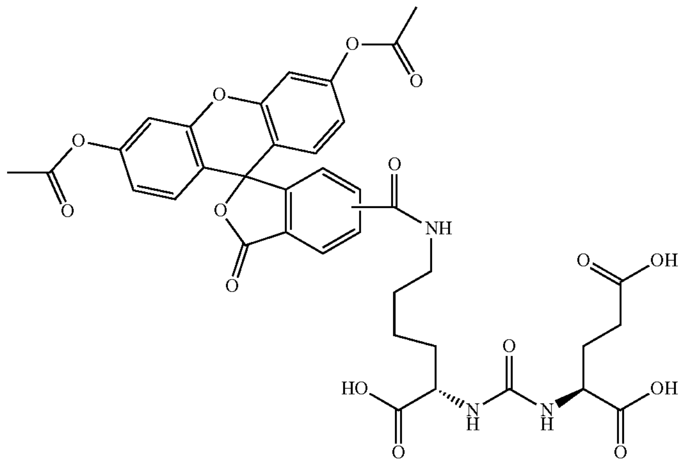 | 761.7 | 761.2 | 1.22 | 99% | | |
| P186 | 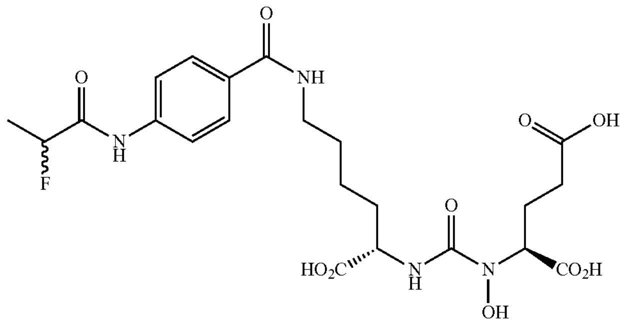 [SMILES: CC(F)C(=O)Nc1ccc(C(=O)NCCCC[C@H](NC(=O)N(O)[C@@H](CCC(=O)O)C(=O)O)C(=O)O)cc1] | 528.5 | 528.2 | 0.33 | 85% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P187 | 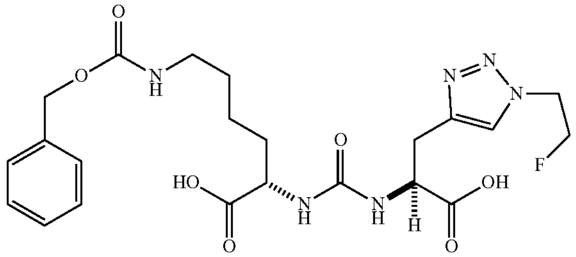 | 508.5 | 508.2 | 0.90 | 77% | | |
| P188 | 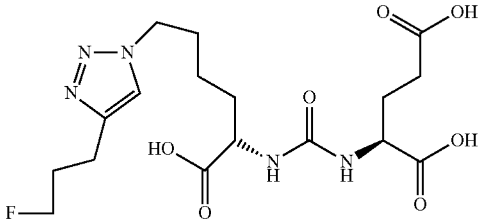 | 431.4 | 431.2 | −0.49 | 99% | | 6.6 |
| P189 | 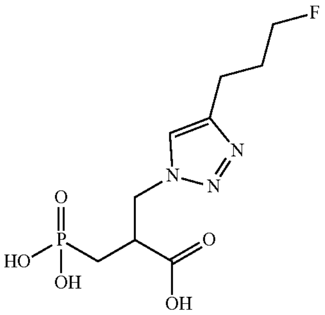 $HO_2C—CF_3$ | 295.2 | 295.1 | −1.50 | 81% | | >688 |
| P190 | 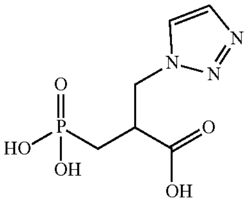 $HO_2C—CF_3$ | 253.1 | 253 | −2.10 | 95% | | 188 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P191 | 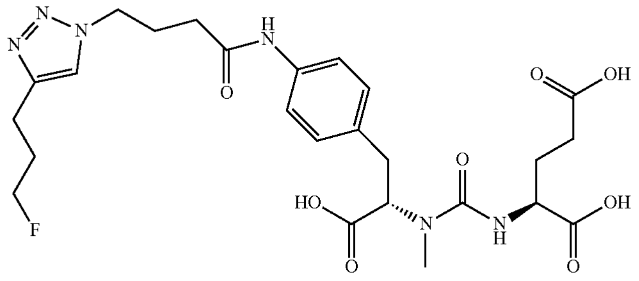 [SMILES: CN(C(=O)N[C@@H](CCC(=O)O)C(=O)O)[C@@H](Cc1ccc(NC(=O)CCCn2cc(CCCF)nn2)cc1)C(=O)O] | 564.6 | 564.2 | 0.22 | 78% | | |
| P192 | 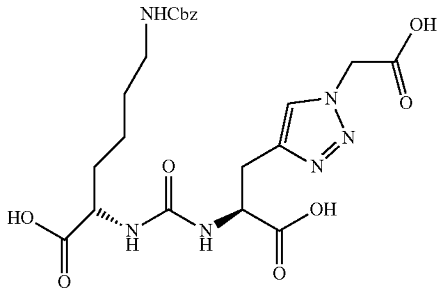 | 520.49 | 520.19 | 0.22 | 29% | | |
| P193 | 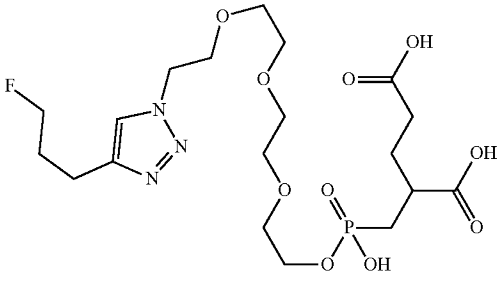 [SMILES: O=C(O)CCC(CP(=O)(O)OCCOCCOCCOCCn1cc(CCCF)nn1)C(=O)O] | 513.5 | 513.2 | −3.67 | 0% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P194 | 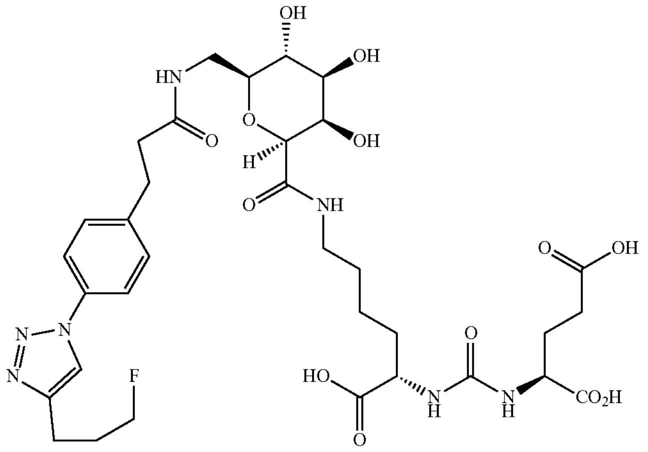 [SMILES: O=C(O)CC[C@H](NC(=O)N[C@@H](CCCCNC(=O)[C@H]1O[C@@H](CNC(=O)CCc2ccc(-n3cc(CCCF)nn3)cc2)[C@H](O)[C@@H](O)[C@H]1O)C(=O)O)C(=O)O] | 767.8 | 767.3 | 1.03 | 96% | | 69 |
| P195 | 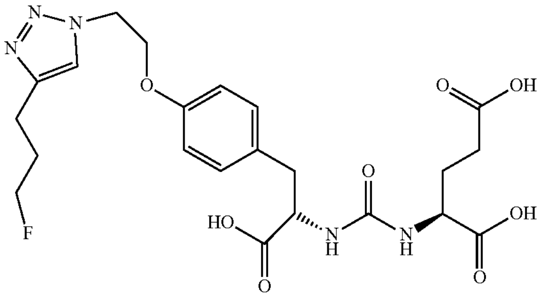 | 509.5 | 509.2 | 1.55 | 96% | | 66 |
| P196 | 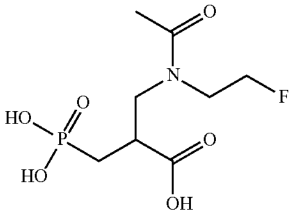 $HO_2C—CF_3$ | 385.2 | 271.1 | −1.72 | 27% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P197 | 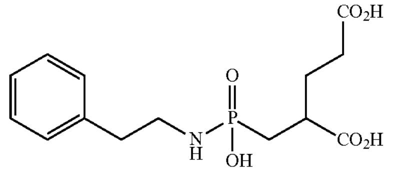 [SMILES: O=C(O)CCC(CP(=O)(O)NCCc1ccccc1)C(=O)O] | 329.3 | 329.1 | −0.88 | 22% | | >3000 |
| P198 | 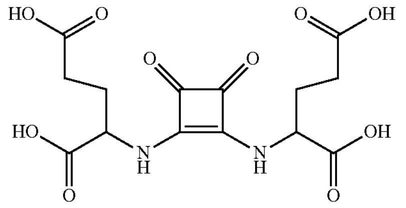 [SMILES: O=C(O)CCC(Nc1c(NC(CCC(=O)O)C(=O)O)c(=O)c1=O)C(=O)O] | 372.3 | 372.1 | −3.22 | 14% | | |
| P199 | 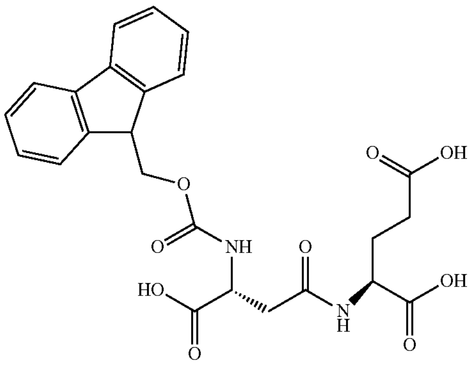 [SMILES: O=C(O)CC[C@H](NC(=O)C[C@@H](NC(=O)OCC1c2ccccc2-c2ccccc21)C(=O)O)C(=O)O] | 484.5 | 484.2 | 1.82 | 82% | | >188 nM |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P200 | 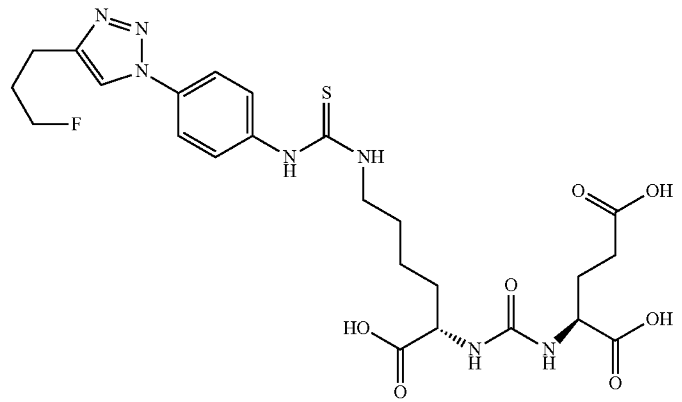 [SMILES: O=C(O)CC[C@H](NC(=O)N[C@@H](CCCCNC(=S)Nc1ccc(-n2cc(CCCF)nn2)cc1)C(=O)O)C(=O)O] | 581.6 | 581.2 | 1.03 | 95% | | <0.3 nM |
| P201 | 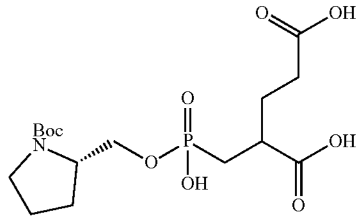 [SMILES: CC(C)(C)OC(=O)N1CCC[C@H]1COP(=O)(O)CC(CCC(=O)O)C(=O)O] | 409.4 | 409.2 | −1.33 | 83% | | >300 |
| P202 | 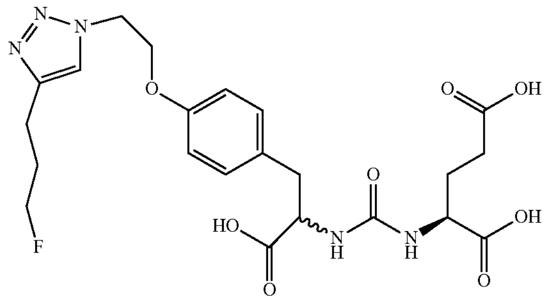 [SMILES: O=C(O)CC[C@H](NC(=O)NC(Cc1ccc(OCCn2cc(CCCF)nn2)cc1)C(=O)O)C(=O)O] | 509.5 | 509.2 | 0.07 | 97% | | 94 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P203 | 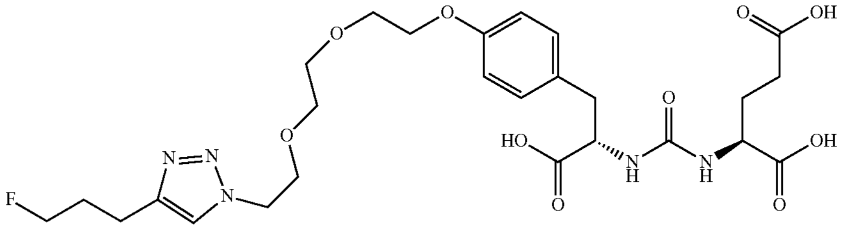 [SMILES: O=C(O)CC[C@H](NC(=O)N[C@@H](Cc1ccc(OCCOCCOCCn2cc(CCCF)nn2)cc1)C(=O)O)C(=O)O] | 597.6 | 597.2 | 0.31 | 97% | | 41 |
| P204 | 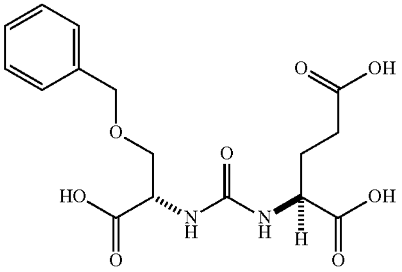 | 368.3 | 368.1 | −0.69 | 98% | | 6.9 |
| P205 | 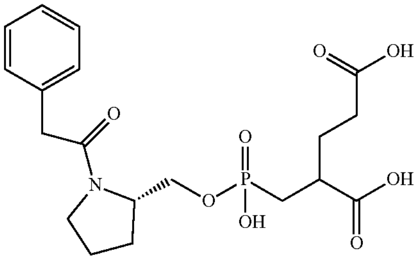 [SMILES: O=C(O)CCC(CP(=O)(O)OC[C@@H]1CCCN1C(=O)Cc1ccccc1)C(=O)O] | 427.4 | 427.1 | −1.73 | 79% | | |
| P206 | 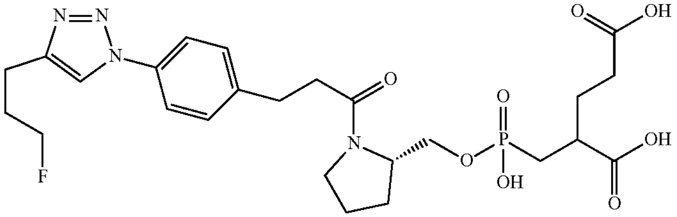 [SMILES: O=C(O)CCC(CP(=O)(O)OC[C@@H]1CCCN1C(=O)CCc1ccc(-n2cc(CCCF)nn2)cc1)C(=O)O] | 568.5 | 568.2 | 1.55 | 81% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P207 | 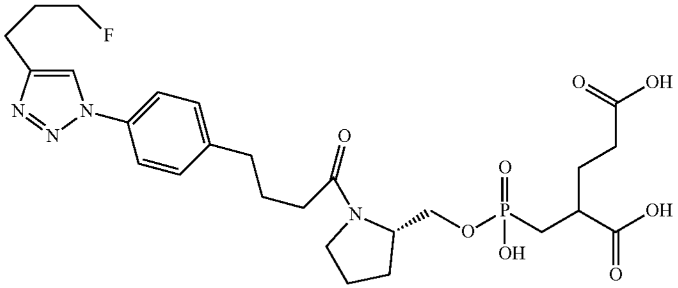 [SMILES: O=C(O)CCC(CP(=O)(O)OC[C@@H]1CCCN1C(=O)CCCc1ccc(-n2cc(CCCF)nn2)cc1)C(=O)O] | 582.6 | 582.2 | −1.22 | 96% | | 18.8 |
| P208 | 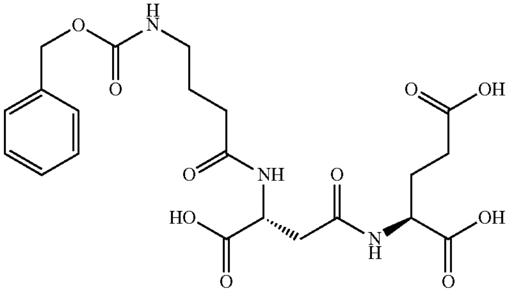 [SMILES: O=C(O)CC[C@H](NC(=O)C[C@@H](NC(=O)CCCNC(=O)OCc1ccccc1)C(=O)O)C(=O)O] | 481.5 | 481.2 | 0.19 | 75% | | |
| P209 | 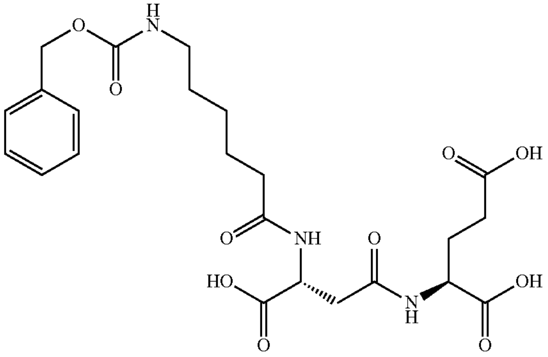 [SMILES: O=C(O)CC[C@H](NC(=O)C[C@@H](NC(=O)CCCCCNC(=O)OCc1ccccc1)C(=O)O)C(=O)O] | 509.5 | 509.2 | 0.39 | 44% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P210 | 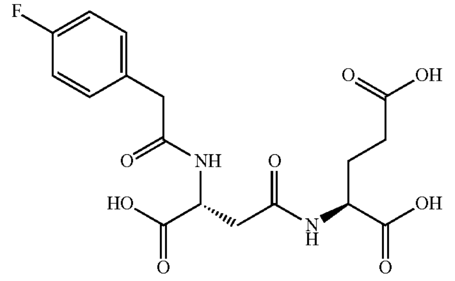 [SMILES: O=C(O)CC[C@H](NC(=O)C[C@@H](NC(=O)Cc1ccc(F)cc1)C(=O)O)C(=O)O] | 398.3 | 398.1 | −0.31 | 16% | | |
| P211 | 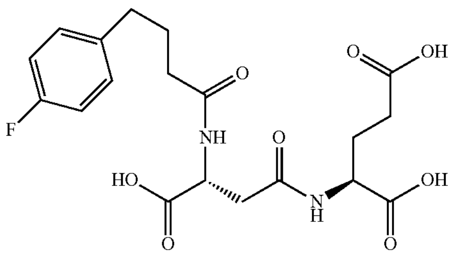 [SMILES: O=C(O)CC[C@H](NC(=O)C[C@@H](NC(=O)CCCc1ccc(F)cc1)C(=O)O)C(=O)O] | 426.4 | 426.1 | 3.31 | 43% | | |
| P212 | 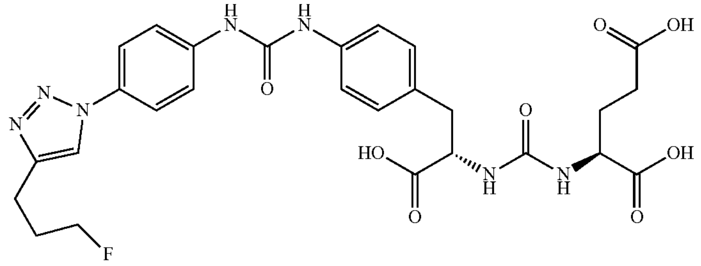 [SMILES: O=C(O)CC[C@H](NC(=O)N[C@@H](Cc1ccc(NC(=O)Nc2ccc(-n3cc(CCCF)nn3)cc2)cc1)C(=O)O)C(=O)O] | 599.6 | 599.2 | 1.95 | 99% | | 3.1 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P213 | 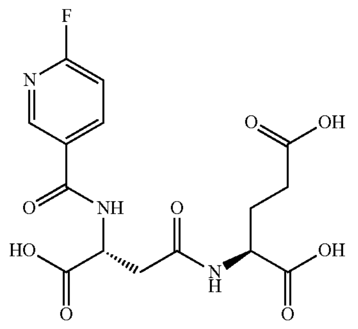 [SMILES: O=C(O)CC[C@H](NC(=O)C[C@@H](NC(=O)c1ccc(F)nc1)C(=O)O)C(=O)O] | 385.3 | 385.1 | −1.20 | 33% | | |
| P214 | 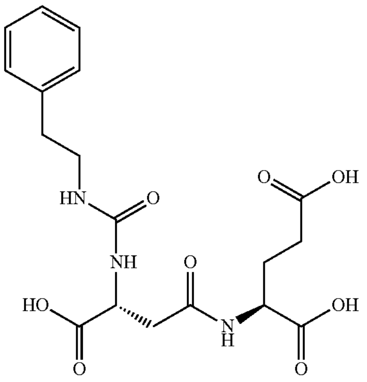 [SMILES: O=C(O)CC[C@H](NC(=O)C[C@@H](NC(=O)NCCc1ccccc1)C(=O)O)C(=O)O] | 409.4 | 409.2 | 0.22 | 34% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P215 | 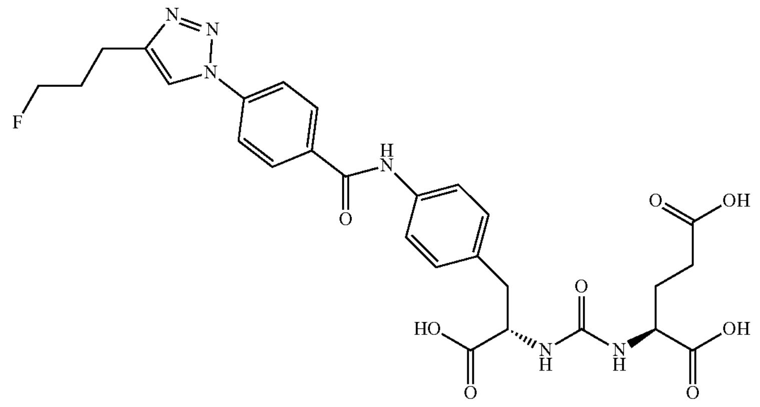 [SMILES: O=C(O)CC[C@H](NC(=O)N[C@@H](Cc1ccc(NC(=O)c2ccc(-n3cc(CCCF)nn3)cc2)cc1)C(=O)O)C(=O)O] | 584.6 | 584.2 | 1.64 | 99% | | 2.2 |
| P216 | 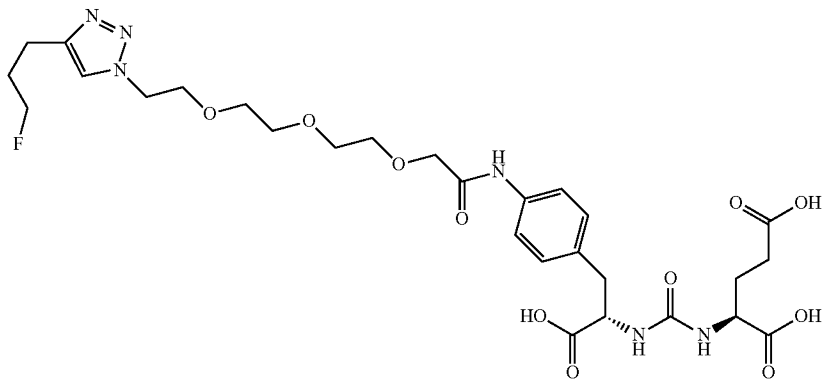 [SMILES: O=C(O)CC[C@H](NC(=O)N[C@@H](Cc1ccc(NC(=O)COCCOCCOCCn2cc(CCCF)nn2)cc1)C(=O)O)C(=O)O] | 654.6 | 654.2 | −0.81 | 98% | | 21.9 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P217 | 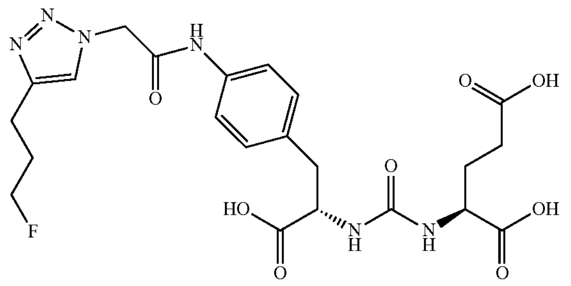 [SMILES: O=C(O)CC[C@H](NC(=O)N[C@@H](Cc1ccc(NC(=O)Cn2cc(CCCF)nn2)cc1)C(=O)O)C(=O)O] | 522.5 | 522.2 | −0.48 | 96% | | 31.3 |
| P218 | 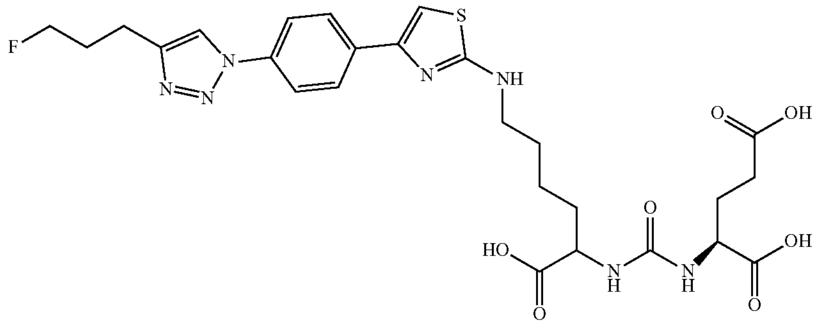 [SMILES: O=C(O)CC[C@H](NC(=O)NC(CCCCNc1nc(-c2ccc(-n3cc(CCCF)nn3)cc2)cs1)C(=O)O)C(=O)O] | 605.6 | 605.2 | 3.08 | 98% | | 0.6 |
| P219 | 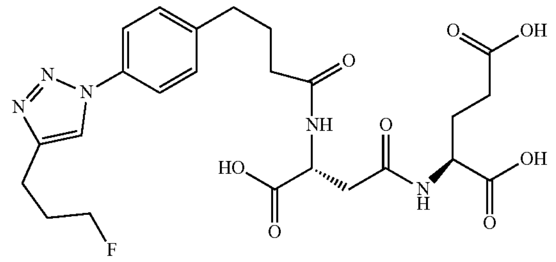 [SMILES: O=C(O)CC[C@H](NC(=O)C[C@@H](NC(=O)CCCc1ccc(-n2cc(CCCF)nn2)cc1)C(=O)O)C(=O)O] | 535.5 | 535.2 | 0.51 | 74% | | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P220 | 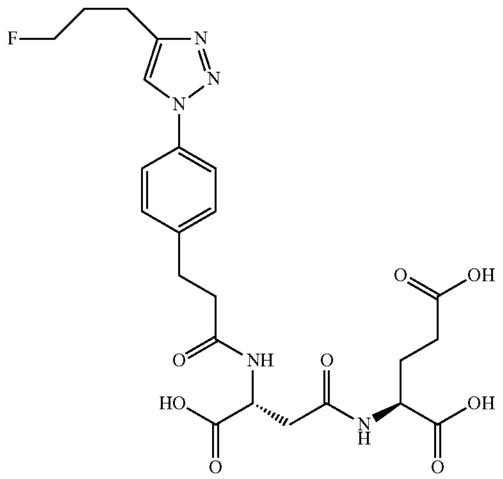 [SMILES: O=C(O)CC[C@H](NC(=O)C[C@@H](NC(=O)CCc1ccc(-n2cc(CCCF)nn2)cc1)C(=O)O)C(=O)O] | 521.5 | 521.2 | 0.13 | | 34% | |
| P221 | 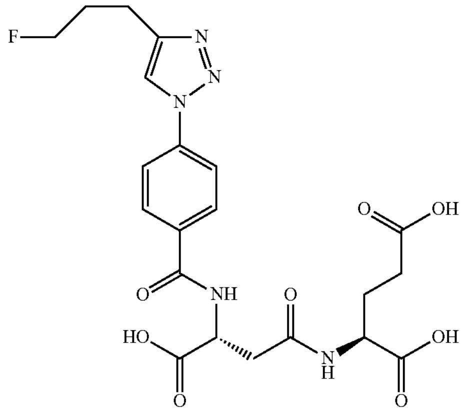 [SMILES: O=C(O)CC[C@H](NC(=O)C[C@@H](NC(=O)c1ccc(-n2cc(CCCF)nn2)cc1)C(=O)O)C(=O)O] | 493.4 | 493.2 | −0.03 | | 15% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P222 | 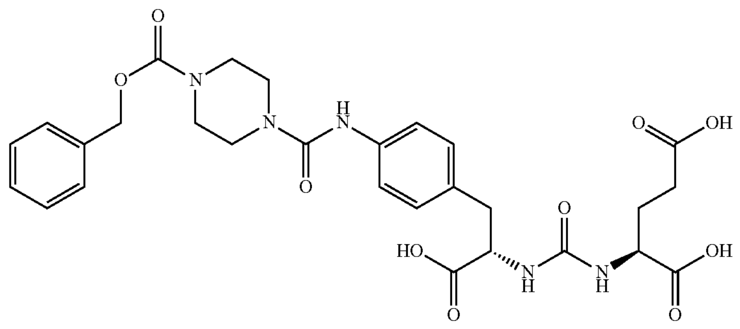 [SMILES: O=C(O)CC[C@H](NC(=O)N[C@@H](Cc1ccc(NC(=O)N2CCN(C(=O)OCc3ccccc3)CC2)cc1)C(=O)O)C(=O)O] | 599.6 | 599.2 | 2.06 | | 98% | 0.56 |
| P223 | 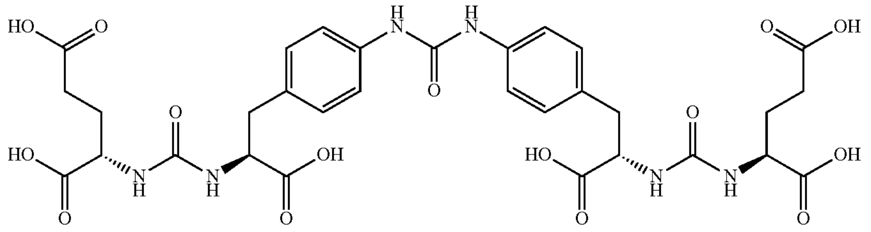 [SMILES: O=C(O)CC[C@H](NC(=O)N[C@@H](Cc1ccc(NC(=O)Nc2ccc(C[C@H](NC(=O)N[C@@H](CCC(=O)O)C(=O)O)C(=O)O)cc2)cc1)C(=O)O)C(=O)O] | 732.7 | 732.2 | −0.28 | | 98% | 1.1 |
| P224 | 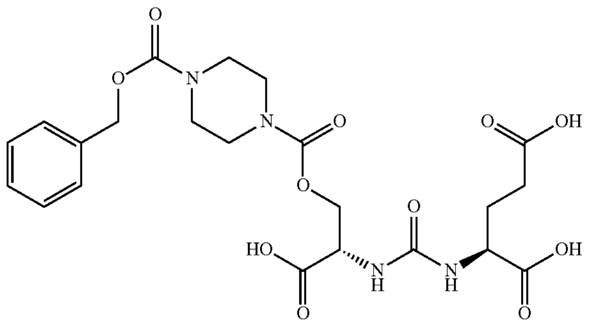 [SMILES: O=C(O)CC[C@H](NC(=O)N[C@@H](COC(=O)N1CCN(C(=O)OCc2ccccc2)CC1)C(=O)O)C(=O)O] | 524.5 | 524.2 | 2.03 | | 65% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P225 | 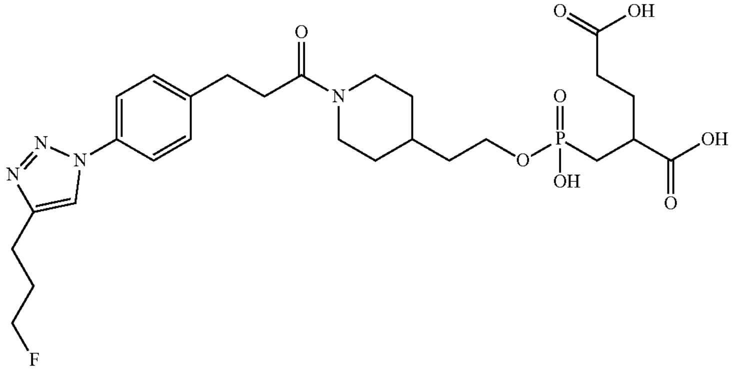 [SMILES: O=C(O)CCC(CP(=O)(O)OCCC1CCN(C(=O)CCc2ccc(-n3cc(CCCF)nn3)cc2)CC1)C(=O)O] | 596.6 | 596.2 | −2.23 | | 7% | |
| P226 | 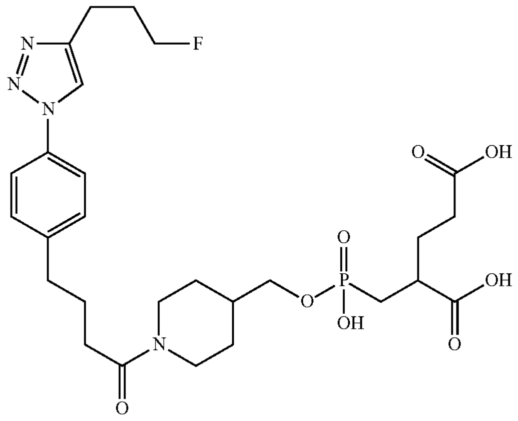 [SMILES: O=C(O)CCC(CP(=O)(O)OCC1CCN(C(=O)CCCc2ccc(-n3cc(CCCF)nn3)cc2)CC1)C(=O)O] | 596.6 | 596.2 | −2.38 | | 32% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P227 | 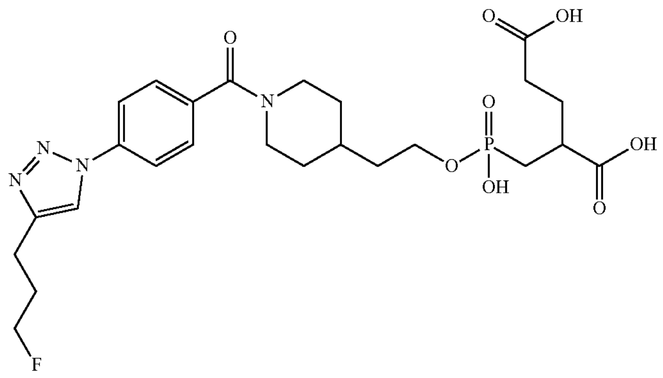 [SMILES: O=C(O)CCC(CP(=O)(O)OCCC1CCN(C(=O)c2ccc(-n3cc(CCCF)nn3)cc2)CC1)C(=O)O] | 568.5 | 568.2 | −2.09 | | 15% | |
| P228 | 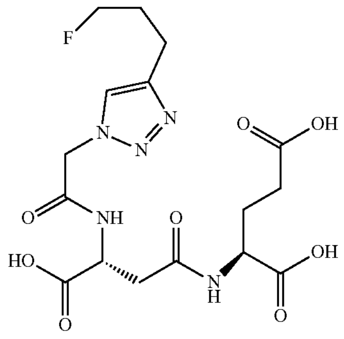 [SMILES: O=C(O)CC[C@H](NC(=O)C[C@@H](NC(=O)Cn1cc(CCCF)nn1)C(=O)O)C(=O)O] | 431.4 | 431.2 | −1.72 | | 24% | |
| P229 | 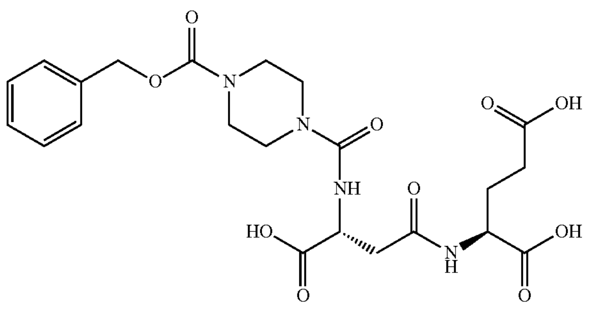 [SMILES: O=C(O)CC[C@H](NC(=O)C[C@@H](NC(=O)N1CCN(C(=O)OCc2ccccc2)CC1)C(=O)O)C(=O)O] | 508.5 | 508.2 | 1.42 | | 25% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P230 | 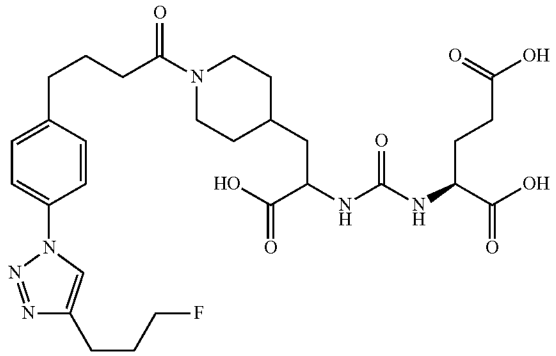 [SMILES: O=C(O)CC[C@H](NC(=O)NC(CC1CCN(C(=O)CCCc2ccc(-n3cc(CCCF)nn3)cc2)CC1)C(=O)O)C(=O)O] | 618.7 | 618.3 | 0.98 | | 95% | 13 |
| P231 | 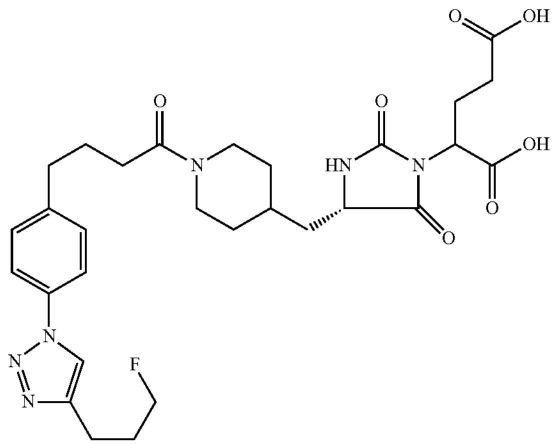 [SMILES: O=C(O)CCC(C(=O)O)N1C(=O)N[C@@H](CC2CCN(C(=O)CCCc3ccc(-n4cc(CCCF)nn4)cc3)CC2)C1=O] | 600.6 | 600.3 | 2.79 | | 63% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P232 | 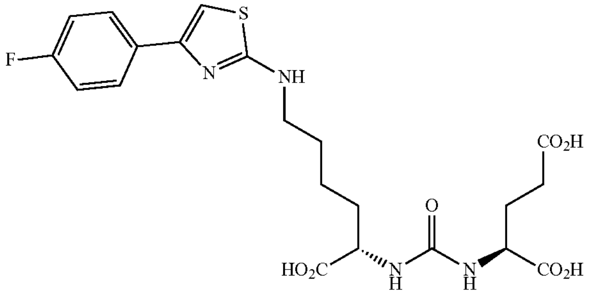 [SMILES: O=C(O)CC[C@H](NC(=O)N[C@@H](CCCCNc1nc(-c2ccc(F)cc2)cs1)C(=O)O)C(=O)O] | 496.5 | 46.1 | 2.73 | | 96% | |
| P233 | 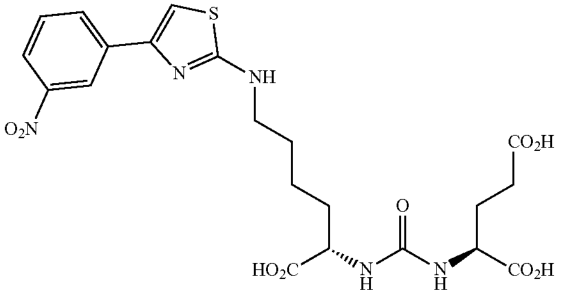 [SMILES: O=C(O)CC[C@H](NC(=O)N[C@@H](CCCCNc1nc(-c2cccc([N+](=O)[O-])c2)cs1)C(=O)O)C(=O)O] | 523.5 | 523.1 | 2.34 | | 96% | |
| P234 | 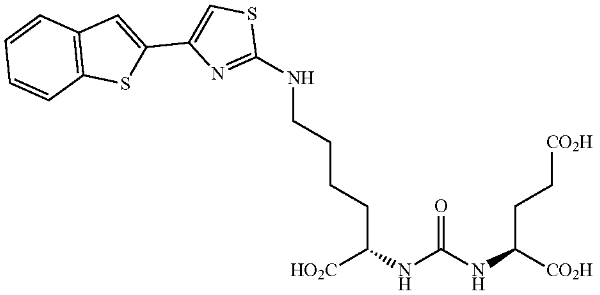 [SMILES: O=C(O)CC[C@H](NC(=O)N[C@@H](CCCCNc1nc(-c2cc3ccccc3s2)cs1)C(=O)O)C(=O)O] | 534.6 | 534.1 | 3.85 | | 86% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P235 | 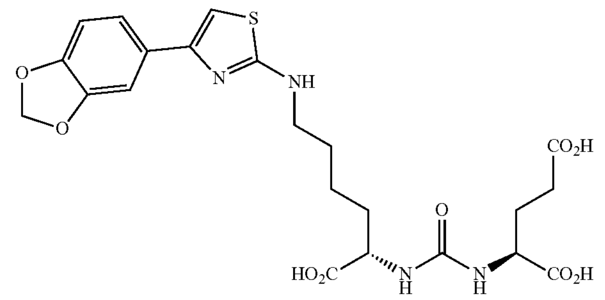 [SMILES: O=C(O)CC[C@H](NC(=O)N[C@@H](CCCCNc1nc(-c2ccc3c(c2)OCO3)cs1)C(=O)O)C(=O)O] | 522.5 | 522.1 | 2.61 | | 100% | <0.3 |
| P236 | 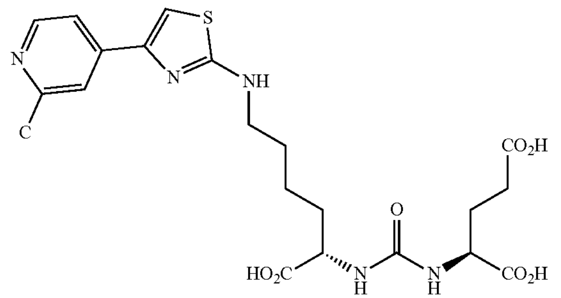 [SMILES: Cc1cc(-c2csc(NCCCC[C@H](NC(=O)N[C@@H](CCC(=O)O)C(=O)O)C(=O)O)n2)ccn1] | 513.9 | 513.1 | 1.95 | | 99% | |
| P237 | 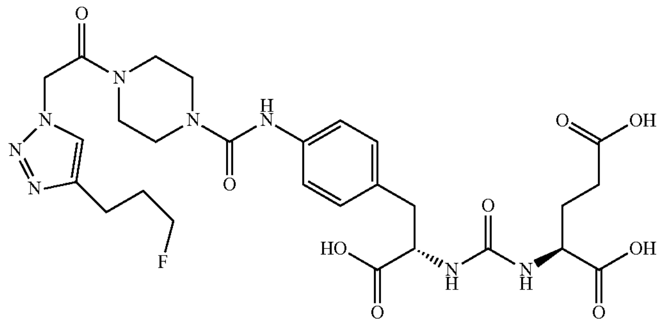 [SMILES: O=C(O)CC[C@H](NC(=O)N[C@@H](Cc1ccc(NC(=O)N2CCN(C(=O)Cn3cc(CCCF)nn3)CC2)cc1)C(=O)O)C(=O)O] | 634.6 | 634.3 | 1.03 | | 100% | 3.8 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P238 | 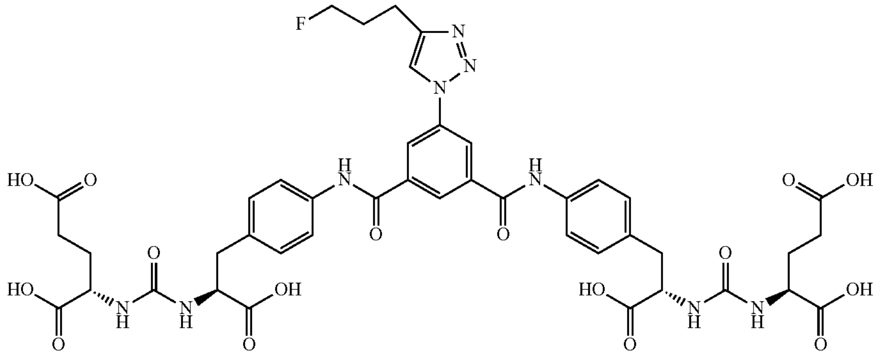 [SMILES: O=C(O)CC[C@H](NC(=O)N[C@@H](Cc1ccc(NC(=O)c2cc(C(=O)Nc3ccc(C[C@H](NC(=O)N[C@@H](CCC(=O)O)C(=O)O)C(=O)O)cc3)cc(-n3cc(CCCF)nn3)c2)cc1)C(=O)O)C(=O)O] | 963.9 | 963.3 | | | 100% | <0.3 |
| P239 | 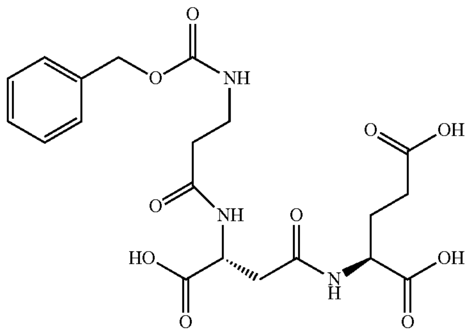 [SMILES: O=C(O)CC[C@H](NC(=O)C[C@@H](NC(=O)CCNC(=O)OCc1ccccc1)C(=O)O)C(=O)O] | 467.4 | 467.2 | −0.08 | | 33% | |
| P240 | 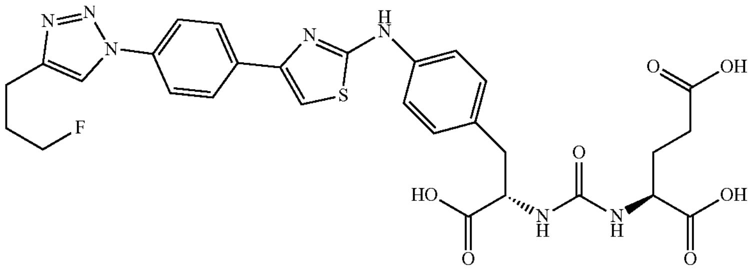 [SMILES: O=C(O)CC[C@H](NC(=O)N[C@@H](Cc1ccc(Nc2nc(-c3ccc(-n4cc(CCCF)nn4)cc3)cs2)cc1)C(=O)O)C(=O)O] | 639.7 | 639.3 | 3.97 | | 94% | 28 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P241 | 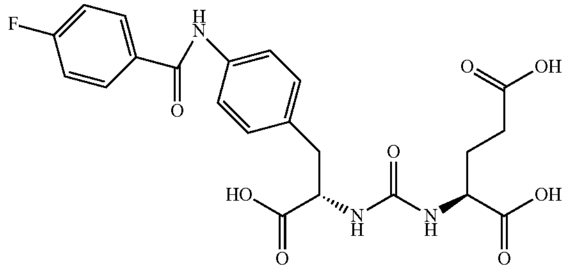 [SMILES: O=C(O)CC[C@H](NC(=O)N[C@@H](Cc1ccc(NC(=O)c2ccc(F)cc2)cc1)C(=O)O)C(=O)O] | 475.4 | 475.2 | 1.35 | | 94% | 0.38 |
| P242 | 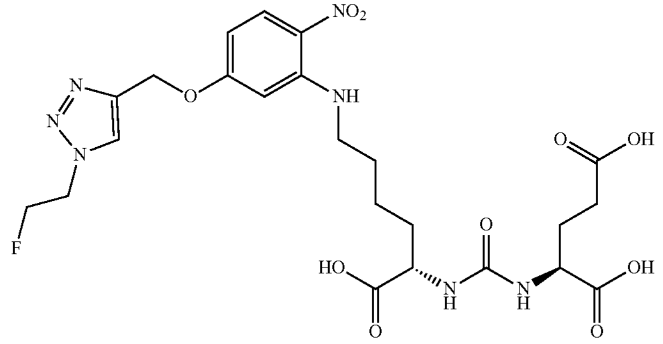 [SMILES: O=C(O)CC[C@H](NC(=O)N[C@@H](CCCCNc1cc(OCc2cn(CCF)nn2)ccc1[N+](=O)[O-])C(=O)O)C(=O)O] | 583.5 | 583.2 | 1.05 | | 99% | 0.07 |
| P243 | 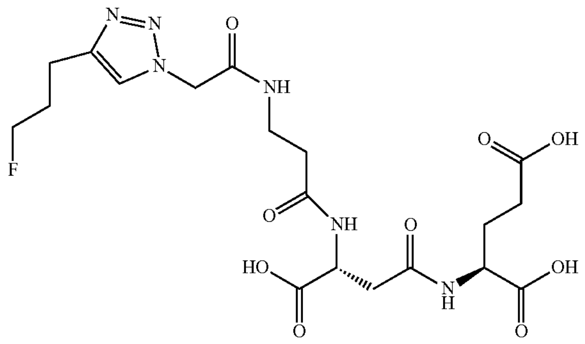 [SMILES: O=C(O)CC[C@H](NC(=O)C[C@@H](NC(=O)CCNC(=O)Cn1cc(CCCF)nn1)C(=O)O)C(=O)O] | 502.5 | 502.2 | −2.08 | | 5% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P244 | 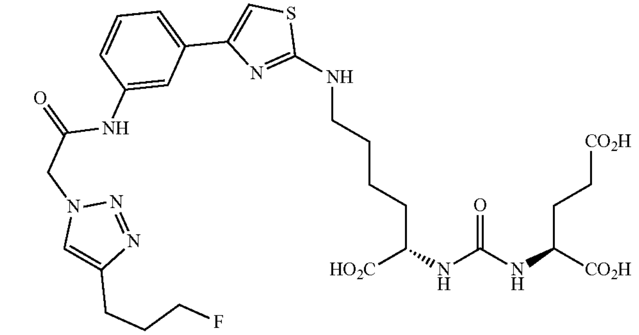 [SMILES: O=C(O)CC[C@H](NC(=O)N[C@@H](CCCCNc1nc(-c2cccc(NC(=O)Cn3cc(CCCF)nn3)c2)cs1)C(=O)O)C(=O)O] | 662.7 | 662.2 | 2.01 | | 98% | 0.38 |
| P245 | 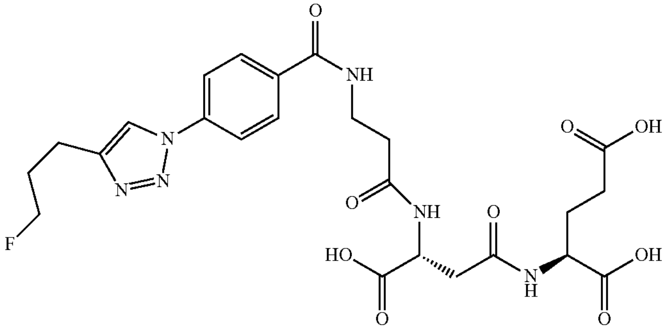 [SMILES: O=C(O)CC[C@H](NC(=O)C[C@@H](NC(=O)CCNC(=O)c1ccc(-n2cc(CCCF)nn2)cc1)C(=O)O)C(=O)O] | 564.5 | 564.2 | —0.13 | | 62% | 156 |
| P246 | 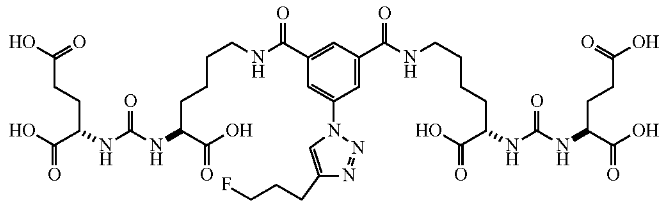 | 895.8 | 895.3 | | | 100% | 0.16 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P247 | 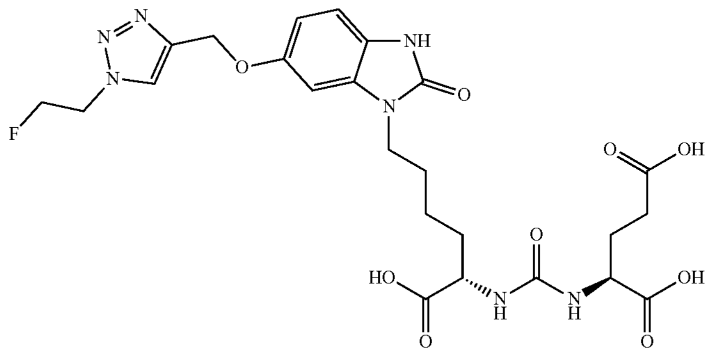 [SMILES: O=C(O)CC[C@H](NC(=O)N[C@@H](CCCCn1c(=O)[nH]c2ccc(OCc3cn(CCF)nn3)cc21)C(=O)O)C(=O)O] | 579.5 | 579.2 | 0.45 | | 100% | 0.63 |
| P248 | 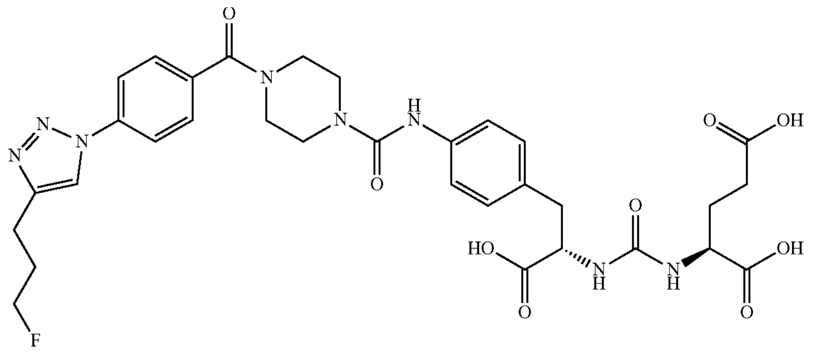 [SMILES: O=C(O)CC[C@H](NC(=O)N[C@@H](Cc1ccc(NC(=O)N2CCN(C(=O)c3ccc(-n4cc(CCCF)nn4)cc3)CC2)cc1)C(=O)O)C(=O)O] | 696.7 | 696.3 | 0.90 | | 100% | 3.4 |
| P249 | 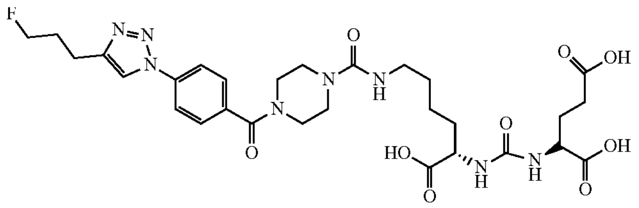 | 662.7 | 662.4 | 0.53 | | | 9.4 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P250 | 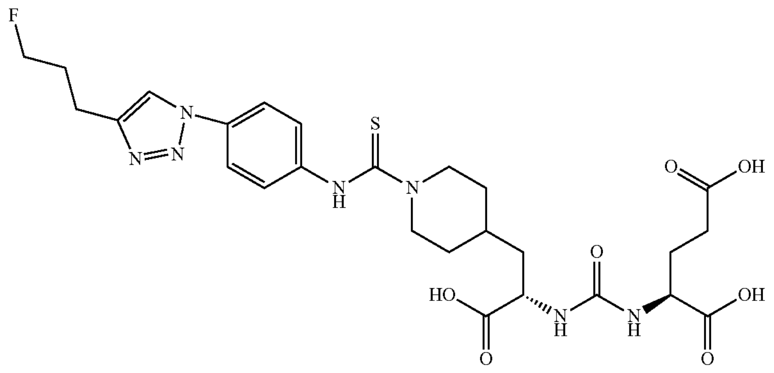 [SMILES: O=C(O)CC[C@H](NC(=O)N[C@@H](CC1CCN(C(=S)Nc2ccc(-n3cc(CCCF)nn3)cc2)CC1)C(=O)O)C(=O)O] | 607.6 | 607.2 | 1.51 | | 96% | 4.1 |
| P251 | 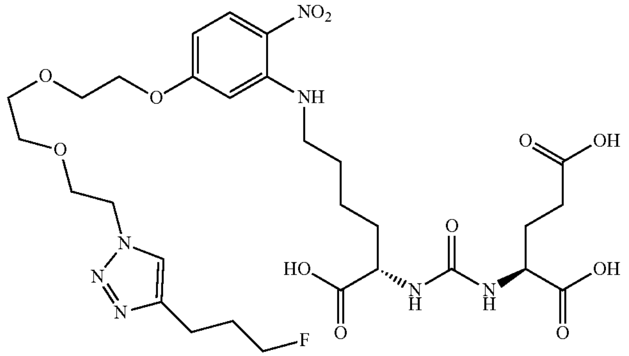 [SMILES: O=C(O)CC[C@H](NC(=O)N[C@@H](CCCCNc1cc(OCCOCCOCCn2cc(CCCF)nn2)ccc1[N+](=O)[O-])C(=O)O)C(=O)O] | 699.7 | 699.3 | 1.59 | | 100% | 0.34 |
| P252 | 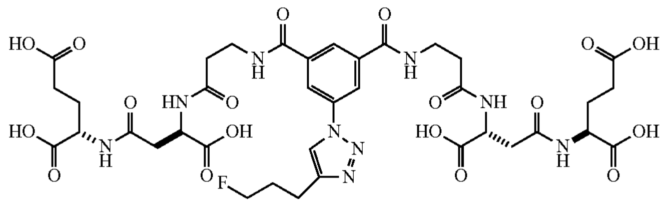 | 923.8 | 923.3 | | | 59% | 94 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P253 | 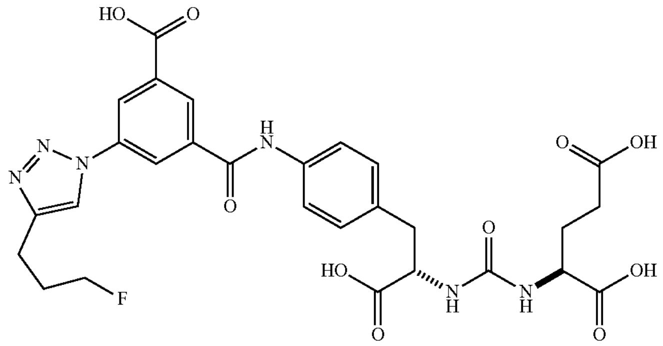 | 628.6 | 628.2 | 1.53 | | 96% | 0.2 |
| P254 | 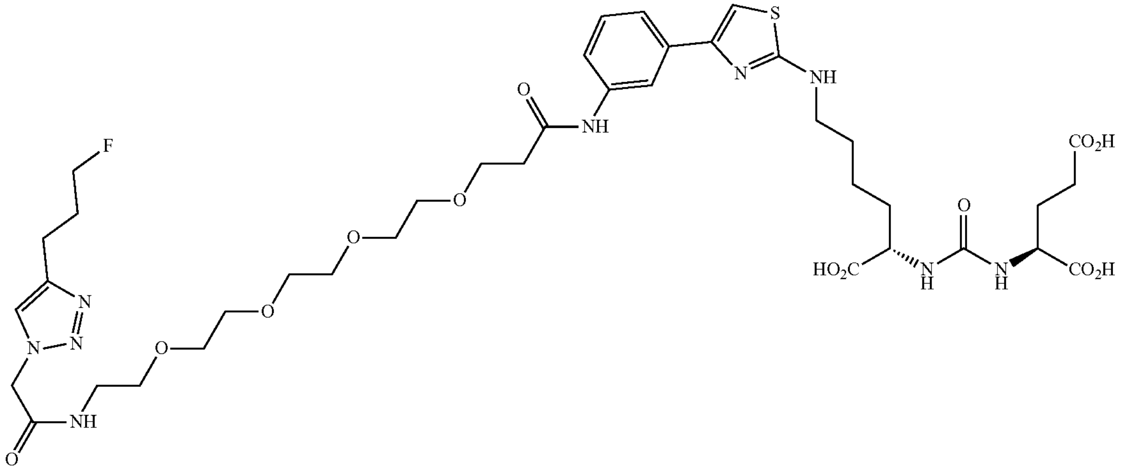 [SMILES: O=C(O)CC[C@H](NC(=O)N[C@@H](CCCCNc1nc(-c2cccc(NC(=O)CCOCCOCCOCCOCCNC(=O)Cn3cc(CCCF)nn3)c2)cs1)C(=O)O)C(=O)O] | 909.9 | 909.4 | | | 95% | 0.4 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P255 | 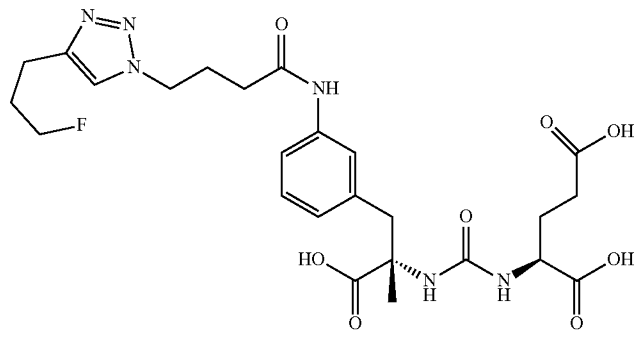 [SMILES: C[C@@](Cc1cccc(NC(=O)CCCn2cc(CCCF)nn2)c1)(NC(=O)N[C@@H](CCC(=O)O)C(=O)O)C(=O)O] | 564.6 | 564.2 | 0.27 | | 62% | |
| P256 | 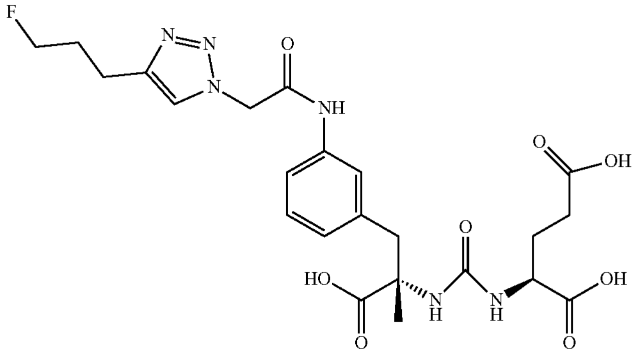 [SMILES: C[C@@](Cc1cccc(NC(=O)Cn2cc(CCCF)nn2)c1)(NC(=O)N[C@@H](CCC(=O)O)C(=O)O)C(=O)O] | 536.5 | 536.2 | −0.17 | | 27% | |
| P257 | 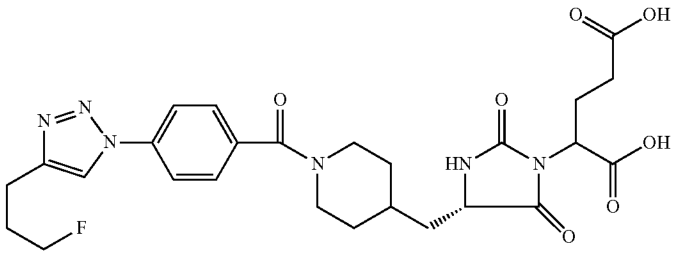 [SMILES: O=C(O)CCC(C(=O)O)N1C(=O)N[C@@H](CC2CCN(C(=O)c3ccc(-n4cc(CCCF)nn4)cc3)CC2)C1=O] | 558.6 | 558.2 | −0.45 | | 5% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P258 | 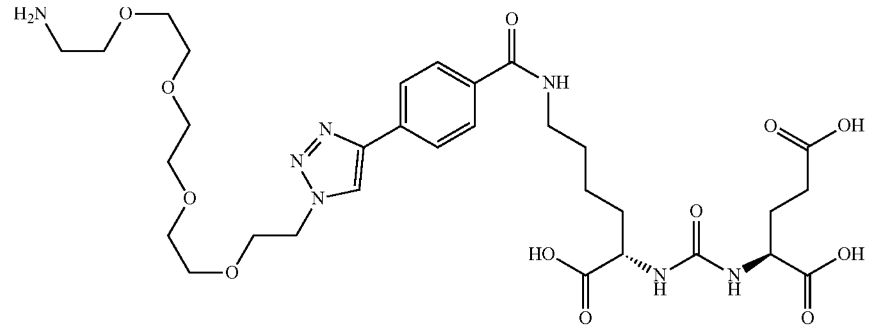 [SMILES: NCCOCCOCCOCCOCCn1cc(-c2ccc(C(=O)NCCCC[C@H](NC(=O)N[C@@H](CCC(=O)O)C(=O)O)C(=O)O)cc2)nn1] | 709.7 | 709.3 | | | | 41 |
| P259 | 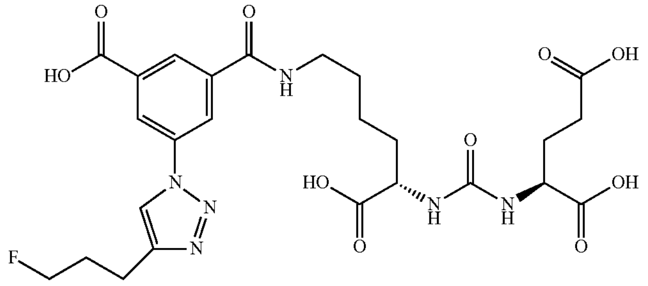 [SMILES: O=C(O)CC[C@H](NC(=O)N[C@@H](CCCCNC(=O)c1cc(C(=O)O)cc(-n2cc(CCCF)nn2)c1)C(=O)O)C(=O)O] | 594.6 | 594.2 | 0.83 | | 98% | |
| P260 | 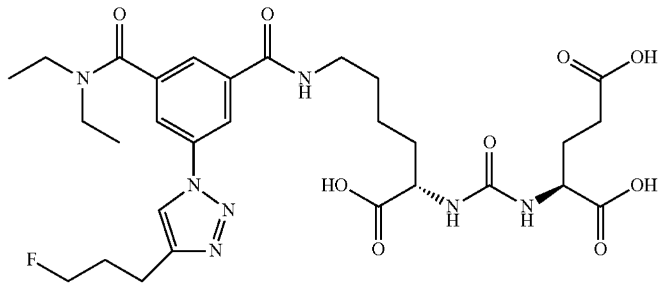 [SMILES: CCN(CC)C(=O)c1cc(C(=O)NCCCC[C@H](NC(=O)N[C@@H](CCC(=O)O)C(=O)O)C(=O)O)cc(-n2cc(CCCF)nn2)c1] | 649.7 | 649.3 | 0.64 | | 81% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P261 | 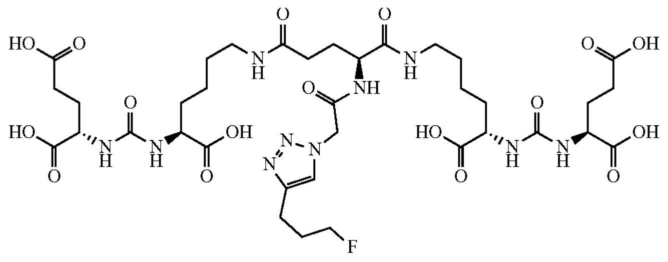 [SMILES: O=C(O)CC[C@H](NC(=O)N[C@@H](CCCCNC(=O)CC[C@H](NC(=O)Cn1cc(CCCF)nn1)C(=O)NCCCC[C@H](NC(=O)N[C@@H](CCC(=O)O)C(=O)O)C(=O)O)C(=O)O)C(=O)O] | 918.9 | 918.4 | | | 98% | 1.0 |
| P262 | 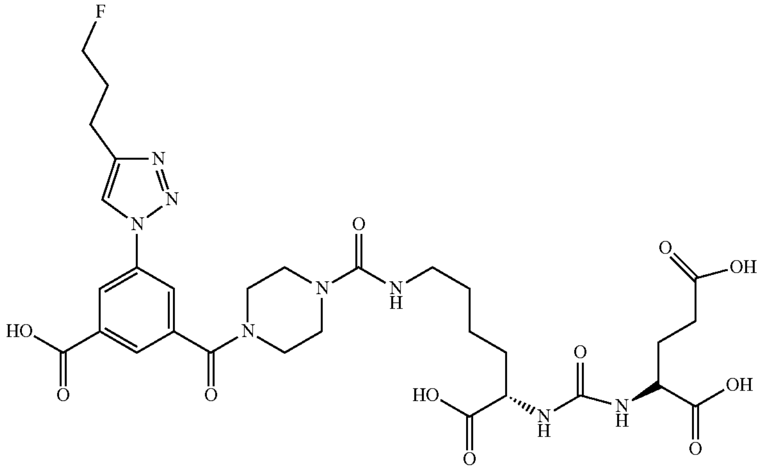 | 706.7 | 706.3 | 0.36 | | 96% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P263 | 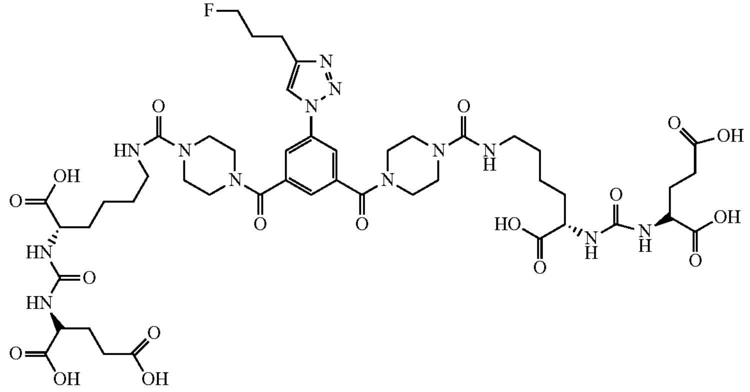 | 1120.1 | 1119.5 | | | 98% | 1.3 |
| P264 | 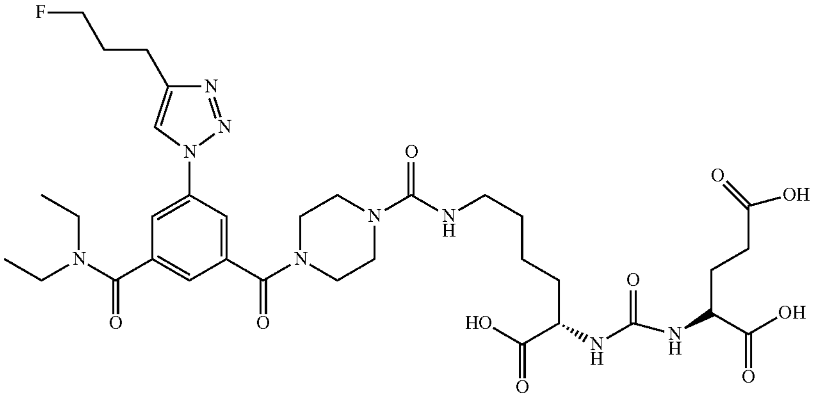 | 761.8 | 761.4 | | | 96% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P265 | 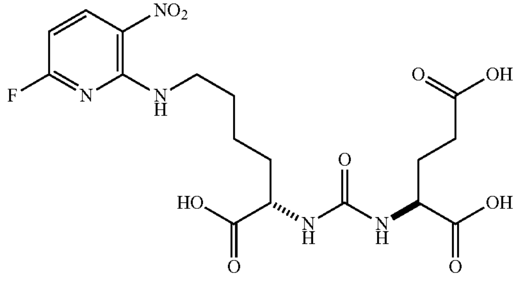 | 459.4 | 459.1 | 0.92 | | 97% | |
| P266 | 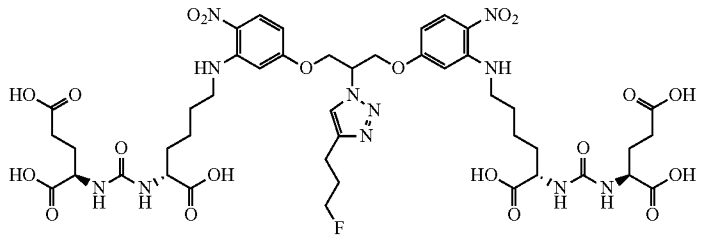 [SMILES: O=C(O)CC[C@H](NC(=O)N[C@@H](CCCCNc1cc(OCC(COc2ccc([N+](=O)[O-])c(NCCCC[C@@H](NC(=O)N[C@H](CCC(=O)O)C(=O)O)C(=O)O)c2)n2cc(CCCF)nn2)ccc1[N+](=O)[O-])C(=O)O)C(=O)O] | 1080 | 1079.4 | | | 98% | 0.3 |
| P267 | 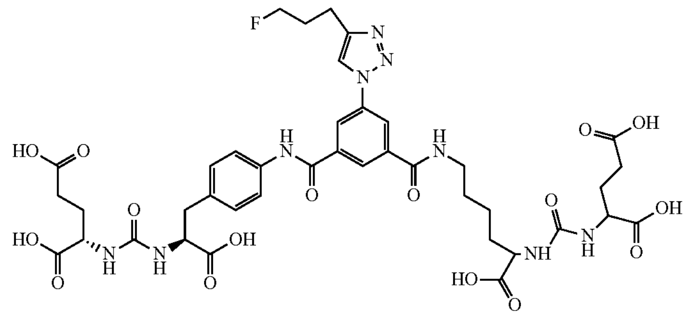 [SMILES: O=C(O)CCC(NC(=O)NC(CCCCNC(=O)c1cc(C(=O)Nc2ccc(C[C@H](NC(=O)N[C@@H](CCC(=O)O)C(=O)O)C(=O)O)cc2)cc(-n2cc(CCCF)nn2)c1)C(=O)O)C(=O)O] | 929.9 | 929.3 | | | 82% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P268 | 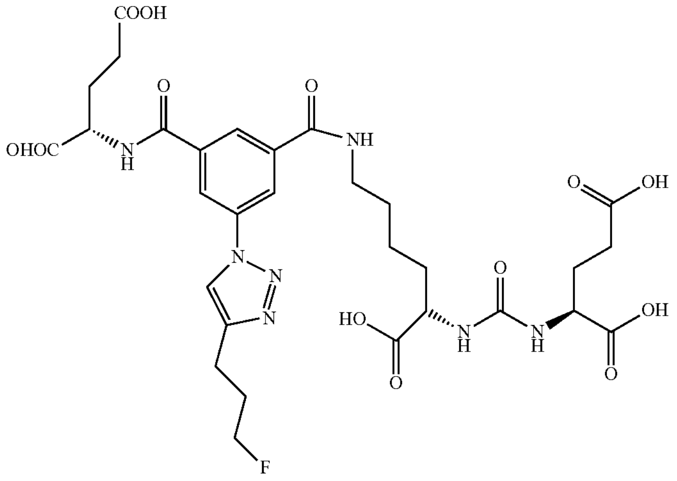 | 723.7 | 723.3 | −1.00 | | 68% | |
| P269 | 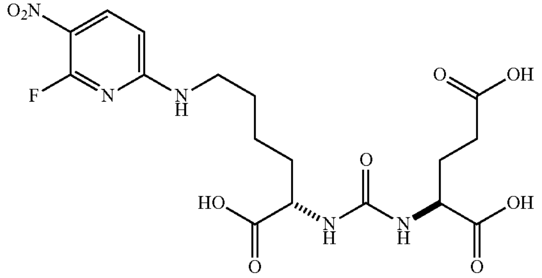 | 459.4 | 459.1 | 0.47 | | 66% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P270 | 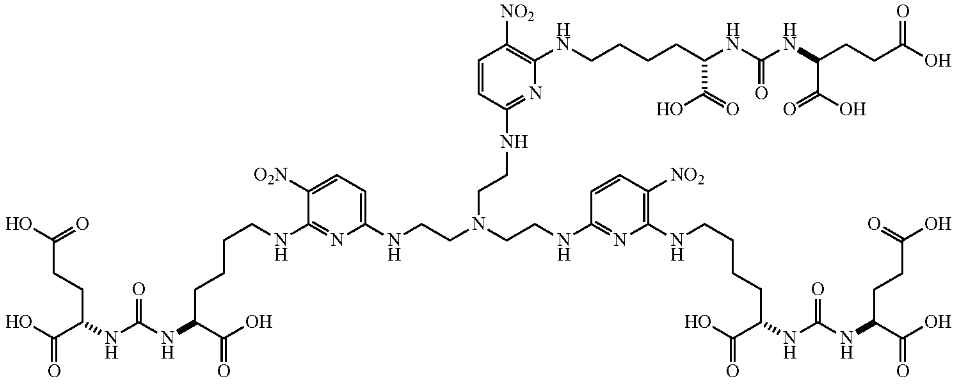 | 1464.4 | 1463.6 | | | 71% | 0.2 nM |
| P271 | 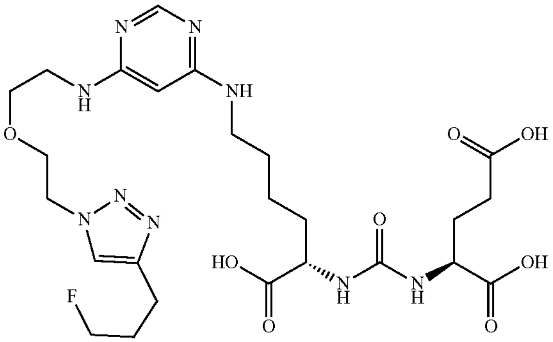 [SMILES: O=C(O)CC[C@H](NC(=O)N[C@@H](CCCCNc1cc(NCCOCCn2cc(CCCF)nn2)ncn1)C(=O)O)C(=O)O] | 611.6 | 611.3 | 0.89 | | 98% | 0.8 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P272 | 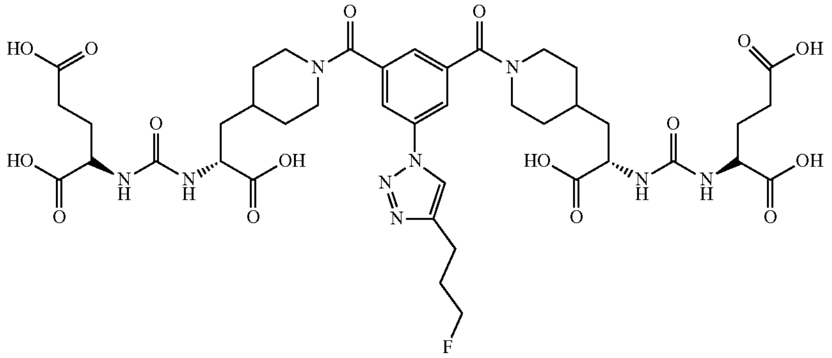 | 947.9 | 947.4 | | | 97% | 2.5 |
| P273 | 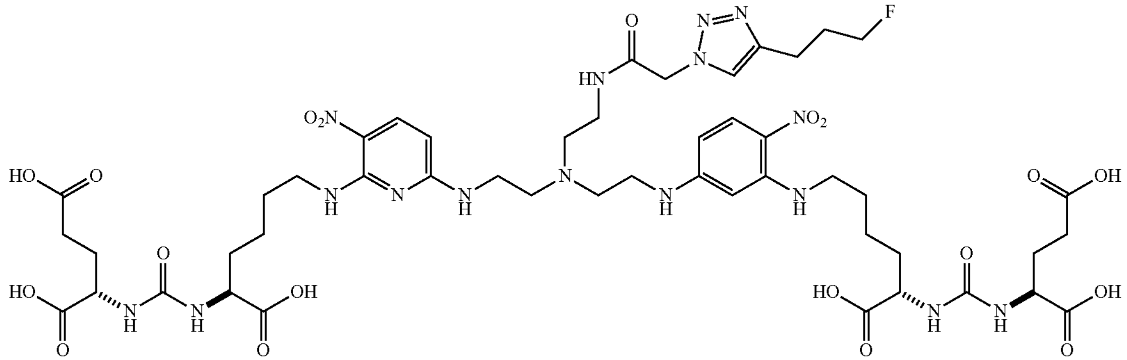 | 1194.1 | 1193.5 | | | 97% | 0.2 |
| P274 | 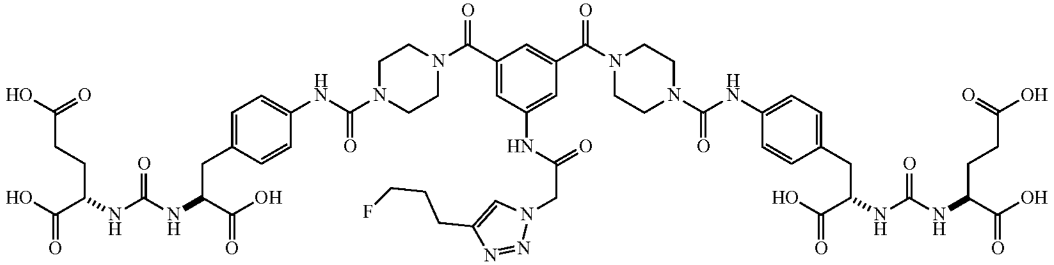 | 1245.2 | 1244.5 | | | | 13.1 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P275 | 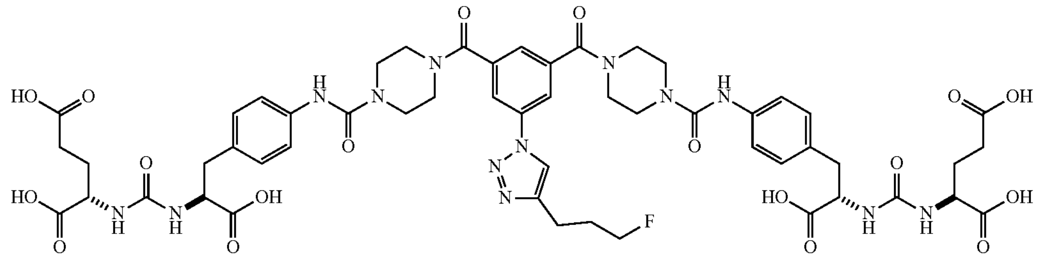 | 1188.1 | 1187.4 | | | | 6.6 |
| P276 | 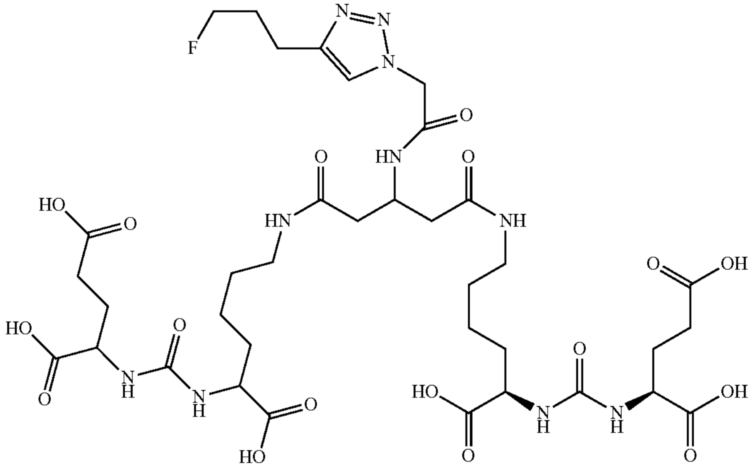 [SMILES: O=C(O)CCC(NC(=O)NC(CCCCNC(=O)CC(CC(=O)NCCCC[C@@H](NC(=O)N[C@@H](CCC(=O)O)C(=O)O)C(=O)O)NC(=O)Cn1cc(CCCF)nn1)C(=O)O)C(=O)O] | 918.9 | 918.4 | | | | 1.3 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P277 | 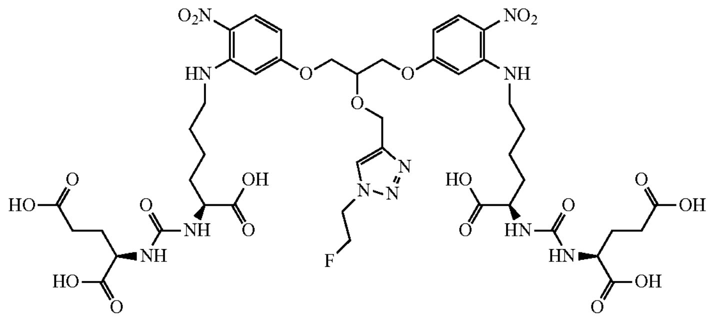 [SMILES: O=C(O)CC[C@H](NC(=O)N[C@H](CCCCNc1cc(OCC(COc2ccc([N+](=O)[O-])c(NCCCC[C@H](NC(=O)N[C@H](CCC(=O)O)C(=O)O)C(=O)O)c2)OCc2cn(CCF)nn2)ccc1[N+](=O)[O-])C(=O)O)C(=O)O] | 1095.99 | 1095.4 | | | | 0.4 |
| P278 | 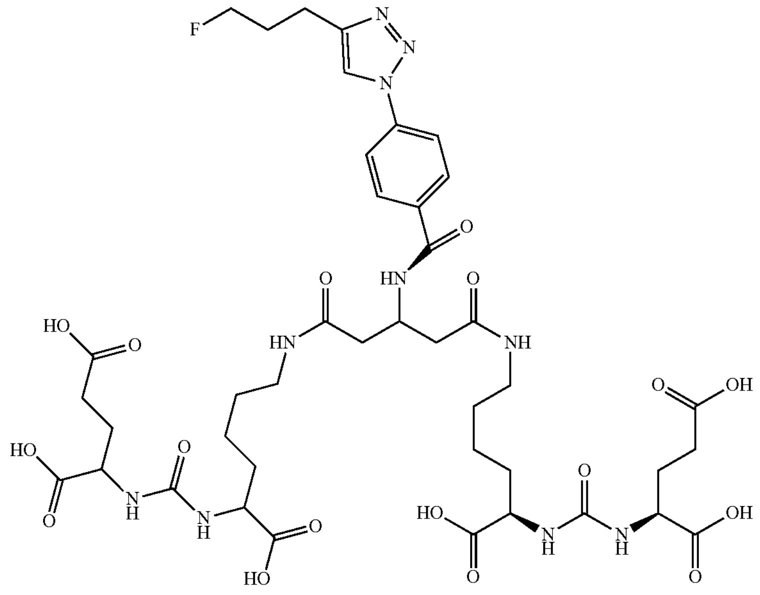 | 980.95 | 980.4 | | | | 0.2 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P279 | 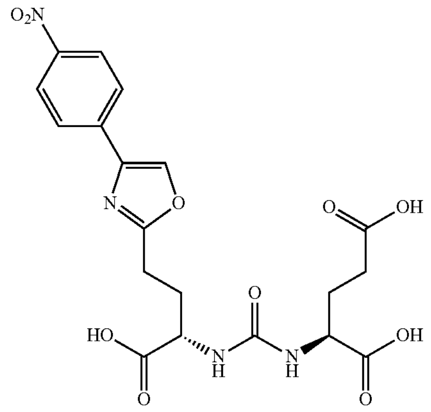 [SMILES: O=C(O)CC[C@H](NC(=O)N[C@@H](CCc1nc(-c2ccc([N+](=O)[O-])cc2)co1)C(=O)O)C(=O)O] | 464.4 | 464.1 | 0.35 | | | 1.6 |
| P280 | 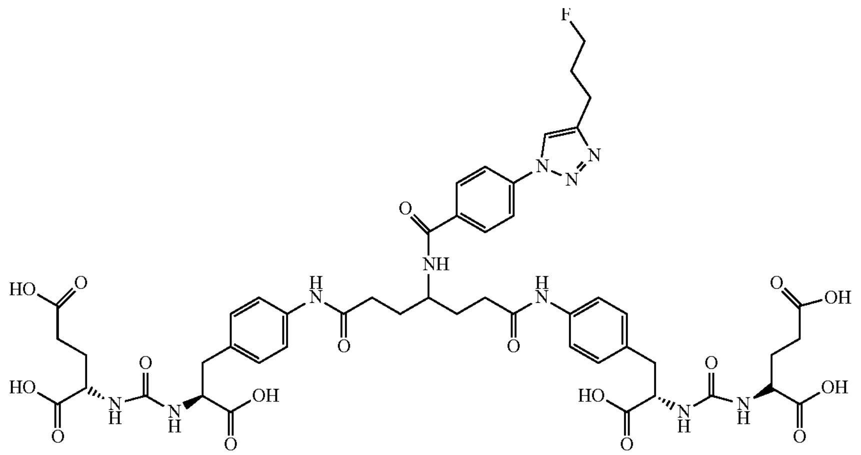 | 1076.4 | 1076.1 | | | | 0.9 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P281 | 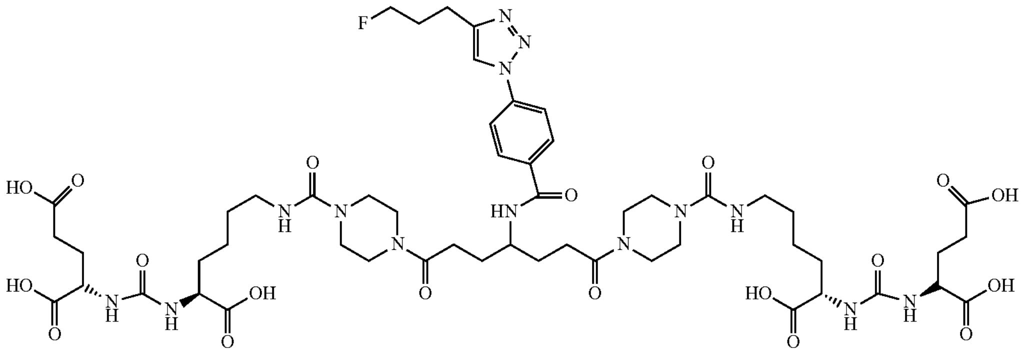 | 1232.6 | 1232.2 | | | | 1.3 |
| P282 | 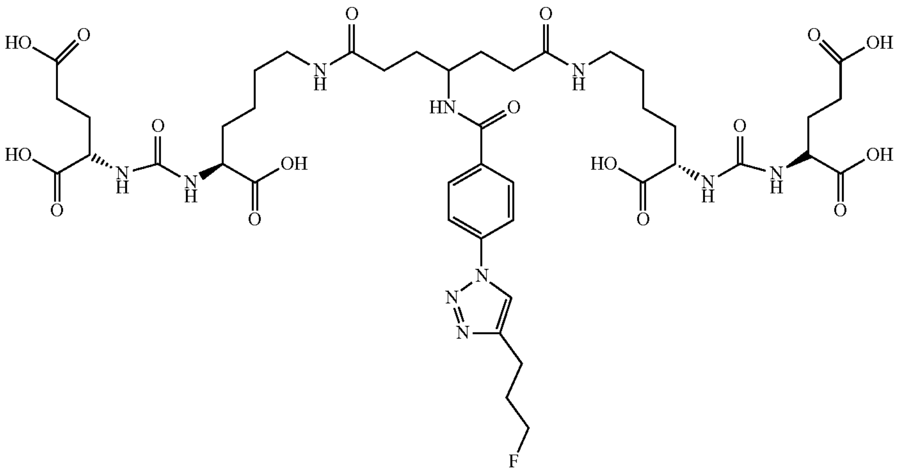 | 1008.4 | 1008.1 | | | | 1.1 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P283 | 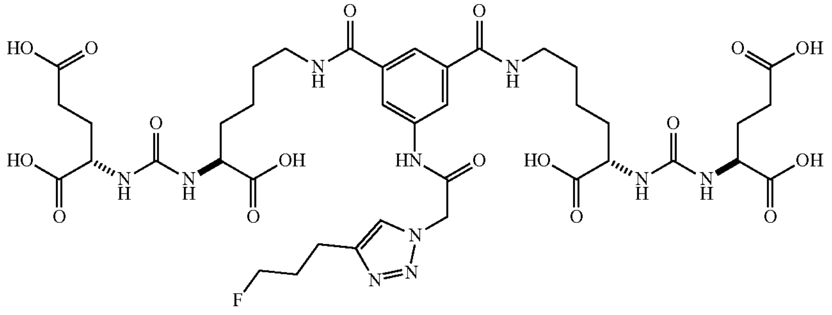 | 982.9 | 952.4 | | | 98% | 0.9 |
| P284 | 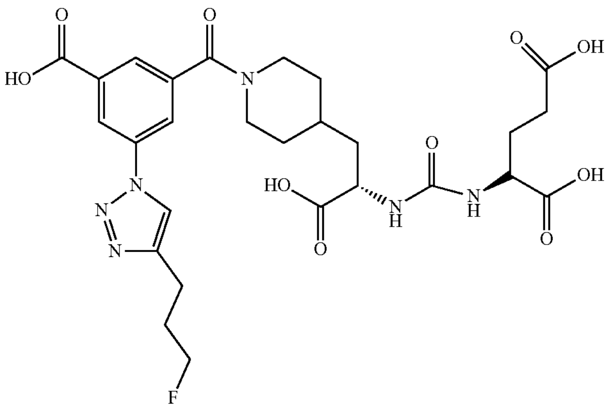 | 620.2 | 620.1 | 0.58 | | 96% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P285 | 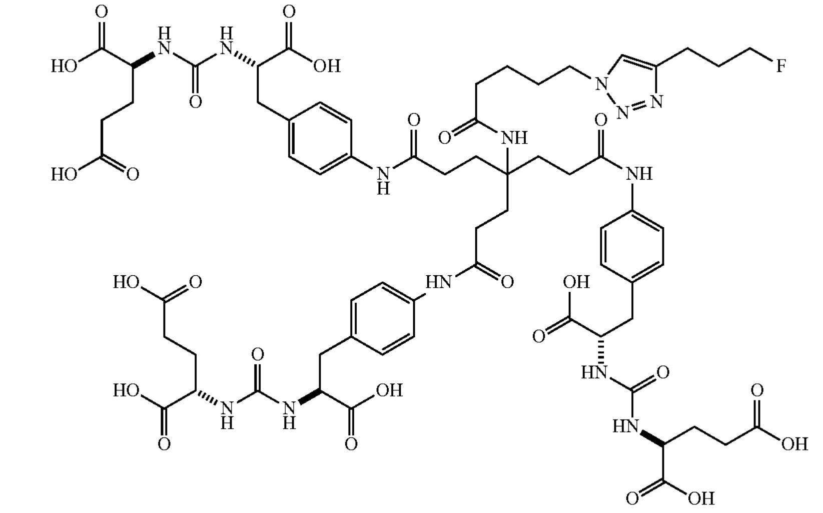 | 1464.4 | 1463.6 | | | | 0.5 |
| P286 | 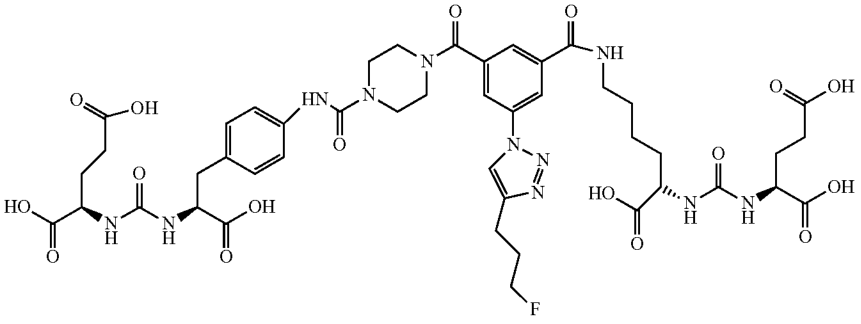 | 1041.99 | 1041.3 | | | 92% | 12.5 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P287 | 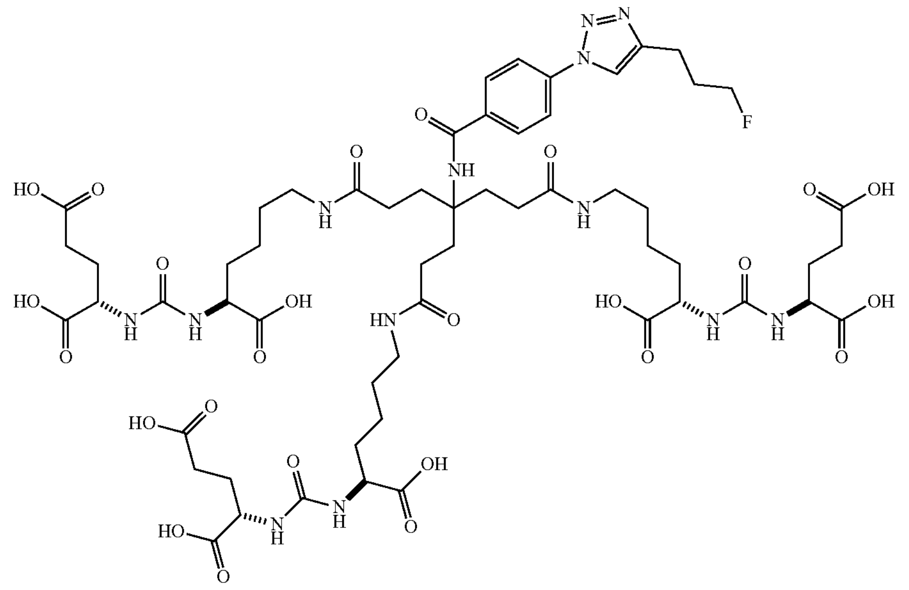 | 1382.4 | 1381.6 | | | 95% | 1 |
| P288 | 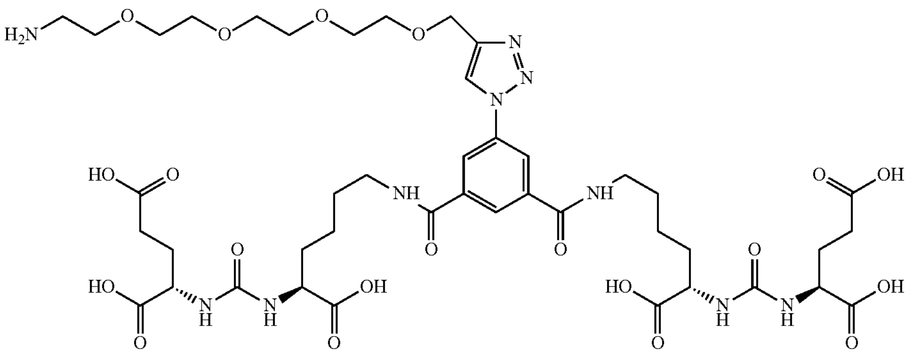 [SMILES: NCCOCCOCCOCCOCc1cn(-c2cc(C(=O)NCCCC[C@H](NC(=O)N[C@@H](CCC(=O)O)C(=O)O)C(=O)O)cc(C(=O)NCCCC[C@H](NC(=O)N[C@@H](CCC(=O)O)C(=O)O)C(=O)O)c2)nn1] | 1041 | 1040.4 | | | 85% | 9.7 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P289 | 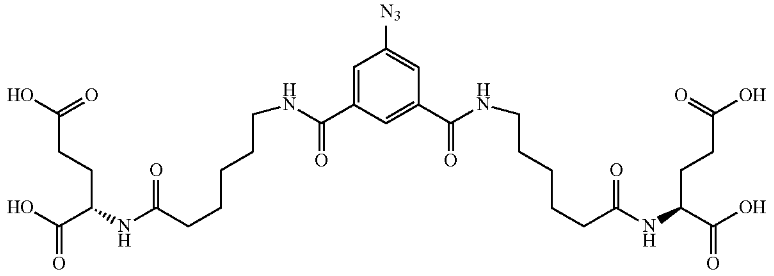 [SMILES: [N-]=[N+]=Nc1cc(C(=O)NCCCCCC(=O)N[C@@H](CCC(=O)O)C(=O)O)cc(C(=O)NCCCCCC(=O)N[C@@H](CCC(=O)O)C(=O)O)c1] | 691.7 | 691.3 | | | 0% | |
| P290 | 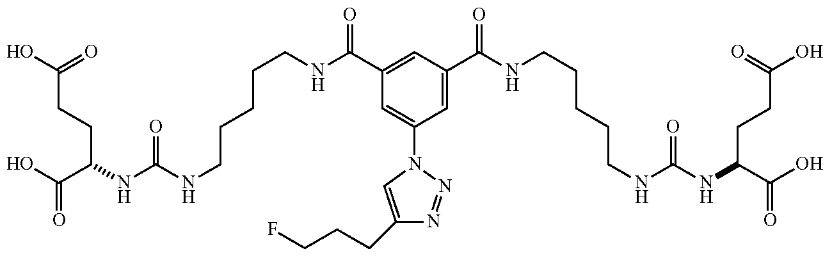 | 807.8 | 807.4 | | | 0% | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P291 | 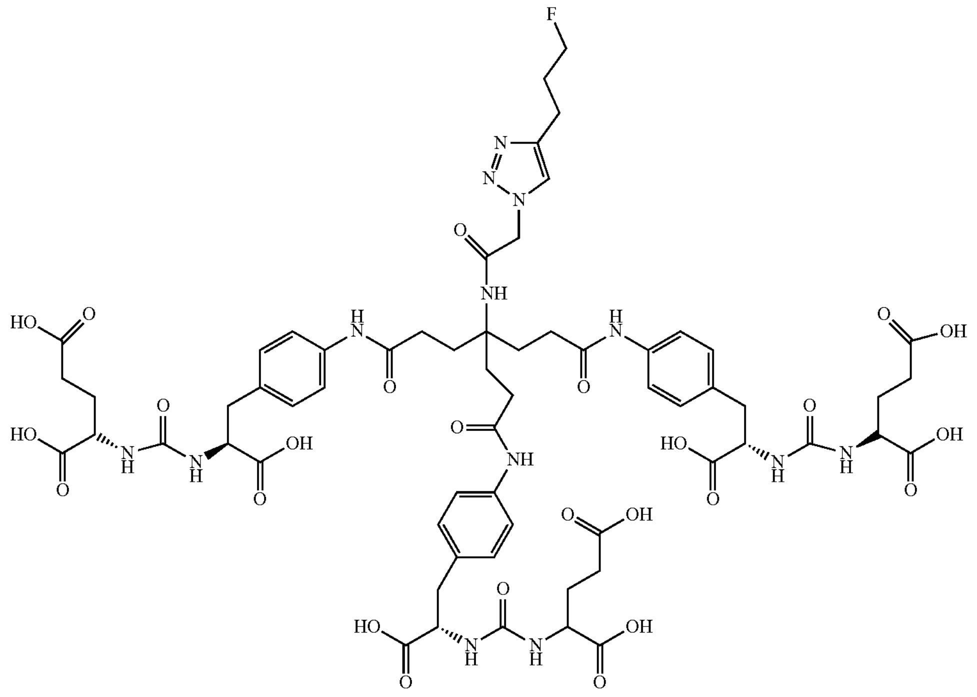 | 1421.5 | 1421.3 | | | 95% | 5 |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P292 | 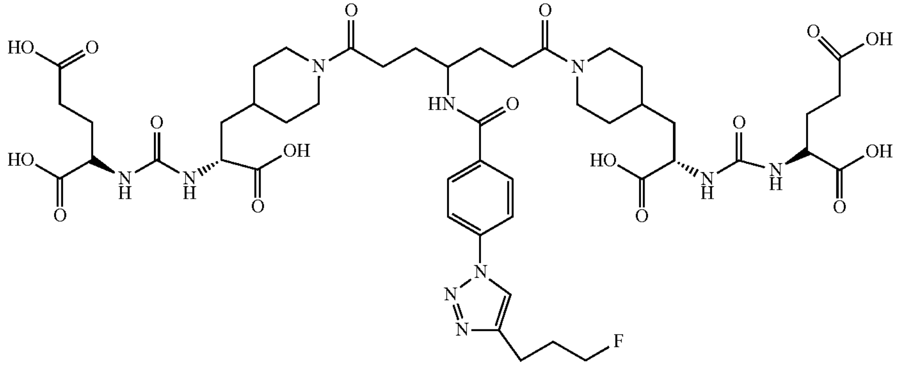 | 1060.5 | 1060.3 | | | 96% | 0.7 |
| P293 | 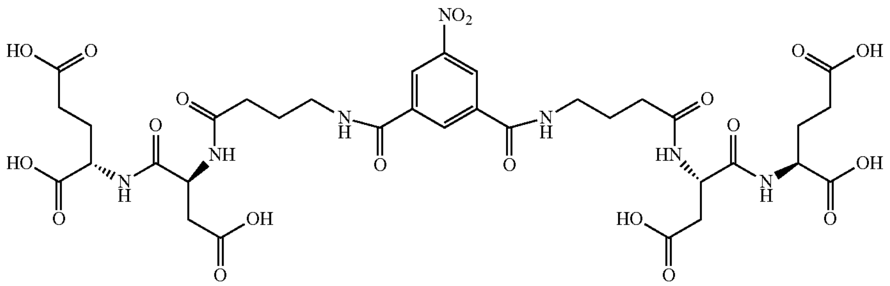 [SMILES: O=C(O)CC[C@H](NC(=O)[C@H](CC(=O)O)NC(=O)CCCNC(=O)c1cc(C(=O)NCCCC(=O)N[C@@H](CC(=O)O)C(=O)N[C@@H](CCC(=O)O)C(=O)O)cc([N+](=O)[O-])c1)C(=O)O] 90% | 869.7 | 869.3 | | | 45 | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P294 | 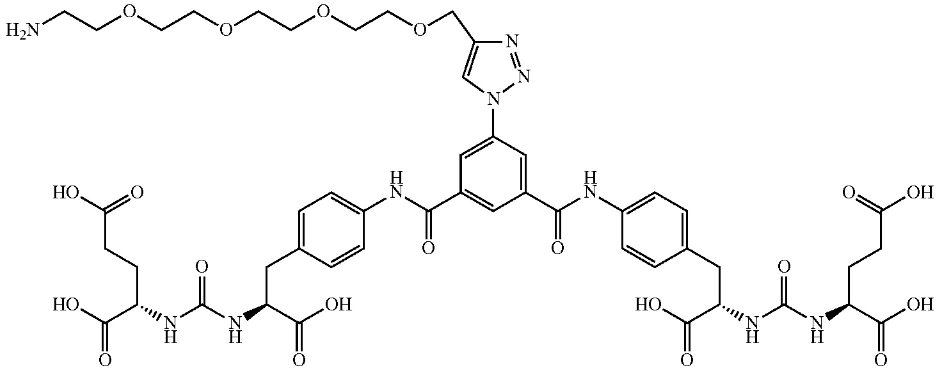 [SMILES: NCCOCCOCCOCCOCc1cn(-c2cc(C(=O)Nc3ccc(C[C@H](NC(=O)N[C@@H](CCC(=O)O)C(=O)O)C(=O)O)cc3)cc(C(=O)Nc3ccc(C[C@H](NC(=O)N[C@@H](CCC(=O)O)C(=O)O)C(=O)O)cc3)c2)nn1] | 1109.1 | 1108.4 | | | 99 | |
| P295 | 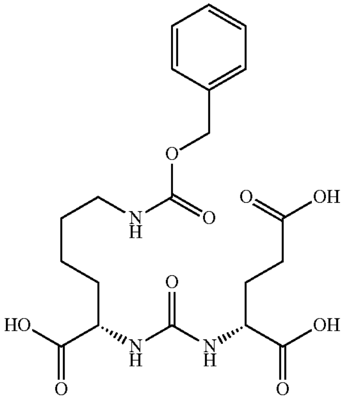 [SMILES: O=C(O)CC[C@@H](NC(=O)N[C@@H](CCCCNC(=O)OCc1ccccc1)C(=O)O)C(=O)O] | 453.4 | 453.2 | 1.05 | | 45 | |

TABLE 1-continued
| ID | Structure | MW | Exact Mass | CLogP | PSMA Blkg % (10 μM) | PSMA Blkg % (1.0 μM) | PSMA Ki (nM) |
|---|---|---|---|---|---|---|---|
| P296 | 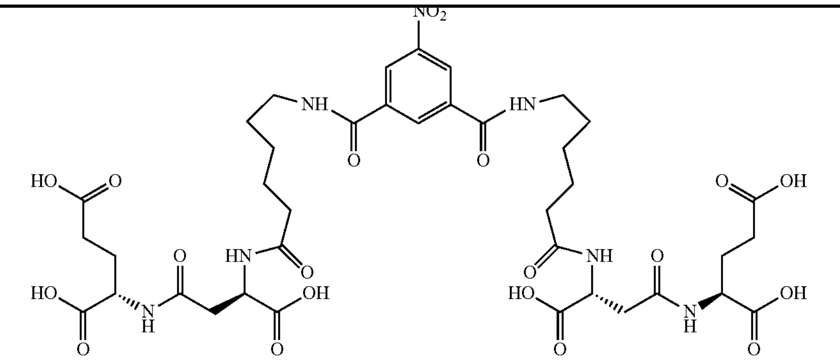 | 925.9 | 925.3 | | | 72% | |
| P297 | 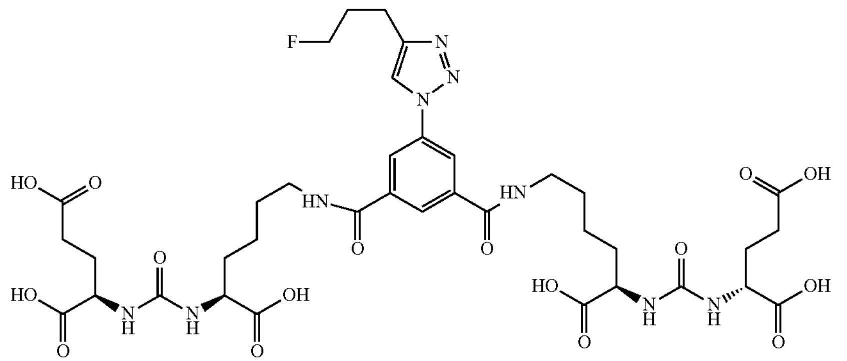 [SMILES: O=C(O)CC[C@@H](NC(=O)N[C@@H](CCCCNC(=O)c1cc(C(=O)NCCCC[C@@H](NC(=O)N[C@H](CCC(=O)O)C(=O)O)C(=O)O)cc(-n2cc(CCCF)nn2)c1)C(=O)O)C(=O)O] | 895.8 | 895.3 | | | 31% | |
| P298 | 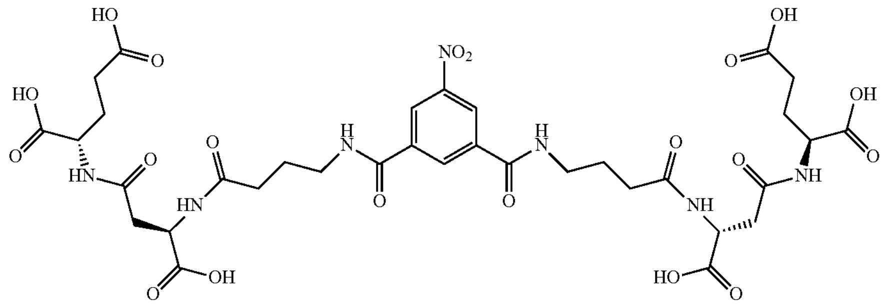 [SMILES: O=C(O)CC[C@H](NC(=O)C[C@@H](NC(=O)CCCNC(=O)c1cc(C(=O)NCCCC(=O)N[C@H](CC(=O)N[C@@H](CCC(=O)O)C(=O)O)C(=O)O)cc([N+](=O)[O-])c1)C(=O)O)C(=O)O] | 869.7 | 869.3 | | | 88% | |

It will be understood that the halogens may be replaced by radiolabeled atoms such as 11C and 18F. Radioactive atoms may also be used with those compounds that do not show a halogen or radioactive atom. It will also be understood that these compounds may be precursors. As such, they may comprise an alkyne or azide or protecting group.

EXAMPLES

A general reaction scheme for forming monomeric compounds of the present invention is shown below. Other synthesis methods may be used.

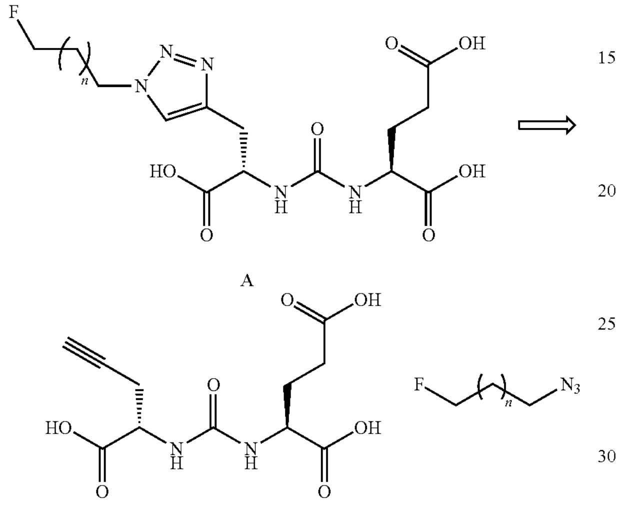

A

A general reaction scheme for forming compounds of the present invention is shown below. Other synthesis methods may be used.

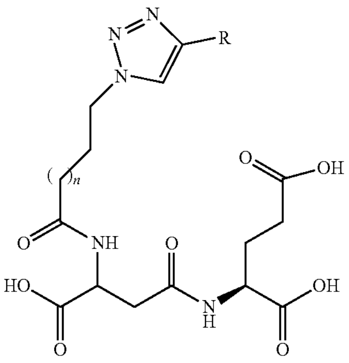

target compounds

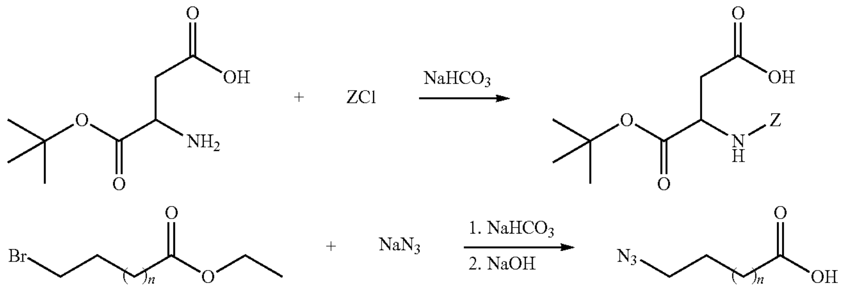

-continued
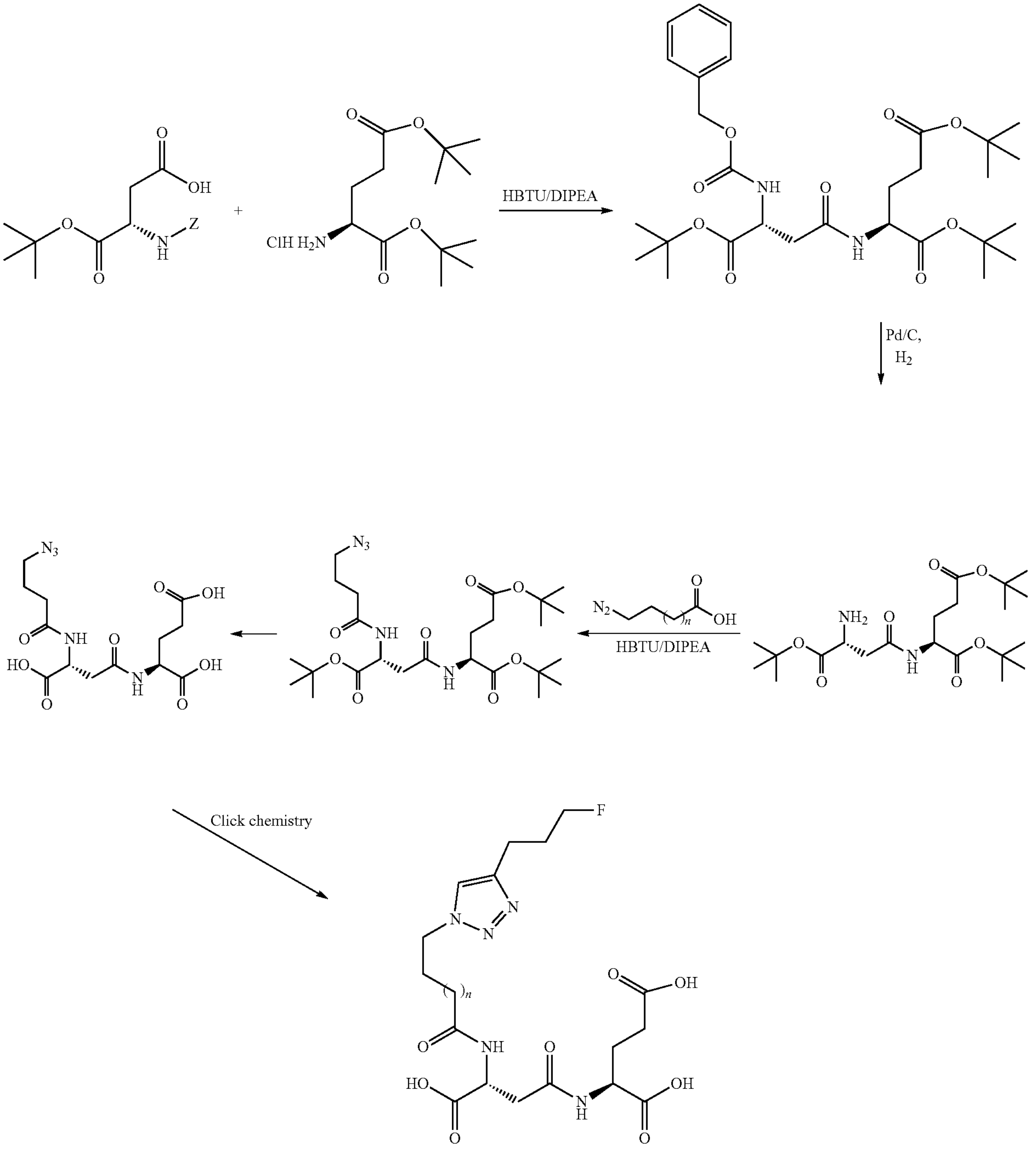
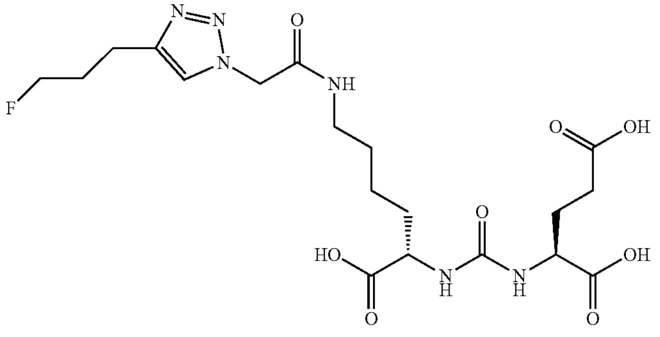
P005

-continued
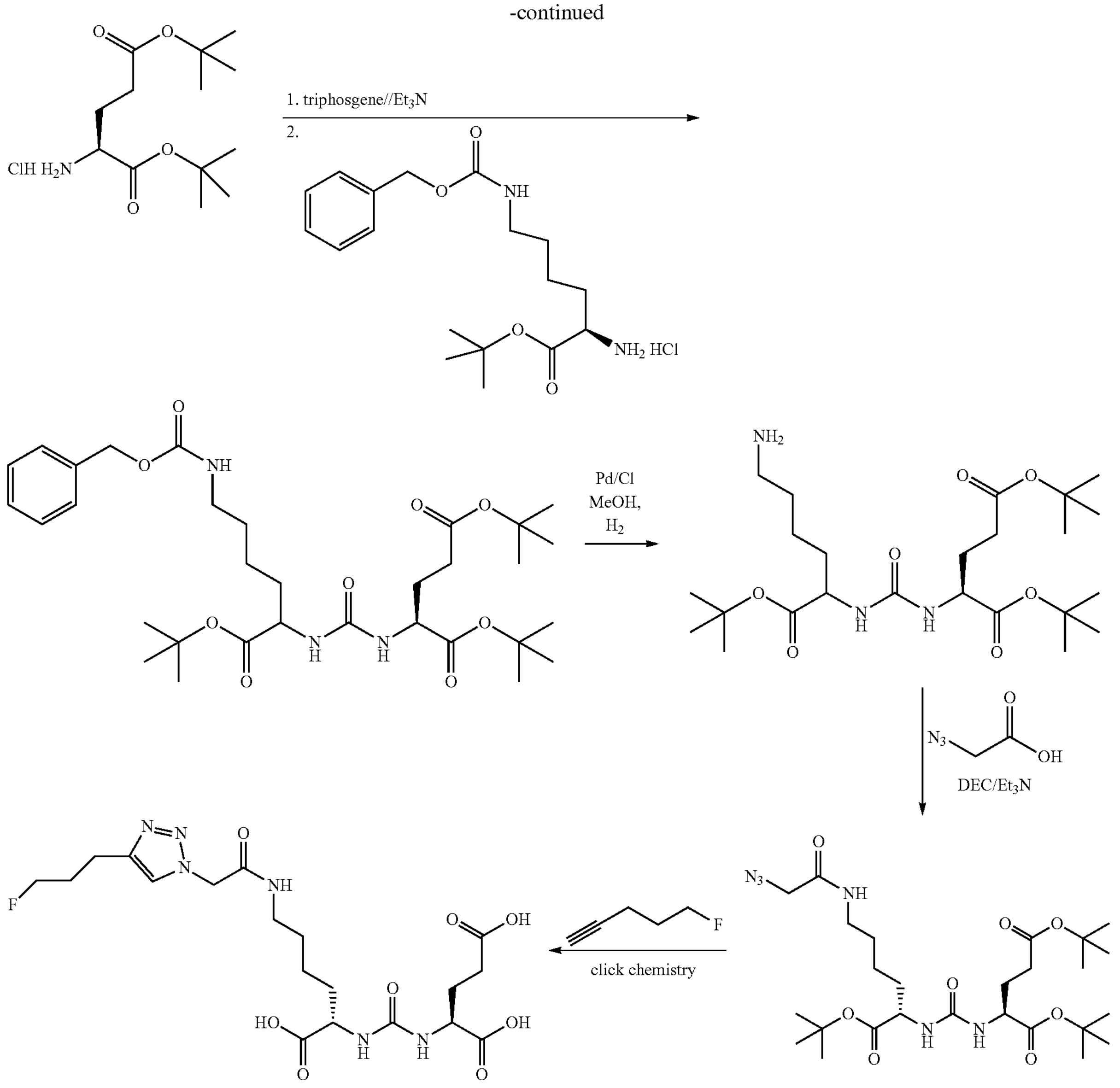
P005
Experimental Data
a. Chemical Synthesis
i. General Reaction Procedures:
1. General Procedure for the Formation of Amide:
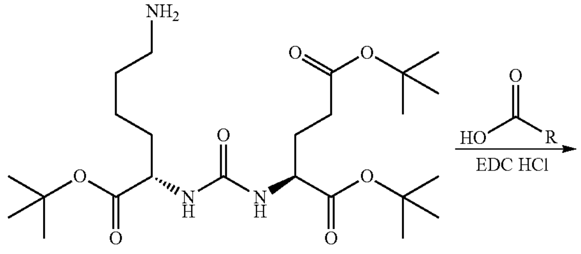
1
-continued
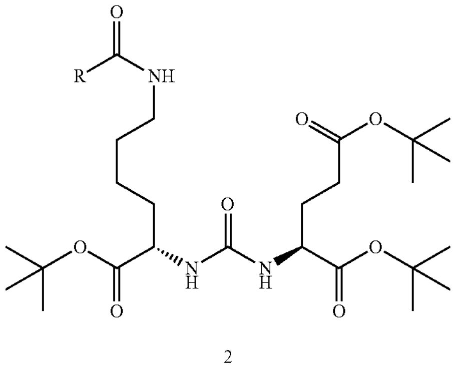
2
A mixture of 1 (1.0 equv.), various acid (1.0 equv.), EDC HCl (1.0 equiv.), and HOBt (1.0 equiv.) in DMF (4.0 mL)

was stirred at room temperature overnight, concentrated in vacuo. The residue was purified on flash column chromatography (silical gel, 20-80% EtOAc/hexanes) to give the desired product.

2. General Procedure for the Removal of Tert-Butyl Group from Esters:

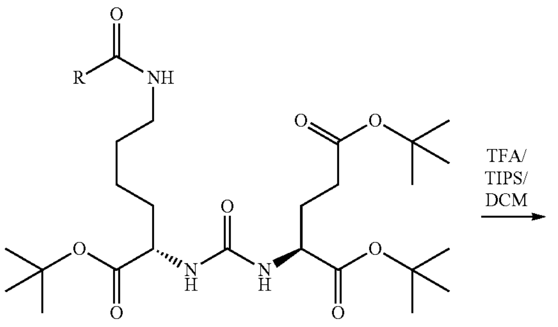

2

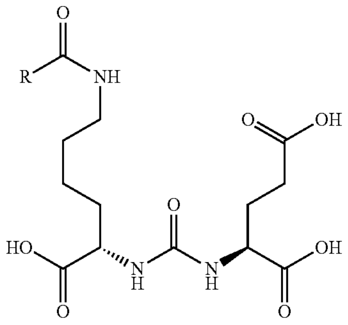

A mixture of compound 2 in TFA/DCM/TIPS (1:1:0.01) was stirred at room temperature for 1-2 hrs, concentrated in vacuo. The residue was purified by either HPLC.

3. General Procedure for the N-Alkylation:

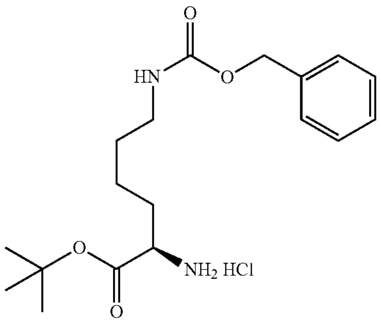

+

-continued

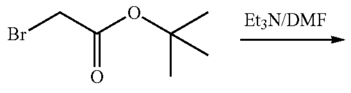

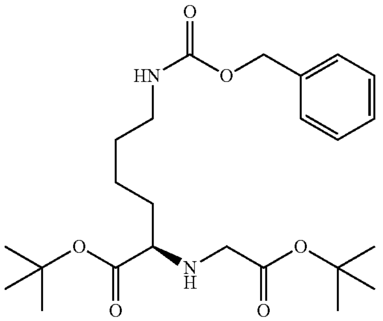

A mixture of amine (1.0 equiv.), bromide (1.1 equiv.), and triethylamine (3.0 equiv.) in DMF (8.0 mL) was stirred at room temperature for 3 days, and then concentrated in vacuo. The residue was purified on flash column chromatography (silica gel, 5-50% EtOAc/hexanes) to give the desired product.

4. General Procedure for "Click Chemistry":

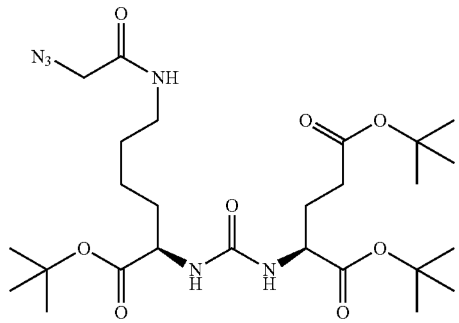

2

+

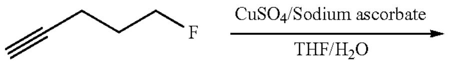

-continued

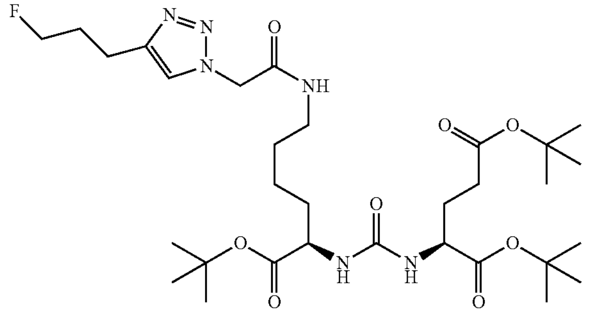

To a solution of 2 (1.0 equiv.), 5-fluoropent-1-yne (1.0 equiv.), and aqueous $CuSO_4$ solution (0.1 M, 1.0 equiv.) in THE (2.0 mL) was added sodium ascorbate (2.1 equiv.). The resulting mixture was stirred at room temperature for 1 hr, and then concentrated in vacuo. The residue was diluted with water, extracted with DCM (2×10 mL). The combined organic layers were dried ($MgSO_4$), filtered, and concentrated in vacuo. The residue was either purified by HPLC or used directly in the next step without any further purification.

5. General Procedure for Removal of Benzyl Group:

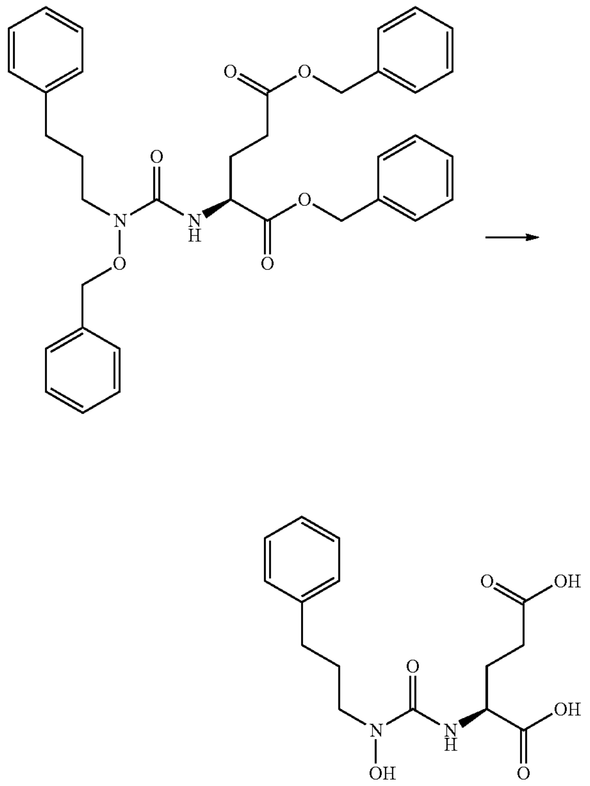 [SMILES: O=C(CC[C@H](NC(=O)N(CCCc1ccccc1)OCc1ccccc1)C(=O)OCc1ccccc1)OCc1ccccc1 ; O=C(O)CC[C@H](NC(=O)N(O)CCCc1ccccc1)C(=O)O]

A mixture of a benzylated compound and Pd/C (10%, catalytic amount) in MeOH (15 mL) was stirred at room temperature under $H_2$ atmosphere (1 atm) for 2-4 hrs. The mixture was then filtered through a short Celite pad, washed with MeOH. The filtrate was concentrated in vacuo. The residue was either purified by HPLC or used directly in the next step without any further purification.

6. General Procedure for Urea Formation:

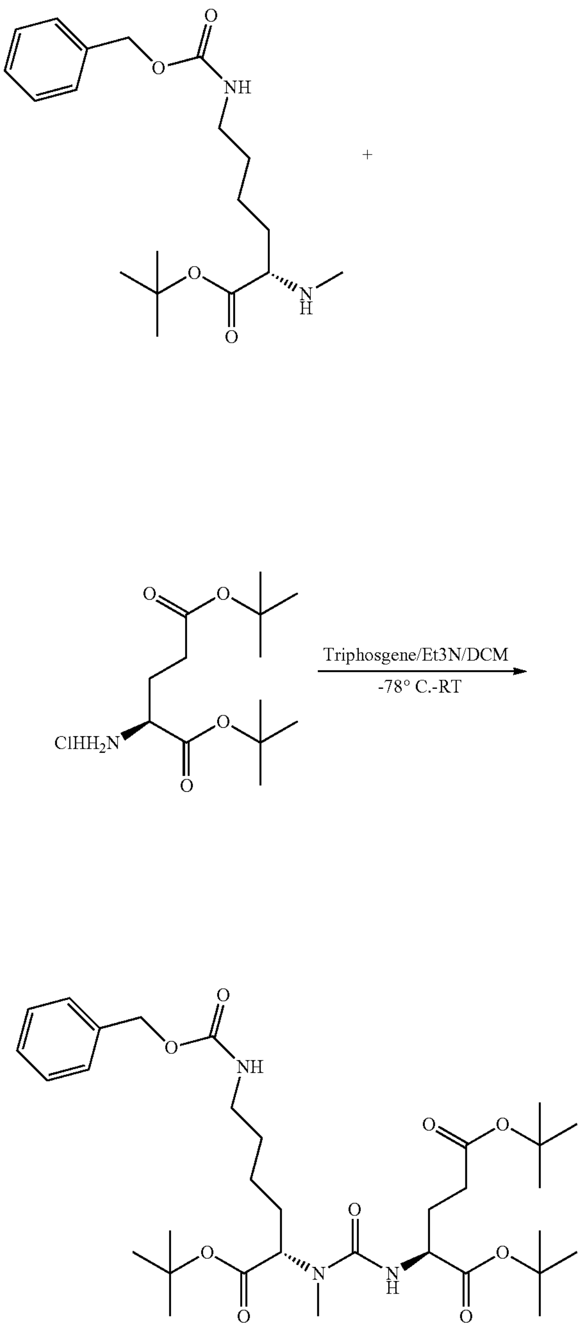

(9S, 13S)-Tri-tert-butyl-10-methyl-3,11-dioxo-1-phenyl-2-oxa-4,10,12-triazapentadecane-9,13,15-tricarboxylate: To a cooled (−78° C.) stirring solution of (S)-glutamic acid di-tert-butyl ester HCl salt (1 mmol, 1 eq) and triphosgene (0.5 mmol, 0.5eq) in dry DCM (5 ml), $Et_3N$ (1.4 mL, 10 eq) was added. The reaction mixture was stirred at −78° C. for 1 h then at 0° C. for 1 h. A solution of CBZ-lysine-N-methyl tert-butyl ester (1 mmol, 1eq) in DCM (3 ml) was added to the above isocyanete solution and continued the stirring 0° C. to RT for 16 h. The volatiles were removed and the residue was purified on flash column chromatography (silical gel, 20-80% EtOAc/hexanes) to give the desired product.

7. General Click Labeling for Dimers (e.g., Compound 297):
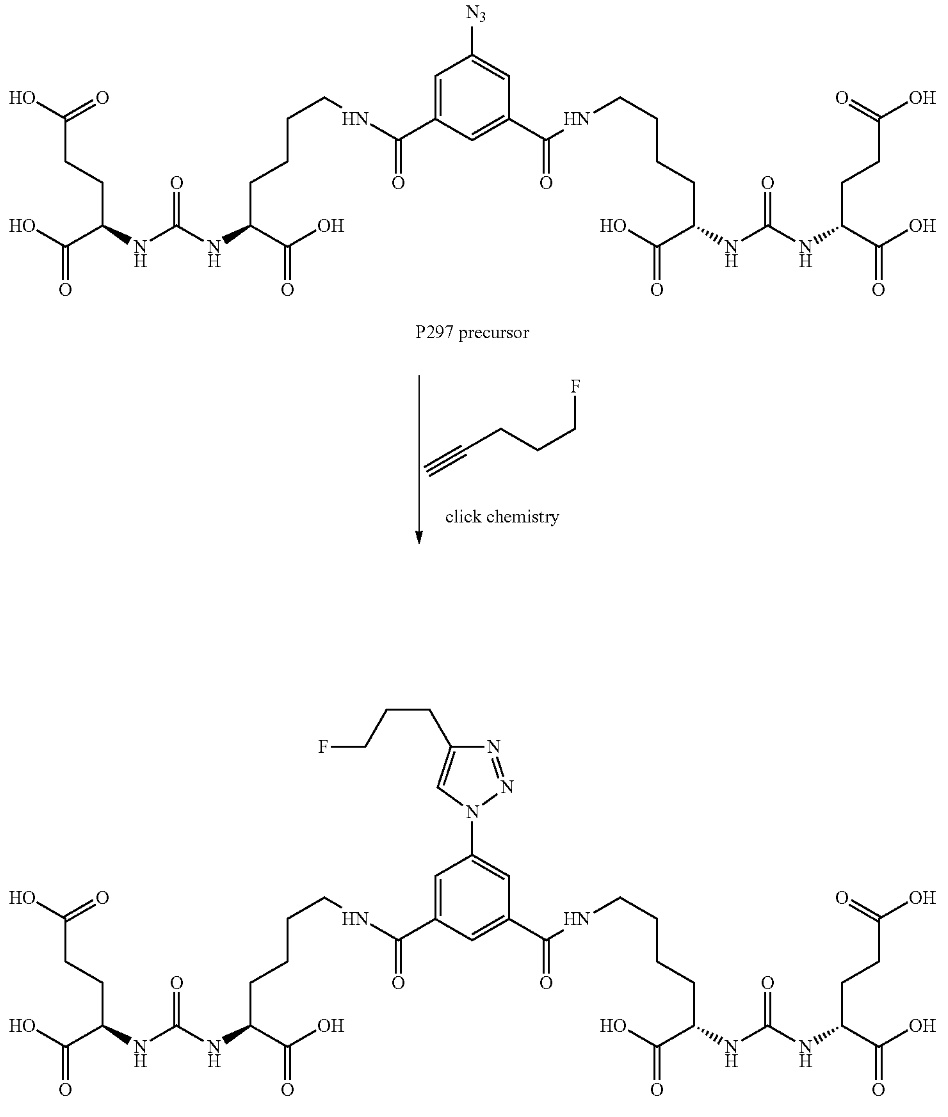
P297 precursor
P297
Preparation of Dimer Precursor (e.g., P238)
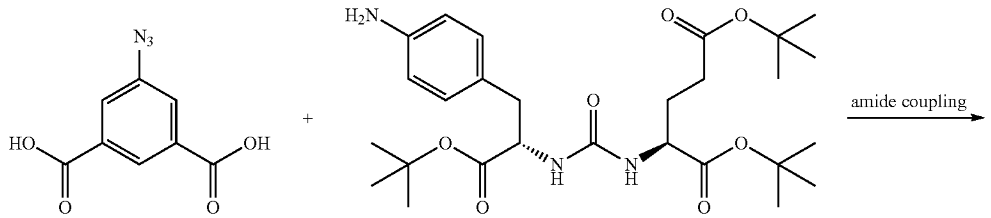

-continued

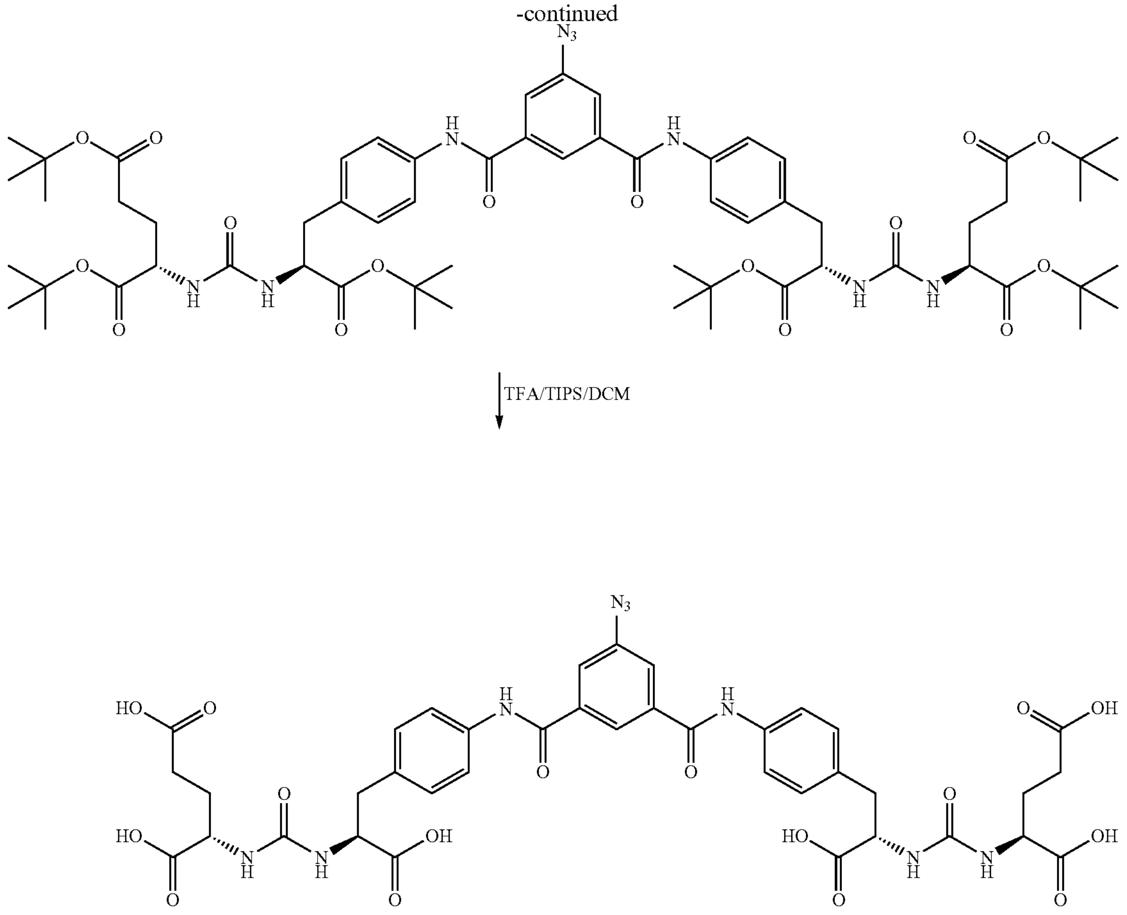

P238 precursor

Synthesized Compounds:

(S)-Di-tert-butyl-2-(3-((S)-1-(tert-butoxy)-6-(6-fluoronicotinamido)-1-oxohexan-2-yl)ureido)pentanedioate

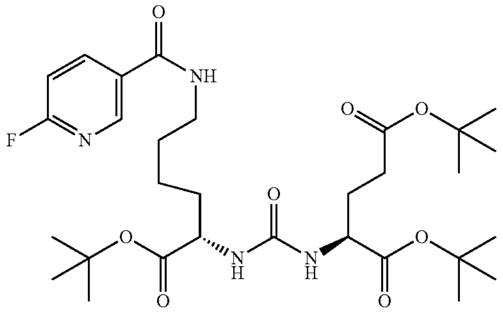 [SMILES: CC(C)(C)OC(=O)CC[C@H](NC(=O)N[C@@H](CCCCNC(=O)c1ccc(F)nc1)C(=O)OC(C)(C)C)C(=O)OC(C)(C)C]

General experimental procedure for amide formation was followed. Reaction was performed on a 10 mg scale. Product was purified on a Biotage purification system eluting out in 20-50% EtOAc:Hexanes mixture in a gradient elution to give the title compound (11 mg, 48%). MS: m/z=611 (M+H$^+$).

(S)-2-(3-((S)-1-Carboxy-5-(6-fluoronicotinamido)pentyl)ureido)pentanedioic acid (P002)

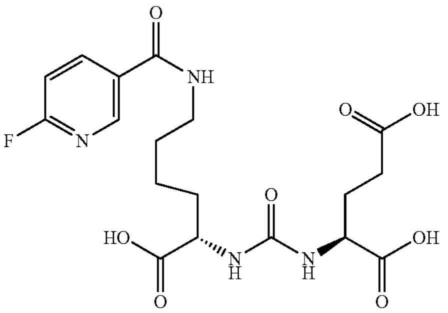 [SMILES: O=C(O)CC[C@H](NC(=O)N[C@@H](CCCCNC(=O)c1ccc(F)nc1)C(=O)O)C(=O)O]

General procedure for the removal of tert-butyl group from esters was followed. Reaction was performed on 11 mg scale. After HPLC purification, P002 (5 mg, 63%) was obtained. MS: m/z=443 (M+H$^+$).

(S)-Di-tert-butyl 2-(3-((S)-1-(tert-butoxy)-6-(6-chloronicotinamido)-1-oxohexan-2-yl)ureido)pentanedioate

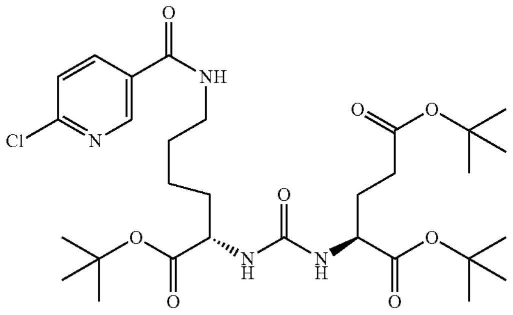 [SMILES: CC(C)(C)OC(=O)CC[C@H](NC(=O)N[C@@H](CCCCNC(=O)c1ccc(Cl)nc1)C(=O)OC(C)(C)C)C(=O)OC(C)(C)C]

General experimental procedure for amide formation was followed. Reaction was performed on an 18 mg scale. Product was purified on a Biotage purification system eluting out in 20-50% EtOAc:Hexanes mixture in a gradient elution to give the title compound (11 mg, 48%). MS: m/z=627 ($M+H^+$).

(S)-2-(3-((S)-1-Carboxy-5-(6-chloronicotinamido)pentyl)ureido)pentanedioic acid (P003)

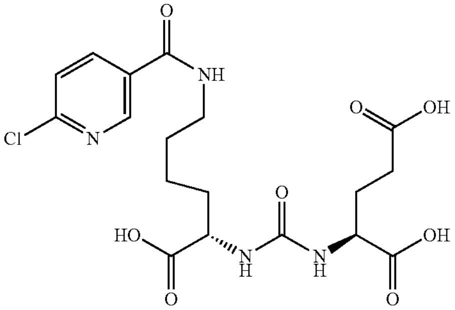 [SMILES: O=C(O)CC[C@H](NC(=O)N[C@@H](CCCCNC(=O)c1ccc(Cl)nc1)C(=O)O)C(=O)O]

General procedure for the removal of tert-butyl group from esters was followed. Reaction was performed on 11 mg scale. After HPLC purification, P003 (3.9 mg, 49%) was obtained. $^1H$ NMR ($CD_3OD$, 400 MHz) δ 8.67-8.70 (m 1H), 8.07-8.10 (m, 1H), 7.42-7.48 (m, 1H), 4.16-4.23 (m, 2H), 3.26-3.33 (m, 2H), 2.27-2.34 (m, 2H), 1.99-2.09 (m, 1H), 1.73-1.84 (m, 2H), 1.50-1.65 (m, 3H), 1.35-1.44 (m, 2H). MS: m/z=459 ($M+H^+$).

(S)-Di-tert-butyl 2-(3-((S)-1-(tert-butoxy)-6-(2-fluoroisonicotinamido)-1-oxohexan-2-yl)ureido)pentanedioate

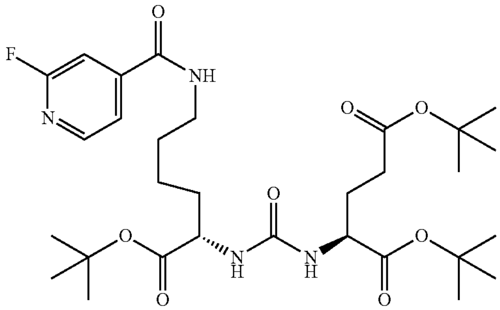 [SMILES: CC(C)(C)OC(=O)CC[C@H](NC(=O)N[C@@H](CCCCNC(=O)c1ccnc(F)c1)C(=O)OC(C)(C)C)C(=O)OC(C)(C)C]

General experimental procedure for amide formation was followed. Reaction was performed on a 17 mg scale. Product was purified on a Biotage purification system eluting out in 20-50% EtOAc:Hexanes mixture in a gradient elution to give the title compound (21 mg, 100%). MS: m/z=611 ($M+H^+$).

(S)-2-(3-((S)-1-Carboxy-5-(2-fluoroisonicotinamido)pentyl)ureido)pentanedioic acid (P004)

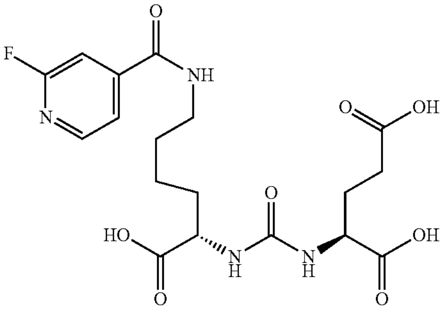 [SMILES: O=C(O)CC[C@H](NC(=O)N[C@@H](CCCCNC(=O)c1ccnc(F)c1)C(=O)O)C(=O)O]

General procedure for the removal of tert-butyl group from esters was followed. Reaction was performed on 11 mg scale. After HPLC purification, P004 (3.9 mg, 49%) was obtained. $^1H$ NMR ($CD_3OD$, 400 MHz) δ 8.21-8.24 (m 1H), 7.53-7.56 (m, 1H), 7.31-7.33 (m, 1H), 4.16-4.23 (m, 2H), 3.30 (t, J=6.8 Hz, 2H), 2.27-2.34 (m, 2H), 1.99-2.07 (m, 1H), 1.73-1.84 (m, 2H), 1.51-1.65 (m, 3H), 1.35-1.44 (m, 2H). MS: m/z=443 ($M+H^+$).

(S)-Di-tert-butyl 2-(3-((S)-6-(2-azidoacetamido)-1-(tert-butoxy)-1-oxohexan-2-yl)ureido)pentanedioate

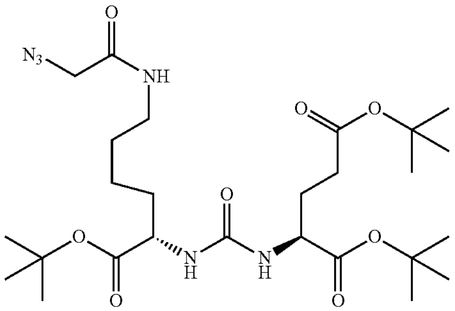 [SMILES: CC(C)(C)OC(=O)CC[C@H](NC(=O)N[C@@H](CCCCNC(=O)CN=[N+]=[N-])C(=O)OC(C)(C)C)C(=O)OC(C)(C)C]

General experimental procedure for amide formation was followed. Reaction was performed on a 126 mg scale. Product was purified on a Biotage purification system eluting out in 0-20% EtOAc:Hexanes mixture in a gradient elution to give the title compound (98 mg, 67%). MS: m/z=571 (M+H$^+$).

(S)-2-(3-((S)-5-(2-Azidoacetamido)-1-carboxypentyl)ureido)pentanedioic acid (P005Precursor)

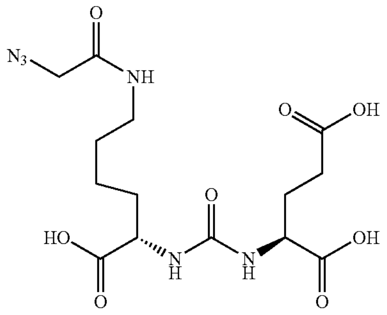 [SMILES: [N-]=[N+]=NCC(=O)NCCCC[C@H](NC(=O)N[C@@H](CCC(=O)O)C(=O)O)C(=O)O]

General procedure for the removal of tert-butyl group from esters was followed. Reaction was performed on 68 mg scale. After HPLC purification, P005 Precursor (45 mg, 95%) was obtained. $^1$H NMR ($CD_3OD$, 400 MHz) δ 4.21-4.32 (m, 2H), 3.84 (s, 2H), 3.21 (t, J=8.0 Hz, 2H), 2.34-2.43 (m, 2H), 2.06-2.17 (m, 1H), 1.77-1.93 (m, 2H), 1.34-1.69 (m, 5H). MS: m/z=403 (M+H$^+$).

(S)-2-(3-((S)-1-Carboxy-5-(2-(4-(3-fluoropropyl)-1H-1,2,3-triazol-1-yl)acetamido)pentyl)ureido)pentanedioic acid (P005)

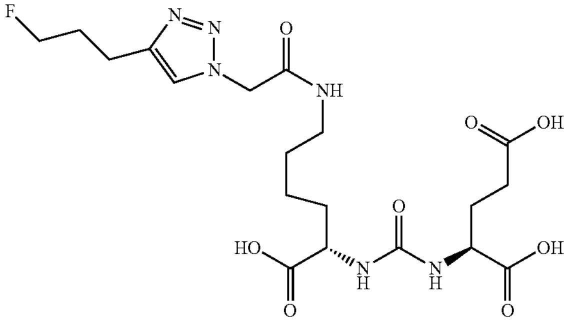 [SMILES: O=C(O)CC[C@H](NC(=O)N[C@@H](CCCCNC(=O)Cn1cc(CCCF)nn1)C(=O)O)C(=O)O]

General experimental procedure for click chemistry of (S)-2-(3-((S)-5-(2-Azidoacetamido)-1-carboxypentyl)ureido)-pentanedioic acid and 5-fluoropent-1-yne was followed. Reaction was performed on a 4 mg scale. After HPLC purification, P005 (3 mg, 60%) was obtained. $^1$H NMR ($CD_3OD$, 400 MHz) δ 7.78 (s, 1H), 5.08 (s, 2H), 4.56 (dt, J=47.6, 5.6 Hz, 2H), 4.22-4.32 (m, 2H), 3.16-3.26 (m, 2H), 2.82 (t, J=8.0 Hz, 2H), 2.36-2.44 (m, 2H), 1.96-2.18 (m, 3H), 1.76-1.93 (m, 1H), 1.39-1.68 (m, 6H). MS: m/z=489 (M+H$^+$).

(S)-Dimethyl 5-(3-(3-(4-hydroxyphenyl)-1-methoxy-1-oxopropan-2-yl)ureido)isophthalate

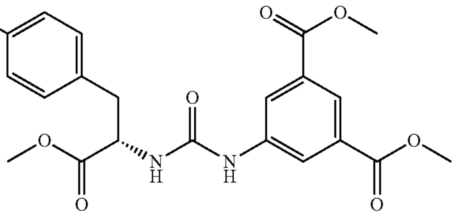

General experimental procedure for the formation of urea was followed. Reaction was performed on a 500 mg scale. Product was purified on a Biotage purification system eluting out in 5-50% EtOAc:Hexanes mixture in a gradient elution to give the title compound (564 mg, 55%). $^1$H NMR ($CDCl_3$, 400 MHz) δ 8.27 (t, J=1.6 Hz, 1H), 8.13 (d, J=1.6 Hz, 1H), 7.59 (br s, 1H), 6.88 (d, J=8.4 Hz, 2H), 6.61 (d, J=8.4 Hz, 2H), 5.48-5.56 (m, 1H), 4.69-4.85 (m, 1H), 3.87 (s, 6H), 3.72 (s, 3H), 3.02 (d, J=6.0 Hz, 2H). MS: m/z=431 (M+H$^+$).

(S)-5-(3-(1-Carboxy-2-(4-(2-fluoroethoxy)phenyl) ethyl)ureido)isophthalic acid (P006)

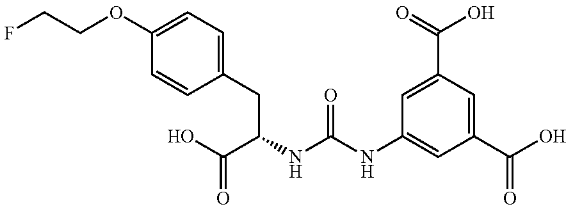 [SMILES: O=C(Nc1cc(C(=O)O)cc(C(=O)O)c1)N[C@@H](Cc1ccc(OCCF)cc1)C(=O)O]

A mixture of (S)-Dimethyl 5-(3-(3-(4-hydroxyphenyl)-1-methoxy-1-oxopropan-2-yl)ureido)isophthalate (33 mg, 0.08 mmol), 1-bromo-2-fluoroethane (excess), and $Cs_2CO_3$ (33 mg, 0.1 mmol) in acetone (10 m) was heated at 75° C. for 4 hrs, cooled and concentrated in vacuo. The residue was used directly in the next step without any further purification. It was mixed with THF/120 (10.0/1.0 mL) containing LiOH (3 equiv.). The resulting mixture was stirred at room temperature for 2 hrs. The reaction mixture was concentrated in vacuo. The residue was acidified with HCl, and then purified by HPLC to give the desired product (4.5 mg, 13%). $^1H$ NMR ($CD_3OD$, 400 MHz) δ 8.15 (s, 3H), 8.07 (d, J=8.8 Hz, 2H), 6.79 (d, J=8.4 Hz, 2H), 4.65 (t, J=4.0 Hz, 1H), 4.49-4.51 (m, 2H), 4.11 (t, J=4.0 Hz, 1H), 4.04 (t, J=4.0 Hz, 1H), 2.91-2.99 (m, 1H), 3.01-3.09 (m, 1H). MS: m/z=435 ($M+H^+$).

(S)-Dimethyl 5-(3-(6-(((benzyloxy)carbonyl)amino)-1-(tert-butoxy)-1-oxohexan-2-yl)ureido)isophthalate

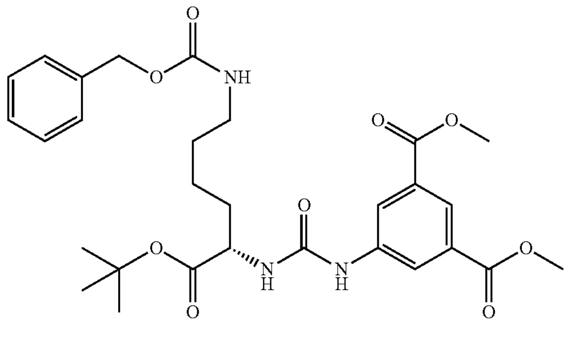 [SMILES: COC(=O)c1cc(NC(=O)N[C@@H](CCCCNC(=O)OCc2ccccc2)C(=O)OC(C)(C)C)cc(C(=O)OC)c1]

General experimental procedure for the formation of urea was followed. Reaction was performed on a 500 mg scale. Product was purified on a Biotage purification system eluting out in 5-50% EtOAc:Hexanes mixture in a gradient elution to give the title compound (150 mg, 11%). $^1H$ NMR ($CDCl_3$, 400 MHz) δ 8.10-8.25 (m, 2H), 7.71 (s, 1H), 7.22-7.38 (m 5H), 5.07 (s, 2H), 4.41 (m, 1H), 3.83 (s, 6H), 3.12-3.28 (m, 2H), 1.49-1.92 (m, 6H), 1.42 (s, 9H). MS: m/z=572 ($M+H^+$).

(S)-Dimethyl 5-(3-(6-(2-azidoacetamido)-1-(tert-butoxy)-1-oxohexan-2-yl)ureido)isophthalate

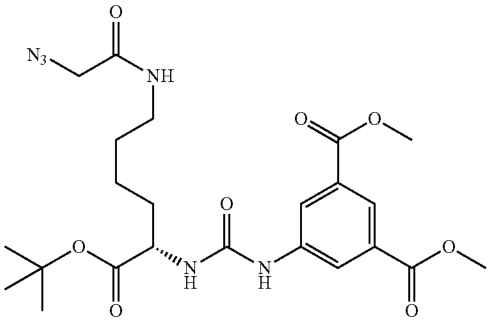 [SMILES: COC(=O)c1cc(NC(=O)N[C@@H](CCCCNC(=O)CN=[N+]=[N-])C(=O)OC(C)(C)C)cc(C(=O)OC)c1]

A mixture of (S)-Dimethyl 5-(3-(6-(((benzyloxy)carbonyl)-amino)-1-(tert-butoxy)-1-oxohexan-2-yl)ureido)isophthalate (200 mg, 0.35 mmol) and Pd/C (10%, catalytic amount) in MeOH (10 mL) was stirred under $H_2$ (1.0 atm) for 4 hrs. The resulting mixture was passed through a short Celite pad. The filtrate was concentrated in vacuo. The residue was used directly in the next step without any further purification. It was then coupled with 2-azidoacetic acid using the general experimental procedure for the formation of amide. The crude product was purified on flash column chromatography (silica gel, 0-5% MeOH/DCM) to give the desired product (96 mg, 54%). $^1H$ NMR ($CDCl_3$, 400 MHz) δ 8.29 (s, 1H), 8.22 (s, 2H), 7.31 (brs, 1H), 6.48-6.55 (br s, 1H), 4.37-4.43 (m, 1H), 4.01 (s, 2H), 3.90 (s, 6H), 3.28-3.34 (m, 2H), 1.49-1.89 (m, 6H), 1.46 (s, 9H). MS: m/z=521 ($M+H^+$).

(S)-5-(3-(1-Carboxy-5-(2-(4-(3-fluoropropyl)-1H-1,2,3-triazol-1-yl)acetamido)pentyl)-ureido)isophthalic acid (P007)

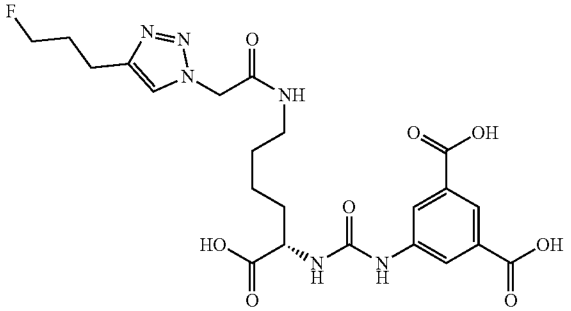 [SMILES: O=C(Cn1cc(CCCF)nn1)NCCCC[C@H](NC(=O)Nc1cc(C(=O)O)cc(C(=O)O)c1)C(=O)O]

General experimental procedure for click chemistry of (S)-Dimethyl 5-(3-(6-(2-azidoacetamido)-1-(tert-butoxy)-1-oxohexan-2-yl)ureido)isophthalate and 5-fluoropent-1-yne was followed. Reaction was performed on 20 mg scale. The crude product from click chemistry was hydrolyzed first under TFA/DCM/TIPS condition, and then under basic condition. After HPLC purification, P007 (8 mg, 40%) was obtained. $^1H$ NMR ($CD_3OD$, 400 MHz) δ 8.32 (s, 1H), 8.27 (s, 1H), 8.23 (s, 1H), 7.75 (s, 1H), 5.06 (s, 2H), 4.50 (t, J=60 Hz, 1H), 4.35-4.42 (m, 2H), 3.19-3.24 (m, 2H), 2.80 (t, J=7.6 Hz, 2H), 1.49-2.11 (m, 6H). MS: m/z=523 ($M+H^+$).

(S)-tert-Butyl 6-(((benzyloxy)carbonyl)amino)-2-((2-(tert-butoxy)-2-oxoethyl)amino)hexanoate

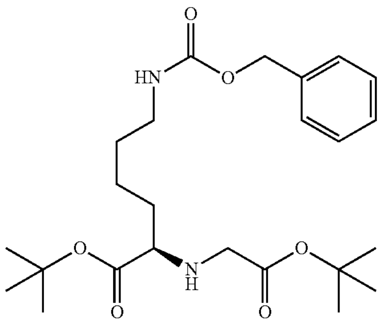 [SMILES: CC(C)(C)OC(=O)CN[C@H](CCCCNC(=O)OCc1ccccc1)C(=O)OC(C)(C)C]

General experimental procedure for N-alkylation was followed. Reaction was performed on a 500 mg scale. Product was purified on a Biotage purification system eluting out in 10-50% EtOAc:Hexanes mixture in a gradient elution to give the title compound (482 mg, 80%). %). $^{1}$H NMR ($CDCl_3$, 400 MHz) δ 7.25-7.32 (m, 5H), 5.10 (s, 2H), 4.85 (br s, 1H), 3.31 (s, 2H), 3.16-3.22 (m, 3H), 1.59-1.79 (m, 2H), 1.29-1.58 (m, 22H). MS: m/z=451 ($M+H^+$).

Benzyl 2-(2-(tert-butoxy)-2-oxoethyl)hydrazinecarboxylate

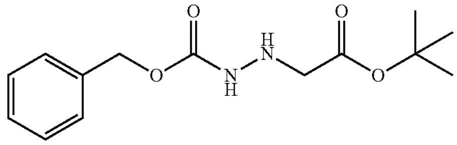 [SMILES: CC(C)(C)OC(=O)CNNC(=O)OCc1ccccc1]

General experimental procedure for N-alkylation was followed. Reaction was performed on a 1000 mg scale. Product was purified on a Biotage purification system eluting out in 5-50% EtOAc:Hexanes mixture in a gradient elution to give the title compound (920 mg, 54%). $^{1}$H NMR ($CDCl_3$, 400 MHz) δ 7.31-7.42 (m, 5H), 6.79 (brs, 1H), 5.15 (s, 2H), 3.58 (s, 2H), 1.47 (s, 9H). MS: m/z=281 ($M+H^+$).

Di-tert-butyl 2,2'-(2-((benzyloxy)carbonyl)hydrazine-1,1-diyl)diacetate

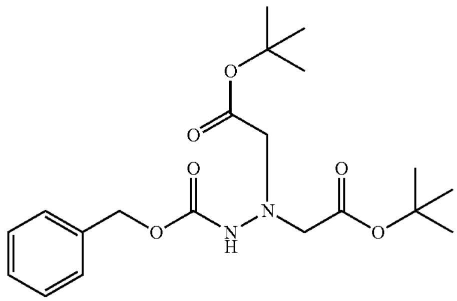 [SMILES: CC(C)(C)OC(=O)CN(CC(=O)OC(C)(C)C)NC(=O)OCc1ccccc1]

General experimental procedure for N-alkylation was followed. Reaction was performed on a 1.13 g scale. Product was purified on a Biotage purification system eluting out in 0-15% EtOAc:Hexanes mixture in a gradient elution to give the title compound (1.05 g, 66%). %). $^{1}$H NMR ($CDCl_3$, 400 MHz) δ 7.26-7.42 (m, 5H), 3.67 (s, 4H), 1.43 (s, 18H). MS: m/z=395 ($M+H^+$).

Benzyl 2-(2-(tert-butoxy)-2-oxoethyl)-2-(3-(tert-butoxy)-3-oxopropyl)-hydrazinecarboxylate

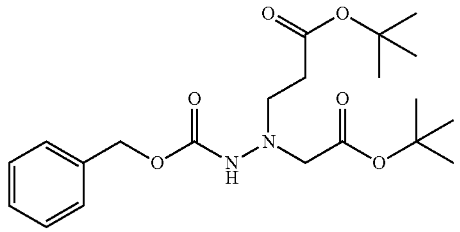 [SMILES: CC(C)(C)OC(=O)CCN(CC(=O)OC(C)(C)C)NC(=O)OCc1ccccc1]

General experimental procedure for N-alkylation was followed. Reaction was performed on a 250 mg scale. Product was purified on a Biotage purification system eluting out in 5-30% EtOAc:Hexanes mixture in a gradient elution to give the title compound (270 mg, 78%). $^{1}$H NMR ($CDCl_3$, 400 MHz) δ 7.25-7.42 (m, 5H), 6.95 (br s, 1H), 5.10 (s, 2H), 3.58 (s, 2H), 3.15 (t, J=7.2 Hz, 2H), 2.35-2.52 (m, 2H). MS: m/z=409 ($M+H^+$).

(S)-tert-Butyl 6-(((benzyloxy)carbonyl)amino)-2-((2-ethoxy-2-oxoethyl)amino)hexanoate

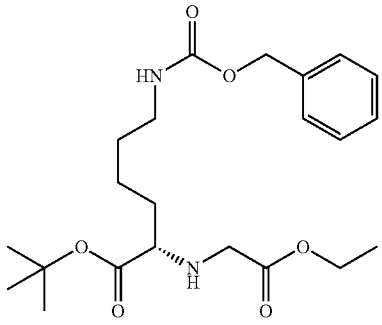 [SMILES: CCOC(=O)CN[C@@H](CCCCNC(=O)OCc1ccccc1)C(=O)OC(C)(C)C]

General experimental procedure for N-alkylation was followed. Reaction was performed on a 1000 mg scale. Product was purified on a Biotage purification system eluting out in 5-50% EtOAc:Hexanes mixture in a gradient elution to give the title compound (929 mg, 82%). $^{1}$H NMR ($CDCl_3$, 400 MHz) δ 7.25-7.39 (m, 5H), 5.09 (s, 2H), 4.87 (br s, 1H), 4.18 (q, J=7.2 Hz, 2H), 3.36 (m, 2H), 3.09-3.25 (m, 3H), 1.36-1.72 (m, 15H), 1.27 (t, J=7.2 Hz, 3H). MS: m/z=423 ($M+H^+$).

Di-tert-butyl 2,2'-(hydrazine-1,1-diyl)diacetate

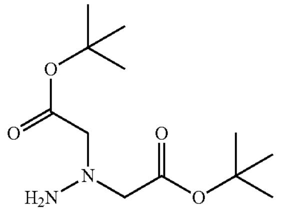 [SMILES: CC(C)(C)OC(=O)CN(N)CC(=O)OC(C)(C)C]

A solution of di-tert-butyl 2,2'-(2-((benzyloxy)carbonyl) hydrazine-1,1-diyl)diacetate (1.05 g, 2.7 mmol) and Pd/C (10%, catalytic amount) in MeOH (20 mL) was stirred under $H_2$ atmosphere (1 atm) for 2 hrs. It was filtered through a short Celite pad, washed with MeOH. The filtrate was concentrated in vacuo. The residue was used directly in the next step without any further purification. MS: m/z=261 $(M+H^+)$.

tert-Butyl 3-(1-(2-(tert-butoxy)-2-oxoethyl)hydrazinyl)propanoate

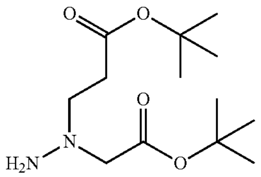 [SMILES: CC(C)(C)OC(=O)CCN(N)CC(=O)OC(C)(C)C]

A solution of benzyl 2-(2-(tert-butoxy)-2-oxoethyl)-2-(3-(tert-butoxy)-3-oxopropyl)hydrazinecarboxylate (0.27 g, 0.67 mmol) and Pd/C (10%, catalytic amount) in MeOH (20 mL) was stirred under $H_2$ atmosphere (1 atm) for 2 hrs. It was filtered through a short Celite pad, washed with MeOH. The filtrate was concentrated in vacuo. The residue was used directly in the next step without any further purification. MS: m/z=275 $(M+H^+)$.

(S)-3-(((Benzyloxy)carbonyl)amino)-4-(tert-butoxy)-4-oxobutanoic acid

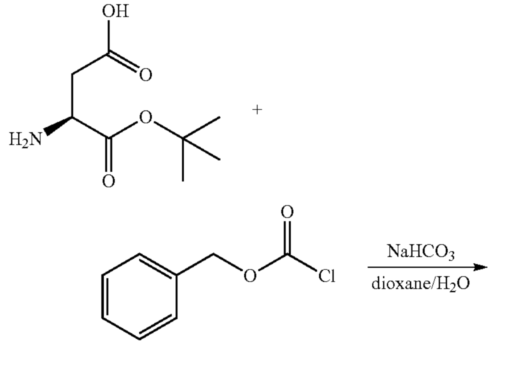

-continued

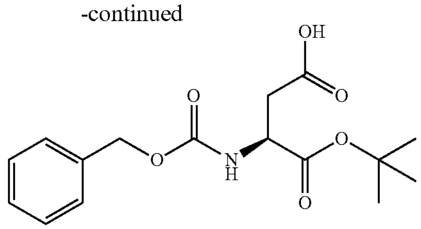

To a solution of (S)-3-amino-4-(tert-butoxy)-4-oxobutanoic acid (1.0 g, 5.3 mmol) and $NaHCO_3$ (1.33 g, 15.8 mmol) in dioxane/H2O (1:1, 20 mL) was added a solution of benzyl chlooroformate (0.9 g, 5.3 mmol) during 2 hrs. The resulting mixture was stirred at room temperature overnight, diluted with EtOAc (20 mL). The layers were separated. The aq. layer was washed with EtOAc (2×20 mL), and then it was acidified with 6N HCl to pH 2. It was then extracted with EtOAc (2×20 mL). The combined organic layers were dried (MgSO4), filtered, and concentrated. It was used directly in the next step without any further purification.

(9S,13S)-tri-tert-Butyl 10-(2-(tert-butoxy)-2-oxoethyl)-3,11-dioxo-1-phenyl-2-oxa-4,10,12-triazapentadecane-9,13,15-tricarboxylate

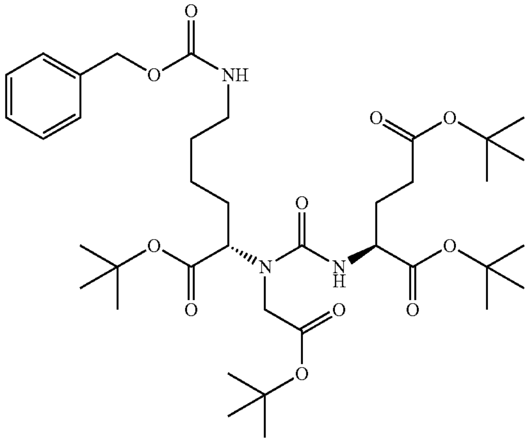 [SMILES: CC(C)(C)OC(=O)CC[C@H](NC(=O)N(CC(=O)OC(C)(C)C)[C@@H](CCCCNC(=O)OCc1ccccc1)C(=O)OC(C)(C)C)C(=O)OC(C)(C)C]

General experimental procedure for the formation of urea was followed. Reaction was performed on a 475 mg scale. Product was purified on a Biotage purification system eluting out in 5-50% EtOAc:Hexanes mixture in a gradient elution to give the title compound (373 mg, 47%). $^1H$ NMR ($CDCl_3$, 400 MHz) δ 7.27-7.38 (m, 5H), 5.84 (d, J=7.2 Hz, 1H), 5.08 (s, 2H), 5.04 (br s, 1H), 4.64 (br s, 1H), 4.32 (q, J=5.2 Hz, 1H), 3.97 (d, J=17.6 Hz, 1H), 3.78 (d, J=17.6 Hz, 1H), 3.18 (d, J=6.0 Hz, 2H), 2.19-2.41 (m, 2H), 2.03-2.14 (m, 1H), 1.81-1.95 (m, 2H), 1.32-1.72 (m, 40H). MS: m/z=736 $(M+H^+)$.

(9S,13S)-10-(Carboxymethyl)-3,11-dioxo-1-phenyl-2-oxa-4,10,12-triazapentadecane-9,13,15-tricarboxylic acid: P008

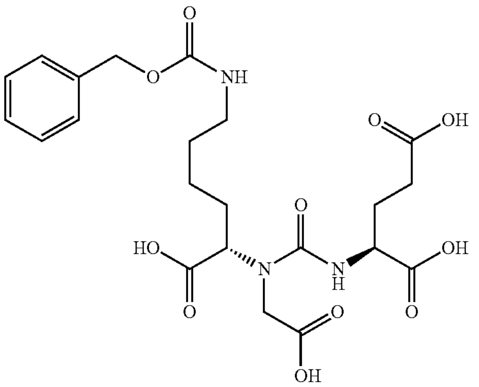 [SMILES: O=C(O)CC[C@H](NC(=O)N(CC(=O)O)[C@@H](CCCCNC(=O)OCc1ccccc1)C(=O)O)C(=O)O]

General procedure for the removal of tert-butyl group from esters was followed. Reaction was performed on 65 mg scale. After HPLC purification, P008 (4 mg, 8%) was obtained. $^1H$ NMR ($CD_3OD$, 400 MHz) δ 7.14-7.28 (m, 5H), 4.96 (s, 2H), 4.50-4.62 (m, 1H), 4.21 (dd, J=9.2, 4.4 Hz, 1H), 4.06 (d, J=18 Hz, 1H), 3.87 (d, J=18 Hz, 1H), 3.01 (t, J=6.4 Hz, 2H), 2.32 (t, J=7.2 Hz, 2H), 2.01-2.12 (m, 1H), 1.78-1.93 (m, 2H), 1.58-1.72 (m, 1H), 1.19-1.52 (m, 4H). MS: m/z=512 (M+H$^+$).

(S)-2-(3-(Carboxymethyl)-3-phenethylureido)pentanedioic acid: P010

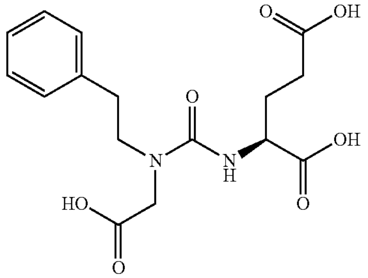 [SMILES: O=C(O)CC[C@H](NC(=O)N(CCc1ccccc1)CC(=O)O)C(=O)O]

General experimental procedure for urea formation and tert-butyl deprotection reaction was followed. Reaction was performed on a 100 mg scale of tert-butyl 2-(phenethylamino)acetate. Isolated 14.1 mg (9.4%) of P010 as a white solid. $^1H$ NMR ($CD_3OD$, 400 MHz) δ 7.23-7.29 (m, 4H), 7.15-7.22 (1H, m), 4.29 (dd, J=9.6, 4.8 Hz, 1H), 3.89 (d, J=18.4 Hz, 1H), 3.77 (d, J=18.4 Hz, 1H), 3.46-3.59 (m, 2H), 2.82-2.94 (m, 2H), 2.39 (t, J=7.6 Hz, 2H), 2.10-2.20 (m, 1H), 1.88-1.98 (m, 1H); MS: m/z=353 (M+H$^+$).

(S)-2-(1-(Carboxymethyl)-2-(2-phenylacetyl)hydrazinecarboxamido)pentanedioic acid: P011

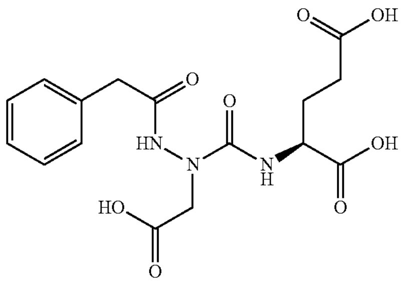 [SMILES: O=C(O)CC[C@H](NC(=O)N(CC(=O)O)NC(=O)Cc1ccccc1)C(=O)O]

General experimental procedure for urea formation and tert-butyl deprotection reaction was followed. Reaction was performed on a 120 mg scale of tert-butyl 2-(2-(2-phenylacetyl)hydrazinyl)acetate. Isolated 10.0 mg (5.8%) of P011 as a white solid. $^1H$ NMR ($CD_3OD$, 400 MHz) δ 7.23-7.31 (m, 4H), 7.20-7.22 (m, 1H), 4.28 (dd, J=9.2, 4.4 Hz, 1H), 3.60 (s, 2H), 2.32 (bt, J=7.4 Hz, 2H), 2.08-2.18 (m, 1H), 1.82-1.92 (m, 1H); MS: m/z=382 (M+H$^+$).

(9S,13S)-9-tert-Butyl 13,15-dimethyl 10-(2-ethoxy-2-oxoethyl)-3,11-dioxo-1-phenyl-2-oxa-4,10,12-triazapentadecane-9,13,15-tricarboxylate

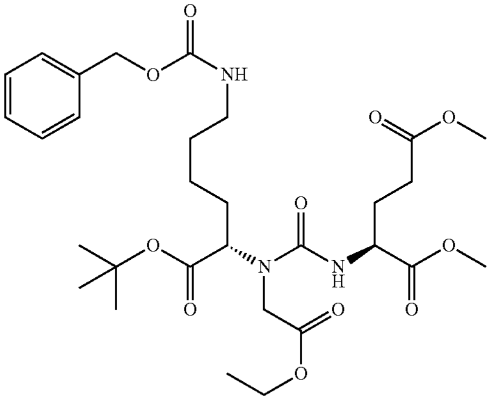 [SMILES: CCOC(=O)CN(C(=O)N[C@@H](CCC(=O)OC)C(=O)OC)[C@@H](CCCCNC(=O)OCc1ccccc1)C(=O)OC(C)(C)C]

General experimental procedure for the formation of urea was followed. Reaction was performed on a 280 mg scale. Product was purified on a Biotage purification system eluting out in 5-50% EtOAc:Hexanes mixture in a gradient elution to give the title compound (367 mg, 54%). $^1H$ NMR ($CDCl_3$, 400 MHz) δ 7.20-7.31 (m, 5H), 5.93 (d, J=6.4 Hz, 1H), 5.05 (br s, 1H), 5.03 (s, 2H), 4.35-4.59 (m, 2H), 4.15 (q, J=13.6, 7.2 Hz, 2H), 4.01 (d, J=18.0 Hz, 1H), 3.85 (d, J=17.6 Hz, 1H), 3.66 (s, 3H), 3.61 (s, 3H), 3.05-3.36 (m, 2H), 2.06-2.18 (m, 1H), 1.74-2.04 (m, 2H), 1.38-1.71 (m, 4H), 1.40 (s, 9H), 1.22 (t, J=7.2 Hz, 3H). MS: m/z=624 (M+H$^+$).

(S)-2-(3-((S)-6-(((Benzyloxy)carbonyl)amino)-1-(hydroxyamino)-1-oxohexan-2-yl)-3-(carboxymethyl)ureido)pentanedioic acid: P012

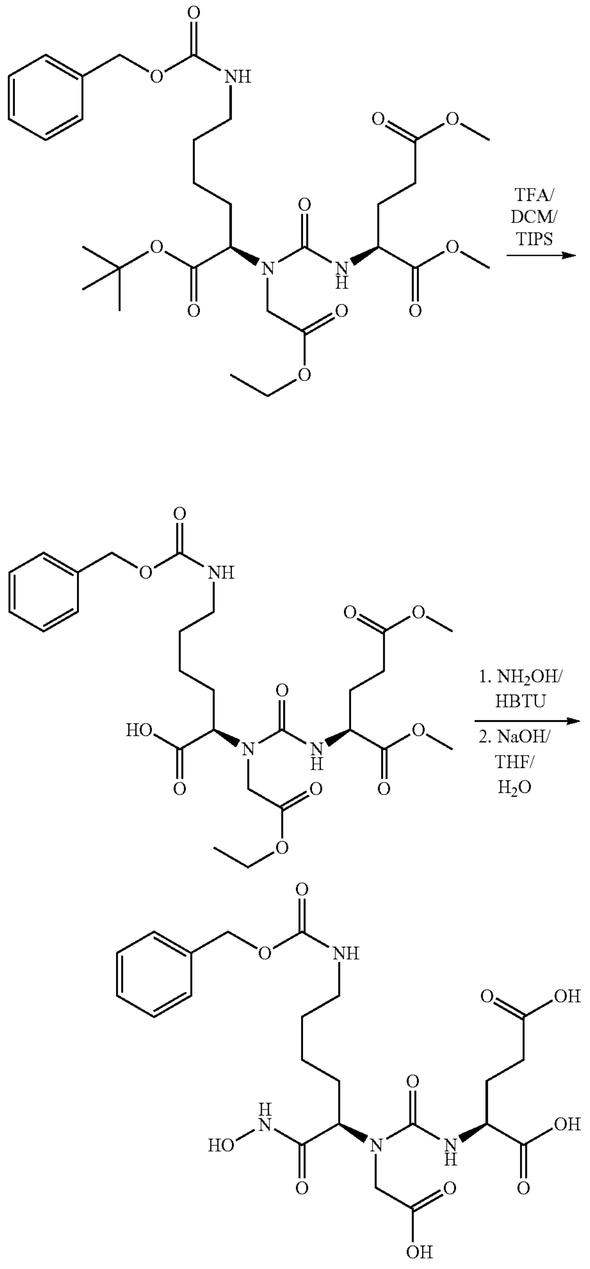

General procedure for the removal of tert-butyl group from esters was followed. Reaction was performed on 367 mg scale. The free acid was then coupled with hydroxylamine, followed by hydrolysis with aqueous NaOH solution. After acidify with HCl, the crude product was purified by HPLC, P012 (8 mg, 28%) was obtained. $^1$H NMR ($CDCl_3$, 400 MHz) δ 7.21-7.38 (m, 5H), 5.05 (br s, 1H), 5.03 (s, 2H), 4.62-4.70 (m, 1H), 4.42 (d, J=18 Hz, 1H), 4.11-4.23 (m, 3H), 3.59-3.74 (m, 3H), 3.08-3.21 (m, 2H), 2.38-2.52 (m, 2H), 1.68-1.96 (m, 2H), 1.19-1.67 (m, 5H). MS: m/z=527 (M+H$^+$).

Di-tert-butyl 2,2'-(2-((3-(benzylthio)-1-methoxy-1-oxopropan-2-yl)carbamoyl)hydrazine-1,1-diyl)diacetate

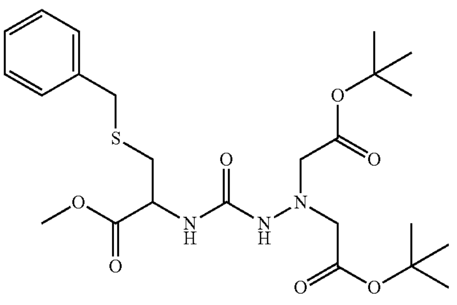 [SMILES: COC(=O)C(CSCc1ccccc1)NC(=O)NN(CC(=O)OC(C)(C)C)CC(=O)OC(C)(C)C]

General experimental procedure for the formation of urea was followed. Reaction was performed on a 352 mg scale. Product was purified on a Biotage purification system eluting out in 5-50% EtOAc:Hexanes mixture in a gradient elution to give the title compound (422 mg, 47%). $^1$H NMR ($CDCl_3$, 400 MHz) δ 7.19-7.35 (m, 5H), 6.60 (br s, 1H), 4.65-4.71 (m, 1H), 3.74 (s, 2H), 3.72 (s, 3H), 3.54-3.66 (m, 4H), 2.74-2.93 (m 2H), 1.44 (s, 9H). MS: m/z=512 (M+H$^+$).

2,2'-(2-((2-(Benzylthio)-1-carboxyethyl)carbamoyl)hydrazine-1,1-diyl)diacetic acid: P013

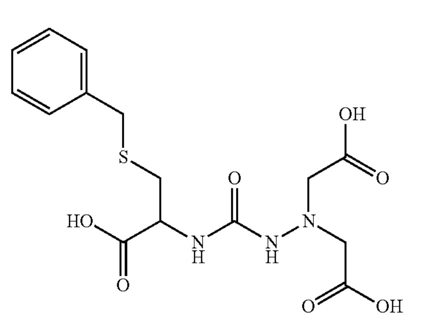 [SMILES: O=C(O)CN(CC(=O)O)NC(=O)NC(CSCc1ccccc1)C(=O)O]

General procedure for the removal of tert-butyl group from esters was followed. Reaction was performed on 211 mg scale. The reaction mixture was then under basic hydrolysis to give crude tri acid. After HPLC purification, P013 (8 mg, 28%) was obtained. $^1$H NMR ($CD_3OD$, 400 MHz) δ 7.18-7.35 (m, 5H), 4.52 (dd, J=7.2, 4.8 Hz, 1H), 3.79 (s, 6H), 2.79-2.96 (m, 2H). MS: m/z=386 (M+H$^+$).

Methyl 3-(benzylthio)-2-(2-(2-(tert-butoxy)-2-oxo-ethyl)-2-(3-(tert-butoxy)-3-oxopropyl)hydrazinecarboxamido)propanoate

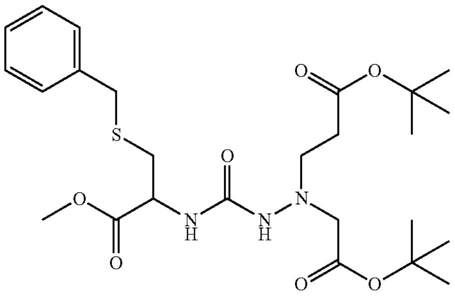 [SMILES: COC(=O)C(CSCc1ccccc1)NC(=O)NN(CCC(=O)OC(C)(C)C)CC(=O)OC(C)(C)C]

General experimental procedure for the formation of urea was followed. Reaction was performed on a 175 mg scale. Product was purified on a Biotage purification system eluting out in 5-50% EtOAc:Hexanes mixture in a gradient elution to give the title compound (260 mg, 74%). $^1$H NMR ($CDCl_3$, 400 MHz) δ 7.16-7.32 (m, 5H), 4.61-4.67 (m, 1H), 3.93 (d, J=17.6 Hz, 1H), 3.83 (d, J=17.6 Hz, 1H), 3.69 (br s, 5H), 3.51-3.57 (m, 2H), 2.88 (dd, J=13.6, 5.2 Hz, 1H), 2.80 (dd, J=13.6, 6.0 Hz, 1H), 2.53 (t, J=6.0 Hz, 2H), 1.43 (s, 9H), 1.41 (s, 9H). MS: m/z=526 ($M+H^+$).

3-(Benzylthio)-2-(2-(2-carboxyethyl)-2-(carboxymethyl)-hydrazinecarboxamido)propanoic acid: P017

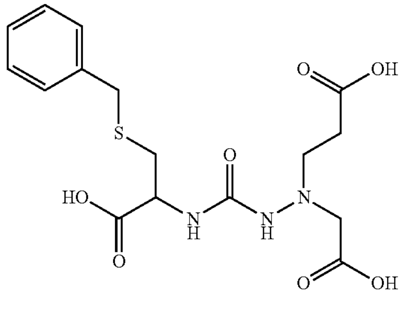 [SMILES: O=C(O)CCN(CC(=O)O)NC(=O)NC(CSCc1ccccc1)C(=O)O]

General procedure for the removal of tert-butyl group from esters was followed. Reaction was performed on 260 mg scale. The reaction mixture was then under basic hydrolysis to give crude tri acid. After HPLC purification, P017 (5 mg, 3%) was obtained. $^1$H NMR ($CD_3OD$, 400 MHz) δ 7.17-7.34 (m, 5H), 4.43-4.49 (m, 1H), 4.03-4.11 (m, 2H), 3.56-3.76 (m, 4H), 2.60-2.92 (m, 4H). MS: m/z=400 ($M+H^+$).

(S)-Di-tert-butyl 2-((S)-2-((((9H-fluoren-9-yl)methoxy)carbonyl)amino)-4-(tert-butoxy)-4-oxobutanamido)pentanedioate

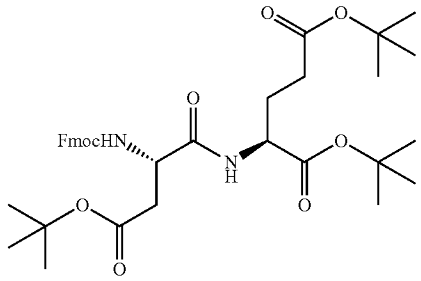

General experimental procedure for the formation of amide was followed. Reaction was performed on a 500 mg scale. Product was purified on a Biotage purification system eluting out in 20-50% EtOAc:Hexanes mixture in a gradient elution to give the title compound (190 mg, 23%). MS: m/z=653 ($M+H^+$).

(S)-Di-tert-butyl 2-((S)-3-(((benzyloxy)carbonyl)amino)-4-(tert-butoxy)-4-oxobutanamido)pentanedioate

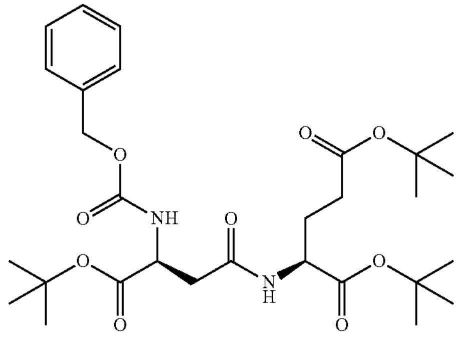 [SMILES: CC(C)(C)OC(=O)CC[C@H](NC(=O)C[C@H](NC(=O)OCc1ccccc1)C(=O)OC(C)(C)C)C(=O)OC(C)(C)C]

General experimental procedure for the formation of amide was followed. Reaction was performed on a 1.09 g scale. Product was purified on a Biotage purification system eluting out in 10-60% EtOAc:Hexanes mixture in a gradient elution to give the title compound (1.5 g, 79%). MS: m/z=565 ($M+H^+$).

(S)-Di-tert-butyl 2-((S)-2-amino-4-(tert-butoxy)-4-oxobutanamido)pentanedioate

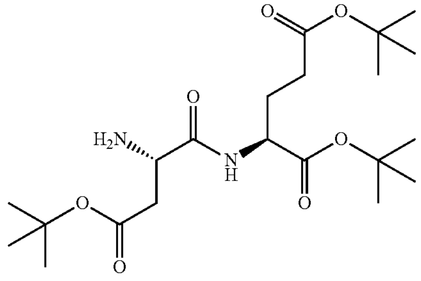 [SMILES: CC(C)(C)OC(=O)CC[C@H](NC(=O)[C@@H](N)CC(=O)OC(C)(C)C)C(=O)OC(C)(C)C]

A solution of (S)-di-tert-butyl 2-((S)-2-((((9H-fluoren-9-yl)methoxy)carbonyl)amino)-4-(tert-butoxy)-4-oxobutanamido)pentanedioate (0.19 g, 0.285 mmol) in 20% solution of piperidine in DMF (10 mL) was stirred at room temperature for 1 hr, and then concentrated in vacuo. The residue was purified on flash column chromatography (silica gel, 10-50% EtOAc/hexanes) to give the desired product (0.078 g, 64%). $^1$H NMR ($CDCl_3$, 400 MHz) δ 7.88 (d, J=8.4 Hz, 1H), 4.39-4.48 (m, 1H), 3.64 (q, J=8.0, 3.6 Hz, 1H), 2.78 (dd, J=16.8, 4.0 Hz, 1H), 2.56 (dd, J=16.8, 8.0 Hz, 1H), 2.19-2.35 (m, 2H), 2.07-2.17 (m, 1H), 1.81-1.93 (m, 1H), 1.45 (s, 9H), 1.43 (s, 9H), 1.42 (s, 9H). MS: m/z=431 (M+H$^+$).

(S)-Di-tert-butyl 2-((S)-3-amino-4-(tert-butoxy)-4-oxobutanamido)pentanedioate

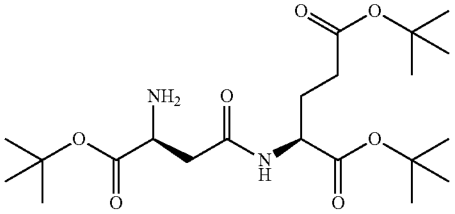 [SMILES: CC(C)(C)OC(=O)CC[C@H](NC(=O)C[C@H](N)C(=O)OC(C)(C)C)C(=O)OC(C)(C)C]

A solution of (S)-di-tert-butyl 2-((R)-3-(((benzyloxy)carbonyl)amino)-4-(tert-butoxy)-4-oxobutanamido)pentanedioate (0.16 g, 0.285 mmol) in 20% solution of piperidine in DMF (10 mL) was stirred at room temperature for 1 hr, and then concentrated in vacuo. The residue was used directly in the next step without any further purification. MS: m/z=431 (M+H$^+$).

(S)-Di-tert-butyl 2-((S)-2-(2-azidoacetamido)-4-(tert-butoxy)-4-oxobutanamido)pentanedioate

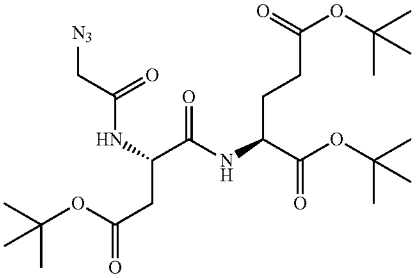 [SMILES: CC(C)(C)OC(=O)CC[C@H](NC(=O)[C@H](CC(=O)OC(C)(C)C)NC(=O)CN=[N+]=[N-])C(=O)OC(C)(C)C]

General experimental procedure for the formation of amide was followed. Reaction was performed on a 78 mg scale. Product was purified on a Biotage purification system eluting out in 30-50% EtOAc:Hexanes mixture in a gradient elution to give the title compound (94 mg, 100%). $^1$H NMR ($CDCl_3$, 400 MHz) δ 7.47 (d, J=8.4 Hz, 1H), 7.13 (d, J=7.6 Hz, 1H), 4.71-4.81 (m, 1H), 4.35-4.42 (m, 1H), 3.99 (s, 2H), 2.88 (dd, J=17.2, 4.0 Hz, 1H), 2.55 (dd, J=17.2, 6.4 Hz, 1H), 2.14-2.32 (m, 2H), 2.03-2.13 (m, 1H), 1.81-1.91 (m, 1H), 1.41 (s, 9H), 1.40 (s, 9H), 1.39 (s, 9H). MS: m/z=514 (M+H$^+$).

(S)-Di-tert-butyl 2-((S)-3-(2-azidoacetamido)-4-(tert-butoxy)-4-oxobutanamido)pentanedioate

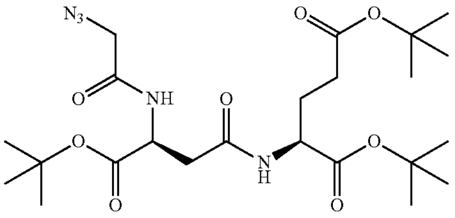 [SMILES: CC(C)(C)OC(=O)CC[C@H](NC(=O)C[C@H](NC(=O)CN=[N+]=[N-])C(=O)OC(C)(C)C)C(=O)OC(C)(C)C]

General experimental procedure for the formation of amide was followed. Reaction was performed on a 123 mg scale. Product was purified on a Biotage purification system eluting out in 30-50% EtOAc:Hexanes mixture in a gradient elution to give the title compound (114 mg, 78%). $^1$H NMR ($CDCl_3$, 400 MHz) δ 7.43 (d, J=7.6 Hz, 1H), 6.22 (d, J=7.6 Hz, 1H), 4.65-4.73 (m, 1H), 4.49-4.54 (m, 1H), 3.97 (s, 2H), 2.90 (dd, J=16.0, 4.4 Hz, 1H), 2.71 (dd, J=16.0, 4.4 Hz, 1H), 2.16-2.46 (m, 2H), 2.04-2.15 (m, 1H), 1.78-1.91 (m, 1H), 1.45 (s, 9H), 1.44 (s, 9H), 1.42 (s, 9H). MS: m/z=514 (M+H$^+$).

(S)-di-tert-butyl 2-((S)-3-(4-azidobutanamido)-4-(tert-butoxy)-4-oxobutanamido)pentanedioate

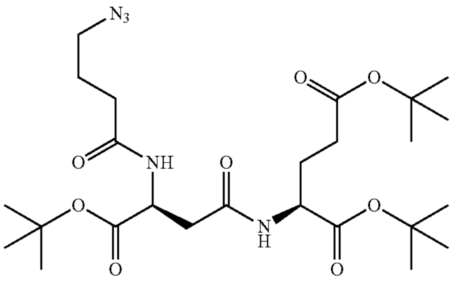 [SMILES: CC(C)(C)OC(=O)CC[C@H](NC(=O)C[C@H](NC(=O)CCCN=[N+]=[N-])C(=O)OC(C)(C)C)C(=O)OC(C)(C)C]

General experimental procedure for the formation of amide was followed. Reaction was performed on a 123 mg scale. Product was purified on a Biotage purification system eluting out in 5-50% EtOAc:Hexanes mixture in a gradient elution to give the title compound (210 mg, 95%). $^1$H NMR ($CDCl_3$, 400 MHz) δ 7.43 (d, J=7.6 Hz, 1H), 6.22 (d, J=7.6 Hz, 1H), 4.63-4.72 (m, 1H), 4.50-4.55 (m, 1H), 2.90 (dd, J=16.0, 4.4 Hz, 1H), 2.71 (dd, J=16.0, 4.4 Hz, 1H), 2.16-2.46 (m, 4H), 2.04-2.15 (m, 2H), 1.62-1.81 (m, 4H), 1.45 (s, 9H), 1.44 (s, 9H), 1.42 (s, 9H). MS: m/z=542 (M+H$^+$).

(S)-Di-tert-butyl 2-((S)-4-(tert-butoxy)-4-oxo-2-(2-(4-(p-tolyl)-1H-1,2,3-triazol-1-yl)acetamido)butanamido)pentanedioate

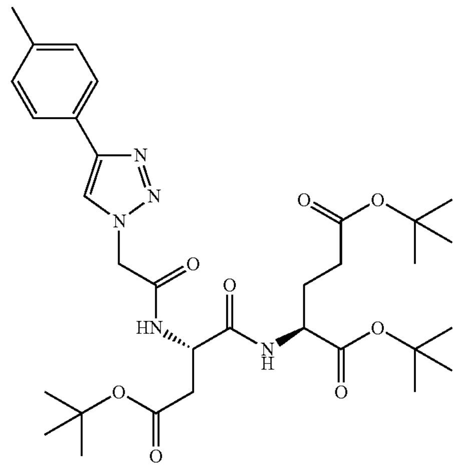 [SMILES: Cc1ccc(-c2cn(CC(=O)N[C@@H](CC(=O)OC(C)(C)C)C(=O)N[C@@H](CCC(=O)OC(C)(C)C)C(=O)OC(C)(C)C)nn2)cc1]

General experimental procedure for click chemistry was followed. Reaction was performed on a 60 mg scale. The crude product was examined with LC-MS, which shows a single peak with desired product mass. MS: m/z=630 $(M+H^+)$.

(S)-2-((S)-3-Carboxy-3-(2-(4-(p-tolyl)-1H-1,2,3-triazol-1-yl)acetamido)-propanamido)pentanedioic acid: P014

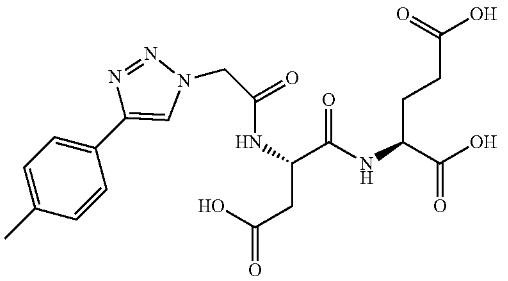 [SMILES: Cc1ccc(-c2cn(CC(=O)N[C@@H](CC(=O)O)C(=O)N[C@@H](CCC(=O)O)C(=O)O)nn2)cc1]

General procedure for the removal of tert-butyl group from esters was followed. Reaction was performed on 74 mg scale. After HPLC purification, P014 (28 mg, 52%) was obtained. $^1$H NMR ($CD_3OD$, 400 MHz) δ 8.75 (d, J=7.6 Hz, 1H), 8.32 (d, J=7.6 Hz, 1H), 7.70 (d, J=8.0 Hz, 2H), 7.25 (d, J=8.0 Hz, 2H), 5.27 (s, 2H), 4.79-4.82 (m, 1H), 4.41-4.49 (m, 1H), 2.72-2.92 (m, 2H), 2.42 (t, J=8.0 Hz, 2H), 2.37 (s, 3H), 2.16-2.26 (m, 1H), 1.91-2.03 (m, 1H). MS: m/z=462 $(M+H^+)$.

(S)-2-((S)-3-(((Benzyloxy)carbonyl)amino)-3-carboxypropanamido)pentanedioic acid: P015

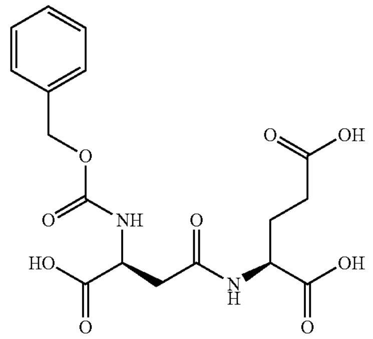 [SMILES: O=C(O)CC[C@H](NC(=O)C[C@H](NC(=O)OCc1ccccc1)C(=O)O)C(=O)O]

General procedure for the removal of tert-butyl group from esters was followed. Reaction was performed on 17 mg scale. After HPLC purification, P015 (10 mg, 84%) was obtained. $^1$H NMR ($CD_3OD$, 400 MHz) δ 7.20-7.35 (m, 5H), 5.08 (s, 2H), 4.53 (t, J=7.4 Hz, 1H), 4.39-4.45 (m, 1H), 2.78 (d, J=6.4 Hz, 2H), 2.36 (t, J=8.0 Hz, 2H), 2.09-2.21 (m, 1H), 1.82-1.95 (m, 1H). MS: m/z=397 $(M+H^+)$.

(S)-Di-tert-butyl 2-((S)-4-(tert-butoxy)-4-oxo-3-(2-(4-(p-tolyl)-1H-1,2,3-triazol-1-yl)acetamido)butanamido)pentanedioate

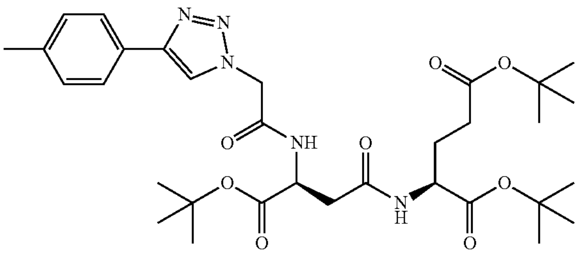 [SMILES: Cc1ccc(-c2cn(CC(=O)N[C@@H](CC(=O)N[C@@H](CCC(=O)OC(C)(C)C)C(=O)OC(C)(C)C)C(=O)OC(C)(C)C)nn2)cc1]

General experimental procedure for click chemistry was followed. Reaction was performed on a 6 mg scale. The crude product was diluted with water, extracted with DCM (2×20 mL). The combined organic layers were dried ($MgSO_4$), filtered, and concentrated in vacuo. The residue was purified on flash column chromatography (silica gel, 20-60% EtOAc/hexanes) to give the desired product. $^1$H NMR ($CDCl_3$, 400 MHz) δ 7.95 (s, 1H), 7.70 (d, J=8.2 Hz, 2H), 7.20 (d, J=8.2 Hz, 2H), 6.34 (d, J=8.0 Hz, 1H), 5.12 (s, 2H), 4.65-4.73 (m, 1H), 3.97-4.45 (m, 1H), 2.86 (dd, J=16.0, 4.4 Hz, 1H), 2.73 (dd, J=16.0, 4.6 Hz, 1H), 2.35 (s, 3H), 2.17-2.34 (m, 2H), 2.03-2.15 (m, 1H), 1.80-1.92 (m, 1H), 1.45 (s, 9H), 1.42 (s, 9H), 1.41 (s, 9H). MS: m/z=630 $(M+H^+)$.

(S)-2-((S)-3-Carboxy-3-(2-(4-(p-tolyl)-1H-1,2,3-triazol-1-yl)acetamido)-propanamido)pentanedioic acid: P016

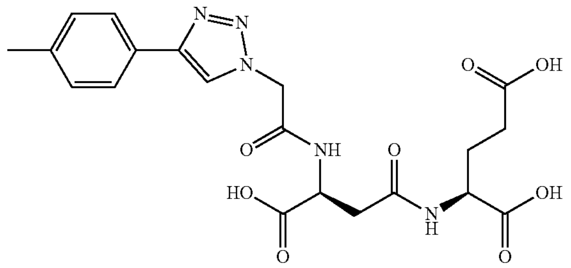 [SMILES: Cc1ccc(-c2cn(CC(=O)N[C@@H](CC(=O)N[C@@H](CCC(=O)O)C(=O)O)C(=O)O)nn2)cc1]

General procedure for the removal of tert-butyl group from esters was followed. Reaction was performed on 7 mg scale. After HPLC purification, P016 (3 mg, 51%) was obtained. $^1H$ NMR ($CDCl_3$, 400 MHz) δ 8.19 (s, 1H), 7.60 (d, J=8.0 Hz, 2H), 7.15 (d, J=8.0 Hz, 2H), 5.17 (s, 2H), 4.67-4.72 (m, 1H), 4.33-4.38 (m, 1H), 2.79 (d, J=6.0 Hz, 2H), 2.32 (t, J=7.6 Hz, 2H), 2.27 (s, 3H), 2.03-2.15 (m, 1H), 1.82-1.95 (m, 1H). MS: m/z=462 (M+H$^+$).

(S)-Di-tert-butyl 2-((S)-4-(tert-butoxy)-3-(4-(4-(3-fluoropropyl)-1H-1,2,3-triazol-1-yl)butanamido)-4-oxobutanamido)pentanedioate

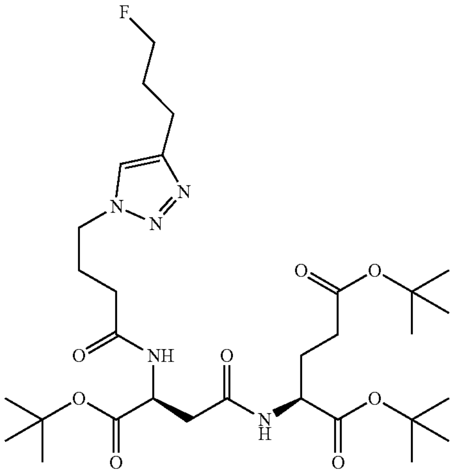 [SMILES: CC(C)(C)OC(=O)CC[C@H](NC(=O)C[C@H](NC(=O)CCCn1cc(CCCF)nn1)C(=O)OC(C)(C)C)C(=O)OC(C)(C)C]

General experimental procedure for click chemistry was followed. Reaction was performed on a 12 mg scale. The crude product was diluted with water, extracted with DCM (2×20 mL). The combined organic layers were dried ($MgSO_4$), filtered, and concentrated in vacuo. The residue was purified on flash column chromatography (silica gel, 20-60% EtOAc/hexanes) to give the desired product (9.4 mg, 64%). MS: m/z=600 (M+H$^+$).

(9S,13S)-Tri-tert-butyl 10-methyl-3,11-dioxo-1-phenyl-2-oxa-4,10,12-triazapentadecane-9,13,15-tricarboxylate

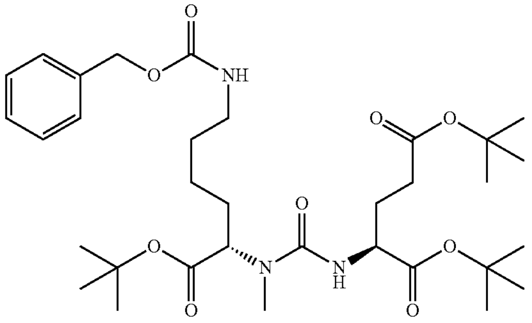 [SMILES: CN(C(=O)N[C@@H](CCC(=O)OC(C)(C)C)C(=O)OC(C)(C)C)[C@@H](CCCCNC(=O)OCc1ccccc1)C(=O)OC(C)(C)C]

General experimental procedure for the formation of urea was followed. Reaction was performed on a 169 mg scale. Product was purified on a Biotage purification system eluting out in 5-50% EtOAc:Hexanes mixture in a gradient elution to give the title compound (53 mg, 15%). $^1H$ NMR ($CDCl_3$, 400 MHz) δ 7.25-7.35 (m 5H), 5.04 (s, 2H), 4.8-4.91 (m, 1H), 4.26-4.38 (m, 1H), 3.08-3.22 (m, 2H), 2.78 (s, 3H), 2.19-2.42 (m, 4H), 1.44-2.12 (m, 4H), 1.45 (s, 9H), 1.42 (s, 9H), 1.41 (s, 9H), 1.22-1.36 (m, 2H). MS: m/z=636 (M+H$^+$).

(9S,13S)-10-Methyl-3,11-dioxo-1-phenyl-2-oxa-4,10,12-triazapentadecane-9,13,15-tricarboxylic acid: P018

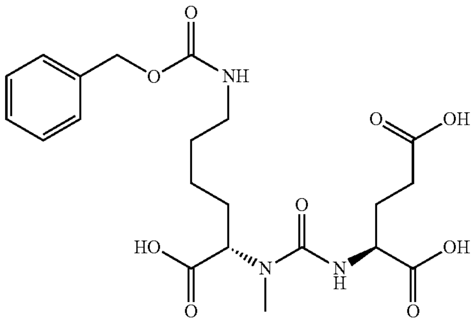

General procedure for the removal of tert-butyl group from esters was followed. Reaction was performed on 164 mg scale. After HPLC purification, P018 (7.1 mg, 6%) was obtained. $^1H$ NMR ($CD_3OD$, 400 MHz) δ 7.21-7.31 (m, 5H), 5.04 (s, 2H), 4.68-4.76 (m, 1H), 4.22-4.32 (m, 1H), 3.09 (t, J=7.2 Hz, 2H), 2.83 (s, 3H), 2.44 (t, J=7.2 Hz, 2H), 2.12-2.22 (m, 1H), 1.86-2.25 (m, 2H), 1.66-1.82 (m, 1H), 1.42-1.56 (m, 2H), 1.25-1.38 (m, 2H). MS: m/z=468 (M+H$^+$).

(9S,13S)-Tri-tert-butyl 12-methyl-3,11-dioxo-1-phenyl-2-oxa-4,10,12-triazapentadecane-9,13,15-tricarboxylate

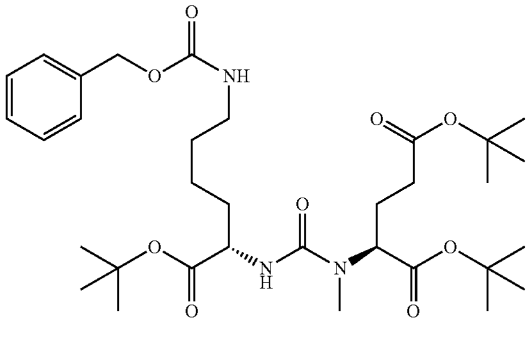 [SMILES: CN(C(=O)N[C@@H](CCCCNC(=O)OCc1ccccc1)C(=O)OC(C)(C)C)[C@@H](CCC(=O)OC(C)(C)C)C(=O)OC(C)(C)C]

General experimental procedure for the formation of urea was followed. Reaction was performed on a 228 mg scale. Product was purified on a Biotage purification system eluting out in 5-50% EtOAc:Hexanes mixture in a gradient elution to give the title compound (205 mg, 38%). $^1$H NMR ($CDCl_3$, 400 MHz) δ 7.22-7.38 (m 5H), 5.04 (s, 2H), 4.28-4.42 (m, 2H), 3.15-3.22 (m, 2H), 2.78 (s, 3H), 2.19-2.42 (m, 4H), 1.44-2.12 (m, 4H), 1.45 (s, 9H), 1.42 (s, 9H), 1.41 (s, 9H), 1.22-1.36 (m, 2H). MS: m/z=636 (M+H$^+$).

(9S,13S)-12-Methyl-3,11-dioxo-1-phenyl-2-oxa-4,10,12-triazapentadecane-9,13,15-tricarboxylic acid: P019

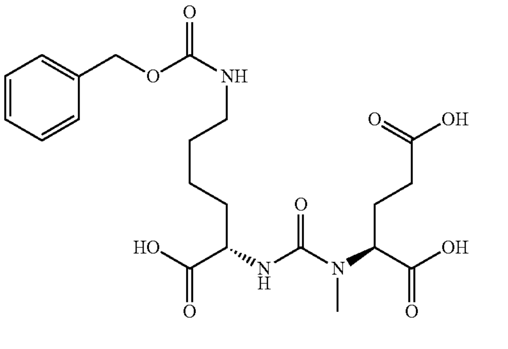 [SMILES: CN(C(=O)N[C@@H](CCCCNC(=O)OCc1ccccc1)C(=O)O)[C@@H](CCC(=O)O)C(=O)O]

General procedure for the removal of tert-butyl group from esters was followed. Reaction was performed on 164 mg scale. After HPLC purification, P019 (7.1 mg, 6%) was obtained. $^1$H NMR ($CD_3OD$, 400 MHz) δ 7.19-7.25 (m, 5H), 4.96 (s, 2H), 4.72-4.85 (m, 1H), 4.15-4.21 (m, 1H), 3.03 (t, J=7.2 Hz, 2H), 2.75 (s, 3H), 2.12-2.25 (m, 3H), 1.62-1.95 (m, 3H), 1.28-1.51 (m, 4H). MS: m/z=468 (M+H$^+$).

(S)-Di-tert-butyl 2-((S)-4-(tert-butoxy)-3-(2-(4-(3-fluoropropyl)-1H-1,2,3-triazol-1-yl)acetamido)-4-oxobutanamido)pentanedioate

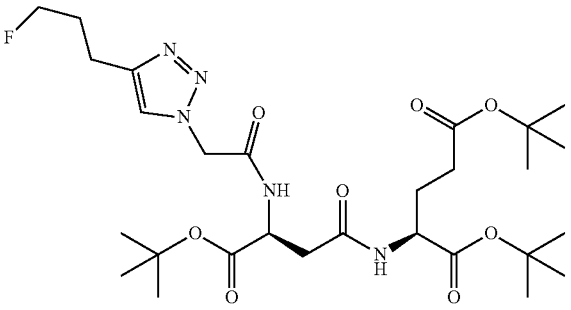 [SMILES: CC(C)(C)OC(=O)CC[C@H](NC(=O)C[C@H](NC(=O)Cn1cc(CCCF)nn1)C(=O)OC(C)(C)C)C(=O)OC(C)(C)C]

General experimental procedure for click chemistry was followed. Reaction was performed on a 120 mg scale. The crude product was diluted with water, extracted with DCM (2×20 mL). The combined organic layers were dried ($MgSO_4$), filtered, and concentrated in vacuo. The residue was purified on flash column chromatography (silica gel, 30-80% EtOAc/hexanes) to give the desired product (9.3 mg, 6%). $^1$H NMR ($CDCl_3$, 400 MHz) δ 7.51 (s, 1H), 5.18 (s, 2H), 4.61-4.72 (m, 1H), 4.38-4.55 (m, 3H), 2.82-2.89 (m, 2H), 2.67-2.78 (m, 2H), 2.01-2.43 (m, 4H), 1.56-1.78 (m, 2H), 1.45 (s, 9H), 1.42 (s, 9H), 1.41 (s, 9H). MS: m/z=600 (M+H$^+$).

(S)-2-((S)-3-Carboxy-3-(2-(4-(3-fluoropropyl)-1H-1,2,3-triazol-1-yl)acetamido)-propanamido)pentanedioic acid: P020

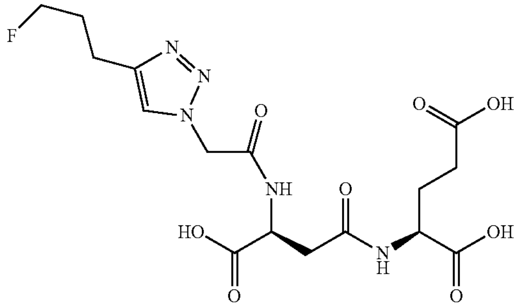 [SMILES: O=C(O)CC[C@H](NC(=O)C[C@H](NC(=O)Cn1cc(CCCF)nn1)C(=O)O)C(=O)O]

General procedure for the removal of tert-butyl group from esters was followed. Reaction was performed on 6 mg scale. After HPLC purification, P020 (1.2 mg, 27%) was obtained. $^1$H NMR ($CD_3OD$, 400 MHz) δ 7.88 (s, 1H), 5.18 (s, 2H), 4.58-4.68 (m, 1H), 4.38-4.46 (m, 3H), 2.78-2.85 (m, 4H), 2.39 (t, J=7.6 Hz, 2H), 1.91-2.32 (m, 4H). MS: m/z=432 (M+H$^+$).

(S)-2-(2-(Benzyloxycarbonyl)-1-(carboxymethyl) hydrazinecarboxamido) pentanedioic acid: P021

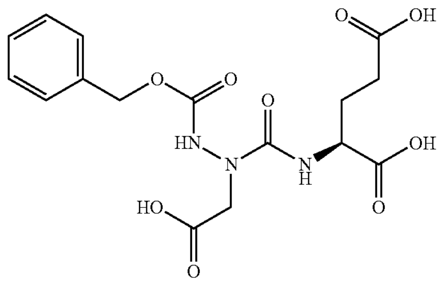 [SMILES: O=C(O)CC[C@H](NC(=O)N(CC(=O)O)NC(=O)OCc1ccccc1)C(=O)O]

General experimental procedure for urea formation and tert-butyl deprotection reaction was followed. Reaction was performed on a 117 mg scale of benzyl 2-(2-tert-butoxy-2-oxoethyl)hydrazinecarboxylate. Isolated 23.5 mg (14.2%) of P021 as a white solid. $^1$H NMR ($CD_3OD$, 400 MHz) δ 7.26-7.40 (m, 5H), 5.17 (s, 2H), 4.31 (dd, J=9.0, 4.4 Hz, 1H), 3.96 (s, 2H), 2.36 (bt, J=7.4 Hz, 2H), 2.14-2.24 (m, 1H), 1.88-1.98 (m, 1H); MS: m/z=398 ($M+H^+$).

(S)-di-tert-butyl 2-(3-(2-(tert-butoxy)-2-oxoethyl) ureido)pentanedioate

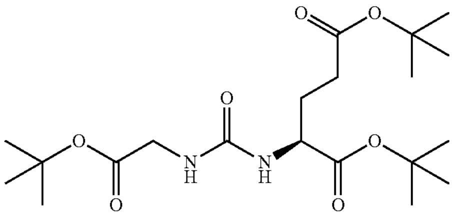 [SMILES: CC(C)(C)OC(=O)CC[C@H](NC(=O)NCC(=O)OC(C)(C)C)C(=O)OC(C)(C)C]

General experimental procedure for the formation of urea was followed. Reaction was performed on a 97 mg scale. Product was purified on a Biotage purification system eluting out in 5-50% EtOAc:Hexanes mixture in a gradient elution to give the title compound (125 mg, 90%). $^1$H NMR ($CDCl_3$, 400 MHz) δ 4.29-4.39 (m, 1H), 3.79-3.94 (m, 2H), 2.21-2.38 (m, 2H), 2.01-2.11 (m, 1H), 1.81-1.91 (m, 1H), 1.45 (s, 9H), 1.42 (s, 9H), 1.41 (s, 9H). MS: m/z=417 ($M+H^+$).

(S)-2-(3-(Carboxymethyl)ureido)pentanedioic acid: P022

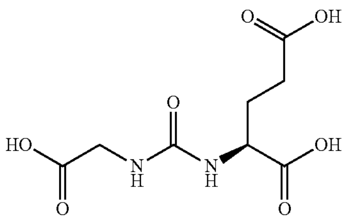 [SMILES: O=C(O)CC[C@H](NC(=O)NCC(=O)O)C(=O)O]

General procedure for the removal of tert-butyl group from esters was followed. Reaction was performed on 9.3 mg scale. After HPLC purification, P022 (5.0 mg, 90%) was obtained. $^1$H NMR ($CD_3OD$, 400 MHz) δ 4.20-4.33 (m, 1H), 3.70-3.84 (m, 2H), 2.28-2.35 (m, 2H), 2.01-2.12 (m, 1H), 1.78-1.86 (m, 1H). MS: m/z=249 ($M+H^+$).

(S)-2-((S)-3-(4-Azidobutanamido)-3-carboxypropanamido)pentanedioic acid: P023

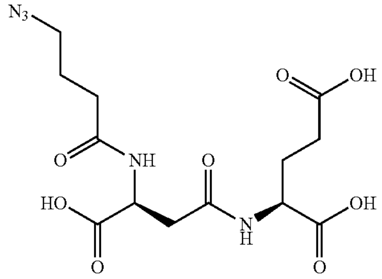 [SMILES: [N-]=[N+]=NCCCC(=O)N[C@@H](CC(=O)N[C@@H](CCC(=O)O)C(=O)O)C(=O)O]

General procedure for the removal of tert-butyl group from esters was followed. Reaction was performed on 5.5 mg scale. After HPLC purification, P023 (3.0 mg, 79%) was obtained. $^1$H NMR ($CD_3OD$, 400 MHz) δ 4.65 (t, J=6.0 Hz, 1H), 4.30-4.39 (m, 1H), 3.26 (t, J=6.8 Hz, 2H), 2.72 (d, J=6.0 Hz, 2H), 2.22-2.35 (m, 4H), 2.02-2.16 (m, 1H), 1.75-1.89 (m, 3H). MS: m/z=374 ($M+H^+$).

(S)-2-(3-((S)-1,5-Di-tert-butoxy-1,5-dioxopentan-2-yl)-1-methylureido)propanoic acid

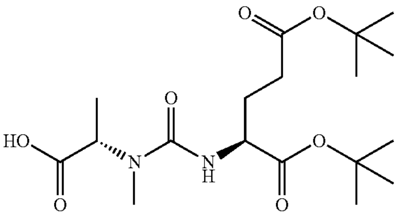 [SMILES: C[C@@H](C(=O)O)N(C)C(=O)N[C@@H](CCC(=O)OC(C)(C)C)C(=O)OC(C)(C)C]

General experimental procedure for the formation of urea was followed. Reaction was performed on a 160 mg scale. Product was purified on a Biotage purification system eluting out in 30-100% EtOAc:Hexanes mixture in a gradient elution to give the title compound (149 mg, 69%). MS: m/z=389 ($M+H^+$).

(S)-2-(3-((S)-1-carboxyethyl)-3-methylureido)pentanedioic acid: P024

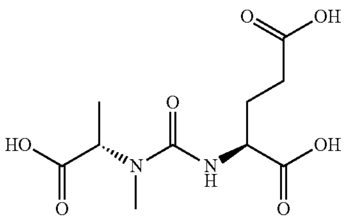

General procedure for the removal of tert-butyl group from esters was followed. Reaction was performed on 149 mg scale. After HPLC purification, P024 (100 mg, 94%) was obtained. $^{1}H$ NMR ($CD_3OD$, 400 MHz) δ 4.75-4.82 (m, 1H), 3.99-4.18 (m, 1H), 2.94 (s, 3H), 2.30-2.55 (m, 4H), 1.43 (d, J=7.2 Hz, 3H). MS: m/z=277 (M+$H^+$).

(S)-Dimethyl 2-(3-((S)-1-methoxy-1-oxopropan-2-yl)ureido)pentanedioate

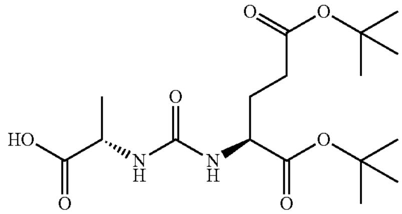 [SMILES: C[C@H](NC(=O)N[C@@H](CCC(=O)OC(C)(C)C)C(=O)OC(C)(C)C)C(=O)O]

General experimental procedure for the formation of urea was followed. Reaction was performed on a 160 mg scale. Product was purified on a Biotage purification system eluting out in 30-100% EtOAc:Hexanes mixture in a gradient elution to give the title compound (16 mg, 8%). MS: m/z=375 (M+$H^+$).

(S)-2-(3-((S)-1-Carboxyethyl)ureido)pentanedioic acid: P025

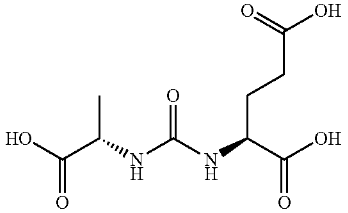

General procedure for the removal of tert-butyl group from esters was followed. Reaction was performed on 16 mg scale. After HPLC purification, P025 (3.0 mg, 26%) was obtained. $^{1}H$ NMR ($CD_3OD$, 400 MHz) δ 4.20-4.32 (m, 2H), 2.35-2.41 (m, 2H), 2.05-2.16 (m, 1H), 1.80-1.91 (m, 1H), 1.35 (d, J=7.2 Hz, 3H). MS: m/z=263 (M+$H^+$).

(S)-Di-tert-butyl 2-(3-(3-ethoxy-3-oxopropyl)ureido)pentanedioate

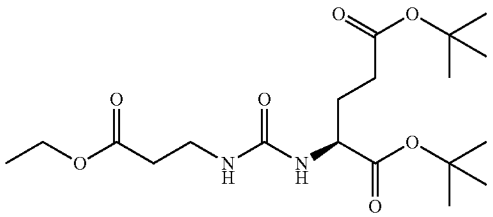 [SMILES: CCOC(=O)CCNC(=O)N[C@@H](CCC(=O)OC(C)(C)C)C(=O)OC(C)(C)C]

General experimental procedure for the formation of urea was followed. Reaction was performed on a 160 mg scale. Product was purified on a Biotage purification system eluting out in 5-50% EtOAc:Hexanes mixture in a gradient elution to give the title compound (139 mg, 61%). MS: m/z=403 (M+$H^+$).

(S)-2-(3-(2-Carboxyethyl)ureido)pentanedioic acid: P026

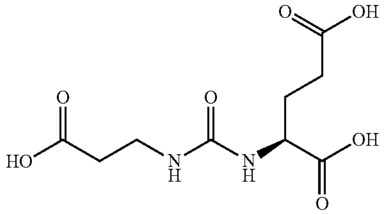 [SMILES: O=C(O)CCNC(=O)N[C@@H](CCC(=O)O)C(=O)O]

General procedure for the removal of tert-butyl group from esters was followed. Reaction was performed on 139 mg scale. The reaction mixture was then under basic hydrolysis to give crude tri acid. After HPLC purification, P026 (3.4 mg, 4%) was obtained. $^{1}H$ NMR ($CD_3OD$, 400 MHz) δ 4.09-4.15 (m, 1H), 3.62-3.75 (m, 2H), 2.58-2.64 (m, 2H), 2.31-2.48 (m 2H), 2.02-2.12 (m, 1H), 1.85-1.99 (m, 1H). MS: m/z=263 (M+$H^+$).

(S)-Di-tert-butyl 2-(((2-(tert-butoxy)-2-oxoethoxy)carbonyl)amino)pentanedioate

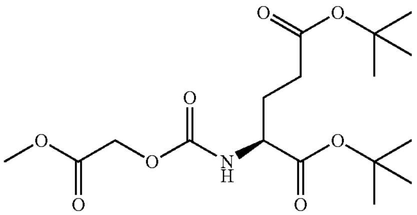 [SMILES: COC(=O)COC(=O)N[C@@H](CCC(=O)OC(C)(C)C)C(=O)OC(C)(C)C]

General experimental procedure for the formation of urea was followed. Reaction was performed on a 200 mg scale. Product was purified on a Biotage purification system eluting out in 5-50% EtOAc:Hexanes mixture in a gradient elution to give the title compound (92 mg, 36%). MS: m/z=286 (M+$H^+$).

(S)-2-(((Carboxymethoxy)carbonyl)amino)pentanedioic acid: P027

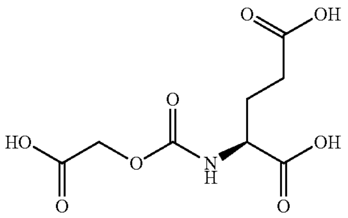

General procedure for the removal of tert-butyl group from esters was followed. Reaction was performed on 92 mg scale. The reaction mixture was then under basic hydrolysis to give crude tri acid. After HPLC purification, P027 (3.5 mg, 6%) was obtained. $^{1}H$ NMR ($CD_3OD$, 400 MHz) δ 4.44-4.62 (m, 2H), 4.16-4.22 (m, 1H), 2.45 (t, J=6.8 Hz, 2H), 2.11-21 (m, 1H), 1.86-1.95 (m, 1H). MS: m/z=250 ($M+H^+$).

Dimethyl 2,2'-((2-(tert-butoxy)-2-oxoethyl) azanediyl)diacetate

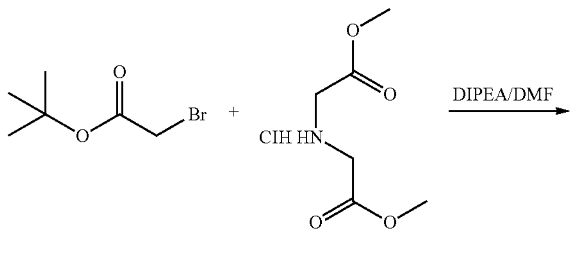

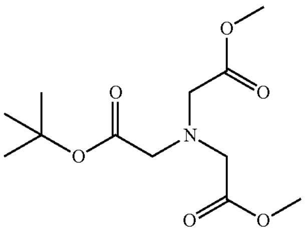

A mixture of tert-butyl 2-bromoacetate (0.55 g, 2.82 mmol), dimethyl 2,2'-azanediylacetate hydrochloride (0.557, 2.82 mmol), and DIPEA (1.47 mL, 8.5 mmol) in DMF (3.0 mL) was stirred at room temperature overnight and then concentrated in vacuo. The residue was purified on flask column chromatoigraphy (silica gel, 5-30% EtOAc/hexanes) to give the desired product (0.58 g, 75%). MS: m/z=276 ($M+H^+$).

2-(Bis(2-methoxy-2-oxoethyl)amino)acetic acid

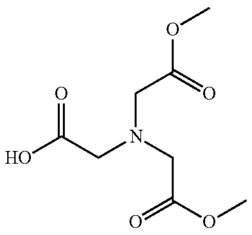

General procedure for the removal of tert-butyl group from esters was followed. Reaction was performed on 580 mg scale. After the removal of solvents, the desired product (460 mg, 99%) was obtained. MS: m/z=220 ($M+H^+$).

(S)-Dimethyl 2,2'-((2-((3-(benzylthio)-1-methoxy-1-oxopropan-2-yl)amino)-2-oxoethyl)azanediyl)diacetate

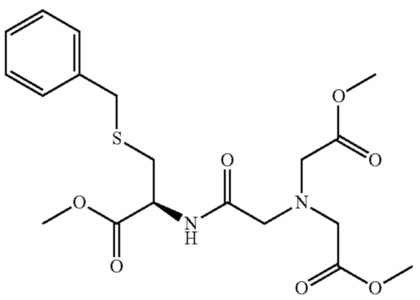 [SMILES: COC(=O)CN(CC(=O)N[C@H](CSCc1ccccc1)C(=O)OC)CC(=O)OC]

General experimental procedure for the formation of amide was followed. Reaction was performed on 460 mg scale. Product was purified on a Biotage purification system eluting out in 5-40% EtOAc:Hexanes mixture in a gradient elution to give the title compound (430 mg, 48%). MS: m/z=427 ($M+H^+$).

(S)-2,2'-((2-((2-(Benzylthio)-1-carboxyethyl)amino)-2-oxoethyl)azanediyl)diacetic acid: P028

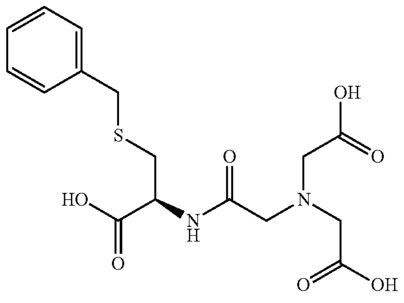 [SMILES: O=C(O)CN(CC(=O)O)CC(=O)N[C@H](CSCc1ccccc1)C(=O)O]

A mixture of (S)-Dimethyl 2,2'-((2-((3-(benzylthio)-1-methoxy-1-oxopropan-2-yl)amino)-2-oxoethyl)azanediyl) diacetate (460 mg, 0.58 mmol) and aqueous NaOH (1.0 M, 2.04 mL, 2.04 mmol) in THF/NaOH (1:1, 4 mL) was stirred at room temperature for 3 hrs, coated in vacuo. The residue was acidified with 1 N aqueous HCl solution and purified by HPLC to give the desired product (125 mg, 56%). $^{1}H$ NMR (DMSO-$d_6$, 400 MHz) δ 8.35 (d, J=8.4 Hz, 1H), 7.18-7.31 (m, 5H), 4.41-4.51 (m, 1H), 3.72 (s, 2H), 3.51 (s, 4H), 3.41 (s, 2H), 2.74-2.82 (m, 1H), 2.62-2.71 (m, 1H). MS: m/z=385 ($M+H^+$).

(S)-Di-tert-butyl 2-(5-ethoxy-5-oxopentanamido) pentanedioate

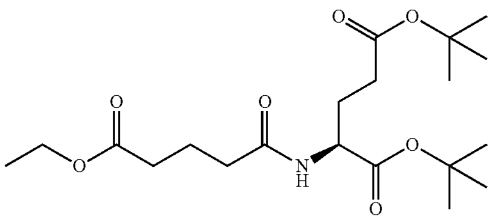 [SMILES: CCOC(=O)CCCC(=O)N[C@@H](CCC(=O)OC(C)(C)C)C(=O)OC(C)(C)C]

General experimental procedure for the formation of amide was followed. Reaction was performed on a 200 mg scale. Product was purified on a Biotage purification system eluting out in 5-60% EtOAc:Hexanes mixture in a gradient elution to give the title compound (139 mg, 51%). MS: m/z=402 (M+H$^+$).

(S)-2-(4-Carboxybutanamido)pentanedioic acid: P030

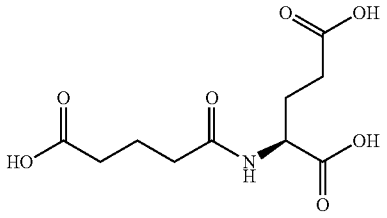 [SMILES: O=C(O)CCCC(=O)N[C@@H](CCC(=O)O)C(=O)O]

General procedure for the removal of tert-butyl group from esters was followed. Reaction was performed on 99 mg scale. The reaction mixture was then under basic hydrolysis to give crude tri acid. After HPLC purification, P030 (5.7 mg, 9%) was obtained. $^1$H NMR ($CD_3OD$, 400 MHz) δ 4.37-4.42 (m, 1H), 2.25-2.41 (m 6H), 2.10-2.20 (m, 1H), 1.82-1.95 (m, 3H). MS: m/z=262 (M+H$^+$).

(S)-Di-tert-butyl 2-(5-ethoxy-N-methyl-5-oxopentanamido)pentanedioate

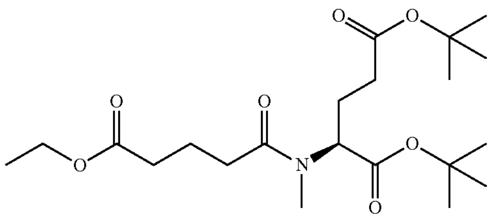 [SMILES: CCOC(=O)CCCC(=O)N(C)[C@@H](CCC(=O)OC(C)(C)C)C(=O)OC(C)(C)C]

To a solution NaH (12 mg, 0.299 mmol) in DMF (2.0 mL) was added (S)-di-tert-butyl 2-(5-ethoxy-5-oxopentanamido) pentanedioate (120 mg, 0.299 mmol). The resulting mixture was stirred at room temperature for 20 min, and than MeI (excess) was added. The reaction mixture was stirred at room temperature overnight, concentrated in vacuo. The residue was purified on flash column chromatography (silica gel, 0-50% EtOac/hexanes) to give the desired product (104 mg, 84%). MS: m/z=416 (M+H$^+$).

(S)-2-(4-Carboxy-N-methylbutanamido)pentanedioic acid: P029

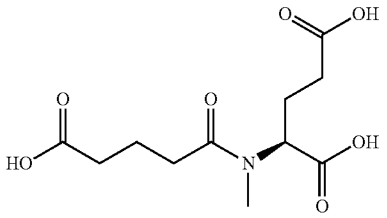 [SMILES: CN(C(=O)CCCC(=O)O)[C@@H](CCC(=O)O)C(=O)O]

General procedure for the removal of tert-butyl group from esters was followed. Reaction was performed on 104 mg scale. The reaction mixture was then under basic hydrolysis to give crude tri acid. After HPLC purification, P029 (1.2 mg, 2%) was obtained. $^1$H NMR ($CD_3OD$, 400 MHz) δ 4.99-5.09 (m, 1H), 2.96 (s, 3H), 2.47 (t, J=7.2 Hz, 2H), 2.15-2.41 (m 6H), 2.95-2.10 (m, 1H), 1.82-1.95 (m, 1H). MS: m/z=262 (M+H$^+$).

(S)-2-((S)-2-(4-Azidobutanamido)propanamido) pentanedioic acid: P031

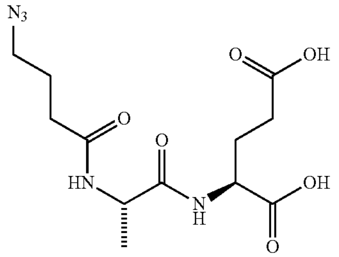 [SMILES: C[C@H](NC(=O)CCCN=[N+]=[N-])C(=O)N[C@@H](CCC(=O)O)C(=O)O]

General experimental procedure for amidation and methyl ester deprotection reaction was followed. Reaction was performed on a 10 mg scale of (S)-2-((S)-2-aminopropanamido)pentanedioic acid. Isolated 2.0 mg (15.0%) of P031 as a white gum. $^1$H NMR ($CDCl_3$, 400 MHz) δ 4.39-4.46 (m, 1H), 4.34 (dd, J=14.4, 7.2 Hz, 1H), 3.32 (t, J=6.8 Hz, 2H), 2.40 (t, J=7.6 Hz, 2H), 2.31 (dt, J=7.6, 2.8 Hz, 2H), 2.13-2.23 (m, 1H), 1.81-1.97 (m, 3H), 1.33 (d, J=7.2 Hz, 3H). MS: m/z=330 (M+H$^+$).

(S)-Tert-butyl-6-(((benzyloxy)carbonyl)amino)-2-(methylamino)hexanoate

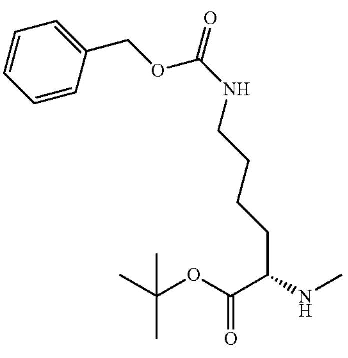 [SMILES: CN[C@@H](CCCCNC(=O)OCc1ccccc1)C(=O)OC(C)(C)C]

To a 50 mL round bottomed flask equipped with a magnetic stir bar containing DMF (2 ml) was placed lysine CBZ compound (1 equiv). To this reaction mixture added DIPEA (2.5 eq) and MeI (1.5 equiv) and stir at room temp overnight. After reaction was complete, DMF was removed in vacuo. The residue was used directly for urea reaction. MS: m/z=351 (M+H$^+$).

(S)-Di-tert-butyl 2 (3-((S)-6-amino-1-(tert-butoxy)-1-oxohexane-2-yl)-3-methylureido)pentanedioate

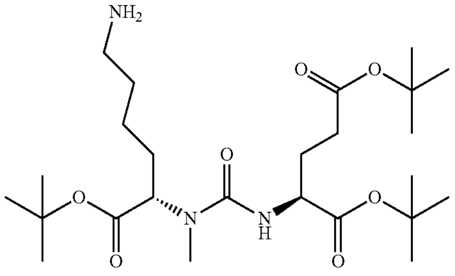 [SMILES: CN(C(=O)N[C@@H](CCC(=O)OC(C)(C)C)C(=O)OC(C)(C)C)[C@@H](CCCCN)C(=O)OC(C)(C)C]

General experimental procedure for the removal of benzyl group was followed. Reaction was performed on a 125 mg scale. The crude product was used directly in the next step without any further purification. MS: m/z=502 (M+H$^+$).

(S)-2-(3-((S)-1-Carboxy-5-(2-(4-(3-fluoropropyl)-1H-1,2,3-triazol-1-yl)acetamido)pentyl)-3-methylureido)pentanedioic acid: P032

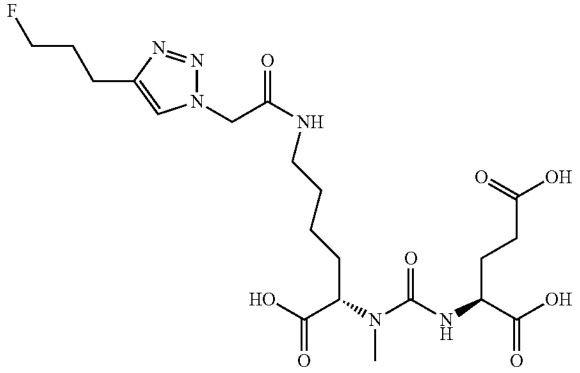 [SMILES: CN(C(=O)N[C@@H](CCC(=O)O)C(=O)O)[C@@H](CCCCNC(=O)Cn1cc(CCCF)nn1)C(=O)O]

General procedure for click chemistry was followed. Reaction was performed on a 20 mg scale. Product was purified by HPLC purification system (0.05% TFA in water-acetonitrile, 20-65%) afforded the title compound (4.5 mg, 22%). $^1$H NMR (CD$_3$OD, 400 MHz) δ 8.21 (br, 1H), 5.09 (d, J=1.6 Hz, 2H), 4.53-4.50 (t, J=6.0 Hz, 1H), 4.41-4.38 (t, J=6.0 Hz, 1H), 4.30-4.27 (dd, J=9.6, 4.8 Hz, 2H), 3.26-3.19 (m, 2H), 2.84 (s, 3H), 2.82 (t, J=7.2 Hz, 2H), 2.22-2.14 (m, 1H), 2.10-1.88 (m, 4H), 1.82-1.72 (m, 1H), 1.62-1.46 (m, 2H), 1.39-1.26 (m, 2H). MS: m/z=503 (M+H$^+$).

(9S,13S)-3,11-Dioxo-1-phenyl-2-oxa-4,10,12-triazapentadecane-9,13,15-tricarboxylic acid: P033

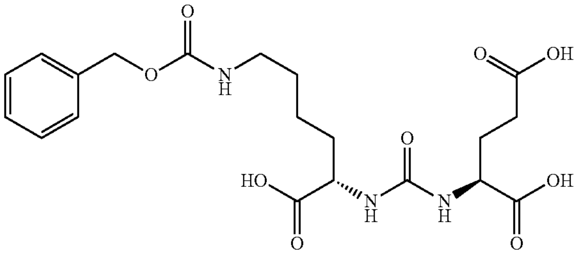 [SMILES: O=C(O)CC[C@H](NC(=O)N[C@@H](CCCCNC(=O)OCc1ccccc1)C(=O)O)C(=O)O]

General procedure for the removal of tert-butyl group from esters was followed. Reaction was performed on 10 mg scale. The reaction mixture was then under basic hydrolysis to give crude tri acid. After HPLC purification, P033 (5.2 mg, 72%) was obtained. $^1$H NMR (CD$_3$OD, 400 MHz): δ 7.23-7.35 (m, 5H), 5.04 (s, 2H), 4.29 (dd, J=8.8, 5.2 Hz, 1H), 4.23 (dd, J=8.0, 4.8 Hz, 1H), 3.10 (d, J=6.8 Hz, 1H), 2.31-2.46 (m, 2H), 2.07-2.17 (m, 1H), 1.76-1.91 (m, 2H, m), 1.59-1.69 (m, 1H), 1.35-1.55 (m, 4H). MS: m/z=454 (M+H$^+$).

(S)-2-(3-((S)-5-(2-Azidoacetamido)-1-carboxypentyl)-3-methylureido)pentanedioic acid: P034

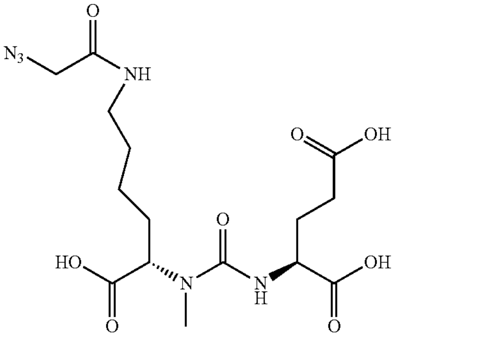 [SMILES: CN(C(=O)N[C@@H](CCC(=O)O)C(=O)O)[C@@H](CCCCNC(=O)CN=[N+]=[N-])C(=O)O]

General experimental procedures for amide formation of amide and removal of tert-butyl group were followed. Reaction was performed on a 50 mg scale. Product was purified on a Biotage purification system as well as on HPLC purification system afforded the title compound P034 (20 mg, 42%). $^1$H NMR (CD$_3$OD, 400 MHz) δ 4.30-4.27 (dd, J=9.6, 4.4 Hz, 1H), 3.84 (s, 2H), 3.23-3.18 (td, J=6.8, 2.0 Hz, 1H), 2.84 (s, 3H), 2.45 (t, J=7.2 Hz, 2H), 2.22-2.14 (m, 1H), 2.03-1.89, 1.82-1.72 (m, 1H), 1.61-1.44 (m, 2H), 1.40-1.26 9m, 2H). MS: m/z=417 (M+H$^+$).

(9S, 13S)-10-Ethyl-3,11-dioxo-1-phenyl-2-oxa-4,10,12-triazapentadecane-9,13,15-tricarboxyllic acid: P035

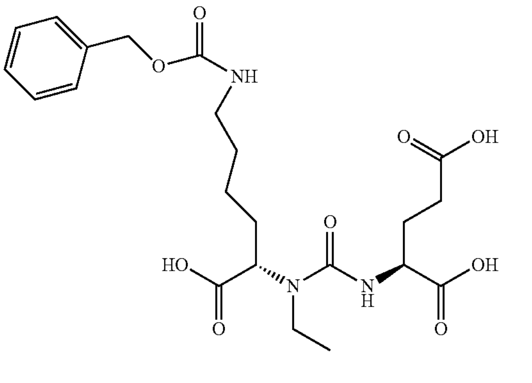 [SMILES: CCN(C(=O)N[C@@H](CCC(=O)O)C(=O)O)[C@@H](CCCCNC(=O)OCc1ccccc1)C(=O)O]

General experimental procedure for N-ethylation of lysine followed by urea formation with glutamic acid and tert-butyl removal were used to prepare the title compound. Reaction was performed on a 50 mg scale. Product was purified on HPLC purification system afforded the title compound P035 (24 mg, 65%). $^1$H NMR ($CD_3OD$, 400 MHz): δ 7.32-7.25 (m, 5H), 5.03 (s, 2H), 4.66-4.63 (dd, J=10.4, 4.8 Hz, 2H), 4.18 (t, J=4.8 Hz, 1H), 3.65-3.56 (m, 1H), 3.18-3.02 (m, 3H), 2.44-2.28 (m, 4H), 1.94-1.82 (m, 2H), 1.54-1.45 (m, 2H), 1.38-1.22 (m, 2H), 1.14 (t, J=7.2 Hz, 3H). MS: m/z=482 (M+H$^+$).

(S)-2-(3-((S)-1-Carboxy-5-(2-(4-(4-methoxyphenyl)-1H-1,2,3-triazol-1-yl)acetamido)-pentyl)3-methylureido)pentanedioic acid: P036

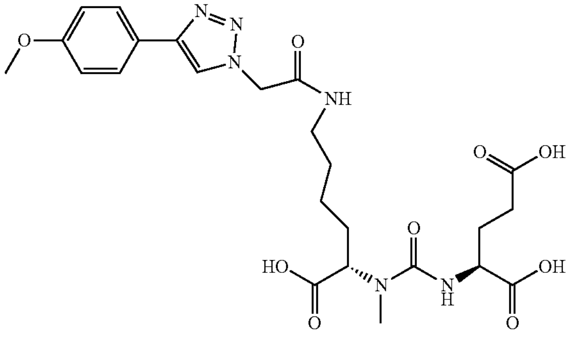 [SMILES: COc1ccc(-c2cn(CC(=O)NCCCC[C@@H](C(=O)O)N(C)C(=O)N[C@@H](CCC(=O)O)C(=O)O)nn2)cc1]

General procedure for click chemistry was followed. Reaction was performed on a 15 mg scale. Product was purified by HPLC purification system using 0.05% TFA in water and acetonitrile as a solvent yielded the title compound P036 (13 mg, 78%). $^1$H NMR ($CD_3OD$, 400 MHz): δ 8.20 (br, 1H), 8.08 (s, 1H), 7.67-7.63 (m, 1H), 6.92-6.88 (m, 2H), 5.08 (d, J=1.6 Hz, 2H), 4.23-4.19 (dd, J=9.6, 4.4 Hz, 2H), 3.73 (s, 3H), 3.19-3.14 (m, 2H), 2.76 (s, 3H), 2.38 (t, J=8.0 Hz, 2H), 2.16-2.06 (m, 1H), 1.96-1.62 (m, 2H), 1.76-1.62 (m, 1H), 1.56-1.40 (m, 2H), 1.34-1.98 (m, 2H). MS: m/z=549 (M+H$^+$).

(S)-Di-tert-butyl 2-((4-(ethoxycarbonyl)oxazol-2-yl) amino)pentanedioate

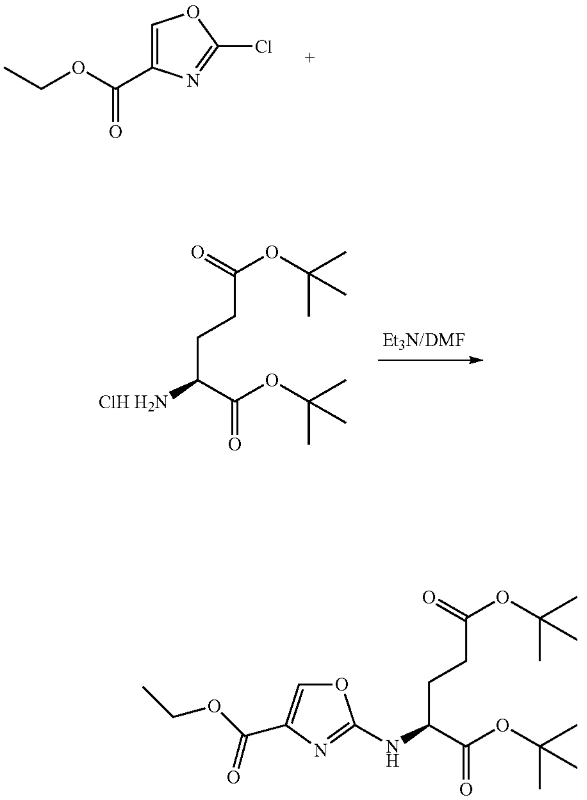

The mixture was microwaved at 120° C. for 1.5 hrs, cooled and concentrated in vacuo. The residue was purified on flash column chromatography (silica gel, 0-50% EtOAc/hexanes) to give the desired product with a small amount of impurities. It was used directly in the next step without any further purification. MS: m/z=399 (M+H$^+$).

(S)-2-((4-Carboxyoxazol-2-yl)amino)pentanedioic acid: P037

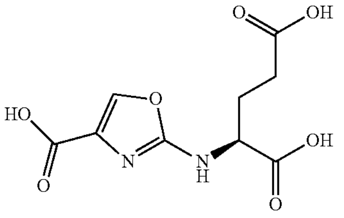 [SMILES: O=C(O)CC[C@H](Nc1nc(C(=O)O)co1)C(=O)O]

General procedure for the removal of tert-butyl group from esters was followed. Reaction was performed on 260 mg scale. The reaction mixture was then under basic hydrolysis to give crude tri acid. After HPLC purification, P037 (5 mg, 3%) was obtained. $^1$H NMR ($CD_3OD$, 400 MHz) δ 7.91 (s, 1H), 4.32-4.41 (m, 1H), 2.41-2.55 (m, 2H), 2.21-2.38 (m, 1H), 1.99-2.09 (m, 1H). MS: m/z=400 (M+H$^+$).

O-Benzyl-N-(3-phenylpropyl)hydroxylamine

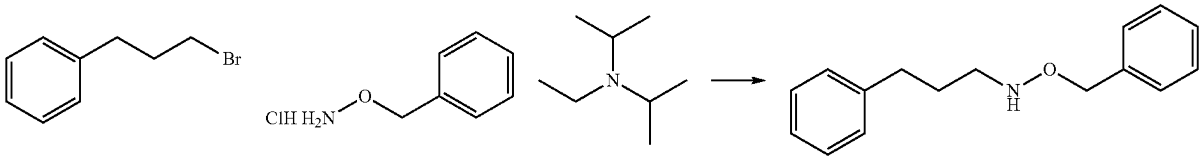

A mixture of 3-phenylpropyl bromide (500 mg, 2.51 mm01), 0-bezylhydroxylamine hydrochloride (802 mg, 5.02 mmol), and DIPEA (1.34 mL, 7.53 mmol) in DMF (5.0 mL) was stirred at room temperature overnight and then heated at 80° C. for 24 hrs, concentrated in vacuo. The residue was purifie don flash column chromatography (silica gel, 0-20% EtOAc/hexanes) to give the desired product (193 mg, 32%). MS: m/z=242 (M+H$^+$).

(S)-Dibenzyl 2-(3-(benzyloxy)-3-(3-phenylpropyl)ureido)pentanedioate

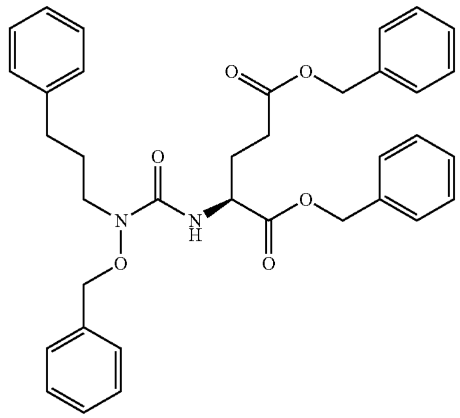 [SMILES: O=C(CC[C@H](NC(=O)N(CCCc1ccccc1)OCc1ccccc1)C(=O)OCc1ccccc1)OCc1ccccc1]

General experimental procedure for the formation of urea was followed. Reaction was performed on a 193 mg scale. Product was purified on a Biotage purification system eluting out in 5-40% EtOAc:Hexanes mixture in a gradient elution to give the title compound (170 mg, 73%). MS: m/z=595 (M+H$^+$).

(S)-2-(3-Hydroxy-3-(3-phenylpropyl)ureido)pentanedioic acid: P038

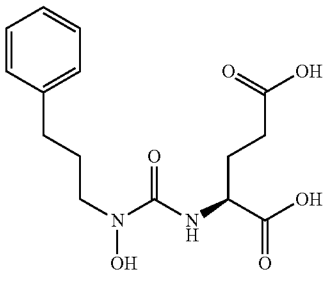 [SMILES: O=C(O)CC[C@H](NC(=O)N(O)CCCc1ccccc1)C(=O)O]

General experimental procedure for the removal of benzyl group was followed. Reaction was performed on a 170 mg scale. After HPLC purification, P038 (25 mg, 27%) was obtained. $^1$H NMR ($CD_3OD$, 400 MHz) δ 7.09-7.25 (m, 5H), 4.28-4.35 (m, 1H), 3.47 (t, J=7.2 Hz, 2H), 2.62 (t, J=7.2 Hz, 2H), 2.36-2.45 (m, 2H), 2.14-2.24 (m, 1H), 1.84-1.20 (m, 3H). MS: m/z=325 (M+H$^+$).

(10S,14S)-2,2-Dimethyl-4,12-dioxo-3-oxa-5,11,13-triazahexadecane-10,14,16-tricarboxylic acid: P039

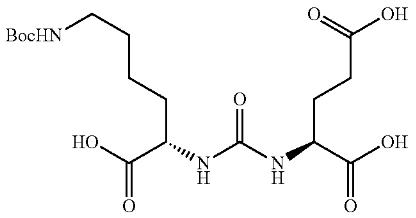 [SMILES: CC(C)(C)OC(=O)NCCCC[C@H](NC(=O)N[C@@H](CCC(=O)O)C(=O)O)C(=O)O]

To a solution of (S)-2-(3-((S)-5-amino-1-carboxypentyl)ureido)pentanedioic acid (3.3 mg, 0.010 mmol) in 1 N NaOH solution (1.0 mL) was added di-tert-butyl dicarbonate (23 mg, 0.10 mmol) in dioxane (1.0 mL). The mixture was stirred at room temperature for 2 hours and acidified with acetic acid to pH ~5. HPLC purification was performed to give 2.3 mg (53%) of P039 as a white solid. $^1$H NMR ($CD_3OD$, 400 MHz) δ 4.29 (dd, J=8.8, 5.2 Hz, 1H), 4.23 (dd, J=8.0, 4.8 Hz, 1H), 3.01 (d, J=6.8 Hz, 1H), 2.32-2.46 (m, 2H), 2.08-2.18 (m, 1H), 1.76-1.92 (m, 2H), 1.58-1.68 (m, 1H), 1.35-1.52 (m, 13H). MS: m/z=420 (M+H$^+$).

(S)-2-(2-(N-(4-(tert-Butoxycarbonylamino)butyl)acetamido)acetamido)pentanedioic acid: P040

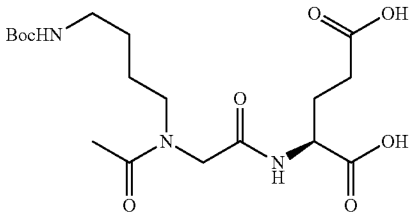 [SMILES: CC(=O)N(CCCCNC(=O)OC(C)(C)C)CC(=O)N[C@@H](CCC(=O)O)C(=O)O]

General experimental procedure for amidation and hydrogenolysis de-benzylation was followed. Reaction was performed on a 15 mg scale of (S)-dibenzyl 2-(2-(4-(tert-butoxycarbonylamino)butylamino)acetamido)pentanedioate. Isolated 10.3 mg (91%) of P040 as a white solid. $^1$H NMR ($CD_3OD$, 400 MHz) δ 4.41-4.49 (m, 1H), 4.08 and 3.99 (d, J=16.0 Hz, two rotamers, total 2H), 3.33-3.41 (m, 2H), 2.99-3.07 (m, 2H), 2.36-2.44 (m, 2H), 2.13-2.25 (m, 1H), 2.14 and 2.04 (two s, two rotamers, total 2H), 1.88-1.99 (m, 1H), 1.37-1.54 (m, 13H). MS: m/z=418 ($M+H^+$).

(10S,14S)-2,2-Dimethyl-4,12-dioxo-3-oxa-5,11,13-triazahexadecane-10,14,16-tricarboxylic acid: P041

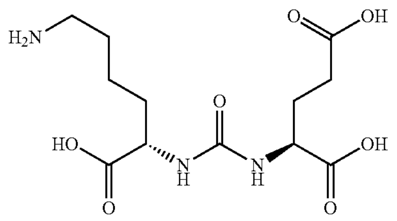 [SMILES: NCCCC[C@H](NC(=O)N[C@@H](CCC(=O)O)C(=O)O)C(=O)O]

General experimental procedure hydrogenolysis was followed. Reaction was performed on a 20 mg scale of (9S,13S)-3,11-dioxo-1-phenyl-2-oxa-4,10,12-triazapentadecane-9,13,15-tricarboxylic acid. Isolated 6.0 mg (43%) of P041 as a white solid. $^1$H NMR ($CD_3OD$, 400 MHz) δ 4.10-4.18 (m, 2H), 2.82-2.94 (m, 2H), 2.36 (t, J=8.0 Hz, 2H), 2.04-2.12 (m, 1H), 1.80-1.94 (m, 2H), 1.58-1.72 (m, 3H), 1.38-1.52 (m, 2H). MS: m/z=320 ($M+H^+$).

(S)-2-(2-(1-(4-(tert-Butoxycarbonylamino)butyl)-3-hydroxyureido)acetamido) pentanedioic acid: P042

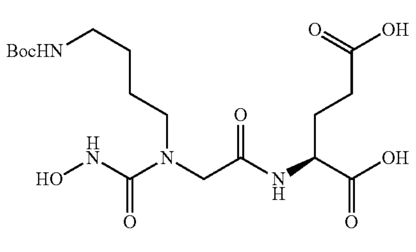 [SMILES: CC(C)(C)OC(=O)NCCCCN(CC(=O)N[C@@H](CCC(=O)O)C(=O)O)C(=O)NO]

General experimental procedure for urea formation and hydrogenolysis de-benzylation was followed. Reaction was performed on a 20 mg scale of (S)-dibenzyl 2-(2-(4-(tert-butoxycarbonylamino)butylamino)acetamido)pentanedioate. Isolated 2.2 mg (14%) of P042 as a white solid. $^1$H NMR ($CD_3OD$, 400 MHz): δ 4.45 (dd, J=9.2, 4.8 Hz, 1H), 4.00, 3.95, 3.94, 3.89 (ABq, J=16.8 Hz, 2H), 3.22-3.26 (m, 2H), 3.03 (t, J=6.8 Hz, 2H), 2.40 (t, J=7.4 Hz, 2H), 2.16-2.26 (m, 1H), 1.90-2.00 (m, 1H), 1.50-1.60 (m, 2H), 1.38-1.48 (m, 11H). MS: m/z=435 ($M+H^+$).

(S)-2-(3-((S)-1-Carboxy-5-(2-(4-2((2-nitro-1H-imidazo-1-yl)-methyl)-1H-1,2,3-triazol-1-yl)acetamido) pentyl)ureido)pentanedioic acid: P043

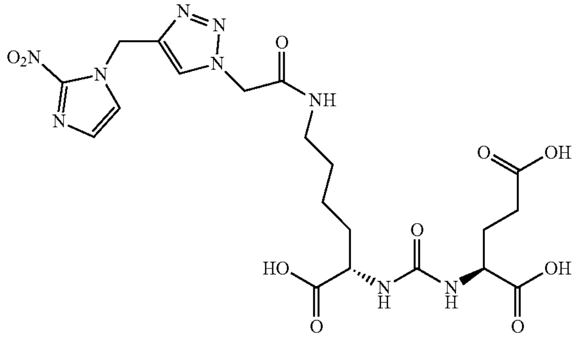 [SMILES: O=C(O)CC[C@H](NC(=O)N[C@@H](CCCCNC(=O)Cn1cc(Cn2ccnc2[N+](=O)[O-])nn1)C(=O)O)C(=O)O]

General procedure for "click chemistry was followed. Reaction was performed on a 15 mg scale. Product was purified by HPLC purification system using 0.05% TFA in water and acetonitrile as a solvent yielded the title compound (1 mg, 7%). $^1$H NMR ($CD_3OD$, 400 MHz) δ 8.30 (br, 1H), 7.54 (d, J=1.2 Hz, 1H), 7.13 (d, J=1.2 Hz, 1H), 5.76 (s, 2H), 5.12 (s, 2H), 4.31-4.27 (m, 2H), 3.23-3.21 (m, 2H), 2.42-2.37 (m, 2H), 2.17-2.04 (m, 1H), 1.90-1.79 (m, 2H), 1.66-1.39 (m, 5H). MS: m/z=554 ($M+H^+$).

(S)-2-(3-((S)-1-Carboxy-5-(2-(4-2((2-nitro-1H-imidazo-1-yl)methyl)-1H-1,2,3-triazol-1-yl)acetamido) pentyl)-3-methylureido)pentanedioic acid: P044

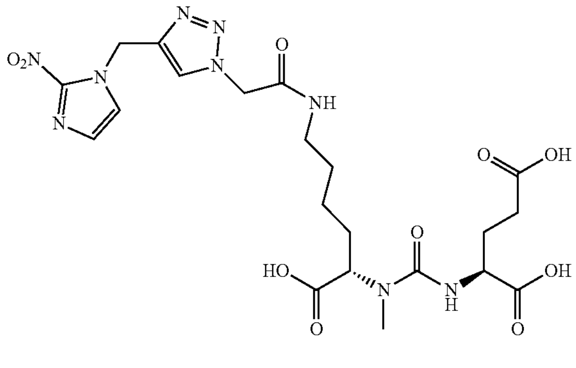 [SMILES: CN(C(=O)N[C@@H](CCC(=O)O)C(=O)O)[C@@H](CCCCNC(=O)Cn1cc(Cn2ccnc2[N+](=O)[O-])nn1)C(=O)O]

General procedure for "click chemistry was followed. Reaction was performed on a 15 mg scale. Product was purified by HPLC purification system using 0.05% TFA in water and acetonitrile as a solvent yielded the title compound (2 mg, 13%). $^1$H NMR ($CD_3OD$, 400 MHz) δ 8.24 (br, 1H), 8.08 (s, 1H), 7.55 (d, J=1.2 Hz, 1H), 7.13 (d, J=1.2 Hz, 1H), 5.76 (s, 2H), 5.12 (s, 2H), 4.30-4.27 (dd, J=9.6, 4.8 Hz, 2H), 3.23-3.19 (m, 2H), 2.83 (s, 3H), 2.45 (t, J=7.7 Hz, 2H), 2.22-2.14 (m, 1H), 2.04-1.88 (m, 2H), 1.82-1.70 (m, 5H), 1.62-1.24 (m, 4H). MS: m/z=568 ($M+H^+$).

(S)-2-(3-((S)-1-Carboxy-5-(4-(4-(3-fluoropropyl)-1H-1,2,3-triazol-1-yl)-butanamido)pentyl)ureido) pentanedioic acid: P045

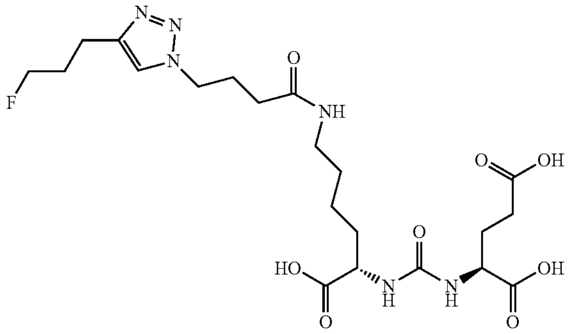 [SMILES: O=C(O)CC[C@H](NC(=O)N[C@@H](CCCCNC(=O)CCCn1cc(CCCF)nn1)C(=O)O)C(=O)O]

General procedure for click chemistry was followed. Reaction was performed on a 28 mg scale. Product was purified by HPLC purification system using 0.05% TFA in water and acetonitrile as a solvent yielded the title compound (7.0 mg, 29%). $^{1}$H NMR ($CD_3OD$, 400 MHz) δ 7.79 (s, 1H), 4.51 ((td, J=6.0, 1.6 Hz, 1H), 4.41-4.37 (m, 3H), 4.30-4.23 (m, 2H), 3.22-3.08 (m, 2H), 2.80 (t, J=7.2 Hz, 2H), 2.41-2.38 (m, 2H), 2.20-1.96 (m, 7H), 1.92-1.76 (m, 2H), 1.70-1.38 (m, 5H). MS: m/z=517 (M+H$^+$).

(S)-2-(3-((S)-1-Carboxy-5-(4-(4-(3-fluoropropyl)-1H-1,2,3-triazol-1-yl)-butanamido)pentyl)-3-methylureido)pentanedioic acid: P046

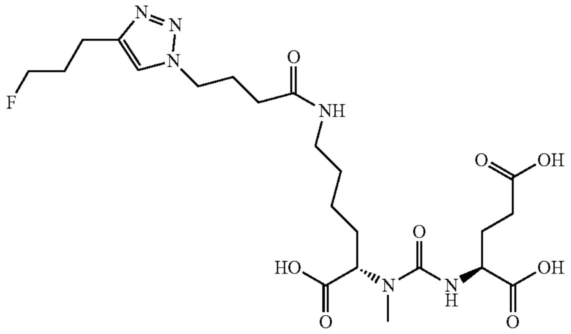 [SMILES: CN(C(=O)N[C@@H](CCC(=O)O)C(=O)O)[C@@H](CCCCNC(=O)CCCn1cc(CCCF)nn1)C(=O)O]

General procedure for click chemistry was followed. Reaction was performed on a 28 mg scale. Product was purified by HPLC purification system using 0.05% TFA in water and actenitrile as a solvent yielded the title compound (5.0 mg, 20%). $^{1}$H NMR ($CD_3OD$, 400 MHz) δ 7.80 (s, 1H), 4.51 ((td, J=6.0, 1.6 Hz, 1H), 4.41-4.37 (m, 2H), 4.29-4.26 (m, 1H), 3.22-3.10 (m, 1H), 2.84 (s, 3H), 2.80 (t, J=7.6 Hz, 1H), 2.45 (t, J=7.6 Hz, 1H), 2.22-1.90 (m, 5H), 1.82-1.72 (m, 1H), 1.58-1.26 (m, 2H). MS: m/z=531 (M+H$^+$).

(S)-2-(2-(1-(4-(tert-Butoxycarbonylamino)butyl) ureido)acetamido)pentanedioic acid: P047

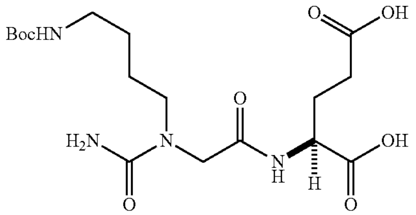

General experimental procedure for urea formation and hydrogenolysis de-benzylation was followed. Reaction was performed on a 30 mg scale of (S)-dibenzyl 2-(2-(4-(tert-butoxycarbonylamino)butylamino)acetamido)pentanedioate. Isolated 11.3 mg (50%) of P047 as a white solid. $^{1}$H NMR ($CD_3OD$, 400 MHz) δ 4.45 (dd, J=9.2, 5.2 Hz, 1H), 4.02, 3.97, 3.96, 3.91 (ABq, J=16.8 Hz, 2H), 3.24-3.28 (m, 2H), 3.04 (t, J=6.8 Hz, 2H), 2.39 (t, J=7.6 Hz, 2H), 2.16-2.26 (m, 1H), 1.92-2.02 (m, 1H), 1.52-1.62 (m, 2H), 1.38-1.48 (m, 11H). MS: m/z=419 (M+H$^+$).

(S)-2-(2-(1-(4-(tert-Butoxycarbonylamino)butyl)-3-carbamoylureido)acetamido) pentanedioic acid: P048

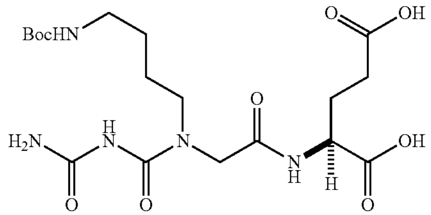

General experimental procedure for urea formation and hydrogenolysis de-benzylation was followed. Reaction was performed on a 30 mg scale of (S)-dibenzyl 2-(2-(4-(tert-butoxycarbonylamino)butylamino)acetamido)pentanedioate. Isolated 5.6 mg (25%) of P048 as a white solid. $^{1}$H NMR ($CD_3OD$, 400 MHz) δ 4.46 (dd, J=9.0, 4.8 Hz, 1H), 4.09, 4.05, 4.03, 3.98 (ABq, J=17.0 Hz, 2H), 3.36 (t, J=6.8 Hz, 2H), 3.04 (t, J=6.8 Hz, 2H), 2.39 (t, J=7.6 Hz, 2H), 2.16-2.24 (m, 1H), 1.92-2.00 (m, 1H), 1.52-1.60 (m, 2H), 1.38-1.48 (m, 11H). MS: m/z=419 (M+H$^+$).

(S)-2-(2-((4-(tert-Butoxycarbonylamino)butyl)(carboxymethyl)amino)acetamido) pentanedioic acid: P049

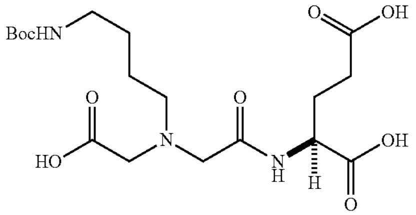

General experimental procedure for alkylation and hydrogenolysis de-benzylation was followed. Reaction was performed on a 25 mg scale of (S)-dibenzyl 2-(2-(4-(tert-butoxycarbonylamino)butylamino)acetamido)pentanedioate. Isolated 6.9 mg (35%) of P049 as a white solid. $^1H$ NMR ($CD_3OD$, 400 MHz) δ 4.49 (dd, J=9.2, 5.2 Hz, 1H), 4.12 (s, 2H), 4.09 (s, 2H), 3.26-3.32 (m, 2H), 3.05 (t, J=6.8 Hz, 2H), 2.41 (t, J=7.6 Hz, 2H), 2.18-2.28 (m, 1H), 1.90-2.02 (m, 1H), 1.68-1.76 (m, 2H), 1.45-1.55 (m, 2H), 1.42 (s, 9H). MS: m/z=434 ($M+H^+$).

(S)-2-(4-(4-(tert-Butoxycarbonylamino)butyl)-2,6-dioxopiperazin-1-yl)pentanedioic acid: P050

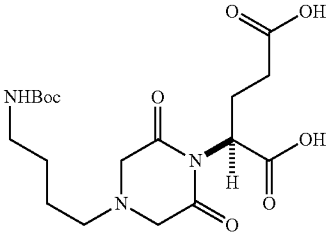

General experimental procedure for alkylation and hydrogenolysis de-benzylation was followed. Reaction was performed on a 25 mg scale of (S)-dibenzyl 2-(2-(4-(tert-butoxycarbonylamino)butylamino)acetamido)pentanedioate. Isolated 2.3 mg (12%) of P050 as a white solid. $^1H$ NMR ($CD_3OD$, 400 MHz) δ 5.22 (1H, dd, J=9.6, 4.4 Hz), 3.54 (4H, bs), 3.03 (2H, t, J=6.8 Hz), 2.59 (2H, t, J=6.8 Hz), 2.38-2.48 (1H, m), 2.28-2.34 (2H, m), 2.14-2.22 (2H, m), 1.44-1.56 (4H, m), 1.41 (9H, s). MS: m/z=416 ($M+H^+$).

(S)-2-(2-(4-(tert-Butoxycarbonylamino)butylamino) acetamido)pentanedioic acid: P051

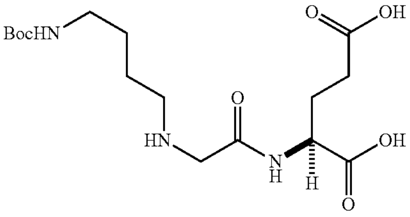

General experimental procedure for hydrogenolysis de-benzylation was followed. Reaction was performed on a 15 mg scale of (S)-dibenzyl 2-(2-(4-(tert-butoxycarbonylamino)butylamino)acetamido)pentanedioate. Isolated 6.6 mg (65%) of P051 as a white solid. $^1H$ NMR ($CD_3OD$, 400 MHz) δ 4.51 (dd, J=9.2, 5.2 Hz, 1H), 3.82 (s, 2H), 3.00-3.08 (m, 4H), 2.40 (t, J=7.6 Hz, 2H), 2.16-2.26 (m, 1H), 1.88-1.98 (m, 1H), 1.64-1.72 (m, 2H), 1.46-1.56 (m, 2H), 1.42 (s, 9H). MS: m/z=376 ($M+H^+$).

N-phenethylethanesulfonamide

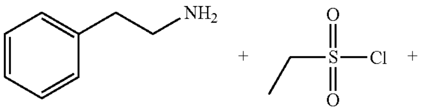

-continued

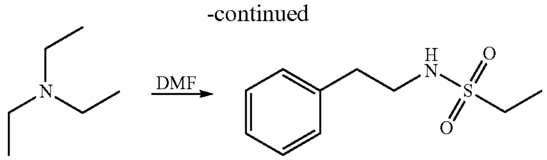

To a solution of pheylethylamin (500 mg, 4.13 mmol) and triethylamine (0.863 mL, 6.19 mmol) in DCM (10 mL) was added a solution of ethansulfonyl chloride (531 mg, 4.13 mmol) in DCM (2.0 mL). The resulting mixture was stirred at room temperature overnight, concentrated in vacuo. The residue was purified on flash column chromatography (silica gel, 0-20% EtOAc/hexanes) to give the desire product (840 mg, 95%). MS: m/z=214 ($M+H^+$).

tert-Butyl 2-(N-phenethylethylsulfonamido)acetate

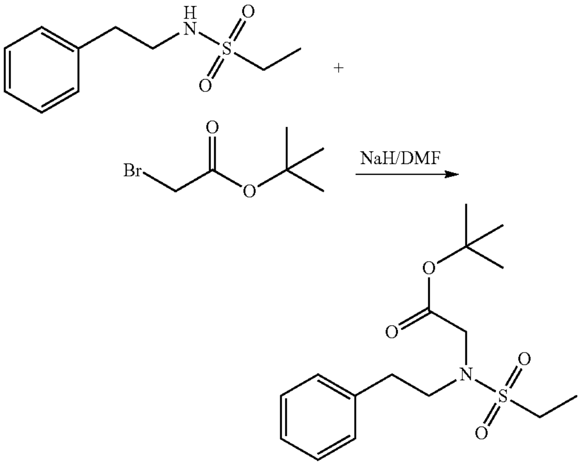

To a solution N-phenethylethanesulfonamide (840 mg, 3.94 mmol) in DMF (5.0 mL) was added NaH (173 mg, 4.33 mmol). The resulting mixture was stirred at room temperature for 20 min, and then a solution of tert-butyl 2-bromoacetate (768 mg, 3.94 mmol) in DMF (1.0 mL) was added. The reaction mixture was stirred at room temperature overnight, concentrated in vacuo. The residue was purified on flash column chromatography (silica gel, 0-50% EtOAc/hexanes) to give the desired product (775 mg, 60%). MS: m/z=328 ($M+H^+$).

2-(N-phenethylethylsulfonamido)acetic acid

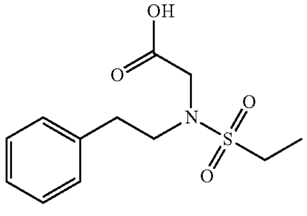 [SMILES: CCS(=O)(=O)N(CCc1ccccc1)CC(=O)O]

General procedure for the removal of tert-butyl group from esters was followed. Reaction was performed on 775 mg scale. After stirring at room temperature for 2 hrs, it was concentrated in vacuo. The residue was used directly in the next step without any further purification. MS: m/z=272 (M+H$^+$).

Di-tert-butyl 2-(2-(N-phenethylethylsulfonamido) acetamido)pentanedioate

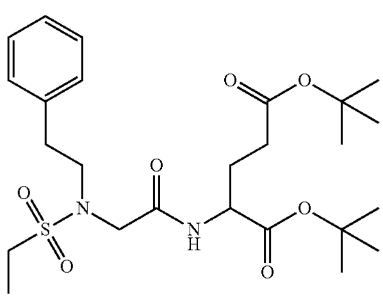 [SMILES: CCS(=O)(=O)N(CCc1ccccc1)CC(=O)NC(CCC(=O)OC(C)(C)C)C(=O)OC(C)(C)C]

General experimental procedure for the formation of amide was followed. Reaction was performed on a 642 mg scale. Product was purified on a Biotage purification system eluting out in 5-40% EtOAc:Hexanes mixture in a gradient elution to give the title compound (1000 mg, 82%). MS: m/z=513 (M+H$^+$).

2-(2-(N-Phenethylethylsulfonamido)acetamido)pentanedioic acid: P052

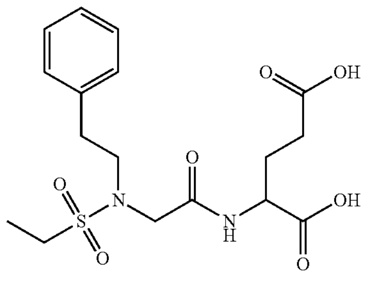 [SMILES: CCS(=O)(=O)N(CCc1ccccc1)CC(=O)NC(CCC(=O)O)C(=O)O]

General procedure for the removal of tert-butyl group from esters was followed. Reaction was performed on 65 mg scale. After HPLC purification, P052 (35 mg, 65%) was obtained. $^1$H NMR (CD$_3$OD, 400 MHz) δ 7.18-7.25 (m 5H), 4.41-4.49 (m, 1H), 3.99 (s, 2H), 3.48-3.53 (m, 2H), 3.07 (q, J=14.8, 6.8 Hz, 2H), 2.89 (t, J=8.0 Hz, 2H), 2.39 (t, J=7.6 Hz, 2H), 2.15-2.25 (m, 1H), 1.89-2.01 (m, 1H), 1.26 (t, J=7.6 Hz, 3H). MS: m/z=401 (M+H$^+$).

(S)-2-(3-((S)-1-Carboxy-5-(4-(4-(3-fluoropropyl)-1H-1,2,3-triazol-1-yl)benzamido) pentyl)-3-methylureido)pentanedioic acid: P053

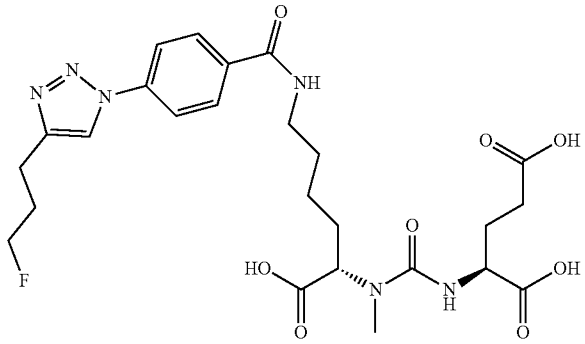 [SMILES: CN(C(=O)N[C@@H](CCC(=O)O)C(=O)O)[C@@H](CCCCNC(=O)c1ccc(-n2cc(CCCF)nn2)cc1)C(=O)O]

General experimental procedure for "click chemistry was followed. Reaction was performed on a 65 mg scale. Product was purified by HPLC purification system using 0.05% TFA in water and actenitrile to affor the tile compound. (12 mg, 20%). $^1$H NMR (CD$_3$OD, 400 MHz) δ 8.42 (s, 1H), 8.01-7.93 (m, 4H), 4.56 (t, J=5.6 Hz, 2H), 4.44 ((t, J=5.6 Hz, 1H), 4.30-4.27 (dd, J=9.6, 4.8 Hz, 1H), 3.44-3.36 (m, 2H), 2.90 (t, J=7.2 Hz, 2H), 2.84 (s, 3H), 2.44 (t, J=7.2 Hz, 2H), 2.22-1.94 (m, 5H), 1.88-1.58 and 1.50-1.32 (m, 2H each). MS: m/z=565 (M+H$^+$).

(S)-2-(3-((S)-1-Carboxy-5-(4-(4-(3-fluoropropyl)-1H-1,2,3-triazol-1-yl)-butanamido)-pentyl)ureido) pentanedioic acid: P054

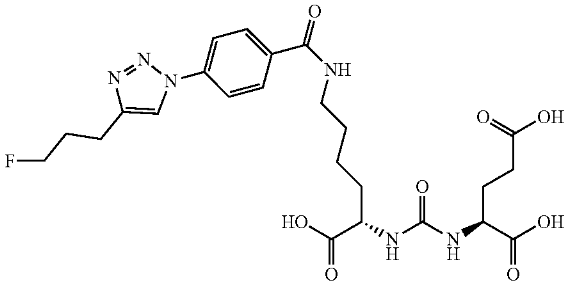 [SMILES: O=C(O)CC[C@H](NC(=O)N[C@@H](CCCCNC(=O)c1ccc(-n2cc(CCCF)nn2)cc1)C(=O)O)C(=O)O]

General experimental procedure for click chemistry was followed. Reaction was performed on a 65 mg scale. Product was purified by HPLC purification system using 0.05% TFA in water and acetonitrile to afford the title compound (17 mg, 30%). $^1$H NMR (CD$_3$OD, 400 MHz) δ 8.42 (d, J=0.8 Hz, 1H), 8.01 (dd, J=8.8, 2.0 Hz, 2H), 7.96 (dd, J=8.8, 2.0 Hz, 2H), 4.59 ((t, J=6.0 Hz, 1H), 4.46 (t, J=6.0 Hz, 1H), 4.31-4.27 (m, 2H), 3.44-3.38 (m, 2H), 2.92 (t, J=7.6 Hz, 2H), 2.42-2.38 (m, 2H), 2.18-2.07 (m, 3H), 1.94-1.82 (m, 2H), 1.76-1.62 (m, 3H), 1.56-1.48 (m, 2H). MS: m/z=551 (M+H$^+$).

(S)-2-(3-((S)-5-(Benzyloxycarbonylamino)-1-carboxypentyl)-2,4,6-trioxotetrahydropyrimidin-1(2H)-yl)pentanedioic acid: P055

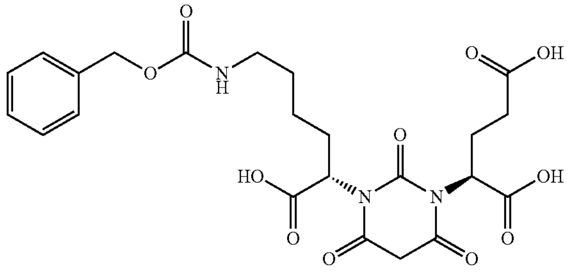 [SMILES: O=C(O)CC[C@@H](C(=O)O)N1C(=O)CC(=O)N([C@@H](CCCCNC(=O)OCc2ccccc2)C(=O)O)C1=O]

To a microwave tube was added a solution of (9S,13S)-tri-tert-butyl 3,11-dioxo-1-phenyl-2-oxa-4,10,12-triazapentadecane-9,13,15-tricarboxylate (107 mg, 0.172 mmol) in dry DCM (1.0 mL) followed by malonyl dichloride (17 μL, 0.175 mmol). The mixture was microwave heated at 80° C. for 20 minutes. The crude mixture was purified by flush chromatography (EtOAc/hexane, 0 to 50%) to give the (S)-di-tert-butyl 2-(3-((S)-6-(benzyloxycarbonylamino)-1-tert-butoxy-1-oxohexan-2-yl)-2,4,6-trioxotetrahydropyrimidin-1(2H)-yl)pentanedioate 30 mg (65%). 5.0 mg of above intermediate was deprotected with general condition to give 1.3 mg (34%) of P055 as a white solid. $^1H$ NMR ($CD_3OD$, 400 MHz) δ 7.23-7.35 (m, 5H), 5.33 (dd, J=10.0, 4.4 Hz, 1H), 5.27 (dd, J=10.0, 5.0 Hz, 1H), 5.03 (s, 2H), 3.07 (t, J=6.8 Hz, 2H), 2.40-2.50 (m, 1H), 2.36 (t, J=6.8 Hz, 2H), 2.20-2.28 (m, 1H), 2.08-2.18 (m, 1H), 1.98-2.08 (m, 1H), 1.40-1.58 (m, 2H), 1.28-1.38 (m, 2H). MS: m/z=522 ($M+H^+$).

(S)-Di-tert-Butyl 2-(2 ((benzyloxy)carbonyl)hydrazinecarboxamido)pentanedioate

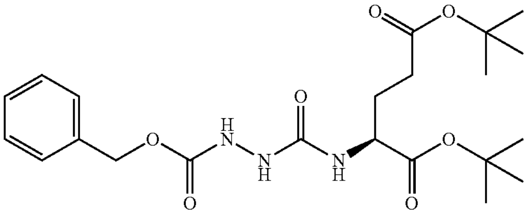 [SMILES: CC(C)(C)OC(=O)CC[C@H](NC(=O)NNC(=O)OCc1ccccc1)C(=O)OC(C)(C)C]

General experimental procedure for the formation of urea was followed. Reaction was performed on 1000 mg scale. Product was purified on a Biotage purification system eluting out in 5-40% EtOAc:Hexanes mixture in a gradient elution to give the title compound (1000 mg, 66%). MS: m/z=452 ($M+H^+$).

(S)-2-(2-((Benzyloxy)carbonyl)hydrazinecarboxamido)pentanedioic acid: P056

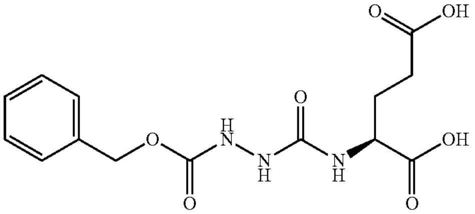 [SMILES: O=C(O)CC[C@H](NC(=O)NNC(=O)OCc1ccccc1)C(=O)O]

General procedure for the removal of tert-butyl group from esters was followed. Reaction was performed on 10 mg scale. After HPLC purification, P056 (5.8 mg, 77%) was obtained. $^1H$ NMR ($CD_3OD$, 400 MHz) δ 7.23-7.41 (5H), 5.13 (s, 2H), 4.29-4.37 (m, 1H), 2.31-2.42 (m 2H), 2.08-2.22 (m, 1H), 1.84-1.95 (m, 1H). MS: m/z=340 ($M+H^+$).

(S)-2-(3-((S)-5-(4-Azidobenzamido)-1-carboxypentyl)-2,4,6-trioxotetrahydro pyrimidin-1(2H)-yl)pentanedioic acid: P057

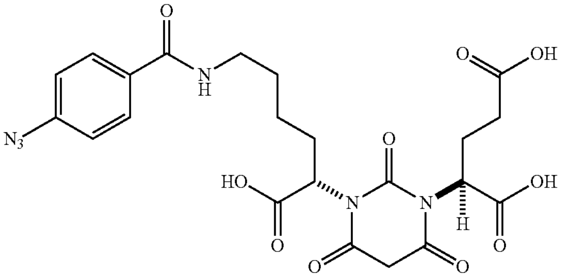

General experimental procedure for amidation and deprotection was followed. Reaction was performed on a 9.9 mg scale of (S)-di-tert-butyl 2-(3-((S)-6-amino-1-tert-butoxy-1-oxohexan-2-yl)-2,4,6-trioxotetrahydropyrimidin-1(2H)-yl) pentanedioate. Isolated 4.3 mg (56%) of P057 as a white solid. $^1H$ NMR ($CD_3OD$, 400 MHz) δ 7.73 (m, 2H), 7.03 (m, 2H), 5.25 (dd, J=10.0, 4.4 Hz, 1H), 5.21 (dd, J=9.6, 4.8 Hz, 1H), 5.03 (s, 2H), 3.23 (m, 2H), 2.30-2.40 (m, 1H), 2.28 (t, J=7.0 Hz, 2H), 2.04-2.20 (m, 2H), 1.92-2.02 (m, 1H), 1.44-1.52 (m, 2H), 1.28-1.38 (m, 2H). MS: m/z=533 ($M+H^+$).

(S)-2-(3-((S)-5-(4-Azidobenzamido)-1-carboxypentyl)ureido)pentanedioic acid: P058

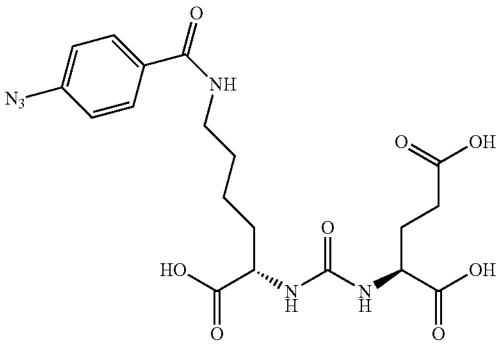 [SMILES: [N-]=[N+]=Nc1ccc(C(=O)NCCCC[C@H](NC(=O)N[C@@H](CCC(=O)O)C(=O)O)C(=O)O)cc1]

General experimental procedures for amide formation and the removal of tert-butyl ester group were used to obtain the compound. Reaction was performed on a 100 mg scale. Product was purified on a Biotage and HPLC purification system to afford the title compound (13 mg, 35%, in two steps), $^{1}$H NMR ($CD_3OD$, 400 MHz) δ 7.76-7.74 (dd, J=6.4, 1.2 Hz, 2H), 7.06-7.04 (dd, J=6.4, 1.2 Hz, 2H), 4.21-4.16 (m, 2H), 3.30-3.22 (m, 2H), 2.33-2.28 (m, 2H), 2.10-2.00 (m, 1H), 1.82-1.72 (m, 2H), 1.66-1.50 (m, 3H), 1.42-1.35 (m, 2H). MS: m/z=465 (M+H$^+$).

(S)-2-(3-((S)-5-(4-Azidobenzamido)-1-carboxypentyl)-3-methylureido)pentanedioic acid: P059

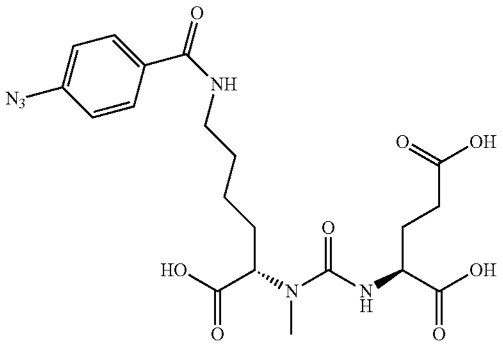 [SMILES: CN(C(=O)N[C@@H](CCC(=O)O)C(=O)O)[C@@H](CCCCNC(=O)c1ccc(N=[N+]=[N-])cc1)C(=O)O]

General experimental procedures for amide formation and removal of tert-butyl ester group were followed. Reaction was performed on a 100 mg scale. Product was purified on a Biotage and HPLC purification system to afford the title compound (11 mg, 28%), $^{1}$H NMR ($CD_3OD$, 400 MHz) δ 7.76-7.74 (dd, J=6.4, 1.2 Hz, 2H), 7.05-7.03 (dd, J=6.4, 1.2 Hz, 2H), 4.21-4.18 (dd, J=9.6, 4.4 Hz, 2H), 3.34-3.26 (m, 4H), 2.76 (s, 3H), 2.36 (t, J=7.2 Hz, 4H), 2.16-2.06 (m, 2H), 1.96-1.66 (m, 5H), 1.64-1.44 (m, 7H). MS: m/z=479 (M+H$^+$).

(S)-2-(Hydrazinecarboxamido)pentanedioic acid: P061

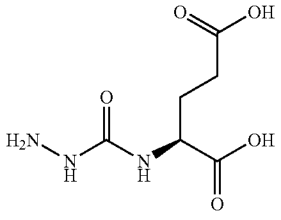 [SMILES: NNC(=O)N[C@@H](CCC(=O)O)C(=O)O]

First, general experimental procedure for the removal of benzyl group was followed. Reaction was performed on an 81 mg scale. Second, the general experimental procedure for the removal of tert-butyl group from esters was followed. Reaction was performed on a 10 mg scale. After HPLC purification of fully deprotected product, P061 (1.1 mg, 17%) was obtained. $^{1}$H NMR ($CD_3OD$, 400 MHz) δ 4.31-4.39 (m, 1H), 2.39 (t, J=8.0 Hz, 2H), 2.14-2.23 (m, 1H), 1.86-1.99 (m, 1H). MS: m/z=206 (M+H$^+$).

(S)-2-(3-((S)-2-(4-(4-Azidobutaneamido)phenyl)-1-carboxyethyl)-ureido)-pentanedioic acid: P062

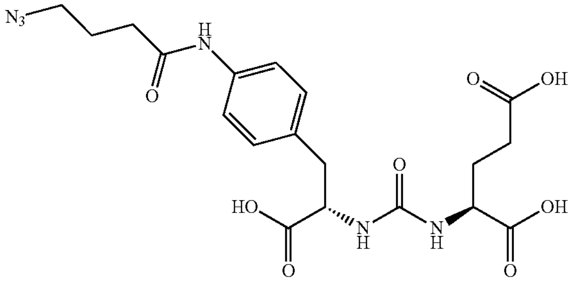 [SMILES: [N-]=[N+]=NCCCC(=O)Nc1ccc(C[C@H](NC(=O)N[C@@H](CCC(=O)O)C(=O)O)C(=O)O)cc1]

General experimental procedures for amide formation and removal of ester groups (tert-butyl and methyl) were followed. Reaction was performed on a 40 mg scale. Product was purified by HPLC purification system using 0.05% TFA in water and acetonitrile as a solvent yielded the title compound (13 mg, 42%). $^{1}$H NMR ($CD_3OD$, 400 MHz) δ 7.37-7.35 (dd, J=6.4, 1.6 Hz, 2H), 7.09-7.07 (dd, J=6.4, 1.6 Hz, 2H), 4.44-4.41 (m, 1H), 4.20-4.16 (m, 1H), 3.28 (t, J=6.4 Hz, 2H), 3.03-2.98 (m, 1H), 2.91-2.82 (m, 1H), 2.36 (t, J=6.4 Hz, 2H), 2.31-2.22 (m, 2H), 2.07-1.98 (m, 1H), 1.88-1.72 (m, 3H). MS: m/z=465 (M+H$^+$).

(S)-2-(3-((S)-2-(4-(4-Azidobutaneamido)phenyl)-1-carboxyethyl)-3-methylureido)-pentanedioic acid: P063

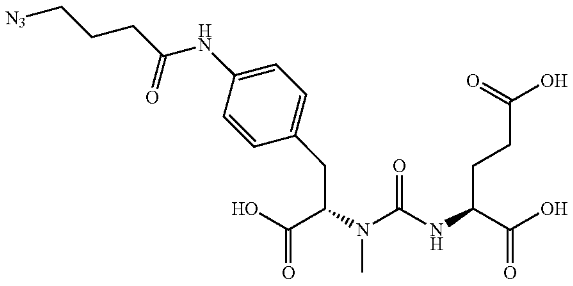 [SMILES: CN(C(=O)N[C@@H](CCC(=O)O)C(=O)O)[C@@H](Cc1ccc(NC(=O)CCCN=[N+]=[N-])cc1)C(=O)O]

General experimental procedures for amide formation of and removal of ester groups (tert-butyl and methyl) were followed. Reaction was performed on a 40 mg scale. Product was purified by HPLC purification system using 0.05% TFA in water and acetonitrile as a solvent yielded the title compound (11 mg, 35%). $^{1}$H NMR ($CD_3OD$, 400 MHz) δ 7.40-7.37 (m, 2H), 7.02-6.99 (m, 2H), 4.48-4.33 (dd, J=11.2, 4.0 Hz, 1H), 4.28-4.19 (m, 1H), 3.31-3.26 (m, 3H), 3.15-3.10 (m, 1H), 3.05-3.0 (m, 1H), 2.94, 2.89 (s, 3H each), 2.38-2.32 (m, 2H), 2.30-2.08 (m, 1H), 2.02-1.82 (m, 3H), 1.66-1.50 (m, 2H). MS: m/z=478 (M+H$^+$).

(S)-2-(3-((S)-1-Carboxy-5-(4-(4-(3-fluoropropyl)-1H-1,2,3-triazol-1-yl)benzamido) pentyl)-2,4,6-trioxotetrahydropyrimidin-1(2H)-yl)pentanedioic acid: P064

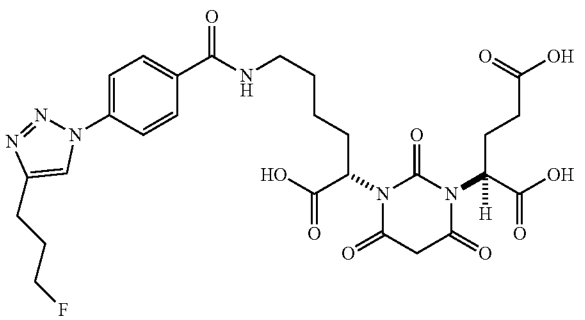

General experimental procedure for click reaction was followed. Reaction was performed on a 2.0 mg scale of (S)-2-(3-((S)-5-(4-azidobenzamido)-1-carboxypentyl)-2,4,6-trioxotetrahydropyrimidin-1(2H)-yl)pentanedioic acid. Isolated 1.0 mg (43%) of P064 as a white solid. $^1$H NMR ($CD_3OD$, 400 MHz) δ 8.43 (s, 1H), 7.99 (d, J=8.8 Hz, 2H), 7.94 (d, J=8.8 Hz, 2H), 5.27-5.36 (m, 2H), 4.57 (t, J=5.8 Hz, 2H), 4.45 (d, J=5.8 Hz, 2H), 3.38 (m, 2H), 2.91 (t, J=7.6 Hz, 2H), 2.40-2.48 (m, 1H), 2.36 (t, J=6.8 Hz, 2H), 2.04-2.26 (m, 3H), 1.58-1.68 (m, 2H), 1.28-1.38 (m, 2H). MS: m/z=619 (M+H$^+$).

(S)-2-(3-((S)-1-Carboxy-2-(4-(4-(4-(3-fluoropropyl)-1H-1,2,3-triazol-1-yl)phenyl)ethyl)ureido)pentanedioic acid: P065

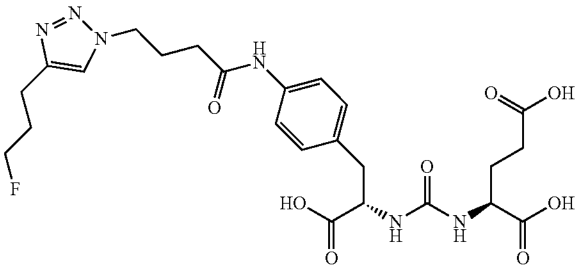 [SMILES: O=C(O)CC[C@H](NC(=O)N[C@@H](Cc1ccc(NC(=O)CCCn2cc(CCCF)nn2)cc1)C(=O)O)C(=O)O]

General procedure for click chemistry was followed. Reaction was performed on a 4 mg scale. Product was purified by HPLC purification system using 0.05% TFA in water and acetonitrile as a solvent yielded the title compound (3 mg, 64%). $^1$H NMR ($CD_3OD$, 400 MHz) δ 7.79 (s, 1H), 7.43-7.41 (dd, J=7.6, 0.8 Hz, 2H), 7.14 (t, J=7.6 Hz, 2H), 4.51-4.43 (m, 4H), 4.38 (t, J=7.6 Hz, 2H), 3.28 (t, J=6.0 Hz, 1H), 4.28-4.24 (m, 1H), 3.17-3.05 (m, 1H), 2.98-2.91 (m, 1H), 2.78 (t, J=7.2 Hz, 2H), 2.40-2.22 (m, 7H), 2.14-1.94 (m, 3H), 1.87-1.78 (m, 1H). MS: m/z=551 (M+H$^+$).

(S)-Di-tert-butyl 2-(2-(4-(1,3-dioxoisoindolin-2-yl)butyl)hydrazinecarboxamido)-pentanedioate

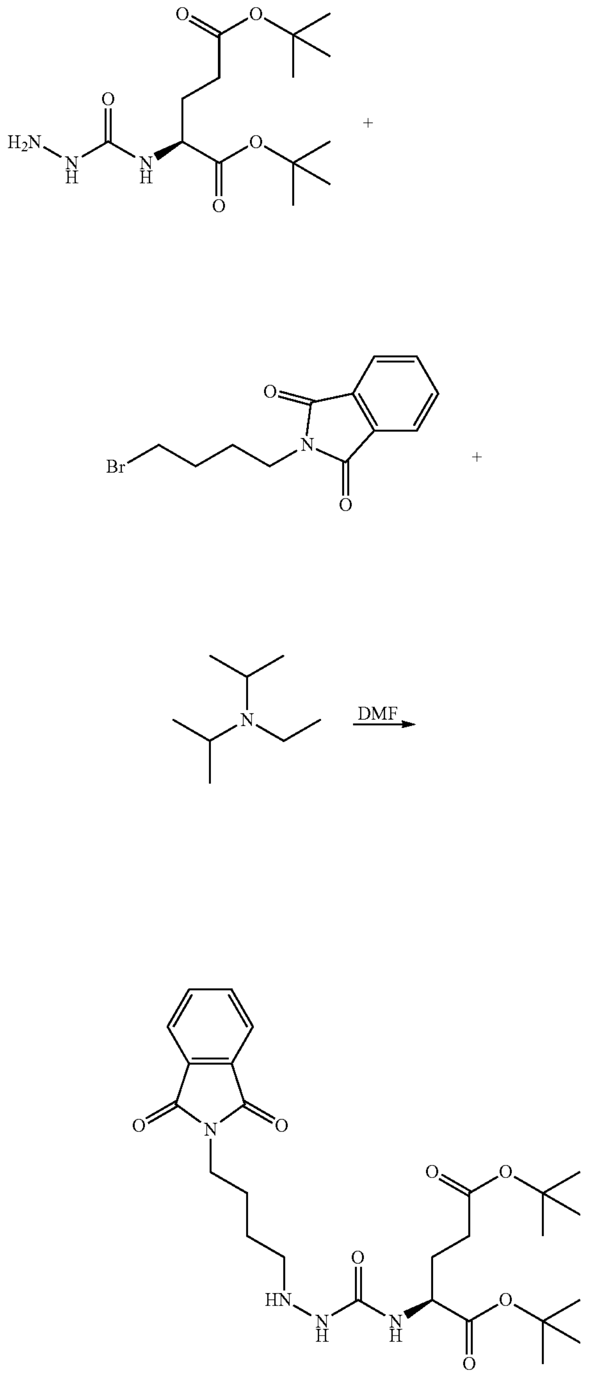

A mixture of (S)-di-tert-butyl 2-(hydrazinecarboxamido)pentanedioate (50 mg, 0.16 mmol), 2-(4-bromobutyl)isoindoline-1,3-dione (44 mg, 0.16 mmol), and DIPEA (0.082 mL, 0.472 mmol) in DMF (2.0 mL) was stirred at room temperature overnight, concentrated in vacuo. The residue was purified on flash column chromatography (silica gel, 40-80% EtOAc/hexanes) to give the desired product (35 mg, 43%). MS: m/z=519 (M+H$^+$).

(S)-2-(2-Acetyl-2-(4-(1,3-dioxoisoindolin-2-yl)butyl)hydrazinecarboxamido)-pentanedioic acid: P066

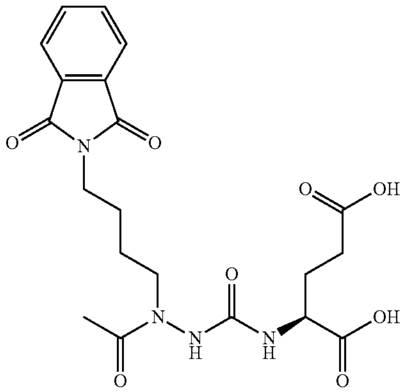 [SMILES: CC(=O)N(CCCCN1C(=O)c2ccccc2C1=O)NC(=O)N[C@@H](CCC(=O)O)C(=O)O]

First, a solution (S)-di-tert-butyl 2-(2-(4-(1,3-dioxoisoindolin-2-yl)butyl)hydrazinecarboxamido)-pentanedioate (35 mg, 0.067 mmol), acetyl chloride (5.3 mg, 0.067 mmol), and triethylamine (0.024 mL, 0.169 mmol) in DCM (2.0 mL) was tirred at room temperature overnight, and then concentrated in vacuo. The residue was used directly in the next step withouy any further purification. General procedure for the removal of tert-butyl group from esters was followed. Reaction was performed on 38 mg scale. After HPLC purification, P066 (20 mg, 66%) was obtained. $^{1}$H NMR ($CD_3OD$, 400 MHz) δ 7.74-7.86 (m, 4H), 4.23-4.33 (m, 1H), 3.83-3.99 (m, 1H), 3.68 (t, J=7.6 Hz, 2H), 2.39 (t, J=7.6 Hz, 2H), 2.12-2.24 (m, 2H), 2.12 (s, 3H), 1.86-1.95 (m, 1H), 1.52-1.74 (m, 4H). MS: m/z=449 (M+H$^+$).

(S)-2-(3-((S)-1-Carboxy-2-(4-(6-(4-(3-fluoropropyl)-1H-1,2,3-triazol-1-yl)hexamido)phenyl)ethyl)ureido)pentanedioic acid: P067

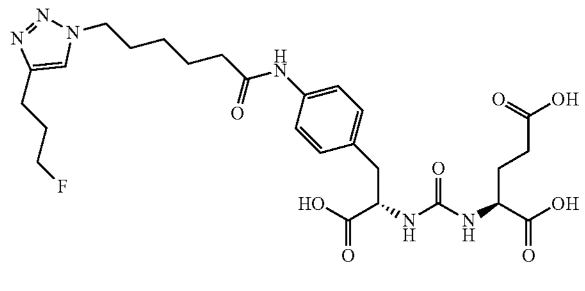 [SMILES: O=C(O)CC[C@H](NC(=O)N[C@@H](Cc1ccc(NC(=O)CCCCCn2cc(CCCF)nn2)cc1)C(=O)O)C(=O)O]

General procedure for click chemistry was followed. Reaction was performed on a 53 mg scale. Product was purified by HPLC purification system using 0.05% TFA in water and acetonitrile as a solvent yielded the title compound (16 mg. 33%). $^{1}$H NMR ($CD_3OD$, 400 MHz) δ 7.70 (s, 1H), 7.38-7.35 (m, 2H), 7.08-7.05 (m, 2H), 4.48-4.28 (m, 6H), 3.00-2.90 (m, 2H), 2.70 (t, J=7.2 Hz, 2H), 2.25 (t, J=7.2 Hz, 2H), 2.06-1.50 (m, 9H), 1.32-1.20 (m, 2H). MS: m/z=579 (M+H$^+$).

(S)-2-(3-((S)-1-Carboxy-2-(4-(6-(4-(3-fluoropropyl)-1H-1,2,3-triazol-1-yl)hexamido)phenyl)ethyl-3-methylureido)pentanedioic acid: P068

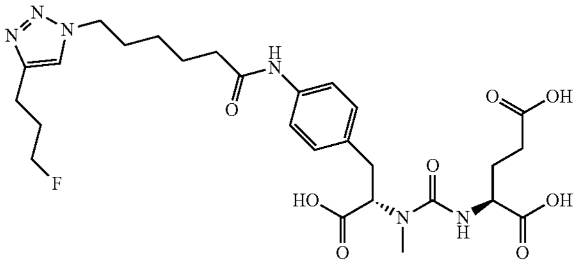 [SMILES: CN(C(=O)N[C@@H](CCC(=O)O)C(=O)O)[C@@H](Cc1ccc(NC(=O)CCCCCn2cc(CCCF)nn2)cc1)C(=O)O]

General procedure for click chemistry was followed. Reaction was performed on a 53 mg scale. Product was purified by HPLC purification system using 0.05% TFA in water and acetonitrile as a solvent yielded the title compound (5 mg. 10%). $^{1}$H NMR ($CD_3OD$, 400 MHz) δ 7.76 (s, 1H), 7.46-7.43 (m, 2H), 7.10-7.06 (td, J=8.4, 1.6 Hz, 2H), 4.56-4.27 (m, 6H), 4.14 (t, J=7.2 Hz, 1H), 3.23-3.09 (m, 2H), 3.02, 2.97 (s, 3H), 2.78 (t, J=8.0 Hz, 2H), 2.30 (t, J=8.0 Hz, 2H), 2.28-2.17 (m, 1H), 2.10-1.82 (m, 10H), 1.37-1.30 (m, 2H). MS: m/z=593 (M+H$^+$).

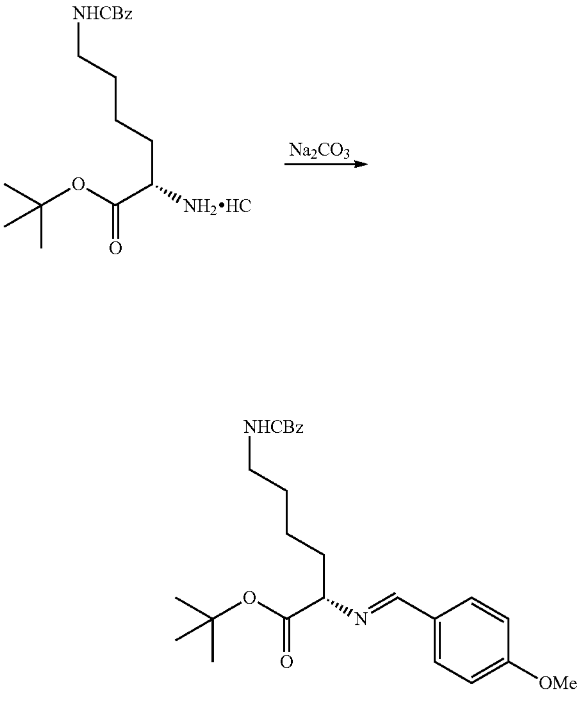

A mixture of (S)-tert-butyl 2-amino-6-(((benzyloxy)carbonyl)amino)hexanoate HCl salt (1.5 g, 4 mmol), 4-methoxybenzaldehyde (571 mg, 4.2 mmol), and sodium bicarbonate (636 mg, 6 mmol) in 5 mL of MeOH was stirred at rt for 18 h. I was filtered and the solid was washed withy MeOH (2 mL). The filtrate was added 3 mL of ether and let sit for 2 h. The mixture was filtered again and the filtrate was concentrated to afford (E)-tert-butyl 6-(((benzyloxy)carbonyl)amino)-2-((4-methoxybenzylidene)amino)hexanoate as a clear oil. MS(ESI): m/z=455 (M+H$^+$).

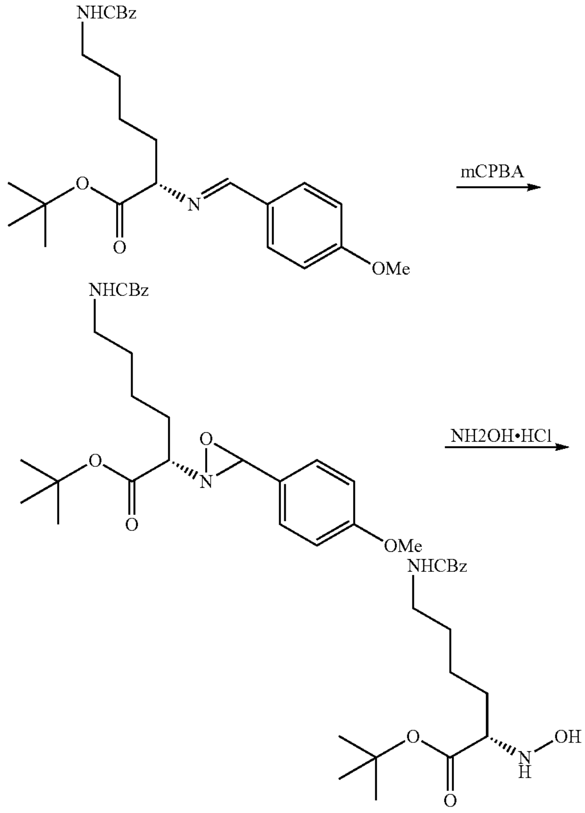

To above compound in DCM (5.0 mL) at −15° C. was added a mCPBA (1.27 g, 5.7 mmol) suspension in DCM (10 mL). The mixture was stirred at rt for 15 h and diluted with EtOAc (60 mL). It was washed with $NaHCO_3$ (3×50 mL) and brine (50 mL), and dried over $MgSO_4$ and concentrated to afford tert-butyl 6-(((benzyloxy)carbonyl)amino)-2-(3-(4-methoxyphenyl)-1,2-oxaziridin-2-yl)hexanoate as a clear oil. To this oil in MeOH (10 mL) was added hydroxylamine HCl (635 mg, 9.2 mmol). The mixture was stirred at rt for 24 h. Solvent was removed and the residue was taken up to EtOAc (80 mL) and washed with water (2×50 mL) and $NaHCO_3$ (2×50 mL), and brine (50 mL). Solvent was removed and the residue was purified by chromatography to afford tert-butyl 6-(((benzyloxy)carbonyl)amino)-2-(hydroxyamino)hexanoate as a thick oil (1.25 g, 87%). MS: m/z=353 ($M+H^+$).

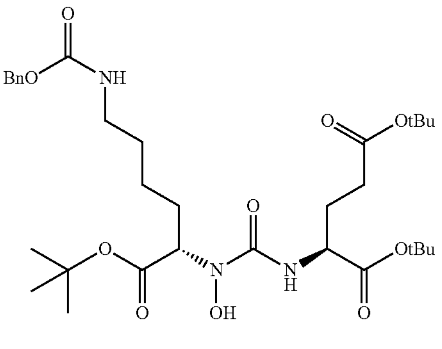 [SMILES: CC(C)(C)OC(=O)CC[C@H](NC(=O)N(O)[C@@H](CCCCNC(=O)OCc1ccccc1)C(=O)OC(C)(C)C)C(=O)OC(C)(C)C]

The above compound (352 mg, 1 mmol) was reacted with isocyanate using the standard condition for urea formation. The crude product was purified by chromatography (hexane/EtOAc) to afford (9S,13S)-tri-tert-butyl 10-hydroxy-3,11-dioxo-1-phenyl-2-oxa-4,10,12-triazapentadecane-9,13,15-tricarboxylate as a white wax (350 mg, 55%). MS: m/z=638 ($M+H^+$).

(13S)-10-Hydroxy-3,11-dioxo-1-phenyl-2-oxa-4,10,12-triazapentadecane-9,13,15-tricarboxylic acid: P069

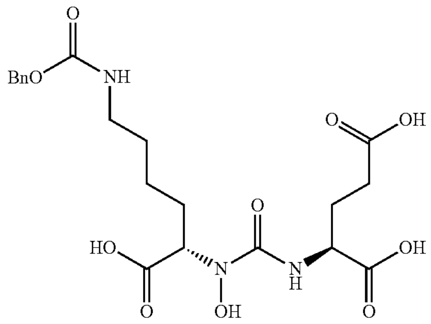 [SMILES: O=C(O)CC[C@H](NC(=O)N(O)[C@@H](CCCCNC(=O)OCc1ccccc1)C(=O)O)C(=O)O]

General procedure for the removal of tert-butyl group from esters was followed. The crude product was purified by RP-HPLC (MeCN/TFA) to afford (13S)-10-Hydroxy-3,11-dioxo-1-phenyl-2-oxa-4,10,12-triazapentadecane-9,13,15-tricarboxylic acid, P069, as a fluffy solid (10 mg, 70%). $^1H$ NMR ($CD_3CN$, 400 MHz) δ 7.40-7.30 (m, 5H), 6.67 (d, J=8.4 Hz, 1H), 5.73 (m, 1H), 5.05 (m, 2H), 4.70 (t, J=7.6 Hz, 1H), 4.31 (m, 1H), 3.21-3.03 (m, 2H), 2.42-2.38 (m, 2H), 2.19-2.09 (m, 1H), 1.88-1.81 (m, 2H), 1.55-1.30 (m, 4H). MS: m/z=470 ($M+H^+$).

(13S)-3-Oxo-1-phenyl-11-thioxo-2-oxa-4,10,12-triazapentadecane-9,13,15-tricarboxylic acid: P070

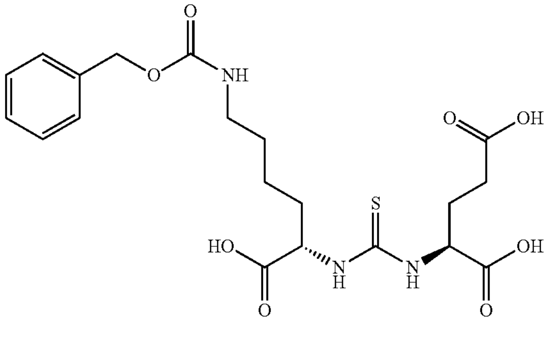 [SMILES: O=C(O)CC[C@H](NC(=S)N[C@@H](CCCCNC(=O)OCc1ccccc1)C(=O)O)C(=O)O]

General experimental procedures for urea formation and tert-butyl deprotection were followed. The reaction was carried out on a 30 mg scale. After HPLC purification, P070 was obtained. $^1H$ NMR ($CD_3CN$, 400 MHz) δ 7.84 (d, J=8.0 Hz, 1H), 7.40-7.30 (m, 5H), 5.95 (dd, J=10.8, 4.4 Hz, 1H), 5.75 (m, 1H), 5.10-5.01 (m, 2H), 4.99-4.94 (m, 1H), 3.21-3.02 (m, 2H), 2.44-2.39 (m, 2H), 2.29-2.21 (m, 1H), 2.11-1.98 (m, 1H), 1.59-1.36 (m, 5H). MS: m/z=470 ($M+H^+$).

(13S)-10-Hydroxy-3-oxo-1-phenyl-11-thioxo-2-oxa-4,10,12-triazapentadecane-9,13,15-tricarboxylic acid: P071

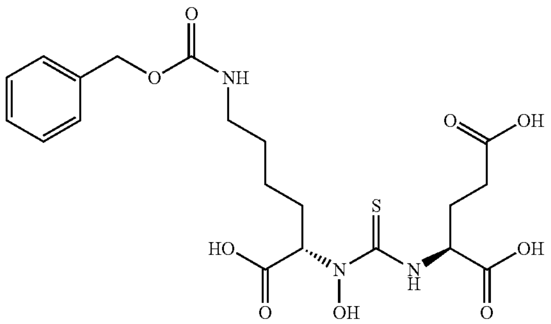 [SMILES: O=C(O)CC[C@H](NC(=S)N(O)[C@@H](CCCCNC(=O)OCc1ccccc1)C(=O)O)C(=O)O]

General experimental procedures for urea formation and tert-butyl deprotection were followed. The reaction was carried out on a 30 mg scale. After HPLC purification, P071 was obtained as a white fluffy solid. MS: m/z=486 (M+H$^+$).

(S)-2-(3-((S)-5-(Benzyloxycarbonylamino)-1-carboxypentyl)-2,4,5-trioxoimidazolidin-1-yl)pentanedioic acid: P072

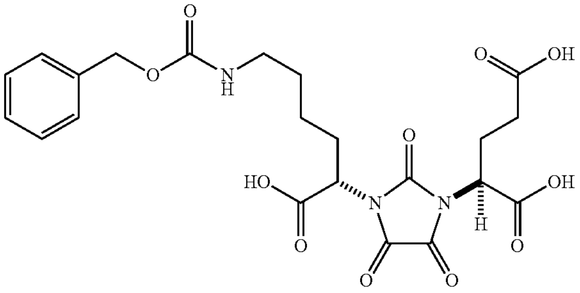

To a solution of (9S,13S)-tri-tert-butyl 3,11-dioxo-1-phenyl-2-oxa-4,10,12-triazapentadecane-9,13,15-tricarboxylate (200 mg, 0.322 mmol) in dry DCM (2.0 mL) was added oxalyl chloride (0.32 mL, 0.64 mmol, 2.0 M solution in DCM). The mixture was heated at 50° C. for 2 hours. The crude mixture was purified by flush chromatography (EtOAc/hexane, 0 to 40%) to give the intermediate which was deprotected with general condition to give 8.5 mg (5.2%) of P072 as a white solid. $^1H$ NMR ($CD_3OD$, 400 MHz) δ 7.23-7.36 (m, 5H), 5.03 (s, 2H), 4.88 (m, 1H), 4.78 (bt, J=7.4 Hz, 1H), 3.09 (bt, J=6.6 Hz, 2H), 2.30-2.50 (m, 4H), 2.14-2.22 (m, 2H), 1.34-1.58 (m, 4H). MS: m/z=508 (M+H$^+$).

(S)-2-(3-((S)-5-(5-Azidopentanamido)-1-carboxypentyl)-2,4,6-trioxotetrahydro pyrimidin-1(2H)-yl) pentanedioic acid: P073

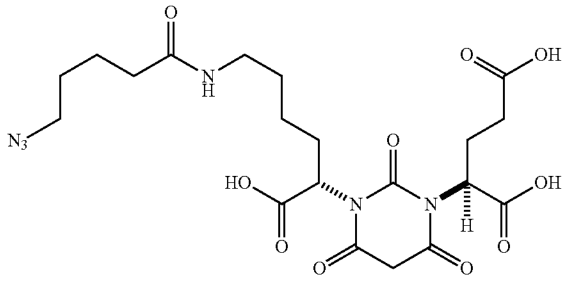

General experimental procedures for amidation and tert-butyl deprotection were followed. Reaction was performed on a 19.7 mg scale of (S)-di-tert-butyl 2-(3-((S)-6-amino-1-tert-butoxy-1-oxohexan-2-yl)-2,4,6-trioxotetrahydropyrimidin-1(2H)-yl)pentanedioate. Isolated 10.0 mg (55%) of P073 as a white solid. $^1H$ NMR ($CD_3OD$, 400 MHz) δ 5.35 (dd, J=10.0, 4.4 Hz, 1H), 5.27 (dd, J=9.6, 4.8 Hz, 1H), 3.25 (m, 2H), 3.08-3.18 (m, 2H), 2.40-2.50 (m, 1H), 2.38 (t, J=7.6 Hz, 2H), 2.10-2.28 (m, 4H), 1.96-2.04 (m, 1H), 1.40-1.64 (m, 6H), 1.28-1.38 (m, 2H). MS: m/z=513 (M+H$^+$).

(S)-2-(3-((S)-5-(2-Azidoacetamido)-1-carboxypentyl)-2,4,6-trioxotetrahydro pyrimidin-1(2H)-yl)pentanedioic acid: P074 Precursor

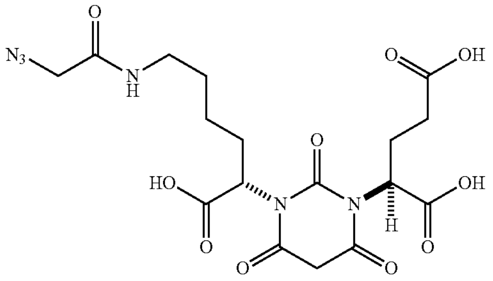

General experimental procedures for amidation and tert-butyl deprotection were followed. Reaction was performed on a 19.7 mg scale of (S)-di-tert-butyl 2-(3-((S)-6-amino-1-tert-butoxy-1-oxohexan-2-yl)-2,4,6-trioxotetrahydropyrimidin-1(2H)-yl)pentanedioate. Isolated 7.3 mg (44%) of P074 precursor as a white solid. $^1H$ NMR ($CD_3OD$, 400 MHz) δ 5.35 (dd, J=10.0, 4.4 Hz, 1H), 5.27 (dd, J=9.8, 5.0 Hz, 1H), 4.90 (s, 2H), 3.18 (t, J=7.0 Hz, 2H), 2.40-2.50 (m, 1H), 2.38 (t, J=6.8 Hz, 2H), 2.20-2.30 (m, 1H), 2.10-2.18 (m, 1H), 1.98-2.06 (m, 1H), 1.42-1.58 (m, 2H), 1.28-1.38 (m, 2H). MS: m/z=471 (M+H$^+$).

(S)-2-(3-((S)-1-Carboxy-5-(2-(4-(3-fluoropropyl)-1H-1,2,3-triazol-1-yl)acetamido) pentyl)-2,4,6-trioxotetrahydropyrimidin-1(2H)-yl)pentanedioic acid: P074

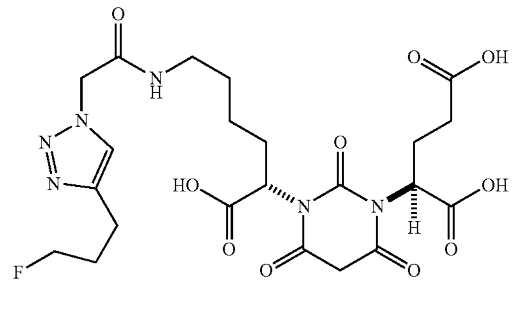

General experimental procedures for amidation and tert-butyl deprotection were followed. Reaction was performed on a 2.6 mg scale of (S)-2-(3-((S)-5-(2-azidoacetamido)-1-carboxypentyl)-2,4,6-trioxotetrahydropyrimidin-1(2H)-yl) pentanedioic acid. Isolated 1.1 mg (35%) of P074 as a white solid. $^1$H NMR ($CD_3OD$, 400 MHz) δ 7.76 (s, 1H), 5.35 (dd, J=10.0, 4.4 Hz, 1H), 5.26 (dd, J=9.6, 5.2 Hz, 1H), 5.06 (s, 2H), 4.52 (t, J=5.8 Hz, 2H), 4.40 (t, J=5.8 Hz, 2H), 3.20 (t, J=6.8 Hz, 2H), 2.82 (t, J=7.8 Hz, 2H), 2.42-2.50 (m, 1H), 2.37 (t, J=6.8 Hz, 2H), 2.20-2.30 (m, 1H), 1.98-2.18 (m, 4H), 1.44-1.60 (m, 2H), 1.28-1.38 (m, 2H). MS: m/z=557 ($M+H^+$).

(S)-2-((S)-2-Carboxypyrrolidine-1-carboxamido) pentanedioic acid: P075

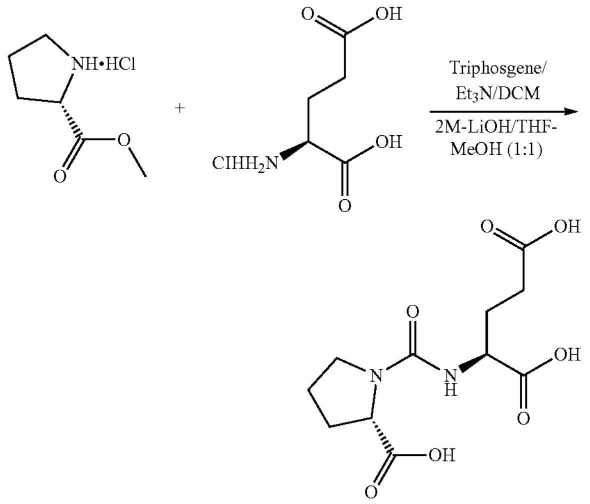

General procedures for urea formation and base hydrolysis of methyl ester were followed to prepare the proline-glutamic acid urea derivative. The reaction was performed on a 211 mg scale. Product was purified by HPLC purification system using 0.05% TFA in water and acetonitrile as a solvent yielded the title compound (218 mg. 86%). $^1$H NMR ($CD_3OD$, 400 MHz) δ 4.12-4.02 (m, 1H), 3.97-3.93 (dd, J=8.8, 6.0 Hz, 1H), 3.40-3.35 (m, 1H), 3.25-3.1.8 (m, 1H), 2.34-1.92 (m, 8H). MS: m/z=289 ($M+H^+$).

(S)-2-(3-((S)-1-Carboxy-5-(5-(4-(3-fluoropropyl)-1H-1,2,3-triazol-1-yl)pentanamido) pentyl)-2,4,6-trioxotetrahydropyrimidin-1(2H)-yl)pentanedioic acid: P076

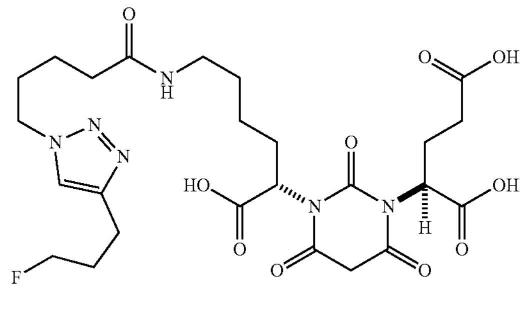

General experimental procedure for click reaction was followed. Reaction was performed on a 2.0 mg scale of (S)-2-(3-((S)-5-(5-azidopentanamido)-1-carboxypentyl)-2,4,6-trioxotetrahydropyrimidin-1(2H)-yl)pentanedioic acid. After HPLC purification, P076 (1.0 mg, 43%) was isolated as a white solid. $^1$H NMR ($CD_3OD$, 400 MHz) δ 7.76 (s, 1H), 5.34 (dd, J=10.0, 4.5 Hz, 1H), 5.25 (dd, J=9.4, 5.1 Hz, 1H), 4.50 (t, J=5.9 Hz, 1H), 4.34-4.40 (m, 3H), 3.08-3.16 (m, 2H), 2.77-2.82 (m, 2H), 2.34-2.50 (m, 3H), 2.10-2.29 (m, 4H), 1.95-2.08 (m, 3H), 1.83-1.91 (m, 2H), 1.40-1.60 (m, 4H), 1.26-1.38 (m, 2H). MS: m/z=599 ($M+H^+$).

(S)-2-(3-((S)-5-(Benzyloxycarbonylamino)-1-carboxypentyl)-5,5-dimethyl-2,4,6-trioxotetrahydropyrimidin-1(2H)-yl)pentanedioic acid: P077

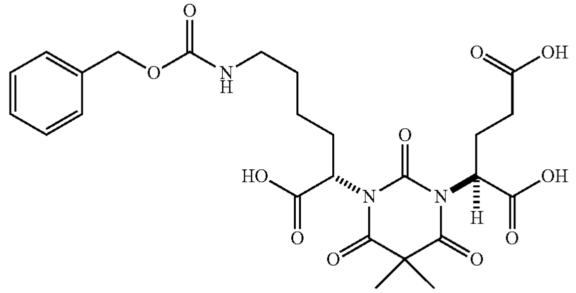

General experimental procedure for alkylation reaction was followed. Reaction was performed on a 30 mg scale of (S)-di-tert-butyl 2-(3-((S)-6-(benzyloxycarbonylamino)-1-tert-butoxy-1-oxohexan-2-yl)-2,4,6-trioxotetrahydropyrimidin-1(2H)-yl)pentanedioate. After HPLC purification, P077 (8.5 mg, 36%) was isolated as a white solid. $^1$H NMR ($CD_3OD$, 400 MHz) δ 7.26-7.34 (m, 4H), 5.31 (dd, J=9.6, 4.9 Hz, 1H), 5.24 (dd, J=9.8, 5.1 Hz, 1H), 5.02 (s, 2H), 3.03-3.11 (m, 2H), 2.45 (ddd, J=14.1, 6.5, 4.9 Hz, 1H), 2.22-2.36 (m, 3H), 2.10-2.20 (m, 1H), 1.98-2.09 (m, 1H), 1.45-1.56 (m, 8H), 1.26-1.39 (m, 2H). MS: m/z=550 ($M+H^+$).

(2S)-2-(3-((S)-5-(Benzyloxycarbonylamino)-1-carboxypentyl)-5-ethyl-2,4,6-trioxotetrahydropyrimidin-1(2H)-yl)pentanedioic acid: P078

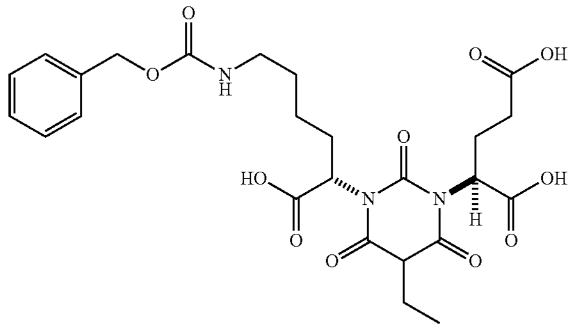

General experimental procedure for alkylation reaction was followed. Reaction was performed on a 27 mg scale of (S)-di-tert-butyl 2-(3-((S)-6-(benzyloxycarbonylamino)-1-tert-butoxy-1-oxohexan-2-yl)-2,4,6-trioxotetrahydropyrimidin-1(2H)-yl)pentanedioate. After HPLC purification, P078 (8.5 mg, 23%) was isolated as a white solid. $^1H$ NMR ($CD_3OD$, 400 MHz) δ 7.24-7.37 (m, 4H), 5.22-5.42 (m, 2H), 5.02 (s, 2H), 3.04-3.12 (m, 2H), 2.42-2.52 (m, 1H), 2.10-2.37 (m, 6H), 1.97-2.07 (m, 1H), 1.40-1.58 (m, 2H), 1.24-1.38 (m, 3H), 0.96 (td, J=7.4, 4.3 Hz, 3H). MS: m/z=550 ($M+H^+$).

(S)-2-(3-((S)-5-(Benzyloxycarbonylamino)-1-carboxypentyl)-5,5-diethyl-2,4,6-trioxotetrahydropyrimidin-1(2H)-yl)pentanedioic acid: P079

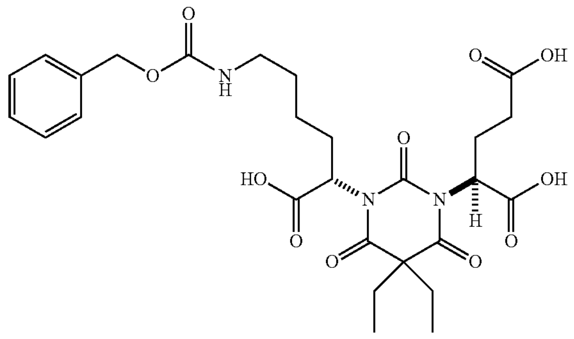

General experimental procedure for alkylation reaction was followed. Reaction was performed on a 27 mg scale of (S)-di-tert-butyl 2-(3-((S)-6-(benzyloxycarbonylamino)-1-tert-butoxy-1-oxohexan-2-yl)-2,4,6-trioxotetrahydropyrimidin-1(2H)-yl)pentanedioate. After HPLC purification, P079 (8.5 mg, 42%) was isolated as a white solid. $^1H$ NMR ($CD_3OD$, 400 MHz) δ 7.26-7.34 (m, 4H), 5.31-5.45 (m, 2H), 4.95-5.09 (m, 2H), 3.03-3.12 (m, 2H), 2.47-2.56 (m, 1H), 2.12-2.37 (m, 4H), 1.96-2.10 (m, 5H), 1.41-1.60 (m, 2H), 1.23-1.37 (m, 2H), 0.86 (q, J=7.6 Hz, 6H). MS: m/z=578 ($M+H^+$).

(S)-2-(3-((S)-1-Carboxy-5-(6-(4-(3-fluoropropyl)-1H-1,2,3-triazol-1-yl)-hexamido)pentyl)-3-methylureido)pentanedioic acid: P080

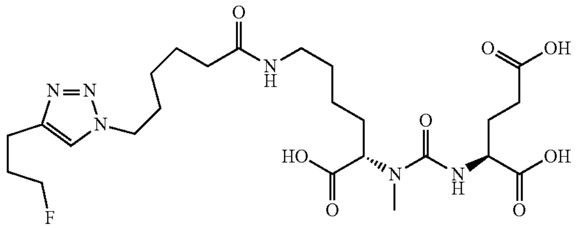 [SMILES: CN(C(=O)N[C@@H](CCC(=O)O)C(=O)O)[C@@H](CCCCNC(=O)CCCCCn1cc(CCCF)nn1)C(=O)O]

General procedure for click chemistry was followed. Reaction was performed on a 13 mg scale. Product was purified by HPLC purification system (0.05% TFA in water-acetonitrile, 20-65%) afforded the title compound (11.5 mg, 77%). $^1H$ NMR ($CD_3OD$, 400 MHz) δ 7.78 (s, 1H), 4.84 (m, 1H), 4.50 (t, J=6.0 Hz, 1H), 4.40-4.34 (m, 2H), 4.30-4.26 (dd, J=9.6, 4.4 Hz, 1H), 3.18-3.08 (m, 2H), 2.84 (s, 3H), 2.80 (t, J=7.6 Hz, 1H), 2.44 (t, J=7.2 Hz, 1H), 2.20-2.12 (m, 2H), 2.15 (t, J=7.2 Hz, 1H), 2.18-1.70 (m, 7H), 1.66-1.28 (m, 8H). MS: m/z=559 ($M+H^+$).

2-((2S)-2-Carboxy-4-(5-(4-(3-fluoropropyl)-1H-1,2,3-triazol-1-yl)pentanamido)pyrrolidine-1-carboxamido)pentanedioic acid: P081

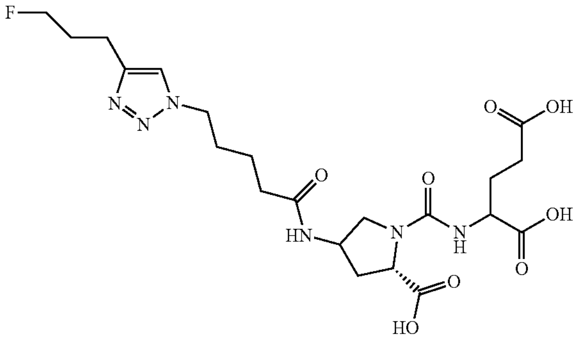 [SMILES: O=C(O)CCC(NC(=O)N1CC(NC(=O)CCCCn2cc(CCCF)nn2)C[C@H]1C(=O)O)C(=O)O]

General experimental procedures for urea, amidation, click chemistry, and tert-butyl deprotection were followed. After HPLC purification, P081 was obtained as a white fluffy solid. 1H NMR ($CD_3OD$, 400 MHz) δ 8.96 (s, 1H), 5.89 (t, J=6.0 Hz, 1H), 5.79-5.73 (m, 3H), 5.68 (t, J=6.8 Hz, 2H), 5.59 (dd, J=10.4, 6.6 Hz, 1H), 5.00 (dd, J=9.6, 6.4 Hz, 1H), 4.67-4.58 (m, 2H), 4.52 (dd, J=10, 6.4 Hz, 1H), 3.77 (m, 2H), 3.66-3.60 (m, 1H), 3.51-3.39 (m, 5H), 3.20 (m, 2H), 2.88 (m, 2H). MS: m/z=515 ($M+H^+$).

(S)-dibenzyl 2-(3-((S)-1-(tert-butoxy)-1-oxopropan-2-yl)ureido)pentanedioate

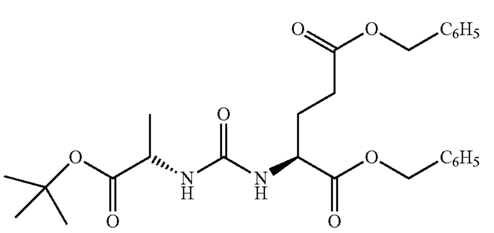

General experimental procedure for urea coupling was followed. Reaction was performed on a 0.2 g scale. Isolated 0.4 g (73%) of the desired product as a white solid. MS m/z=499.1 (M+H$^+$).

(S)-2-(3-((S)-1,5-bis(benzyloxy)-1,5-dioxopentan-2-yl)ureido)propanoic acid

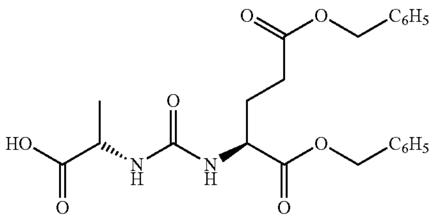

General experimental procedure for N-Boc deprotection was followed. Reaction was performed on a 0.4 g scale. Isolated 0.4 g (93%) of the desired product as a white solid. MS m/z=443.1 (M+H$^+$).

(S)-dibenzyl 2-(3-((S)-1-((2-fluoroethyl)amino)-1-oxopropan-2-yl)ureido)pentanedioate

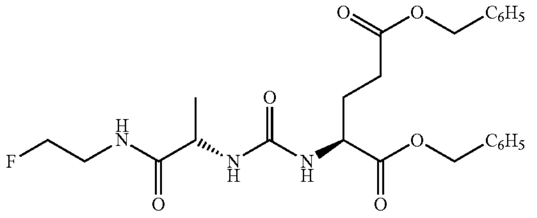

General experimental procedure for amide coupling was followed. Reaction was performed on a 0.4 g scale. Isolated 0.2 g (42%) of the desired product as a white solid. MS m/z=488.1 (M+H$^+$).

(S)-2-(3-((S)-1-((2-Fluoroethyl)amino)-1-oxopropan-2-yl)ureido)pentanedioic acid: P082

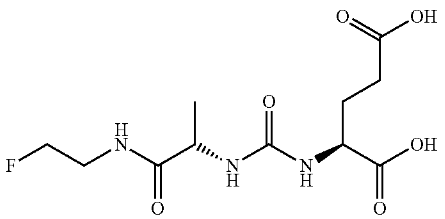

General experimental procedure for benzyl deprotection was followed. Reaction was performed on a 0.05 g scale. After HPLC purification, P082 (10 mg, 31%) was obtained as a white solid. H NMR ($CD_3OD$, 400 MHz) 4.43 (td, J=47.6, 5.2 Hz, 2H), 4.32-4.26 (m, 1H), 3.46 (td, J=26.8, 4.8 Hz, 2H), 3.40-3.36 (m, 2H), 2.42-2.34 (m, 4H), 2.17-2.05 (m, 1H), 1.95-1.84 (m, 1H), MS: m/z=308.1 (M+H$^+$).

(9S,13S)-4-Methyl-3,11-dioxo-1-phenyl-2-oxa-4,10,12-triazapentadecane-9,13,15-tricarboxylic acid: P083

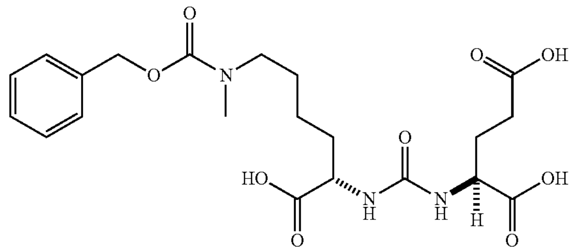

General experimental procedure for alkylation and deprotection reaction was followed. Reaction was performed on a 75 mg scale of (9S,13S)-tri-tert-butyl 3,11-dioxo-1-phenyl-2-oxa-4,10,12-triazapentadecane-9,13,15-tricarboxylate. P083 (7.4 mg, 13%) was isolated as a white solid. $^1$H NMR ($CD_3OD$, 400 MHz) δ 7.27-7.34 (m, 5H), 5.08 (s, 2H), 4.21-4.31 (m, 2H), 3.25-3.32 (m, 2H), 2.89 (d, J=10.2 Hz, 3H), 2.39 (ddd, J=8.7, 6.9, 3.5 Hz, 2H), 2.07-2.16 (m, 1H), 1.74-1.92 (m, 2H), 1.49-1.71 (m, 3H), 1.26-1.43 (m, 2H). MS: m/z=468 (M+H$^+$).

(S)-2-(3-((S)-5-(Benzyloxycarbonylamino)-1-carboxypentyl)-2,4,6-trioxo-1,3,5-triazinan-1-yl)pentanedioic acid: P084

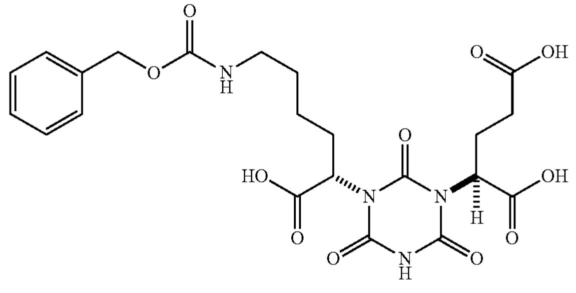

To a solution of (9S,13S)-tri-tert-butyl 3,11-dioxo-1-phenyl-2-oxa-4,10,12-triazapentadecane-9,13,15-tricarboxylate (140 mg, 0.225 mmol) in dry DCM (3.0 mL) was added N-(chlorocarbonyl) isocyanate (22 μL, 0.273 mmol) and pyridine (50 μL, 618 mmol). The mixture was stirred at room temperature for 1 hour and diluted with DCM. The mixture was washed with water, ammonium chloride solution, and brine. The DCM was removed and the residue was purified by flush chromatography (EtOAc/hexane, 0 to 40%) to give (S)-di-tert-butyl 2-(3-((S)-6-(benzyloxycarbonylamino)-1-tert-butoxy-1-oxohexan-2-yl)-2,4,6-trioxo-1,3,5-triazinan-1-yl)pentanedioate 119 mg (76%) as colorless gum. 10.0 mg of above intermediate was deprotected with general condition to give P084 (5.6 mg, 63%) as a white solid. $^1$H NMR ($CD_3OD$, 400 MHz) δ 7.25-7.34 (m, 5H), 5.15-5.28 (m, 2H), 5.03 (s, 2H), 3.04-3.14 (m, 2H), 2.27-2.49 (m, 4H), 2.01-2.18 (m, 2H), 1.30-1.58 (m, 4H). MS: m/z=523 ($M+H^+$).

(S)-2-(3-((S)-5-(Benzyloxycarbonylamino)-1-carboxypentyl)-5-methyl-2,4,6-trioxo-1,3,5-triazinan-1-yl)pentanedioic acid: P085

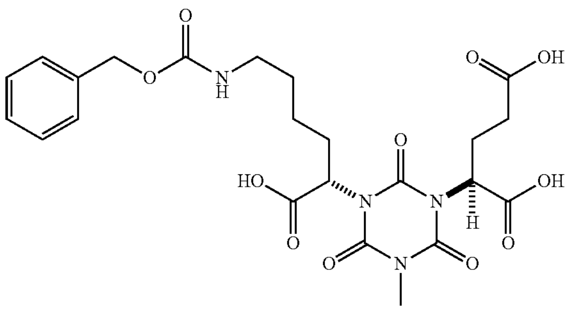

To a solution of (S)-di-tert-butyl 2-(3-((S)-6-(benzyloxycarbonylamino)-1-tert-butoxy-1-oxohexan-2-yl)-2,4,6-trioxo-1,3,5-triazinan-1-yl)pentanedioate (23.4 mg, 0.0334 mmol) in acetonitrile/methanol (1.0 mL, v1:1) was added diazomethane in ether (100 μL, 2.0 M). The mixture was stirred at room temperature for 10 minutes and concentrated. The residue was deprotected with general condition to give P085 (8.4 mg, 46%) as a white solid. $^1$H NMR ($CD_3OD$, 400 MHz) δ 7.26-7.34 (m, 5H), 5.20-5.33 (m, 2H), 5.02 (s, 2H), 3.05-3.27 (m, 2H), 2.27-2.49 (m, 4H), 2.01-2.20 (m, 2H), 1.29-1.58 (m, 4H). MS: m/z=537 ($M+H^+$).

2-((S)-4-(4-(4-Azidobenzamido)butyl)-3-methyl-2,5-dioxoimidazolidin-1-yl)-pentanedioic acid: P086

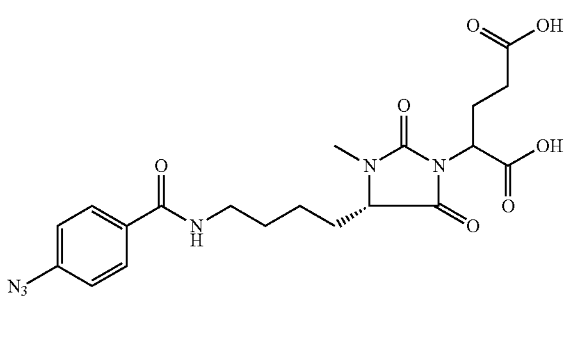 [SMILES: CN1C(=O)N(C(CCC(=O)O)C(=O)O)C(=O)[C@@H]1CCCCNC(=O)c1ccc(N=[N+]=[N-])cc1]

The cylized product was obtained during the acid hydrolysis of tert-butyl group of methylated azido-amide P059. Product was purified with HPLC. $^1$H NMR ($CD_3OD$, 400 MHz) δ 7.83-7.80 (m, 2H), 7.13-7.10 (m, 2H), 4.67-4.63 (m, 1H), 4.08 (t, J=4.4 Hz, 1H), 3.42-3.12 (m, 1H), 2.91 (s, 3H), 2.46-2.28 (m, 4H), 1.98-1.91 (m, 2H), 1.68-1.58 (m, 2H), 1.42-1.36 (m, 2H). MS: m/z=460 ($M+H^+$).

(S)-Di-tert-butyl 2-((5-(ethoxycarbonyl)-4-methylthiazol-2-yl)amino)pentanedioate

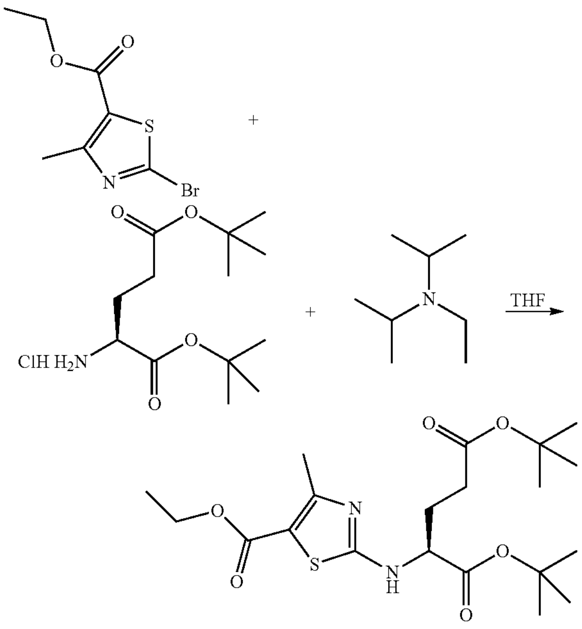

A mixture of ethyl 2-bromo-4-methylthiazole-5-carboxylate (100 mg, 0.4 mmol), (S)-di-tert-butyl 2-aminopentanedioate hydrochloride (118 mg, 0.4 mmol), and DIPEA (0.139 mL, 0.8 mmol) in THE (2.0 mL) was microwaved at 120° C. for 15 min, cooled and concentrated in vacuo. The residue was used directly in the next step without any further purification.

(S)-2-((5-Carboxy-4-methylthiazol-2-yl)amino)pentanedioic acid: P087

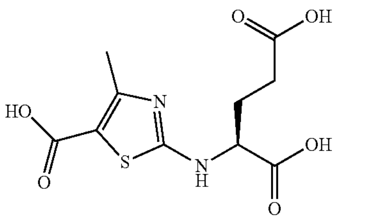 [SMILES: Cc1nc(N[C@@H](CCC(=O)O)C(=O)O)sc1C(=O)O]

General procedure for the removal of tert-butyl group from esters was followed. Reaction was performed on 80 mg scale. The reaction mixture was then under basic hydrolysis to give crude tri acid. After HPLC purification, P087 (3.5 mg, 7%) was obtained. $^1$H NMR ($CD_3OD$, 400 MHz) δ

4.40-4.51 (m, 1H), 2.49 (s, 3H), 2.46 (t, J=7.6 Hz, 2H), 2.22-2.38 (m, 1H), 2.01-2.20 (m, 1H). MS: m/z=289 ($M+H^+$).

(2S)-2-(3-((S)-5-(Benzyloxycarbonylamino)-1-carboxypentyl)-5-nitroso-2,4,6-trioxotetrahydropyrimidin-1(2H)-yl)pentanedioic acid: P088

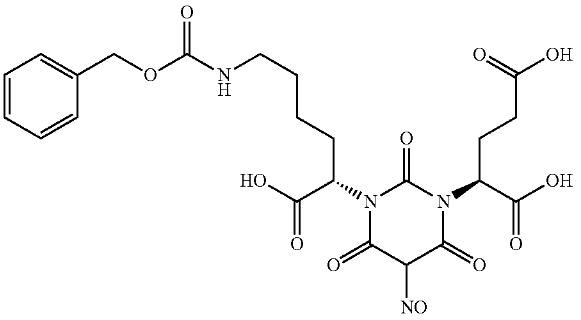

To a solution of (S)-di-tert-butyl 2-(3-((S)-6-(benzyloxycarbonylamino)-1-tert-butoxy-1-oxohexan-2-yl)-2,4,6-trioxotetrahydropyrimidin-1(2H)-yl)pentanedioate (15 mg, 0.022 mmol) in THE (0.5 mL) was added 1M solution of sulfuric acid (0.5 mL) followed by solid sodium nitrite (3.0 mg, 0.043 mmol). The mixture was stirred at room temperature for 10 minutes and concentrated. The residue was deprotected with general condition to give P088 (1.5 mg, 13%) as a white solid. $^1$H NMR ($CD_3OD$, 400 MHz) δ 7.24-7.34 (m, 5H), 5.29-5.46 (m, 2H), 5.01 (s, 2H), 3.05-3.12 (m, 2H), 2.45-2.54 (m, 1H), 2.15-2.41 (m, 4H), 1.98-2.11 (m, 1H), 1.39-1.57 (m, 2H), 1.36 (m, 2H). MS: m/z=551 ($M+H^+$).

(2S)-2-(3-((S)-1-Carboxy-5-((((4-nitrobenzyl)oxy)carbonyl)amino)pentyl)-5-nitro-2,4,6-trioxotetrahydropyrimidin-1(2H)-yl)pentanedioic acid: P089

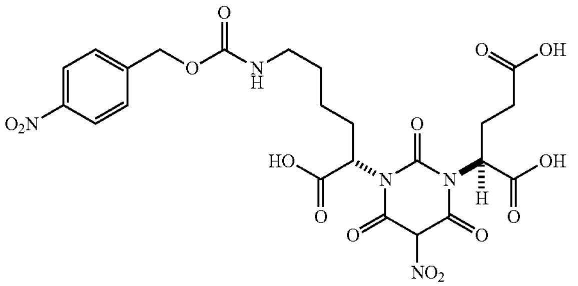

To a solution of (S)-di-tert-butyl 2-(3-((S)-6-(benzyloxycarbonylamino)-1-tert-butoxy-1-oxohexan-2-yl)-2,4,6-trioxotetrahydropyrimidin-1(2H)-yl)pentanedioate (15 mg, 0.022 mmol) in chloroform (0.5 mL) was added $HNO_3$ (conc.) (0.1 mL) followed by TFA (0.5 mL). The mixture was stirred at room temperature for 1 hour and concentrated. The residue was purified by HPLC to give P089 (1.4 mg, 12%) as a white solid. $^1$H NMR ($CD_3OD$, 400 MHz) δ 8.21 (m, 2H), 7.51-7.66 (m, 2H), 5.34-5.48 (m, 2H), 5.08-5.22 (m, 2H), 3.04-3.27 (m, 2H), 2.39-2.50 (m, 1H), 2.24-2.37 (m, 3H), 2.11 (m, 2H), 1.41-1.58 (m, 2H), 1.24-1.40 (m, 2H). MS: m/z=612 ($M+H^+$).

(S)-Dibenzyl 2-(2-((benzyloxy)amino)acetamido)pentanedioate

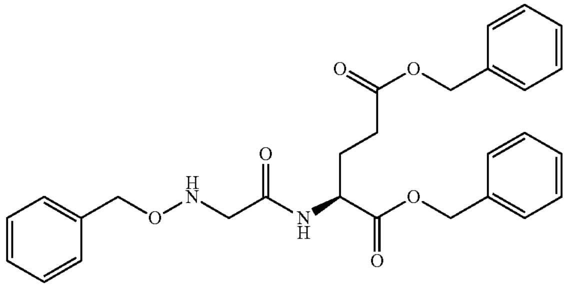 [SMILES: O=C(CNOCc1ccccc1)N[C@@H](CCC(=O)OCc1ccccc1)C(=O)OCc1ccccc1]

First, general experimental procedure for the formation of amide was followed. Reaction was performed on a 525 mg scale. Product was purified on a Biotage purification system eluting out in 5-50% EtOAc:Hexanes mixture in a gradient elution to give a bromide (269 mg, 57%). MS: m/z=449 ($M+H^+$). Second, The bromide was treated with benzylhydroxylamine hydrochloride in the present of DIPEA which gives the title compound (86 mg, 29%). MS: m/z=491 ($M+H^+$).

(S)-Dibenzyl 2-(2-(4-(4-azidophenyl)-N-(benzyloxy)butanamido)acetamido)-pentanedioate

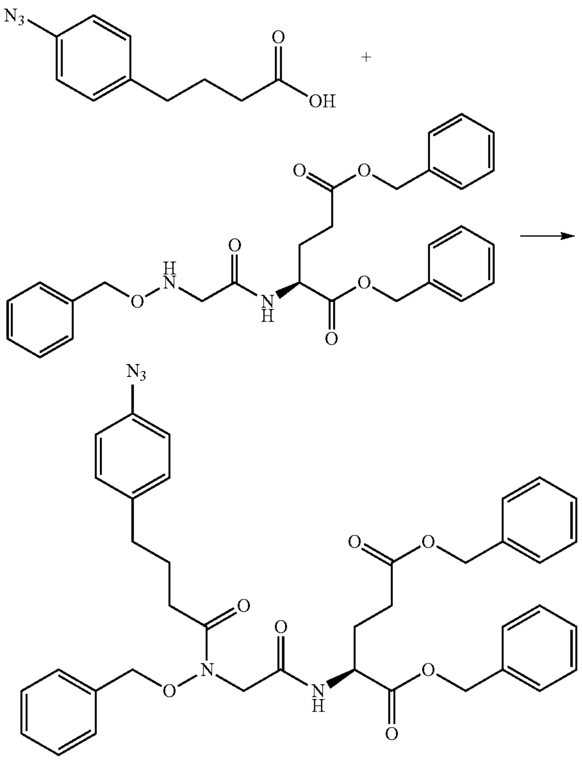

General experimental procedure for the formation of amide was followed. Reaction was performed on a 43 mg scale. Product was purified on a Biotage purification system eluting out in 5-50% EtOAc:Hexanes mixture in a gradient elution to give a bromide (38 mg, 64%). MS: m/z=678 (M+H$^+$).

(S)-2-(2-(4-(4-(4-(3-Fluoropropyl)-1H-1,2,3-triazol-1-yl)phenyl)-N-hydroxybutanamido)acetamido)pentanedioic acid: P090

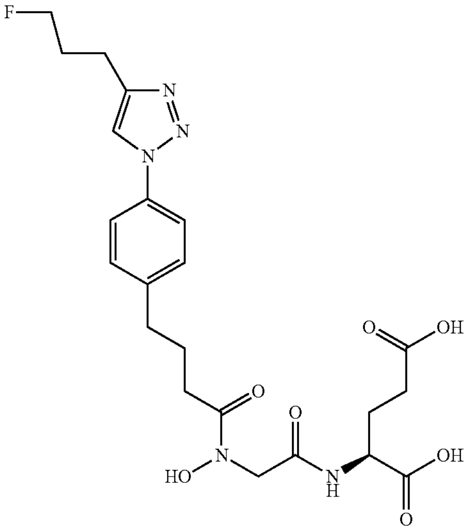 [SMILES: O=C(O)CC[C@H](NC(=O)CN(O)C(=O)CCCc1ccc(-n2cc(CCCF)nn2)cc1)C(=O)O]

First, general experimental procedure for click chemistry was followed. Reaction was performed on a 38 mg scale. The crude product was used directly in the next step without any further purification. Second, general experimental procedure for the removal of benzyl group was followed. Reaction was performed on a 43 mg scale. After HPLC purification, P090 (10 mg, 37%) was obtained. $^1$H NMR ($CD_3OD$, 400 MHz) δ 8.21 (s, 1H), 7.64 (d, J=8.4 Hz, 2H), 7.34 (d, J=8.4 Hz, 2H), 4.46 (dt, J=47.2, 6.0 Hz, 2H), 4.32-4.43 (m, 1H), 4.24 (s, 2H), 2.81 (t, J=3.6 Hz, 2H), 2.67 (t, J=8.4 Hz, 2H), 2.51 (t, J=7.2 Hz, 2H), 2.31 (t, J=8.0 Hz, 2H), 1.78-2.16 (m 6H). MS: m/z=494 (M+H$^+$).

(2S)-2-(5-Amino-3-((S)-5-(benzyloxycarbonylamino)-1-carboxypentyl)-2,4,6-trioxotetrahydropyrimidin-1(2H)-yl)pentanedioic acid: P091

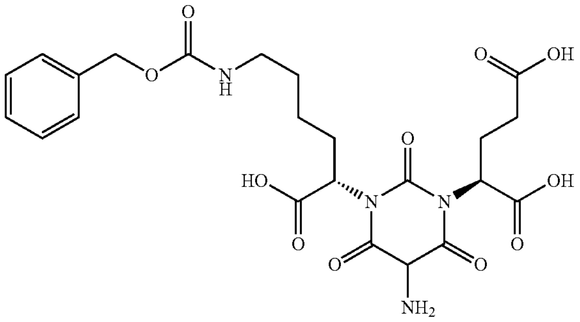 [SMILES: NC1C(=O)N([C@@H](CCCCNC(=O)OCc2ccccc2)C(=O)O)C(=O)N([C@@H](CCC(=O)O)C(=O)O)C1=O]

To a solution of (2S)-2-(3-((S)-5-(benzyloxycarbonylamino)-1-carboxypentyl)-5-nitroso-2,4,6-trioxotetrahydropyrimidin-1(2H)-yl)pentanedioic acid (1.5 mg, 0.0027 mmol) in acetonitrile/water/TFA (10 mL, 50:50:0.05) was added sodium hydrogen sulfite (10 mg, 0.057 mmol). The mixture was stirred at room temperature for 30 minutes and concentrated and purified by HPLC to give P091 (1.0 mg, 68%) as a white solid. $^1$H NMR ($CD_3OD$, 400 MHz) δ 7.15-7.27 (m, 5H), 5.15-5.37 (m, 2H), 4.94 (s, 2H), 2.84-3.06 (m, 2H), 2.28-2.49 (m, 1H), 1.96-2.45 (m, 5H), 1.31-1.52 (m, 2H), 1.11-1.30 (m, 2H). MS: m/z=537 (M+H$^+$).

(S)-2-(3-((S)-1-Carboxy-5-(4-(4-(3-fluoropropyl)-1H-1,2,3-triazol-1-yl)benzamido)pentyl)-3-hydroxyureido)pentanedioic acid: P092

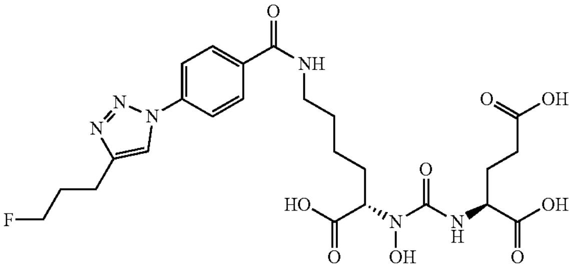 [SMILES: O=C(O)CC[C@H](NC(=O)N(O)[C@@H](CCCCNC(=O)c1ccc(-n2cc(CCCF)nn2)cc1)C(=O)O)C(=O)O]

Compound P092 was synthesized using the same procedures for the preparation of P069. After HPLC purification, P092 was obtained. 1H NMR ($CD_3OD$, 400 MHz) δ 8.26 (s, 1H), 8.00-7.97 (m, 2H), 7.92-7.90 (m, 2H), 4.74-4.70 (m, 1H), 4.60 (t, J=6.0 Hz, 1H), 4.48 (t, J=5.6 Hz, 1H), 4.36-4.32 (m, 1H), 3.50-3.30 (m, 2H), 2.90 (m, 2H), 2.42 (m, 2H), 2.22-2.05 (m, 4H), 1.95-1.88 (m, 2H), 1.69-1.61 (m, 2H), 1.52-1.42 (m, 2H). MS: m/z=567 (M+H$^+$).

(S)-Dibenzyl 2-(2-(5-azido-N-(benzyloxy)pentanamido)acetamido)pentanedioate

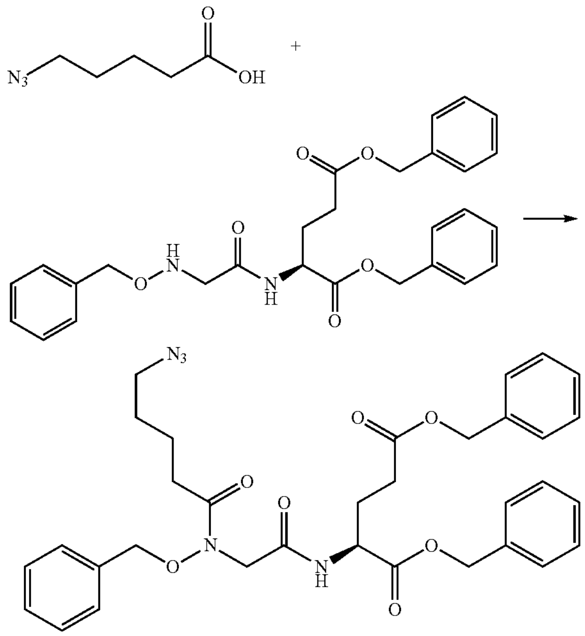

General experimental procedure for the formation of amide was followed. Reaction was performed on a 43 mg scale. Product was purified on a Biotage purification system eluting out in 5-50% EtOAc:Hexanes mixture in a gradient elution to give a bromide (37 mg, 69%). MS: m/z=616 ($M+H^+$).

(S)-2-(2-(5-(4-(3-Fluoropropyl)-1H-1,2,3-triazol-1-yl)-N-hydroxypentanamido)-acetamido)pentanedioic acid: P093

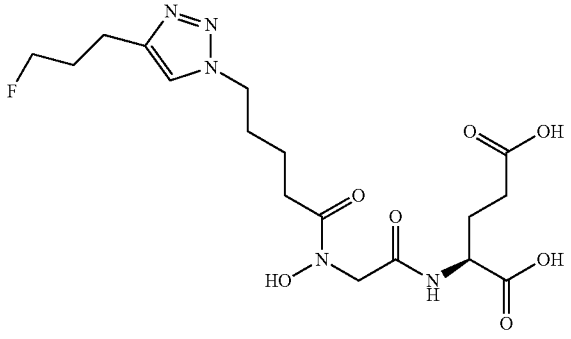 [SMILES: O=C(O)CC[C@H](NC(=O)CN(O)C(=O)CCCCn1cc(CCCF)nn1)C(=O)O]

First, general experimental procedure for click chemistry was followed. Reaction was performed on a 37 mg scale. The crude product was used directly in the next step without any further purification. Second, general experimental procedure for the removal of benzyl group was followed. Reaction was performed on a 43 mg scale. After HPLC purification, P093 (15 mg, 60%) was obtained. $^1H$ NMR ($CD_3OD$, 400 MHz) δ 7.80 (s, 1H), 4.44-4.53 (m, 2H), 4.35-4.42 (m, 3H), 4.31 (s, 2H), 2.80 (t, J=4.4 Hz, 2H), 2.54-2.62 (m, 2H), 2.38 (t, J=8.0 Hz, 2H), 2.12-2.23 (m, 1H), 1.86-2.09 (m, 4H), 1.56-1.65 (m, 2H). MS: m/z=432 ($M+H^+$).

General experimental procedure for amidation and deprotection was followed. Reaction was performed on a 26 mg scale of (S)-di-tert-butyl 2-(3-((S)-6-amino-1-tert-butoxy-1-oxohexan-2-yl)-2,4,6-trioxotetrahydropyrimidin-1(2H)-yl) pentanedioate. Isolated 1.4 mg (5.2%) of P094 precursor as a white solid. MS: m/z=575 ($M+H^+$).

(S)-2-(3-((S)-1-Carboxy-5-(4-(4-(4-(3-fluoropropyl)-1H-1,2,3-triazol-1-yl)phenyl)butanamido)pentyl)-2,4,6-trioxotetrahydropyrimidin-1(2H)-yl)pentanedioic acid: P094

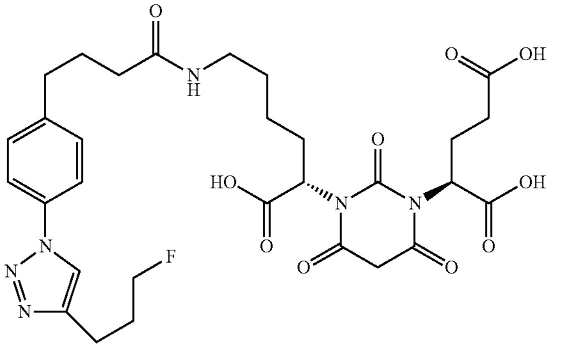 [SMILES: O=C(O)CC[C@@H](C(=O)O)N1C(=O)CC(=O)N([C@@H](CCCCNC(=O)CCCc2ccc(-n3cc(CCCF)nn3)cc2)C(=O)O)C1=O]

General experimental procedure for click reaction was followed. Reaction was performed on a 1.4 mg scale of (S)-2-(3-((S)-5-(4-(4-azidophenyl)butanamido)-1-carboxypentyl)-2,4,6-trioxotetrahydropyrimidin-1(2H)-yl)pentanedioic acid. After HPLC purification, P094 (0.8 mg, 50%) was obtained as a white solid. $^1H$ NMR ($CD_3OD$, 400 MHz) δ 8.30 (s, 1H), 7.73 (d, J 8.6 Hz, 2H), 7.41 (d, J=8.6 Hz, 2H), 5.24-5.40 (m, 2H), 4.55-4.61 (m, 1H), 4.42-4.50 (m, 1H), 3.12-3.15 (m, 2H), 2.88-2.93 (m, 2H), 2.69-2.73 (m, 2H), 2.43-2.50 (m, 1H), 2.36-2.42 (m, 2H), 2.03-2.25 (m, 7H), 1.92-1.97 (m, 2H), 1.44-1.62 (m, 2H), 1.28-1.38 (m, 2H). MS: m/z=661 ($M+H^+$).

(S)-2-(3-Benzyl-2,4,6-trioxotetrahydropyrimidin-1(2H)-yl)pentanedioic acid: P095

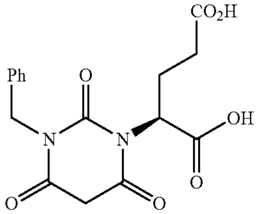 [SMILES: O=C(O)CC[C@@H](C(=O)O)N1C(=O)CC(=O)N(Cc2ccccc2)C1=O]

General experimental procedure for the removal of tert-butyl group from esters was followed. $^1H$ NMR ($CD_3OD$, 400 MHz) δ: 7.35-7.26 (m 5H), 5.37 (m, 1H), 5.08-4.98 (m, 4H), 2.56-2.20 (m, 4H); MS: m/z=370.8 ($M+Na^+$)

(S,E)-2-(3-Benzyl-5-(2-(4-(3-fluoropropyl)-1H-1,2,3-triazol-1-yl)-1-hydroxyethylidene)-2,4,6-trioxotetrahydropyrimidin-1(2H)-yl)pentanedioic acid: P096

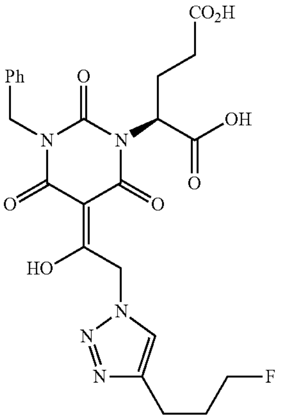 [SMILES: O=C(O)CC[C@@H](C(=O)O)N1C(=O)/C(=C(/O)Cn2cc(CCCF)nn2)C(=O)N(Cc2ccccc2)C1=O]

General experimental procedure for the removal of tert-butyl group from esters was followed. $^1H$ NMR ($CD_3OD$, 400 MHz) δ: 7.71 (s, 1H), 7.36-7.24 (m 5H), 5.51 (m, 1H), 5.20-5.00 (m, 3H), 4.52-4.38 (m, 2H), 2.84-2.81 (m, 2H), 2.56-2.36 (m, 5H), 2.15-1.98 (m, 2H); MS: m/z=517.7 ($M+H^+$)

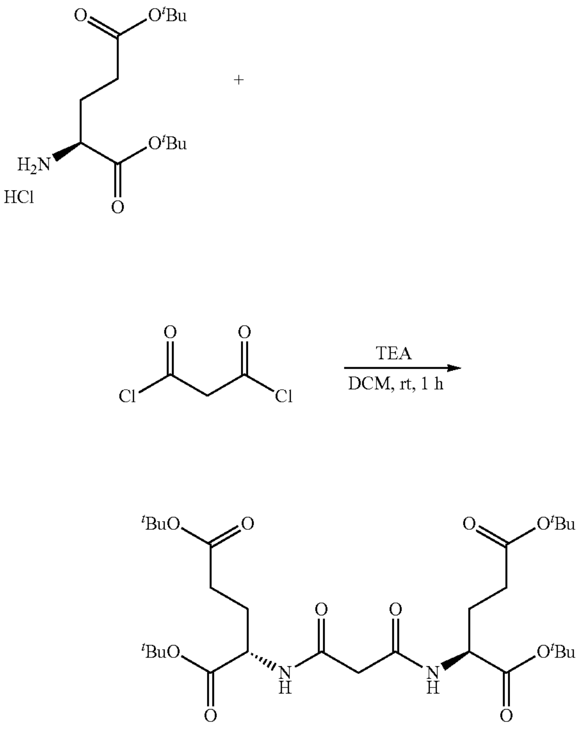

To (S)-di-tert-butyl 2-aminopentanedioate HCl (148 mg, 0.5 mmol) in dry DCM (5.0 mL) was added TEA (252 mg, 2.5 mmol). The mixture was cooled to 0° C. and added malonyl dichloride (35 mg, 0.25 mmol) dropwise. The mixture was stirred at rt for 1 h and diluted with ETOAc. It was washed with water (3×50 mL) and concentrated. The crude product was purified by silica chromatography to afford (2S,2'S)-tetra-tert-butyl 2,2'-(malonylbis(azanediyl))dipentanedioate as a clear oil (140 mg, 47%). MS: m/z=587 $(M+H^+)$.

2,2'-(Malonylbis(azanediyl))dipentanedioic acid: P097

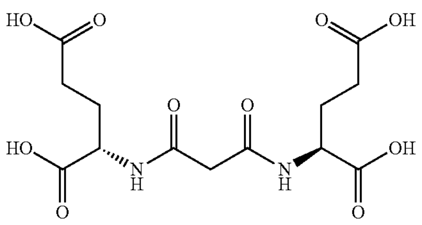 [SMILES: O=C(O)CC[C@H](NC(=O)CC(=O)N[C@@H](CCC(=O)O)C(=O)O)C(=O)O]

General experimental procedure for the removal of tert-butyl group from esters was followed. The reaction was carried out on a 30 mg scale. After HPLC purification, P097 (10 mg, 61%) was obtained as a white fluffy solid. $^1H$ NMR ($D_2O$, 400 MHz) δ 4.29 (dd, J=23, 13 Hz, 2H), 3.21 (s, 2H), 2.32 (t, J=7.6 Hz, 4H), 2.09-2.00 (m, 2H), 1.88-1.80 (m, 2H). MS: m/z=363 $(M+H^+)$.

(2'S)-2,2'-(Oxalylbis(azanediyl))dipentanedioic acid: P098

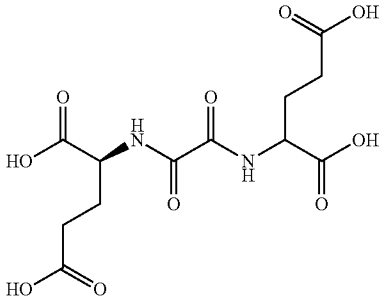 [SMILES: O=C(O)CCC(NC(=O)C(=O)N[C@@H](CCC(=O)O)C(=O)O)C(=O)O]

General experimental procedures for amide formation and the removal of tert-butyl group from esters was followed. The reaction was carried out on a 30 mg scale. After HPLC purification, P098 (8.0 mg, 51%) was obtained as a white fluffy solid. $^1H$ NMR ($D_2O$, 400 MHz) δ 4.53-4.48 (m, 2H), 2.43 (t, J=7.2 Hz, 4H), 2.32-2.24 (m, 2H), 2.11-2.02 (m, 2H). MS: m/z=349 $(M+H^+)$.

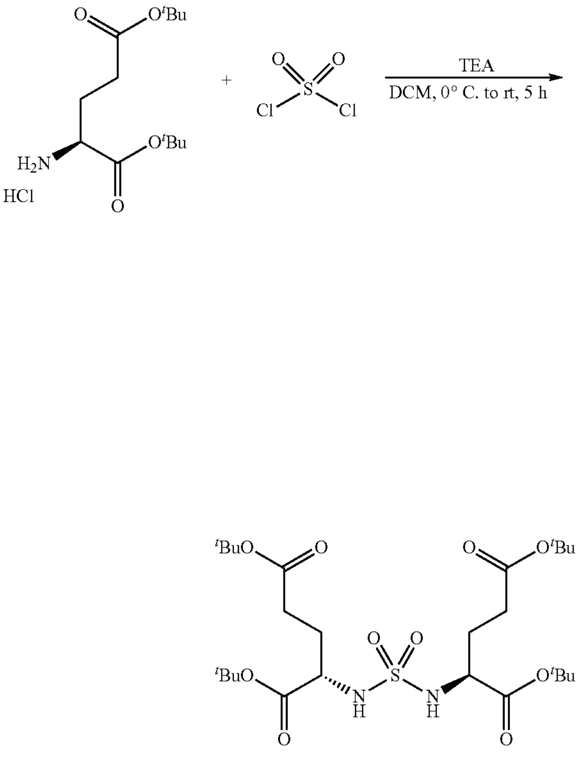

To (S)-di-tert-butyl 2-aminopentanedioate HCl (148 mg, 0.5 mmol) in 5 mL dry DCM was added TEA (252 mg, 2.5 mmol). The mixture was cooled to 0° C. and added sulfuryl dichloride (33 mg, 0.25 mmol) dropwise. The mixture was stirred at rt for 5 h and diluted with ETOAc. It was washed with water (3×50 mL) and concentrated. The crude product was purified by silica chromatography to afford (2S,2'S)-tetra-tert-butyl 2,2'-(sulfonylbis(azanediyl))dipentanedioate as a clear oil (86 mg, 29%). MS: m/z=581 $(M+H^+)$.

(2S)-2,2'-(Sulfonylbis(azanediyl))dipentanedioic acid: P099

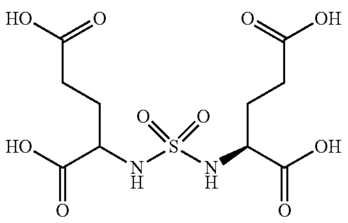 [SMILES: O=C(O)CCC(NS(=O)(=O)N[C@@H](CCC(=O)O)C(=O)O)C(=O)O]

General experimental procedure for the removal of tert-butyl group from esters was followed. The reaction was carried out on a 30 mg scale. After HPLC purification, P099 (10 mg, 55%) was obtained as a white fluffy solid. $^1$H NMR ($D_2O$, 400 MHz) δ 4.01 (dd, J=8, 5.6 Hz, 2H), 2.50 (m, 4H), 2.13 (m, 2H), 1.95 (m, 2H). MS: m/z=357 (M+H$^+$).

(S)-Di-tert-butyl 2-(2-(4-(4-azidophenyl)butanoyl) hydrazinecarboxamido)-pentanedioate

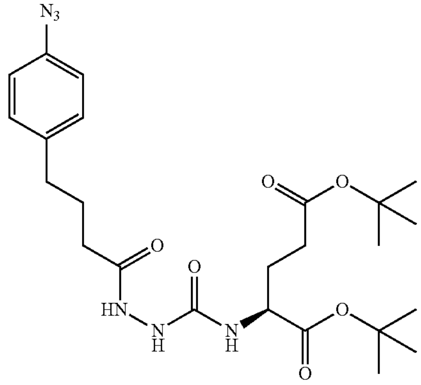 [SMILES: CC(C)(C)OC(=O)CC[C@H](NC(=O)NNC(=O)CCCc1ccc(N=[N+]=[N-])cc1)C(=O)OC(C)(C)C]

General experimental procedure for the formation of amide was followed. Reaction was performed on a 93 mg scale. Product was purified on a Biotage purification system eluting out in 50-80% EtOAc:Hexanes mixture in a gradient elution to give a bromide (89 mg, 60%). MS: m/z=505 (M+H$^+$).

(S)-2-(2-(4-(4-(4-(3-Fluoropropyl)-1H-1,2,3-triazol-1-yl)phenyl)butanoyl)-hydrazinecarboxamido)pentanedioic acid: P100

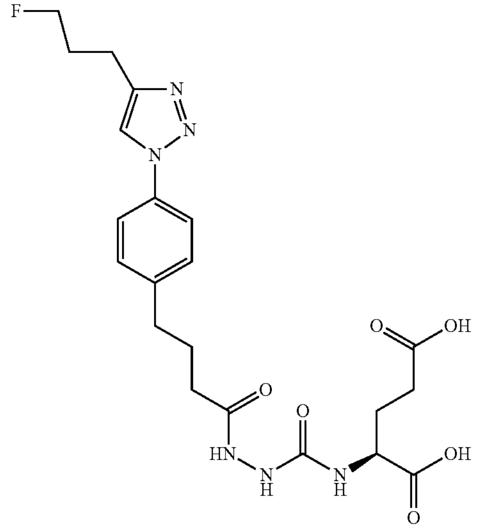 [SMILES: O=C(O)CC[C@H](NC(=O)NNC(=O)CCCc1ccc(-n2cc(CCCF)nn2)cc1)C(=O)O]

First, general experimental procedure for click chemistry was followed. Reaction was performed on an 89 mg scale. The crude product was used directly in the next step without any further purification. Second, general experimental procedure for the removal of tert-butyl group from esters was followed. Reaction was performed on a 100 mg scale. After HPLC purification, P100 (10 mg, 12%) was obtained. $^1$H NMR ($CD_3OD$, 400 MHz) δ 8.28 (s, 1H), 7.72 (d, J=8.4 Hz, 2H), 7.42 (d, J=8.4 Hz, 2H), 4.50 (dt, J=47.6, 6.0 Hz, 2H), 4.31-4.36 (m, 1H), 2.89 (t, J=8.0 Hz, 2H), 2.74 (t, J=8.0 Hz, 2H), 2.35-2.43 (m, 2H), 2.28 (t, J=7.2 Hz, 2H), 1.86-2.22 (m, 6H). MS: m/z=479 (M+H$^+$).

(S,Z)-2-(3-Benzyl-5-(4-(4-(4-(3-fluoropropyl)-1H-1,2,3-triazol-1-yl)phenyl)-1-hydroxybutylidene)-2,4,6-trioxotetrahydropyrimidin-1(2H)-yl)pentanedioic acid: P101

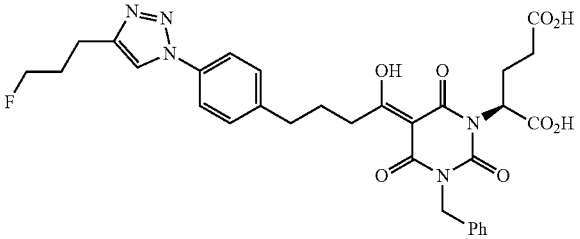 [SMILES: O=C(O)CC[C@@H](C(=O)O)N1C(=O)/C(=C(\O)CCCc2ccc(-n3cc(CCCF)nn3)cc2)C(=O)N(Cc2ccccc2)C1=O]

General experimental procedure for the removal of tert-butyl group from esters was followed. $^1$H NMR ($CD_3OD$, 400 MHz) δ 8.26 (s, 1H), 7.69 (m 2H), 7.42-7.20 (m, 7H), 5.48-5.42 (m, 1H), 5.08-5.03 (m, 2H), 4.56-4.44 (m, 2H), 3.20-3.08 (m, 2H), 2.92-2.79 (m, 4H), 2.56-2.30 (m, 4H), 2.15-1.98 (m, 4H). MS: m/z=622.1 (M+H$^+$)

(S,Z)-2-(3-Benzyl-5-(5-(4-(3-fluoropropyl)-1H-1,2,3-triazol-1-yl)-1-hydroxypentylidene)-2,4,6-trioxotetrahydropyrimidin-1(2H)-yl)pentanedioic acid: P102

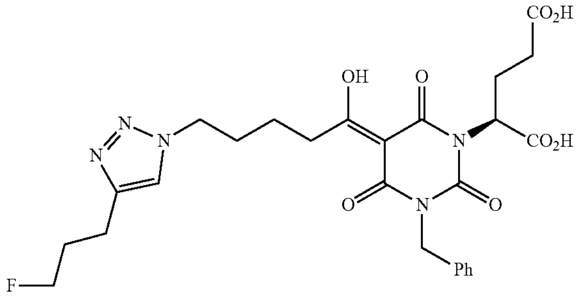 [SMILES: O=C(O)CC[C@@H](C(=O)O)N1C(=O)/C(=C(\O)CCCCn2cc(CCCF)nn2)C(=O)N(Cc2ccccc2)C1=O]

General experimental procedure for the removal of tert-butyl group from esters was followed. $^1$H NMR ($CD_3OD$, 400 MHz), δ7.81 (s, 1H), 7.32-7.26 (m, 5H), 5.48 (m, 1H), 5.08-5.03 (m, 2H), 4.49-4.37 (m, 4H), 3.17-3.10 (m, 2H), 2.79-2.75 (m, 2H), 2.56-2.30 (m, 4H), 2.10-1.92 (m, 4H), 1.68-1.65 (m, 2H). MS: m/z=559.7 ($M+H^+$)

(S)-2-(3-((S)-5-(4-(4-Azidophenyl)butanamido)1-carboxypentyl)-3-methylureido)-pentanedioic acid

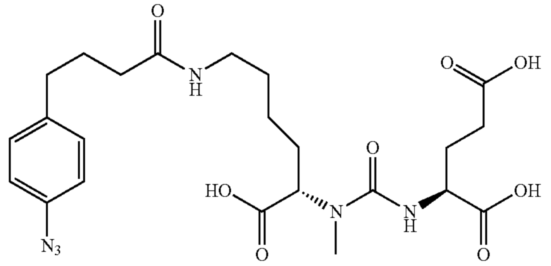 [SMILES: CN(C(=O)N[C@@H](CCC(=O)O)C(=O)O)[C@@H](CCCCNC(=O)CCCc1ccc(N=[N+]=[N-])cc1)C(=O)O]

General experimental procedures for amide formation and removal of tert-butyl ester groups were followed. Reaction was performed on a 125 mg scale. Product was purified by HPLC purification system using 0.05% TFA in water and acetonitrile as a solvent yielded the title compound (5 mg, 5%, in two steps). MS: m/z=478 ($M+H^+$).

(S)-2-(3-((S)-1-Carboxy-5-(4-(4-(4-(3-fluoropropyl)-1H-1,2,3-triazol-1-yl)phenyl)-butanamido)phenyl)-3-methylureido)pentanedioic acid: P103

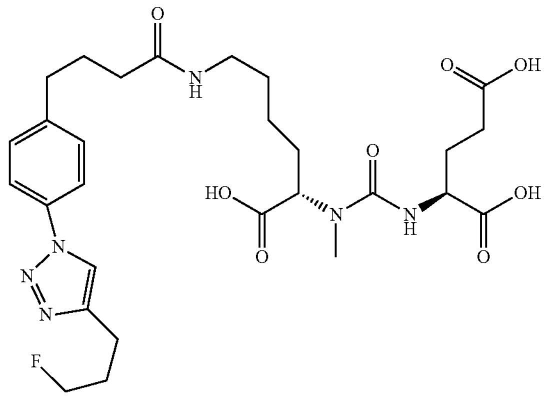 [SMILES: CN(C(=O)N[C@@H](CCC(=O)O)C(=O)O)[C@@H](CCCCNC(=O)CCCc1ccc(-n2cc(CCCF)nn2)cc1)C(=O)O]

General procedure for click chemistry was followed. Reaction was performed on a 2 mg scale. Product was purified by HPLC purification system using 0.05% TFA in water and acetonitrile as a solvent yielded the title compound (1.2 mg. 49%). $^1$H NMR ($CD_3OD$, 400 MHz) δ 8.28 (s, 1H), 7.27-7.70 (dd, J=6.4, 2.0 Hz, 2H), 7.38 (d, J=6.4 Hz, 2H), 4.55 (t, J=6.0 Hz, 1H), 4.44 (t, J=6.0 Hz, 1H), 4.30-4.26 (dd, J=9.6, 4.8 Hz, 1H), 3.22-3.11 (m, 2H), 2.88 (t, J=7.6 Hz, 2H), 2.83 (m, 3H), 2.67 (t, J=7.2 Hz, 2H), 2.44 (t, J=7.2 Hz, 2H), 2.24-1.88 (m, 8H), 1.80-1.70 (m, 1H), 1.60-1.36 (m, 3H); MS: m/z=607 ($M+H^+$).

(S)-2-(3-((S)-5-(Bis(4-nitrobenzyl)amino)-1-carboxypentyl)-5,5-diethyl-2,4,6-trioxotetrahydropyrimidin-1(2H)-yl)pentanedioic acid: P104

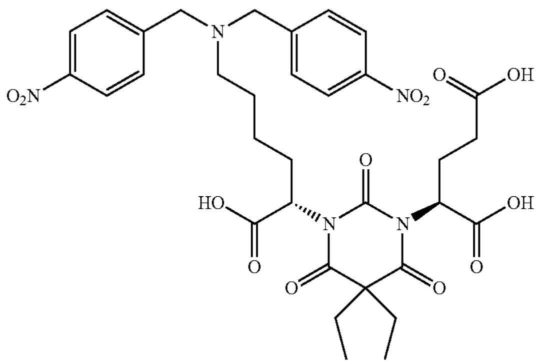 [SMILES: CCC1(CC)C(=O)N([C@@H](CCCCN(Cc2ccc([N+](=O)[O-])cc2)Cc2ccc([N+](=O)[O-])cc2)C(=O)O)C(=O)N([C@@H](CCC(=O)O)C(=O)O)C1=O]

General experimental procedure for reductive amination and deprotection was followed. Reaction was performed on a 40 mg scale of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate. Isolated 9.0 mg (19%) of P104 as a white solid. $^1$H NMR ($CD_3OD$, 400 MHz) δ 8.28-8.33 (m, 4H), 7.70-7.75 (m, 4H), 5.43 (dd, J=9.6, 4.9 Hz, 1H), 5.32 (dd, J=9.6, 4.9 Hz, 1H), 4.27-4.45 (m, 4H), 2.94 (t, J=7.6 Hz, 2H), 2.46-2.62 (m, 1H), 2.13-2.37 (m, 4H), 1.91-2.07 (m, 5H), 1.76-1.90 (m, 2H), 1.29-1.40 (m, 2H), 0.84 (dt, J=12.2, 7.4 Hz, 6H). MS: m/z=714 ($M+H^+$).

(S)-2-(3-((S)-1-Carboxy-5-(5-(4-(3-fluoropropyl)-1H-1,2,3-triazol-1-yl)-N-(4-nitrobenzyl)pentanamido)pentyl)-5,5-diethyl-2,4,6-trioxotetrahydropyrimidin-1(2H)-yl)pentanedioic acid: P105

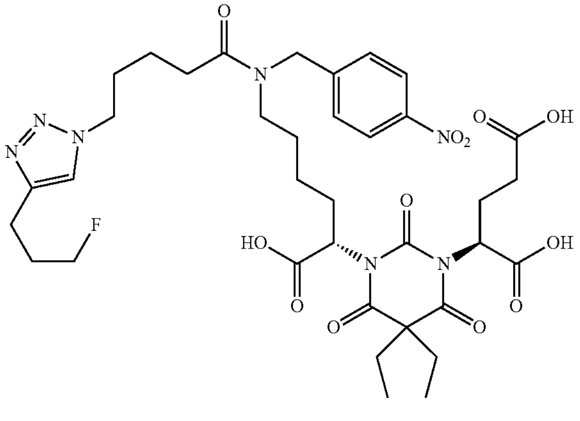 [SMILES: CCC1(CC)C(=O)N([C@@H](CCCCN(Cc2ccc([N+](=O)[O-])cc2)C(=O)CCCCn2cc(CCCF)nn2)C(=O)O)C(=O)N([C@@H](CCC(=O)O)C(=O)O)C1=O]

General experimental procedure for chlick reaction was followed. Reaction was performed on a 5.0 mg scale of (S)-2-(3-((S)-5-(5-azido-N-(4-nitrobenzyl)pentanamido)-1-carboxypentyl)-5,5-diethyl-2,4,6-trioxotetrahydropyrimidin-1(2H)-yl)pentanedioic acid. After HPLC purification, P105 (3.2 mg, 57%) was obtained as a white solid. $^1$H NMR ($CD_3OD$, 400 MHz) δ 8.24 and 8.18 (d, J=8.6 Hz, two rotomers, total 2H), 7.77 and 7.81 (s, two rotomers, total 1H), 7.44 (d, J=8.6 Hz, 2H), 5.43 (dd, J=9.6, 4.9 Hz, 1H), 5.31-5.37 (m, 1H), 4.72-4.82 (m, 1H), 4.65-4.77 (m, 2H), 4.50-4.54 (m, 1H), 4.33-4.45 (m, 3H), 2.78-2.85 (m, 2H), 2.48-2.58 (m, 2H), 2.13-2.40 (m, 5H), 1.93-2.11 (m, 8H), 1.84-1.92 (m, 1H), 1.52-1.75 (m, 4H), 1.23-1.38 (m, 2H), 0.86 (q, J=7.4 Hz, 6H). MS: m/z=790 (M+H$^+$).

(2S)-2-(8-((S)-5-(Benzyloxycarbonylamino)-1-carboxypentyl)-5,7,9-trioxo-6,8-diazaspiro[3.5]nonan-6-yl)pentanedioic acid: P106

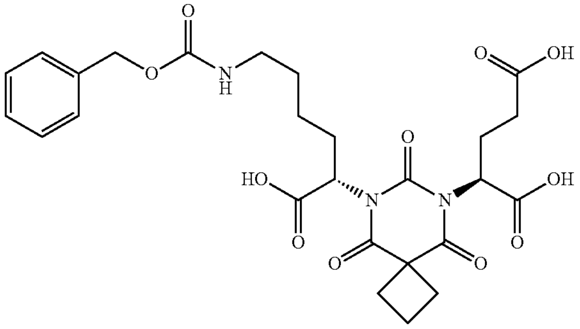 [SMILES: O=C(O)CC[C@@H](C(=O)O)N1C(=O)N([C@@H](CCCCNC(=O)OCc2ccccc2)C(=O)O)C(=O)C2(CCC2)C1=O]

To a solution of (9S,13S)-tri-tert-butyl 3,11-dioxo-1-phenyl-2-oxa-4,10,12-triazapentadecane-9,13,15-tricarboxylate (30 mg, 0.048 mmol) in dry DCM (2.0 mL) was added cyclobutane-1,1-dicarbonyl dichloride (26 mg, 0.144 mmol). The mixture was heated at 70° C. for 1 hour. The mixture was deprotected with general condition to give P106 (10.0 mg, 28%) as a white solid. $^1$H NMR ($CD_3OD$, 400 MHz) δ 7.26-7.40 (m, 5H), 5.34 (dd, J=9.8, 4.7 Hz, 1H), 5.22-5.30 (m, 1H), 5.04 (s, 2H), 3.09 (t, J=6.8 Hz, 2H), 2.50-2.71 (m, 4H), 2.25-2.49 (m, 4H), 2.01-2.24 (m, 4H), 1.39-1.63 (m, 2H), 1.33 (d, J=6.3 Hz, 2H). MS: m/z=562 (M+H$^+$).

(S)-2-(3-((S)-1-Carboxy-5-(4-nitrophenylsulfonamido)pentyl)-5,5-diethyl-2,4,6-trioxotetrahydropyrimidin-1(2H)-yl)pentanedioic acid: P107

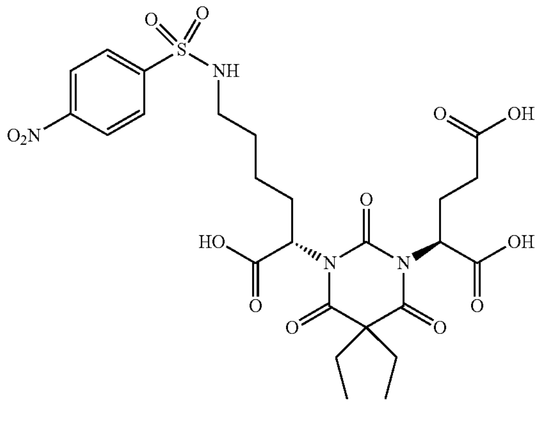 [SMILES: CCC1(CC)C(=O)N([C@@H](CCCCNS(=O)(=O)c2ccc([N+](=O)[O-])cc2)C(=O)O)C(=O)N([C@@H](CCC(=O)O)C(=O)O)C1=O]

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (10 mg, 0.016 mmol) in DCM (1.0 mL) was added 4-nitrobenzenesulfonyl chloride (5.4 mg, 0.024 mmol) and triethylamine (10 μL, 0.072 mmol). The mixture was stirred at room temperature for 1 hour and further deprotected with general condition to give P107 (4.7 mg, 46%) as a white solid. $^1$H NMR ($CD_3OD$, 400 MHz) δ 8.39-8.42 (m, 2H), 8.04-8.08 (m, 2H), 5.43 (dd, J=9.2, 4.9 Hz, 1H), 5.28 (dd, J=9.8, 5.1 Hz, 1H), 2.90 (t, J=7.0 Hz, 2H), 2.49-2.58 (m, 1H), 2.18-2.38 (m, 3H), 1.92-2.14 (m, 6H), 1.38-1.56 (m, 2H), 1.22-1.37 (m, 2H), 0.81-0.92 (m, 6H). MS: m/z=629 (M+H$^+$).

(S)-2-(3-((S)-5-(3-benzylureido)-1-carboxypentyl)-5,5-diethyl-2,4,6-trioxotetrahydropyrimidin-1(2H)-yl) pentanedioic acid: P108

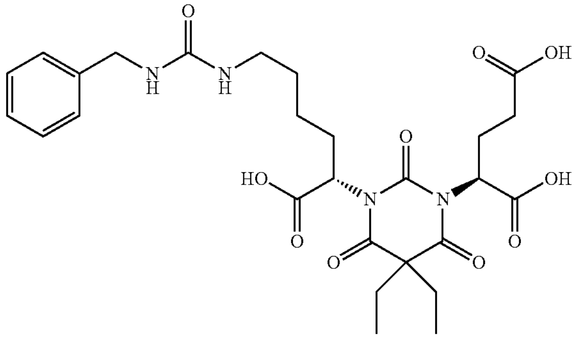 [SMILES: CCC1(CC)C(=O)N([C@@H](CCCCNC(=O)NCc2ccccc2)C(=O)O)C(=O)N([C@@H](CCC(=O)O)C(=O)O)C1=O]

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (10 mg, 0.016 mmol) in DCM (1.0 mL) was added benzyl isocyanate (6.5 mg, 0.049 mmol) and triethylamine (10 μL, 0.072 mmol). The mixture was stirred at room temperature for 1 hour and further deprotected with general condition to give P108 (5.4 mg, 57%) as a white solid. $^1$H NMR ($CD_3OD$, 400 MHz) δ 7.19-7.32 (m, 5H), 5.42-5.51 (m, 1H), 5.35-5.47 (m, 2H), 4.29 (s, 2H), 3.05-3.17 (m, 2H), 2.48-2.58 (m, 1H), 2.14-2.36 (m, 4H), 1.99-2.12 (m, 5H), 1.42-1.59 (m, 2H), 1.26-1.41 (m, 2H), 0.88 (td, J=7.4, 4.3 Hz, 6H). MS: m/z=577 (M+H$^+$).

2-(4-(((2-oxo-2H-chromen-7-yl)oxy)methyl)-1H-1,2,3-triazol-1-yl)pentanedioic acid: P109

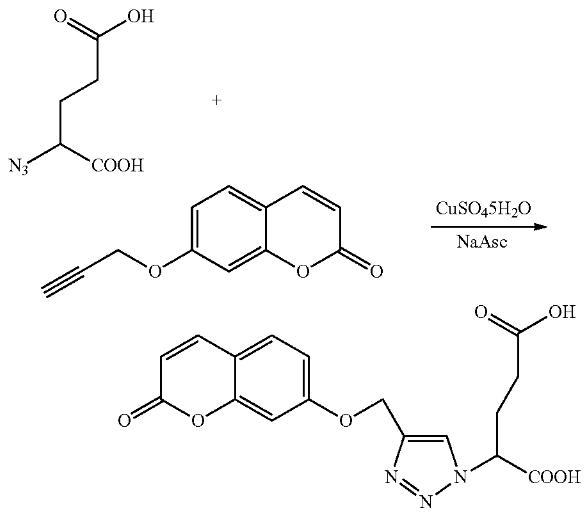

P109

General experimental procedure for click reaction was followed. Reaction was performed on a 0.05 g scale. After HPLC purification, P109 (50 mg, 50%) was obtained as a white solid. $^1$H NMR ($CD_3OD$, 400 MHz) 8.25 (s, 1H), 7.87 (d, J=9.6 Hz, 1H), 7.54 (d, J=8.8 Hz, 1H), 7.06 (d, J=2.4 Hz, 1H), 7.02 (dd, J=8.4, 2.4 Hz, 1H), 6.25 (d, J=9.6 Hz, 1H), 5.53 (dd, J=10.0, 4.8 Hz, 1H), 5.29 (s, 2H), 2.67-2.58 (m, 1H), 2.49-2.39 (m, 1H), 2.23 (t, J=8.0 Hz, 2H). MS: m/z=374.1 ($M+H^+$).

(S)-2-(3-((S)-1-carboxy-5-(4-nitrobenzylamino)pentyl)-5,5-diethyl-2,4,6-trioxotetrahydropyrimidin-1(2H)-yl)pentanedioic acid: P110

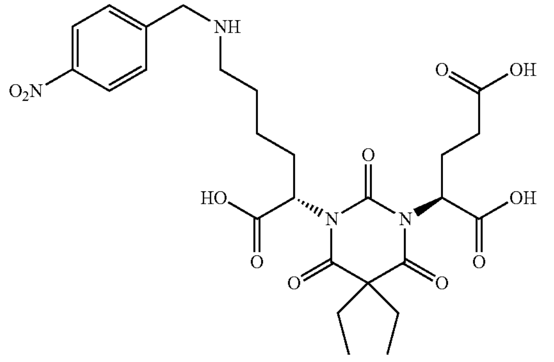 [SMILES: CCC1(CC)C(=O)N([C@@H](CCCCNCc2ccc([N+](=O)[O-])cc2)C(=O)O)C(=O)N([C@@H](CCC(=O)O)C(=O)O)C1=O]

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (10 mg, 0.016 mmol) in DCE (1.0 mL) was added 4-nitrobenzaldehyde (3.0 mg, 0.020 mmol), acetic acid (18 μL, 0.315 mmol), and sodium $NaBH(OAc)_3$ (18 mg, 0.085 mmol). The mixture was stirred at room temperature for 2 hours and further deprotected with general condition to give P110 (6.4 mg, 67%) as a white solid.

$^1$H NMR ($CD_3OD$, 400 MHz) δ 8.31-8.34 (m, 2H), 7.71-7.75 (m, 2H), 5.34-5.48 (m, 2H), 4.34 (s, 2H), 3.08 (ddd, J=9.2, 7.0, 1.8 Hz, 2H), 2.49-2.59 (m, 1H), 2.21-2.37 (m, 4H), 1.96-2.11 (m, 5H), 1.68-1.90 (m, 2H), 1.36-1.51 (m, 2H), 0.88 (t, J=7.4 Hz, 6H). MS: m/z=579 ($M+H^+$).

tert-Butyl 3-((benzyloxy)amino)propanoate

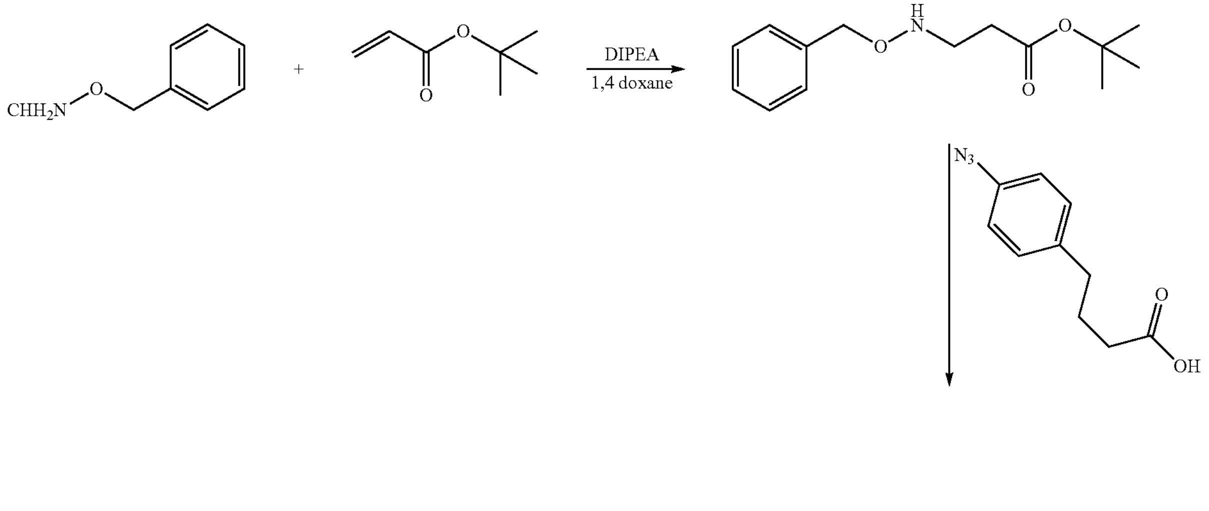

-continued

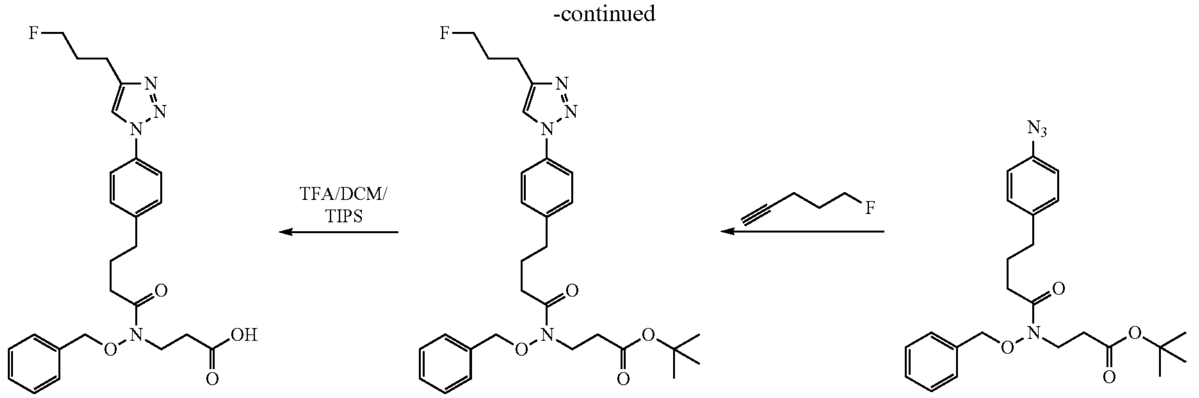

A mixture of O-benzylhydroxylamie hydrochloride (500 mg, 3.13 mmol), tert-butyl acrylate (401 mg, 3.13 mmol), and DIPEA (0.546 mL, 3.13 mmol) in 1,4-dioxane (3.0 mL) was microwaved at 120° C. for 20 min, cooled and concentrated in vacuo. The residue was purified on flash column chromatography (silica gel, 0-40% EtOAc/hexanes) to give the title compound (53 mg, 6.7%). MS: m/z=252 ($M+H^+$).

tert-Butyl 3-(4-(4-azidophenyl)-N-(benzyloxy)butanamido)propanoate: General experimental procedure for the formation of amide was followed. Reaction was performed on a 53 mg scale. Product was purified on a Biotage purification system eluting out in 0-35% EtOAc:Hexanes mixture in a gradient elution to give a bromide (80 mg, 87%). MS: m/z=439 ($M+H^+$).

tert-Butyl 3-(N-(benzyloxy)-4-(4-(4-(3-fluoropropyl)-1H-1,2,3-triazol-1-yl)phenyl)butanamido)propanoate: General experimental procedure for click chemistry was followed. Reaction was performed on an 80 mg scale. The crude product was purified on flash column chromatography (silica gel, 30-80% EtOAc/hexanes) to give the desired compound (59 mg, 62%). MS: m/z=525 ($M+H^+$).

3-(N-(Benzyloxy)-4-(4-(4-(3-fluoropropyl)-1H-1,2,3-triazol-1-yl)phenyl)-butanamido)propanoic acid: General experimental procedure for the removal of tert-butyl group from esters was followed. Reaction was performed on a 59 mg scale. The crude product was used directly in the next step without any further purification.

(S)-Dibenzyl 2-(3-(N-(benzyloxy)-4-(4-(4-(3-fluoropropyl)-1H-1,2,3-triazol-1-yl)phenyl)butanamido)propanamido)pentanedioate

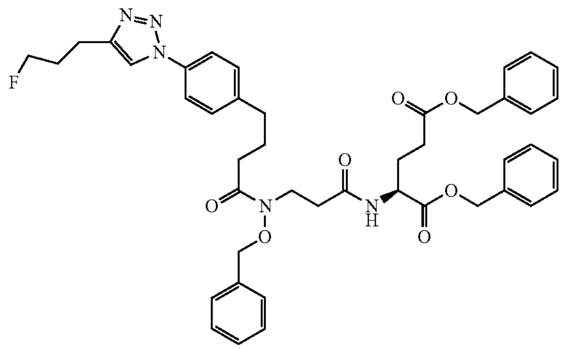 [SMILES: O=C(CCN(OCc1ccccc1)C(=O)CCCc1ccc(-n2cc(CCCF)nn2)cc1)N[C@@H](CCC(=O)OCc1ccccc1)C(=O)OCc1ccccc1]

General experimental procedure for the formation of amide was followed. Reaction was performed on a 53 mg scale. Product was purified on a Biotage purification system eluting out in 30-100% EtOAc:Hexanes mixture in a gradient elution to give a bromide (71 mg, 81%). MS: m/z=778 ($M+H^+$).

(S)-2-(3-(4-(4-(4-(3-Fluoropropyl)-1H-1,2,3-triazol-1-yl)phenyl)-N-hydroxybutanamido)propanamido)pentanedioic acid: P111

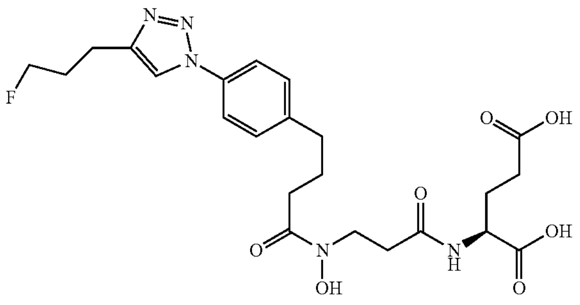 [SMILES: O=C(O)CC[C@H](NC(=O)CCN(O)C(=O)CCCc1ccc(-n2cc(CCCF)nn2)cc1)C(=O)O]

General experimental procedure for the removal of benzyl group was followed. Reaction was performed on a 71 mg scale. After HPLC purification, P111 (17 mg, 37%) was obtained. $^1H$ NMR ($CD_3OD$, 400 MHz) δ 8.30 (s, 1H), 7.73 (d, J=8.4 Hz, 2H), 7.42 (d, J=8.4 Hz, 2H), 4.52 (dt, J=47.2, 6.0 Hz, 2H), 4.40-4.46 (m, 1H), 3.85-93 (m, 1H), 2.91 (t, J=8.0 Hz, 2H), 2.74 (t, J=8.0 Hz, 2H), 2.47-2.62 (4H), 2.40 (t, J=8.0 Hz, 2H), 2.03-2.23 (m, 3H), 1.88-1.99 (m, 3H). MS: m/z=508 ($M+H^+$).

(S)-2-(3-((S)-1-Carboxy-5-(4-methoxybenzylamino)pentyl)-5,5-diethyl-2,4,6-trioxotetrahydropyrimidin-1(2H)-yl)pentanedioic acid: P112

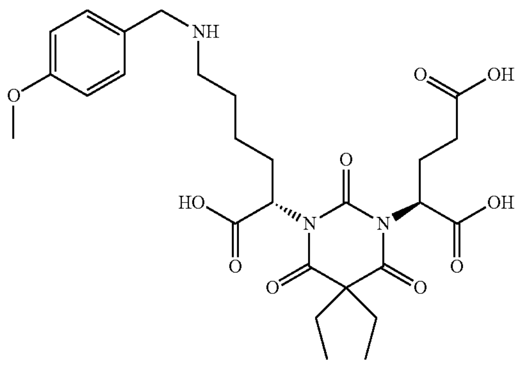 [SMILES: CCC1(CC)C(=O)N([C@@H](CCCCNCc2ccc(OC)cc2)C(=O)O)C(=O)N([C@@H](CCC(=O)O)C(=O)O)C1=O]

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (12 mg, 0.020 mmol) in DCE (1.0 mL) was added 4-nitrobenzaldehyde (3.2 mg, 0.024 mmol), acetic acid (18 μL, 0.315 mmol), and sodium $NaBH(OAc)_3$ (20 mg, 0.094 mmol). The mixture was stirred at room temperature for 2 hours and further deprotected with general condition to give P112 (9.5 mg, 86%) as a white solid. $^1H$ NMR ($CD_3OD$, 400 MHz) δ 7.28-7.33 (m, 2H), 6.89-6.93 (m, 2H), 5.26-5.39 (m, 2H), 4.03 (s, 2H), 3.73 (s, 3H), 2.91 (t, J=8.2 Hz, 2H), 2.40-2.51 (m, 1H), 2.12-2.29 (m, 4H), 1.90-2.02 (m, 5H), 1.58-1.82 (m, 2H), 1.23-1.43 (m, 2H), 0.80 (td, J=7.4, 1.6 Hz, 6H). MS: m/z=564 ($M+H^+$).

(S)-2-(3-((S)-1-Carboxy-5-(6-fluoronicotinamido)pentyl)-5,5-diethyl-2,4,6-trioxotetrahydropyrimidin-1(2H)-yl)pentanedioic acid: P113

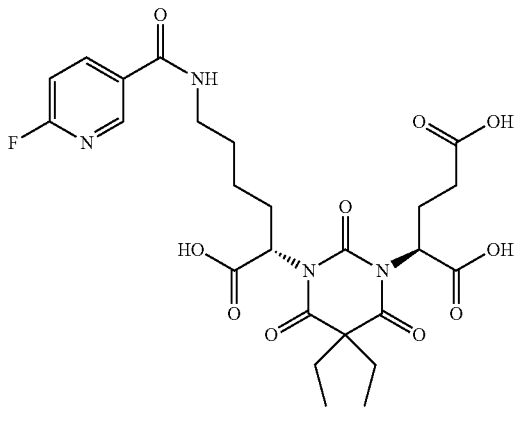 [SMILES: CCC1(CC)C(=O)N([C@@H](CCCCNC(=O)c2ccc(F)nc2)C(=O)O)C(=O)N([C@@H](CCC(=O)O)C(=O)O)C1=O]

General experimental procedure for amidation and deprotection was followed. Reaction was performed on a 12.0 mg scale of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate. After HPLC purification, P113 (4.6 mg, 41%) was obtained as a white solid. $^1H$ NMR ($CD_3OD$, 400 MHz) δ 8.60-8.69 (m, 1H), 8.27-8.41 (m, 1H), 7.15 (m, 1H), 5.42 (m, 2H), 3.33-3.49 (m, 2H), 2.54 (m, 1H), 2.18-2.40 (m, 4H), 2.12 (m, 1H), 1.97-2.07 (m, 4H), 1.54-1.76 (m, 2H), 1.40 (m, 2H), 0.81-0.92 (m, 6H). MS: m/z=567 ($M+H^+$).

(S)-2-(3-((S)-5-((E)-3-(4-Azidophenyl)allylamino)-1-carboxypentyl)-5,5-diethyl-2,4,6-trioxotetrahydropyrimidin-1(2H)-yl)pentanedioic acid: P114 precursor

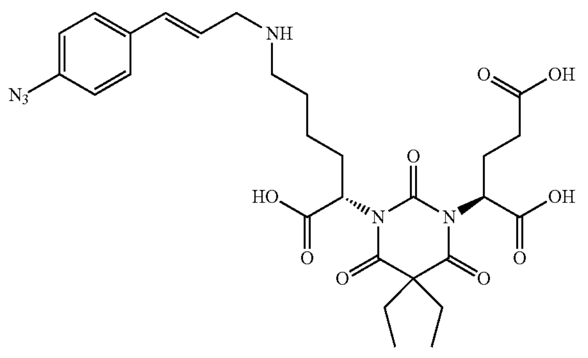 [SMILES: CCC1(CC)C(=O)N([C@@H](CCCCNC/C=C/c2ccc(N=[N+]=[N-])cc2)C(=O)O)C(=O)N([C@@H](CCC(=O)O)C(=O)O)C1=O]

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (12 mg, 0.020 mmol) in DCE (1.0 mL) was added 4-nitrobenzaldehyde (3.4 mg, 0.020 mmol), acetic acid (12 μL, 0.210 mmol), and sodium $NaBH(OAc)_3$ (12.5 mg, 0.059 mmol). The mixture was stirred at room temperature for 2 hours and further deprotected with general condition to give P114 precursor (4.0 mg, 34%) as a white solid. $^1H$ NMR ($CD_3OD$, 400 MHz) δ 7.51 (d, J=8.2 Hz, 2H), 7.07 (d, J=8.6 Hz, 2H), 6.84 (d, J=16.0 Hz, 1H), 6.22 (dt, J=15.8, 7.3 Hz, 1H), 5.30-5.52 (m, 2H), 3.79 (d, J=7.4 Hz, 2H), 2.95-3.08 (m, 2H), 2.47-2.61 (m, 1H), 2.28-2.35 (m, 4H), 2.00-2.12 (m, 5H), 1.65-1.88 (m, 2H), 1.35-1.55 (m, 2H), 0.88 (td, J=7.3, 1.4 Hz, 6H). MS: m/z=601 ($M+H^+$).

(S)-2-(3-((S)-1-Carboxy-5-((E)-3-(4-(4-(3-fluoropropyl)-1H-1,2,3-triazol-1-yl)phenyl)allylamino)pentyl)-5,5-diethyl-2,4,6-trioxotetrahydropyrimidin-1(2H)-yl)pentanedioic acid: P114

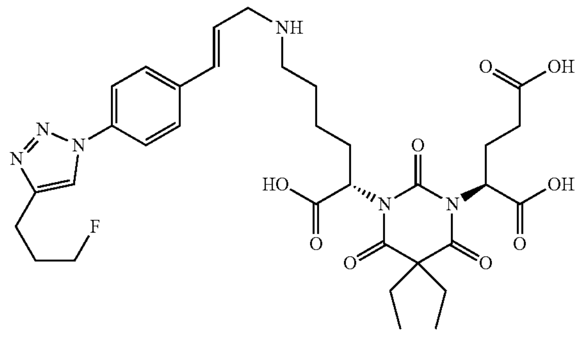 [SMILES: CCC1(CC)C(=O)N([C@@H](CCCCNC/C=C/c2ccc(-n3cc(CCCF)nn3)cc2)C(=O)O)C(=O)N([C@@H](CCC(=O)O)C(=O)O)C1=O]

General experimental procedure for click reaction was followed. Reaction was performed on a 2.0 mg scale of (S)-2-(3-((S)-5-((E)-3-(4-azidophenyl)allylamino)-1-carboxypentyl)-5,5-diethyl-2,4,6-trioxotetrahydropyrimidin-1(2H)-yl)pentanedioic acid. After HPLC purification, P114

(0.8 mg, 35%) was obtained as a white solid. $^1H$ NMR ($CD_3OD$, 400 MHz) δ 8.38 (s, 1H), 7.88 (d, J 8.6 Hz, 2H), 7.70 (d, J=8.6 Hz, 2H), 6.95 (d, J=16.0 Hz, 1H), 6.32-6.47 (m, 1H), 5.36-5.52 (m, 2H), 4.59 (t, J=5.9 Hz, 1H), 4.47 (t, J=5.9 Hz, 1H), 3.85 (d, J=7.4 Hz, 2H), 3.06 (t, J=8.0 Hz, 2H), 2.87-2.96 (m, 2H), 2.46-2.62 (m, 1H), 1.97-2.40 (m, 11H), 1.64-1.91 (m, 2H), 1.35-1.54 (m, 2H), 0.89 (t, J=7.4 Hz, 6H). MS: m/z=687 (M+H$^+$).

(S)-Di-tert-butyl 2-((S)-4-(tert-butoxy)-3-(5-(4-(4-(3-fluoropropyl)-1H-1,2,3-triazol-1-yl)phenyl)pentanamido)-4-oxobutanamido)pentanedioate

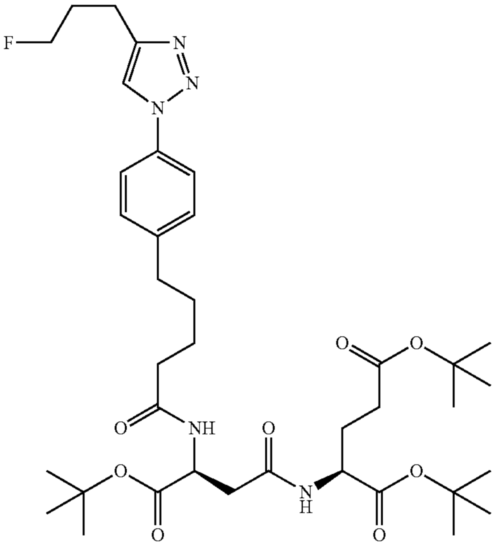 [SMILES: CC(C)(C)OC(=O)CC[C@H](NC(=O)C[C@H](NC(=O)CCCCc1ccc(-n2cc(CCCF)nn2)cc1)C(=O)OC(C)(C)C)C(=O)OC(C)(C)C]

General experimental procedure for the formation of amide was followed. Reaction was performed on a 41 mg scale. The crude product was used directly in the next step without any further purification. MS: m/z=704 (M+H$^+$).

(S)-2-((S)-3-Carboxy-3-(5-(4-(4-(3-fluoropropyl)-1H-1,2,3-triazol-1-yl)phenyl)pentanamido)propanamido)pentanedioic acid: P115

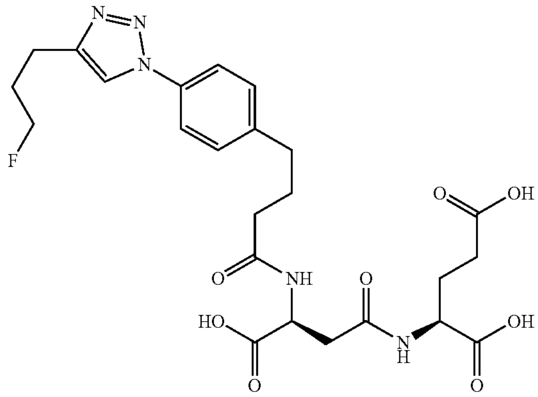 [SMILES: O=C(O)CC[C@H](NC(=O)C[C@H](NC(=O)CCCc1ccc(-n2cc(CCCF)nn2)cc1)C(=O)O)C(=O)O]

General experimental procedure for the removal of tert-butyl group from esters was followed. Reaction was performed on a 60 mg scale. After HPLC purification, P115 (23 mg, 49%) was obtained. $^1H$ NMR ($CD_3OD$, 400 MHz) δ 8.30 (s, 1H), 7.73 (d, J=8.4 Hz, 2H), 7.42 (d, J=8.4 Hz, 2H), 4.75 (t, J=6.4 Hz, 1H), 4.52 (dt, J=47.2, 6.0 Hz, 2H), 4.41-4.46 (m, 1H), 2.91 (t, J=7.6 Hz, 2H), 2.79-2.83 (m, 2H), 2.74 (t, J=8.0 Hz, 2H), 2.38 (t, J=8.0 Hz, 2H), 2.30 (t, J=8.0 Hz, 2H), 1.85-2.24 (m, 6H). MS: m/z=536 (M+H$^+$).

(10S,14S)-Tri-tert-butyl 3,8,12-trioxo-1-phenyl-2-oxa-4,9,13-triazahexadecane-10,14,16-tricarboxylate

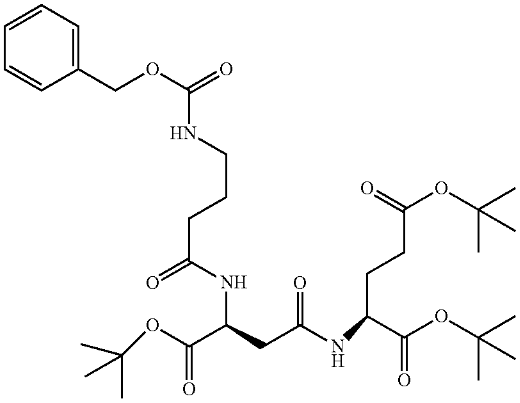 [SMILES: CC(C)(C)OC(=O)CC[C@H](NC(=O)C[C@H](NC(=O)CCCNC(=O)OCc1ccccc1)C(=O)OC(C)(C)C)C(=O)OC(C)(C)C]

General experimental procedure for the formation of amide was followed. Reaction was performed on a 50 mg scale. The crude product was used directly in the next step without any further purification. MS: m/z=650 (M+H$^+$).

(10S,14S)-3,8,12-Trioxo-1-phenyl-2-oxa-4,9,13-triazahexadecane-10,14,16-tricarboxylic acid: P116

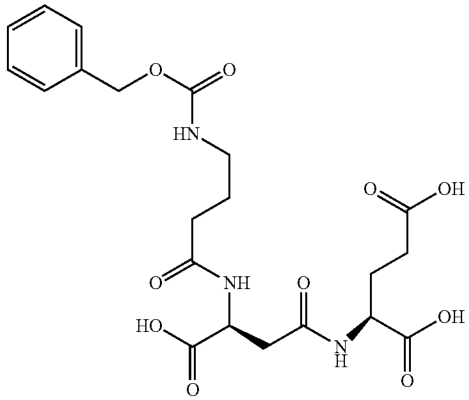 [SMILES: O=C(O)CC[C@H](NC(=O)C[C@H](NC(=O)CCCNC(=O)OCc1ccccc1)C(=O)O)C(=O)O]

General experimental procedure for the removal of tert-butyl group from esters was followed. Reaction was performed on a 75 mg scale. After HPLC purification, P116 (30 mg, 54%) was obtained. $^1H$ NMR ($CD_3OD$, 400 MHz) δ 7.22-7.29 (m, 5H), 5.07 (s, 2H), 4.74 (t, J=6.0 Hz, 1H), 4.39-4.45 (m, 1H), 3.15 (t, J=7.6 Hz, 2H), 2.81 (d, J=6.4 Hz, 2H), 2.38 (t, J=8.0 Hz, 2H), 2.27 (t, J=8.0 Hz, 2H), 2.11-2.23 (m, 1H), 1.82-1.95 (m, 1H), 1.75-1.82 (m, 2H). MS: m/z=482 (M+H$^+$).

(2S)-2-((Z)-5-(4-(((9H-Fluoren-9-yl)methoxy)carbonyl)amino)4-carboxy-1-hydroxybutylidene)-2,4,6-trioxotetrahydropyrimidin-1(2H)-yl)pentanedioic acid: P117

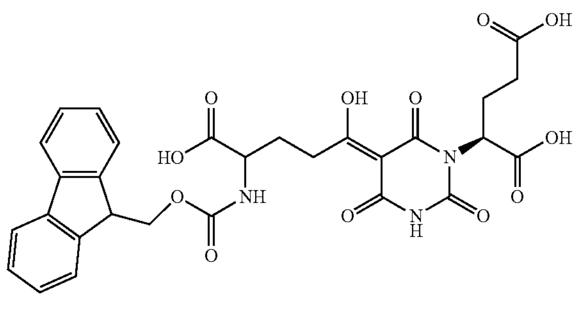 [SMILES: O=C(O)CC[C@@H](C(=O)O)N1C(=O)NC(=O)/C(=C(/O)CCC(NC(=O)OCC2c3ccccc3-c3ccccc32)C(=O)O)C1=O]

General experimental procedures for amide formation and the removal of benzyl group were followed. Reaction was performed on a 15 mg scale. Product was purified by HPLC purification system using 0.05% TFA in water and acetonitrile as a solvent yielded the title compound (1.5 mg, 7%). $^1$H NMR ($CD_3OD$, 400 MHz) δ 7.78 (d, J=6.8 Hz, 2H), 7.69-7.66 (m, 2H), 7.37-7.28 (m, 4H), 5.37 (br, 1H), 4.37-4.22 (m, 2H), 2.50-2.0 (m, 3H). MS: m/z=610 (M+H$^+$).

(S)-2-(3-((S)-1-Carboxy-5-((4-nitrobenzyloxy)carbonylamino)pentyl)-5,5-diethyl-2,4,6-trioxotetrahydropyrimidin-1(2H)-yl)pentanedioic acid: P118

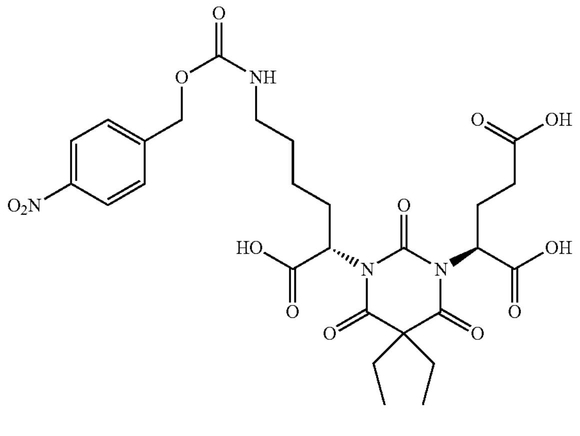 [SMILES: CCC1(CC)C(=O)N([C@@H](CCCCNC(=O)OCc2ccc([N+](=O)[O-])cc2)C(=O)O)C(=O)N([C@@H](CCC(=O)O)C(=O)O)C1=O]

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (20 mg, 0.032 mmol) in DCM (1.0 mL) was added 4-nitrobenzyl chloroformate (10.6 mg, 0.049 mmol) and triethylamine (15 μL, 0.108 mmol). The mixture was stirred at room temperature for 1 hour and further deprotected with general condition to give P118 (8.5 mg, 42%) as a white solid. $^1$H NMR ($CD_3OD$, 400 MHz) δ 8.23 (d, J=9.0 Hz, 2H), 7.58 (d, J=8.6 Hz, 2H), 5.33-5.47 (m, 2H), 5.18 (s, 2H), 3.06-3.18 (m, 2H), 2.49-2.59 (m, 1H), 2.15-2.38 (m, 4H), 1.98-2.12 (m, 5H), 1.45-1.62 (m, 2H), 1.26-1.42 (m, 2H), 0.84-0.92 (m, 6H). MS: m/z=623 (M+H$^+$).

(S)-Di-tert-butyl 2-((S)-3-(5-benzamidopentanamido)-4-(tert-butoxy)-4-oxobutanamido)pentanedioate

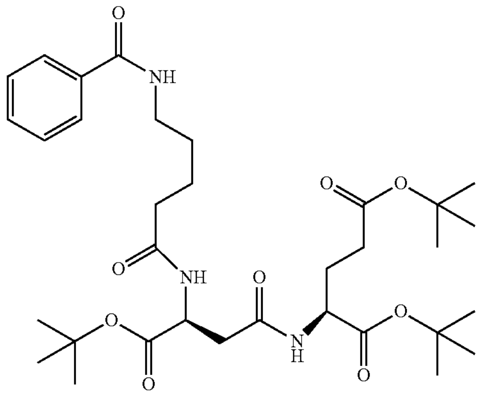 [SMILES: CC(C)(C)OC(=O)CC[C@H](NC(=O)C[C@H](NC(=O)CCCCNC(=O)c1ccccc1)C(=O)OC(C)(C)C)C(=O)OC(C)(C)C]

General experimental procedure for the formation of amide was followed. Reaction was performed on a 42 mg scale. The crude product was used directly in the next step without any further purification. MS: m/z=634 (M+H$^+$).

(S)-2-((S)-3-(5-Benzamidopentanamido)-3-carboxypropanamido)pentanedioic acid: P119

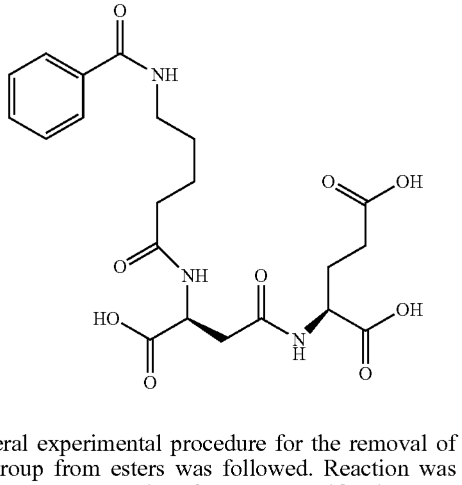

General experimental procedure for the removal of tert-butyl group from esters was followed. Reaction was performed on a 62 mg scale. After HPLC purification, P119 (20 mg, 44%) was obtained. $^1$H NMR ($CD_3OD$, 400 MHz) δ 7.78-7.83 (m, 2H), 7.41-7.55 (m, 3H), 4.74 (t, J=6.0 Hz, 1H), 3.39 (t, J=6.4 Hz, 2H), 2.81 (d, J=6.4 Hz, 2H), 2.39 (t, J=8.0 Hz, 2H), 2.31*t, J=7.2 Hz, 2H), 2.11-2.23 (m, 1H), 1.84-1.97 (m, 1H), 1.61-1.75 (4H). MS: m/z=466 (M+H$^+$).

(S)-2-(3-((S)-1-Carboxy-5-((4-nitrobenzyloxy)carbonylamino)pentyl)-2,4,6-trioxotetrahydropyrimidin-1(2H)-yl)pentanedioic acid: P120

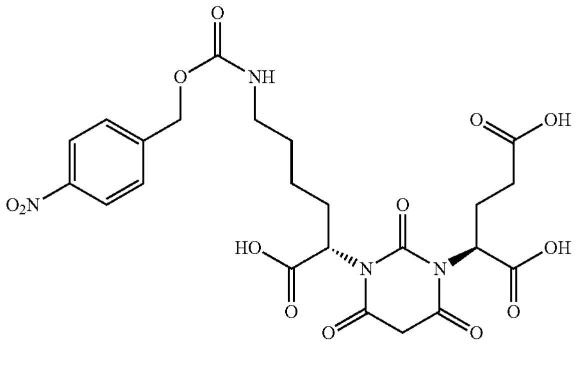 [SMILES: O=C(O)CC[C@@H](C(=O)O)N1C(=O)CC(=O)N([C@@H](CCCCNC(=O)OCc2ccc([N+](=O)[O-])cc2)C(=O)O)C1=O]

To solution of (S)-di-tert-butyl 2-(3-((S)-6-amino-1-tert-butoxy-1-oxohexan-2-yl)-2,4,6-trioxotetrahydropyrimidin-1(2H)-yl)pentanedioate (23 mg, 0.041 mmol) in DCM (1.5 mL) was added 4-nitrobenzyl chloroformate (10.7 mg, 0.050 mmol) and triethylamine (18 μL, 0.130 mmol). The mixture was stirred at room temperature for 2 hour and further deprotected with general condition to give P120 (13.4 mg, 57%) as a white solid. $^{1}$H NMR ($CD_3OD$, 400 MHz) δ 8.23 (d, J 9.0 Hz, 2H), 7.58 (d, J=8.6 Hz, 2H), 5.23-5.38 (m, 2H), 5.18 (s, 2H), 3.07-3.16 (m, 2H), 2.36-2.52 (m, 3H), 2.12-2.33 (m, 2H), 1.99-2.09 (m, 1H), 1.43-1.59 (m, 2H), 1.29-1.41 (m, 2H). MS: m/z=567 ($M+H^+$).

5-Amino-5-oxo-2-(4-(((2-oxo-2H-chromen-7-yl)oxy)methyl)-1H-1,2,3-triazol-1-yl)pentanoic acid: P121

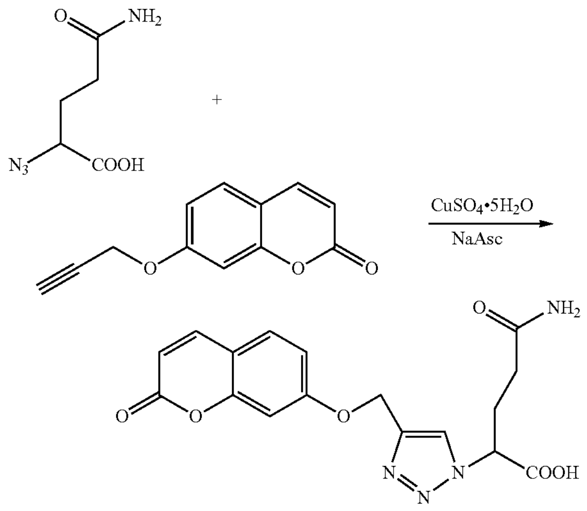

P121

General experimental procedure for click reaction was followed. Reaction was performed on a 0.032 g scale. After HPLC purification, P121 (0.05 g, 72%) was obtained as a white solid. $^{1}$H NMR ($CD_3OD$, 400 MHz) 8.25 (s, 1H), 7.87 (d, J=9.2 Hz, 1H), 7.55 (d, J=8.8 Hz, 1H), 7.06 (d, J=2.4 Hz, 1H), 7.02 (dd, J=8.8, 2.4 Hz, 1H), 6.25 (d, J=9.6 Hz, 1H), 5.49 (dd, J=10.4, 4.8 Hz, 1H), 5.28 (s, 2H), 2.69-2.60 (m, 1H), 2.50-2.41 (m, 1H), 2.23-2.12 (m, 2H). MS: m/z=373.1 ($M+H^+$).

(S)-Di-tert-butyl 2-((S)-4-(tert-butoxy)-3-(4-(4-methoxyphenyl)butanamido)-4-oxobutanamido)pentanedioate

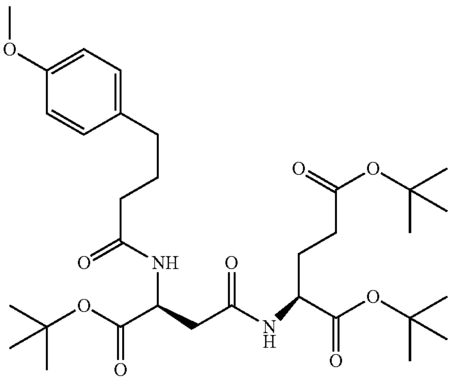 [SMILES: COc1ccc(CCCC(=O)N[C@@H](CC(=O)N[C@@H](CCC(=O)OC(C)(C)C)C(=O)OC(C)(C)C)C(=O)OC(C)(C)C)cc1]

General experimental procedure for the formation of amide was followed. Reaction was performed on a 47 mg scale. The crude product was used directly in the next step without any further purification. MS: m/z=607 ($M+H^+$).

(S)-2-((S)-3-Carboxy-3-(4-(4-methoxyphenyl)butanamido)propanamido)-pentanedioic acid: P122

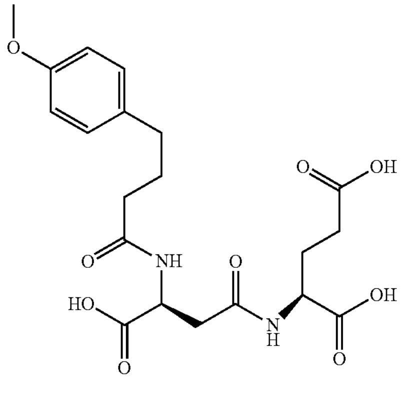 [SMILES: COc1ccc(CCCC(=O)N[C@@H](CC(=O)N[C@@H](CCC(=O)O)C(=O)O)C(=O)O)cc1]

General experimental procedure for the removal of tert-butyl group from esters was followed. Reaction was performed on a 68 mg scale. After HPLC purification, P122 (33 mg, 67%) was obtained. $^{1}$H NMR ($CD_3OD$, 400 MHz) δ 7.10 (d, J=8.8 Hz, 2H), 6.81 (d, J=8.8 Hz, 2H), 4.73 (t, J=6.8 Hz, 1H), 4.59-4.66 (m, 1H), 3.75 (s, 3H), 2.78-2.83 (m, 2H), 2.57 (t, J=8.0 Hz, 2H), 2.38 (t, J=8.0 Hz, 2H), 2.24 (t, J=7.6 Hz, 2H), 2.11-2.21 (m, 1H), 1.82-1.95 (m, 3H). MS: m/z=439 ($M+H^+$).

(S)-Di-tert-butyl 2-((S)-4-(tert-butoxy)-3-(4-(4-nitrophenyl)butanamido)-4-oxobutanamido)pentanedioate

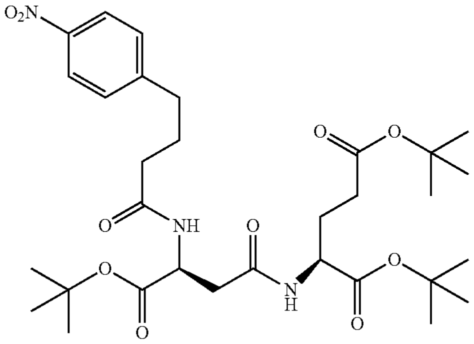 [SMILES: CC(C)(C)OC(=O)CC[C@H](NC(=O)C[C@H](NC(=O)CCCc1ccc([N+](=O)[O-])cc1)C(=O)OC(C)(C)C)C(=O)OC(C)(C)C]

General experimental procedure for the formation of amide was followed. Reaction was performed on a 47 mg scale. The crude product was used directly in the next step without any further purification. MS: m/z=622 (M+H$^+$).

(S)-2-((S)-3-Carboxy-3-(4-(4-nitrophenyl)butanamido)propanamido)pentanedioic acid: P123

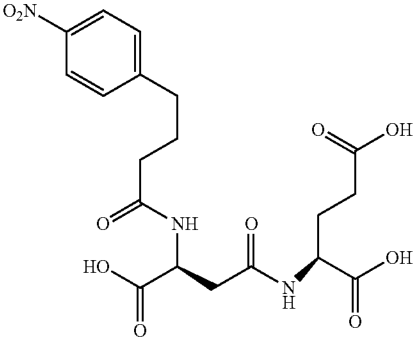 [SMILES: O=C(O)CC[C@H](NC(=O)C[C@H](NC(=O)CCCc1ccc([N+](=O)[O-])cc1)C(=O)O)C(=O)O]

General experimental procedure for the removal of tert-butyl group from esters was followed. Reaction was performed on a 68 mg scale. After HPLC purification, P123 (25 mg, 50%) was obtained. $^1$H NMR (CD$_3$OD, 400 MHz) δ 8.15 (d, J=8.8 Hz, 2H), 7.46 (d, J=8.8 Hz, 2H), 4.74 (t, J=6.0 Hz, 1H), 3.39-4.46 (m, 1H), 2.74-2.84 (m, 4H), 2.38 (t, J=8.0 Hz, 2H), 2.29 (t, J=7.2 Hz, 2H), 2.11-2.22 (m, 1H), 1.85-2.03 (m, 3H). MS: m/z=454 (M+H$^+$).

2-(4-(2-Amino-3-methoxy-3-oxopropyl)-1H-1,2,3-triazol-1-yl)pentanedioic acid

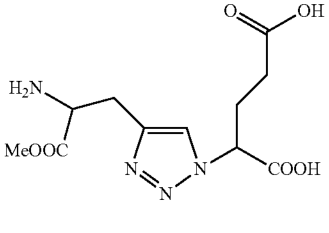 [SMILES: COC(=O)C(N)Cc1cn(C(CCC(=O)O)C(=O)O)nn1]

General experimental procedure for click reaction was followed. Reaction was performed on a 0.05 g scale. The title compound (50 mg, 54%) was obtained as a white solid. MS: m/z=301.1 (M+H$^+$).

2-(4-(2-(((Benzyloxy)carbonyl)amino)-3-methoxy-3-oxopropyl)-1H-1,2,3-triazol-1-yl)pentanedioic acid: P124

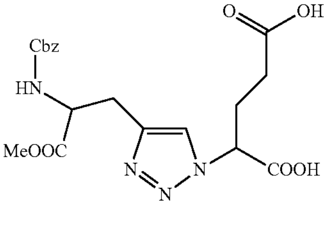 [SMILES: COC(=O)C(Cc1cn(C(CCC(=O)O)C(=O)O)nn1)NC(=O)OCc1ccccc1]

General experimental procedures for benzoylation were followed. Reaction was performed on a 0.054 g scale. After HPLC purification, P124 (70 mg, 77%) was obtained as a white solid. $^1$H NMR (CD$_3$OD, 400 MHz) 7.84 (s, 1H), 7.32-7.25 (m, 5H), 5.44 (dd, J=9.2, 4.0 Hz, 1H), 5.04 (ABq, $J_{AB}$=12.4 Hz, 2H), 4.48 (dd, J=8.8, 4.8 Hz, 1H), 3.33-3.30 (m, 1H), 3.14-3.08 (m, 1H), 2.61-2.52 (m, 1H), 2.39-2.32 (m, 1H), 2.18 (t, J=7.6, Hz, 2H). MS: m/z=435.1 (M+H$^+$).

(S)-4-(Formyloxy)-4-(picolinamido)butanoic acid: P125

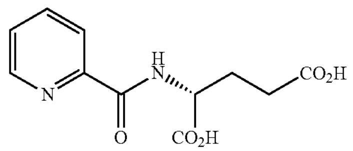 [SMILES: O=C(O)CC[C@@H](NC(=O)c1ccccn1)C(=O)O]

General experimental procedure for amide formation and tert-butyl deprotection was followed. $^1$H NMR (CD$_3$OD, 400 MHz) δ 8.65 (s, 1H), 8.06 (d, J=30 Hz, 1H), 8.01 (m 1H), 7.60 (m, 1H), 4.68-4.66 (m, 1H), 2.45-2.41 (m, 3H), 2.20-2.05 (m, 1H). MS: m/z=252.8 (M+H$^+$)

(S,Z)-2-(5-((4-Aminophenyl)(hydroxy)methylene)-2,4,6-trioxotetrahydropyrimidin-1(2H)-yl)pentanedioic acid: P127

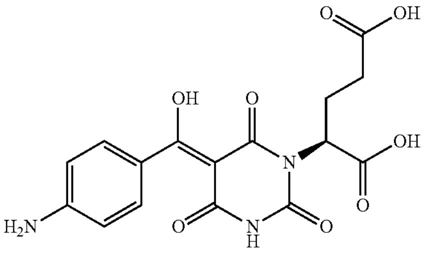 [SMILES: Nc1ccc(/C(O)=C2\C(=O)NC(=O)N([C@@H](CCC(=O)O)C(=O)O)C2=O)cc1]

General experimental procedures for amide formation and hydrogenation method for debenzylation were followed. Reaction was performed on a 23 mg scale. Product was purified by HPLC purification system using 0.05% TFA in water and acetonitrile as a solvent yielded the title compound (1.5 mg, 8%). $^1$H NMR (400 $CD_3OD$, 400 MHz) δ 7.51-7.49 (dd, J=6.8, 1.6 Hz, 1H), 7.39-7.37 (m, 1H), 6.52-6.46 (dd, J=6.8, 1.6 Hz, 1H), 6.44-6.41 (m, 1H), 5.30-5.26 (m, 1H), 2.41-2.25 (m, 4H). MS: m/z=378 (M+H$^+$).

(S)-2-(3-((S)-1-Carboxy-5-(4-nitrophenylsulfonamido)pentyl)-2,4,6-trioxotetrahydropyrimidin-1(2H)-yl)pentanedioic acid: P128

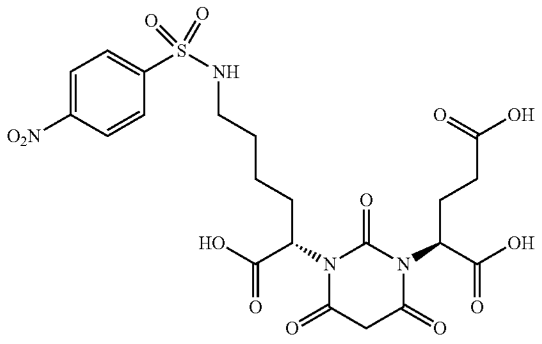 [SMILES: O=C(O)CC[C@@H](C(=O)O)N1C(=O)CC(=O)N([C@@H](CCCCNS(=O)(=O)c2ccc([N+](=O)[O-])cc2)C(=O)O)C1=O]

To solution of (S)-di-tert-butyl 2-(3-((S)-6-amino-1-tert-butoxy-1-oxohexan-2-yl)-2,4,6-trioxotetrahydropyrimidin-1(2H)-yl)pentanedioate (10.0 mg, 0.018 mmol) in DCM (1.0 mL) was added 4-nitrobenzenesulfonyl chloride (6.0 mg, 0.027 mmol) and triethylamine (10 μL, 0.072 mmol). The mixture was stirred at room temperature for 2 hour and further deprotected with general condition to give P128 (4.7 mg, 46%) as a white solid. $^1$H NMR ($CD_3OD$, 400 MHz) δ 8.39-8.42 (m, 2H), 8.05-8.08 (m, 2H), 5.35 (dd, J=10.0, 4.5 Hz, 1H), 5.20 (dd, J=9.8, 5.1 Hz, 1H), 2.91 (t, J=6.8 Hz, 2H), 2.34-2.52 (m, 3H), 2.20-2.33 (m, 1H), 1.90-2.13 (m, 2H), 1.28-1.54 (m, 4H). MS: m/z=573 (M+H$^+$).

(S)-2-(3-((S)-5-(3-Benzylureido)-1-carboxypentyl)-2,4,6-trioxotetrahydropyrimidin-1(2H)-yl)pentanedioic acid: P129

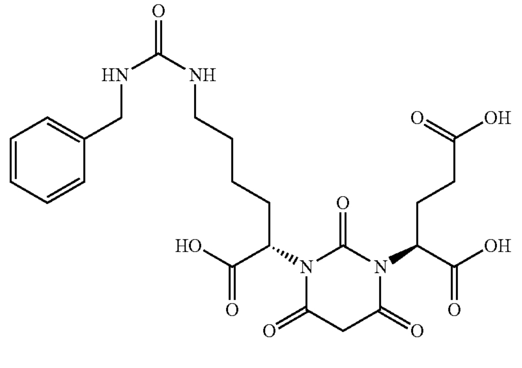 [SMILES: O=C(O)CC[C@@H](C(=O)O)N1C(=O)CC(=O)N([C@@H](CCCCNC(=O)NCc2ccccc2)C(=O)O)C1=O]

To solution of (S)-di-tert-butyl 2-(3-((S)-6-amino-1-tert-butoxy-1-oxohexan-2-yl)-2,4,6-trioxotetrahydropyrimidin-1(2H)-yl)pentanedioate (10.0 mg, 0.018 mmol) in DCM (1.0 mL) was added benzyl isocyanate (2.9 mg, 0.022 mmol) and triethylamine (10 μL, 0.072 mmol). The mixture was stirred at room temperature for 2 hour and further deprotected with general condition to give P129 (4.7 mg, 55%) as a white solid. $^1$H NMR ($CD_3OD$, 400 MHz) δ 7.19-7.32 (m, 4H), 5.27-5.39 (m, 2H), 4.30 (s, 2H), 3.07-3.17 (m, 2H), 2.35-2.52 (m, 3H), 2.12-2.33 (m, 2H), 1.99-2.09 (m, 1H), 1.31-1.57 (m, 4H). MS: m/z=521 (M+H$^+$).

(S)-2-(3-((S)-5-(3-(4-Azidophenyl)thioureido)-1-carboxypentyl)-5,5-diethyl-2,4,6-trioxotetrahydropyrimidin-1(2H)-yl)pentanedioic acid: P130 precursor

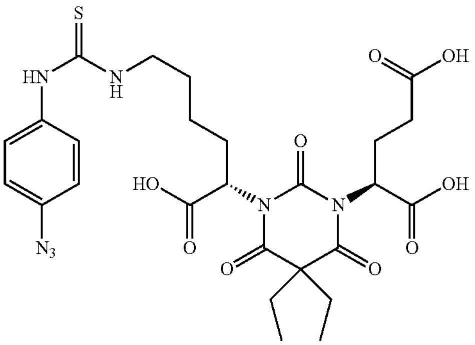 [SMILES: CCC1(CC)C(=O)N([C@@H](CCCCNC(=S)Nc2ccc(N=[N+]=[N-])cc2)C(=O)O)C(=O)N([C@@H](CCC(=O)O)C(=O)O)C1=O]

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (24 mg, 0.039 mmol) in DCM (1.5 mL) was added 4-azidophenyl isothiocyanate (8.3 mg, 0.047 mmol) and triethylamine (20 μL, 0.144 mmol). The mixture was stirred at room temperature for 1 hour and further deprotected with general condition to give P130 precursor (13.5 mg, 56%) as a white solid. $^1$H NMR ($CD_3OD$, 400 MHz) δ 7.31-7.36 (m, 2H), 7.04-7.08 (m, 2H), 5.36-5.47 (m, 2H), 3.44-3.64 (m, 2H), 2.50-2.59 (m, 1H), 2.18-2.39 (m, 4H), 2.00-2.13 (m, 5H), 1.58-1.73 (m, 2H), 1.29-1.45 (m, 2H), 0.89 (td, J=7.4, 3.5 Hz, 6H). MS: m/z=620 (M+H$^+$).

(S)-2-(3-((S)-1-Carboxy-5-(3-(4-(4-(3-fluoropropyl)-1H-1,2,3-triazol-1-yl)phenyl)thioureido)pentyl)-5,5-diethyl-2,4,6-trioxotetrahydropyrimidin-1(2H)-yl) pentanedioic acid: P130

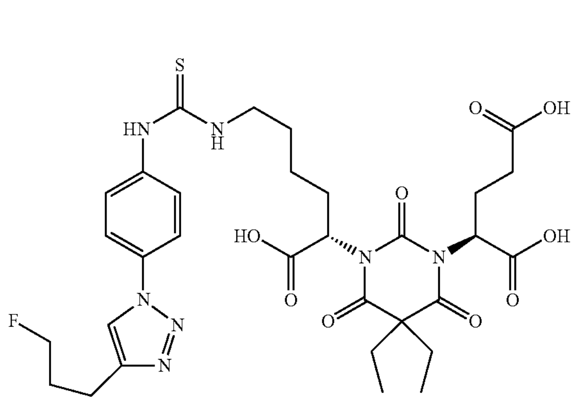 [SMILES: CCC1(CC)C(=O)N([C@@H](CCCCNC(=S)Nc2ccc(-n3cc(CCCF)nn3)cc2)C(=O)O)C(=O)N([C@@H](CCC(=O)O)C(=O)O)C1=O]

General experimental procedure for click reaction was followed. Reaction was performed on a 5.7 mg scale of (S)-2-(3-((S)-5-(3-(4-azidophenyl)thioureido)-1-carboxypentyl)-5,5-diethyl-2,4,6-trioxotetrahydropyrimidin-1(2H)-yl)pentanedioic acid. After HPLC purification, P130 (3.7 mg, 57%) was obtained as a white solid. $^1$H NMR ($CD_3OD$, 400 MHz) δ 8.32 (s, 1H), 7.78-7.82 (m, 2H), 7.58-7.62 (m, 2H), 5.38-5.48 (m, 2H), 4.58 (t, J=5.9 Hz, 1H), 4.46 (t, J=5.9 Hz, 1H), 3.47-3.67 (m, 2H), 2.89-2.94 (m, 2H), 2.50-2.59 (m, 1H), 2.31-2.37 (m, 2H), 2.21-2.30 (m, 2H), 2.00-2.19 (m, 7H), 1.60-1.76 (m, 2H), 1.29-1.47 (m, 2H), 0.90 (td, J=7.4, 2.0 Hz, 6H). MS: m/z=706 (M+H$^+$).

(S)-2-(2-(5-Benzamido-N-hydroxypentanamido)acetamido)pentanedioic acid: P131

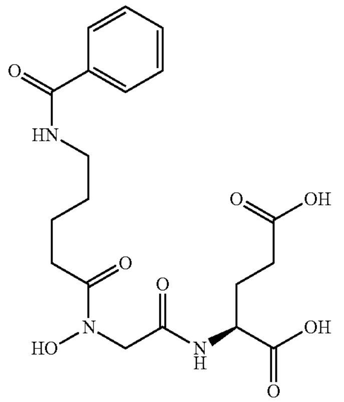 [SMILES: O=C(O)CC[C@H](NC(=O)CN(O)C(=O)CCCCNC(=O)c1ccccc1)C(=O)O]

General experimental procedure for the removal of benzyl group was followed. Reaction was performed on a 75 mg scale. After HPLC purification, P131 (17 mg, 37%) was obtained. $^1$H NMR ($CD_3OD$, 400 MHz) δ 7.78-7.84 (m, 2H), 7.41-7.55 (m 3H), 4.44-4.52 (m, 1H), 4.33 (s, 2H), 3.37-3.45 (m, 2H), 2.56-2.66 (m, 2H), 2.40 (t, J=8.0 Hz, 2H), 2.13-2.25 (m, 1H), 1.89-2.01 (m, 1H), 1.64-1.78 (m, 4H). MS: m/z=424 (M+H$^+$).

(S)-2-(2-(N-Hydroxy-4-(4-methoxyphenyl)butanamido)acetamido)pentanedioic acid: P132

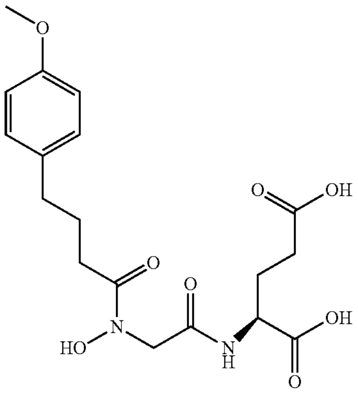 [SMILES: COc1ccc(CCCC(=O)N(O)CC(=O)N[C@@H](CCC(=O)O)C(=O)O)cc1]

General experimental procedure for the removal of benzyl group was followed. Reaction was performed on a 68 mg scale. After HPLC purification, P132 (33 mg, 80%) was obtained. $^1$H NMR ($CD_3OD$, 400 MHz) δ 7.11 (d, J=8.4 Hz, 2H), 6.82 (d, J=8.8 Hz, 2H), 4.45-4.53 (m, 1H), 4.32 (s, 2H), 3.75 (s, 3H), 2.60 (t, J=8.0 Hz, 2H), 2.51-2.58 (m, 2H), 2.40 (t, J=8.0 Hz, 2H), 2.14-2.25 (m, 1H), 1.84-2.01 (m, 3H). MS: m/z=397 (M+H$^+$).

(S)-2-(3-((S)-1-Carboxy-5-(6-fluoronicotinamide)pentyl)-3-methylureido)-pentanedioic acid: P133

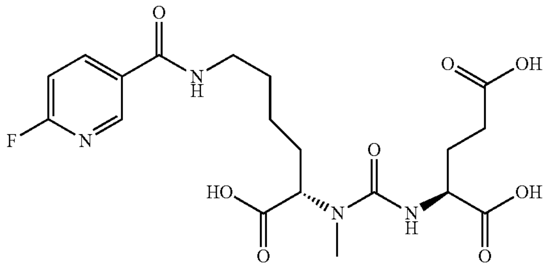 [SMILES: CN(C(=O)N[C@@H](CCC(=O)O)C(=O)O)[C@@H](CCCCNC(=O)c1ccc(F)nc1)C(=O)O]

General experimental procedures for amide formation and removal of tert-butyl group from esters were followed. Reaction was performed on a 70 mg scale. Product was purified on a Biotage and HPLC purification system afforded the title compound (10 mg, 16%). $^1$H NMR ($CD_3OD$, 400 MHz) δ 8.65 (d, J=2.0 Hz, 1H), 8.36-8.31 (m, 1H), 8.16-8.14 (dd, J=8.8, 2.8 Hz, 1H), 4.31-4.28 (dd, J=9.6, 4.8 Hz, 1H), 3.42-3.37 (m, 1H), 2.85 (s, 3H), 2.46 (t, J=7.6 Hz, 2H), 2.23-2.15 (m, 1H), 2.04-1.95 (m, 1H), 1.86-1.58 (m, 4H), 1.46-1.38 (m, 2H). MS: m/z=457 (M+H$^+$).

(S)-Di-tert-butyl 2-(3-((S)-1-(tert-butoxy)-6-(6-nitronicotinamide)-1-oxohexan-2-yl)-3-methylureido)-pentanedioate: P133 Precursor 1

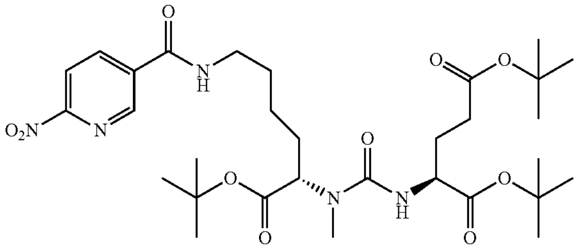 [SMILES: CN(C(=O)N[C@@H](CCC(=O)OC(C)(C)C)C(=O)OC(C)(C)C)[C@@H](CCCCNC(=O)c1ccc([N+](=O)[O-])nc1)C(=O)OC(C)(C)C]

General experimental procedure for amide formation was followed. Reaction was performed on a 100 mg scale. Product was purified on a HPLC purification system using water-acetonitrile with 0.05% TFA (30-90%) afforded the protected amide-ester (30 mg, 24%). $^1$H NMR ($CD_3OD$, 400 MHz) δ 8.98-8.97 (dd, J=2.0, 0.4 Hz, 1H), 8.85 (br, 1H), 8.55-8.52 (dd, J=8.4, 2.4 Hz, 1H), 8.39-8.37 (dd, J=8.4, 2.4 Hz, 1H), 4.76-4.72 (m, 1H), 4.19-4.15 (d, J=9.6, 4.8 Hz, 1H), 3.45-3.41 (m, 2H), 2.97 (s, 3H), 2.36 (t, J=7.2 Hz, 1H), 2.11-2.04 (m, 1H), 1.98-1.60 (m, 5H), 1.44-1.22 (m, 11H). MS: m/z=652 (M+H$^+$).

(S)-Di-tert-butyl 2-(3-((S)-1-(tert-butoxy)-6-(6-bromonicotinamide)-1-oxohexan-2-yl)-3-methylureido)-pentanedioate: P133 Precursor 2

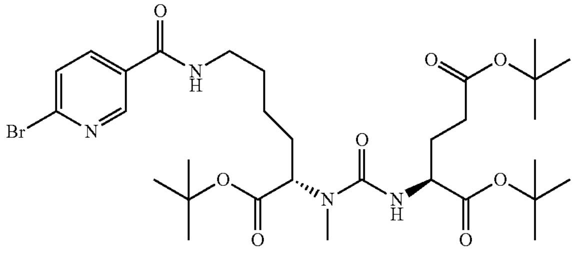 [SMILES: CN(C(=O)N[C@@H](CCC(=O)OC(C)(C)C)C(=O)OC(C)(C)C)[C@@H](CCCCNC(=O)c1ccc(Br)nc1)C(=O)OC(C)(C)C]

General experimental procedure for amide formation was followed. Reaction was performed on a 115 mg scale. Product was purified on a HPLC purification system using water-acetonitrile with 0.05% TFA (30-90%) afforded the protected amide-ester (50 mg, 24%). $^1$H NMR ($CD_3CN$, 400 MHz) δ 8.73-8.72 (dd, J=2.4, 0.4 Hz, 1H), 8.01-7.98 (dd, J=8.4, 2.4 Hz, 1H), 7.63 (dd, J=8.4, 2.4 Hz, 1H), 7.25 (br s, 1H), 5.42 (d, J=8.0 Hz, 1H), 4.73-4.69 (dd, J=10.8, 5.2 Hz, 1H), 4.14-4.08 (m, 1H), 3.40-3.28 (m, 2H), 2.76 (s, 3H), 2.06-2.0 (m, 1H), 1.88-1.52 (m, 6H), 1.44-1.22 (m, 11H). MS: m/z=685 and 687 ($M+H^+$ and $M+2H^+$).

(S)-2-(2-(4-(4-Aminophenyl)-N-hydroxybutanamido)acetamido)pentanedioic acid: P134

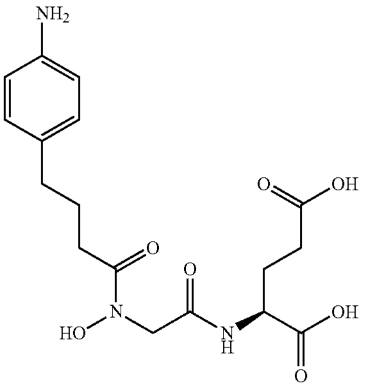 [SMILES: Nc1ccc(CCCC(=O)N(O)CC(=O)N[C@@H](CCC(=O)O)C(=O)O)cc1]

General experimental procedure for the removal of benzyl group was followed. Reaction was performed on a 97 mg scale. After HPLC purification, P134 (10 mg, 18%) was obtained. $^1$H NMR ($CD_3OD$, 400 MHz) δ 7.39 (d, J=8.8 Hz, 2H), 7.26 (d, J=8.8 Hz, 2H), 4.45-4.53 (m, 1H), 4.33 (s, 2H), 2.73 (t, J=8.0 Hz, 2H), 2.58 (t, J=8.0 Hz, 2H), 2.40 (t, J=8.0 Hz, 2H), 2.13-2.26 (m, 1H), 1.87-2.03 (m, 3H). MS: m/z=382 ($M+H^+$).

(R)-2-(3-((S)-3-(Benzylamino)-1-carboxy-3-oxopropyl)-3-hydroxyureido)pentanedioic acid: P135

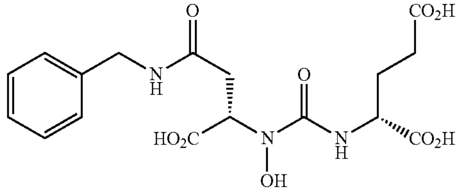 [SMILES: O=C(O)CC[C@@H](NC(=O)N(O)[C@@H](CC(=O)NCc1ccccc1)C(=O)O)C(=O)O]

General experimental procedures for amide formation and removal of tert-butyl group from esters were followed. $^1$H NMR ($CD_3OD$, 400 MHz) δ 7.28-7.20 (m, 6H), 5.14 (m 1H), 4.45-4.30 (m, 4H), 3.71-3.65 (m, 1H), 3.06-3.02 (m, 1H), 2.67-2.62 (m, 1H), 2.37-2.33 (m, 2H), 2.30-2.20 (m, 1H), 2.00-1.90 (m, 1H). MS: m/z=411.9 ($M+H^+$)

(S)-Di-tert-butyl 2-(((cyanoimino)(methylthio)methyl)amino)pentanedioate

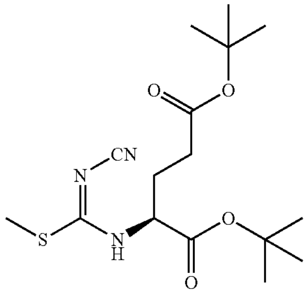 [SMILES: CS/C(=N/C#N)N[C@@H](CCC(=O)OC(C)(C)C)C(=O)OC(C)(C)C]

(S)-di-tert-butyl 2-aminopentanedioate hydrochloride (2 g, 6.76 mmol), dimethyl cyanocarbonimidodithioate (1.29 g, 8.82 mmol), and Triethylamine (1.885 ml, 13.52 mmol) were added in Acetonitrile (Volume: 22.54 ml). The reaction was heated for 1 hour at 90° C. The reaction was cooled to room temperature and purified by combiflash using 40% ethyl acetate in hexanes to afford (S)-di-tert-butyl 2-(((cyanoimino)(methylthio)methyl)amino)pentanedioate (1.2 g, 3.36 mmol, 49.6%) MS: m/z=358 ($M+H^+$).

(9S,13S)-Tri-tert-butyl 11-(cyanoimino)-3-oxo-1-phenyl-2-oxa-4,10,12-triazapentadecane-9,13,15-tricarboxylate

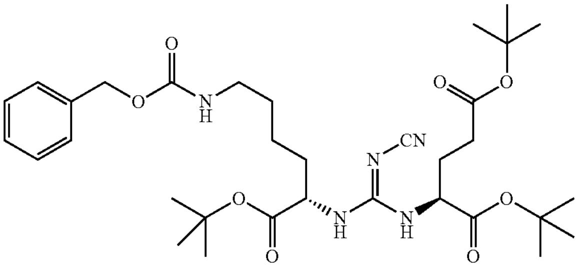 [SMILES: CC(C)(C)OC(=O)CC[C@H](N/C(=N\C#N)N[C@@H](CCCCNC(=O)OCc1ccccc1)C(=O)OC(C)(C)C)C(=O)OC(C)(C)C]

Silver nitrate (0.513 g, 3.02 mmol) was added to a solution containing, (S)-tert-butyl 2-amino-6-(((benzyloxy)

carbonyl)amino)hexanoate hydrochloride (0.42 g, 1.126 mmol)(S)-di-tert-butyl 2-(((cyanoimino)(methylthio) methyl)amino)pentanedioate (0.36 g, 1.007 mmol), and Triethylamine (0.281 ml, 2.014 mmol) in DMF (Volume: 5 ml). Heated the reaction to 80° C. for 20 minutes in MW. Let the reaction cool to room temperature and filtered. Concentrated and purified by prep HPLC to afford (9S,13S,Z)-tri-tert-butyl 11-(cyanoimino)-3-oxo-1-phenyl-2-oxa-4,10,12-triazapentadecane-9,13,15-tricarboxylate (0.4 g, 0.619 mmol, 61.5% yield) MS: m/z=646 (M+H$^+$)

(9S,13S)-11-(Cyanoimino)-3-oxo-1-phenyl-2-oxa-4,10,12-triazapentadecane-9,13,15-tricarboxylic acid: P136

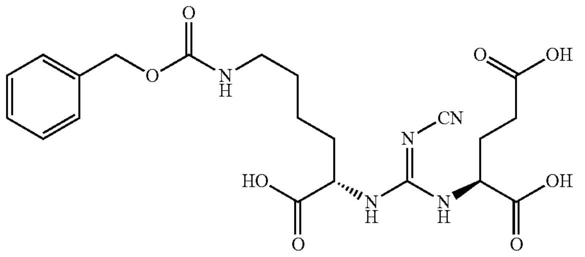 [SMILES: N#C/N=C(/N[C@@H](CCCCNC(=O)OCc1ccccc1)C(=O)O)N[C@@H](CCC(=O)O)C(=O)O]

General experimental procedure for the deprotection of the tert-butyl group was followed. Reaction was performed on a 50 mg scale. After HPLC purification, P136 (9.0 mg, 24%) was obtained. $^1$H NMR ($CD_3OD$, 400 MHz) δ 7.29 (m, 5H), 5.04 (s, 2H), 4.46 (m, 2H), 3.11 (m, 2H), 2.45 (m, 2H), 2.15 (m, 1H), 1.95 (m, 2H), 1.78 (m, 1H), 1.48 (m, 4H). MS: m/z=478 (M+H$^+$).

2-(4-(2-(4-(4-Azidophenyl)butanamido)-3-methoxy-3-oxopropyl)-1H-1,2,3-triazol-1-yl)pentanedioic acid

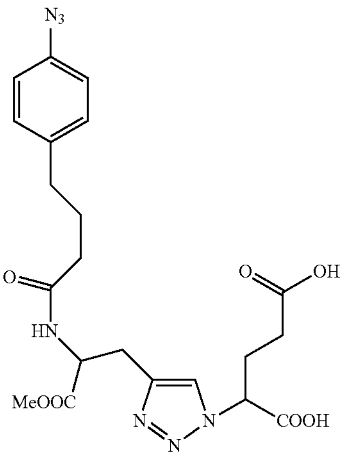 [SMILES: COC(=O)C(Cc1cn(C(CCC(=O)O)C(=O)O)nn1)NC(=O)CCCc1ccc(N=[N+]=[N-])cc1]

General experimental procedure for coupling reaction was followed. Reaction was performed on a 0.07 g scale. The title compound (30 mg, 26%) was obtained as a white solid. MS: m/z=488.1 (M+H$^+$).

2-(4-(2-(4-(4-Azidophenyl)butanamido)-2-carboxyethyl)-1H-1,2,3-triazol-1-yl)pentanedioic acid: P137 Precursor General experimental procedure for hydrolysis was followed. Reaction was performed on a 0.03 g scale. After HPLC purification, P137 Precursor (10 mg, 34%) was obtained as a white solid. $^1$H NMR ($CD_3OD$, 400 MHz) 7.78 (s, 1H), 7.11 (d, J=8.4 Hz, 2H), 6.86 (d J=8.4 Hz, 2H), 5.36 (dd, J=10.4, 5.2 Hz, 1H), 4.64 (dd, J=9.6, 4.8, Hz, 1H), 3.08-3.01 (m, 2H), 2.53-2.44 (m, 2H), 2.32-2.23 (m, 1H), 2.13-2.08 (m, 5H), 1.79-1.71 (m, 2H). MS: m/z=474.1 (M+H$^+$).

(S)-2-(3-((S)-5-(Benzyloxycarbonylamino)-1-carboxypentyl)-5,5-diethyl-4,6-dioxo-2-thioxotetrahydropyrimidin-1(2H)-yl)pentanedioic acid P138

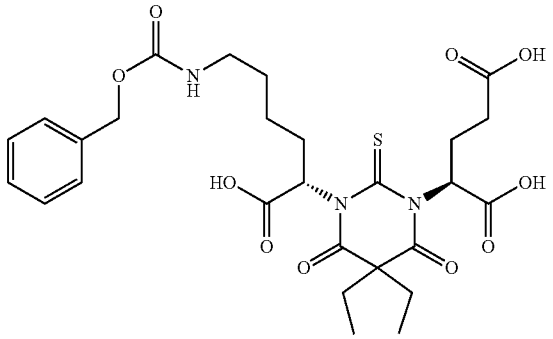 [SMILES: CCC1(CC)C(=O)N([C@@H](CCCCNC(=O)OCc2ccccc2)C(=O)O)C(=S)N([C@@H](CCC(=O)O)C(=O)O)C1=O]

To microwave tube was added a solution of (9S,13S)-tri-tert-butyl 3-oxo-1-phenyl-11-thioxo-2-oxa-4,10,12-triazapentadecane-9,13,15-tricarboxylate (110 mg, 0.173 mmol) in dry DCM (2.0 mL) followed by diethyl malonyl dichloride (40 mg, 0.272 mmol). The mixture was microwave heated at 80° C. for 30 minutes. The crude mixture was purified by flush chromatography (EtOAc/hexane, 0 to 30%) to give the (S)-di-tert-butyl 2-(3-((S)-6-(benzyloxycarbonylamino)-1-tert-butoxy-1-oxohexan-2-yl)-5,5-diethyl-4,6-dioxo-2-thioxotetrahydropyrimidin-1(2H)-yl)pentanedioate 66 mg (50%). 22.0 mg of above intermediate was deprotected with general condition to give P138 (1.2 mg, 7%) as a white solid. $^1$H NMR ($CD_3OD$, 400 MHz) δ 7.27-7.37 (m, 5H), 5.05 (s, 2H), 4.74-4.87 (m, 2H), 4.62 (dd, J=10.8, 4.9 Hz, 1H), 3.05-3.22 (m, 2H), 2.23-2.47 (m, 5H), 2.01-2.23 (m, 5H), 1.39-1.59 (m, 2H), 1.24-1.38 (m, 4H), 0.79-0.90 (m, 6H). MS: m/z=594 (M+H$^+$).

(8S,12S)-9-Hydroxy-3,10-dioxo-1-phenyl-2-oxa-4,9,11-triazatetradecane-8,12,14-tricarboxylic acid: P139

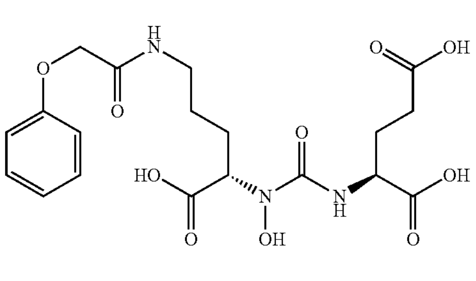 [SMILES: O=C(O)CC[C@H](NC(=O)N(O)[C@@H](CCCNC(=O)COc1ccccc1)C(=O)O)C(=O)O]

General experimental procedure for urea formation and tert-butyl deprotection was followed. Reaction was performed on a 352 mg scale of (S)-tert-butyl 5-(benzyloxycarbonylamino)-2-(hydroxyamino)pentanoate. After HPLC purification, P139 (17.5 mg, 36% in two steps) was obtained as a white solid. $^1$H NMR ($CD_3OD$, 400 MHz) δ 7.27-7.37 (m, 5H), 5.00-5.12 (m, 2H), 4.71 (dd, J=11.0, 4.3 Hz, 1H), 4.40 (dd, J=9.0, 4.7 Hz, 1H), 3.10-3.22 (m, 2H), 2.41-2.51 (m, 2H), 2.19-2.29 (m, 1H), 1.92-2.04 (m, 2H), 1.78-1.89 (m, 1H), 1.47-1.74 (m, 2H). MS: m/z=456 (M+H$^+$).

(9S,13S)-12-Hydroxy-3,11-dioxo-1-phenyl-2-oxa-4,10,12-triazapentadecane-9,13,15-tricarboxylic acid: P140

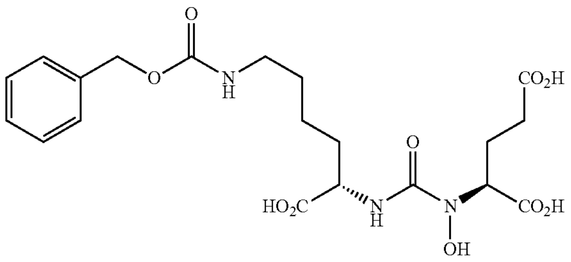 [SMILES: O=C(O)CC[C@@H](C(=O)O)N(O)C(=O)N[C@@H](CCCCNC(=O)OCc1ccccc1)C(=O)O]

General experimental procedure for urea formation and tert-butyl deprotection was followed. Reaction was performed on a 352 mg scale of (S)-tert-butyl 5-(benzyloxycarbonylamino)-2-(hydroxyamino)pentanoate. After HPLC purification, P140 (17.5, 36%) was obtained as a white solid. $^1$H NMR ($CD_3OD$, 400 MHz) δ 7.32-7.31 (m 5H), 5.03 (s, 2H), 4.78-4.72 (m, 1H), 4.34-4.32 (m, 1H), 3.09 (m, 2H), 2.50-2.42 (m, 2H), 2.22-2.18 (m, 1H), 2.10-2.00 (m, 1H), 1.90-1.80 (m, 1H), 1.75-1.70 (m, 1H), 1.60-1.40 (m, 4H). MS: m/z=470 (M+H$^+$).

(S)-2-(2-(4-(4-(4-(3-Fluoropropyl)-1H-1,2,3-triazol-1-yl)benzamido)-N-hydroxybutanamido)acetamido)pentanedioic acid: P141

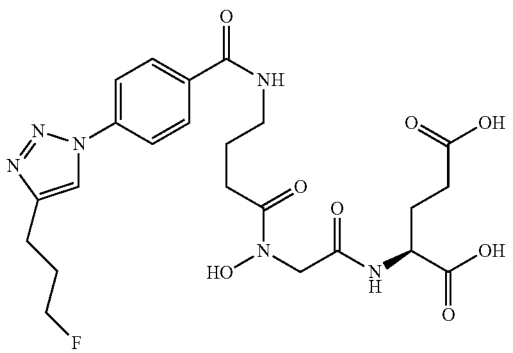 [SMILES: O=C(O)CC[C@H](NC(=O)CN(O)C(=O)CCCNC(=O)c1ccc(-n2cc(CCCF)nn2)cc1)C(=O)O]

General experimental procedure for the removal of benzyl group was followed. Reaction was performed on a 30 mg scale. After HPLC purification, P141 (5.0 mg, 25%) was obtained. $^1$H NMR ($CD_3OD$, 400 MHz) δ 8.44 (s, 1H), 7.91-8.07 (m, 4H), 4.52 (dt, J=47.2, 6.0 Hz, 2H), 4.34-4.37 (m, 1H), 4.31 (s, 2H), 3.45-3.55 (m, 2H), 2.56-2.66 (m, 2H), 2.40 (t, J=8.0 Hz, 2H), 2.13-2.25 (m, 1H), 1.89-2.01 (m, 1H), 1.64-1.78 (m, 6H). MS: m/z=537 (M+H$^+$).

(S)-2-(2-(4-(2-(4-(3-Fluoropropyl)-1H-1,2,3-triazol-1-yl)acetamido)-N-hydroxybutanamido)acetamido)pentanedioic acid: P142

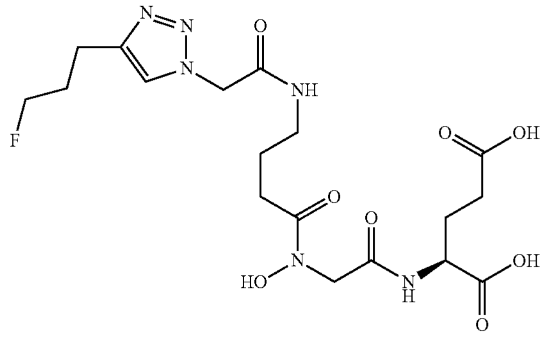 [SMILES: O=C(O)CC[C@H](NC(=O)CN(O)C(=O)CCCNC(=O)Cn1cc(CCCF)nn1)C(=O)O]

General experimental procedure for the removal of benzyl group was followed. Reaction was performed on a 22 mg scale. After HPLC purification, P142 (6.2 mg, 44%) was obtained. $^1$H NMR ($CD_3OD$, 400 MHz) δ 7.81 (s, 1H), 5.10 (s, 2H), 4.47 (dt, J=47.6 6.0 Hz, 2H), 4.45-4.52 (m, 1H), 4.35 (br s, 2H), 2.83 (t, J=8.0 Hz, 2H), 2.60 (t, J=6.4 Hz, 2H), 2.40 (t, J=8.0 Hz, 2H), 1.79-2.32 (m, 6H). MS: m/z=475 (M+H$^+$).

(9S,13S)-10-Methyl-3-oxo-1-phenyl-11-thioxo-2-oxa-4,10,12-triazapentadecane-9,13,15-tricarboxylic acid: P143

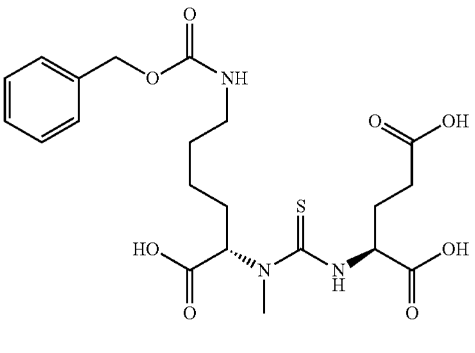 [SMILES: CN(C(=S)N[C@@H](CCC(=O)O)C(=O)O)[C@@H](CCCCNC(=O)OCc1ccccc1)C(=O)O]

General experimental procedure for the removal of benzyl group was followed. Reaction was performed on a 37 mg scale. After HPLC purification, P143 (3.4 mg, 12%) was obtained. $^1$H NMR ($CD_3OD$, 400 MHz) δ 7.20-7.40 (m, 5H), 5.18-5.22 (m, 1H), 5.11-5.16 (m, 1H), 5.06 (s, 2H), 3.08-3.17 (m, 2H), 3.03 (s, 3H), 2.39-2.53 (m, 2H), 2.19-2.37 (m, 1H), 1.98-2.18 (m, 2H), 1.77-1.95 (m, 1H), 1.29-1.51 (m, 4H). MS: m/z=484 (M+H$^+$).

(S)-2-(2-(3-(4-(4-(3-Fluoropropyl)-1H-1,2,3-triazol-1-yl)phenyl)-N-hydroxypropanamido)acetamido) pentanedioic acid: P144

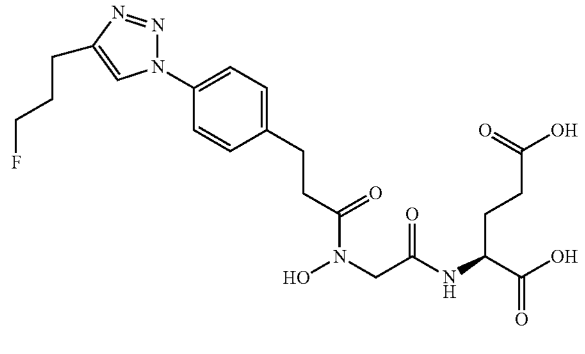 [SMILES: O=C(O)CC[C@H](NC(=O)CN(O)C(=O)CCc1ccc(-n2cc(CCCF)nn2)cc1)C(=O)O]

General experimental procedure for the removal of benzyl group was followed. Reaction was performed on a 120 mg scale. After HPLC purification, P144 (35 mg, 46%) was obtained. $^1$H NMR ($CD_3OD$, 400 MHz) δ 8.32 (s, 1H), 7.75 (d, J=8.4 Hz, 2H), 7.49 (d, J=8.4 Hz, 2H), 4.41-4.61 (m 3H), 4.36 (s, 2H), 2.98-3.12 (m, 2H), 2.85-2.96 (m, 4H), 2.38-2.43 (m, 2H), 1.89-2.25 (m, 4H). MS: m/z=480 $(M+H^+)$.

(S)-2-(2-(4-(4-(4-(3-Fluropropyl)-1H-1,2,3-triazol-1-yl)phenyl)-N-hydroxy-butanamido)ethanethioamido) pentanedioic acid: P145

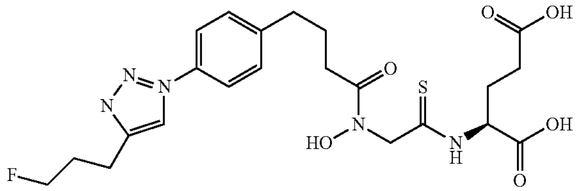

General experimental procedure for urea formation and tert-butyl deprotection was followed. Reaction was performed on a 200 mg scale of (S)-tert-butyl 5-(benzyloxycarbonylamino)-2-(hydroxyamino)pentanoate. After HPLC purification, P145 (17.5, 45%) was obtained as a white solid. $^1$H NMR ($CD_3OD$, 400 MHz) δ 8.30 (s, 1H), 7.74-7.72 (dd, J=6.8, 2.0 Hz, 2H), 7.44 (d, J=8.4 Hz, 2H), 5.14-5.11 (dd, J=8.4, 5.2 Hz, 2H), 4.64 (s, 2H), 4.57 (t, J=6.0 Hz, 1H), 4.45 (t, J=6.0 Hz, 1H), 2.90 (t, J=6.8 Hz, 2H), 2.78 (t, J=7.6 Hz, 2H), 2.62 (t, J=6.8 Hz, 2H), 2.45-2.28 (m, 2H), 2.16-1.98 (m, 4H). MS: m/z=510 $(M+H^+)$.

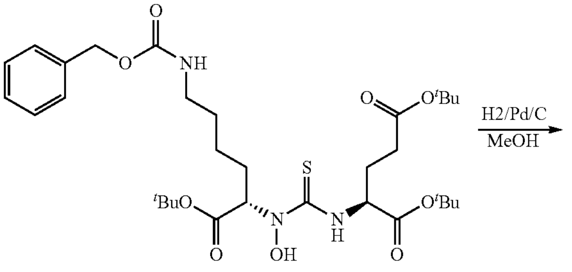

-continued

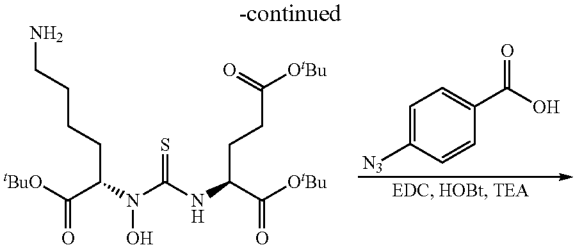

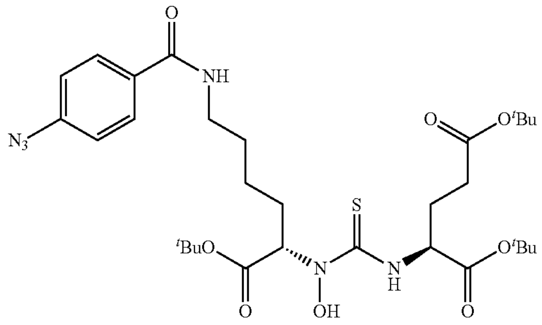

General experimental procedures for the removal of benzyl group and amide formation were followed. Reaction was performed on a 65 mg scale. After purification on column (silca gel) to give (S)-di-tert-butyl 2-(3-((S)-6-(4-azidobenzamido)-1-(tert-butoxy)-1-oxohexan-2-yl)-3-hydroxythioureido)pentanedioate (23 mg, 34% in two steps) as a yellow wax. MS: m/z=665 $(M+H^+)$.

(S)-2-(3-((S)-1-Carboxy-5-(4-(4-(3-fluoropropyl)-1H-1,2,3-triazol-1-yl)benzamido)pentyl)-3-hydroxythioureido)pentanedioic acid: P146

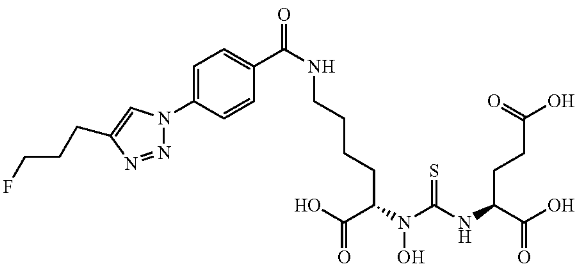 [SMILES: O=C(O)CC[C@H](NC(=S)N(O)[C@@H](CCCCNC(=O)c1ccc(-n2cc(CCCF)nn2)cc1)C(=O)O)C(=O)O]

General experimental procedure for click chemistry and tert-butyl deprotection was followed. Reaction was performed on a 9.0 mg scale. After HPLC purification, P146 was obtained. MS: m/z=583 $(M+H^+)$.

(S)-2-(3-((S)-1-Carboxy-5-(4-(4-(4-(3-fluoropropyl)-1H-1,2,3-triazol-1-yl)phenyl)butanamido)pentyl)-1-hydroxyureido)pentanedioic acid: P147

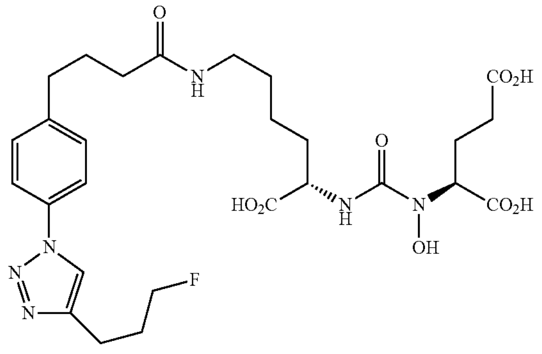 [SMILES: O=C(O)CC[C@@H](C(=O)O)N(O)C(=O)N[C@@H](CCCCNC(=O)CCCc1ccc(-n2cc(CCCF)nn2)cc1)C(=O)O]

General experimental procedure for urea formation and tert-butyl deprotection was followed. Reaction was performed on a 352 mg scale of (S)-tert-butyl 5-(benzyloxycarbonylamino)-2-(hydroxyamino)pentanoate. P147 was obtained as a white solid. $^{1}H$ NMR ($CD_3OD$, 400 MHz) δ 9.30 (s, 1H), 7.72-7.70 (m, 2H), 7.39-7.37 (m, 2H), 4.74-4.72 (m, 1H), 4.59-4.56 (m, 1H), 4.44-4.42 (m, 1H), 4.37-4.36 (m, 1H), 3.16-3.14 (m, 2H), 2.89-2.87 (m, 2H), 2.70-2.68 (m, 2H), 2.50-2.39 (m, 2H), 2.30-1.90 (m, 9H), 1.80-1.72 (m, 1H), 1.58-1.40 (m, 2H). MS: 609 ($M+H^+$).

(S)-2-(3-((S)-1-Carboxy-5-(2-(4-(3-fluoropropyl)-1H-1,2,3-triazol-1-yl)acetamido)pentyl)-1-hydroxyureido)pentanedioic acid: P148

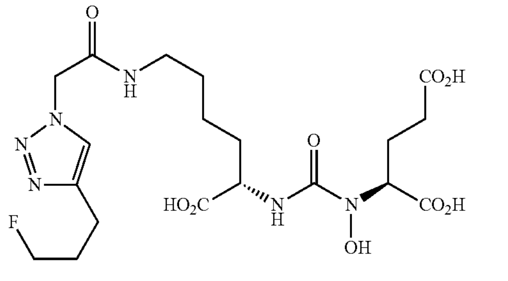 [SMILES: O=C(O)CC[C@@H](C(=O)O)N(O)C(=O)N[C@@H](CCCCNC(=O)Cn1cc(CCCF)nn1)C(=O)O]

General experimental procedure for urea formation and tert-butyl deprotection was followed. Reaction was performed on a 352 mg scale of (S)-tert-butyl 5-(benzyloxycarbonylamino)-2-(hydroxyamino)pentanoate. P148 was obtained as a white solid. $^{1}H$ NMR ($CD_3OD$, 400 MHz) δ 7.79 (s, 1H), 5.01 (s, 2H), 4.80-4.78 (m, 2H), 4.53-4.51 (m, 1H), 4.41-4.35 (m, 2H), 3.23-3.22 (m, 2H), 2.83-2.80 (m, 2H), 2.45-2.40 (m, 2H), 2.30-2.20 (m, 1H), 2.10-1.90 (m, 4H), 1.80-1.70 (m, 1H), 1.60-1.42 (m, 4H). MS: 609 ($M+H^+$).

(S)-2-(2-(3-(3,4-Dimethoxyphenethyl)-1-hydroxyureido)acetamido)pentanedioic acid: 149

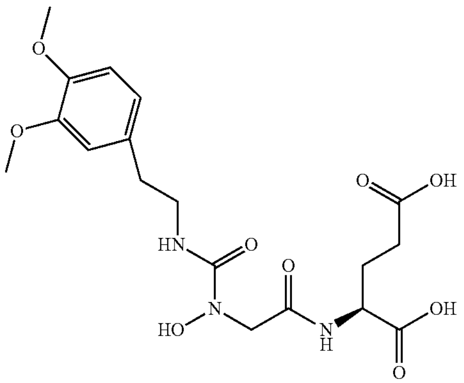 [SMILES: COc1ccc(CCNC(=O)N(O)CC(=O)N[C@@H](CCC(=O)O)C(=O)O)cc1OC]

General experimental procedure for the removal of benzyl group was followed. Reaction was performed on a 87 mg scale. After HPLC purification, P149 (33 mg, 62%) was obtained. $^{1}H$ NMR ($CD_3OD$, 400 MHz) δ 6.87-6.92 (m, 1H), 6.86 (s, 1H), 6.74-6.81 (m, 1H), 4.47-4.52 (m 1H), 4.16 (d, J=2.8 Hz, 2H), 3.82 (s, 3H), 3.79 (s, 3H), 3.38 (t, J=8.0 Hz, 2H), 2.76 (t, J=7.2 Hz, 2H), 2.35-2.44 (m, 2H), 2.14-2.25 (m, 1H), 1.98-2.01 (m, 1H). MS: m/z=428 ($M+H^+$).

(S)-2-(3-((S)-5-Azido-1-carboxypentyl)-5,5-diethyl-2,4,6-trioxotetrahydropyrimidin-1(2H)-yl)pentanedioic acid: P150 precursor

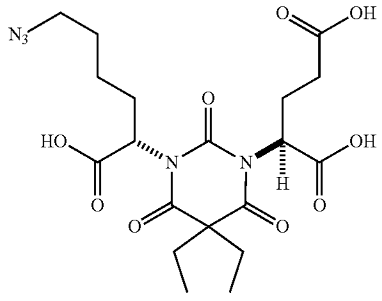

To solution of (S)-di-tert-butyl 2-(3-((S)-6-amino-1-tert-butoxy-1-oxohexan-2-yl)-5,5-diethyl-2,4,6-trioxotetrahydropyrimidin-1(2H)-yl)pentanedioate (186 mg, 0.304 mmol) in methanol (3.0 mL) was 1H-imidazole-1-sulfonyl azide hydrochloride (150 mg, 0.715 mmol), potassium carbonate (150 mg, 1.09 mmol), and copper(II) sulfate pentahydrate (3.5 mg, 0.014 mmol). The mixture was stirred at room temperature for 4 hours and concentrated. The residue was partitioned between DCM and water and the DCM layer was further deprotected with general condition to give P150 precursor (73.8 mg, 52%) as a white solid. $^{1}H$ NMR ($CD_3OD$, 400 MHz) δ 5.37-5.49 (m, 2H), 3.28 (t, J=8.0 Hz, 2H), 2.49-2.60 (m, 1H), 2.31-2.36 (m, 2H), 2.01-2.29 (m, 7H), 1.51-1.72 (m, 2H), 1.30-1.46 (m, 2H), 0.90 (td, J=7.4, 3.5 Hz, 6H). MS: m/z=470 ($M+H^+$).

(S)-2-(3-((S)-1-Carboxy-5-(4-(3-fluoropropyl)-1H-1,2,3-triazol-1-yl)pentyl)-5,5-diethyl-2,4,6-trioxotetrahydropyrimidin-1(2H)-yl)pentanedioic acid: P150

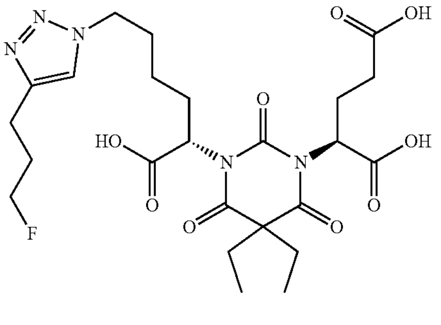 [SMILES: CCC1(CC)C(=O)N([C@@H](CCCCn2cc(CCCF)nn2)C(=O)O)C(=O)N([C@@H](CCC(=O)O)C(=O)O)C1=O]

General experimental procedure for click reaction was followed. Reaction was performed on a 8.5 mg scale of ((S)-2-(3-((S)-5-azido-1-carboxypentyl)-5,5-diethyl-2,4,6-trioxotetrahydropyrimidin-1(2H)-yl)pentanedioic acid. After HPLC purification, P150 (7.1 mg, 71%) was obtained as a white solid. $^1$H NMR ($CD_3OD$, 400 MHz) δ 7.80 (s, 1H), 5.33-5.47 (m, 2H), 4.52 (t, J=5.7 Hz, 1H), 4.35-4.42 (m, 3H), 2.79-2.84 (m, 2H), 2.49-2.59 (m, 1H), 2.17-2.40 (m, 4H), 1.87-2.13 (m, 9H), 1.21-1.40 (m, 2H), 0.81-0.89 (m, 6H). MS: m/z=556 ($M+H^+$).

(S)-2-(3-((S)-1-Carboxy-5-(4-((2-(2-(2,4-dinitrophenylamino)ethoxy)ethoxy)methyl)-1H-1,2,3-triazol-1-yl)pentyl)-5,5-diethyl-2,4,6-trioxotetrahydropyrimidin-1(2H)-yl)pentanedioic acid: P151

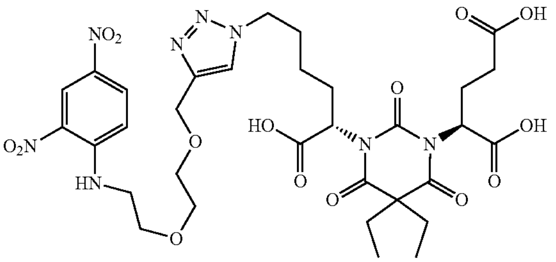 [SMILES: CCC1(CC)C(=O)N([C@@H](CCCCn2cc(COCCOCCNc3ccc([N+](=O)[O-])cc3[N+](=O)[O-])nn2)C(=O)O)C(=O)N([C@@H](CCC(=O)O)C(=O)O)C1=O]

General experimental procedure for click reaction was followed. Reaction was performed on a 2.5 mg scale of ((S)-2-(3-((S)-5-azido-1-carboxypentyl)-5,5-diethyl-2,4,6-trioxotetrahydropyrimidin-1(2H)-yl)pentanedioic acid. After HPLC purification, P151 (7.1 mg, 53%) was obtained as a yellow solid. $^1$H NMR ($CD_3OD$, 400 MHz) δ 9.03 (d, J=2.7 Hz, 1H), 8.27 (dd, J=9.4, 2.7 Hz, 1H), 7.93 (s, 1H), 7.21 (d, J=9.4 Hz, 1H), 5.31-5.44 (m, 2H), 4.60 (s, 2H), 4.39 (t, J=6.8 Hz, 2H), 3.77-3.82 (m, 2H), 3.64-3.72 (m, 6H), 2.43-2.62 (m, 1H), 2.15-2.39 (m, 4H), 1.89-2.05 (m, 6H), 1.20-1.38 (m, 2H), 0.79-0.88 (m, 6H). MS: m/z=779 ($M+H^+$).

(S)-2-(3-((S)-1-Carboxy-5-(4-(4-(3-fluoropropyl)-1H-1,2,3-triazol-1-yl)benzamido)pentyl)-1-hydroxyureido)pentanedioic acid: P152

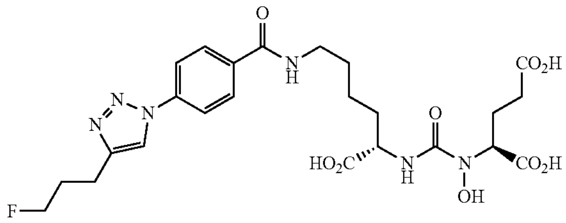 [SMILES: O=C(O)CC[C@@H](C(=O)O)N(O)C(=O)N[C@@H](CCCCNC(=O)c1ccc(-n2cc(CCCF)nn2)cc1)C(=O)O]

General experimental procedure for urea formation and tert-butyl deprotection was followed. P152 was obtained as a white solid. $^1$H NMR ($CD_3OD$, 400 MHz) δ 8.34 (s, 1H), 7.99-7.85 (m, 4H), 4.75-4.70 (m, 1H), 4.49-4.47 (m, 1H), 4.38-4.36 (m, 1H), 4.35-4.30 (m, 1H), 3.32-3.25 (m, 2H), 2.85-2.80 (m, 2H), 2.42-2.30 (m, 2H), 2.20-1.80 (m, 6H), 1.75-1.40 (m, 6H). MS: m/z=567 ($M+H^+$).

(S)-2-(3-((S)-1-Carboxy-5-(4-(4-(3-fluoropropyl)-1H-1,2,3-triazol-1-yl)benzamido)pentyl)-2-cyanoguanidino)pentanedioic acid: P153

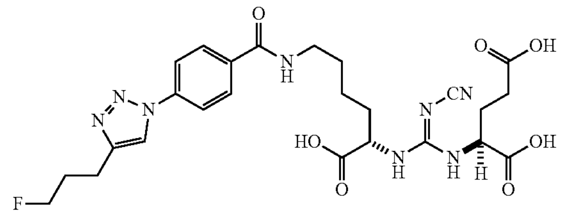

General experimental procedure for the deprotection of the tert-butyl group was followed. Reaction was performed on a 100 mg scale. The crude product was examined with LC-MS, which shows a single peak with desired product mass. After HPLC purification, P153 (7.0 mg, 14%) was obtained. $^1$H NMR ($CD_3OD$, 400 MHz) δ 8.42 (s, 1H), 8.08 (s, 1H), 7.95 (m, 3H), 4.56 (m, 1H), 4.43 (m, 3H), 3.41 (m, 2H), 2.90 (m, 2H), 2.43 (m, 2H), 2.13 (m, 6H), 1.67 (m, 2H), 1.50 (m, 2H). MS: m/z=575 ($M+H^+$).

(S)-2-(2-(4-(4-Fluorophenyl)-N-hydroxybutanamido)acetamido)pentanedioic acid: P154

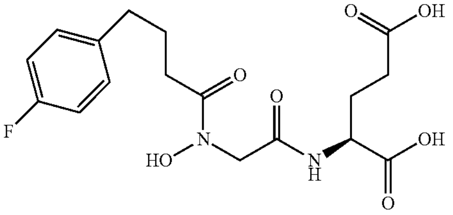 [SMILES: O=C(O)CC[C@H](NC(=O)CN(O)C(=O)CCCc1ccc(F)cc1)C(=O)O]

General experimental procedure for the removal of benzyl group was followed. Reaction was performed on a 95 mg scale. After HPLC purification, P149 (29 mg, 52%) was obtained. $^1$H NMR ($CD_3OD$, 400 MHz) δ 7.19-7.25 (m, 2H), 6.95-7.01 (m, 2H), 4.43-4.52 (m, 1H), 4.32 (s, 2H), 2.65 (t, J=8.0 Hz, 2H), 2.56 (t, J=8.0 Hz, 2H), 2.40 (t, J=8.4 Hz, 2H), 2.17-2.12 (m, 1H), 1.89-2.08 (m, 3H). MS: m/z=385 (M+H$^+$).

(S)-2-(3-((S)-1-Carboxy-5-(4-fluorobenzamido)pentyl)-3-methylureido)pentanedioic acid: P156

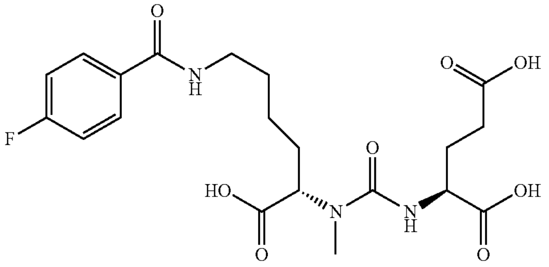 [SMILES: CN(C(=O)N[C@@H](CCC(=O)O)C(=O)O)[C@@H](CCCCNC(=O)c1ccc(F)cc1)C(=O)O]

General experimental procedure for amide formation and removal of tert-butyl ester group was followed. Reaction was performed on a 105 mg scale. Product was purified on a HPLC purification system using water-acetonitrile with 0.05% TFA (30-65%) afforded the title compound (12 mg, 13%, in two steps). $^1$H NMR ($CD_3OD$, 400 MHz) δ 7.87-7.84 (m, 2H), 7.17 (t, J=8.8 Hz, 2H), 4.31-4.27 (dd, J=9.6, 4.8 Hz, 2H), 4.38-4.32 (m, 2H), 2.85 (s, 3H), 2.46 (t, J=7.6 Hz, 2H), 2.24-2.14 (m, 2H), 2.04-1.95 (m, 2H), 1.86-1.76 (m, 1H), 1.72-1.56 (m, 2H), 1.46-1.34 (m, 2H). MS: m/z=456 (M+H$^+$).

(2S)-2-(3-((1S)-1-Carboxy-5-(4-(2-fluoropropanamido)benzamido)pentyl)-3-hydroxyureido)pentanedioic acid: P157

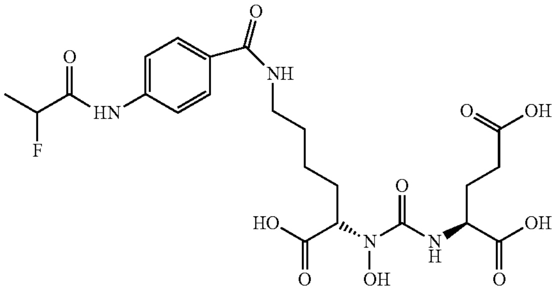

General experimental procedure for Staudinger reaction was followed. Reaction was performed on a 0.008 g scale. After HPLC purification, P157 (5.0 mg, 41%) was isolated as a white solid. $^1$H NMR ($CD_3OD$, 400 MHz) δ 7.79 (dd, J=8.8, 2.0 Hz, 2H), 7.72 (d, J=8.8 Hz, 2H), 5.11 (qd, J=49.0, 6.4 Hz, 1H), 4.70 (dd, J=10.0, 5.2, Hz, 1H), 4.37 (dd, J=9.2, 4.8, Hz, 1H), 3.39-3.34 (m, 2H), 2.46-2.42 (m, 2H), 2.25-2.19 (m, 2H), 1.98-1.89 (m, 2H), 1.69-1.60 (m, 2H), 1.59 (dd, J=24.4, 6.8 Hz, 3H), 1.41-1.35 (m, 2H). MS: m/z 529.1 (M+H$^+$).

(2S)-2-(3-((1S)-1-Carboxy-5-(4-(2-fluoropropanamido)benzamido)pentyl)-3-methylureido)pentanedioic acid: P158

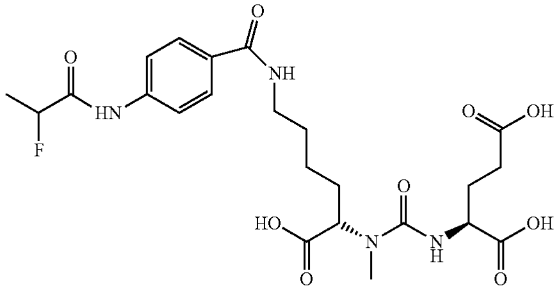

General experimental procedure for Staudinger reaction was followed. Reaction was performed on a 0.007 g scale. After HPLC purification, P158 (4.0 mg, 36%) was isolated as a white solid. $^1$H NMR ($CD_3OD$, 400 MHz) δ 7.79 (d, J=8.8 Hz, 2H), 7.71 (d, J=8.8 Hz, 2H), 5.11 (qd, J=48.8, 6.8 Hz, 1H), 4.28 (dd, J=9.2, 4.8, Hz, 1H), 3.39-3.34 (m, 2H), 2.81 (s, 3H), 2.44 (t, J=7.2 Hz, 2H), 2.22-2.13 (m, 2H), 2.03-1.94 (m, 2H), 1.87-1.77 (m, 1H), 1.69-1.60 (m, 2H), 1.59 (dd, J=24.0, 6.8 Hz, 3H), 1.41-1.35 (m, 2H). MS: m/z 527.1 (M+H$^+$).

(S)-2-((S)-3-Carboxy-2-(4-(4-(3-fluoropropyl)-1H-1,2,3-triazol-1-yl)benzamido)-N-methylpropanamido)pentanedioic acid: P159

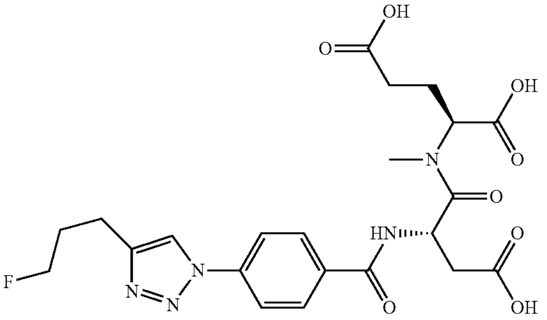 [SMILES: CN(C(=O)[C@H](CC(=O)O)NC(=O)c1ccc(-n2cc(CCCF)nn2)cc1)[C@@H](CCC(=O)O)C(=O)O]

General experimental procedures for amide formation, click chemistry, and tert-butyl deprotection was followed. $^1$H NMR ($CD_3OD$, 400 MHz) δ 8.45-8.43 (m, 1H), 8.06-7.93 (m, 4H), 5.52-5.42 (m, 1H), 5.04-4.96 (m, 1H), 4.59-4.46 (m, 2H), 3.20 (s, 3H), 3.13-2.62 (m, 5H), 2.42-2.25 (m, 3H), 2.20-2.05 (m, 2H). MS: m/z=507.8 (M+H$^+$).

(S)-2-(3-((S)-1-Carboxy-5-(4-(2-fluoroethoxy)benzamido)pentyl)ureido)pentanedioic acid: P160

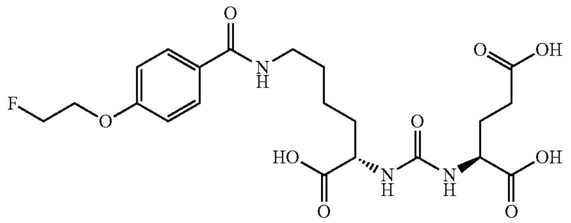 [SMILES: O=C(O)CC[C@H](NC(=O)N[C@@H](CCCCNC(=O)c1ccc(OCCF)cc1)C(=O)O)C(=O)O]

General experimental procedure for amide formation of and removal of tert-butyl ester group was followed. Reaction was performed on a 50 mg scale. After HPLC purification, P160 (16 mg, 32%) was obtained. $^1H$ NMR ($CD_3OD$, 400 MHz) δ 7.79-7.77 (dd, J=6.8, 1.6 Hz, 2H), 7.01-6.99 (dd, J=6.8, 1.6 Hz, 2H), 4.79-4.77 (dd, J=5.2, 4.0 Hz, 1H), 4.67-4.65 (dd, J=5.2, 4.0 Hz, 1H), 4.32-4.21 (m, 4H), 3.38-3.33 (m, 2H), 2.48-2.38 (m, 2H), 2.19-2.08 (m, 1H), 1.93-1.82 (m, 2H), 1.74-1.58 (m, 3H), 1.52-1.46 (m, 2H). MS: m/z=486 ($M+H^+$).

(S)-2-(3-((S)-1-Carboxy-5-(4-fluoroethoxy)benzamido)pentyl)-3-methylureido)-pentanedioic acid: P161

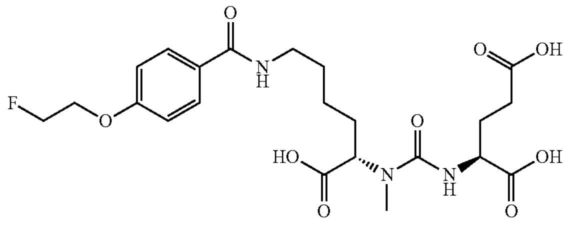 [SMILES: CN(C(=O)N[C@@H](CCC(=O)O)C(=O)O)[C@@H](CCCCNC(=O)c1ccc(OCCF)cc1)C(=O)O]

General experimental procedure for amide formation and removal of tert-butyl ester group was followed. Reaction was performed on a 50 mg scale. Product was purified on a HPLC purification system using water-acetonitrile with 0.05% TFA (30-65%) afforded the amide-acid (16 mg, 32%). $^1H$ NMR ($CD_3OD$, 400 MHz) δ 7.80-7.77 (m, 2H), 7.01-6.99 (dd, J=6.8, 1.6 Hz, 1H), 4.79-4.77 (t, J=4.4 Hz, 1H), 4.67-4.65 (t, J=4.4 Hz, 1H), 4.31-4.22 (m, 4H), 3.41-3.32 (m, 2H), 2.85 (s, 3H), 2.48-2.44 (t, J=7.6 Hz, 2H), 2.22-2.15 (m, 1H), 2.05-1.95 (m, 2H), 1.86-1.58 (m, 3H), 1.44-1.32 (m, 2H). MS: m/z=500 ($M+H^+$).

(S)-2-(3-((S)-1-Carboxy-5-(4-fluorobenzamido)pentyl)-1-hydroxyureido)pentanedioic acid: P162

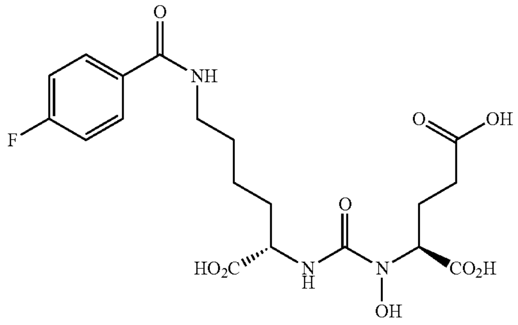 [SMILES: O=C(O)CC[C@@H](C(=O)O)N(O)C(=O)N[C@@H](CCCCNC(=O)c1ccc(F)cc1)C(=O)O]

General experimental procedure for urea formation and tert-butyl deprotection was followed. $^1H$ NMR ($CD_3OD$, 400 MHz) δ 7.88 (m, 2H), 7.18 (m 2H), 4.80-4.75 (m, 1H), 4.39-4.35 (m, 1H), 3.42-3.38 (m, 2H), 2.50-2.40 (m, 2H), 2.25 (m, 1H), 2.10-1.95 (m, 2H), 1.70-1.45 (m, 5H). MS: m/z=458.1 ($M+H^+$)

(S)-2-((S)-3-Carboxy-2-(4-fluorobenzamido)-N-methylpropanamido)pentanedioic acid: P163

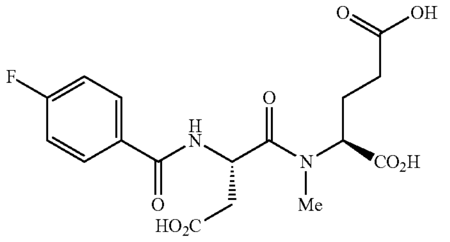 [SMILES: CN(C(=O)[C@H](CC(=O)O)NC(=O)c1ccc(F)cc1)[C@@H](CCC(=O)O)C(=O)O]

General experimental procedure for amide formation and tert-butyl deprotection was followed. $^1H$ NMR ($CD_3OD$, 400 MHz) δ 7.91-7.81 (m, 2H), 7.20-7.13 (m, 2H), 5.47-5.38 (m, 1H), 5.00-5.98 (m, 1H), 3.17 (s, 3H), 2.99-2.70 (m, 2H), 2.40-2.30 (m, 3H), 2.18-2.03 (m, 1H). MS: m/z=398.2 ($M+H^+$)

(S)-2-(3-((S)-1-Carboxy-5-(4-(6-fluoronicotinamido)benzamido)pentyl)-3-hydroxyureido)pentanedioic acid: P164

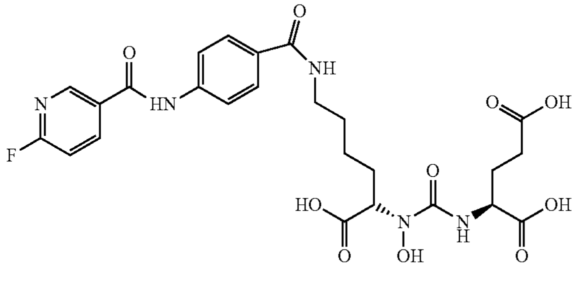

General experimental procedure for amide formation and tert-butyl deprotection was followed. Reaction was performed on a 0.015 g scale. After HPLC purification, P164 (6.3 mg, 48%) was isolated as a white solid. $^1$H NMR ($CD_3OD$, 400 MHz) δ 8.78 (d, J=2.8, Hz, 1H), 8.48-8.43 (m, 4H), 7.20 (dd, J=8.4, 2.4 Hz, 2H), 4.71 (dd, J=8.0, 5.6, Hz, 1H), 4.37 (dd, J=8.8, 4.4 Hz, 1H), 3.46-3.34 (m, 2H), 2.46-2.42 (m, 1H), 2.26-2.18 (m, 1H), 2.01-1.90 (m, 2H), 1.71-1.54 (m, 4H), 1.47-1.41 (m, 2H). MS: m/z 578.1 ($M+H^+$).

(S)-2-(3-((S)-1-Carboxy-5-(2-(4-(3-fluoropropyl)-1H-1,2,3-triazol-1-yl)acetamido)pentyl)-3-hydroxyureido)pentanedioic acid: P166

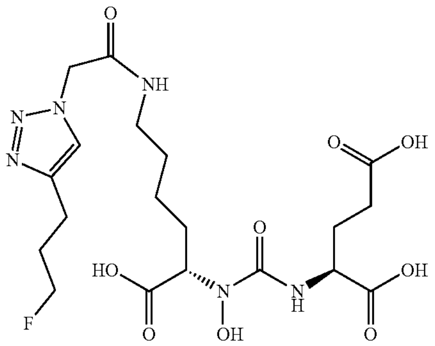 [SMILES: O=C(O)CC[C@H](NC(=O)N(O)[C@@H](CCCCNC(=O)Cn1cc(CCCF)nn1)C(=O)O)C(=O)O]

General experimental procedure for urea formation and tert-butyl deprotection was followed. After HPLC purification, P166 was obtained. $^1$H NMR ($D_2O$, 400 MHz) δ 7.64 (s, 1H), 5.00 (s, 2H), 4.41 (t, J=6.0 Hz, 1H), 4.30 (t, J=6.0 Hz, 1H), 4.16 (dd, J=4.8 Hz, 1H), 3.08 (t, J=6.4 Hz, 2H), 2.67 (t, J=7.2 Hz, 2H), 2.35 (t, J=8.0 Hz, 2H), 2.11-2.02 (m, 1H), 1.95-1.80 (m, 3H), 1.77-1.67 (m, 2H), 1.44-1.35 (m, 2H), 1.31-1.16 (m, 2H). MS: m/z=505 ($M+H^+$).

(S)-2-(3-((S)-1-Carboxy-5-(4-(2-fluoroethoxy)benzamido)pentyl)-3-hydroxyureido)pentanedioic acid: P167

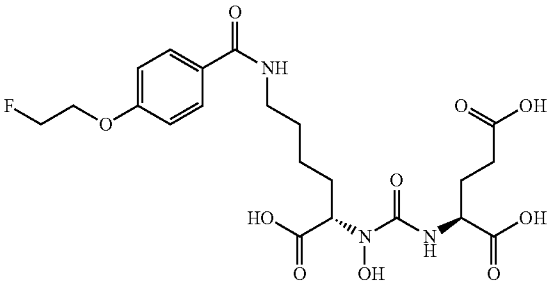 [SMILES: O=C(O)CC[C@H](NC(=O)N(O)[C@@H](CCCCNC(=O)c1ccc(OCCF)cc1)C(=O)O)C(=O)O]

General experimental procedure for urea formation and tert-butyl deprotection was followed. After HPLC purification, P167 was obtained. $^1$H NMR ($CD_3CN$, 400 MHz) δ 7.57-7.54 (m, 2H), 6.92-6.89 (m, 2H), 4.72-4.50 (m, 3H), 4.24-4.22 (m, 1H), 4.17-4.11 (m, 2H), 3.24-3.20 (m, 2H), 2.32 (t, J=8.0 Hz, 2H), 2.08-2.00 (m, 1H), 1.88-1.73 (m, 3H), 1.54-1.42 (m, 2H), 1.40-1.20 (m, 2H). MS: m/z=502 ($M+H^+$).

(S)-2-(3-((S)-1-Carboxy-5-(4-ethynylbenzamido)pentyl)-3-hydroxyureido)pentanedioic acid: P168

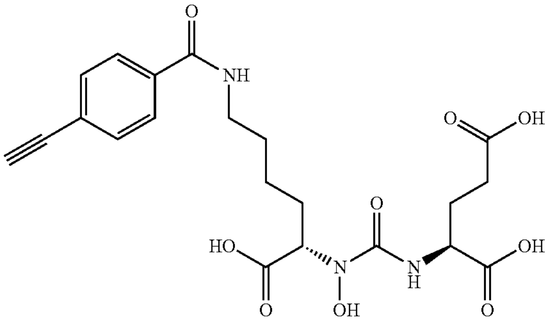 [SMILES: C#Cc1ccc(C(=O)NCCCC[C@@H](C(=O)O)N(O)C(=O)N[C@@H](CCC(=O)O)C(=O)O)cc1]

General experimental procedure for urea formation and tert-butyl deprotection was followed. After HPLC purification, P168 was obtained. $^1$H NMR ($CD_3CN$, 400 MHz) δ 7.89-7.86 (m, 2H), 7.68-7.65 (m, 2H), 4.81-4.77 (m, 1H), 4.40 (dd, J=9.2, 4.8 Hz, 1H), 3.69 (s, 1H), 3.56-3.49 (m, 1H), 3.43-3.36 (m, 1H), 2.51 (t, J=7.6 Hz, 2H), 2.30-2.21 (m, 1H), 2.02-1.95 (m, 3H), 1.80-1.61 (m, 2H), 1.60-1.42 (m, 2H). MS: m/z=464 ($M+H^+$).

(S)-2-(3-((S)-1-Carboxy-5-(4-fluorobenzamido)pentyl)-3-hydroxyureido)pentanedioic acid: P169

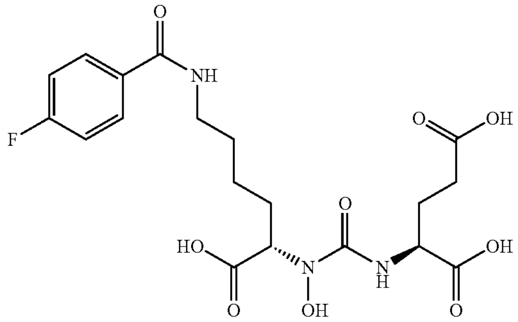

General experimental procedure for urea formation and tert-butyl deprotection was followed. After HPLC purification, P169 was obtained. $^1$H NMR ($D_2O$, 400 MHz) δ 7.60-7.56 (m, 2H), 7.06-7.01 (m, 2H), 4.15 (dd, J=9.6, 5.2 Hz, 1H), 3.22 (t, J=6.8 Hz, 2H), 2.33 (m, 2H), 2.10-2.01 (m, 2H), 1.88-1.72 (m, 3H), 1.55-1.42 (m, 2H), 1.38-1.20 (m, 2H). MS: m/z=458 ($M+H^+$).

(S)-2-((S)-3-Carboxy-2-(3-(4-(4-(3-fluoropropyl)-1H-1,2,3-triazol-1-yl)phenyl)propanamido)-N-methylpropanamido)pentanedioic acid: P170

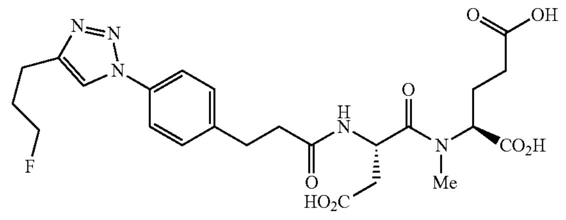 [SMILES: CN(C(=O)[C@H](CC(=O)O)NC(=O)CCc1ccc(-n2cc(CCCF)nn2)cc1)[C@@H](CCC(=O)O)C(=O)O]

General experimental procedure for amide formation and tert-butyl deprotection was followed. $^{1}H$ NMR ($CD_3OD$, 400 MHz) δ 8.28 (s, 1H), 7.77-7.75 (m, 2H), 7.42-7.40 (m, 2H), 5.30-5.20 (m, 1H), 4.58-4.45 (m, 2H), 3.09-3.02 (m, 1H), 2.99 (s, 3H), 2.96-2.78 (m, 4H), 2.60-2.40 (m, 3H), 2.30 (m, 2H), 2.20-1.99 (m, 3H). MS: m/z=535.8 ($M+H^+$)

(S)-2-(3-((S)-1-Carboxy-5-(4-(4-fluorobenzamido)benzamido)pentyl)-3-hydroxyureido)pentanedioic acid: P171

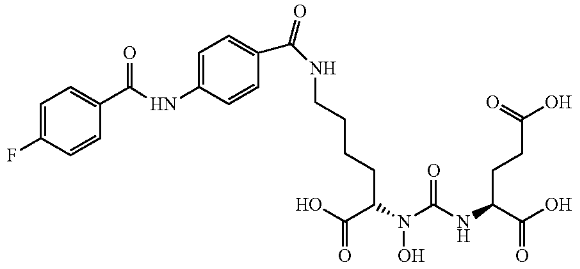

General experimental procedure for urea formation and tert-butyl deprotection was followed. Reaction was performed on a 0.02 g scale. After HPLC purification, P171 (12.0 mg, 68%) was isolated as a white solid. $^{1}H$ NMR ($CD_3OD$, 400 MHz) δ 7.99 (dd, J=8.8, 5.2, Hz, 2H), 7.81 (ABq, $J_{AB}$=9.2 Hz, 4H), 7.23 (t, J=8.8 Hz, 2H), 4.71 (dd, J=8.0, 5.6, Hz, 1H), 4.37 (dd, J=9.2, 4.8 Hz, 1H), 3.46-3.34 (m, 2H), 2.46-2.42 (m, 1H), 2.26-2.18 (m, 1H), 2.01-1.90 (m, 2H), 1.71-1.54 (m, 4H), 1.47-1.41 (m, 2H). MS: m/z 577.1 ($M+H^+$).

(S)-2-(3-((S)-1-Carboxy-5-(4-((2-(2-(2,4-dinitrophenylamino)ethoxy)ethoxy)methyl)-1H-1,2,3-triazol-1-yl)pentyl)-3-methylureido)pentanedioic acid: P172

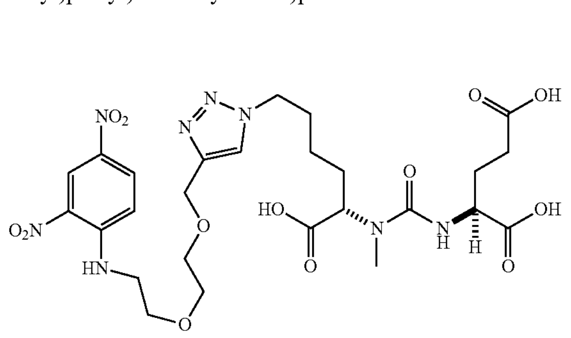

General experimental procedure for click reaction was followed. Reaction was performed on a 5.5 mg scale of (S)-2-(3-((S)-5-azido-1-carboxypentyl)-3-methylureido)pentanedioic acid. After HPLC purification, P172 (3.3 mg, 32%) was isolated as a yellow solid. $^{1}H$ NMR ($CD_3OD$, 400 MHz) δ 9.03 (d, J=2.7 Hz, 1H), 8.26 (dd, J=9.6, 2.5 Hz, 1H), 7.97 (s, 1H), 7.21 (d, J=9.4 Hz, 1H), 4.62 (s, 2H), 4.40 (t, J=7.0 Hz, 2H), 4.29 (dd, J=9.8, 4.7 Hz, 1H), 3.75-3.83 (m, 2H), 3.64-3.73 (m, 6H), 2.83 (s, 3H), 2.46 (t, J=7.2 Hz, 2H), 2.13-2.24 (m, 1H), 1.76-2.05 (m, 5H), 1.24-1.39 (m, 2H). MS: m/z=669 ($M+H^+$).

(S)-2-(3-((S)-1-Carboxy-5-(4-(3-fluoropropyl)-1H-1,2,3-triazol-1-yl)pentyl)-3-methylureido)pentanedioic acid: P173

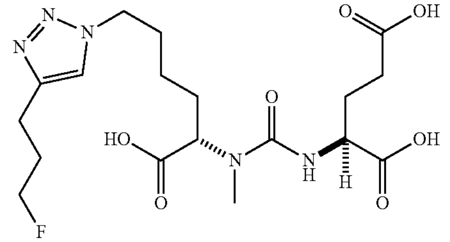

General experimental procedure for click reaction was followed. Reaction was performed on a 5.5 mg scale of (S)-2-(3-((S)-5-azido-1-carboxypentyl)-3-methylureido)pentanedioic acid. After HPLC purification, P173 (5.0 mg, 71%) was isolated as a white solid. $^{1}H$ NMR ($CD_3OD$, 400 MHz) δ 7.85 (s, 1H), 4.50-4.55 (m, 1H), 4.36-4.43 (m, 3H), 4.29 (dd, J=9.4, 4.7 Hz, 1H), 2.81-2.85 (m, 5H), 2.44-2.49 (m, 2H), 2.15-2.25 (m, 1H), 1.79-2.10 (m, 6H), 1.79-1.86 (m, 1H), 1.25-1.38 (m, 2H). MS: m/z=446 ($M+H^+$).

(S)-2-((S)-3-Carboxy-2-(2-(2-(4-fluorobenzamido)ethoxy)acetamido)-N-methylpropanamido)pentanedioic acid: P174

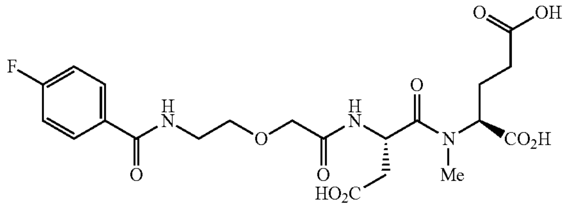 [SMILES: CN(C(=O)[C@H](CC(=O)O)NC(=O)COCCNC(=O)c1ccc(F)cc1)[C@@H](CCC(=O)O)C(=O)O]

General experimental procedure for amide formation and tert-butyl deprotection was followed. $^{1}H$ NMR ($CD_3OD$, 400 MHz) δ 7.92-7.88 (m, 2H), 7.22-7.18 (m, 2H), 5.39-5.28 (m, 1H), 4.05-3.95 (m, 2H), 3.72-3.58 (m, 4H), 3.13 (s, 3H), 3.04-3.80 (m, 2H), 2.67-2.57 (m, 1H), 2.45-2.25 (m, 3H), 2.15-2.00 (m, 1H). MS: m/z=499.8 ($M+H^+$)

(9S,13S)-10-Methyl-3,11-dioxo-1-phenyl-2,4,10,12-tetraazapentadecane-9,13,15-tricarboxylic acid: P175

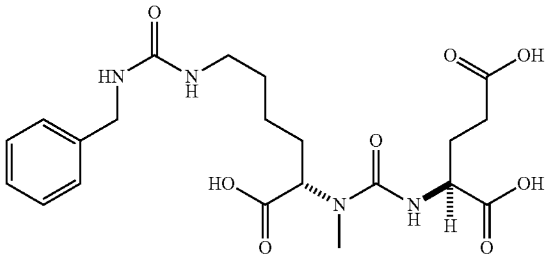

To solution of (S)-di-tert-butyl 2-(3-((S)-6-amino-1-tert-butoxy-1-oxohexan-2-yl)-3-methylureido)pentanedioate (10.0 mg, 0.020 mmol) in DCM (1.0 mL) was added benzyl isocyanate (5.3 mg, 0.040 mmol) and triethylamine (10 μL, 0.072 mmol). The mixture was stirred at room temperature for 1 hour and further deprotected with general condition to give P175 (4.8 mg, 52%) as a white solid. $^1H$ NMR ($CD_3OD$, 400 MHz) δ 7.19-7.32 (m, 5H), 4.85-4.89 (m, 1H), 4.27-4.33 (m, 3H), 3.08-3.21 (m, 2H), 2.85 (s, 3H), 2.41-2.50 (m, 2H), 2.14-2.24 (m, 1H), 1.90-2.05 (m, 2H), 1.71-1.85 (m, 1H), 1.41-1.59 (m, 2H), 1.26-1.40 (m, 2H). MS: m/z=467 (M+H$^+$).

(9S,13S)-10-Methyl-1-(4-nitrophenyl)-3,11-dioxo-2-oxa-4,10,12-triazapentadecane-9,13,15-tricarboxylic acid: P176

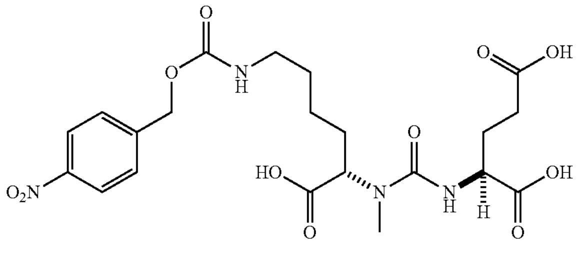

To solution of (S)-di-tert-butyl 2-(3-((S)-6-amino-1-tert-butoxy-1-oxohexan-2-yl)-3-methylureido)pentanedioate (10.0 mg, 0.020 mmol) in DCM (1.0 mL) was added 4-nitrobenzyl chloroformate (6.5 mg, 0.030 mmol) and triethylamine (10 μL, 0.072 mmol). The mixture was stirred at room temperature for 1 hour and further deprotected with general condition to give P176 (3.6 mg, 35%) as a white solid. $^1H$ NMR ($CD_3OD$, 400 MHz) δ 8.23 (d, J=8.6 Hz, 2H), 7.58 (d, J=8.6 Hz, 2H), 5.19 (s, 2H), 4.85-4.89 (m, 1H), 4.31 (dd, J=9.4, 4.7 Hz, 1H), 3.10-3.18 (m, 2H), 2.85 (s, 3H), 2.46 (t, J=7.4 Hz, 2H), 2.15-2.24 (m, 1H), 1.91-2.05 (m, 2H), 1.72-1.83 (m, 1H), 1.45-1.61 (m, 2H), 1.27-1.42 (m, 2H). MS: m/z=513 (M+H$^+$).

(S)-2-(3-((S)-1-Carboxy-5-(4-methylphenylsulfonamido)pentyl)-3-methylureido)pentanedioic acid: P177

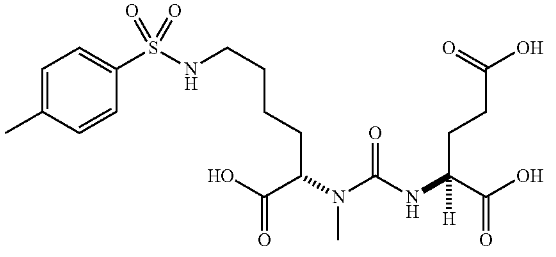

To solution of (S)-di-tert-butyl 2-(3-((S)-6-amino-1-tert-butoxy-1-oxohexan-2-yl)-3-methylureido)pentanedioate (15.0 mg, 0.030 mmol) in DCM (1.0 mL) was added 4-nitrobenzyl chloroformate (8.8 mg, 0.045 mmol) and triethylamine (15 μL, 0.108 mmol). The mixture was stirred at room temperature for 1 hour and further deprotected with general condition to give P177 (8.0 mg, 55%) as a white solid. $^1H$ NMR ($CD_3OD$, 400 MHz) δ 7.70-7.73 (m, 2H), 7.37 (m, 2H), 4.79 (dd, J=11.0, 4.7 Hz, 1H), 4.30 (dd, J=9.4, 4.7 Hz, 1H), 2.78-2.91 (m, 5H), 2.41-2.48 (m, 5H), 2.15-2.26 (m, 1H), 1.95-2.05 (m, 1H), 1.79-1.89 (m, 1H), 1.63-1.73 (m, 1H), 1.21-1.50 (m, 4H). MS: m/z=488 (M+H$^+$).

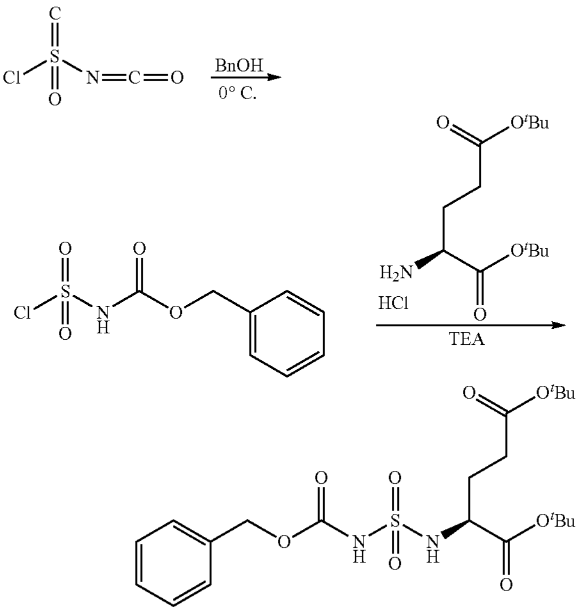

To sulfurisocyanatidic chloride (141 mg, 1 mmol) in dry DCM (3.0 mL) was added benzyl alcohol (113 mg, 1.05 mmol) dropwise at 0° C. The reaction was stirred at 0° C. for 1 h. This mixture was added dropwise to a mixture of (S)-di-tert-butyl 2-aminopentanedioate HCl (296 mg, 1 mmol) in dry DCM (5.0 mL) and TEA (303 mg, 3 mmol) at rt. The reaction was stirred for 30 min and quenched by adding EtOAc (50 mL). It was washed with 0.5 M HCl (2×50 mL) and water (50 mL) and dried over $MgSO_4$. The crude product was purified by silica chromatography to afford (S)-di-tert-butyl 2-((N-((benzyloxy)carbonyl)sulfamoyl)amino)pentanedioate (305 mg, 64%) as a clear oil. MS: m/z=473 ($M+H^+$).

(S)-2-((N-((Benzyloxy)carbonyl)sulfamoyl)amino) pentanedioic acid: P178

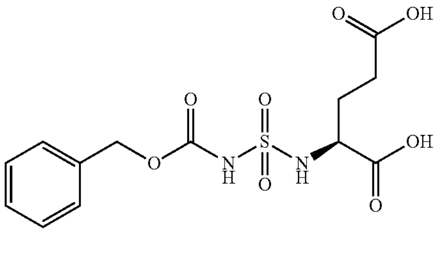 [SMILES: O=C(O)CC[C@H](NS(=O)(=O)NC(=O)OCc1ccccc1)C(=O)O]

General experimental procedure for tert-butyl deprotection was followed. The reaction was carried out on a 30 mg scale. After HPLC purification, P178 (13 mg, 60%) was obtained as a white fluffy solid. $^1H$ NMR ($CD_3CN$, 400 MHz) δ 8.88 (s, 1H), 7.42-7.36 (m, 5H), 6.34 (d, J=8.4 Hz, 1H), 5.15 (s, 2H), 4.12 (dt, J=8.8, 4.4 Hz, 1H), 2.44-2.40 (m, 2H), 2.14-2.06 (m, 1H), 1.89-1.80 (m, 1H). MS: m/z=361 ($M+H^+$).

(S)-2-((N-((Benzyloxy)carbonyl)sulfamoyl)(hydroxy)amino)pentanedioic acid: P179

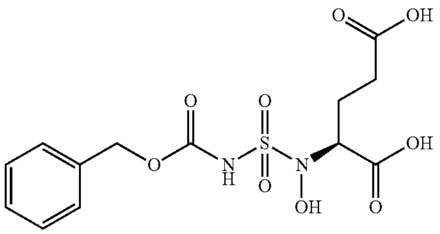 [SMILES: O=C(O)CC[C@@H](C(=O)O)N(O)S(=O)(=O)NC(=O)OCc1ccccc1]

Similar experimental procedures to prepare P178 were used to synthesize P179. $^1H$ NMR ($CD_3CN$, 400 MHz δ 7.42-7.36 (m, 5H), 5.17 (s, 2H), 4.62 (dd, J=10.0, 4.4 Hz, 1H), 2.50-2.46 (m, 2H), 2.22-2.13 (m, 1H), 2.09-1.99 (m, 1H). MS: m/z=377 ($M+H^+$).

(S)-2-((((Benzyloxy)carbonyl)oxy)(sulfamoyl) amino)pentanedioic acid: P180

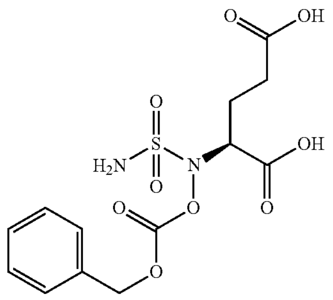 [SMILES: NS(=O)(=O)N(OC(=O)OCc1ccccc1)[C@@H](CCC(=O)O)C(=O)O]

Similar experimental procedures to prepare P178 were used to synthesize P180. $^1H$ NMR ($CD_3OD$, 400 MHz δ 7.42-7.31 (m, 5H), 5.15 (s, 2H), 5.04 (s, 1H), 4.58 (dd, J=9.6 Hz, 1H), 2.52-2.47 (m, 2H), 2.27-2.18 (m, 1H), 2.11-2.02 (m, 1H). MS: m/z=377 ($M+H^+$).

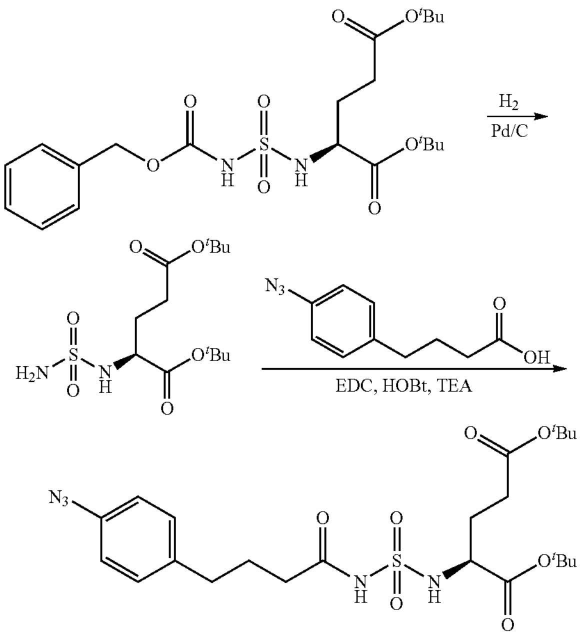

(S)-Di-tert-butyl 2-((N-((benzyloxy)carbonyl)sulfamoyl) amino)pentanedioate was hydrogenated in MeOH for 2 h at rt and 1 atm in the presence of Pd/C. The mixture was filtered and the filtrate was concentrated to afford (S)-di-tert-butyl 2-(sulfamoylamino)pentanedioate as white solid (100%). MS: m/z=339 ($M+H^+$). It was used directly in the next step without any further purification. It was then reacted with 4-(4-azidophenyl)butanoic acid under standard amide coupling condition to afford (S)-di-tert-butyl 2-((N-(4-(4-azidophenyl)butanoyl)sulfamoyl)amino)pentanedioate as a yellow oil (45%). MS: m/z=526 ($M+H^+$).

(S)-2-((N-(4-(4-Azidophenyl)butanoyl)sulfamoyl) amino)pentanedioic acid: P181

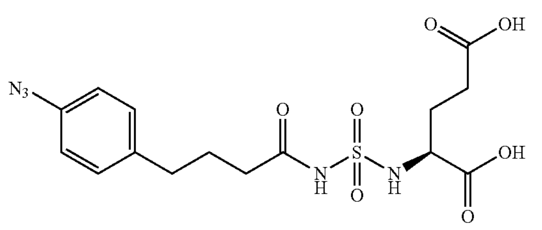 [SMILES: [N-]=[N+]=Nc1ccc(CCCC(=O)NS(=O)(=O)N[C@@H](CCC(=O)O)C(=O)O)cc1]

General experimental procedure for tert-butyl deprotection was followed. The reaction was carried out on a 30 mg scale. After HPLC purification, P181 (13 mg, 55%) was obtained as a white fluffy solid. $^1H$ NMR ($CD_3CN$, 400 MHz δ 7.26 (d, J=10 Hz, 2H), 6.77 (d, J=10 Hz, 2H), 6.29 (m, 2H), 4.09 (m, 1H), 2.43-2.38 (m, 2H), 2.22 (t, J=7.2 Hz, 2H), 2.11-2.04 (m, 2H), 1.82-1.77 (m, 2H), 1.46-1.42 (m, 2H). MS: m/z=414 ($M+H^+$).

(S)-2-(3-((S)-1-Carboxy-5-(6-fluoronicotinamido) pentyl)-3-hydroxyureido)pentanedioic acid: P182

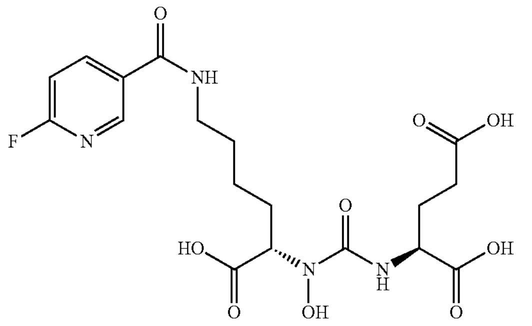

General experimental procedure for urea formation and tert-butyl deprotection was followed. After HPLC purification, P182 was obtained. $^1$H NMR ($D_2O$, 400 MHz δ 8.69 (m, 1H), 8.38 (m, 1H), 7.22 (m, 1H), 4.77 (m, 1H), 4.38 (dd, J=9.2, 4.4 Hz, 1H), 3.48-3.40 (m, 2H), 2.51 (t, J=7.2 Hz, 2H), 2.28-2.20 (m, 1H), 2.02-1.93 (m, 3H), 1.75-1.65 (m, 2H), 1.58-1.44 (m, 2H). MS: m/z=459 (M+H$^+$).

(S)-2-((N-(5-Azidopentanoyl)sulfamoyl)amino)pentanedioic acid: P183

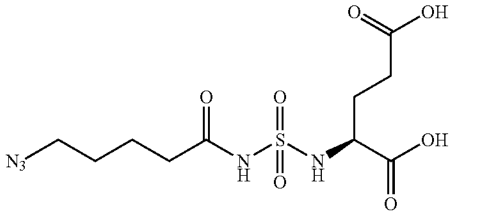 [SMILES: [N-]=[N+]=NCCCCC(=O)NS(=O)(=O)N[C@@H](CCC(=O)O)C(=O)O]

Similar procedures for the preparation of P181 were used to synthesize P183. After HPLC purification, P183 was obtained. $^1$H NMR ($CD_3CN$, 400 MHz δ 9.26 (brs, 1H), 6.24 (d, J=8.4 Hz, 1H), 4.10 (m, 1H), 2.47-2.36 (m, 2H), 2.26 (t, J=7.2 Hz, 2H), 2.13-2.04 (m, 1H), 1.89-1.80 (m, 1H), 1.66-1.55 (m, 6H). MS: m/z=352 (M+H$^+$).

(S)-2-(3-((S)-1-Carboxy-5-(4-fluorobenzylamino) pentyl)-3-methylureido)pentanedioic acid: P184

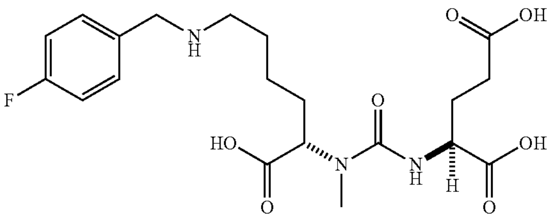

To solution of (S)-di-tert-butyl 2-(3-((S)-6-amino-1-tert-butoxy-1-oxohexan-2-yl)-3-methylureido)pentanedioate (15 mg, 0.030 mmol) in DCE (1.0 mL) was added 4-fluorobenzaldehyde (5.6 mg, 0.045 mmol), acetic acid (10 μL, 0.175 mmol), and sodium $NaBH(OAc)_3$ (32 mg, 0.151 mmol). The mixture was stirred at room temperature for 18 hours and further deprotected with general condition to give P184 (4.8 mg, 86%) as a white solid. $^1$H NMR ($CD_3CN$, 400 MHz): δ 8.11 (br. s., 1H), 7.69 (br. s., 1H), 7.48-7.54 (m, 2H), 7.13-7.19 (m, 2H), 5.80 (d, J=7.4 Hz, 1H), 4.89 (dd, J=10.2, 5.5 Hz, 2H), 4.07-4.21 (m, 4H), 2.92-3.06 (m, 2H), 2.77 (s, 3H), 2.41-2.46 (m, 2H), 2.03-2.19 (m, 1H), 1.92-2.01 (m, 1H), 1.75-1.87 (m, 2H), 1.62-1.74 (m, 2H), 1.34-1.49 (m, 1H), 1.13-1.31 (m, 1H). MS: 442 (M+H$^+$).

(S)-2-(3-((S)-1-Carboxy-5-(3',6'-diacetoxy-3-oxo-3H-spiro[isobenzofuran-1,9'-xanthen]-6-ylcarboxamido)pentyl)ureido)pentanedioic acid: P185

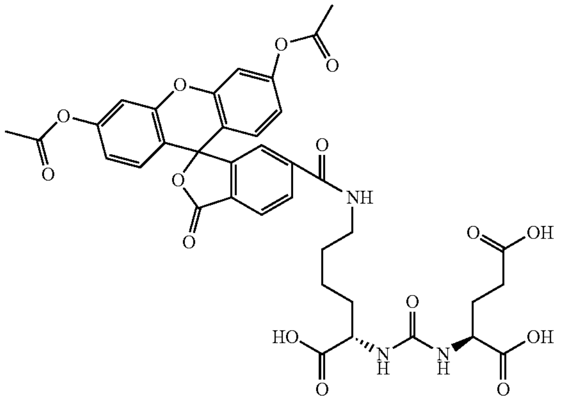 [SMILES: CC(=O)Oc1ccc2c(c1)Oc1cc(OC(C)=O)ccc1C21OC(=O)c2ccc(C(=O)NCCCC[C@H](NC(=O)N[C@@H](CCC(=O)O)C(=O)O)C(=O)O)cc21]

General experimental procedure for urea formation and tert-butyl deprotection was followed. P185 (2.0 mg, 6%) was obtained as a white solid. MS: m/z=762 (M+H$^+$).

(S)-2-(3-((S)-1-Carboxy-5-(4-(2-fluoropropanamido) benzamido)pentyl)-1-hydroxyureido)pentanedioic acid: P186

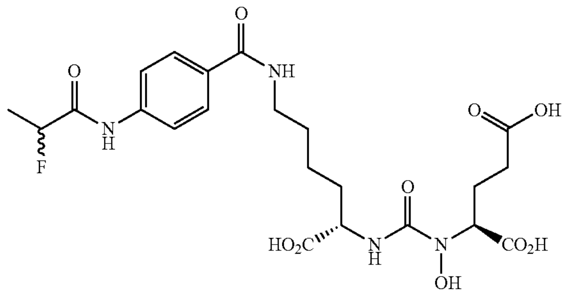

General experimental procedure for urea formation and tert-butyl deprotection was followed. P186 was obtained as a white solid. MS: 529 (M+H$^+$).

(S)-Methyl 2-amino-3-(1-(2-fluoroethyl)-1H-1,2,3-triazol-4-yl)propanoate

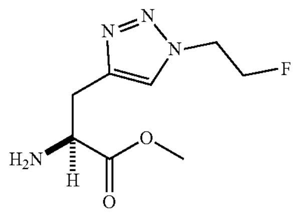

General experimental procedure for click chemistry was followed. Reaction was performed on a 272 mg scale. He crude product was examined with LC-MS, which shows a single peak with desired product mass. MS: m/z=217 ($M+H^+$).

(9S,13S)-Methyl 9-(tert-butoxycarbonyl)-13-((1-(2-fluoroethyl)-1H-1,2,3-triazol-4-yl)methyl)-3,11-dioxo-1-phenyl-2-oxa-4,10,12-triazatetradecan-14-oate

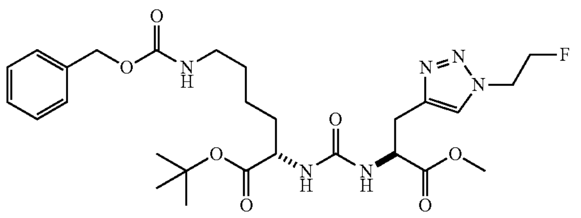

Triphosgene (0.159 g, 0.536 mmol) was added to a solution of (S)-tert-butyl 2-amino-6-(((benzyloxy)carbonyl)amino)hexanoate hydrochloride (0.4 g, 1.073 mmol) and Triethylamine (1.495 ml, 10.73 mmol) in DCM (Volume: 3 ml) at 0° C. Let the reaction stir for 15 minutes. Added (S)-methyl 2-amino-3-(1-(2-fluoroethyl)-1H-1,2,3-triazol-4-yl)propanoate (0.232 g, 1.073 mmol) in 1 mL DCM to the reaction mixture and stirred for 30 minutes. Let the reaction warm to room temperature. Diluted with ethyl acetate and washed with water. Separated layers, combined organics, dried with $MgSO_4$, filtered and concentrated. Purified by prep HPLC to afford (9S,13S)-methyl 9-(tert-butoxycarbonyl)-13-((1-(2-fluoroethyl)-1H-1,2,3-triazol-4-yl)methyl)-3,11-dioxo-1-phenyl-2-oxa-4,10,12-triazatetradecan-14-oate (0.12 g, 19.33%). MS: m/z=579 ($M+H^+$).

(9S,13S)-9-Carboxy-13-((1-(2-fluoroethyl)-1H-1,2,3-triazol-4-yl)methyl)-3,11-dioxo-1-phenyl-2-oxa-4,10,12-triazatetradecan-14-oic acid: P187

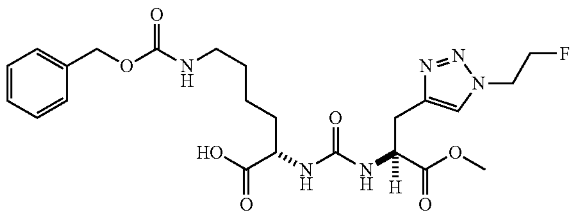

Hydrogen chloride (1 ml, 4.00 mmol) 4M in dioxanes was added to (9S,13S)-methyl 9-(tert-butoxycarbonyl)-13-((1-(2-fluoroethyl)-1H-1,2,3-triazol-4-yl)methyl)-3,11-dioxo-1-phenyl-2-oxa-4,10,12-triazatetradecan-14-oate (0.05 g). Added Water (0.5 ml) to the reaction mixture and the solution became hot. Stirred for 1 hour. Purified by prep HPLC to afford P187 (7.0 mg, 16%). $^1H$ NMR ($CD_3CN$, 400 MHz) δ 7.73 (s, 1H), 7.36 (m, 5H), 5.84 (m, 2H), 5.73 (m, 1H), 5.04 (m, 4H), 4.84 (m, 1H), 4.74 (m, 1H), 4.67 (m, 1H), 4.61 (m, 1H), 4.56 (m, 1H), 4.17 (m, 1H), 3.21 (m, 2H), 3.15 (m, 2H), 1.77 (m, 1H), 1.62 (m, 1H), 1.47 (m, 2H), 1.35 (m, 2H). MS: m/z=509 ($M+H^+$).

(S)-2-(3-((S)-1-Carboxy-5-(4-(3-fluoropropyl)-1H-1,2,3-triazol-1-yl)pentyl)ureido)-pentanedioic acid: P188

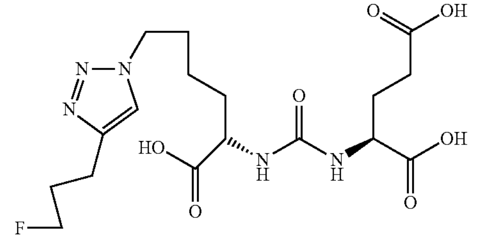

General experimental procedure for tert-butyl deprotection was followed. Reaction was performed on a 0.015 g scale. After HPLC purification, P188 (12 mg, 42%) was obtained as a white solid. $^1H$ NMR ($CD_3OD$, 400 MHz) δ 7.78 (s, 1H), 4.52 (t, J=6.0 Hz, 1H), 4.40 (t, J=6.0 Hz, 1H), 4.37 (t, J=6.8 Hz, 1H), 4.30 (dd, J=8.8, 5.2 Hz, 1H), 4.27 (dd, J=8.4, 4.8 Hz, 1H), 2.81 (t, J=8.0 Hz, 1H), 2.43-2.38 (m, 2H), 2.18-2.01 (m, 2H), 2.08-1.97 (m, 2H), 1.96-1.82 (m, 4H), 1.72-1.63 (m, 2H), 1.44-1.37 (m, 2H). MS: m/z 432.1 ($M+H^+$).

3-(4-(3-Fluoropropyl)-1H-1,2,3-triazol-1-yl)-2-(phosphonomethyl)propanoic acid: P189

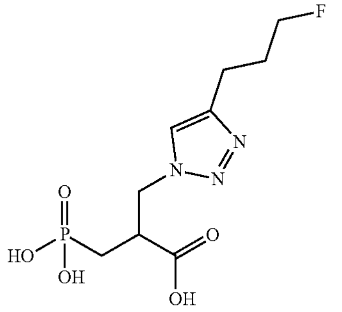 [SMILES: O=C(O)C(Cn1cc(CCCF)nn1)CP(=O)(O)O]

Hydrobromic acid (1.314 µl, 0.024 mmol) and benzyl 3-(dimethoxyphosphoryl)-2-((4-(3-fluoropropyl)-1H-1,2,3-triazol-1-yl)methyl)propanoate (0.01 g, 0.024 mmol) were stirred for 3 hours. Concentrated and purified by PREP HPLC to afford P189 (2.0 mg, 28%). MS: m/z=296 ($M+H^+$).

2-((1H-1,2,3-Triazol-1-yl)methyl)-3-phosphonopropanoic acid: P190

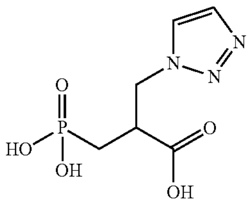 [SMILES: O=C(O)C(Cn1ccnn1)CP(=O)(O)O]

Hydrobromic acid 48% (0.5 mL, 9.21 mmol) and benzyl 3-(dimethoxyphosphoryl)-2-((4-(trimethylsilyl)-1H-1,2,3-triazol-1-yl)methyl)propanoate (0.06 g, 0.141 mmol) were stirred for 2 hours. Concentrated and purified by PREP HPLC to afford P190 (5.0 mg, 2%). MS: m/z=236 (M+H$^+$).

(S)-2-(3-((S)-1-Carboxy-2-(4-(4-(4-(3-fluoropropyl)-1H-1,2,3-triazol-1-yl)-butanamido)phenyl)-ethyl)-3-methylureido)pentanedioic acid: P191

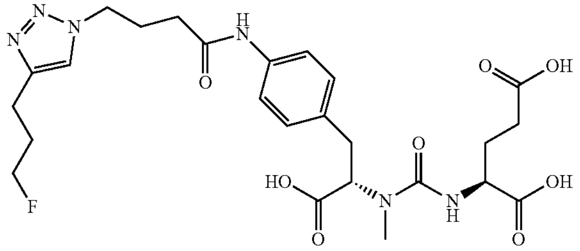 [SMILES: CN(C(=O)N[C@@H](CCC(=O)O)C(=O)O)[C@@H](Cc1ccc(NC(=O)CCCn2cc(CCCF)nn2)cc1)C(=O)O]

General procedure for click chemistry was followed. Reaction was performed on a 6 mg scale. After HPLC purification, P191 (2.4 mg. 49%) was obtained. $^1$H NMR ($CD_3OD$, 400 MHz) δ 7.80 (br s, 1H), 7.44-7.42 (m, 2H), 7.19-7.17 (m, 2H), 4.52-4.38 (m, 5H), 4.21 (br m, 1H), 3.28-3.24 (m, 2H), 3.16-2.98 (m, 1H), 2.84-2.76 (m, 5H), 2.42-2.22 (br m, 7H), 2.00-1.80 (br m, 3H). MS: m/z=565 (M+H$^+$).

(9S,13S)-Methyl 9-(tert-butoxycarbonyl)-3,11-dioxo-1-phenyl-13-(prop-2-yn-1-yl)-2-oxa-4,10,12-triazatetradecan-14-oate

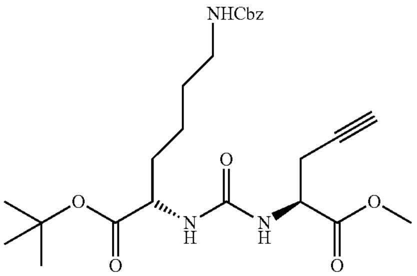

General experimental procedure for urea formation was followed. Reaction was performed on a 0.2 g scale. The title compound (110 mg, 17%) was obtained as a white solid. MS: m/z=490.1 (M+H$^+$).

(9S,13S)-9-Carboxy-13-((1-(carboxymethyl)-1H-1,2,3-triazol-4-yl)methyl)-3,11-dioxo-1-phenyl-2-oxa-4,10,12-triazatetradecan-14-oic acid: P192

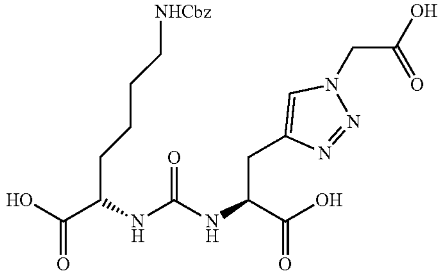

General experimental procedures for click chemistry and tert-butyl and Me deprotection were followed. Reaction was performed on a 0.011 g scale. After HPLC purification, P192 (60 mg, 51%) was obtained as a white solid. $^1$H NMR ($CD_3OD$, 400 MHz) δ 7.84 (s, 1H), 7.34-7.29 (m, 5H), 5.23 (s, 2H), 5.05 (s, 2H), 4.61-4.58 (m, 1H), 4.24-4.20 (m, 1H), 3.17-3.09 (m, 2H), 1.84-1.80 (m, 1H), 1.67-1.63 (m, 1H), 1.53-1.51 (m, 2H), 1.43-1.39 (m, 2H). MS: m/z 521.1 (M+H$^+$).

2-(((2-(2-(2-(2-(4-(3-Fluoropropyl)-1H-1,2,3-triazol-1-yl)ethoxy)ethoxy)ethoxy)ethoxy)(hydroxy)phosphoryl)methyl)pentanedioic acid: P193

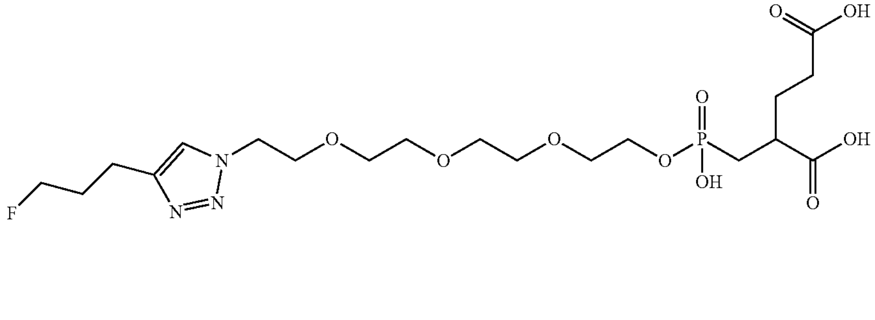 [SMILES: O=C(O)CCC(CP(=O)(O)OCCOCCOCCOCCn1cc(CCCF)nn1)C(=O)O]

General experimental procedures for click chemistry and tert-butyl and Me deprotection were followed. After HPLC purification, P193 was obtained. $^1H$ NMR ($CD_3OD$, 400 MHz) δ 9.04 (s, 1H), 5.88 (t, J=6.0 Hz, 1H), 5.83 (t, J=4.8 Hz, 2H), 5.76 (t, J=6.0 Hz, 1H), 5.34 (m, 2H), 5.18 (t, J=4.8 Hz, 2H), 4.95-4.87 (m, 9H), 4.60-4.58 (m, 4H), 4.12 (t, J=7.6 Hz, H), 3.73-3.62 (m, 2H), 3.42-3.10 (m, 4H). MS: m/z=514 ($M+H^+$).

(S)-2-(3-((S)-1-Carboxy-5-((2S,3R,4R,5R,6S)-6-((3-(4-(4-(3-fluoropropyl)-1H-1,2,3-triazol-1-yl)phenyl)propanamido)methyl)-3,4,5-trihydroxytetrahydro-2H-pyran-2-carboxamido)pentyl)ureido)pentanedioic acid: P194

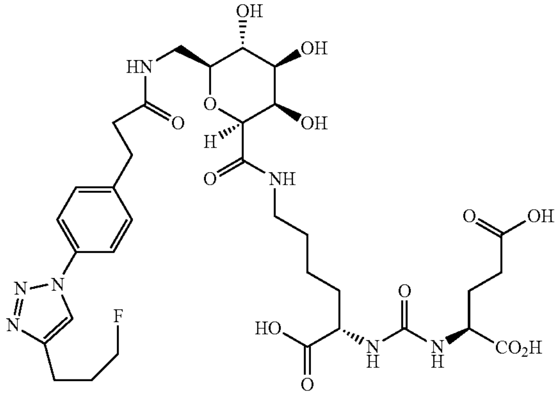 [SMILES: O=C(O)CC[C@H](NC(=O)N[C@@H](CCCCNC(=O)[C@H]1O[C@@H](CNC(=O)CCc2ccc(-n3cc(CCCF)nn3)cc2)[C@H](O)[C@@H](O)[C@H]1O)C(=O)O)C(=O)O]

General experimental procedure for Boc-deprotection was followed. MS: m/z=768.4 ($M+H^+$)

(S)-2-(3-((S)-1-Carboxy-2-(4-(2-(4-(3-fluoropropyl)-1H-1,2,3-triazol-1-yl)ethoxy)phenyl)ethyl)ureido)pentanedioic acid: P195

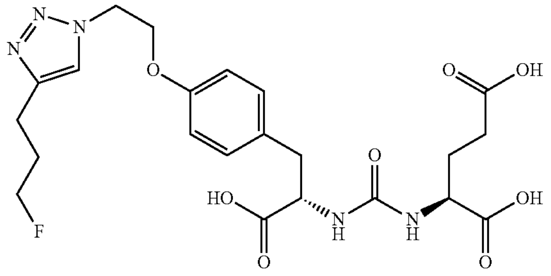 [SMILES: O=C(O)CC[C@H](NC(=O)N[C@@H](Cc1ccc(OCCn2cc(CCCF)nn2)cc1)C(=O)O)C(=O)O]

General experimental procedure for deprotection of Me and t-Bu ester with HCl/dioxane reaction was followed. Reaction was performed on a 0.05 g scale. After HPLC purification, P195 (10 mg, 25%) was obtained as a white solid. $^1H$ NMR ($CD_3OD$, 400 MHz) 7.85 (s, 1H), 7.11 (dd, J=9.2, 8.0 Hz, 2H), 6.82 (dd, J=8.8, 1.6 Hz, 2H), 4.75 (t, J=5.2 Hz, 2H), 4.52-4.47 (m, 2H), 4.40-4.34 (m, 3H), 4.29-4.25 (m, 1H), 3.08-3.04 (m, 1H), 2.96-2.88 (m, 1H), 2.82 (t, J=7.6 Hz, 2H), 2.39-2.29 (m, 2H), 2.16-1.96 (m, 4H), 1.90-1.81 (m, 1H). MS: m/z=510 ($M+H^+$).

3-(N-(2-Fluoroethyl)acetamido)-2-(phosphonomethyl)propanoic acid: P196

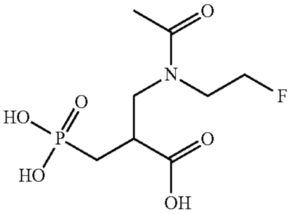 [SMILES: CC(=O)N(CCF)CC(CP(=O)(O)O)C(=O)O]

Hydrobromic acid 48% (0.013 ml, 0.231 mmol) and benzyl 3-(dimethoxyphosphoryl)-2-((N-(2-fluoroethyl)acetamido)methyl)propanoate (0.09 g, 0.231 mmol) were stirred for 1 hour. Concentrated and purified by PREP HPLC to afford P196 (3.0 mg, 5%). MS: m/z=272 ($M+H^+$).

2-((Hydroxy(phenethylamino)phosphoryl)methyl)pentanedioic acid: P197

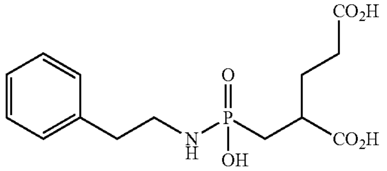 [SMILES: O=C(O)CCC(CP(=O)(O)NCCc1ccccc1)C(=O)O]

General experimental procedure for tert-butyl deprotection was followed. $^1H$ NMR ($CD_3OD$, 400 MHz) δ 7.32-7.13 (m, 5H), 3.50-3.45 (s, 1H), 3.42-3.40 (m, 1H), 2.85-2.75 (m, 2H), 2.61-2.52 (m, 1H), 2.22-2.18 (m, 2H), 2.02-1.65 (m, 4H). MS: m/z=330.1 ($M+H^+$).

2,2'-[(3,4-Dioxocyclobut-1-ene-1,2-diyl)bis(azanediyl)]dipentanedioic acid: P198

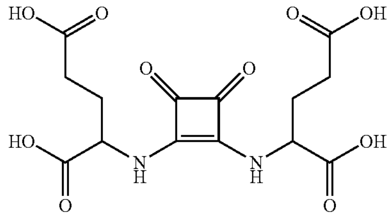 [SMILES: O=C(O)CCC(Nc1c(NC(CCC(=O)O)C(=O)O)c(=O)c1=O)C(=O)O]

General experimental procedure for tert-butyl deprotection reaction was followed. After HPLC purification, P198 (3.1 mg, 16%) was obtained. $^1H$ NMR ($CD_3OD$, 400 MHz) δ 4.73-4.82 (m, 2H), 2.21-2.42 (m, 4H), 2.02-2.20 (m, 4H). MS: m/z=373 ($M+H^+$).

(S)-2-[(R)-((((9H-Fluoren-9-yl)methoxy)carbonyl)amino)-3-carboxypropanamido]pentanedioic acid: P199

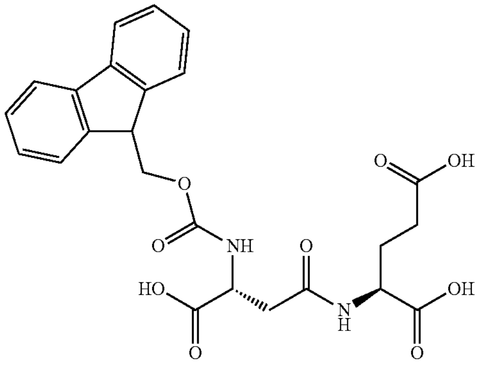 [SMILES: O=C(O)CC[C@H](NC(=O)C[C@@H](NC(=O)OCC1c2ccccc2-c2ccccc21)C(=O)O)C(=O)O]

General procedures for amide formation and and tert-butyl deprotection reaction were followed. After HPLC purification, P199 (9.1 mg, 27%) was obtained. $^1$H NMR ($CD_3OD$, 400 MHz) δ 7.78 (d, J=7.6 Hz, 2H), 7.67 (d, J=7.6 Hz, 2H), 7.36 (t, J=7.2 Hz, 2H), 7.31 (t, J=7.6 Hz, 2H), 4.57 (t, J=7.6 Hz, 2H), 4.42-4.51 (m, 2H), 4.32 (d, J=7.2 Hz, 2H), 4.24 (t, J=7.2 Hz, 1H), 2.82-2.91 (m, 1H), 2.68-2.78 (m, 1H), 2.40 (t, J=7.6 Hz, 2H), 2.12-2.24 (m, 1H), 1.87-2.20 (m, 1H). MS: m/z=485 (M+H$^+$).

(S)-Di-tert-butyl 2-(3-((S)-6-(3-(4-azidophenyl)thioureido)-1-(tert-butoxy)-1-oxohexan-2-yl)ureido)pentanedioate

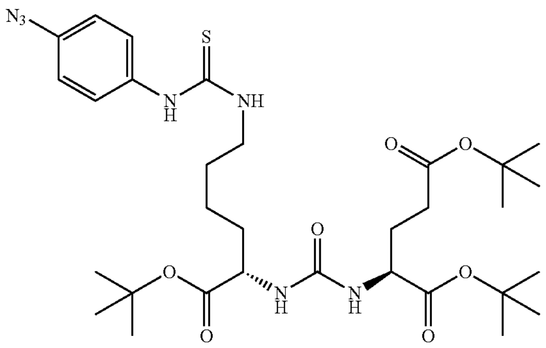 [SMILES: CC(C)(C)OC(=O)CC[C@H](NC(=O)N[C@@H](CCCCNC(=S)Nc1ccc(N=[N+]=[N-])cc1)C(=O)OC(C)(C)C)C(=O)OC(C)(C)C]

General procedures for urea formation reaction were followed. The crude product was purified on column (silica gel, hexanes/EtoAc) to give the title compound as a yellow wax (40 mg, 60%). MS: m/z=664 (M+H$^+$).

(S)-2-(3-((S)-1-Carboxy-5-(3-(4-(4-(3-fluoropropyl)-1H-1,2,3-triazol-1-yl)phenyl)thioureido)pentyl)-ureido)pentanedioic acid: P200

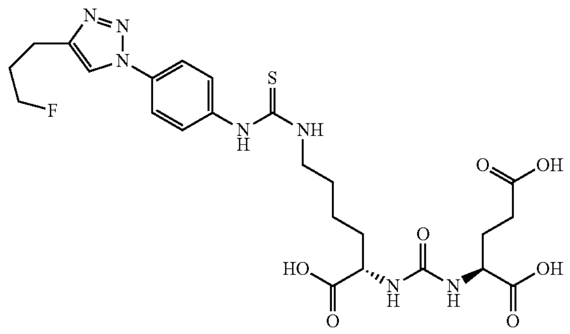 [SMILES: O=C(O)CC[C@H](NC(=O)N[C@@H](CCCCNC(=S)Nc1ccc(-n2cc(CCCF)nn2)cc1)C(=O)O)C(=O)O]

General procedures for click chemistry and and tert-butyl deprotection reaction were followed. After HPLC purification, P200 (12 mg, 50%) was obtained. $^1$H NMR ($CD_3OD$, 400 MHz) δ 8.30 (s, 1H), 7.79-7.77 (m, 2H), 7.60-7.58 (m, 2H), 4.56 (t, J=5.6 Hz, 1H), 4.44 (t, J=5.8 Hz, 1H), 4.28 (m, 2H), 3.58 (s, 2H), 3.20 (m, 1H), 2.90 (m, 2H), 2.41-2.37 (m, 2H), 2.16-2.05 (m, 3H), 1.90-1.80 (m, 2H), 1.71-1.60 (m, 3H), 1.47 (m, 2H), 1.36-1.26 (m, 5H). MS: m/z=582 (M+H$^+$).

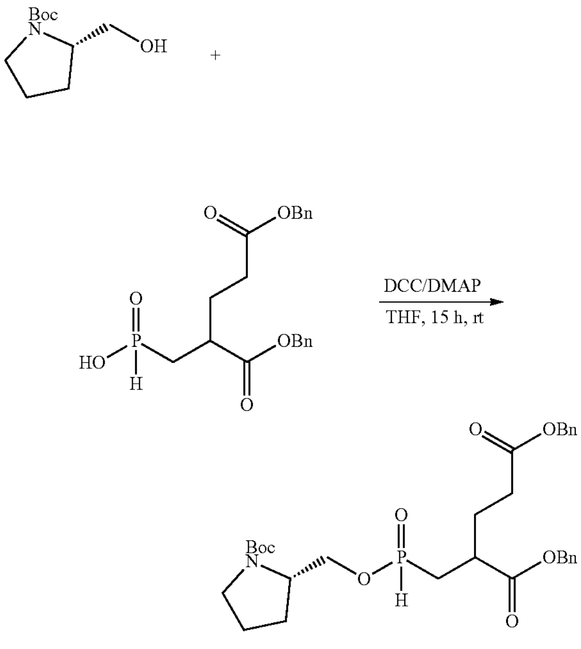

To (S)-tert-butyl 2-(hydroxymethyl)pyrrolidine-1-carboxylate (100 mg, 0.5 mmol), (5-(benzyloxy)-2-((benzyloxy)carbonyl)-5-oxopentyl)phosphinic acid (180 mg, 0.46 mmol), and DMAP (11 mg, 0.09 mmol) in THF (5.0 mL) was added DCC (284 mg, 1.38 mmol). The mixture was stirred at rt for 15 h. It was concentrated and the residue was chromatographed (silica gel, hexane/EtOAc) to afford phosphinic acid as a clear wax (150 mg, 56%). MS: m/z=574 (M+H$^+$).

Dibenzyl 2-(((((S)-1-(tert-butoxycarbonyl)pyrrolidin-2-yl)methoxy)(hydroxy)phosphoryl)methyl)-pentanedioate

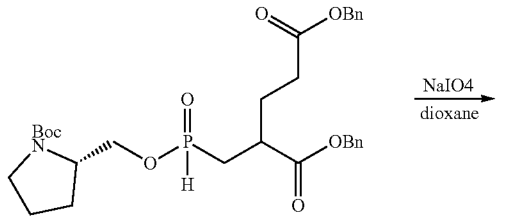

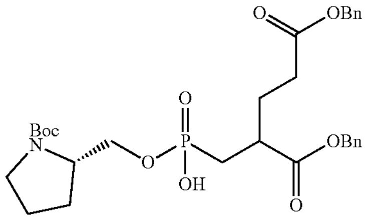

To above phosphinic acid in a mixed solvent of dioxane (3.0 mL) and water (0.6 mL) was added NaIO4 (84 mg, 0.39 mmol). The mixture was stirred at rt for 5 h and then diluted with MeCN (3 mL) and filtered. The filtrate was concentrated and purified by HPLC to afford the title compound as a white fluffy solid (100 mg, 65%). MS: m/z=590 (M+H$^+$).

2-(((((S)-1-(tert-butoxycarbonyl)pyrrolidin-2-yl)methoxy)(hydroxy)phosphoryl)methyl)-pentanedioic acid: P201

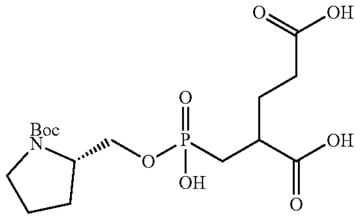 [SMILES: CC(C)(C)OC(=O)N1CCC[C@H]1COP(=O)(O)CC(CCC(=O)O)C(=O)O]

General experimental procedure for the removal of benzyl group was followed. After HPLC purification, P201 (7.0 mg, 85%) was obtained. MS: m/z=410 (M+H$^+$).

(2S)-2-(3-(1-Carboxy-2-(4-(2-(4-(3-fluoropropyl)-1H-1,2,3-triazol-1-yl)ethoxy)phenyl)ethyl)ureido) pentanedioic acid: P202

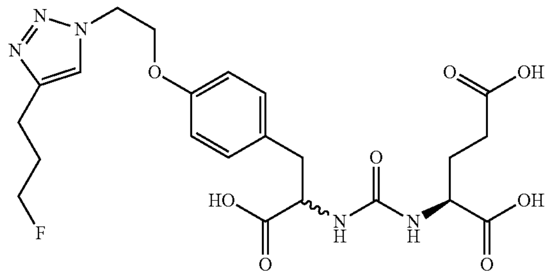 [SMILES: O=C(O)CC[C@H](NC(=O)NC(Cc1ccc(OCCn2cc(CCCF)nn2)cc1)C(=O)O)C(=O)O]

General experimental procedure for deprotection of Me and t-Bu ester with HCl/dioxane reaction was followed. Reaction was performed on a 0.09 g scale. After HPLC purification, P202 (10 mg, 25%) was obtained as a white solid. $^1$H NMR (CD$_3$OD, 400 MHz) 7.84 (s, 1H), 7.11 (t, J=8.8 Hz, 2H), 6.82 (dd, J=8.8, 1.6 Hz, 2H), 4.74 (t, J=4.8 Hz, 2H), 4.52-4.48 (m, 2H), 4.40-4.34 (m, 3H), 4.30-4.25 (m, 1H), 3.08-3.01 (m, 1H), 2.96-2.88 (m, 1H), 2.82 (t, J=7.6 Hz, 2H), 2.39-2.29 (m, 2H), 2.12-1.96 (m, 3H), 1.90-1.81 (m, 1H). MS: m/z=510 (M+H$^+$).

(S)-2-(3-((S)-1-Carboxy-2-(4-(2-(2-(2-(4-(3-fluoropropyl)-1H-1,2,3-triazol-1-yl)ethoxy)ethoxy)ethoxy)phenyl)ethyl)ureido)pentanedioic acid: P203

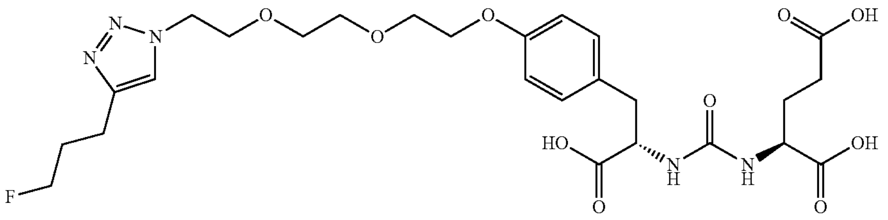 [SMILES: O=C(O)CC[C@H](NC(=O)N[C@@H](Cc1ccc(OCCOCCOCCn2cc(CCCF)nn2)cc1)C(=O)O)C(=O)O]

General experimental procedure for the deprotection of the tert-butyl group was followed. Reaction was performed on a 50 mg scale. After HPLC purification, P203 (3.0, 8%) was obtained. MS: m/z=598 (M+H$^+$).

(S)-2-(3-((S)-2-(Benzyloxy)-1-carboxyethyl)ureido)pentanedioic acid: P204

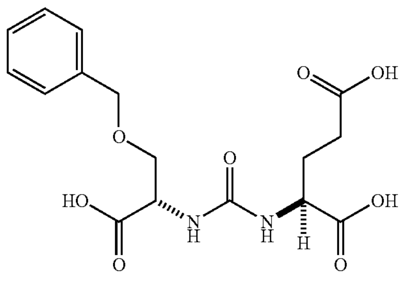

General experimental procedure for urea formation and tert-butyl deprotection reaction was followed. Reaction was performed on a 570 mg scale of (S)-tert-butyl 2-amino-3-(benzyloxy)propanoate. After HPLC purification, P204 (1.8 mg, 43% in two steps) was obtained as a white solid. $^1$H NMR ($CD_3OD$, 400 MHz) δ 7.25-7.35 (m, 5H), 4.51-4.59 (m, 2H), 4.46 (t, J=3.5 Hz, 1H), 4.33 (dd, J=8.6, 5.1 Hz, 1H), 3.92 (dd, J=9.4, 3.5 Hz, 1H), 3.70 (dd, J=9.4, 3.5 Hz, 1H), 2.36-2.49 (m, 2H), 2.10-2.19 (m, 1H), 1.85-1.94 (m, 1H). MS: m/z=369 (M+H$^+$).

2-((Hydroxy(((S)-1-(2-phenylacetyl)pyrrolidin-2-yl)methoxy)phosphoryl)methyl)pentanedioic acid: P205

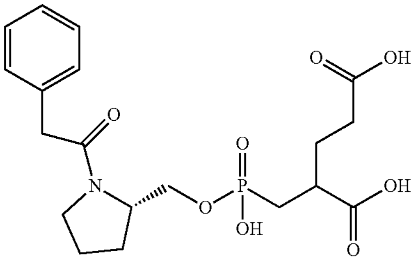 [SMILES: O=C(O)CCC(CP(=O)(O)OC[C@@H]1CCCN1C(=O)Cc1ccccc1)C(=O)O]

Similar procedures for the preparation of P207 were used to synthesize P205. After HPLC purification, P205 was obtained. $^1$H NMR ($CD_3CN$, 400 MHz) δ 7.33-7.23 (m, 5H), 4.30-4.4.05 (m, 2H), 3.70-3.37 (m, 5H), 2.61 (m, 1H), 2.32 (m, 2H), 2.00-1.56 (m, 6H), 1.35 (m, 2H). MS: m/z=569 (M+H$^+$).

2-(((((S)-1-(3-(4-(4-(3-Fluoropropyl)-1H-1,2,3-triazol-1-yl)phenyl)propanoyl)pyrrolidin-2-yl)methoxy)(hydroxy)phosphoryl)methyl)pentanedioic acid: P206

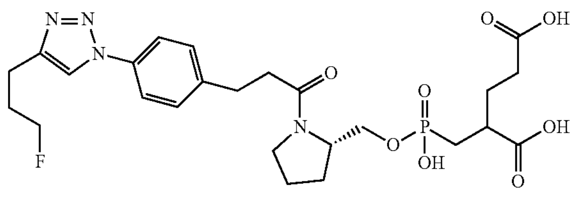 [SMILES: O=C(O)CCC(CP(=O)(O)OC[C@@H]1CCCN1C(=O)CCc1ccc(-n2cc(CCCF)nn2)cc1)C(=O)O]

Similar procedures for the preparation of P207 were used to synthesize P206. After HPLC purification, P206 was obtained. $^1$H NMR ($CD_3OD/CD_3CN$, 400 MHz) δ 8.01 (s, 1H), 7.69-7.67 (m, 2H), 7.43-7.40 (m, 2H), 4.90 (m, 1H), 4.59 (m, 1H), 4.47 (m, 1H), 4.09-4.03 (m, 2H), 3.67-3.58 (m, 3H), 3.08-2.85 (m, 5H), 2.55-2.70 (m, 2H), 2.34 (m, 2H), 2.16-2.11 (m, 4H), 1.63-1.52 (m, 5H). MS: m/z=569 (M+H$^+$).

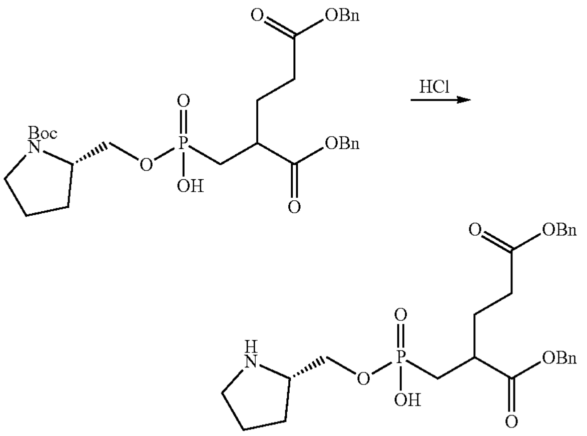

Dibenzyl 2-((hydroxy((S)-pyrrolidin-2-ylmethoxy)phosphoryl)methyl)pentanedioate

General procedure for the removal tert-butyl group was followed. The crude product was used directly in the next step without any further purification. MS: m/z=490 (M+H$^+$).

2-(((((S)-1-(4-(4-(4-(3-Fluoropropyl)-1H-1,2,3-triazol-1-yl)phenyl)butanoyl)pyrrolidin-2-yl)methoxy)(hydroxy)phosphoryl)methyl)pentanedioic acid: P207

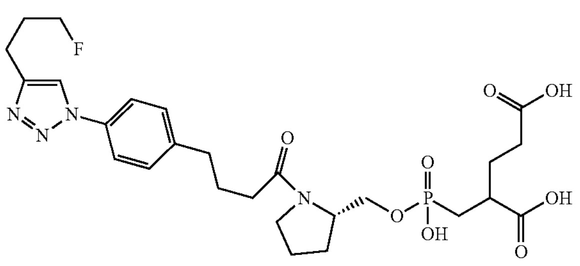 [SMILES: O=C(O)CCC(CP(=O)(O)OC[C@@H]1CCCN1C(=O)CCCc1ccc(-n2cc(CCCF)nn2)cc1)C(=O)O]

General procedures for click chemistry and debenzylation reaction were followed. After HPLC purification, P207 was obtained. $^1$H NMR ($CD_3OD/CD_3CN$, 400 MHz) δ 8.05 (s, 1H), 7.64 (m, 2H), 7.38 (m, 2H), 4.58-4.44 (m, 4H), 4.05 (m, 1H), 3.67-3.58 (m, 2H), 3.08-2.85 (m, 4H), 2.55-2.70 (m, 2H), 2.34 (m, 2H), 2.16-2.11 (m, 4H), 1.55-1.62 (m, 4H). MS: m/z=583 ($M+H^+$).

(10R,14S)-3,8,12-Trioxo-1-phenyl-2-oxa-4,9,13-triazahexadecane-10,14,16-tricarboxylic acid: P208

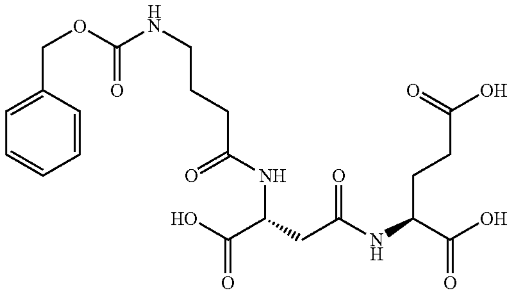 [SMILES: O=C(O)CC[C@H](NC(=O)C[C@@H](NC(=O)CCCNC(=O)OCc1ccccc1)C(=O)O)C(=O)O]

General experimental procedure for urea formation and tert-butyl deprotection reaction was followed. After HPLC purification, P208 (2.2 mg, 19%) was obtained. $^1$H NMR ($CD_3OD$, 400 MHz) δ 7.21-7.39 m, 5H), 5.06 (s, 2H), 4.73 (t, J=7.6 Hz, 1H), 4.39-4.4.48 (m, 1H), 3.15 (t, J=7.2 Hz, 2H), 2.79-2.88 (m, 1H), 2.68-2.78 (m, 1H), 2.39 (t, J=7.6 Hz, 2H), 2.26 (t, J=7.2 Hz, 2H), 2.12-2.22 (m, 1H), 1.86-1.98 (m, 1H), 1.74-1.84 (m, 2H) MS: m/z=482 ($M+H^+$).

(12R,16S)-3,10,14-Trioxo-1-phenyl-2-oxa-4,11,15-triazaoctadecane-12,16,18-tricarboxylic acid: P209

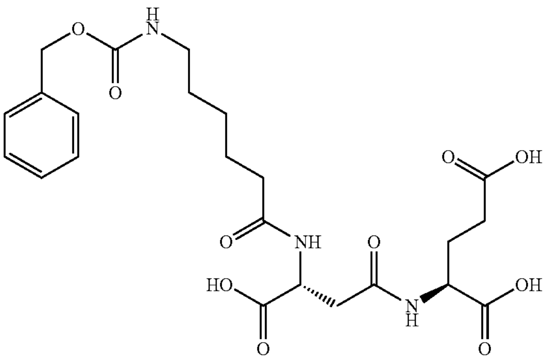 [SMILES: O=C(O)CC[C@H](NC(=O)C[C@@H](NC(=O)CCCCCNC(=O)OCc1ccccc1)C(=O)O)C(=O)O]

General experimental procedure for urea formation and tert-butyl deprotection reaction was followed. After HPLC purification, P209 (3.3 mg, 21%) was obtained. $^1$H NMR ($CD_3OD$, 400 MHz) δ 7.21-7.39 (m, 5H), 5.06 (s, 2H), 4.68-4.76 (m, 1H), 4.41-4.48 (m, 1H), 3.10 (t, J=7.2 Hz, 2H), 2.79-2.889 (m, 1H), 2.67-2.78 (m, 1H), 2.39 (t, J=7.6 Hz, 2H), 2.24 (t, J=7.6 Hz, 2H), 2.12-2.23 (m, 1H), 1.85-1.98 (m, 1H), 1.56-1.66 (m, 2H), 1.45-1.55 (m, 2H), 1.28-1.41 (m, 2H). MS: m/z=510 ($M+H^+$).

(S)-2-((R)-3-Carboxy-3-(2-(4-fluorophenyl)acetamido)propanamido)pentanedioic acid: P210

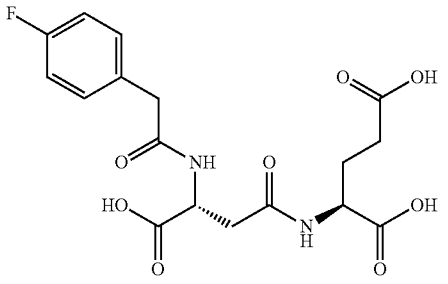 [SMILES: O=C(O)CC[C@H](NC(=O)C[C@@H](NC(=O)Cc1ccc(F)cc1)C(=O)O)C(=O)O]

General experimental procedure for urea formation and tert-butyl deprotection reaction was followed. After HPLC purification, P210 (8.1 mg, 42%) was obtained. $^1$H NMR ($CD_3OD$, 400 MHz) δ 7.28-7.32 (m, 2H), 7.02 (t, J=8.8 Hz, 2H), 4.69-4.74 (m, 1H), 4.39-4.48 (m, 1H), 2.72-2.89 (m, 2H), 2.38 (t, J=7.6 Hz, 2H), 2.11-2.23 (m, 1H), 1.85-1.98 (m, 1H). MS: m/z=399 ($M+H^+$).

(S)-2-((R)-3-Carboxy-3-(4-(4-fluorophenyl)butanamido)propanamido)pentanedioic acid: P211

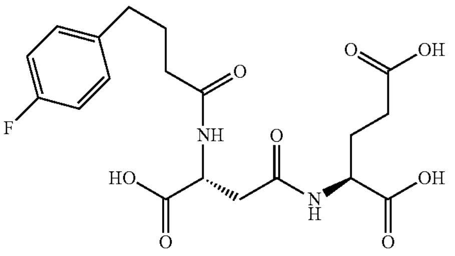 [SMILES: O=C(O)CC[C@H](NC(=O)C[C@@H](NC(=O)CCCc1ccc(F)cc1)C(=O)O)C(=O)O]

General experimental procedure for urea formation and tert-butyl deprotection reaction was followed. After HPLC purification, P211 (3.6 mg, 37%) was obtained. $^1$H NMR ($CD_3OD$, 400 MHz) δ 7.17-7.23 (m, 2H), 6.97 (t, J=8.8 Hz, 2H), 4.51-4.53 (m, 1H), 4.41-4.47 (m, 1H), 2.85 (dd, J=15.2, 5.2 Hz, 1H), 2.73 (dd, J=15.2, 7.6 Hz, 1H), 2.62 (t, J=8.0 Hz, 2H), 2.39 (t, J=8.0 Hz, 2H), 2.25 (t, J=7.2 Hz, 2H), 2.12-2.23 (m, 1H), 1.84-1.97 (m, 3H). MS: m/z=427 ($M+H^+$).

(S)-2-(3-((S)-1-Carboxy-2-(4-(3-(4-(4-(3-fluoropropyl)-1H-1,2,3-triazol-1-yl)phenyl)ureido)phenyl)ethyl)ureido)pentanedioic acid: P212

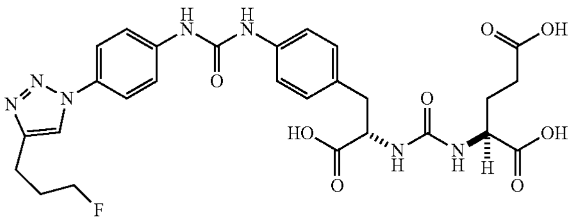

General experimental procedure for click reaction was followed. Reaction was performed on a 7.5 mg scale of (S)-2-(3-((S)-2-(4-(3-(4-azidophenyl)thioureido)phenyl)-1-carboxyethyl)ureido)pentanedioic acid. After HPLC purification, P212 (1.2 mg, 14%) was obtained as a white solid. $^1$H NMR ($CD_3OD$, 400 MHz) δ 8.30 (s, 1H), 7.73-7.77 (m, 2H), 7.62-7.66 (m, 2H), 7.35-7.39 (m, 2H), 7.15-7.20 (m, 2H), 4.44-4.59 (m, 3H), 4.29 (dd, J=8.6, 5.1 Hz, 1H), 3.08-3.17 (m, 1H), 2.89-3.02 (m, 3H), 2.34-2.44 (m, 2H), 1.99-2.18 (m, 3H), 1.82-1.92 (m, 1H). MS: m/z=600 (M+H$^+$).

(S)-2-((R)-3-Carboxy-3-(6-fluoronicotinamido)propanamido)pentanedioic acid: P213

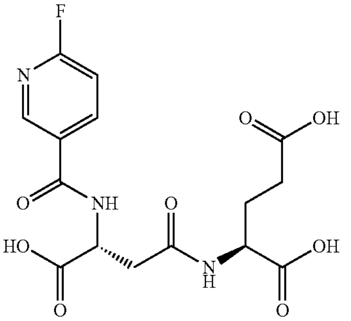 [SMILES: O=C(O)CC[C@H](NC(=O)C[C@@H](NC(=O)c1ccc(F)nc1)C(=O)O)C(=O)O]

General experimental procedure for urea formation and tert-butyl deprotection reaction was followed. After HPLC purification, P213 was obtained. $^1$H NMR ($CD_3OD$, 400 MHz) δ 8.33 (d, J=0.8 Hz, 1H), 7.67 (d, J=5.2 Hz, 1H), 7.44-7.46 (m, 1H), 4.89-4.99 (m, 1H), 4.41-4.49 (m, 1H), 2.99 (dd, J=15.2, 5.2 Hz, 1H), 2.85 (dd, J=15.2, 8.4 Hz, 1H), 2.39 (t, J=7.6 Hz, 2H), 2.13-2.24 (m, 1H), 1.87-1.99 (m, 1H). MS: m/z=386 (M+H$^+$).

(S)-2-((R)-3-Carboxy-3-(3-phenethylureido)propanamido)pentanedioic acid: P214

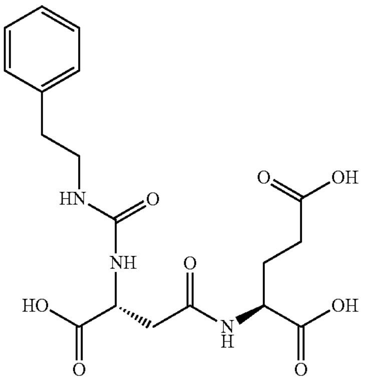 [SMILES: O=C(O)CC[C@H](NC(=O)C[C@@H](NC(=O)NCCc1ccccc1)C(=O)O)C(=O)O]

General experimental procedure for urea formation and tert-butyl deprotection reaction was followed. After HPLC purification, P214 was obtained. $^1$H NMR ($CD_3OD$, 400 MHz) δ 7.15-7.31 (m, 5H), 4.59 (t, J=5.6 Hz, 1H), 4.41-4.49 (m, 1H), 3.31-3.39 (m, 2H), 2.71-2.83 (m, 4H), 2.39 (t, J=7.6 Hz, 2H), 2.11-2.23 (m, 1H), 1.85-1.99 (m, 1H). MS: m/z=410 (M+H$^+$).

(S)-2-(3-((S)-1-Carboxy-2-(4-(4-(4-(3-fluoropropyl)-1H-1,2,3-triazol-1-yl)-benzamido)-phenyl)ethyl)ureido)pentanedioic acid: P215

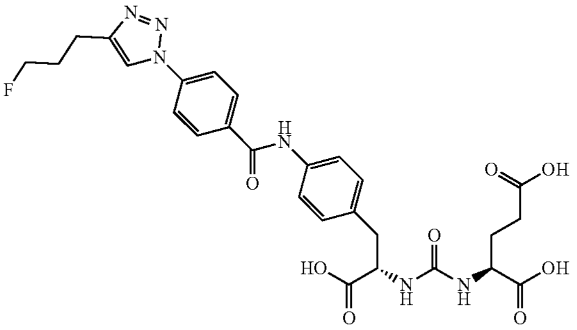 [SMILES: O=C(O)CC[C@H](NC(=O)N[C@@H](Cc1ccc(NC(=O)c2ccc(-n3cc(CCCF)nn3)cc2)cc1)C(=O)O)C(=O)O]

General procedure for click chemistry and tert-butyl ester group deprotection was followed. Reaction was performed on a 50 mg scale. After HPLC purification, P215 (23 mg, 35% in two steps) was obtained. $^1$H NMR ($CD_3OD$, 400 MHz) δ 8.47 (s, 1H), 8.13 (d, J=8.4 Hz, 2H), 8.01 (d, J=8.4 Hz, 2H), 7.63 (d, J=8.4 Hz, 2H), 7.26 (d, J=8.4 Hz, 2H), 4.60-4.54 (m, 2H), 4.47 (t, J=6.0 Hz, 1H), 4.31-4.28 (dd, J=8.4, 4.8 Hz, 1H), 3.17-3.12 (dd, J=14.0, 5.2 Hz, 1H), 3.05-2.99 (dd, J=14.0, 5.2 Hz, 1H), 2.94 (t, J=7.2 Hz, 2H), 2.41-2.37 (m, 2H), 2.20-2.07 (m, 3H), 1.91-1.84 (m, 1H). MS: m/z=585 (M+H$^+$).

(S)-2-(3-((S)-2-(4-(4-Azidobenzamido)phenyl)-1-carboxyethyl)ureido)pentanedioic acid: P215 Precursor

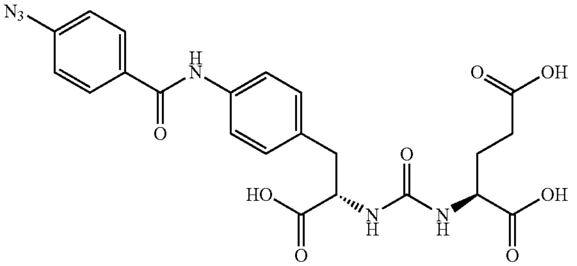 [SMILES: [N-]=[N+]=Nc1ccc(C(=O)Nc2ccc(C[C@H](NC(=O)N[C@@H](CCC(=O)O)C(=O)O)C(=O)O)cc2)cc1]

General procedure for amide coupling was followed on ureaamine-tbutyl ester. Reaction was performed on a 100 mg scale. After HPLC purification, P215 Precursor (6.0 mg, 25%) was obtained. $^1$H NMR ($CD_3OD$, 400 MHz) δ 7.98-7.94 (m, 2H), 7.60-7.58 (m, 2H), 7.25-7.16 (m, 4H), 4.55 (t, J=5.2 Hz, 1H), 4.28 (dd, J=8.8, 5.2 Hz, 1H), 3.16-3.08 (m, 1H), 3.01 (dd, J=13.6, 6.2 Hz, 1H), 2.41-2.36 (m, 2H), 2.18-2.08 (m, 1H), 1.91-1.81 (m, 1H). MS: m/z=499 [M+H$^+$].

(S)-2-(3-((S)-1-Carboxy-2-(4-(4-(4-(3-fluoropropyl)-1H-1,2,3-triazol-1-yl)-ethoxy)-ethoxy)ethoxy)acetamido)phenyl)ethyl)ureido)pentanedioic acid: P216

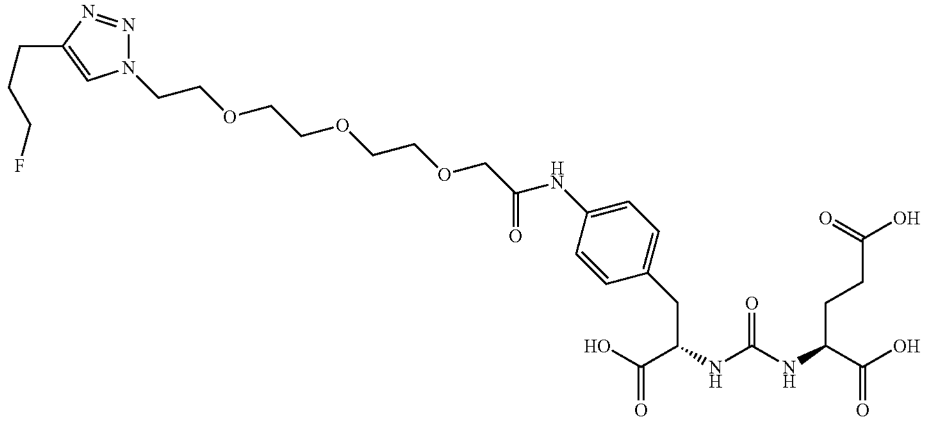 [SMILES: O=C(O)CC[C@H](NC(=O)N[C@@H](Cc1ccc(NC(=O)COCCOCCOCCn2cc(CCCF)nn2)cc1)C(=O)O)C(=O)O]

General procedure for click chemistry was followed. Reaction was performed on a 10 mg scale. After HPLC purification, P216 (4 mg, 35%) was obtained. $^1$H NMR ($CD_3OD$, 400 MHz) δ 7.74 (s, 1H), 7.49-7.47 (dd, J=8.4, 1.6 Hz, 2H), 7.19 (d, J=8.4 Hz, 2H), 4.55-4.46 (m, 4H), 4.37 (t, J=6.0 Hz, 1H), 4.30-4.27 (dd, J=8.8, 5.2 Hz, 1H), 4.11 (s, 2H), 3.81 (t, J=5.2 Hz, 2H), 3.73-3.72 (m, 2H), 3.69-3.61 (m, 7H), 3.15-3.10 (dd, J=14.0, 6.4 Hz, 1H), 3.02-2.96 (dd, J=14.0, 6.4 Hz, 1H), 2.76 (t, J=7.6 Hz, 2H), 2.42-2.37 (m, 2H), 1.98-1.82 (m, 4H). MS: m/z=655 (M+H$^+$).

(S)-2-(3-((S)-1-Carboxy-2-(4-(4-(4-(3-fluoropropyl)-1H-1,2,3-triazol-1-yl)-acetamido)-phenyl)ethyl) ureido)pentanedioic acid: P217

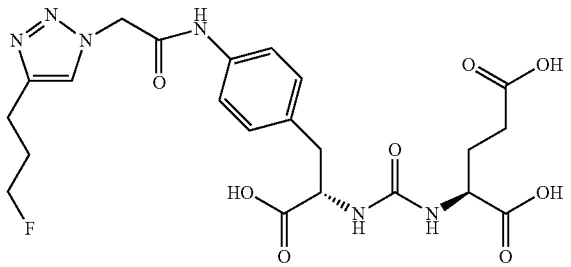 [SMILES: O=C(O)CC[C@H](NC(=O)N[C@@H](Cc1ccc(NC(=O)Cn2cc(CCCF)nn2)cc1)C(=O)O)C(=O)O]

General procedure for click chemistry was followed. Reaction was performed on a 4.6 mg scale. After HPLC purification, P217 (3 mg, 55%) was obtained. $^1$H NMR ($CD_3OD$, 400 MHz) δ 10.22 (s, 1H), 7.85 (s, 1H), 7.49-7.47 (dd, J=8.4, 1.6 Hz, 2H), 7.20 (dd, J=8.4 Hz, 2H), 5.28 (s, 2H), 4.54-4.50 (m, 1H), 4.42 (t, J=6.0 Hz, 1H), 4.29-4.26 (dd, J=8.8, 5.2 Hz, 1H), 3.13-3.08 (dd, J=12.0, 6.8 Hz, 1H), 3.01-2.96 (dd, J=12.0, 6.8 Hz, 1H), 2.85 (t, J=7.2 Hz, 1H), 2.41-2.35 (m, 2H), 1.98-2.02 (m, 2H), 1.92-1.82 (m, 1H). MS: m/z=523 (M+H$^+$).

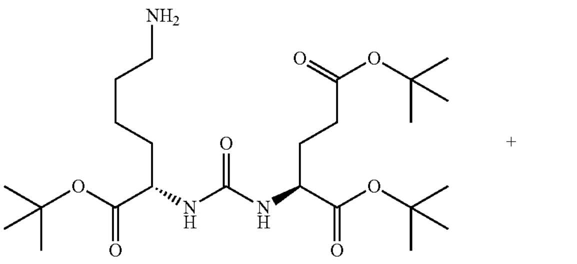

1

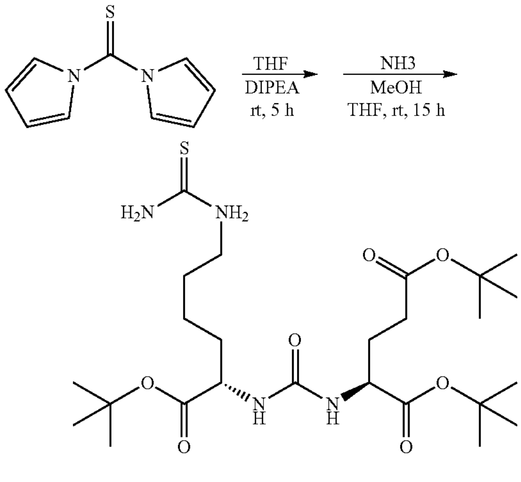

(S)-Di-tert-butyl 2-(3-((S)-1-(tert-butoxy)-1-oxo-6-thioureidohexan-2-yl)ureido)pentanedioate To a mixture of 1 (97 mg, 0.2 mmol) and di(1H-pyrrol-1-yl)methanethione (35 mg, 0.2 mmol) in THF (2.0 mL) was added DIPEA (26 mg, 0.2 mmol). The mixture was stirred at rt for 5 h and then quenched by adding ammonia solution (2 M in MeOH, 3.0 mL). The mixture was stirred for 15 h at rt and concentrated. The residue was purified chromatography (hexane/EtOAc) to afford (S)-di-tert-butyl 2-(3-((S)-

1-(tert-butoxy)-1-oxo-6-thioureidohexan-2-yl)ureido)pentanedioate as a yellow wax (75 mg, 68%). MS: m/z=547 (M+H+).

(S)-Di-tert-butyl 2-(3-((S)-6-((4-(4-azidophenyl)thiazol-2-yl)amino)-1-(tert-butoxy)-1-oxohexan-2-yl)ureido)pentanedioate

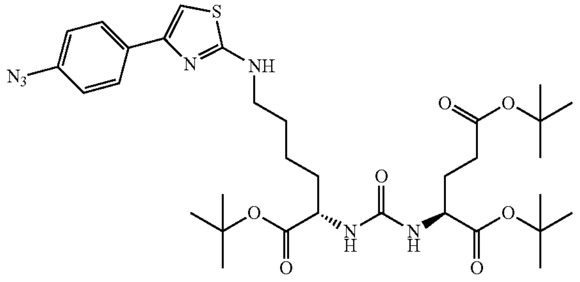 [SMILES: CC(C)(C)OC(=O)CC[C@H](NC(=O)N[C@@H](CCCCNc1nc(-c2ccc(N=[N+]=[N-])cc2)cs1)C(=O)OC(C)(C)C)C(=O)OC(C)(C)C]

A mixture of above compound and 1-(4-azidophenyl)-2-bromoethanone (33 mg, 0.13 mmol) in dry EtOH (2.0 mL) was stirred at rt for 15 h. Solvent was removed under reduced pressure and the residue was purified by chromatography (hexane/EtOAc) to afford (S)-di-tert-butyl 2-(3-((S)-6-((4-(4-azidophenyl)thiazol-2-yl)amino)-1-(tert-butoxy)-1-oxohexan-2-yl)ureido)pentanedioate as a yellow solid (38 mg, 42%). MS: m/z=688 (M+H+).

(S)-2-(3-((S)-1-Carboxy-5-((4-(4-(4-(3-fluoropropyl)-1H-1,2,3-triazol-1-yl)phenyl)thiazol-2-yl)amino)pentyl)ureido)pentanedioic acid: P218

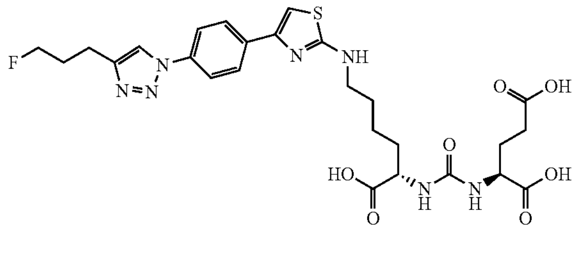 [SMILES: O=C(O)CC[C@H](NC(=O)N[C@@H](CCCCNc1nc(-c2ccc(-n3cc(CCCF)nn3)cc2)cs1)C(=O)O)C(=O)O]

General experimental procedures for click chemistry and tert-butyl deprotection reaction were followed. After HPLC purification, P218 (14 mg, 60%) was obtained. $^1$H NMR ($CD_3OD$, 400 MHz) δ 8.37 (s, 1H), 8.00-7.98 (m, 2H), 7.85-7.83 (m, 2H), 6.96 (s, 1H), 4.58 (t, J=5.6 Hz, 1H), 4.47 (t, J=5.6 Hz, 1H), 4.33-4.28 (m, 2H), 3.38 (t, J=7.2 Hz, 2H), 2.92 (m, 2H), 2.44-2.39 (m, 2H), 2.19-2.04 (m, 3H), 1.96-1.84 (m, 2H), 1.77-1.63 (m, 3H), 1.58-1.50 (m, 2H). MS: m/z=606 (M+H+).

(S)-2-((R)-3-Carboxy-3-(4-(4-(4-(3-fluoropropyl)-1H-1,2,3-triazol-1-yl)phenyl)butanamido)-propanamido)pentanedioic acid: P219

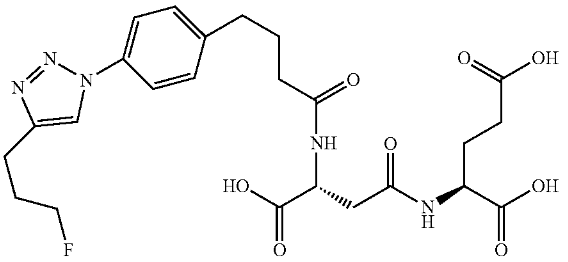 [SMILES: O=C(O)CC[C@H](NC(=O)C[C@@H](NC(=O)CCCc1ccc(-n2cc(CCCF)nn2)cc1)C(=O)O)C(=O)O]

General experimental procedure for urea formation and tert-butyl deprotection reaction was followed. After HPLC purification, P219 was obtained. $^1$H NMR ($CD_3OD$, 400 MHz) δ 8.30 (s, 1H), 7.73 (d, J=8.4 Hz, 2H), 7.42 (d, J=8.4 Hz, 2H), 4.73-4.79 (m, 1H), 4.52 (dt, J=47.2, 6.0 Hz, 2H), 4.41-4.48 (m, 1H), 2.83-2.93 (m, 4H), 2.69-2.78 (m, 4H), 2.39 (t, J=7.6 Hz, 2H), 2.29 (t, J=7.6 Hz, 2H), 1.85-2.15 (m, 4H). MS: m/z=536 (M+H+).

(S)-2-((R)-3-Carboxy-3-(3-(4-(4-(3-fluoropropyl)-1H-1,2,3-triazol-1-yl)phenyl)-propanamido)-propanamido)pentanedioic acid: P220

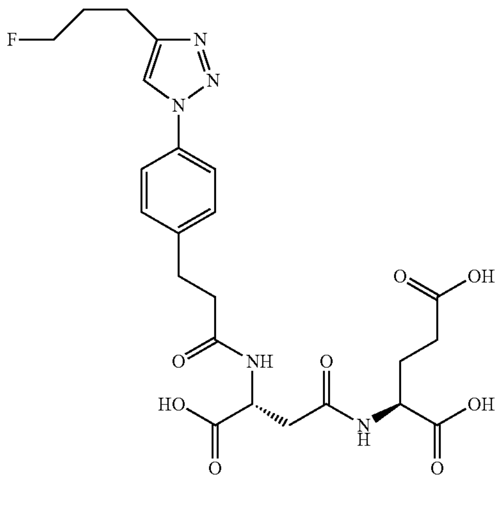 [SMILES: O=C(O)CC[C@H](NC(=O)C[C@@H](NC(=O)CCc1ccc(-n2cc(CCCF)nn2)cc1)C(=O)O)C(=O)O]

General experimental procedure for urea formation and tert-butyl deprotection reaction was followed. After HPLC purification, P220 was obtained. $^1$H NMR ($CD_3OD$, 400 MHz) δ 8.30 (s, 1H), 7.72 (d, J=8.4 Hz, 2H), 7.43 (d, J=8.4 Hz, 2H), 4.71-4.75 (m, 1H), 4.50 (dt, J=47.2, 6.0 Hz, 2H), 4.39-4.49 (m, 1H), 3.00 (t, J=8.0 Hz, 2H), 2.90 (t, J=8.0 Hz, 2H), 2.77-2.85 (m, 1H), 2.65-2.74 (m, 1H), 2.59 (t, J=8.0 Hz, 2H), 2.38 (t, J=7.6 Hz, 2H), 2.02-2.22 (m, 3H), 1.84-1.96 (m, 1H). MS: m/z=522 (M+H+).

(S)-2-((R)-3-Carboxy-3-(4-(4-(3-fluoropropyl)-1H-1,2,3-triazol-1-yl)benzamido)propanamido)-pentanedioic acid: P221

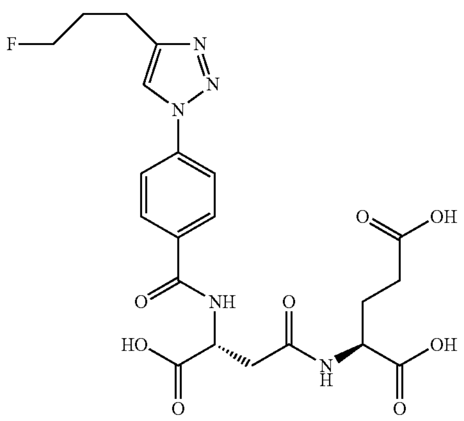 [SMILES: O=C(O)CC[C@H](NC(=O)C[C@@H](NC(=O)c1ccc(-n2cc(CCCF)nn2)cc1)C(=O)O)C(=O)O]

General experimental procedure for urea formation and tert-butyl deprotection reaction was followed. After HPLC purification, P221 was obtained. $^{1}$H NMR ($CD_3OD$, 400 MHz) δ 8.45 (s, 1H), 8.05 (d, J=8.4 Hz, 2H), 7.97 (d, J=8.4 Hz, 2H), 4.93-5.01 (m, 1H), 4.52 (dt, J=47.2, 6.0 Hz, 2H), 4.42-4.51 (m, 1H), 2.84-3.05 (m, 4H), 2.40 (t, J=7.6 Hz, 2H), 2.05-2.25 (m, 3H), 1.88-1.98 (m, 1H). MS: m/z=494 (M+H$^{+}$).

((S)-2-(3-((S)-2-(4-(4-((Benzyloxy)carbonyl)piperazine-1-carboxamido)phenyl)-1-carboxyethyl)ureido) pentanedioic acid: P222

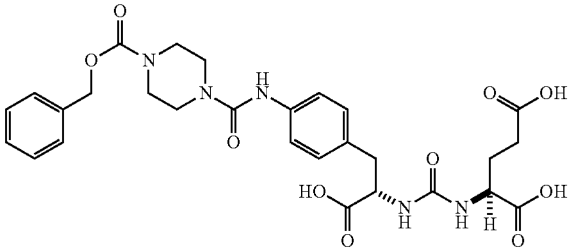

General experimental procedure for urea formation and d tert-butyl eprotection was followed. Reaction was performed on a 15 mg scale of (S)-di-tert-butyl 2-(3-((S)-3-(4-(4-((benzyloxy)carbonyl)piperazine-1-carboxamido)phenyl)-1-(tert-butoxy)-1-oxopropan-2-yl)ureido) pentanedioate. After HPLC purification, P222 (4.2 mg, 36%) was obtained as a white solid. $^{1}$H NMR ($CD_3OD$, 400 MHz) δ 7.15-7.30 (m, 7H), 7.02-7.07 (m, 2H), 5.05 (s, 2H), 4.42 (dd, J=6.7, 5.5 Hz, 1H), 4.18 (dd, J=8.8, 4.9 Hz, 1H), 3.37-3.51 (m, 8H), 2.96-3.04 (m, 1H), 2.83-2.90 (m, 1H), 2.22-2.35 (m, 2H), 1.97-2.06 (m, 1H), 1.71-1.81 (m, 1H). MS: m/z=600 (M+H$^{+}$).

(2S,2'S)-2,2'-(((((1S,1'S)-((Carbonylbis(azanediyl))bis(4,1-phenylene))bis(1-carboxyethane-2,1-diyl))bis(azanediyl))bis(carbonyl))bis(azanediyl))dipentanedioic acid: P223

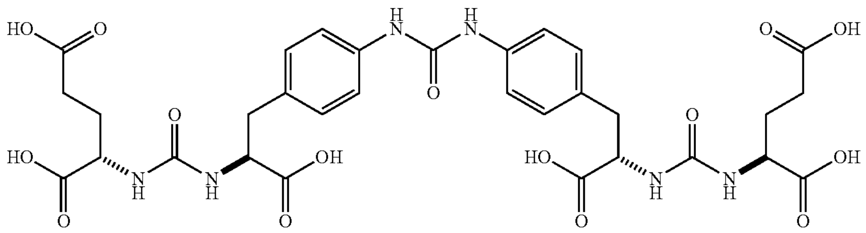

General experimental procedure for urea formation and tert-butyl deprotection was followed. Reaction was performed on a 45 mg scale of (S)-di-tert-butyl 2-(3-((S)-3-(4-aminophenyl)-1-(tert-butoxy)-1-oxopropan-2-yl)ureido) pentanedioate. After HPLC purification, P223 (15 mg, 47%) was obtained as a white solid. $^1$H NMR ($CD_3OD$, 400 MHz) δ 7.34 (d, J=8.2 Hz, 4H), 7.17 (d, J 8.2 Hz, 4H), 4.52 (t, J=6.1 Hz, 2H), 4.29 (dd, J=8.8, 4.9 Hz, 2H), 3.05-3.13 (m, 2H), 2.93-3.03 (m, 2H), 2.31-2.48 (m, 4H), 2.07-2.19 (m, 2H), 1.80-1.93 (m, 2H). MS: m/z=733 (M+H$^+$).

(S)-2-(3-((S)-2-((4-((Benzyloxy)carbonyl)piperazine-1-carbonyl)oxy)-1-carboxyethyl)ureido)pentanedioic acid: P224

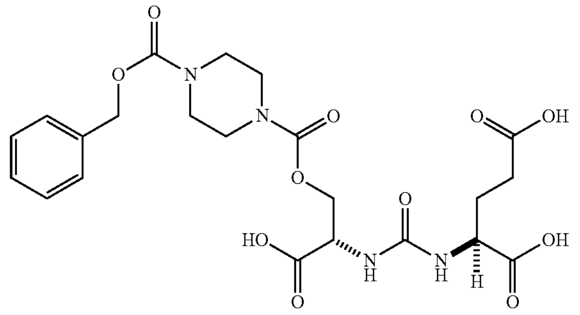

General experimental procedure for tert-butyl deprotection was followed. Reaction was performed on a 10 mg scale of 1-benzyl 4-((S)-3-(tert-butoxy)-2-(3-((S)-1,5-di-tert-butoxy-1,5-dioxopentan-2-yl)ureido)-3-oxopropyl) piperazine-1,4-dicarboxylate. After HPLC purification, P224 (4.8 mg, 63%) was obtained as a white solid. $^1$H NMR ($CD_3OD$, 400 MHz) δ 7.30-7.38 (m, 5H), 5.09-5.16 (m, 2H), 4.61 (t, J=4.3 Hz, 1H), 4.30-4.43 (m, 3H), 3.47 (br. s., 8H), 2.34-2.48 (m, 2H), 2.10-2.19 (m, 1H), 1.84-1.94 (m, 1H). MS: m/z=525 (M+H$^+$).

2-(((2-(1-(3-(4-(4-(3-Fluoropropyl)-1H-1,2,3-triazol-1-yl)phenyl)propanoyl)piperidin-4-yl)ethoxy)(hydroxy)phosphoryl)methyl)pentanedioic acid: P225

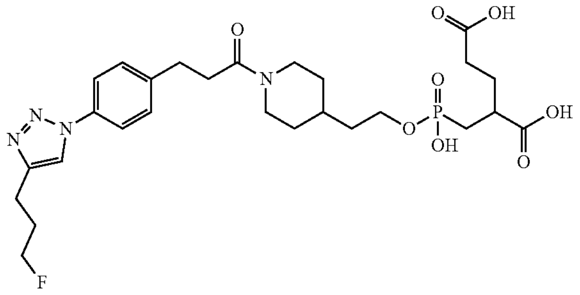 [SMILES: O=C(O)CCC(CP(=O)(O)OCCC1CCN(C(=O)CCc2ccc(-n3cc(CCCF)nn3)cc2)CC1)C(=O)O]

General experimental procedure for tert-butyl deprotection was followed. After HPLC purification, P225 was obtained. MS: m/z=596.9 (M+H$^+$)

2-((((1-(4-(4-(4-(3-Fluoropropyl)-1H-1,2,3-triazol-1-yl)phenyl)butanoyl)piperidin-4-yl)methoxy)(hydroxy)phosphoryl)methyl)pentanedioic acid: P226

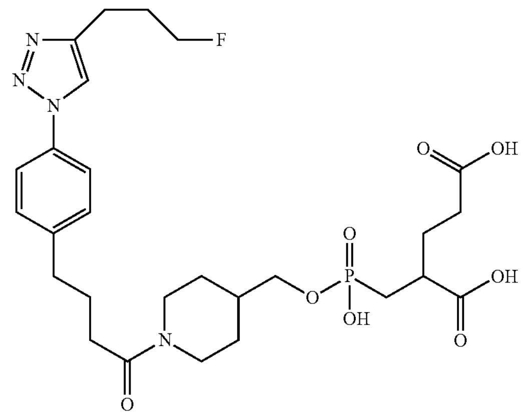 [SMILES: O=C(O)CCC(CP(=O)(O)OCC1CCN(C(=O)CCCc2ccc(-n3cc(CCCF)nn3)cc2)CC1)C(=O)O]

Similar procedures for the preparation of P207 were used to synthesize P226. After HPLC purification, P226 was obtained. MS: m/z=597 (M+H$^+$)

2-(((2-(1-(4-(4-(3-Fluoropropyl)-1H-1,2,3-triazol-1-yl)benzoyl)piperidin-4-yl)ethoxy)(hydroxy)phosphoryl)methyl)pentanedioic acid: P227

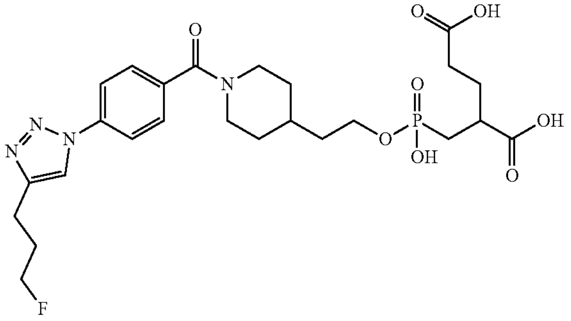 [SMILES: O=C(O)CCC(CP(=O)(O)OCCC1CCN(C(=O)c2ccc(-n3cc(CCCF)nn3)cc2)CC1)C(=O)O]

General experimental procedure for tert-butyl deprotection was followed. After HPLC purification, P227 was obtained. $^1$H NMR ($CD_3OD$, 400 MHz) δ 8.14 (s, 1H), 7.55 (m, 2H), 7.44 (m, 2H), 4.44-4.33 (m, 4H), 3.70 (m, 2H), 3.45 (m, 1H), 3.00 (m, 1H), 2.85-2.75 (m, 3H), 2.58-2.55 (m, 1H), 2.25-2.21 (m, 2H), 2.01-1.39 (m, 10H), 1.20-1.01 (m, 2H). MS: m/z=568.9 (M+H$^+$)

(S)-2-((R)-3-Carboxy-3-(2-(4-(3-fluoropropyl)-1H-1,2,3-triazol-1-yl)acetamido)propanamido)-pentanedioic acid: P228

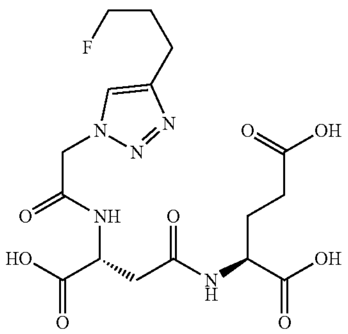 [SMILES: O=C(O)CC[C@H](NC(=O)C[C@@H](NC(=O)Cn1cc(CCCF)nn1)C(=O)O)C(=O)O]

General experimental procedures for urea formation and tert-butyl deprotection reaction were followed. After HPLC purification, P228 (3.3 mg, 20%) was obtained. $^1H$ NMR ($CD_3OD$, 400 MHz) δ 7.81 (s, 1H), 5.19 (s, 2H), 4.75-4.81 (m, 1H), 4.47 (dt, J=47.2, 6.0 Hz, 2H), 4.39-4.50 (m, 1H), 2.74-2.92 (m, 4H), 2.41 (t, J=7.6 Hz, 2H), 1.85-2.31 (m, 4H). MS: m/z=432 ($M+H^+$).

(S)-2-((R)-3-(4-((Benzyloxy)carbonyl)piperazine-1-carboxamido)-3-carboxypropanamido)-pentanedioic acid: P229

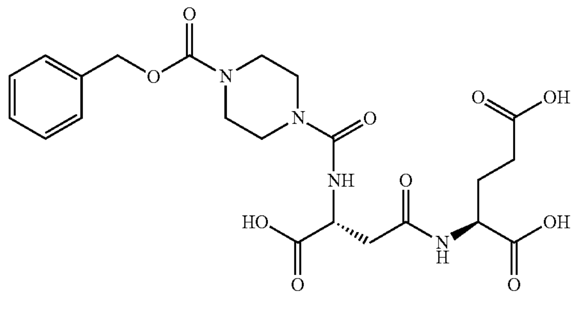 [SMILES: O=C(O)CC[C@H](NC(=O)C[C@@H](NC(=O)N1CCN(C(=O)OCc2ccccc2)CC1)C(=O)O)C(=O)O]

General experimental procedure for urea formation and tert-butyl deprotection reaction was followed. After HPLC purification, P229 (2.3 mg, 13%) was obtained. $^1H$ NMR ($CD_3OD$, 400 MHz) δ 7.32-7.41 (m, 5H), 5.13 (s, 2H), 4.58-4.63 (m, 1H), 4.38-4.40 (m, 1H), 3.34-3.58 (m, 8H), 2.81-2.88 (m, 1H), 2.69-2.79 (m, 1H), 2.39 (t, J=7.6 Hz, 2H), 2.12-2.23 (m, 1H), 1.82-1.97 (m, 1H). MS: m/z=432 ($M+H^+$).

(2S)-2-(3-(1-Carboxy-2-(1-(4-(4-(4-(3-fluoropropyl)-1H-1,2,3-triazol-1-yl)phenyl)butanoyl)-piperidin-4-yl)ethyl)ureido)pentanedioic acid: P230

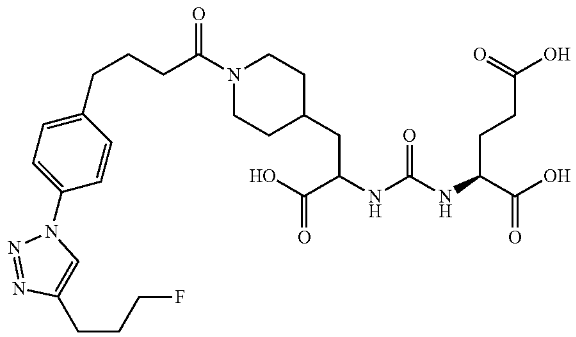 [SMILES: O=C(O)CC[C@H](NC(=O)NC(CC1CCN(C(=O)CCCc2ccc(-n3cc(CCCF)nn3)cc2)CC1)C(=O)O)C(=O)O]

General experimental procedures for urea formation, amide formation, click chemistry, and tert-butyl deprotection reaction were followed. After HPLC purification, P230 was obtained. MS: mz=619 ($M+H^+$).

2-((S)-4-((1-(4-(4-(4-(3-Fluoropropyl)-1H-1,2,3-triazol-1-yl)phenyl)butanoyl)piperidin-4-yl)methyl)-2,5-dioxoimidazolidin-1-yl)pentanedioic acid: P231

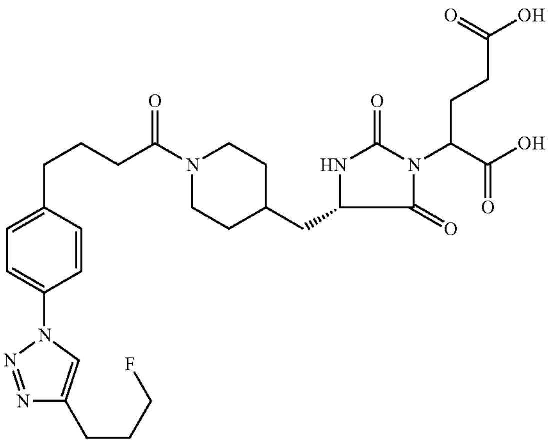 [SMILES: O=C(O)CCC(C(=O)O)N1C(=O)N[C@@H](CC2CCN(C(=O)CCCc3ccc(-n4cc(CCCF)nn4)cc3)CC2)C1=O]

General procedures for the preparation of P230 were followed. After HPLC purification, P231 was obtained. MS: m/z=601 ($M+H^+$).

(S)-2-(3-((S)-1-Carboxy-5-(4-(4-fluorophenyl)thiazol-2-ylamino)pentyl)ureido)pentanedioic acid: P232

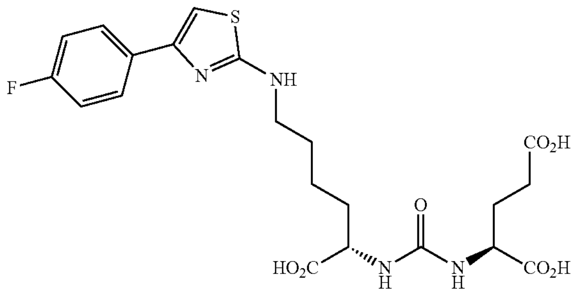 [SMILES: O=C(O)CC[C@H](NC(=O)N[C@@H](CCCCNc1nc(-c2ccc(F)cc2)cs1)C(=O)O)C(=O)O]

General experimental procedure for urea formation and tert-butyl deprotection reaction was followed. $^1$H NMR ($CD_3OD$, 400 MHz) δ 7.75-7.73 (m, 2H), 7.20-7.18 (m, 2H), 6.93 (s, 1H), 4.31-4.28 (m, 2H), 3.44-3.41 (m, 2H), 2.46-2.39 (m, 2H), 2.22-2.13 (m, 1H), 1.93-1.71 (m, 5H), 1.54-1.47 (m, 2H). MS: m/z=497.2 ($M+H^+$)

(S)-2-(3-((S)-1-Carboxy-5-(4-(3-nitrophenyl)thiazol-2-ylamino)pentyl)ureido)pentanedioic acid: P233

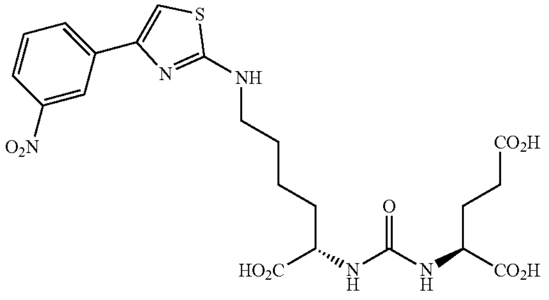 [SMILES: O=C(O)CC[C@H](NC(=O)N[C@@H](CCCCNc1nc(-c2cccc([N+](=O)[O-])c2)cs1)C(=O)O)C(=O)O]

General experimental procedure for urea formation and tert-butyl deprotection reaction was followed. $^1$H NMR ($CD_3OD$, 400 MHz) δ 8.61 (s, 1H), 8.24 (dd, J=8.0, 2.0 Hz, 1H), 8.13 (d, J=8.0 Hz, 1H), 7.68 (t, J=8.0 Hz, 1H), 7.18 (s, 1H), 4.33-4.29 (m, 2H), 3.45-3.41 (m, 2H), 2.42-2.39 (m, 2H), 2.43-2.39 (m, 1H), 1.93-1.55 (m, 5H), 1.52-1.47 (m, 2H). MS: m/z=524.9 ($M+H^+$)

(S)-2-(3-((S)-5-(4-(Benzo[b]thiophen-2-yl)thiazol-2-ylamino)-1-carboxypentyl)ureido) pentanedioic acid: P234

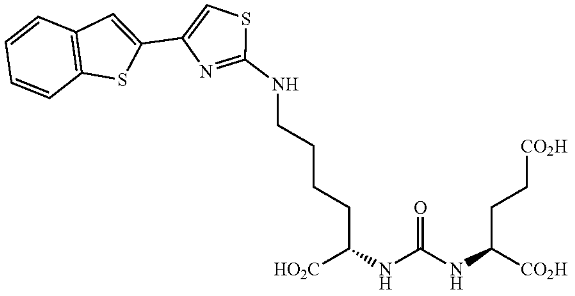 [SMILES: O=C(O)CC[C@H](NC(=O)N[C@@H](CCCCNc1nc(-c2cc3ccccc3s2)cs1)C(=O)O)C(=O)O]

General experimental procedure for urea formation and tert-butyl deprotection reaction was followed. $^1$H NMR ($CD_3OD$, 400 MHz), δ: 8.00-7.95 (m, 2H), 7.54-7.42 (m, 3H), 4.32-4.30 (m, 2H), 3.41-3.35 (m, 2H), 2.41-2.38 (m, 2H), 2.15-2.08 (m, 1H), 1.95-1.70 (m, 5H), 1.56-1.54 (m, 2H). MS: m/z=535.8 ($M+H^+$)

(S)-2-(3-((S)-5-(4-(Benzo[d][1,3]dioxol-5-yl)thiazol-2-ylamino)-1-carboxypentyl)ureido)-pentanedioic acid: P235

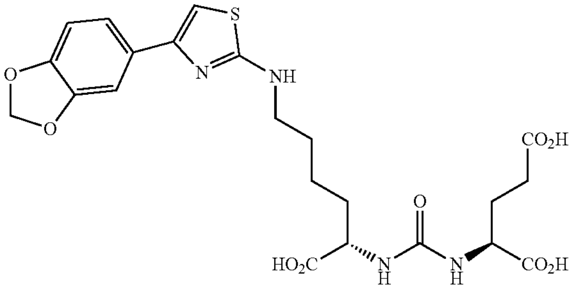 [SMILES: O=C(O)CC[C@H](NC(=O)N[C@@H](CCCCNc1nc(-c2ccc3c(c2)OCO3)cs1)C(=O)O)C(=O)O]

General experimental procedure for urea formation and tert-butyl deprotection reaction was followed. $^1$H NMR ($CD_3OD$, 400 MHz), δ: 7.18 (m, 2H), 6.92 (d, J=9.2 Hz, 1H), 6.86 (s, 1H), 6.03 (s, 2H), 4.32-4.29 (m, 2H), 3.45-3.43 (m, 2H), 2.41-2.40 (m, 2H), 2.20-2.13 (m, 1H), 1.95-1.74 (m, 5H), 1.56-1.54 (m, 2H). MS: m/z=523.2 ($M+H^+$)

(S)-2-(3-((S)-1-Carboxy-5-(4-(2-chloropyridin-4-yl) thiazol-2-ylamino)pentyl)ureido)-pentanedioic acid: P236

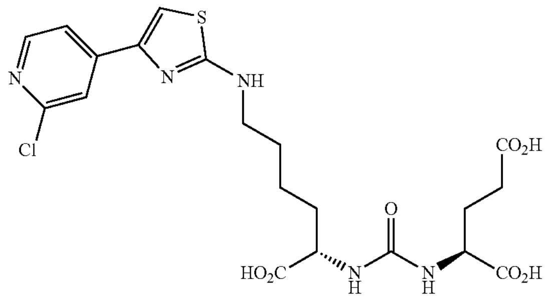 [SMILES: O=C(O)CC[C@H](NC(=O)N[C@@H](CCCCNc1nc(-c2ccnc(Cl)c2)cs1)C(=O)O)C(=O)O]

General experimental procedure for urea formation and tert-butyl deprotection reaction was followed. $^1$H NMR ($CD_3OD$, 400 MHz), δ: 8.34 (d, J=5.2 Hz, 1H), 7.84 (d, J=1.2 Hz, 1H), 7.74 (d, J=5.2 Hz, 1H), 7.35 (s, 1H), 4.35-4.33 (m, 2H), 3.41-3.40 (m, 2H), 2.44-2.42 (m, 2H), 2.20-2.15 (m, 1H), 1.95-1.82 (m, 2H), 1.80-1.72 (m, 3H), 1.60-1.55 (m, 2H). MS: m/z=514.1 (M+H$^+$).

(S)-2-(3-((S)-1-Carboxy-2-(4-(4-(2-(4-(3-fluoropropyl)-1H-1,2,3-triazol-1-yl)acetyl)piperazine-1-carboxamido)phenyl)ethyl)ureido)pentanedioic acid: P237

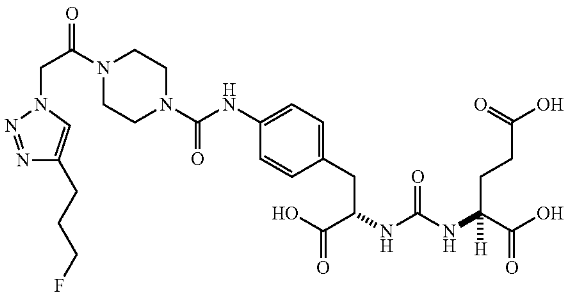

General experimental procedure for click reaction was followed. Reaction was performed on a 7.2 mg scale of (S)-2-(3-((S)-2-(4-(4-(2-azidoacetyl)piperazine-1-carboxamido)phenyl)-1-carboxyethyl)ureido)pentanedioic acid. After HPLC purification, P237 (5.0 mg, 60%) was obtained as a white solid. $^1$H NMR ($CD_3OD$, 400 MHz) δ 7.77 (s, 1H), 7.27-7.31 (m, 2H), 7.14-7.18 (m, 2H), 5.49 (s, 2H), 4.50-4.56 (m, 2H), 4.43 (t, J=5.9 Hz, 1H), 4.28 (dd, J=8.6, 4.7 Hz, 1H), 3.64-3.71 (m, 6H), 3.56-3.63 (m, 2H), 3.07-3.14 (m, 1H), 2.97 (dd, J=13.7, 6.7 Hz, 1H), 2.83-2.88 (m, 2H), 2.32-2.44 (m, 2H), 2.00-2.17 (m, 3H), 1.81-1.91 (m, 1H). MS: m/z=635 (M+H$^+$).

(2S,2'S)-2,2'-(((((1S,1'S)-(((5-(4-(3-Fluoropropyl)-1H-1,2,3-triazol-1-yl)isophthaloyl)bis(azanediyl))bis(4,1-phenylene))bis(1-carboxyethane-2,1-diyl))bis(azanediyl))bis(carbonyl))bis(azanediyl))dipentanedioic acid: P238

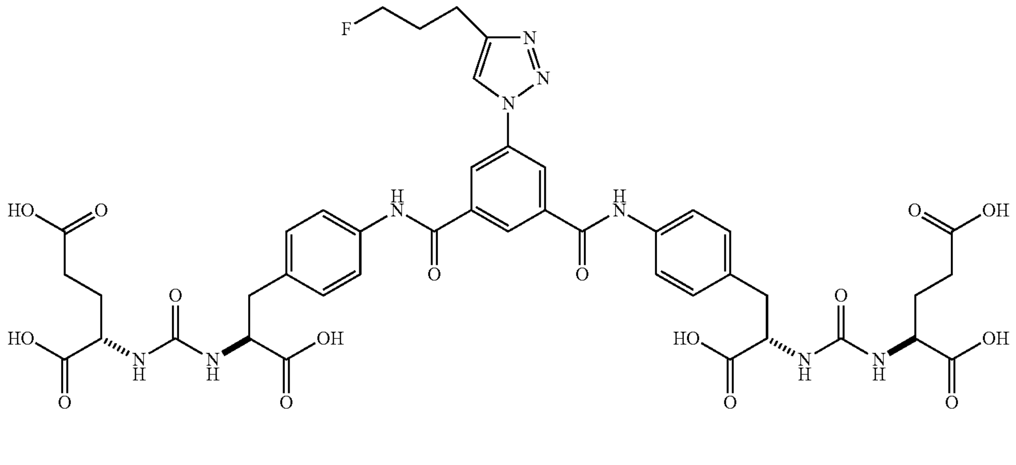

General experimental procedure for click reaction was followed. Reaction was performed on a 16.0 mg scale of (2S,2'S)-2,2'-(((((1S,1'S)-(((5-azidoisophthaloyl)bis(azanediyl))bis(4,1-phenylene))bis(1-carboxyethane-2,1-diyl))bis(azanediyl))bis(carbonyl))bis(azanediyl))-dipentanedioic acid. After HPLC purification, P238 (8.7 mg, 49%) was obtained as a white solid. $^1H$ NMR ($CD_3OD$, 400 MHz) δ 8.52-8.67 (m, 4H), 7.68 (d, J=8.6 Hz, 4H), 7.26-7.30 (m, 4H), 4.47-4.62 (m, 4H), 4.30 (dd, J=8.6, 5.1 Hz, 2H), 3.12-3.19 (m, 2H), 2.94-3.08 (m, 4H), 2.33-2.46 (m, 4H), 2.09-2.22 (m, 4H), 1.82-1.92 (m, 2H). MS: m/z=964 ($M+H^+$).

(9R,13S)-3,7,11-Trioxo-1-phenyl-2-oxa-4,8,12-triazapentadecane-9,13,15-tricarboxylic acid: P239

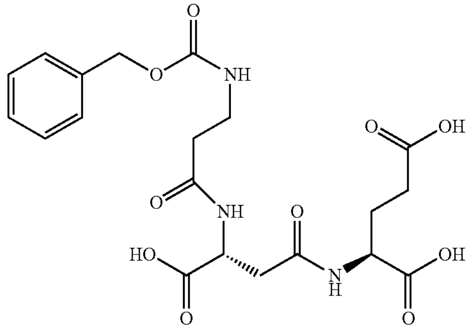 [SMILES: O=C(O)CC[C@H](NC(=O)C[C@@H](NC(=O)CCNC(=O)OCc1ccccc1)C(=O)O)C(=O)O]

General experimental procedure for urea formation and tert-butyl deprotection reaction was followed. After HPLC purification, P239 (5.5 mg, 21%) was obtained. $^1H$ NMR ($CD_3OD$, 400 MHz) δ 7.25-7.41 (m, 5H), 5.06 (s, 2H), 4.70-4.78 (m, 1H), 4.40-4.49 (m, 1H), 3.39 (t, J=6.8 Hz, 2H), 2.79-2.87 (m, 1H), 2.67-2.75 (m, 1H), 2.44 (t, J=7.2 Hz, 2H), 2.39 (t, J=8.0 Hz, 2H), 2.11-2.22 (m, 1H), 1.85-1.97 (m, 1H). MS: m/z=468 ($M+H^+$).

(S)-2-(3-((S)-1-Carboxy-2-(4-(4-(4-(3-fluoropropyl)-1H-1,2,3-triazol-1-yl)-phenyl)-thiazol-2-yl)amino)phenyl)ethyl)ureido)pentanedioic acid: P240

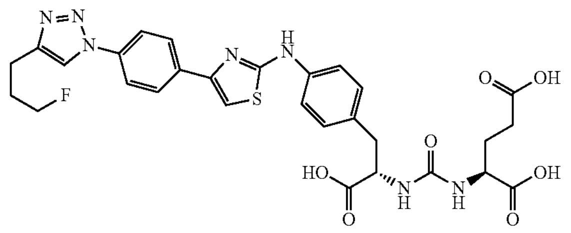 [SMILES: O=C(O)CC[C@H](NC(=O)N[C@@H](Cc1ccc(Nc2nc(-c3ccc(-n4cc(CCCF)nn4)cc3)cs2)cc1)C(=O)O)C(=O)O]

General procedure for click chemistry was followed. Reaction was performed on a 6 mg scale. After HPLC purification system P240 (3.8 mg, 55%) was obtained. $^1H$ NMR ($CD_3OD$, 400 MHz) δ 8.34 (s, 1H), 8.11-8.09 (dd, J=6.8, 2.0 Hz, 2H), 7.89-7.87 (dd, J=6.8, 2.0 Hz, 2H), 7.64-7.62 (dd, J=6.8, 2.0 Hz, 2H), 7.22 (d, J=8.8 Hz, 1H), 7.18 (s, 2H), 4.60-4.46 (m, 3H), 4.31-4.28 (dd, J=8.8, 5.2 Hz, 1H), 3.16-3.09 (m, 1H), 3.04-3.00 (dd, J=14.4, 6.8 Hz, 1H), 2.93 (t, J=7.6 Hz, 1H), 2.41-2.37 (m, 2H), 2.20-2.08 (m, 2H), 1.92-1.82 (m, 1H). MS: m/z=640 ($M+H^+$).

(S)-2-(3-((S)-1-Carboxy-2-(4-(4-fluorobenzamido)-phenyl)-phenyl)ethyl)-ureido)-pentanedioic acid: P241

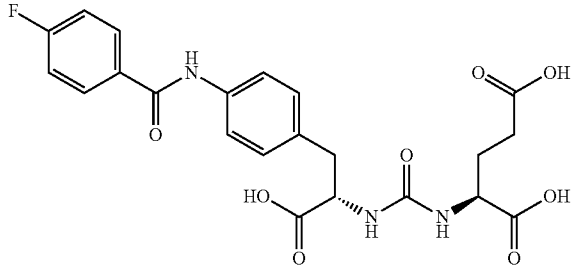 [SMILES: O=C(O)CC[C@H](NC(=O)N[C@@H](Cc1ccc(NC(=O)c2ccc(F)cc2)cc1)C(=O)O)C(=O)O]

General procedure for amide coupling and t-butyl group deprotection was followed. Reaction was performed on 45 mg scale. After HPLC purification, P241 (33 mg, 99%) was obtained. $^1H$ NMR ($CD_3OD$, 400 MHz) δ 7.99-7.96 (m, 2H), 7.60-7.58 (m, 2H), 7.26-7.21 (m, 4H), 4.55 (t, J=4.0 Hz, 1H), 4.30-4.27 (dd, J=8.8, 4.8 Hz, 1H), 3.16-3.11 (m, 1H), 3.04-2.99 (dd, J=16.0, 8.0 Hz, 1H), 2.41-2.36 (m, 2H), 2.18-2.08 (m, 1H), 1.92-1.82 (m, 1H). MS: m/z=4.76 ($M+H^+$).

(S)-2-(3-((S)-1-Carboxy-5-((5-((1-(2-fluoroethyl)-1H-1,2,3-triazol-4-yl)methoxy)-2-nitrophenyl)amino)pentyl)ureido)pentanedioic acid: P242

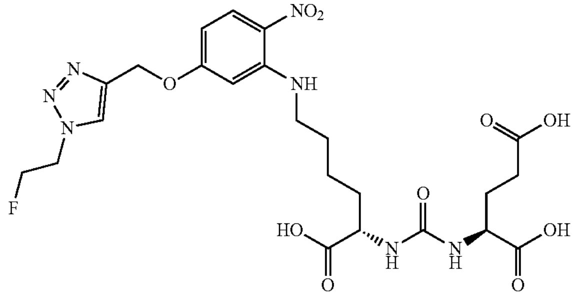 [SMILES: O=C(O)CC[C@H](NC(=O)N[C@@H](CCCCNc1cc(OCc2cn(CCF)nn2)ccc1[N+](=O)[O-])C(=O)O)C(=O)O]

General experimental procedure for the deprotection of the tert-butyl group was followed. Reaction was performed on a 100 mg scale. After HPLC purification, P242 (10 mg, 13%) was obtained. $^1H$ NMR ($CD_3OD$, 400 MHz) δ 8.11 (s, 1H), 8.07 (m, 1H), 6.46 (m, 1H), 6.30 (m, 1H), 5.28 (s, 2H), 4.75 (m, 4H), 4.28 (m, 2H), 3.35 (m, 2H), 2.38 (m, 2H), 2.10 (m, 1H), 1.88 (m, 2H), 1.74 (m, 3H), 1.54 (m, 2H). MS: m/z=584 ($M+H^+$).

(S)-2-((R)-3-Carboxy-3-(3-(2-(4-(3-fluoropropyl)-1H-1,2,3-triazol-1-yl)acetamido)propanamido)-propanamido)pentanedioic acid: P243

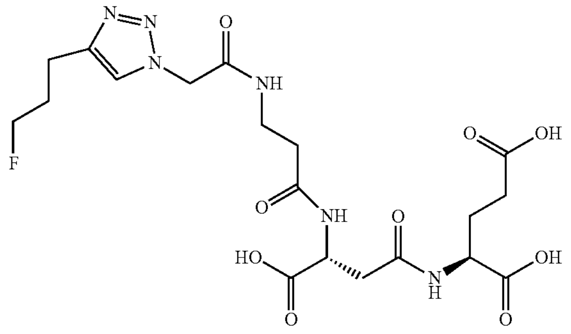 [SMILES: O=C(O)CC[C@H](NC(=O)C[C@@H](NC(=O)CCNC(=O)Cn1cc(CCCF)nn1)C(=O)O)C(=O)O]

General experimental procedure for urea formation and tert-butyl deprotection reaction was followed. After HPLC purification, P243 (4.3 mg, 38%) was obtained. $^1$H NMR ($CD_3OD$, 400 MHz) δ 7.83 (s, 1H), 5.12 (s, 2H), 4.73-4.80 (m, 1H), 4.48 (dt, J=47.2, 6.0 Hz, 2H), 4.38-4.47 (m, 1H), 3.44-3.56 (m, 2H), 2.69-2.88 (m, 4H), 2.36-2.52 (m, 4H), 1.88-2.24 (m, 4H). MS: m/z=503 (M+H$^+$).

(S)-2-(3-((S)-1-Carboxy-5-(4-(3-(2-(4-(3-fluoropropyl)-1H-1,2,3-triazol-1-yl)acetamido)phenyl)thiazol-2-ylamino)pentyl)ureido)pentanedioic acid: P244

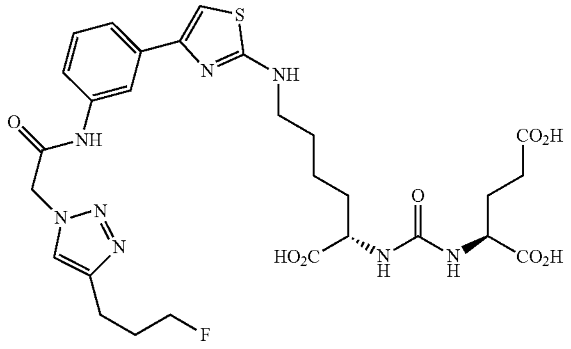 [SMILES: O=C(O)CC[C@H](NC(=O)N[C@@H](CCCCNc1nc(-c2cccc(NC(=O)Cn3cc(CCCF)nn3)c2)cs1)C(=O)O)C(=O)O]

General procedure for click chemistry was followed. $^1$H NMR ($CD_3OD$, 400 MHz) δ 8.06 (s, 1H), 7.88 (s, 1H), 7.46-7.44 (m, 3H), 6.99 (s, 1H), 5.34 (s, 2H), 4.56-4.30 (m, 3H), 3.45-3.41 (m, 2H), 3.21-3.20 (m, 1H), 2.88-2.85 (m, 2H), 2.40-2.39 (m, 2H), 2.18-2.08 (m, 1H), 1.98-1.65 (m, 5H), 1.60-1.55 (m, 2H). MS: m/z=663.1 (M+H$^+$)

(S)-2-((R)-3-Carboxy-3-(3-(4-(4-(3-fluoropropyl)-1H-1,2,3-triazol-1-yl)benzamido)propanamido)-propanamido)pentanedioic acid: P245

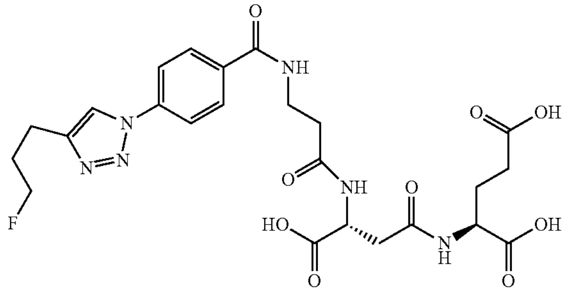 [SMILES: O=C(O)CC[C@H](NC(=O)C[C@@H](NC(=O)CCNC(=O)c1ccc(-n2cc(CCCF)nn2)cc1)C(=O)O)C(=O)O]

General experimental procedure for urea formation and tert-butyl deprotection reaction was followed. After HPLC purification, P245 (7.2 mg, 21%) was obtained. $^1$H NMR ($CD_3OD$, 400 MHz) δ 8.44 (s, 1H), 8.03 (d, J=8.8 Hz, 2H), 7.96 (d, J=8.8 Hz, 2H). 4.72-4.81 (m, 1H), 4.52 (dt, J=47.2, 6.0 Hz, 2H), 4.38-4.42 (m, 1H), 3.58-72 (m, 2H), 2.81-2.98 (m, 2H), 2.68-2.79 (m, 1H), 2.54-2.63 (m, 2H), 2.39 (t, J=7.6 Hz, 2H), 2.03-2.21 (m, 3H), 1.85-1.95 (m, 1H). MS: m/z=565 (M+H$^+$).

(2S,2'S)-2,2'-(((((1S,1'S)-((5-(4-(3-Fluoropropyl)-1H-1,2,3-triazol-1-yl)isophthaloyl)bis(azanediyl))bis(1-carboxypentane-5,1-diyl))bis(azanediyl))bis(carbonyl))bis(azanediyl))dipentanedioic acid: P246

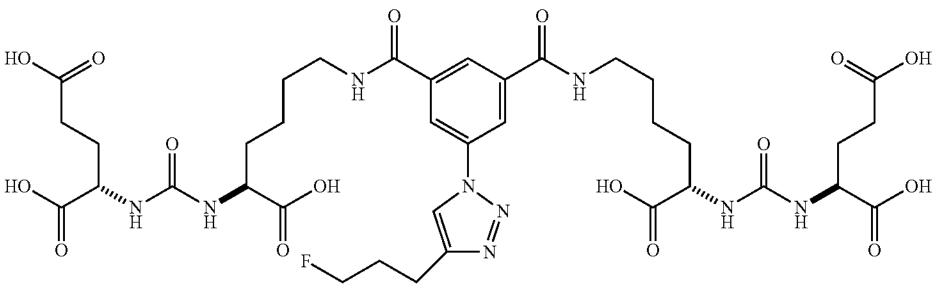

General experimental procedure for click reaction was followed. Reaction was performed on a 7.8 mg scale of (2S,2'S)-2,2'-(((((1S,1'S)-((5-azidoisophthaloyl)bis(azanediyl))bis(1-carboxypentane-5,1-diyl))bis(azanediyl))bis(carbonyl))bis(azanediyl))dipentanedioic acid. After HPLC purification, P246 (5.0 mg, 58%) was obtained as a white solid. $^1$H NMR ($CD_3OD$, 400 MHz) δ 8.76 (t, J=5.7 Hz, 1H), 8.43-8.52 (m, 3H), 8.33-8.41 (m, 1H), 4.60 (t, J=5.9 Hz, 1H), 4.48 (t, J 5.9 Hz, 1H), 4.30 (m, 4H), 3.42-3.49 (m, 4H), 2.92-2.98 (m, 2H), 2.34-2.47 (m, 4H), 2.05-2.22 (m, 4H), 1.82-1.96 (m, 4H), 1.63-1.78 (m, 6H), 1.45-1.61 (m, 4H). MS: m/z=896 (M+H$^+$).

(S)-2-(3-((S)-1-Carboxy-5-(6-((1-(2-fluoroethyl)-1H-1,2,3-triazol-4-yl)methoxy)-2-oxo-2,3-dihydro-1H-benzo[d]imidazol-1-yl)pentyl)ureido)pentanedioic acid: P247

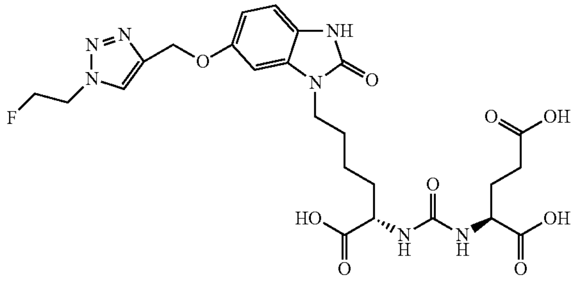 [SMILES: O=C(O)CC[C@H](NC(=O)N[C@@H](CCCCn1c(=O)[nH]c2ccc(OCc3cn(CCF)nn3)cc21)C(=O)O)C(=O)O]

General experimental procedure for the deprotection of the tert-butyl group was followed. Reaction was performed on a 25 mg scale. After HPLC purification, P247 (3.0 mg, 15%) was obtained. $^1$H NMR ($CD_3OD$, 400 MHz) δ 8.01 (s, 1H), 6.86 (m, 1H), 6.80 (s, 1H), 6.63 (m, 1H), 5.11 (s, 2H), 4.77 (m, 2H), 4.66 (m, 3H), 4.19 (m, 2H), 3.77 (m, 2H), 2.30 (m, 2H), 2.02 (m, 1H), 1.78 (m, 2H), 1.62 (m, 2H), 1.37 (m, 2H). MS: m/z=580 (M+H$^+$)

(S)-2-(3-((S)-1-Carboxy-2-(4-(4-(4-(4-(3-fluoropropyl)-1H-1,2,3-triazol-1-yl)benzoyl)piperazine-1-carboxamido)phenyl)ethyl)ureido)pentanedioic acid: P248

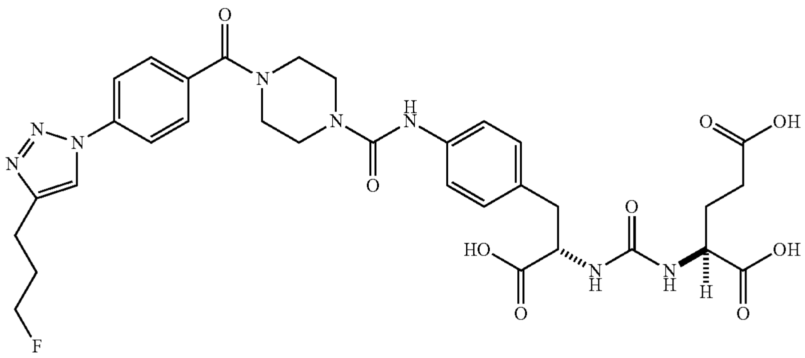

General experimental procedure for click reaction was followed. Reaction was performed on a 25.0 mg scale of (S)-2-(3-((S)-2-(4-(4-(4-azidobenzoyl)piperazine-1-carboxamido)phenyl)-1-carboxyethyl)ureido)pentanedioic acid. After HPLC purification, P248 (19.0 mg, 67%) was obtained as a white solid. $^1$H NMR ($CD_3OD$, 400 MHz) δ 8.44 (s, 1H), 7.97-8.01 (m, 2H), 7.67-7.70 (m, 2H), 7.27-7.30 (m, 2H), 7.14-7.17 (m, 2H), 4.46-4.60 (m, 3H), 4.28 (dd, J=8.6, 4.7 Hz, 1H), 3.83 (br. s., 2H), 3.66 (br. s., 3H), 3.57 (br. s., 3H), 3.04-3.14 (m, 1H), 2.91-3.00 (m, 3H), 2.32-2.43 (m, 2H), 2.03-2.20 (m, 3H), 1.78-1.95 (m, 1H). MS: m/z=697 (M+H$^+$).

(S)-2-(3-((S)-5-(4-(4-Azidobenzoyl)piperazine-1-carboxamido)-1-carboxypentyl)-ureido)pentanedioic acid: P249 Precursor

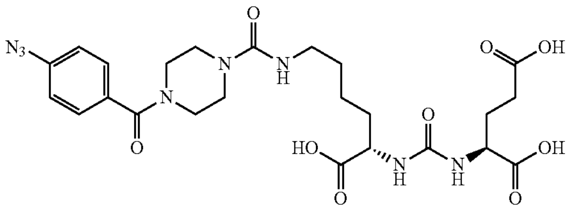 [SMILES: [N-]=[N+]=Nc1ccc(C(=O)N2CCN(C(=O)NCCCC[C@H](NC(=O)N[C@@H](CCC(=O)O)C(=O)O)C(=O)O)CC2)cc1]

General procedure for amide coupling and t-butyl group was followed. Reaction was performed on 88 mg scale. After HPLC purification, P-249 Precursor (39 mg, 46%) was obtained. $^1$H NMR ($CD_3OD$, 400 MHz) δ 7.49-7.47 (m, 2H), 7.18-7.15 (m, 2H), 4.31-4.24 (m, 2H), 3.80-3.55 (br m, 8H), 3.17 (t, J=6.8 Hz, 1H), 2.43-2.38 (m, 2H), 2.18-2.08 (m, 1H), 1.92-1.79 (m, 1H), 1.70-1.38 (m, 5H). MS: m/z=577 (M+H$^+$).

(S)-2-(3-((S)-1-Carboxy-5-(4-(4-(4-(3-fluoropropyl)-1H-1,2,3-triazol-1-yl)benzoyl)-piperizine-1-carboxamido)pentyl)ureido)pentanedioic acid: P249

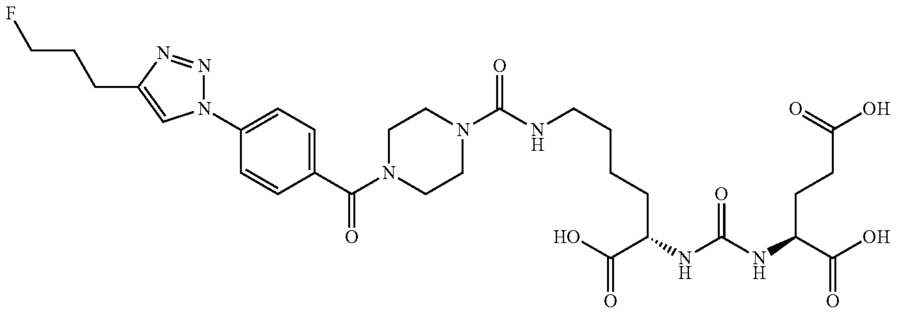 [SMILES: O=C(O)CC[C@H](NC(=O)N[C@@H](CCCCNC(=O)N1CCN(C(=O)c2ccc(-n3cc(CCCF)nn3)cc2)CC1)C(=O)O)C(=O)O]

General procedure for click chemistry was followed. Reaction was performed on a 10 mg scale. After HPLC purification, P249 (9 mg, 78%) was obtained. $^{1}$H NMR ($CD_3OD$, 400 MHz) δ 8.43 (s, 1H), 7.98-7.96 (dd, J=6.4, 1.6 Hz, 2H), 7.67-7.65 (dd, J=6.4, 1.6 Hz, 2H), 4.58 (t, J=6.0 Hz, 1H), 4.46 (t, J=6.0 Hz, 1H), 4.31-4.25 (m, 2H), 3.84-3.52 (br m, 2H), 3.56-3.42 (br m, 6H), 3.17 (t, J=7.2 Hz, 2H), 2.92 ((t, J=7.2 Hz, 2H), 2.44-2.38 (m, 2H), 2.18-2.08 (m, 2H), 1.94-1.80 (m, 2H), 1.70-1.40 (m, 4H). MS: m/z=663 (M+H$^{+}$).

(S)-2-(3-((S)-1-Carboxy-2-(1-((4-(4-(3-fluoropropyl)-1H-1,2,3-triazol-1-yl)phenyl)carbamothioyl)piperidin-4-yl)ethyl)ureido)pentanedioic acid: P250

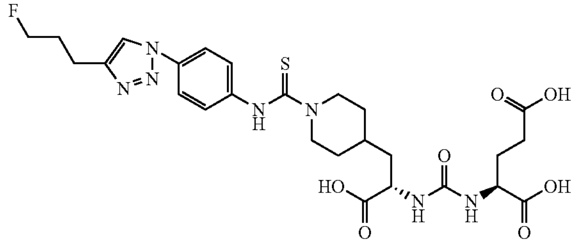 [SMILES: O=C(O)CC[C@H](NC(=O)N[C@@H](CC1CCN(C(=S)Nc2ccc(-n3cc(CCCF)nn3)cc2)CC1)C(=O)O)C(=O)O]

The compound P250 was synthesized using the same procedures for the preparation of P200. $^{1}$H NMR ($CD_3OD$, 400 MHz) δ 8.31 (s, 1H), 7.77-7.74 (m, 2H), 7.49-7.46 (m, 2H), 4.86-4.75 (m, 2H), 4.58 (t, J=6.0 Hz, 1H), 4.46 (t, J=6.0 Hz, 1H), 4.42-4.29 (m, 2H), 3.13 (m, 2H), 2.91 (t, J=7.2 Hz, 2H), 2.41 (m, 2H), 2.20-2.05 (m, 3H), 1096-1.73 (m, 5H), 1.67-1.59 (m, 1H), 1.40-1.24 (m, 2H). MS: m/z=608 (M+H$^{+}$).

(S)-2-(3-((S)-1-Carboxy-5-((5-(2-(2-(2-(4-(3-fluoropropyl)-1H-1,2,3-triazol-1-yl)ethoxy)ethoxy)ethoxy)-2-nitrophenyl)amino)pentyl)ureido)pentanedioic acid: P251

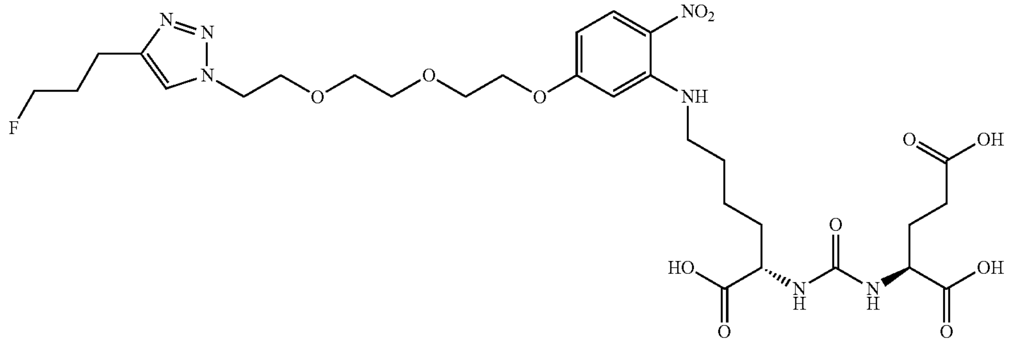 [SMILES: O=C(O)CC[C@H](NC(=O)N[C@@H](CCCCNc1cc(OCCOCCOCCn2cc(CCCF)nn2)ccc1[N+](=O)[O-])C(=O)O)C(=O)O]

General experimental procedure for the deprotection of the tert-butyl group was followed. Reaction was performed on a 40 mg scale. After HPLC purification, P251 (9.0 mg, 28%) was obtained. $^1H$ NMR ($CD_3OD$, 400 MHz) δ 8.06 (m, 1H), 7.80 (s, 1H), 6.30 (s, 1H), 6.23 (m, 1H), 4.53 (m, 2H), 4.46 (m, 1H), 4.34 (m, 1H), 4.29 (m, 2H), 4.18 (m, 2H), 3.86 (m, 2H), 3.79 (m, 2H), 3.63 (m, 4H), 3.33 (m, 2H), 2.74 (m, 2H), 2.39 (m, 2H), 2.13 (m, 1H), 2.12 (m, 2H), 1.99 (m, 2H), 1.85 (m, 3H), 1.54 (m, 2H). MS: m/z=700 (M+$H^+$)

(2S,2'S)-2,2'-(((3R,3'R)-3,3'-((3,3'-((5-(4-(3-Fluoropropyl)-1H-1,2,3-triazol-1-yl)isophthaloyl)bis(azanediyl))bis(propanoyl))bis(azanediyl))bis(3-carboxypropanoyl))bis(azanediyl))dipentanedioic acid: P252

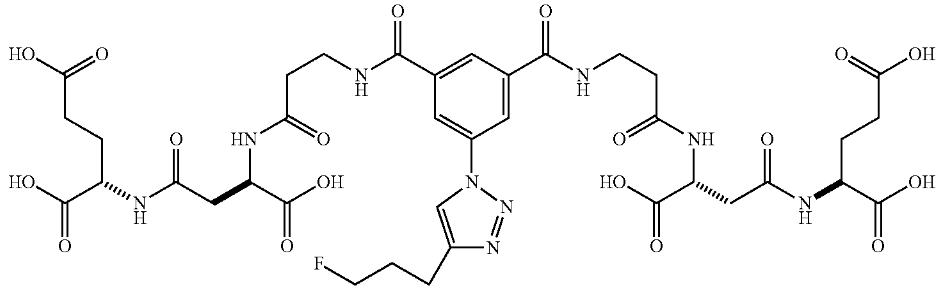

General experimental procedure for click reaction was followed. Reaction was performed on a 12.7 mg scale of (2S,2'S)-2,2'-(((3R,3'R)-3,3'-((3,3'-((5-azidoisophthaloyl)bis(azanediyl))bis(propanoyl))bis(azanediyl))bis(3-carboxypropanoyl))bis(azanediyl))dipentanedioic acid. After HPLC purification, P252 (9.6 mg, 69%) was obtained as a white solid. $^1H$ NMR ($CD_3OD$, 400 MHz) δ 8.46-8.50 (m, 3H), 8.37-8.41 (m, 1H), 4.82 (dd, J=7.8, 5.1 Hz, 2H), 4.59 (t, J=5.9 Hz, 1H), 4.47 (t, J=5.9 Hz, 1H), 4.35 (dd, J=9.0, 5.1 Hz, 2H), 3.67-3.78 (m, 4H), 2.78-2.97 (m, 6H), 2.53-2.68 (m, 4H), 2.37 (t, J=7.6 Hz, 4H), 2.07-2.21 (m, 4H), 1.84-1.94 (m, 2H). MS: m/z=924 (M+$H^+$).

(S)-2-(3-((S)-1-Carboxy-2-(4-(3-carboxy-5-(4-(3-fluoropropyl)-1H-1,2,3-triazol-1-yl)benzamido)phenyl)ethyl)ureido)pentanedioic acid: P253

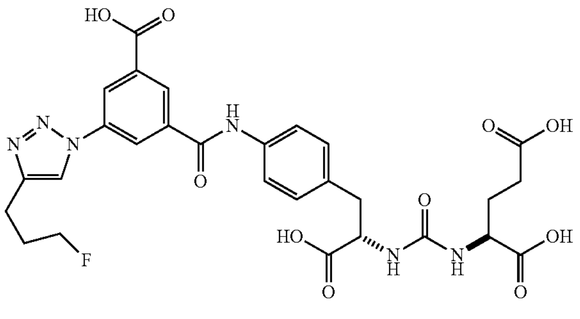

General experimental procedure for click reaction was followed. Reaction was performed on a 3.0 mg scale of (S)-2-(3-((S)-2-(4-(3-azido-5-carboxybenzamido)phenyl)-1-carboxyethyl)ureido)pentanedioic acid. After HPLC purification, P253 (2.5 mg, 71%) was obtained as a white solid. $^1$H NMR ($CD_3OD$, 400 MHz) δ 8.63-8.68 (m, 3H), 8.55 (s, 1H), 7.67 (m, J=8.2 Hz, 2H), 7.27 (m, J=8.2 Hz, 2H), 4.55-4.62 (m, 2H), 4.48 (t, J=5.9 Hz, 1H), 4.30 (dd, J=8.6, 5.1 Hz, 1H), 3.11-3.20 (m, 1H), 2.93-3.07 (m, 3H), 2.33-2.46 (m, 2H), 2.04-2.22 (m, 3H), 1.83-1.94 (m, 1H). MS: m/z=629 (M+H$^+$).

(S)-2-(3-((S)-1-Carboxy-5-(4-(3-(1-(4-(3-fluoropropyl)-1H-1,2,3-triazol-1-yl)-2-oxo-6,9,12,15-tetraoxa-3-azaoctadecanamido)phenyl)thiazol-2-ylamino) pentyl)ureido)-pentanedioic acid: P254

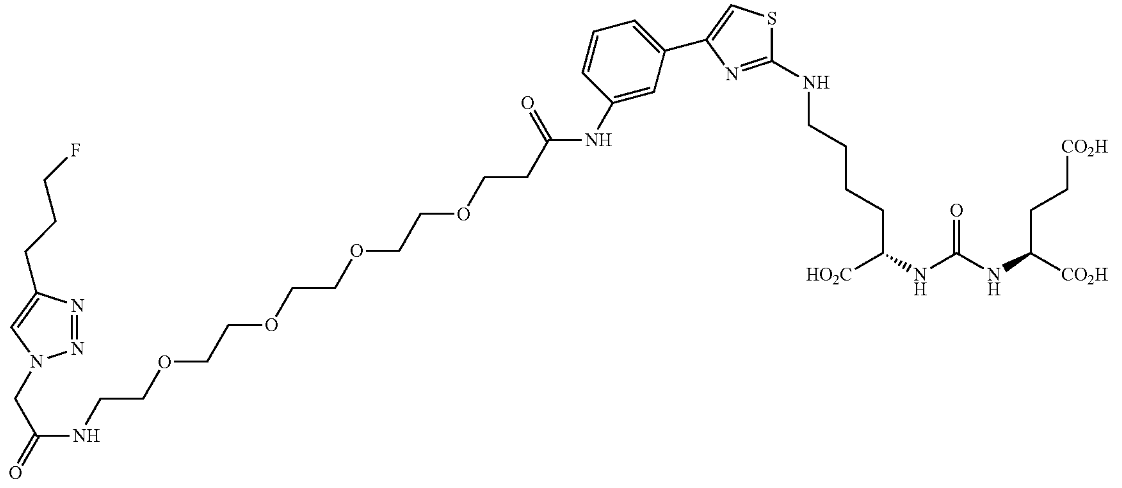 [SMILES: O=C(O)CC[C@H](NC(=O)N[C@@H](CCCCNc1nc(-c2cccc(NC(=O)CCOCCOCCOCCOCCNC(=O)Cn3cc(CCCF)nn3)c2)cs1)C(=O)O)C(=O)O]

General experimental procedure for click reaction was followed. $^1$H NMR ($CD_3OD$, 400 MHz), δ 7.58-7.54 (m, 2H), 7.29-7.22 (m, 3H), 6.77 (s, 1H), 4.91 (s, 2H), 4.36-4.22 (m, 2H), 3.70-3.68 (m, 2H), 3.52-3.36 (m, 14H), 3.33-3.15 (m, 4H), 2.59-2.51 (m, 4H), 2.29-2.27 (m, 2H), 1.85-1.52 (m, 8H), 1.28-1.24 (m, 2H). MS: m/z=910.2 (M+H$^+$).

(S)-2-(3-((S)-2-Carboxy-1-(3-(4-(4-(3-fluoropropyl)-1H-1,2,3-triazol-1-yl)butanamido)-henyl)propan-2-yl)ureido)pentanedioic acid: P255

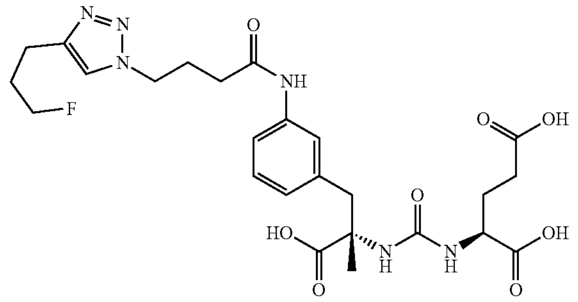 [SMILES: C[C@@](Cc1cccc(NC(=O)CCCn2cc(CCCF)nn2)c1)(NC(=O)N[C@@H](CCC(=O)O)C(=O)O)C(=O)O]

General procedure for click chemistry was followed. Reaction was performed on 8.10 mg scale. After HPLC purification, P255 (6.5 mg. 68%) was obtained. $^1$H NMR ($CD_3OD$, 400 MHz) δ 7.79 (s, 1H), 7.59-7.56 (m, 1H), 7.18 (t, J=7.6 Hz, 2H), 6.90 (d, J=8.0 Hz, 1H), 4.52-4.44 (m, 3H), 4.39 (t, J=6.0 Hz, 1H), 4.35-4.32 (dd, J=8.0 and 4.0 Hz, 1H), 3.33 (d, J=13.2 Hz, 1H), 3.18 (d, J=13.2 Hz, 1H), 2.78 (t, J=8.0 Hz, 2H) 2.46-2.38 (m, 4H), 2.30-2.12 (m, 3H), 2.08-1.86 (m, 3H), 1.54 (s, 3H); MS: m/z=565 (M+H$^+$), 587 (M+Na$^+$).

(S)-2-(3-((S)-2-Carboxy-1-(3-(2-(4-(3-fluoropropyl)-1H-1,2,3-triazol-1-yl)acetamido)-phenyl)propan-2-yl)ureido)pentanedioic acid: P256

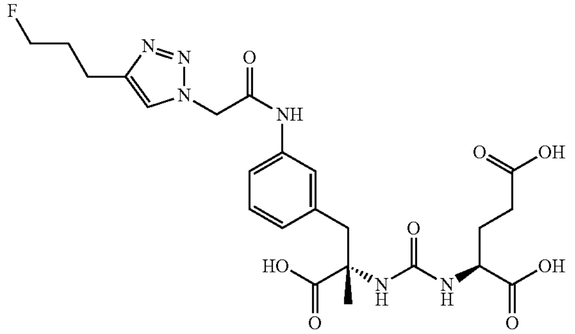 [SMILES: C[C@@](Cc1cccc(NC(=O)Cn2cc(CCCF)nn2)c1)(NC(=O)N[C@@H](CCC(=O)O)C(=O)O)C(=O)O]

General procedure for click chemistry was followed. Reaction was performed on a 10.5 mg scale. After HPLC purification P256 (10.5 mg, 84%) was obtained. $^1$H NMR ($CD_3OD$, 400 MHz) δ 7.84 (s, 1H), 7.56-7.54 (dd, J=8.0, 2.4 Hz, 1H), 7.19 (t, J=8.0 Hz, 2H), 6.93 (d, J=7.6 Hz, 1H), 5.28 (s, 2H), 4.52 (t, J=5.6 Hz, 1H), 4.41 (t, J=5.6 Hz, 1H), 4.35-4.32 (m, 2H), 3.84-3.74 (m, 2H), 3.33 (d, J=13.2 Hz, 1H), 3.20 (d, J=13.2 Hz, 1H), 2.84 (t, J=8.0 Hz, 2H) 2.44-2.39 (m, 2H), 2.21-2.00 (m, 3H), 1.94-1.84 (m, 1H), 1.53 (s, 3H); MS: m/z=537 ($M+H^+$, 559 ($M+Na^+$).

2-((S)-4-((1-(4-(4-(3-Fluoropropyl)-1H-1,2,3-triazol-1-yl)benzoyl)piperidin-4-yl)methyl)-2,5-dioxoimidazolidin-1-yl)pentanedioic acid: P257

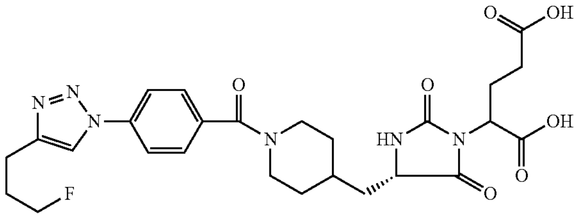 [SMILES: O=C(O)CCC(C(=O)O)N1C(=O)N[C@@H](CC2CCN(C(=O)c3ccc(-n4cc(CCCF)nn4)cc3)CC2)C1=O]

General experimental procedures for click chemistry and the deprotection of the tert-butyl group were followed. After HPLC purification, P257 was obtained. MS: m/z=559 ($M+H^+$).

(S)-2-(3-((S)-5-(4-(1-(14-Amino-3,6,9,12-tetraoxatetradecyl)-1H-1,2,3-triazol-4-yl)benzamido)-1-carboxypentyl)ureido)pentanedioic acid: P258

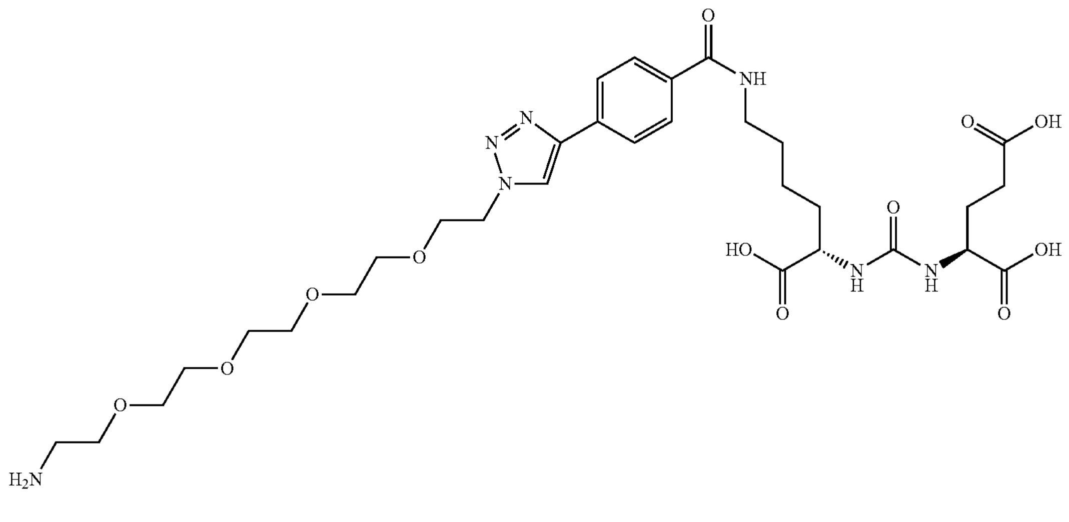 [SMILES: NCCOCCOCCOCCOCCn1cc(-c2ccc(C(=O)NCCCC[C@H](NC(=O)N[C@@H](CCC(=O)O)C(=O)O)C(=O)O)cc2)nn1]

General experimental procedure for the deprotection of the tert-butyl group was followed. Reaction was performed on a 20 mg scale. After HPLC purification, P258 (3.0 mg, 19%) was obtained. $^1H$ NMR ($CD_3OD$, 400 MHz) δ 8.38 (s, 1H), 7.80 (m, 4H) 4.56 (m, 2H), 4.20 (m, 2H), 3.86 (m, 2H), 3.50 (m, 13H), 3.32 (m, 2H), 2.99 (m, 2H), 2.31 (m, 2H), 2.04 (m, 1H), 1.80 (m, 2H), 1.60 (m, 3H), 1.40 (m, 2H), 0.01 (m, 1H). MS: m/z=710 (M+H$^+$).

(S)-2-(3-((S)-1-Carboxy-5-(3-carboxy-5-(4-(3-fluoropropyl)-1H-1,2,3-triazol-1-yl)benzamido)pentyl) ureido)pentanedioic acid: P259

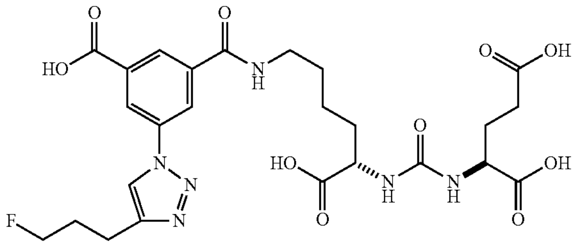

General experimental procedure for click reaction was followed. Reaction was performed on a 5.0 mg scale of (S)-2-(3-((S)-5-(3-azido-5-carboxybenzamido)-1-carboxypentyl)ureido)pentanedioic acid. After HPLC purification, P259 (2.0 mg, 34%) was obtained as a white solid. $^1H$ NMR ($CD_3OD$, 400 MHz) δ 8.84 (t, J=5.5 Hz, 1H), 8.60-8.62 (m, 1H), 8.49-8.57 (m, 3H), 4.59 (t, J=5.9 Hz, 1H), 4.47 (t, J=5.9 Hz, 1H), 4.24-4.34 (m, 2H), 3.37-3.52 (m, 2H), 2.92-2.97 (m, 2H), 2.33-2.44 (m, 2H), 2.03-2.20 (m, 3H), 1.82-1.94 (m, 2H), 1.64-1.76 (m, 3H), 1.46-1.57 (m, 2H). MS: m/z=595 (M+H$^+$).

(S)-2-(3-((S)-1-Carboxy-5-(3-(diethylcarbamoyl)-5-(4-(3-fluoropropyl)-1H-1,2,3-triazol-1-yl)benzamido)pentyl)ureido)pentanedioic acid: P260

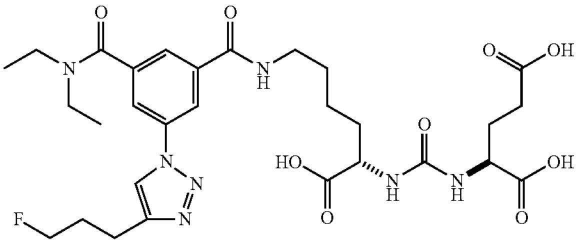

General experimental procedure for click reaction was followed. Reaction was performed on a 7.0 mg scale of (S)-2-(3-((S)-5-(3-azido-5-(diethylcarbamoyl)benzamido)-1-carboxypentyl)ureido)pentanedioic acid. After HPLC purification, P260 (4.3 mg, 53%) was obtained as a white solid. $^1H$ NMR ($CD_3OD$, 400 MHz) δ 8.50 (s, 1H), 8.42 (t, J=1.8 Hz, 1H), 8.07 (t, J=1.6 Hz, 1H), 7.92 (t, J=1.4 Hz, 1H), 4.59 (t, J=5.9 Hz, 1H), 4.47 (t, J=5.9 Hz, 1H), 4.24-4.34 (m, 2H), 3.60 (q, J=7.0 Hz, 2H), 3.33-3.48 (m, 4H), 2.91-2.96 (m, 2H), 2.33-2.44 (m, 2H), 2.04-2.20 (m, 3H), 1.81-1.94 (m, 2H), 1.62-1.76 (m, 3H), 1.43-1.56 (m, 2H), 1.30 (t, J=7.0 Hz, 3H), 1.17 (t, J=7.0 Hz, 3H). MS: m/z=650 (M+H$^+$).

(3S,7S,14S,23S,27S)-14-(2-(4-(3-Fluoropropyl)-1H-1,2,3-triazol-1-yl)acetamido)-5,13,17,25-tetraoxo-4,6,12,18,24,26-hexaazanonacosane-1,3,7,23,27,29-hexacarboxylic acid: P261

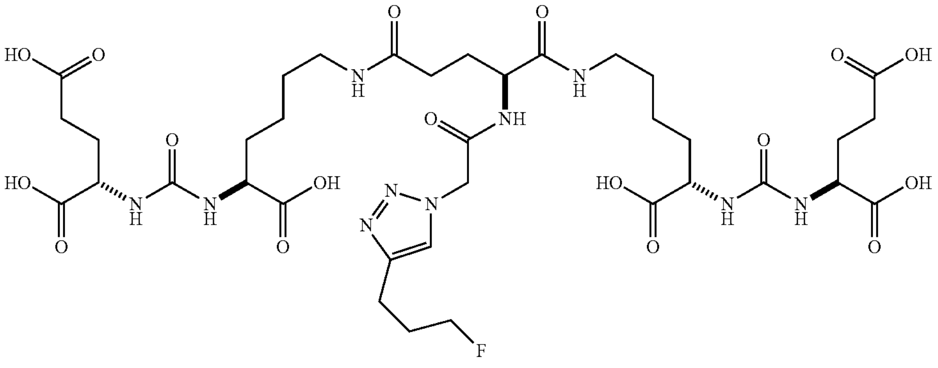

General experimental procedure for click reaction was followed. Reaction was performed on a 3.6 mg scale of (3S,7S,14S,23S,27S)-14-(2-azidoacetamido)-5,13,17,25-tetraoxo-4,6,12,18,24,26-hexaazanonacosane-1,3,7,23,27,29-hexacarboxylic acid. After HPLC purification, P261 (2.5 mg, 63%) was obtained as a white solid. $^1$H NMR ($CD_3OD$, 400 MHz) δ 7.85 (s, 1H), 5.21 (d, J=2.3 Hz, 2H), 4.53 (t, J=5.9 Hz, 1H), 4.41 (t, J=5.9 Hz, 1H), 4.22-4.36 (m, 5H), 3.11-3.26 (m, 4H), 2.84 (t, J=7.6 Hz, 2H), 2.35-2.47 (m, 4H), 2.23-2.35 (m, 2H), 2.06-2.19 (m, 4H), 1.74-2.05 (m, 6H), 1.46-1.70 (m, 6H), 1.33-1.46 (m, 4H). MS: m/z=919 ($M+H^+$).

(S)-2-(3-((S)-1-Carboxy-5-(4-(3-carboxy-5-(4-(3-fluoropropyl)-1H-1,2,3-triazol-1-yl)benzoyl)piperazine-1-carboxamido)pentyl)ureido)pentanedioic acid: P262

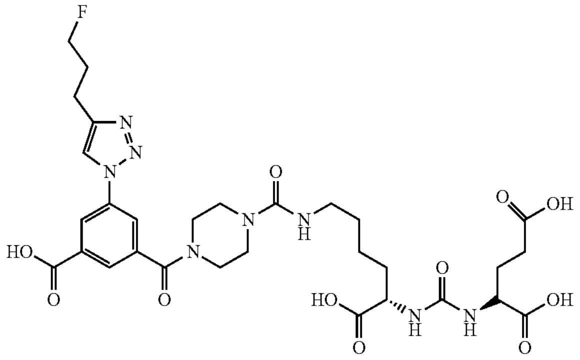

General procedure for "click chemistry was followed. Reaction was performed on a 5 mg scale. After HPLC purification, P262 (2.0 mg. 35%) was obtained; $^1$H NMR ($CD_3OD$, 400 MHz) δ 8.58 (t, J=1.6 Hz, 1H), 8.16 (dt, J=19.2, 1.2 Hz, 2H), 4.58 (t, J=6.0 Hz, 1H), 4.46 (t, J=6.0 Hz, 1H), 4.32-4.22 (m, 2H), 3.84-3.74 (m, 2H), 3.58-3.40 (m, 6H), 3.17 (t, J=6.8 Hz, 2H), 2.93 (t, J=8.0 Hz, 2H) 2.44-2.37 (m, 2H), 2.20-2.06 (m, 4H), 1.94-1.78 (m, 2H), 1.70-1.38 (m, 8H); MS: m/z 707 ($M+H^+$) and 729 ($M+Na^+$).

(2S,2'S)-2,2'-(((((1S,1'S)-((4,4'-(5-(4-(3-Fluoropropyl)-1H-1,2,3-triazol-1-yl)-isophthaloyl)bis(piperazine-1,1'-carbonyl))bis(azanediyl))bis(1-carboxypentane-5,1-diyl))bis(azanediyl))bis(carbonyl))bis(azanediyl))dipentanedioic acid: P263

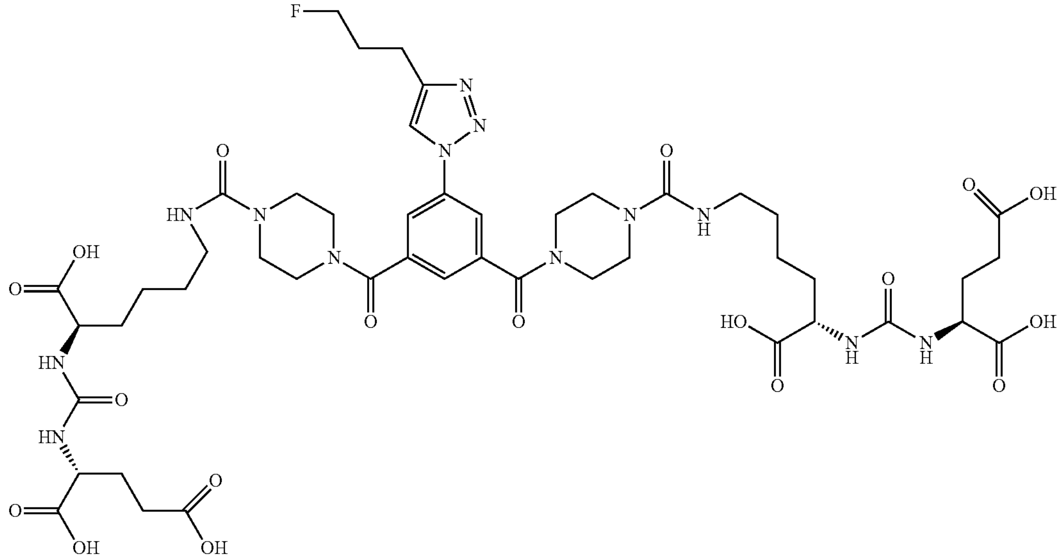 [SMILES: O=C(O)CC[C@H](NC(=O)N[C@@H](CCCCNC(=O)N1CCN(C(=O)c2cc(C(=O)N3CCN(C(=O)NCCCC[C@@H](NC(=O)N[C@H](CCC(=O)O)C(=O)O)C(=O)O)CC3)cc(-n3cc(CCCF)nn3)c2)CC1)C(=O)O)C(=O)O]

General procedure for click chemistry was followed. Reaction was performed on a 22 mg scale. After HPLC purification, P263 (6.0 mg. 25%) was obtained. $^1$H NMR ($CD_3OD$, 400 MHz) δ 8.48 (s, 1H), 8.08 (d, J=1.2 Hz, 2H), 7.60 (t, J=1.2 Hz, 1H), 4.58 (t, J=6.0 Hz, 1H), 4.46 (t, J=6.0 Hz, 1H), 4.32-4.22 (m, 4H), 3.86-3.74 (m, 4H), 3.58-3.40 (m, 12H), 3.17 (t, J=7.2 Hz, 4H), 2.92 (t, J=7.2 Hz, 2H) 2.46-2.34 (m, 4H), 2.18-2.06 (m, 2H), 1.94-1.78 (m, 3H), 1.70-1.38 (m, 8H). MS: m/z=1120 (M+H$^+$).

(2S,2'S)-2,2'-(((((1S,1'S)-((4,4'-(5-Azidoisophthaloyl)bis(piperazine-1,1'-carbonyl))-bis(azanediyl))bis(1-carboxypentane-5,1-diyl))-bis(azanediyl))-bis(carbonyl))-bis(azanediyl))dipentanedioic acid: P-263 Precursor

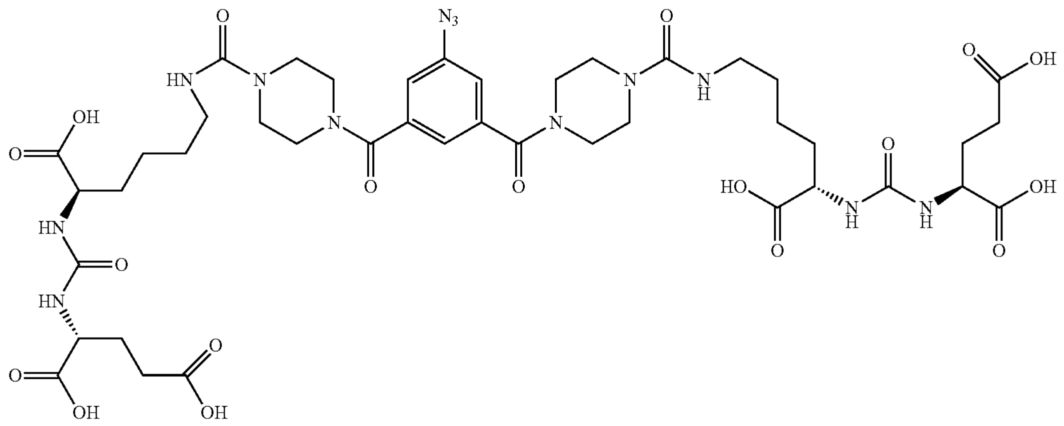 [SMILES: [N-]=[N+]=Nc1cc(C(=O)N2CCN(C(=O)NCCCC[C@H](NC(=O)N[C@@H](CCC(=O)O)C(=O)O)C(=O)O)CC2)cc(C(=O)N2CCN(C(=O)NCCCC[C@@H](NC(=O)N[C@H](CCC(=O)O)C(=O)O)C(=O)O)CC2)c1]

General procedure for amide coupling and t-butyl ester deprotection was followed. Reaction was performed on 67 mg scale. After HPLC purification, P-263 Precursor (44 mg, 44%) was obtained; $^1$H NMR ($CD_3OD$, 400 MHz): δ 7.27 (d, J=1.20 Hz, 1H), 7.26-7.24 (m, 2H), 4.32-4.24 (m, 4H), 3.70-3.60 (m, 4H), 3.55-3.25 (m, 14H), 3.17 (t, J=6.8 Hz, 4H), 2.46-2.34 (m, 4H), 2.18-2.08 (m, 2H), 1.93-1.79 (m, 4H), 1.72-1.38 (m, 10H). MS: m/z=1234 (M+H$^+$).

(S)-2-(3-((S)-1-Carboxy-5-(4-(3-(diethylcarbamoyl)-5-(4-(3-fluoropropyl)-1H-1,2,3-triazol-1-yl)benzoyl)piperazine-1-carboxamido)pentyl)ureido)pentanedioic acid: P264

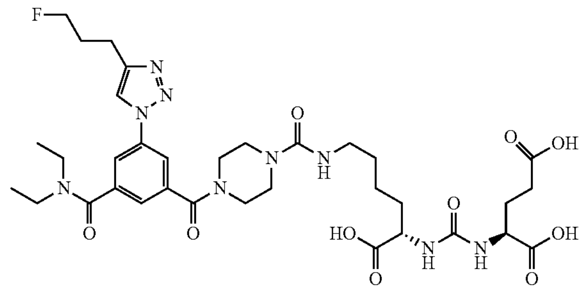 [SMILES: CCN(CC)C(=O)c1cc(C(=O)N2CCN(C(=O)NCCCC[C@H](NC(=O)N[C@@H](CCC(=O)O)C(=O)O)C(=O)O)CC2)cc(-n2cc(CCCF)nn2)c1]

General procedure for click chemistry was followed. Reaction was performed on 14 mg scale. After HPLC purification, P264 (3.0 mg, 19%) was obtained. $^1$H NMR ($CD_3OD$, 400 MHz) δ 8.49 (s, 1H), 8.05-8.01 (m, 2H), 7.54 (t, J=4.0 Hz, 1H), 4.58 (t, J=6.0 Hz, 1H), 4.46 (t, J=6.0 Hz, 1H), 4.31-4.24 (m, 2H), 3.84-3.74 (br, 2H), 3.62-3.40 (m, 9H), 3.30-3.38 (m, 4H), 3.17 (t, J=6.8 Hz, 2H), 2.92 (t, J=7.2 Hz, 2H), 2.44-2.36 (m, 2H), 2.20-2.06 (m, 2H), 1.94-1.78 (m, 1H), 1.70-1.38 (m, 5H), 1.28 and 1.17 (t each, J=8.0 Hz, 3H). MS: m/z=762 (M+H$^+$).

(S)-2-(3-((S)-1-Carboxy-5-((6-fluoro-3-nitropyridin-2-yl)amino)pentyl)ureido)pentanedioic acid: P265

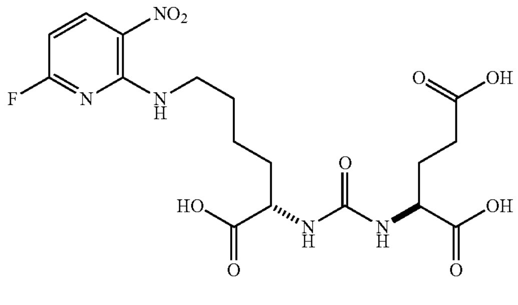

General experimental procedure for N-alkylation and deprotection was followed. Reaction was performed on a 30.0 mg scale of (S)-di-tert-butyl 2-(3-((S)-6-amino-1-(tert-butoxy)-1-oxohexan-2-yl)ureido)pentanedioate. After HPLC purification, P265 (14.7 mg, 52%) was obtained as a yellow solid. $^1$H NMR ($CD_3OD$, 400 MHz) δ 8.58 (dd, J=8.8, 7.2 Hz, 1H), 6.28 (dd, J=8.8, 3.3 Hz, 1H), 4.24-4.34 (m, 2H), 3.52-3.63 (m, 2H), 2.40 (ddd, J=8.6, 6.8, 3.7 Hz, 2H), 2.08-2.18 (m, 1H), 1.83-1.94 (m, 2H), 1.65-1.76 (m, 3H), 1.45-1.55 (m, 2H). MS: m/z=460 (M+H⁺).

(2S)-2-(3-((1S)-1-Carboxy-5-((5-(3-(3-(((S)-5-carboxy-5-(3-((S)-1,3-dicarboxypropyl)ureido)pentyl)amino)-4-nitrophenoxy)-2-(4-(3-fluoropropyl)-1H-1,2,3-triazol-1-yl)propoxy)-2-nitrophenyl)amino)pentyl)ureido)pentanedioic acid: P266

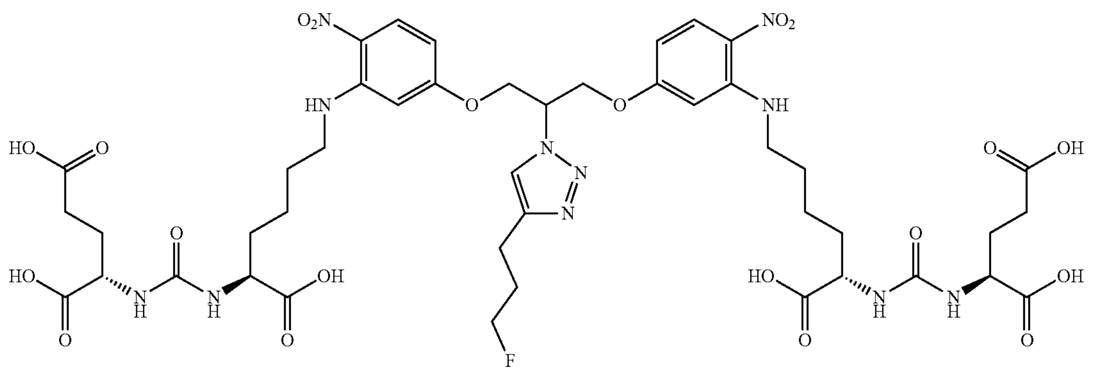 [SMILES: O=C(O)CC[C@H](NC(=O)N[C@@H](CCCCNc1cc(OCC(COc2ccc([N+](=O)[O-])c(NCCCC[C@H](NC(=O)N[C@@H](CCC(=O)O)C(=O)O)C(=O)O)c2)n2cc(CCCF)nn2)ccc1[N+](=O)[O-])C(=O)O)C(=O)O]

General experimental procedure for the deprotection of the tert-butyl group was followed. Reaction was performed on a 45 mg scale. After HPLC purification, P266 (6.0 mg, 12%) was obtained. $^1$H NMR ($CD_3OD$, 400 MHz) δ 8.05 (m, 3H), 6.32 (m, 2H), 6.24 (m, 2H), 5.42 (m, 1H), 4.70 (m, 4H), 4.46 (m, 1H), 4.31 (m, 4H), 3.33 (m, 4H), 2.81 (m, 2H), 2.36 (m, 4H), 2.15 (m, 4H), 1.88 (m, 4H), 1.72 (m, 6H), 1.52 (m, 5H). MS: m/z=1080 (M+H$^+$).

(S)-2-(3-((S)-1-Carboxy-2-(4-(3-(((S)-5-carboxy-5-(3-((S)-1,3-dicarboxypropyl)ureido)pentyl)carbamoyl)-5-(4-(3-fluoropropyl)-1H-1,2,3-triazol-1-yl)benzamido)phenyl)ethyl)ureido)pentanedioic acid: P267

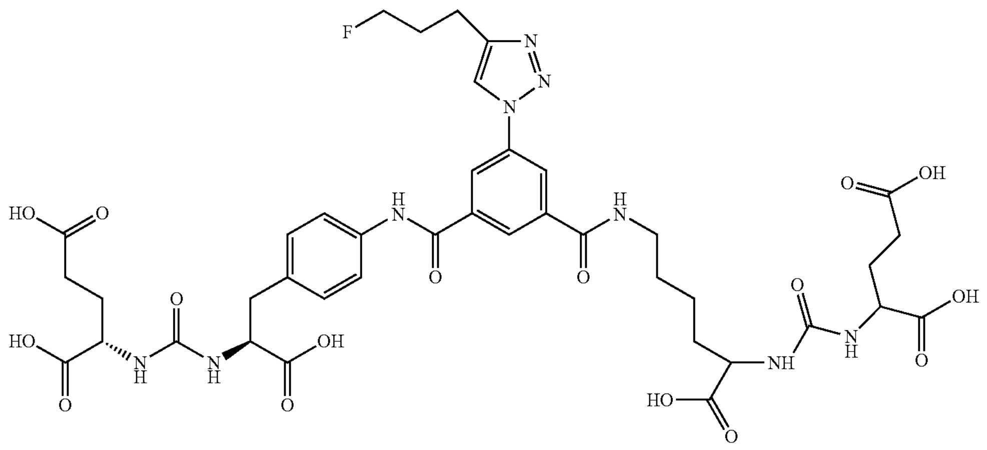 [SMILES: O=C(O)CCC(NC(=O)NC(CCCCNC(=O)c1cc(C(=O)Nc2ccc(C[C@H](NC(=O)N[C@@H](CCC(=O)O)C(=O)O)C(=O)O)cc2)cc(-n2cc(CCCF)nn2)c1)C(=O)O)C(=O)O]

General experimental procedure for the deprotection of the tert-butyl group was followed. Reaction was performed on a 0.06 g scale. After HPLC purification, P267 (10 mg, 22%) was obtained as a white solid. $^1$H NMR ($CD_3OD$, 400 MHz) 8.56 (t, J=2.0 Hz, 1H), 8.51 (s, 1H), 8.51 (t, J=2.0 Hz, 1H), 8.47 (t, J=2.0 Hz, 1H), 7.66 (d, J=8.4 Hz, 2H), 7.27 (d, J=8.8 Hz, 2H), 4.60 (t, J=5.6 Hz, 1H), 4.56 (dd, J=6.8, 5.2 Hz, 1H), 4.48 (t, J=6.0 Hz, 1H), 4.29 (ddd, J=12.4, 8.4, 4.4 Hz, 2H), 3.48-3.44 (m, 3H), 3.18-3.12 (m, 1H), 3.03 (dd, J=7.6 Hz, 1H), 2.95 (t, J=7.6 Hz, 2H), 2.41-2.36 (m, 4H), 2.21-2.08 (m, 4H), 1.93-1.83 (m, 3H), 1.76-1.69 (m, 3H), 1.56-1.51 (m, 2H). MS: m/z=930.1 (M+H$^+$).

(S)-2-(3-((S)-1-Carboxy-5-(3-(((S)-1,3-dicarboxy-propyl)carbamoyl)-5-(4-(3-fluoropropyl)-1H-1,2,3-triazol-1-yl)benzamido)pentyl)ureido)pentanedioic acid: P268

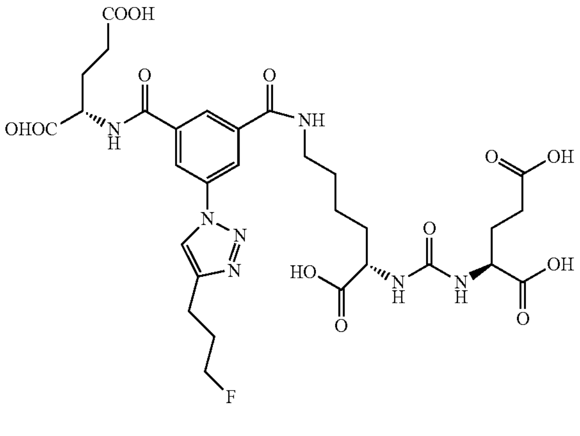

General experimental procedure for the deprotection of the tert-butyl group was followed. Reaction was performed on a 0.06 g scale. After HPLC purification, P268 (10 mg, 23%) was obtained as a white solid. $^1$H NMR ($CD_3OD$, 400 MHz) 8.48 (d, J=1.2, 3H), 8.40 (t, J=1.6 Hz, 1H), 4.69 (dd, J=5.2, 9.6 Hz, 1H), 4.59 (t, J=5.6 Hz, 1H), 4.47 (t, J=5.6 Hz, 1H), 4.32-4.27 (m, 2H), 3.46-3.42 (m, 2H), 2.94 (t, J=7.6 Hz, 2H), 2.52 (t, J=7.6 Hz, 2H), 2.42-2.50 (m, 3H), 2.21-2.07 (m, 4H), 1.94-1.82 (m, 2H), 1.74-1.66 (m, 3H), 1.56-1.50 (m, 2H). MS: m/z=724.1 (M+H$^+$).

(S)-2-(3-((S)-1-Carboxy-5-((6-fluoro-5-nitropyridin-2-yl)amino)pentyl)ureido)pentanedioic acid: P269

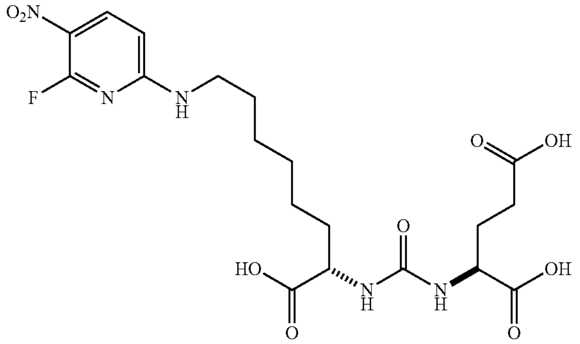

General experimental procedure for the deprotection of the tert-butyl group was followed. Reaction was performed on a 8.0 mg scale of (S)-di-tert-butyl 2-(3-((S)-1-(tert-butoxy)-6-((6-fluoro-5-nitropyridin-2-yl)amino)-1-oxo-hexan-2-yl)ureido)pentanedioate. After HPLC purification, P269 (3.2 mg, 54%) was obtained as a yellow solid. $^1$H NMR ($CD_3OD$, 400 MHz) δ 8.11-8.21 (m, 1H), 6.38 (d, J=8.6 Hz, 1H), 4.26-4.33 (m, 2H), 3.41 (br. s., 2H), 2.34-2.47 (m, 2H), 2.10-2.19 (m, 1H), 1.83-1.93 (m, 2H), 1.59-1.73 (m, 3H), 1.44-1.53 (m, 3H). MS: m/z=460 (M+H$^+$).

(2S,2'S,2"S)-2,2',2"-(((((1S,1'S,1"S)-((6,6',6"-((Nitrilotris(ethane-2,1-diyl))tris(azanediyl))tris(3-nitropyridine-6,2-diyl))tris(azanediyl))tris(1-carboxypentane-5,1-diyl))tris(azanediyl))tris(carbonyl))tris(azanediyl))tripentanedioic acid: P270

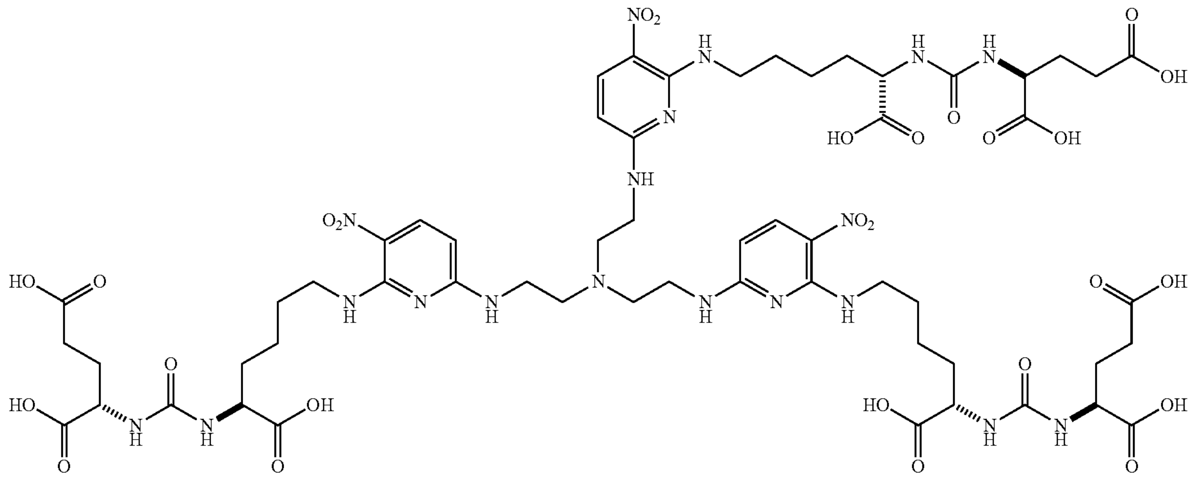

General experimental procedure for N-alkylation and deprotection was followed. Reaction was performed on a 30.0 mg scale of (S)-di-tert-butyl 2-(3-((S)-1-(tert-butoxy)-6-((6-fluoro-3-nitropyridin-2-yl)amino)-1-oxohexan-2-yl) ureido)pentanedioate. After HPLC purification, P270 (13.5 mg, 58%) was obtained as a yellow solid. $^1$H NMR ($CD_3OD$, 400 MHz) δ 8.01 (d, J=9.0 Hz, 3H), 5.89 (d, J=9.4 Hz, 3H), 4.22-4.33 (m, 6H), 3.85-4.01 (m, 6H), 3.72 (t, J=5.9 Hz, 6H), 3.47 (t, J=5.9 Hz, 6H), 2.35-2.47 (m, 6H), 2.09-2.19 (m, 3H), 1.81-1.95 (m, 6H), 1.59-1.73 (m, 9H), 1.42-1.52 (m, 6H). MS: m/z=1464 (M+H$^+$).

(S)-2-(3-((S)-1-Carboxy-5-((6-((2-(2-(4-(3-fluoropropyl)-1H-1,2,3-triazol-1-yl)ethoxy)ethyl)amino) pyrimidin-4-yl)amino)pentyl)ureido)pentanedioic acid: P271

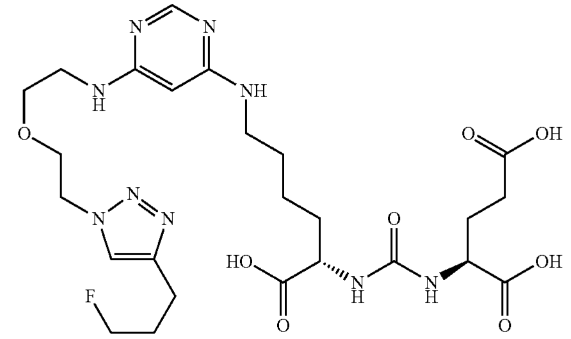 [SMILES: O=C(O)CC[C@H](NC(=O)N[C@@H](CCCCNc1cc(NCCOCCn2cc(CCCF)nn2)ncn1)C(=O)O)C(=O)O]

General experimental procedures for click chemistry and the deprotection of the tert-butyl group were followed. After HPLC purification, P271 was obtained. MS: m/z=612 (M+H$^+$).

(S)-2-(3-((S)-1-Carboxy-2-(1-(3-(4-((S)-2-carboxy-2-(3-((S)-1,3-dicarboxypropyl)-ureido)ethyl)piperidine-1-carbonyl)-5-(4-(3-fluoropropyl)-1H-1,2,3-triazol-1-yl)benzoyl)piperidin-4-yl)ethyl)ureido) pentanedioic acid: P272

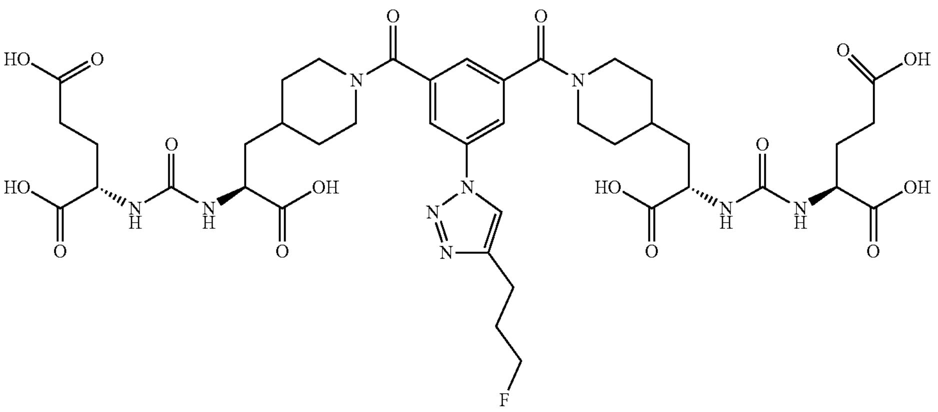 [SMILES: O=C(O)CC[C@H](NC(=O)N[C@@H](CC1CCN(C(=O)c2cc(C(=O)N3CCC(C[C@H](NC(=O)N[C@@H](CCC(=O)O)C(=O)O)C(=O)O)CC3)cc(-n3cc(CCCF)nn3)c2)CC1)C(=O)O)C(=O)O]

General procedure for click chemistry was followed. Reaction was performed on 5.0 mg scale. After HPLC purification, P272 (4.0 mg, 60%) was obtained. $^1$H NMR ($CD_3OD$, 400 MHz) δ 8.49 (s, 1H), 8.15 (s, 2H), 7.50 (s, 1H), 4.54-4.51 (m, 4H), 4.48-4.15 (m, 6H), 3.76-3.68 (m, 2H), 3.22-3.10 (m, 2H), 2.96-2.88 (m, 2H), 2.46-2.38 (m, 4H), 2.20-1.60 (m, 15H), 1.46-1.00 (m, 3H). MS: m/z=948 (M+H$^+$), 970 (M+H$^+$+Na).

(S)-2-(3-((S)-2-(1-(3-Azido-5-(4-((S)-2-carboxy-2-(3-((S)-1,3-dicarboxypropyl)-ureido)ethyl)piperidine-1-carbonyl)benzoyl)piperidin-4-yl)-1-carboxyethyl)-ureido)pentanedioic acid: P272 Precursor

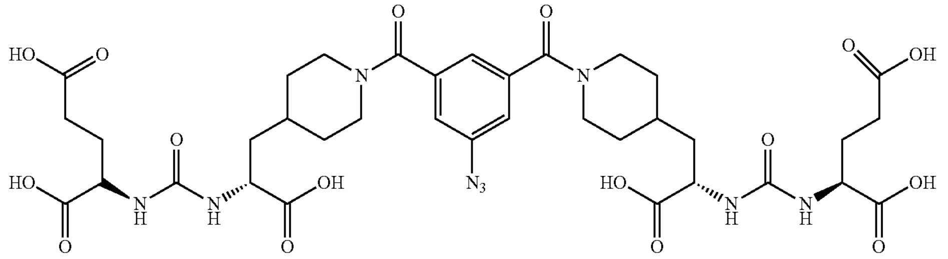

General experimental procedure for amide formation and methyl ester deprotection using 2M HCl at 40° C. for 4 h was followed. Reaction was performed on 80 mg scale. After HPLC purification, P272 Precursor (23 mg, 34%, in two steps) was obtained. $^1$H NMR ($CD_3OD$, 400 MHz) δ 7.07 (s, 3H), 4.52-4.49 (m, 2H), 4.30-4.15 (m, 4H), 3.60-3.51 (m, 2H), 3.08-2.98 (m, 2H), 2.38-2.26 (m, 4H), 2.10-1.46 (m, 15H), 1.30-1.00 (m, 3H); MS: m/z=862 (M+H$^+$).

(2S,2'S)-2,2'-(((((1S,1'S)-((6,6'-((((2-(2-(4-(3-Fluoropropyl)-1H-1,2,3-triazol-1-yl)acetamido)ethyl)azanediyl)bis(ethane-2,1-diyl))bis(azanediyl))bis(3-nitropyridine-6,2-diyl))bis(azanediyl))bis(1-carboxypentane-5,1-diyl))bis(azanediyl))bis(carbonyl))bis(azanediyl))dipentanedioic acid: P273

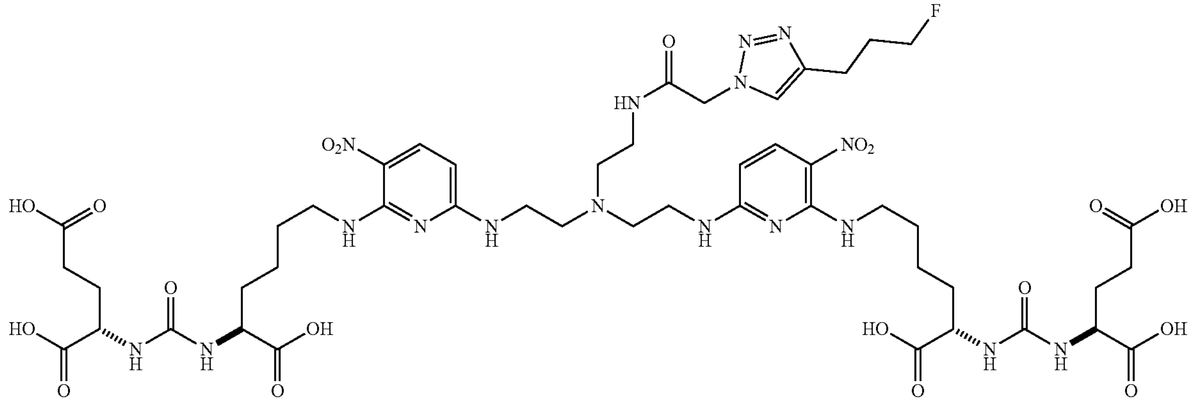

General experimental procedure for click reaction was followed. Reaction was performed on a 7.6 mg scale of (2S,2'S)-2,2'-(((((1S,1'S)-((6,6'-((((2-(2-azidoacetamido) ethyl)azanediyl)bis(ethane-2,1-diyl))bis(azanediyl))bis(3-nitropyridine-6,2-diyl))bis(azanediyl))bis(1-carboxypentane-5,1-diyl))bis(azanediyl))bis(carbonyl))bis(azanediyl)) dipentanedioic acid. After HPLC purification, P273 (2.5 mg, 30%) was obtained as a yellow solid. $^{1}H$ NMR (DMSO-$d_6$, 400 MHz) δ 7.80 (d, J 9.4 Hz, 2H), 5.81 (d, J=9.4 Hz, 2H), 5.06 (s, 2H), 4.51 (t, J=6.1 Hz, 1H), 4.39 (t, J=6.1 Hz, 1H), 3.98-4.10 (m, 4H), 3.32-3.45 (m, 8H), 3.22 (br. s., 2H), 2.65-2.75 (m, 6H), 2.16-2.33 (m, 4H), 1.85-2.01 (m, 4H), 1.56-1.74 (m, 4H), 1.42-1.56 (m, 6H), 1.22-1.32 (m, 4H). MS: m/z=1194 ($M+H^+$).

(2S,2'S)-2,2'-(((((1S,1'S)-(((4,4'-(5-(2-(4-(3-Fluoropropyl)-1H-1,2,3-triazol-1-yl)acetamido)isophthaloyl)bis(piperazine-1,1'-carbonyl))bis(azanediyl))bis(4,1-phenylene))bis(1-carboxyethane-2,1-diyl))bis(azanediyl))bis(carbonyl))bis(azanediyl)) dipentanedioic acid: P274

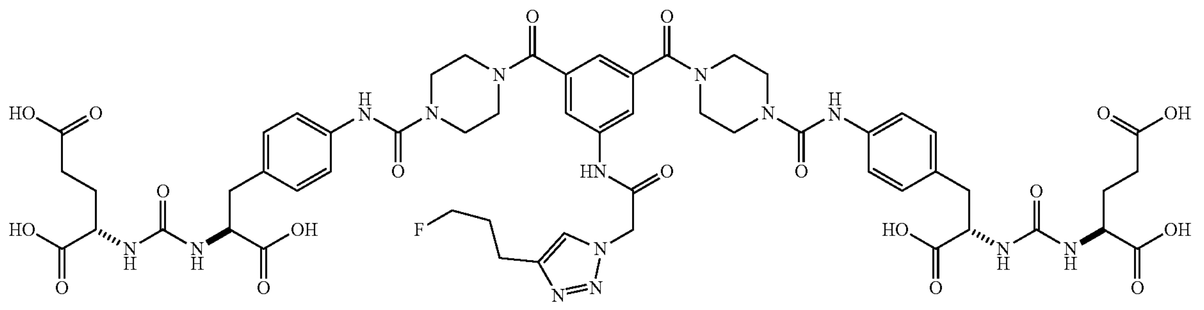

General experimental procedure for click reaction was followed. Reaction was performed on a 5.0 mg scale of (2S,2'S)-2,2'-(((((1S,1'S)-(((4,4'-(5-(2-azidoacetamido) isophthaloyl)bis(piperazine-1,1'-carbonyl))bis(azanediyl)) bis(4,1-phenylene))bis(1-carboxyethane-2,1-diyl))bis (azanediyl))bis(carbonyl))bis(azanediyl))-dipentanedioic acid. After HPLC purification, P274 (2.1 mg, 39%) was obtained as a white solid. $^{1}H$ NMR ($CD_3OD$, 400 MHz) δ 7.87 (s, 1H), 7.81 (d, J=1.2 Hz, 2H), 7.26-7.31 (m, 5H), 7.15 (d, J=8.6 Hz, 4H), 5.35 (s, 2H), 4.50-4.56 (m, 3H), 4.43 (t, J=5.9 Hz, 1H), 4.28 (dd, J=8.8, 4.9 Hz, 2H), 3.81 (br. s., 4H), 3.65 (br. s., 4H), 3.54 (br. s., 8H), 3.09 (dd, J 13.9, 6.8 Hz, 2H), 2.97 (dd, J=13.9, 6.8 Hz, 2H), 2.84-2.89 (m, 2H), 2.33-2.43 (m, 4H), 2.01-2.16 (m, 4H), 1.81-1.91 (m, 2H). MS: m/z=1245 ($M+H^+$).

(2S,2'S)-2,2'-(((((1S,1'S)-(((4,4'-(5-(4-(3-Fluoropropyl)-1H-1,2,3-triazol-1-yl)isophthaloyl)bis(piperazine-1,1'-carbonyl))bis(azanediyl))bis(4,1-phenylene))bis(1-carboxyethane-2,1-diyl))bis(azanediyl))bis(carbonyl))bis(azanediyl)) dipentanedioic acid: P275

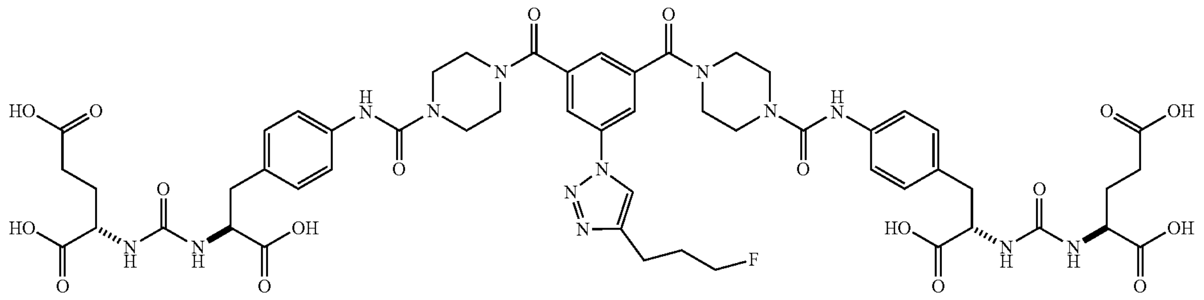

General experimental procedure for click reaction was followed. Reaction was performed on a 6.0 mg scale of (2S,2'S)-2,2'-(((((1S,1'S)-(((4,4'-(5-azidoisophthaloyl)bis(piperazine-1,1'-carbonyl))bis(azanediyl))bis(4,1-phenylene))bis(1-carboxyethane-2,1-diyl))bis(azanediyl))bis(carbonyl))bis(azanediyl))dipentanedioic acid. After HPLC purification, P275 (2.0 mg, 31%) was obtained as a white solid. $^1$H NMR ($CD_3OD$, 400 MHz) δ 8.50 (s, 1H), 8.11 (d, J=1.2 Hz, 2H), 7.65 (t, J=1.4 Hz, 1H), 7.25-7.32 (m, 4H), 7.13-7.18 (m, 4H), 4.45-4.60 (m, 4H), 4.28 (dd, J=8.6, 5.1 Hz, 2H), 3.85 (br. s., 4H), 3.68 (br. s., 4H), 3.57 (br. s., 8H), 3.06-3.16 (m, 2H), 2.90-3.00 (m, 4H), 2.31-2.43 (m, 4H), 2.03-2.20 (m, 4H), 1.77-1.92 (m, 2H). MS: m/z=1188 ($M+H^+$).

(3S,7S,23S,27S)-15-(2-(4-(3-Fluoropropyl)-1H-1,2,3-triazol-1-yl)acetamido)-5,13,17,25-tetraoxo-4,6,12,18,24,26-hexaazanonacosane-1,3,7,23,27,29-hexacarboxylic acid: P276

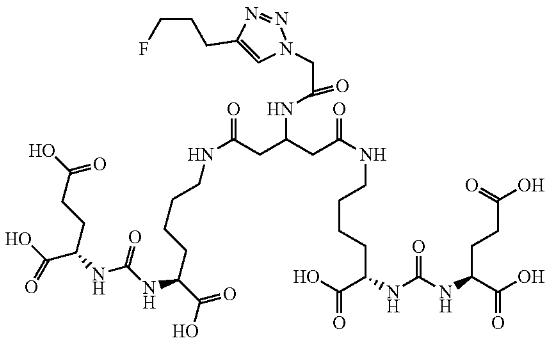 [SMILES: O=C(O)CC[C@H](NC(=O)N[C@@H](CCCCNC(=O)CC(CC(=O)NCCCC[C@H](NC(=O)N[C@@H](CCC(=O)O)C(=O)O)C(=O)O)NC(=O)Cn1cc(CCCF)nn1)C(=O)O)C(=O)O]

General experimental procedure for urea formation and tert-butyl deprotection reaction was followed. After HPLC purification, P276 was obtained. $^1$H NMR ($CD_3OD$, 400 MHz) δ 7.83 (s, 1H), 5.09 (s, 2H), 4.50-4.61 (m, 1H), 4.47 (dt, J=47.2, 6.0 Hz, 2H), 4.21-4.56 (m, 3H), 3.06-3.28 (m, 4H), 2.84 (t, J=8.0 Hz, 2H), 2.32-2.56 (m, 8H), 1.98-2.22 (m, 4H), 1.28-1.96 (m, 12H). MS: m/z=919 ($M+H^+$).

(2S)-2-(3-((1S)-1-Carboxy-5-((5-(3-(3-(((S)-5-carboxy-5-(3-((S)-1,3-dicarboxypropyl)ureido)pentyl)amino)-4-nitrophenoxy)-2-((1-(2-fluoroethyl)-1H-1,2,3-triazol-4-yl)methoxy)propoxy)-2-nitrophenyl)amino)pentyl)ureido)pentanedioic acid: P277

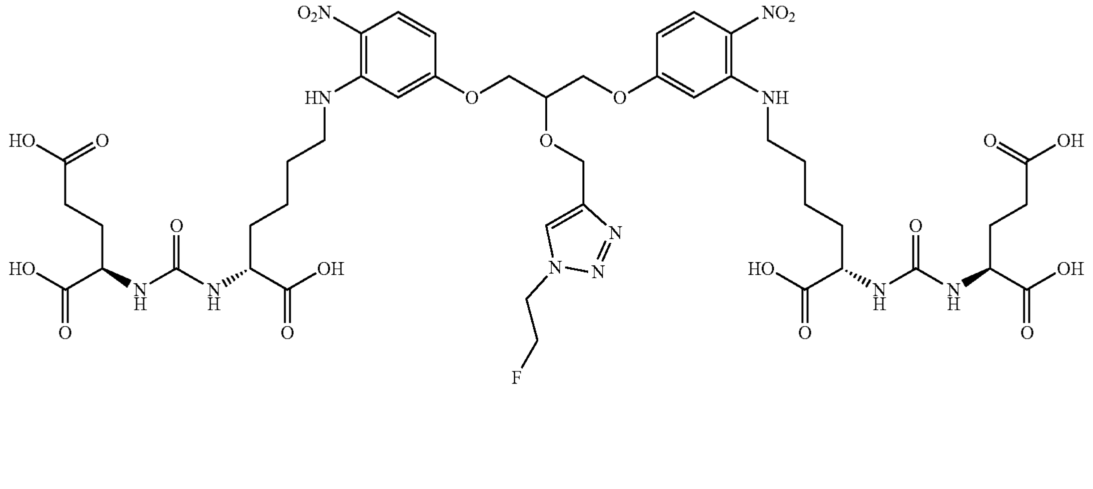 [SMILES: O=C(O)CC[C@H](NC(=O)N[C@@H](CCCCNc1cc(OCC(COc2ccc([N+](=O)[O-])c(NCCCC[C@@H](NC(=O)N[C@H](CCC(=O)O)C(=O)O)C(=O)O)c2)OCc2cn(CCF)nn2)ccc1[N+](=O)[O-])C(=O)O)C(=O)O]

General experimental procedure for the deprotection of the tert-butyl group was followed. Reaction was performed on a 30 mg scale. After HPLC purification, P277 (7 mgs, 30%) was obtained. $^1$H NMR ($CD_3OD$, 400 MHz) δ 8.05 (m, 2H), 7.99 (s, 1H), 6.28 (m, 4H), 4.83 (m, 5H), 4.72 (m, 2H), 4.66 (m, 1H), 4.29 (m, 8H), 3.33 (m, 4H), 2.38 (m, 4H), 2.11 (m, 2H), 1.88 (m, 4H), 1.71 (m, 5H), 1.53 (m, 4H). MS: m/z=1096 (M+H$^+$).

(3S,7S,23S,27S)-15-(4-(4-(3-Fluoropropyl)-1H-1,2,3-triazol-1-yl)benzamido)-5,13,17,25-tetraoxo-4,6,12,18,24,26-hexaazanonacosane-1,3,7,23,27,29-hexacarboxylic acid: P278

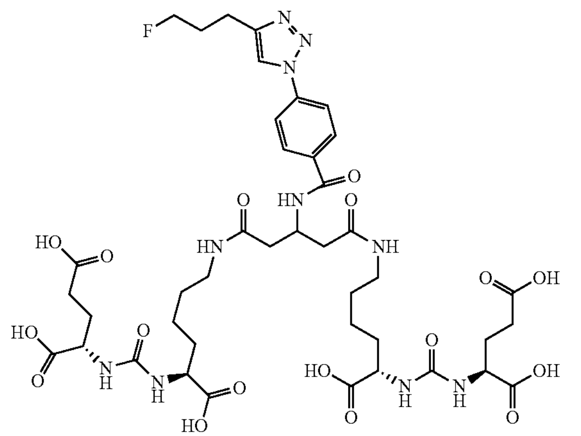 [SMILES: O=C(O)CC[C@H](NC(=O)N[C@@H](CCCCNC(=O)CC(CC(=O)NCCCC[C@H](NC(=O)N[C@@H](CCC(=O)O)C(=O)O)C(=O)O)NC(=O)c1ccc(-n2cc(CCCF)nn2)cc1)C(=O)O)C(=O)O]

General experimental procedure for urea formation and tert-butyl deprotection reaction was followed. After HPLC purification, P278 was obtained. $^1$H NMR ($CD_3OD$, 400 MHz) δ 8.44 (s, 1H), 8.00 (d, J=8.8 Hz, 2H), 7.95 (d, J=8.8 Hz, 2H), 4.69-4.86 (m, 1H), 4.51 (dt, J=47.2, 6.0 Hz, 2H), 4.13-4.33 (m, 4H), 3.04-3.24 (m, 4H), 2.91 (t, J=7.6 Hz, 2H), 2.49-2.64 (m, 4H), 2.32-2.45 (m, 4H), 2.02-2.19 (m, 4H), 1.68-1.94 (m, 4H), 1.28-1.66 (m, 10H). MS: m/z=981 (M+H$^+$).

(S)-2-(3-((S)-1-Carboxy-3-(4-(4-nitrophenyl)oxazol-2-yl)propyl)ureido)pentanedioic acid: P279

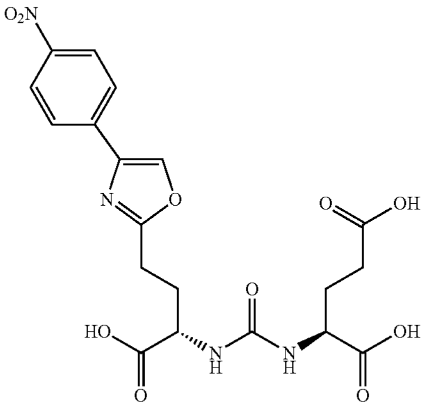 [SMILES: O=C(O)CC[C@H](NC(=O)N[C@@H](CCc1nc(-c2ccc([N+](=O)[O-])cc2)co1)C(=O)O)C(=O)O]

General experimental procedure for urea formation and tert-butyl deprotection reaction was followed. After HPLC purification, P279 was obtained. $^1$H NMR ($CD_3OD$, 400 MHz) δ 8.37 (s, 1H), 8.26 (d, J=8.8 Hz, 2H), 7.97 (d, J=8.8 Hz, 2H), 4.38-4.44 (m, 1H), 4.25-4.33 (m, 1H), 2.91-2.98 (m, 2H), 2.32-2.46 (m, 3H), 2.05-2.18 (m, 2H), 1.82-1.92 (m, 1H). MS: m/z=465 (M+H$^+$).

(2S,2'S)-2,2'(((((1S,1'S)(((4-(4-(4-(3-Fluoropropyl)-1H-1,2,3-triazol-1-yl)-benzamido)-heptanedioyl)-bis(azanediyl))-bis(4,1-phenylene))-bis(1-carboxy-ethane-2,1-diyl))-bis(azanediyl))-bis(carbonyl))-bis(azanediyl))-dipentanedioic acid: P280

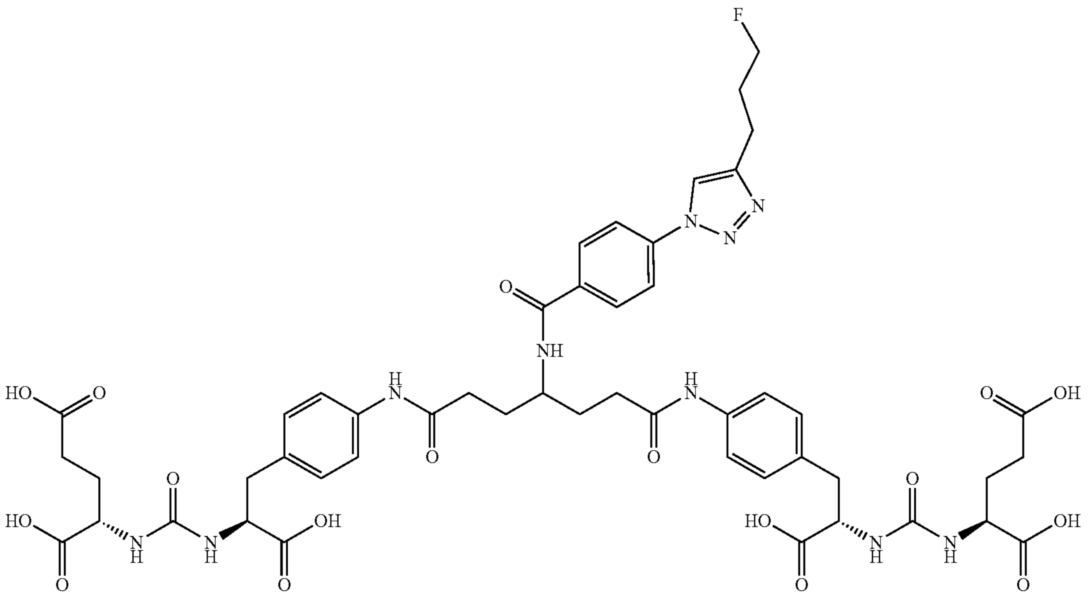 [SMILES: O=C(O)CC[C@H](NC(=O)N[C@@H](Cc1ccc(NC(=O)CCC(CCC(=O)Nc2ccc(C[C@H](NC(=O)N[C@@H](CCC(=O)O)C(=O)O)C(=O)O)cc2)NC(=O)c2ccc(-n3cc(CCCF)nn3)cc2)cc1)C(=O)O)C(=O)O]

General procedure for click chemistry was followed. Reaction was performed on 5.0 mg scale. After HPLC purification, P280 (4.0 mg, 74%) was obtained. $^1$H NMR ($CD_3OD$, 400 MHz) δ 8.40 (s, 1H), 8.21 (br d, J=8.80 Hz, 1H), 7.92 (d, J=8.80 Hz, 2H), 7.80 (d, J=8.80 Hz, 2H), 7.37 (d, J=8.80 Hz, 4H), 7.01 (d, J=8.80 Hz, 4H), 4.57 (t, J=5.60 Hz, 2H), 4.46-4.43 (m, 4H), 4.28-4.22 (m, 3H), 3.72-3.68 (m, 6H), 3.05-2.99 (dd, J=13.6 and 5.2 Hz, 1H), 2.94-2.86 (m, 4H), 2.50-2.31 (m, 6H), 2.18-1.96 (m, 5H), 1.86-1.83 (m, 6H). MS: m/z=1078 (M+H$^+$).

(2S,2'S)-2,2'-(((((1S,1'S)-(((4-(4-Azidobenzamido)-heptanedioyl)-bis(azanediyl))-bis(4,1-phenylene))-bis(1-carboxyethane-2,1-diyl))bis(azanediyl))-bis(carbonyl))-bis(azanediyl))dipentanedioic acid: P280 Precursor

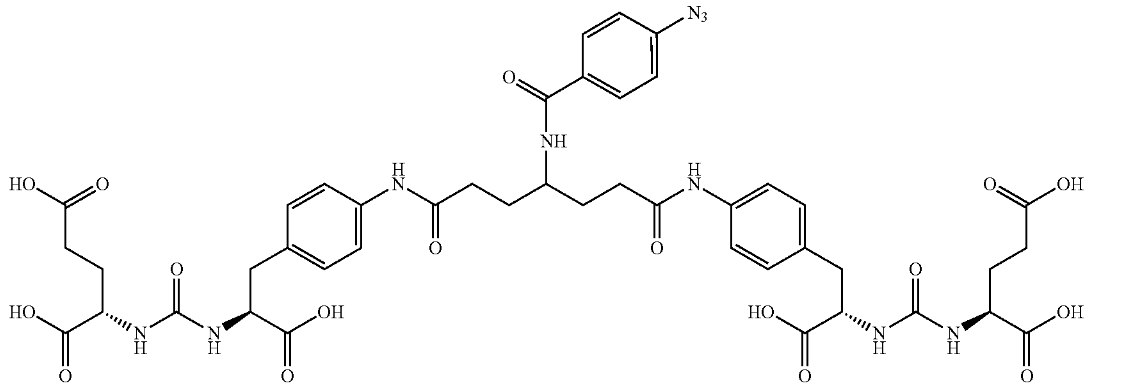 [SMILES: [N-]=[N+]=Nc1ccc(C(=O)NC(CCC(=O)Nc2ccc(C[C@H](NC(=O)N[C@@H](CCC(=O)O)C(=O)O)C(=O)O)cc2)CCC(=O)Nc2ccc(C[C@H](NC(=O)N[C@@H](CCC(=O)O)C(=O)O)C(=O)O)cc2)cc1]

General procedure for amide coupling and t-butyl ester deprotection was followed. Reaction was performed on 81 mg scale. After HPLC purification, P280 Precursor (30 mg, 48%) was obtained. $^1$H NMR ($CD_3OD$, 400 MHz) δ 8.04 (d, J=9.2 Hz, 1H), 7.74-7.71 (m, 2H), 7.31 (d, J=8.40 Hz, 4H), 7.03 (d, J=8.40 Hz, 4H), 6.97-6.93 (m, 2H), 4.41 (t, J=8.0 Hz, 2H), 4.13 (dd, J=8.4, 4.80 Hz, 4H), 4.15-4.05 (m, 1H), 2.92 (dd, J=13.6, 4.0 Hz, 2H), 2.86 (dd, J=13.6, 4.0 Hz, 2H), 2.41-2.21 (m, 8H), 2.08-1.70 (m, 8H). MS: m/z=862 (M+H$^+$).

(2S,2'S)-2,2'-(((((1S,1'S)-((4,4'-(4-(4-(4-(3-Fluoropropyl)-1H-1,2,3-triazol-1-yl)benzamido)heptanedioyl)bis(piperazine-1,1'-carbonyl))bis(azanediyl))bis(1-carboxypentane-5,1diyl))-bis(azanediyl))-bis(carbonyl))-bis(azanediyl))-dipentanedioic acid: P281

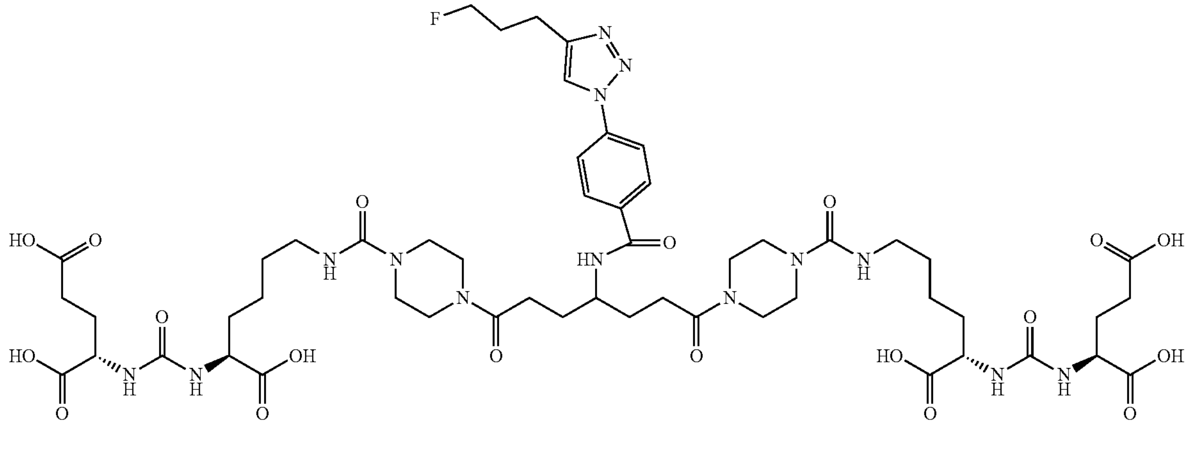 [SMILES: O=C(O)CC[C@H](NC(=O)N[C@@H](CCCCNC(=O)N1CCN(C(=O)CCC(CCC(=O)N2CCN(C(=O)NCCCC[C@H](NC(=O)N[C@@H](CCC(=O)O)C(=O)O)C(=O)O)CC2)NC(=O)c2ccc(-n3cc(CCCF)nn3)cc2)CC1)C(=O)O)C(=O)O]

General procedure for click chemistry was followed. Reaction was performed on 5.0 mg scale. After HPLC purification, P281 (3.5 mg. 65%) was obtained. $^1$H NMR ($CD_3OD$, 400 MHz) δ 8.43 (s, 1H), 8.04-7.95 (m, 4H), 4.56 (t, J=6.0 Hz, 1H), 4.45 (t, J=4.4 Hz, 1H), 4.45 (t, J=4.4 Hz, 1H), 4.30-4.23 (m, 4H), 4.18-4.10 (m, 1H), 3.62-3.22 (m, 16H), 3.15-3.10 m, 4H), 2.9 (t, J=8.0 Hz, 2H), 2.58-2.34 (m, 8H), 2.19-1.77 (m, 8H), 1.70-1.36 (m, 9H). MS: m/z=1233 (M+H$^+$).

(2S,2'S)-2,2'-(((((1S,1'S)-((4,4'-(4-(4-Azidobenzamido)heptanedioyl)bis(piperazine-1,1'-carbonyl)) bis(azanediyl))bis(1-carboxypentane-5,1-diyl))-bis (azanediyl))-bis(carbonyl))bis(azanediyl)) dipentanedioic acid: P281 Precursor

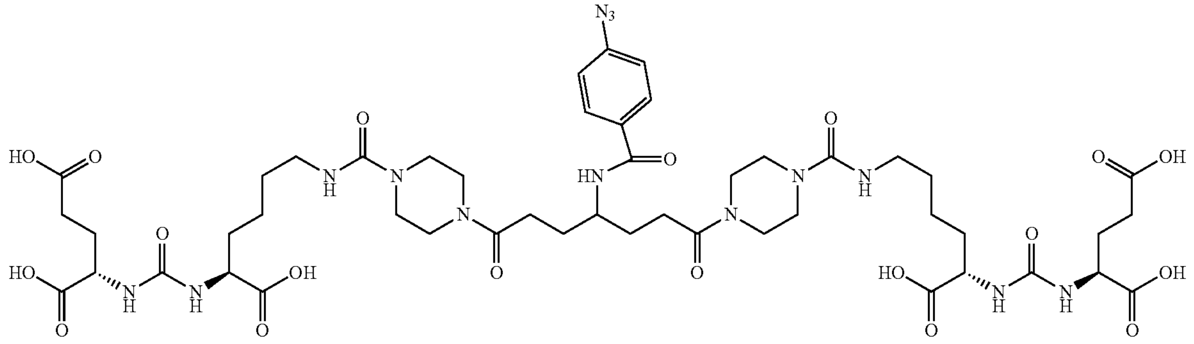 [SMILES: [N-]=[N+]=Nc1ccc(C(=O)NC(CCC(=O)N2CCN(C(=O)NCCCC[C@H](NC(=O)N[C@@H](CCC(=O)O)C(=O)O)C(=O)O)CC2)CCC(=O)N2CCN(C(=O)NCCCC[C@H](NC(=O)N[C@@H](CCC(=O)O)C(=O)O)C(=O)O)CC2)cc1]

General procedure for amide coupling and t-butyl ester deprotection was followed. Reaction was performed on 94 mg scale. After HPLC purification, P281 Precursor (28 mg, 39%, in two steps) was obtained. $^1$H NMR ($CD_3OD$, 400 MHz) δ 7.89-7.86 (m, 2H), 7.17-7.14 (m, 2H), 4.32-4.24 (m, 4H), 4.18-4.10 (m, 1H), 3.60-3.48 (m, 8H), 3.44-3.36 (m, 4H), 3.28-3.12 (m, 6H), 3.58-3.36 (m, 7H), 2.18-1.78 (m, 9H), 1.70-1.38 (m, 9H). MS: m/z=1147 (M+H$^+$).

(3S,7S,25S,29S)-16-(4-(4-(3-Fluoropropyl)-1H-1,2,3-triazol-1-yl)benzamido)-5,13,19,27-tetraoxo-4,6,12,20,26,28-hexaazahentriacontane-1,3,7,25,29,31-hexacarboxylic acid: P282

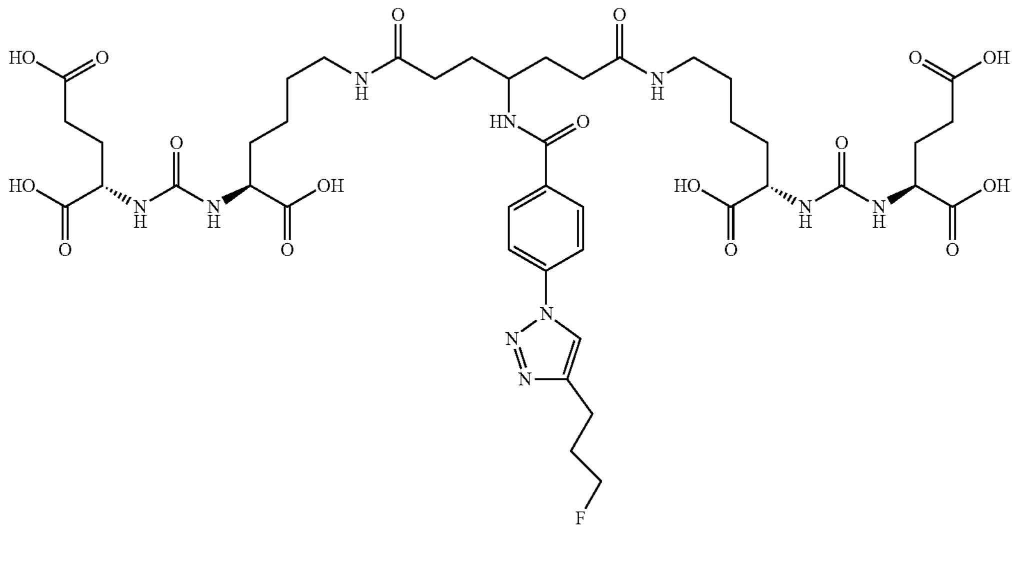 [SMILES: O=C(O)CC[C@H](NC(=O)N[C@@H](CCCCNC(=O)CCC(CCC(=O)NCCCC[C@H](NC(=O)N[C@@H](CCC(=O)O)C(=O)O)C(=O)O)NC(=O)c1ccc(-n2cc(CCCF)nn2)cc1)C(=O)O)C(=O)O]

General procedure for "click chemistry was followed. Reaction was performed on 8.4 mg scale. After HPLC purification, P282 (4.8 mg, 52%) was obtained. $^{1}$H NMR ($CD_3OD$, 400 MHz) δ 8.42 (s, 1H), 8.06-8.04 (m, 2H), 7.97-7.94 (m, 2H), 4.56 (t, J=6.0 Hz, 1H), 4.44 (t, J=6.0 Hz, 1H), 4.31-4.20 (m, 4H), 4.14-4.04 (m, 1H), 3.20-3.02 (m, 4H), 2.91 (t, J=7.2 Hz, 2H), 2.39-2.22 (m, 8H), 2.18-2.01 (m, 4H), 1.98-1.74 (m, 8H), 1.68-1.30 (m, 9H). MS: m/z=1010 (M+H$^+$).
(3S,7S,25S,29S)-16-(4-Azidobenzamido)-5,13,19,27-tetraoxo-4,6,12,20,26,28-hexaazahentriacontane-1,3,7,25,29,31-hexacarboxylic acid: P282 Precursor
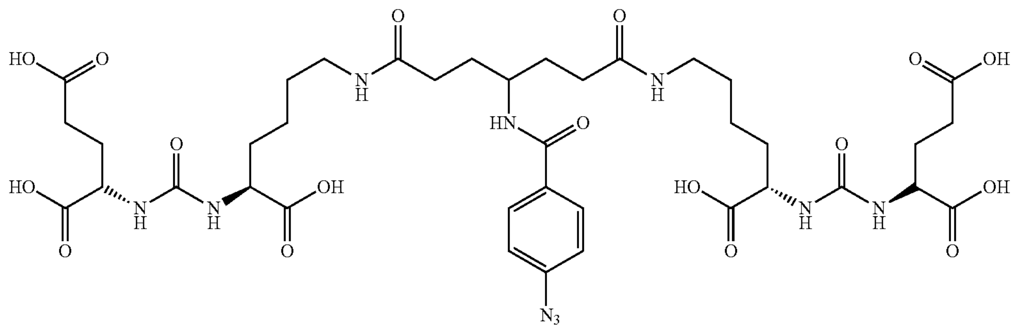

General procedure for amide coupling and removal of tert-butyl ester was followed. Reaction was performed on 76 mg scale. After HPLC purification, P282 Precursor (37 mg, 64%) was obtained. $^1$H NMR ($CD_3OD$, 400 MHz) δ 7.89-7.86 (m, 2H), 7.15-7.11 (m, 2H), 4.29-4.21 (m, 4H), 4.10-4.02 (m, 1H), 3.18-3.01 (m, 4H), 2.39-2.05 (m, 9H), 1.97-1.71 (m, 8H), 1.67-1.33 (m, 9H). MS: m/z=923 (M+H$^+$).

(2S,2'S)-2,2'-(((((1S,1'S)-((5-(2-(4-(3-fluoropropyl)-1H-1,2,3-triazol-1-yl)acetamido)isophthaloyl)bis(azanediyl))bis(1-carboxypentane-5,1-diyl))bis(azanediyl))bis(carbonyl))bis(azanediyl))dipentanedioic acid: P283

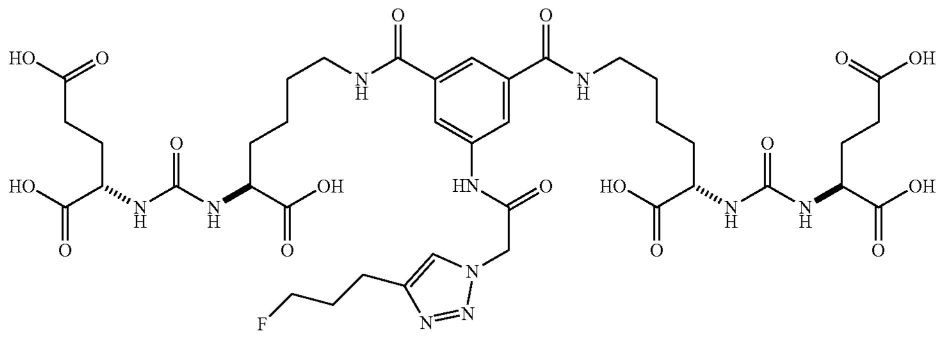

General experimental procedure for click reaction was followed. Reaction was performed on a 7.0 mg scale of (2S,2'S)-2,2'-(((((1S,1'S)-((5-(2-azidoacetamido)isophthaloyl)bis(azanediyl))bis(1-carboxypentane-5,1-diyl))bis(azanediyl))bis(carbonyl))bis(azanediyl))dipentanedioic acid. After HPLC purification, P283 (3.3 mg, 43%) was obtained as a white solid. $^1$H NMR ($CD_3OD$, 400 MHz) δ 8.15 (d, J 1.2 Hz, 2H), 7.96 (t, J=1.4 Hz, 1H), 7.90 (s, 1H), 5.36 (s, 2H), 4.55 (t, J=5.9 Hz, 1H), 4.43 (t, J=5.9 Hz, 1H), 4.25-4.32 (m, 4H), 3.33-3.42 (m, 4H), 2.87 (t, J=7.6 Hz, 2H), 2.30-2.50 (m, 4H), 2.00-2.20 (m, 4H), 1.78-1.94 (m, 4H), 1.59-1.75 (m, 6H), 1.44-1.55 (m, 4H). MS: m/z=953 (M+H$^+$).

(S)-2-(3-((S)-1-Carboxy-2-(1-(3-carboxy-5-(4-(3-fluoropropyl)-1H-1,2,3-triazol-1-yl)benzoyl)piperidin-4-yl)ethyl)ureido)pentanedioic acid: P284

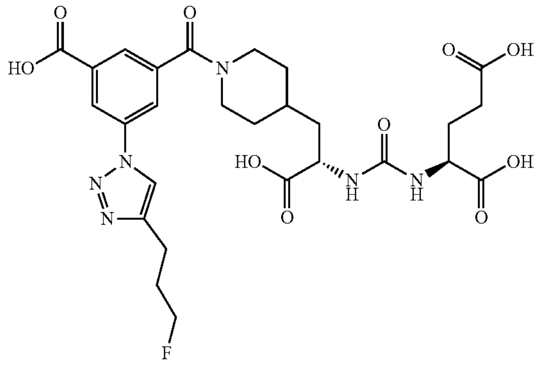 [SMILES: O=C(O)CC[C@H](NC(=O)N[C@@H](CC1CCN(C(=O)c2cc(C(=O)O)cc(-n3cc(CCCF)nn3)c2)CC1)C(=O)O)C(=O)O]

General procedure for click chemistry was followed. Reaction was performed on a 10 mg scale. After HPLC purification, P284 (4.0 mg, 35%) was obtained. $^1$H NMR ($CD_3OD$, 400 MHz) δ 8.55-8.54 (m, 1H), 8.50 (br s, 1H), 8.12-8.11 (m, 1H), 8.07 (t, J=1.6 Hz, 1H), 4.66-4.60 (m, 2H), 4.57 (t, J=8.0 Hz, 1H), 4.45 (t, J=8.0 Hz, 1H), 4.40-4.24 (m, 2H), 3.74-3.64 (m, 1H), 2.91 (t, J=7.2 Hz, 2H) 2.42-2.38 (m, 2H), 2.18-2.06 (m, 2H), 2.00-1.55 (m, 3H), 1.40-1.10 (m, 1H). MS: m/z=621 (M+H$^+$).

(2S,2'S)-2,2'-(((((1S,1'S)-(((4-(3-((4-((S)-2-Carboxy-2-(3-((S)-1,3-dicarboxypropyl)ureido)ethyl)phenyl)amino)-3-oxopropyl)-4-(5-(4-(3-fluoropropyl)-1H-1,2,3-triazol-1-yl)pentanamido)heptanedioyl)bis(azanediyl))bis(4,1-phenylene))bis(1-carboxyethane-2,1-diyl))bis(azanediyl))bis(carbonyl))bis(azanediyl))dipentanedioic acid: P285

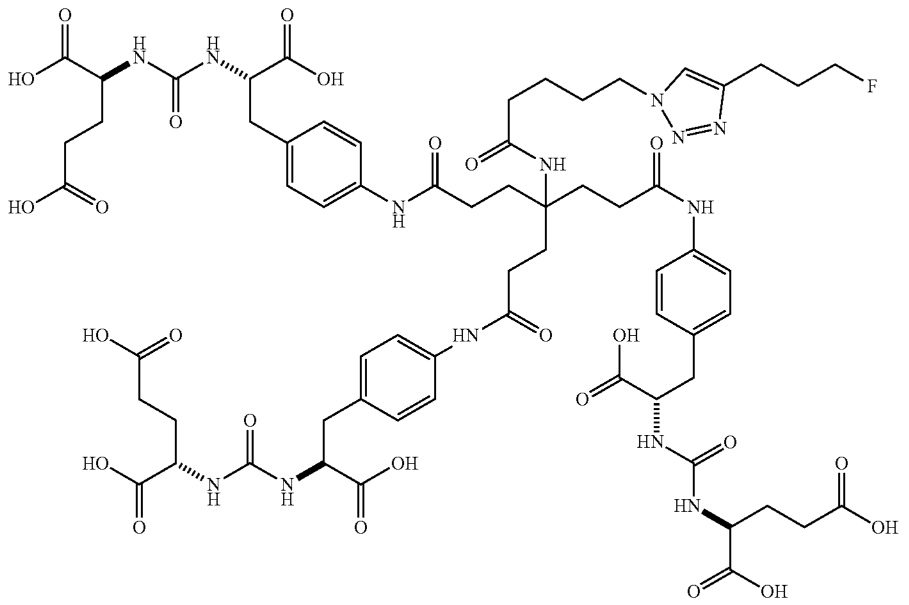

General experimental procedure for click reaction was followed. Reaction was performed on a 10.0 mg scale of (2S,2'S)-2,2'-(((((1S,1'S)-(((4-(5-azidopentanamido)-4-(3-((4-((S)-2-carboxy-2-(3-((S)-1,3-dicarboxypropyl)ureido)ethyl)phenyl)amino)-3-oxopropyl)heptanedioyl)bis(azanediyl))bis(4,1-phenylene))bis(1-carboxyethane-2,1-diyl))bis(azanediyl))bis(carbonyl))bis(azanediyl))dipentanedioic acid. After HPLC purification, P285 (3.9 mg, 37%) was obtained as a white solid. $^1$H NMR ($CD_3OD$, 400 MHz) δ 7.66 (s, 1H), 7.33-7.41 (m, 6H), 7.07 (d, J=8.6 Hz, 6H), 4.36-4.45 (m, 4H), 4.16-4.28 (m, 6H), 2.94-3.04 (m, 3H), 2.81-2.91 (m, 3H), 2.64-2.72 (m, 2H), 2.22-2.33 (m, 11H), 2.12 (t, J=7.4 Hz, 2H), 1.98-2.07 (m, 8H), 1.85-1.96 (m, 2H), 1.71-1.82 (m, 5H), 1.42-1.51 (m, 2H). MS: m/z=1464 (M+H$^+$).

(S)-2-(3-((S)-1-Carboxy-2-(4-(4-(3-(((S)-5-carboxy-5-(3-((S)-1,3-dicarboxypropyl)ureido)pentyl)carbamoyl)-5-(4-(3-fluoropropyl)-1H-1,2,3-triazol-1-yl)benzoyl)piperazine-1-carboxamido)phenyl)ethyl)ureido)pentanedioic acid: P286

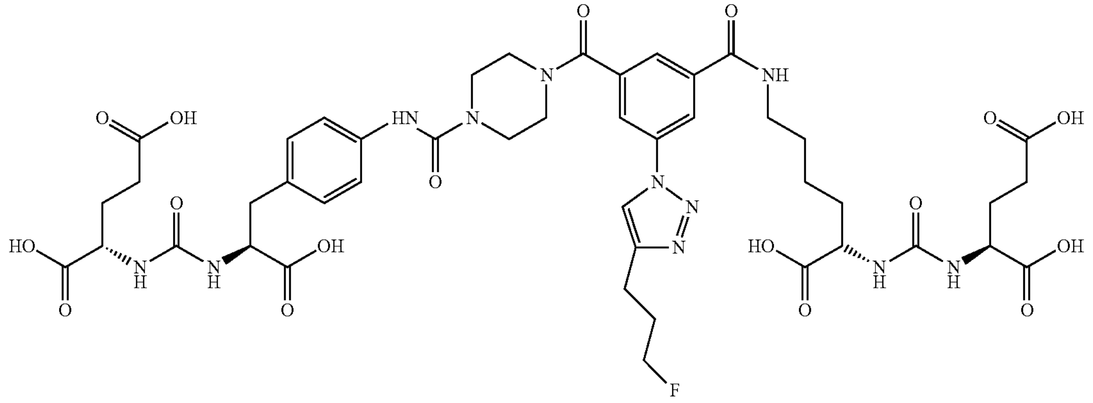

General experimental procedure for click reaction was followed. Reaction was performed on a 0.03 g scale. After HPLC purification, P286 (6.0 mg, 18%) was obtained as a white solid. MS: m/z=1042 (M+H+).

(3S,7S,25S,29S)-16-(3-(((S)-5-Carboxy-5-(3-((S)-1,3-dicarboxypropyl)ureido)pentyl)amino)-3-oxopropyl)-16-(4-(4-(3-fluoropropyl)-1H-1,2,3-triazol-1-yl)benzamido)-5,13,19,27-tetraoxo-4,6,12,20,26,28-hexaazahentriacontane-1,3,7,25,29,31-hexacarboxylic acid: P287

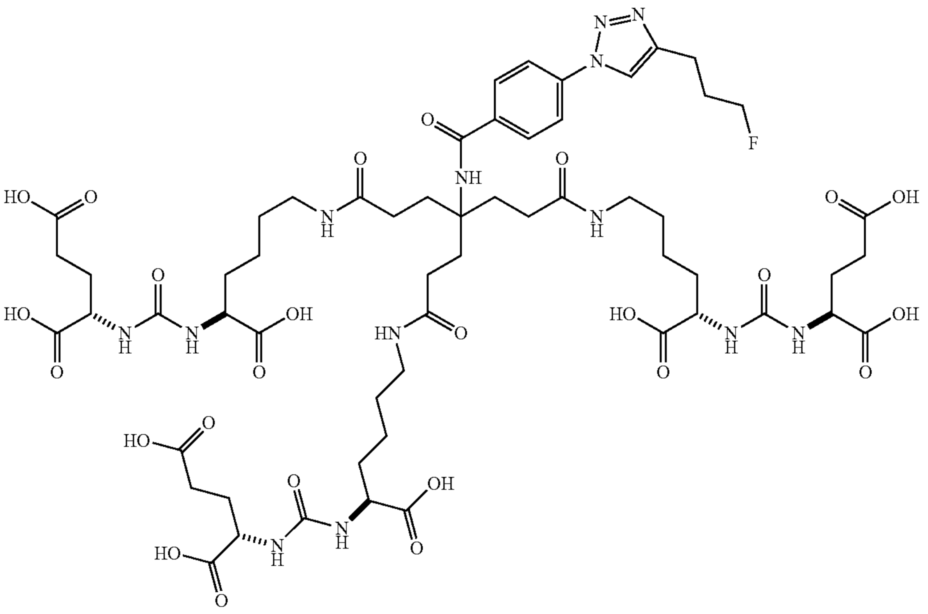

General experimental procedure for click reaction was followed. Reaction was performed on a 6.4 mg scale of (3S,7S,25S,29S)-16-(4-azidobenzamido)-16-(3-(((S)-5-carboxy-5-(3-((S)-1,3-dicarboxypropyl)ureido)pentyl)amino)-3-oxopropyl)-5,13,19,27-tetraoxo-4,6,12,20,26,28-hexaazahentriacontane-1,3,7,25,29,31-hexacarboxylic acid. After HPLC purification, P287 (4.2 mg, 62%) was obtained as a white solid. $^1$H NMR ($CD_3OD$, 400 MHz) δ 8.45 (s, 1H), 8.11 (s, 1H), 8.01-8.07 (m, 2H), 7.93-7.99 (m, 2H), 4.59 (t, J=5.9 Hz, 1H), 4.47 (t, J=5.9 Hz, 1H), 4.24-4.33 (m, 6H), 3.11-3.23 (m, 6H), 2.86-2.99 (m, 2H), 2.37-2.44 (m, 6H), 2.08-2.35 (m, 18H), 1.77-1.94 (m, 6H), 1.57-1.70 (m, 2H), 1.38-1.56 (m, 12H). MS: m/z=1382 (M+H+).

(2S,2'S)-2,2'-(((((1S,1'S)-((5-(4-(13-Amino-2,5,8,11-tetraoxatridecyl)-1H-1,2,3-triazol-1-yl)isophthaloyl)bis(azanediyl))bis(1-carboxypentane-5,1-diyl))bis(azanediyl))bis(carbonyl))-bis(azanediyl))dipentanedioic acid: P288

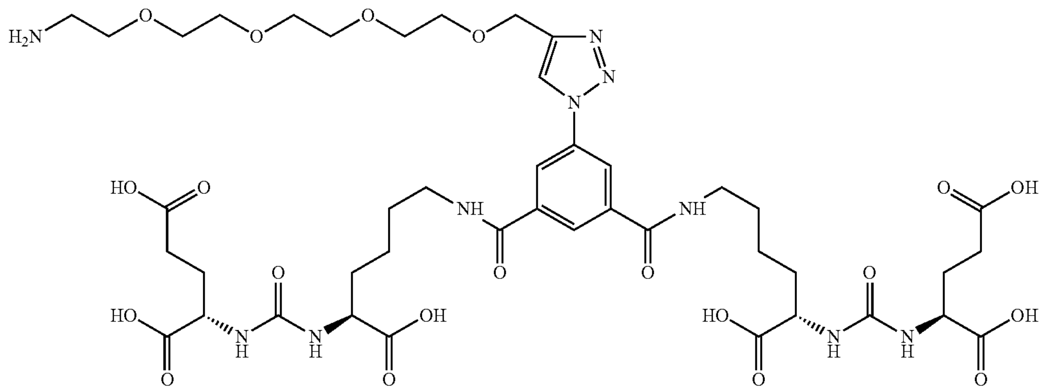 [SMILES: NCCOCCOCCOCCOCc1cn(-c2cc(C(=O)NCCCC[C@H](NC(=O)N[C@@H](CCC(=O)O)C(=O)O)C(=O)O)cc(C(=O)NCCCC[C@H](NC(=O)N[C@@H](CCC(=O)O)C(=O)O)C(=O)O)c2)nn1]

General experimental procedure for urea formation and tert-butyl deprotection reaction was followed. After HPLC purification, P288 (8.0 mg, 45%) was obtained. $^1H$ NMR ($CD_3OD$, 400 MHz) δ 8.66 (s, 1H), 8.45 (brs, 2H), 8.37 (s, 1H), 4.75 (s, 2H), 4.21-4.31 (M, 4H), 3.59-3.78 (m, 19H), 3.39-3.48 (m, 5H), 3.09-3.15 (m, 2H), 2.35-2.43 (m, 3H), 2.03-2.15 (m, 1H), 1.45-1.97 (m, 9H). MS: m/z=1109 ($M+3Na^+$).

(2S,2'S)-2,2'-((6,6'-((5-Azidoisophthaloyl)bis (azanediyl))bis(hexanoyl))-bis(azanediyl))dipentanedioic acid: P289

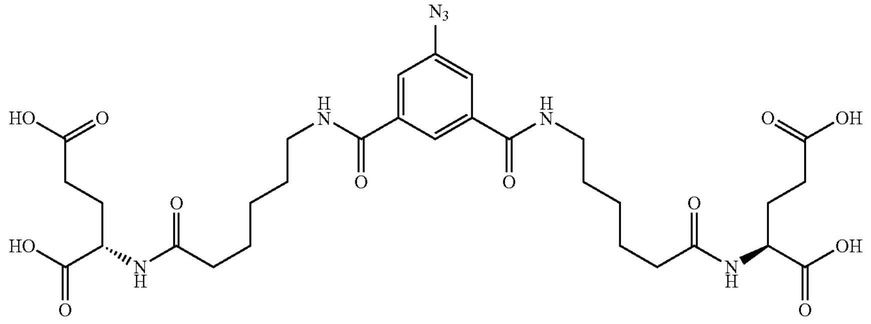 [SMILES: [N-]=[N+]=Nc1cc(C(=O)NCCCCCC(=O)N[C@@H](CCC(=O)O)C(=O)O)cc(C(=O)NCCCCCC(=O)N[C@@H](CCC(=O)O)C(=O)O)c1]

General experimental procedures for amide formation and tert-butyl deprotection reaction were followed. After HPLC purification, P289 (10.0 mg, 35%) was obtained. $^1H$ NMR ($CD_3OD$, 400 MHz) δ 7.96 (s, 1H), 7.55 (s, 2H), 4.30-4.38 (m, 2H), 3.30 (t, J=8.0 Hz, 4H), 2.28 (t, J=8.0 Hz, 4H), 2.19 (t, J=8.0 Hz, 4H), 2.02-2.15 (m, 2H), 1.78-1.89 (m, 2H), 1.50-1.67 (m, 8H), 1.28-1.41 (m, 4H). MS: m/z=692 ($M+H^+$).

(2S,2'S)-2,2'-((((((5-(4-(3-Fluoropropyl)-1H-1,2,3-triazol-1-yl)isophthaloyl)bis(azanediyl))bis(pentane-5,1-diyl))bis(azanediyl))bis(carbonyl))-bis (azanediyl))dipentanedioic acid: P290

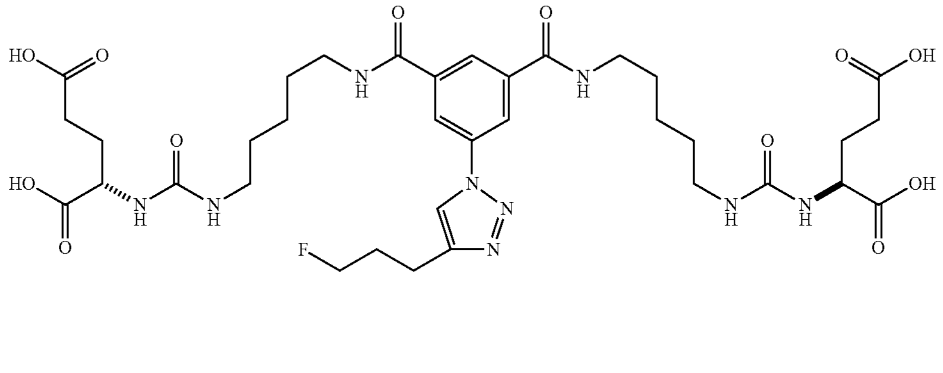

General experimental procedure for click reaction was followed. Reaction was performed on a 6.0 mg scale of (2S,2'S)-2,2'-((((((5-azidoisophthaloyl)bis(azanediyl))bis (pentane-5,1-diyl))bis(azanediyl))bis(carbonyl))bis (azanediyl))dipentanedioic acid. After HPLC purification, P290 (2.5 mg, 37%) was obtained as a white solid. $^1$H NMR ($CD_3OD$, 400 MHz) δ 8.75 (t, J=5.5 Hz, 1H), 8.43-8.49 (m, 3H), 8.37 (t, J=1.4 Hz, 1H), 4.59 (t, J=5.7 Hz, 1H), 4.47 (t, J=5.9 Hz, 1H), 4.28 (dd, J=8.8, 4.9 Hz, 2H), 3.40-3.49 (m, 4H), 3.15 (t, J=6.8 Hz, 4H), 2.92-2.97 (m, 2H), 2.31-2.44 (m, 4H), 2.04-2.21 (m, 4H), 1.82-1.92 (m, 2H), 1.68 (quin, J=7.3 Hz, 4H), 1.40-1.59 (m, 8H). MS: m/z=808 (M+H$^+$).

(2S,2'S)-2,2'-(((((1S,1'S)-((((4S)-4-(3-((4-((2S)-2-Carboxy-2-(3-(1,3-dicarboxypropyl)-ureido)ethyl) phenyl)amino)-3-oxopropyl)-4-(2-(4-(3-fluoropropyl)-1H-1,2,3-triazol-1-yl)acetamido)heptanedioyl) bis(azanediyl))bis(4,1-phenylene))bis(1-carboxyethane-2,1-diyl))bis(azanediyl))bis (carbonyl))bis(azanediyl))dipentanedioic acid: P291

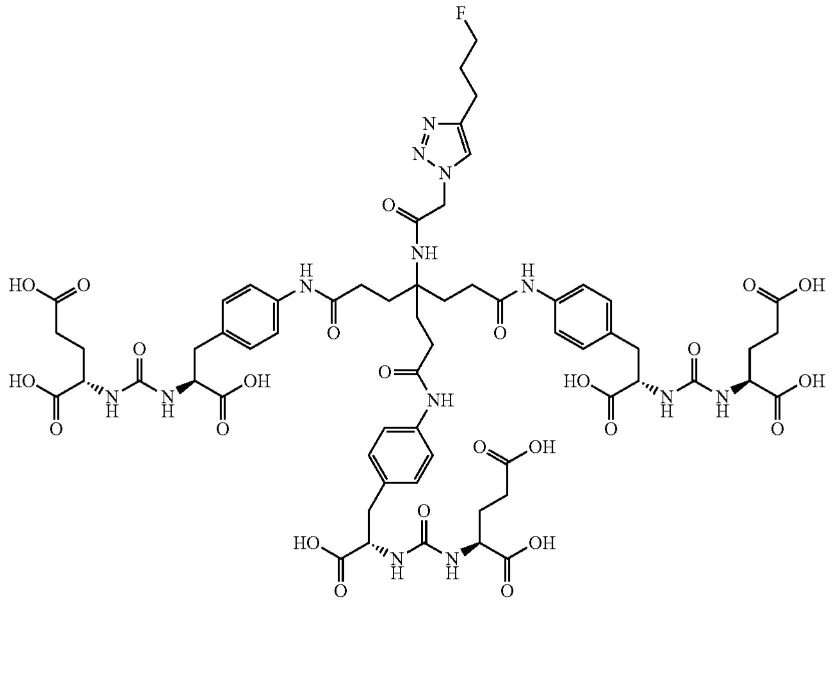 [SMILES: O=C(O)CC[C@H](NC(=O)N[C@@H](Cc1ccc(NC(=O)CCC(CCC(=O)Nc2ccc(C[C@H](NC(=O)N[C@@H](CCC(=O)O)C(=O)O)C(=O)O)cc2)(CCC(=O)Nc2ccc(C[C@H](NC(=O)N[C@@H](CCC(=O)O)C(=O)O)C(=O)O)cc2)NC(=O)Cn2cc(CCCF)nn2)cc1)C(=O)O)C(=O)O]

General procedure for click chemistry was followed. Reaction was performed on a 6 mg scale. After HPLC purification, P291 (2 mg, 38%) was obtained. $^1$H NMR ($CD_3OD$, 400 MHz) δ 7.98 (s, 1H), 7.70 (s, 1H), 7.63 (s, 1H), 7.44 (d, J=8.4 Hz, 6H), 7.15 (d, J=8.4 Hz, 6H), 5.01 (s, 2H), 4.50 (t, J=6.8 Hz, 4H), 4.38 (t, J=6.0 Hz, 1H), 4.28-4.24 (dd, J=8.4 and 4.4 Hz, 3H), 3.12-3.06 (dd, J=14.0 and 6.4 Hz, 3H), 2.96-2.93 (dd, J=14.0 and 6.4 Hz, 3H), 2.80 (t, J=6.4 Hz, 2H), 2.42-2.34 (m, 12H), 2.16-1.81 (m, 16H). MS: m/z=1422 (M+H$^+$).

(2S)-2-(3-((1S)-1-Carboxy-2-(1-(7-(4-((S)-2-carboxy-2-(3-((S)-1,3-dicarboxypropyl)-ureido)-ethyl)-piperidin-1-yl)-4-(4-(4-(3-fluoropropyl)-1H-1,2,3-triazol-1-yl)-benzamido)7-oxoheptanoyl)-piperidin-4-yl)ethyl)ureido)pentanedioic acid: P292

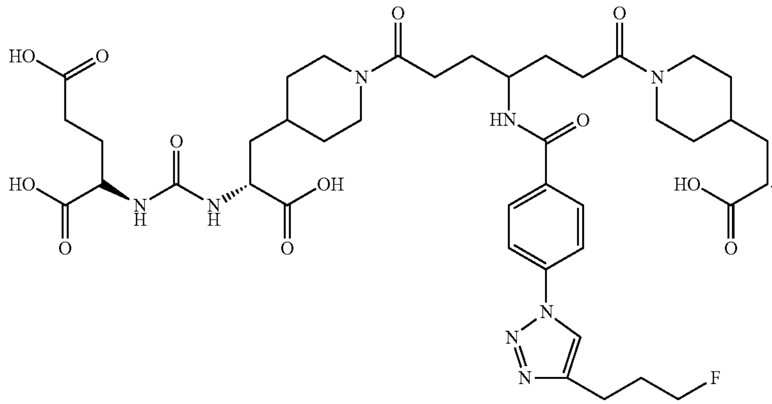

General procedure for click chemistry was followed. Reaction was performed on a 3.3 mg scale. After HPLC purification, P292 (3.2 mg. 89%) was obtained. $^1$H NMR ($CD_3OD$, 400 MHz MHz) δ 8.45 (s, 1H), 8.06-7.97 (m, 4H), 4.58 (t, J=5.6 Hz, 1H), 4.47-4.45 (m, 1H), 4.46 (t, J=5.6 Hz, 1H), 4.34-4.27 (m, 4H), 4.14 (m, 1H), 3.92 (br d, J=13 Hz, 2H), 3.36-3.34 (m, 1H), 3.26-3.21 (m, 1H), 3.06-2.99 (m, 2H), 2.92 (t, J=8.0 Hz, 2H), 2.62-2.38 (m, 9H), 2.19-2.03 (m, 4H), 2.00-1.51 (m, 16H), 1.22-0.85 (m, 4H). MS: m/z=1061 (M+H$^+$).

(2R)-2-(3-((1S)-2-(1-(4-(4-Azidobenzamido)-7-(4-((R)-2-carboxy-2-(3-((S)-1,3-dicarboxypropyl) ureido)ethyl)piperidin-1-yl)-7-oxoheptanoyl)piperidin-4-yl)-1-carboxyethyl)ureido)pentanedioic acid: P292 Precursor

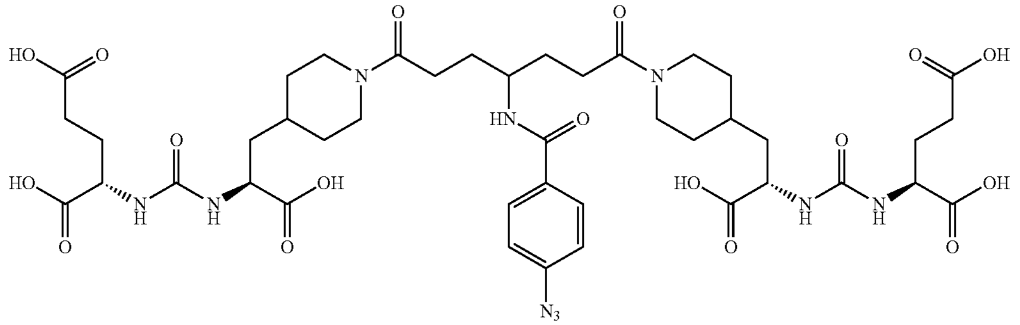 [SMILES: [N-]=[N+]=Nc1ccc(C(=O)NC(CCC(=O)N2CCC(C[C@H](NC(=O)N[C@@H](CCC(=O)O)C(=O)O)C(=O)O)CC2)CCC(=O)N2CCC(C[C@H](NC(=O)N[C@@H](CCC(=O)O)C(=O)O)C(=O)O)CC2)cc1]

General experimental procedure for amide coupling and deprotection of methyl ester group using 2M HCl at 40° C. for 4 h was followed. Reaction was performed on 120 mg scale. After HPLC purification, P292 Precursor (48 mg, 34%, in two steps) was obtained. $^1$H NMR ($CD_3OD$, 400 MHz) δ 7.89-7.86 (m, 2H), 8.15 (d, J=8.0 Hz, 2H), 4.46 (t, J=11.0 Hz, 2H), 4.35-4.27 (m, 4H), 4.15-4.08 (m, 1H), 3.89 (br d, J=12.8 Hz, 2H), 3.03-2.94 (m, 2H), 2.62-2.34 (m, 10H), 2.18-2.09 (m, 2H), 1.96-1.47 (m, 16H), 1.40-1.91 (m, 4H). MS: m/z=975 (M+H$^+$).

(2S,2'S)-2,2'-(((2S,2'S)-2,2'-((4,4'-((5-Nitroisophthaloyl)bis(azanediyl))bis(butanoyl))-bis(azanediyl))bis(3-carboxypropanoyl))bis(azanediyl))dipentanedioic acid: P293

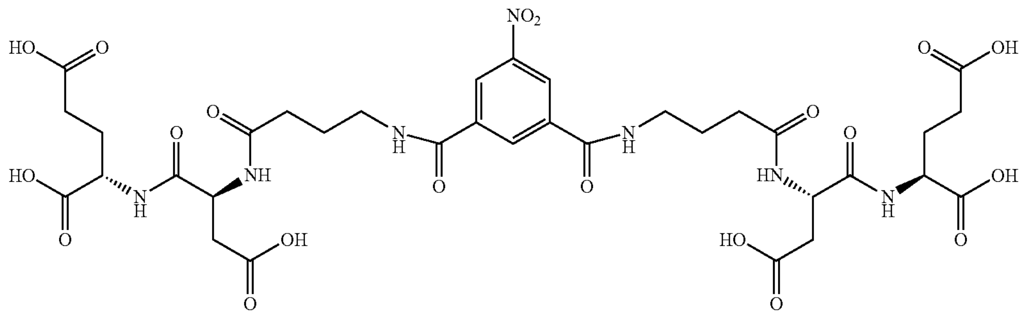 [SMILES: O=C(O)CC[C@H](NC(=O)[C@H](CC(=O)O)NC(=O)CCCNC(=O)c1cc(C(=O)NCCCC(=O)N[C@@H](CC(=O)O)C(=O)N[C@@H](CCC(=O)O)C(=O)O)cc([N+](=O)[O-])c1)C(=O)O]

General experimental procedure for amide formation and tert-butyl deprotection reaction was followed. After HPLC purification, P293 (5.1 mg, 25%) was obtained. $^1$H NMR ($CD_3OD$, 400 MHz) δ 8.82 (s, 2H), 8.69 (s, 1H), 4.69-4.80 (m, 2H), 4.39-4.48 (m, 2H), 3.38-3.58 (m, 4H), 2.61-2.85 (m, 4H), 2.08-2.47 (m, 10H), 1.83-2.03 (m, 6H). MS: m/z=870 (M+H$^+$).

(2S,2'S)-2,2'-(((((1S,1'S)-(((5-(4-(13-Amino-2,5,8,11-tetraoxatridecyl)-1H-1,2,3-triazol-1-yl)isophthaloyl)bis(azanediyl))bis(4,1-phenylene))bis(1-carboxyethane-2,1-diyl))-bis(azanediyl))bis(carbonyl))bis(azanediyl))dipentanedioic acid: P294

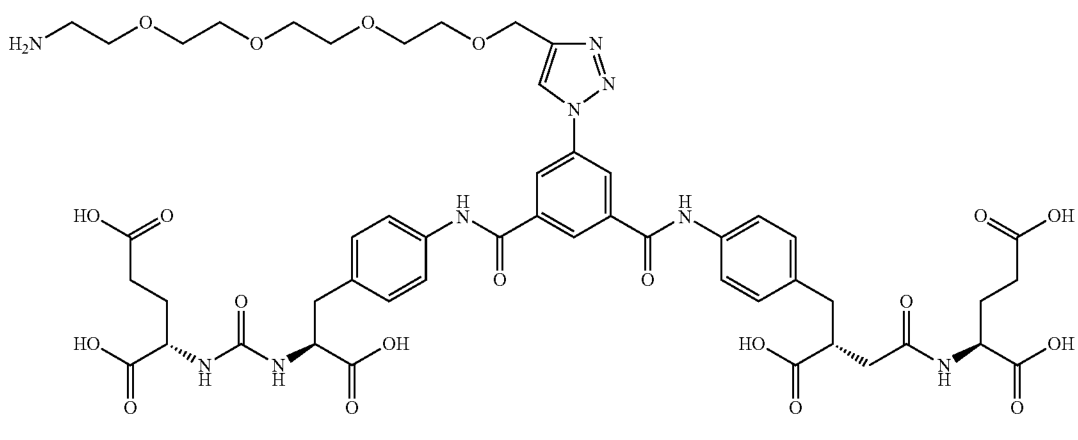 [SMILES: NCCOCCOCCOCCOCc1cn(-c2cc(C(=O)Nc3ccc(C[C@H](CC(=O)N[C@@H](CCC(=O)O)C(=O)O)C(=O)O)cc3)cc(C(=O)Nc3ccc(C[C@H](NC(=O)N[C@@H](CCC(=O)O)C(=O)O)C(=O)O)cc3)c2)nn1]

General experimental procedure for click chemistry and tert-butyl deprotection reaction was followed. After HPLC purification, P294 (3.2 mg, 18%) was obtained. MS: m/z=870 (M+H+).

(9S,13R)-3,11-Dioxo-1-phenyl-2-oxa-4,10,12-triaza-pentadecane-9,13,15-tricarboxylic acid: P295

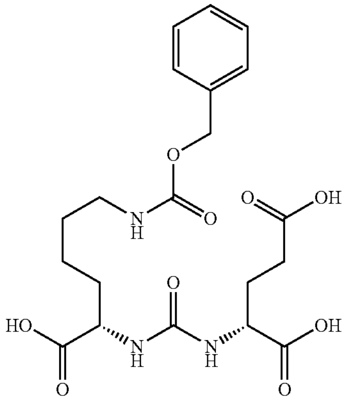 [SMILES: O=C(O)CC[C@@H](NC(=O)N[C@@H](CCCCNC(=O)OCc1ccccc1)C(=O)O)C(=O)O]

General experimental procedure for urea formation and tert-butyl deprotection reaction was followed. After HPLC purification, P295 (15 mg, 56%) was obtained. $^1$H NMR ($CD_3OD$, 400 MHz) δ 7.35-7.46 (m, 5H), 5.09 (s, 2H), 4.51-4.63 (m, 1H), 4.35-4.48 (m, 1H), 3.38 (t, J=7.6 Hz, 2H), 2.39 (t, J=7.6 Hz, 2H), 1.95-2.21 (m, 2H), 1.25-1.86 (m, 6H). MS: m/z=454 (M+H+).

(2S,2'S)-2,2'-(((3R,3'R)-3,3'-((6,6'-((5-nitroisophthaloyl)bis(azanediyl))bis(hexanoyl))-bis(azanediyl))bis(3-carboxypropanoyl))bis(azanediyl))dipentanedioic acid: P296

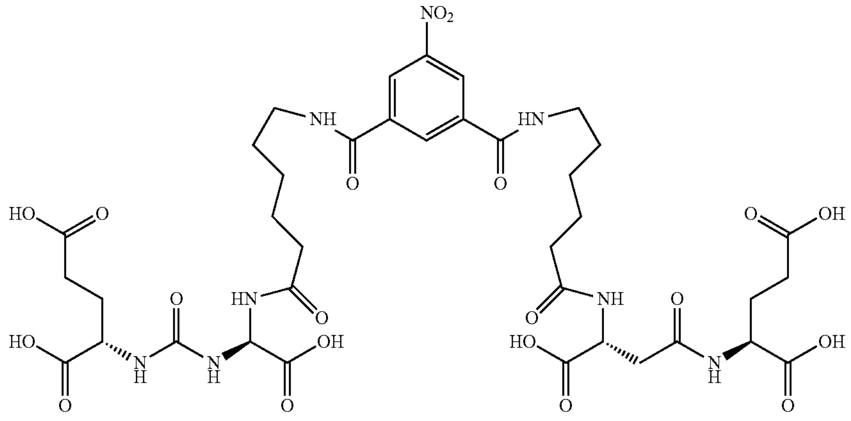 [SMILES: O=C(O)CC[C@H](NC(=O)C[C@@H](NC(=O)CCCCCNC(=O)c1cc(C(=O)NCCCCCC(=O)N[C@H](NC(=O)N[C@@H](CCC(=O)O)C(=O)O)C(=O)O)cc([N+](=O)[O-])c1)C(=O)O)C(=O)O]

General experimental procedure for amide formation and tert-butyl deprotection reaction was followed. After HPLC purification, P296 (8.1 mg, 32%) was obtained. $^{1}H$ NMR ($CD_3OD$, 400 MHz) δ 8.71 (s, 2H), 8.59 (s, 1H), 4.61-4.78 (m, 2H), 4.30-4.37 (m, 2H), 3.33 (t, J=6.8 Hz, 4H), 2.59-2.79 (m, 4H), 2.29 (t, J=7.6 Hz, 4H), 2.18 (t, J=7.6 Hz, 4H), 2.02-2.14 (m, 2H), 1.76-1.88 (m, 2H), 1.51-1.65 (m, 8H), 1.28-1.41 (m, 4H). MS: m/z=926 ($M+H^+$).

(2R,2'R)-2,2'-(((((1S,1'S)-((5-(4-(3-Fluoropropyl)-1H-1,2,3-triazol-1-yl)isophthaloyl)-bis(azanediyl))bis(1-carboxypentane-5,1-diyl))bis(azanediyl))bis(carbonyl))-bis(azanediyl))dipentanedioic acid: P297

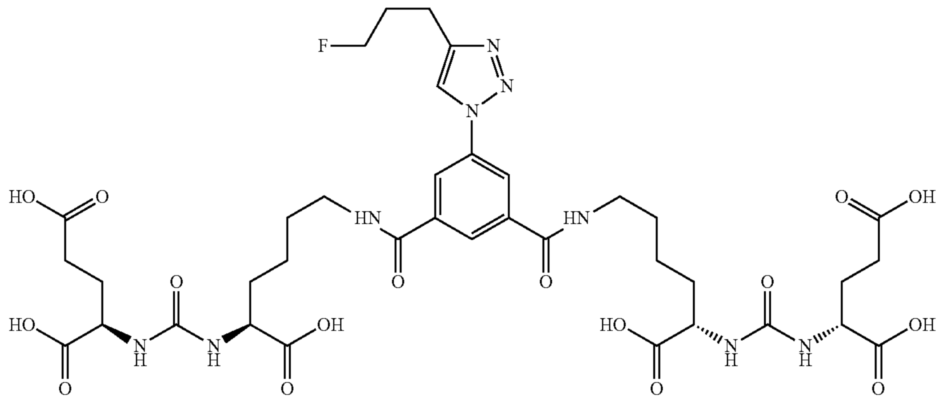 [SMILES: O=C(O)CC[C@@H](NC(=O)N[C@@H](CCCCNC(=O)c1cc(C(=O)NCCCC[C@H](NC(=O)N[C@H](CCC(=O)O)C(=O)O)C(=O)O)cc(-n2cc(CCCF)nn2)c1)C(=O)O)C(=O)O]

General experimental procedure for amide formation and tert-butyl deprotection reaction was followed. After HPLC purification, P297 (12 mg, 36%) was obtained. $^{1}H$ NMR ($CD_3OD$, 400 MHz) δ 8.39 (s, 1H), 8.36 (d, J=1.6 Hz, 2H), 8.27 (t, J=1.6 Hz, 1H), 4.44 (dt, J=47.2, 6.0 Hz, 2H), 4.16-4.25 (m, 4H), 3.35 (t, J=6.8 Hz, 4H), 2.85 (t, J=7.2 Hz, 2H), 2.17-2.33 (m, 4H), 1.96-2.12 (m, 4H), 1.72-1.85 (m, 4H), 1.53-1.71 (m, 6H), 1.35-1.48 (m, 4H). MS: m/z=896 ($M+H^+$).

(2S,2'S)-2,2'-(((3R,3'R)-3,3'-((4,4'-((5-Nitroisophthaloyl)bis(azanediyl))bis(butanoyl))-bis(azanediyl))bis(3-carboxypropanoyl))bis(azanediyl))dipentanedioic acid: P298

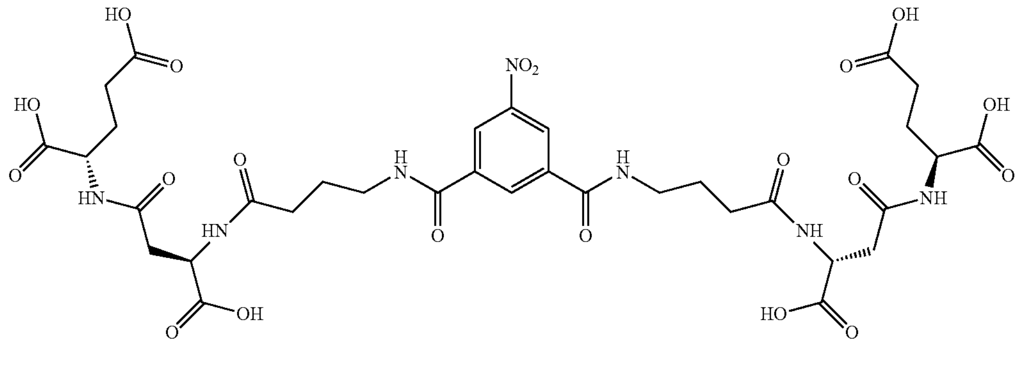 [SMILES: O=C(O)CC[C@H](NC(=O)C[C@@H](NC(=O)CCCNC(=O)c1cc(C(=O)NCCCC(=O)N[C@H](CC(=O)N[C@@H](CCC(=O)O)C(=O)O)C(=O)O)cc([N+](=O)[O-])c1)C(=O)O)C(=O)O]

General experimental procedure for amide formation and tert-butyl deprotection reaction was followed. After HPLC purification, P298 (6.2 mg, 31%) was obtained. $^{1}H$ NMR ($CD_3OD$, 400 MHz) δ 8.73 (s, 2H), 8.59 (s, 1H), 4.61-4.69 (m, 2H), 4.31-4.39 (m, 2H), 3.37 (t, J=6.8 Hz, 4H), 2.61-2.81 (m, 4H), 2.23-2.34 (m, 8H), 2.01-2.12 (m, 2H), 1.76-1.92 (m, 6H). MS: m/z=926 ($M+H^+$).

Enzymatic Assay for In Vitro Evaluation of PSMA Inhibitors

The inhibitory activity of all compounds was determined using a fluorescent assay of human PSMA activity. The enzyme used in the assay was purchased from R&D Systems and stored at ~80° C. The PSMA activity was assayed in a two-step process. In the first step, aliquots of enzyme (0.2 μg/mL) were incubated for 1 h at 37° C. in 50 mM HEPES, 0.1 M NaCl, pH 7.5, in the presence of 20 μM NAAG and the given inhibitor, in a volume of 250 μL, to allow for the accumulation of glutamate produced in the PSMA reaction. In the second step, the amount of accumulated glutamate was measured using the OPA reaction, and the fluorescence was read with a SpectraMax fluorescent plate reader using excitation at 330 nm and emission at 450 nm. The final Ki values for each inhibitor were calculated from the respective IC50 values using the Cheng and Prusoff equation.

Preparation of Radio-F-18 labeled P005, P053, P092, and P188.

1. Preparation of [F-18]Fluoride and Conversion to Anhydrous Form:

Aqueous [F-18]fluoride ion produced in the cyclotron target, is passed through an anion exchange resin cartridge. The [O-18]$H_2O$ readily passes through the anion exchange resin while [F-18]fluoride is retained. The [F-18]fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18]fluoride in the reaction vessel. The Kryptofix sequesters the potassium ions preventing the formation of strong K+/F on-pairs. This increases the chemical reactivity of the [F-18]fluoride ions. The mixture is dried by heating between 68-95° C. under reduced pressure (250 mbar) and a stream of argon. This evaporation step removes the water and converts the [F-18] to an anhydrous complex, which is much more reactive than aqueous [F-18]fluoride.

2. Reaction of Anhydrous [F-18]Fluoride with Pentynyl Tosylate.

A solution of the tosylate precursor, (20 mg, 75 μmol) dissolved in THE or MeCN or DMF (0.5 mL) is added to the reaction vessel containing the anhydrous [F-18]Fluoride. The vessel is heated to approximately 110±5° C. for 3 minutes to induce displacement of the tosylate leaving group by [F-18]fluoride. The 18-F-fluoropentyne is distilled from the reaction vessel into the mixture containing the PSMA (azide) precursor.

3. Coupling of 18F-Fluoropentyne with PSMA Azide Precursor to Prepare [F-18]PSMA Tracer.

The 18F-pentyne is distilled at room temperature (bubbled) into a solution containing Azide-precursor (4 mg) dissolved in 250 μL of 0.1 M $CuSO_4$, sodium ascorbate (40 mg), and EtOH (0.1 mL). The reaction is stirred at room temperature for 15-30 minutes. Prior to purification by HPLC, the reaction is diluted with water (up to 5 mL).

4. HPLC Purification of [F-18]PSMA Tracer.

The reaction mixture containing crude [F-18]PSMA tracer is transferred to the HPLC sample loop (5 mL) and purified via chromatographic separation using a semi-preparative HPLC column (Phenomenex Gemini, C18, 5, 10×250 mm) using appropriate mobile phase with flow rate of 5 mL/min. The column effluent is monitored using UV (220, 254 or 280 nm) and radiometric detectors connected in series. The purified [F-18]PSMA tracer is collected from the column at the retention time window determined for the reference standard which coincides with the time that the radiometric detectors begin showing the main peak.

5. Formulation of Purified [F-18]PSMA Tracer.

The purified [F-18]PSMA tracer fraction is evaporated at 40° C. to dryness and final dose is reformulated in a maximum of 10% EtOH:water.

| Tracer | Synthesis time in min | Mobile phase used | DCY | SA Ci/umol |
|---|---|---|---|---|
| P05 | 69 | MeCN/5 mmol phosphate buffer | 24% | 2.938 |
| P53 | 127 | MeCN/30 mmol phosphate buffer | 5.5% | 4.92 |
| P92 | 98 | MeCN/30 mmol phosphate buffer | 18.6% | 2.416 |
| P188 | 120 | EtOH/5 mmol phosphate buffer | 17% | 1.005 |

The LC trace of F18-PSMA is analyzed using Gemini NX 5u C18 110A, 150×4.6 mm analytical column using the following program.

Small Animal In Vivo PET Imaging

MicroPET/CT. Tumor-bearing mice (LNCaP, PSMA+, PC-3, PSMA−) were anesthetized with 2% isoflurane/98% oxygen and administered with ~250 μCi/mouse of tracer in a total volume of 200 μl saline via bolus intravenous tail vein injection. An INVEON Multimodality scanner (SIEMENS) was used to perform the microPET/CT imaging. For dynamic scans, imaging was performed immediately following the tracer injection for two hours. Animals were kept warm and under anesthesia during this time period. For static scans, the animals first underwent a one hour conscious uptake, and was then anesthetized prior to and during imaging. Animals were scanned for 15-30 minutes and a static image was generated from each scan. All mice underwent a 10 minute micro-CT scan for anatomical registration. Uptake of the tracer was obtained by visually drawing regions of interest (ROIs) based on the fused PET/CT images and the corresponding activity values were determined using the INVEON Research Workplace software. All values are represented as % injected dose per gram tissue (% ID/g). In order to take into account mouse-to-mouse variation of background tracer uptake, tumor uptake values was also normalized to uptake values in the skeletal muscle, represented as tumor-over-muscle (T/M) ratios.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. A variety of modifications to the embodiments described will be apparent to those skilled in the art from the disclosure provided herein. Thus, the present invention may be embodied in other specific forms without departing from the spirit or essential attributes thereof. Various changes may be made without departing from the spirit and scope of the inventions as defined in the following claims.

We claim:

1. A method comprising administering to a patient, a compound of Formula VI:

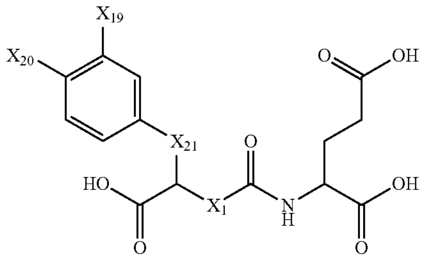

and pharmaceutically acceptable salts and stereoisomers thereof, wherein:

$X_1$ is CH;

$X_{19}$ is selected from the group consisting of: $NO_2$ and $(CH_2)_{1-10}$—$R_{16}$ wherein at least one $CH_2$ of $(CH_2)_{1-10}$ is optionally replaced by CONH, aryl, a triazole or heteroaryl;

$X_{20}$ is selected from the group consisting of: H, $NO_2$, and $(CH_2)_{1-10}$-$R_{16}$ wherein at least one $CH_2$ of $(CH_2)_{1-10}$ is optionally replaced by CONH, aryl, a triazole or heteroaryl; wherein in Formula VI, at least one $CH_2$ of $(CH_2)_{1-10}$-$R_{16}$ of either $X_{19}$ or $X_{20}$ is replaced by triazole;

$X_{21}$ is $(CH_2)_{1-3}$ wherein at least one $CH_2$ of $(CH_2)_{1-3}$ is optionally replaced by a heteroaryl, and $R_{16}$ is selected from the group consisting of $N_3$, alkyne, protecting group, halo and a radioisotope; wherein at least one $R_{16}$ from $X_{19}$ or $X_{20}$ is a radioisotope;

or administering to a patient, a radio labelled-compound of Formula VIII:

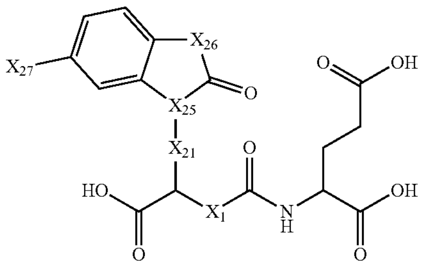

and pharmaceutically acceptable salts and stereoisomers thereof, wherein:

$X_1$ is CH;

$X_{24}$ is $(CH_2)_{1-6}$ wherein at least one $CH_2$ of $(CH_2)_{1-6}$ is optionally replaced by at least one selected from the group consisting of NH, O, or S, $X_{25}$ is N or CH;

$X_{26}$ is NH or $CH_2$;

$X_{27}$ is selected from the group consisting of: H, $NO_2$, and $(CH_2)_{1-10}$-$R_{16}$ wherein at least one $CH_2$ of $(CH_2)_{1-10}$ is optionally replaced by O, CONH, aryl, or heteroaryl; and $R_{16}$ is a radioisotope;

scanning the patient using positron emission tomography or single photon emission computed tomography; and imaging a tissue in the patient.

2. The method of claim 1, wherein in Formula VI, $X_{19}$ is H and $X_{20}$ is $(CH_2)_{1-10}$-$R_{16}$ wherein at least one $CH_2$ of $(CH_2)_{1-10}$ is replaced by CONH.

3. The method of claim 1, wherein in Formula VI, $X_{20}$ is H and $X_{19}$ is $(CH_2)_{1-10}$-$R_{16}$ wherein at least one $CH_2$ of $(CH_2)_{1-10}$ is replaced by CONH.

4. The method of claim 1, wherein in Formula VIII, at least one $CH_2$ of $(CH_2)_{1-6}$ is optionally replaced by O.

5. The method of claim 1, wherein in Formula VIII, $X_{25}$ is N.

6. The method of claim 1, wherein in Formula VIII, $X_{25}$ is CH.

* * * * *